US012157779B2

(12) United States Patent
O'Connor et al.

(10) Patent No.: US 12,157,779 B2
(45) Date of Patent: *Dec. 3, 2024

(54) CYCLODEXTRIN DIMERS, COMPOSITIONS THEREOF, AND USES THEREOF

(71) Applicant: CYCLARITY THERAPEUTICS, INC., Novato, CA (US)

(72) Inventors: Matthew S. O'Connor, Richmond, CA (US); Milo Malanga, Budapest (HU); Michael Kope, El Granada, CA (US); Christina A. T. M. B. Tom, Eugene, OR (US); Amelia M. Anderson, San Jose, CA (US)

(73) Assignee: CYCLARITY THERAPEUTICS, INC., Novato, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/461,069

(22) Filed: Aug. 30, 2021

(65) Prior Publication Data

US 2022/0056158 A1 Feb. 24, 2022

Related U.S. Application Data

(62) Division of application No. 16/733,945, filed on Jan. 3, 2020, now Pat. No. 11,279,774.

(60) Provisional application No. 62/850,334, filed on May 20, 2019, provisional application No. 62/787,869, filed on Jan. 3, 2019.

(51) Int. Cl.
 *C08B 37/16* (2006.01)
 *A61K 31/724* (2006.01)

(52) U.S. Cl.
 CPC ........ *C08B 37/0012* (2013.01); *A61K 31/724* (2013.01)

(58) Field of Classification Search
 CPC ............ C08B 37/0012; C08B 37/0015; A61K 31/724; A61K 47/40
 See application file for complete search history.

(56) References Cited

U.S. PATENT DOCUMENTS

| | | | |
|---|---|---|---|
| 3,420,788 A | 1/1969 | Solms | |
| 3,426,011 A | 2/1969 | Parmerter et al. | |
| 3,453,257 A | 7/1969 | Parmerter et al. | |
| 3,459,731 A | 8/1969 | Gramera et al. | |
| 5,134,127 A | 7/1992 | Stella et al. | |
| 5,208,316 A | 5/1993 | Yoshinaga | |
| 5,241,059 A | 8/1993 | Yoshinaga | |
| 5,276,088 A | 1/1994 | Yoshinaga | |
| 5,324,750 A | 6/1994 | Lincoln et al. | |
| 5,403,828 A | 4/1995 | Lewis et al. | |
| 5,608,015 A | 3/1997 | Yoshinaga | |
| 5,977,070 A | 11/1999 | Piazza et al. | |
| 6,642,214 B1 | 11/2003 | Moser | |
| 6,835,718 B2 | 12/2004 | Kosak | |
| 2002/0094950 A1 | 7/2002 | Moser et al. | |
| 2010/0303754 A1 | 12/2010 | Turpin et al. | |
| 2011/0312914 A1 | 12/2011 | Kano et al. | |
| 2012/0010171 A1 | 1/2012 | Yuan | |
| 2012/0107229 A1 | 5/2012 | Huang et al. | |
| 2013/0237611 A1 | 9/2013 | Kuhn et al. | |
| 2014/0038918 A1 | 2/2014 | Rodriguez-Boulan et al. | |
| 2014/0178925 A1 | 6/2014 | Chen | |
| 2016/0155972 A1 | 6/2016 | Chen | |
| 2019/0209605 A1 | 7/2019 | Kulkarni et al. | |
| 2019/0381091 A1 | 12/2019 | Meigers et al. | |

FOREIGN PATENT DOCUMENTS

| | | |
|---|---|---|
| CN | 1274674 C | 9/2006 |
| CN | 102019171 B | 6/2013 |
| CN | 103641937 A | 3/2014 |
| CN | 103788233 A | 5/2014 |
| CN | 103242827 B | 8/2014 |
| CN | 104072797 A | 10/2014 |
| CN | 104289204 A | 1/2015 |
| CN | 104558253 A | 4/2015 |
| CN | 104610470 A | 5/2015 |
| CN | 104861950 A | 8/2015 |
| CN | 105219007 A | 1/2016 |
| CN | 103965376 B | 5/2016 |
| CN | 106000247 A | 10/2016 |
| CN | 106215891 A | 12/2016 |
| CN | 104861950 B | 8/2017 |
| CN | 107376875 A | 11/2017 |
| CN | 108478532 A | 9/2018 |
| CN | 106984291 B | 4/2020 |
| CN | 108478532 B | 12/2020 |

(Continued)

OTHER PUBLICATIONS

Wu Linsheng, "Design of Two Synthetic Routes of Captive Cyclodextrin DImer," Journal of Chuzhou Teachers College, No. 4, Dec. 31, 1999, pp. 74-75.

Hocquelet, Celine, et al. "Synthesis and inclusion properties study of some mono 6-amino β-cyclodextrin dimers bridged by N, N-succinyldiamide linkers." Journal of Inclusion Phenomena and Macrocyclic Chemistry 69 (2011):75-84.

Menuel, Stéphane, et al. "Unusual Inversion Phenomenon of β-Cyclodextrin Dimers in Water." Chemistry-A European Journal 17.14 (2011): 3949-3955.

Arima, Hidetoshi, Keiichi Motoyama, and Tetsumi Irie. "Recent findings on safety profiles of cyclodextrins, cyclodextrin conjugates, and polypseudorotaxanes." Cyclodextrins in pharmaceutics, cosmetics, and biomedicine (2011): 91-122.

(Continued)

*Primary Examiner* — Leigh C Maier
(74) *Attorney, Agent, or Firm* — Robin L. Teskin; Baker, Donelson, Bearman, Caldwell & Berkowitz PC

(57) ABSTRACT

A new class of synthetic cyclodextrin dimers is described. Exemplary cyclodextrin dimers can treat atherosclerotic plaques by targeting various forms cholesterol both intracellularly and extracellularly. Also provided are methods of depleting atherosclerotic plaques of cholesterol, cholesterol esters, 7-ketocholesterol and 7-ketocholesterol esters by treatment with such cyclodextrins. Further described are subclasses of dimers that have high specificity for 7-ketocholesterol.

20 Claims, 179 Drawing Sheets

(56) References Cited

FOREIGN PATENT DOCUMENTS

| | | |
|---|---|---|
| DE | 2927733 A1 | 1/1980 |
| DE | 102010023790 A1 | 12/2011 |
| EP | 1743907 A1 | 1/2007 |
| EP | 2690105 A1 | 1/2014 |
| ES | 2162552 A1 | 12/2001 |
| FR | 2980976 B1 | 10/2015 |
| GB | 2307176 A | 5/1997 |
| JP | 06206905 | 7/1994 |
| JP | H09241292 A | 9/1997 |
| JP | H11322758 A | 11/1999 |
| JP | 2006002077 | 1/2006 |
| JP | 2006002077 A | 1/2006 |
| JP | 2007106789 A | 4/2007 |
| JP | 2008184548 A | 8/2008 |
| JP | 2009024094 A | 2/2009 |
| JP | 2009127044 A | 6/2009 |
| JP | 2010086864 A | 4/2010 |
| JP | 4803631 B2 | 10/2011 |
| JP | 2012020940 A | 2/2012 |
| JP | 2013231111 | 11/2013 |
| JP | 2013231111 A | 11/2013 |
| JP | 2017052859 A | 3/2017 |
| KR | 20110034260 A | 4/2011 |
| WO | 1991004026 A1 | 4/1991 |
| WO | 1991013100 A1 | 9/1991 |
| WO | 1991018022 | 11/1991 |
| WO | 1991018023 | 11/1991 |
| WO | 1992006127 | 4/1992 |
| WO | 1992009637 | 6/1992 |
| WO | 1994023697 A1 | 10/1994 |
| WO | 2000067716 A1 | 11/2000 |
| WO | 2000067717 A1 | 11/2000 |
| WO | 2001003706 A1 | 1/2001 |
| WO | 2001055222 A1 | 8/2001 |
| WO | 2002043742 A1 | 6/2002 |
| WO | 2003065924 A1 | 8/2003 |
| WO | 2003052060 A3 | 11/2003 |
| WO | 2003063805 A3 | 3/2004 |
| WO | 2004087043 B1 | 1/2005 |
| WO | 2005003089 A2 | 1/2005 |
| WO | 2005030131 A3 | 5/2005 |
| WO | 2007110882 A1 | 10/2007 |
| WO | 2007075963 A3 | 11/2008 |
| WO | 2008151775 A2 | 12/2008 |
| WO | 2009064374 A3 | 5/2010 |
| WO | 2012019500 A1 | 2/2012 |
| WO | 2013155485 A3 | 12/2013 |
| WO | 2014016361 A1 | 1/2014 |
| WO | 2014022841 A1 | 2/2014 |
| WO | 2014047715 A1 | 4/2014 |
| WO | 2015083736 A1 | 6/2015 |
| WO | 2015087016 A1 | 6/2015 |
| WO | 2016040940 A1 | 3/2016 |
| WO | 2016201137 A1 | 12/2016 |
| WO | 2016204854 A1 | 12/2016 |
| WO | 2017006279 A1 | 1/2017 |
| WO | 2017125889 A1 | 7/2017 |
| WO | 2017173111 A1 | 10/2017 |
| WO | 2018051298 A1 | 3/2018 |
| WO | 2020002851 A1 | 1/2020 |
| WO | 2019067269 A3 | 3/2020 |
| WO | 2020092107 A1 | 5/2020 |

OTHER PUBLICATIONS

Tripodo et al. "Efficient synthesis of pure monotosylated beta-cyclodextrin and its dimers." Carbohydrate Research. Nov. 2013; 1-15.
"European Pharmacopenia HydroxypropylBetadex Monograph Details," May 14, 2020. https://extranet.edqm.eu/4DLink1/4DCGI/Web_View/mono/1804.
"Preclinical Formulations for Discovery and Toxicology: Physicochemical Challenges: Expert Opinion on Drug Metabolism & Toxicology: vol. 2, No. 5." Accessed Aug. 5, 2020. https://www.tandfonline.com/doi/abs/10.1517/17425255.2.5.715?journalCode=iemt20.
Addi & Cassi Fund. "Addi & Cassi Fund Hydroxy Propyl-Beta-Cyclodextrin Summary for IND/IRB Submissions," 2010.
Aime, Silvio, Eliana Gianolio, Francesca Arena, Alessandro Barge, Katia Martina, George Heropoulos, and Giancarlo Cravotto. "New Cyclodextrin Dimers and Trimers Capable of Forming Supramolecular Adducts with Shape-Specific Ligands." Org. Biomol. Chem. 7, No. 2 (2009): 370-79. https://doi.org/10.1039/B812172A.
Alcalde, Mercedes Alvarez, Alvaro Antelo, Aida Jover, Francisco Meijide, and José Vázquez Tato. "Solubilization of Cholesterol in Aqueous Solution by Two β-Cyclodextrin Dimers and a Negatively Charged β-Cyclodextrin Derivative." Journal of Inclusion Phenomena and Macrocyclic Chemistry 63, No. 3-4 (Apr. 2009): 309-17. https://doi.org/10.1007/s10847-008-9524-3.
Amar, Marcelo J. A., Maryann Kaler, Amber B. Courville, Robert Shamburek, Maureen Sampson, and Alan T. Remaley. "Randomized Double Blind Clinical Trial on the Effect of Oral α-Cyclodextrin on Serum Lipids." Lipids in Health and Disease 15, No. 1 (Jul. 12, 2016): 115. https://doi.org/10.1186/s12944-016-0284-6.
Anderson, Amelia, Angielyn Campo, Elena Fulton, Anne Corwin, W. Gray Jerome, and Matthew S. O'Connor. "7-Ketocholesterol in Disease and Aging." Redox Biology 29 (Jan. 2020): 101380. https://doi.org/10.1016/j.redox.2019.101380.
Atger, V M, M de la Llera Moya, G W Stoudt, WV Rodrigueza, M C Phillips, and G H Rothblat. "Cyclodextrins as Catalysts for the Removal of Cholesterol from Macrophage Foam Cells." Journal of Clinical Investigation 99, No. 4 (Feb. 15, 1997): 773-80. https://doi.org/10.1172/JCI119223.
Avakyan, V. G., V. B. Nazarov, M. V. Alfimov, A. A. Bagaturyants, and N. I. Voronezheva. "The Role of Intra- and Intermolecular Hydrogen Bonds in the Formation of β-Cyclodextrin Head-to-Head and Head-to-Tail Dimers. The Results of Ab Initio and Semiempirical Quantum-Chemical Calculations." Russian Chemical Bulletin 50, No. 2 (Feb. 1, 2001): 206-16. https://doi.org/10.1023/A:1009557729668.
Aykaç, A, M C Martos-Maldonado, J M Casas-Solvas, L García-Fuentes, and A Vargas-Berenguel. "Binding Ability Properties of β-Cyclodextrin Dimers Linked through Their Secondary Faces towards Cancer Chemotherapeutic Agent Methotrexate." J. Drug Del. Sci. Tech. 22, No. 3 (2012): 270-72.
Bas, G. Le, and G. Tsoucaris. "Two-Dimensional Hydrogen Bond Network in β-Cyclodextrin Complexes." Supramolecular Chemistry 4, No. 1 (Nov. 1994): 13-16. https://doi.org/10.1080/10610279408029857.
Benkovics, et al.. "Homo- and Hetero-Difunctionalized β-Cyclodextrins: Short Direct Synthesis in Gram Scale and Analysis of Regiochemistry." Beilstein Journal of Organic Chemistry 15 (Mar. 18, 2019): 710-20. https://doi.org/10.3762/bjoc.15.66.
Besenicar, Mojca Podlesnik, Andrej Bavdek, Ales Kladnik, Peter Macek, and Gregor Anderluh. "Kinetics of Cholesterol Extraction from Lipid Membranes by Methyl-Beta-Cyclodextrin—a Surface Plasmon Resonance Approach." Biochimica Et Biophysica Acta 1778, No. 1 (Jan. 2008): 175-84. https://doi.org/10.1016/j.bbamem.2007.09.022.
Blaszkiewicz, Claire, Hervé Bricout, Estelle Léonard, Christophe Len, David Landy, Christine Cézard, Florence Djedaïni-Pilard, Eric Monflier, and Sébastien Tilloy. "A Cyclodextrin Dimer as a Supramolecular Reaction Platform for Aqueous Organometallic Catalysis." Chemical Communications 49, No. 62 (2013): 6989. https://doi.org/10.1039/c3cc43647k.
Bodine, Kyle D., David Y. Gin, and Mary S. Gin. "Synthesis of Readily Modifiable Cyclodextrin Analogues via Cyclodimerization of an Alkynyl-Azido Trisaccharide." Journal of the American Chemical Society 126, No. 6 (Feb. 2004): 1638-39. https://doi.org/10.1021/ja039374t.
Bonnet, Pascal, Carlos Jaime, and Luc Morin-Allory. "Structure and Thermodynamics of β-, β-, and γ-Cyclodextrin Dimers. Molecular Dynamics Studies of the Solvent Effect and Free Binding Energies." The Journal of Organic Chemistry 67, No. 24 (Nov. 1, 2002): 8602-9. https://doi.org/10.1021/jo026166v.
Bonnet, Pascal, Carlos Jaime, and Luc Morin-Allory. "α-, β-, and γ-Cyclodextrin Dimers. Molecular Modeling Studies by Molecular

(56) References Cited

OTHER PUBLICATIONS

Mechanics and Molecular Dynamics Simulations." The Journal of Organic Chemistry 66, No. 3 (Feb. 2001): 689-92. https://doi.org/10.1021/jo0008284.

Boubaker Hosouna, Ashraf A.A. Abdusalam, Hassan Y. Aboul-Enein, Hebatallah A. Wagdy. "Molecular Docking and Semi-Empirical Quantum Studies on Cholesterol with Cyclodextrins." Current Nutrition & Food Science 13 (2017): 1-7. https://doi.org/10.2174/1573401313666170525134654.

Breslow, Ronald, and Anthony W. Czarnik. "Transaminations by Pyridoxamine Selectively Attached at C-3 in .Beta.-Cyclodextrin." Journal of the American Chemical Society 105, No. 5 (Mar. 1, 1983): 1390-91. https://doi.org/10.1021/ja00343a063.

Breslow, Ronald, and Biliang Zhang. "Cholesterol Recognition and Binding by Cyclodextrin Dimers." Journal of the American Chemical Society 118, No. 35 (Jan. 1996): 8495-96. https://doi.org/10.1021/ja961567b.

Breslow, Ronald, Noam Greenspoon, Tao Guo, and Ryszard Zarzycki. "Very Strong Binding of Appropriate Substrates by Cyclodextrin Dimers." Journal of the American Chemical Society 111, No. 21 (Oct. 1, 1989): 8296-97. https://doi.org/10.1021/ja00203a050.

Brewster, M.E., T. Loftsson, and N. Bodor. "Applications of Chemically-Modified Cyclodextrins: Use of Hydroxypropyl-β-Cyclodextrin as an Enabling Excipient for Brain Targeting, Redox-Based Derivatives of Estradiol A Review of Preclinical and Clinical Findings." Journal of Drug Delivery Science and Technology 14, No. 1 (2004): 21-34. https://doi.org/10.1016/S1773-2247(04)50002-3.

Brewster, Marcus E., and Thorsteinn Loftsson. "Cyclodextrins as Pharmaceutical Solubilizers." Advanced Drug Delivery Reviews 59, No. 7 (Jul. 2007): 645-66. https://doi.org/10.1016/j.addr.2007.05.012.

Brewster, Marcus E., Kerry S. Estes, Thorsteinn Loftsson, Robert Perchalski, Hartmut Derendorf, Gotelind Mullersman, and Nicholas Bodor. "Improved Delivery through Biological Membranes XXXI: Solubilization and Stabilization of an Estradiol Chemical Delivery System by Modified B-Cyclodextrins." Journal of Pharmaceutical Sciences 77, No. 11 (Nov. 1988): 981-85. https://doi.org/10.1002/jps.2600771118.

Brown, A. J., S. L. Leong, R. T. Dean, and W. Jessup. "7-Hydroperoxycholesterol and Its Products in Oxidized Low Density Lipoprotein and Human Atherosclerotic Plaque." Journal of Lipid Research 38, No. 9 (Sep. 1, 1997): 1730-45.

Brown, Andrew J, and Wendy Jessup. "Oxysterols and Atherosclerosis." Atherosclerosis 142, No. 1 (Jan. 1999): 1-28. https://doi.org/10.1016/S0021-9150(98)00196-8.

Cagno, Massimiliano Pio di. "The Potential of Cyclodextrins as Novel Active Pharmaceutical Ingredients: a Short Overview." Molecules : A Journal of Synthetic Chemistry and Natural Product Chemistry 22, No. 1 (Dec. 25, 2016). https://doi.org/10.3390/molecules22010001.

Caira, Mino, Susan Bourne, Halima Samsodien, and Vincent Smith. "Inclusion Complexes of 2-Methoxyestradiol with Dimethylated and Permethylated β-Cyclodextrins: Models for Cyclodextrin-Steroid Interaction." Beilstein Journal of Organic Chemistry, 2015, 2616-30. https://doi.org/10.3762/bjoc.11.281.

Camargo, Fernando, Robert P. Erickson, William S. Garver, G.Showkat Hossain, Peter N. Carbone, Randall A. Heidenreich, and James Blanchard. "Cyclodextrins in the Treatment of a Mouse Model of Niemann-Pick C Disease." Life Sciences 70, No. 2 (Nov. 2001): 131-42. https://doi.org/10.1016/S0024-3205(01)01384-4.

Carpenter, T. O., A. Gerloczy, and J. Pitha. "Safety of Parenteral Hydroxypropyl Beta-Cyclodextrin." Journal of Pharmaceutical Sciences 84, No. 2 (Feb. 1995): 222-25. https://doi.org/10.1002/jps.2600840220.

Casas-Solvas, Juan M., Indalecio Quesada-Soriano, Dolores Carreño-Gázquez, Juan J. Gimenez-Martínez, Luís García-Fuentes, and Antonio Vargas-Berenguel. "β-Cyclodextrin Dimers Linked through Their Secondary Faces with Rigid Spacer Arms as Hosts for Bile Salts." Langmuir 27, No. 16 (Aug. 16, 2011): 9729-37. https://doi.org/10.1021/la201180u.

Casas-Solvas, Juan M., Manuel C. Martos-Maldonado, and Antonio Vargas-Berenguel. "Synthesis of β-Cyclodextrin Derivatives Functionalized with Azobenzene." Tetrahedron 64, No. 48 (Nov. 2008): 10919-23. https://doi.org/10.1016/j.tet.2008.08.098.

Challa, Rajeswari, Alka Ahuja, Javed Ali, and R. K. Khar. "Cyclodextrins in Drug Delivery: an Updated Review." AAPS PharmSciTech 6, No. 2 (Jun. 2005): E329-57. https://doi.org/10.1208/pt060243.

Chatjigakis, A. K., Ph. J. P. Cardot, A. W. Coleman, and H. Parrot-Lopez. "Retention Properties of Cyclodextrins and Modified Cyclodextrins in Reversed Phase HPLC." Chromatographia 36, No. 1 (Dec. 1993): 174-78. https://doi.org/10.1007/BF02263857.

Chatjigakis, Alexis K., Cecile Donze, Anthony W. Coleman, and Philippe Cardot. "Solubility Behavior of .Beta.-Cyclodextrin in Water/Cosolvent Mixtures." Analytical Chemistry 64, No. 14 (Jul. 15, 1992): 1632-34. https://doi.org/10.1021/ac00038a022.

Chiu, null, null Myles, null Garrell, and null Stoddart. "Novel Ether-Linked Secondary Face-to-Face 2-2' and 3-3' Beta-Cyclodextrin Dimers." The Journal of Organic Chemistry 65, No. 9 (May 9, 2000): 2792-96. https://doi.org/10.1021/jo9910381.

Chmurski, Kazimierz, Pawel Stepniak, and Janusz Jurczak. "Long-Chain-Linked β-Cyclodextrin Dimers: Synthesis and Relationship between Reactivity and Inclusion Complex Formation." Carbohydrate Polymers 138 (Mar. 2016): 8-15. https://doi.org/10.1016/j.carbpol.2015.11.054.

Choi, Yong-Hoon, Chul-Hak Yang, Hyun-Won Kim, and Seunho Jung. "Molecular Modeling Studies of the β-Cyclodextrin in Monomer and Dimer Form as Hosts for the Complexation of Cholesterol," 2000, 6.

Christian, A. E., H. S. Byun, N. Zhong, M. Wanunu, T. Marti, A. Fürer, F. Diederich, R. Bittman, and G. H. Rothblat. "Comparison of the Capacity of Beta-Cyclodextrin Derivatives and Cyclophanes to Shuttle Cholesterol between Cells and Serum Lipoproteins." Journal of Lipid Research 40, No. 8 (Aug. 1999): 1475-82. https://doi.org/10.1016/S0022-2275(20)33390-3.

Christian, A. E., M. P. Haynes, M. C. Phillips, and G. H. Rothblat. "Use of Cyclodextrins for Manipulating Cellular Cholesterol Content." Journal of Lipid Research 38, No. 11 (Nov. 1997): 2264-72.

Christoforides, Elias, Andreas Papaioannou, and Kostas Bethanis. "Crystal Structure of the Inclusion Complex of Cholesterol in β-Cyclodextrin and Molecular Dynamics Studies." Beilstein Journal of Organic Chemistry 14 (Apr. 11, 2018): 838-48. https://doi.org/10.3762/bjoc.14.69.

Clare, K. "Toxicity of Oxysterols to Human Monocyte-Macrophages." Atherosclerosis 118, No. 1 (Nov. 1995): 67-75. https://doi.org/10.1016/0021-9150(95)05594-M.

ClinicalTrials.gov. "Safety and Efficacy of Intravenous Trappsol Cyclo (HPBCD) in Niemann-Pick Type C Patients from ClinicalTrials.Gov." Accessed Apr. 8, 2020. https://clinicaltrials.gov/ct2/show/NCT02912793.

ClinicalTrials.gov. "VTS-270 to Treat Niemann-Pick Type C1 (NPC1) Disease from ClinicalTrials.Gov." Accessed Apr. 8, 2020. https://clinicaltrials.gov/ct2/show/NCT02534844.

Coisne, Caroline, Sébastien Tilloy, Eric Monflier, Daniel Wils, Laurence Fenart, and Fabien Gosselet. "Cyclodextrins as Emerging Therapeutic Tools in the Treatment of Cholesterol-Associated Vascular and Neurodegenerative Diseases." Molecules 21, No. 12 (Dec. 20, 2016): 1748. https://doi.org/10.3390/molecules21121748.

Colles, Scott M, Julie M Maxson, Sara G Carlson, and Guy M Chisolm. "Oxidized LDL-Induced Injury and Apoptosis in Atherosclerosis" 11, No. 3 (2001): 8.

Collins, Christopher J., Bradley P. Loren, Md Suhail Alam, Yawo Mondjinou, Joseph L. Skulsky, Cheyenne R. Chaplain, Kasturi Haldar, and David H. Thompson. "Pluronic Based β-Cyclodextrin Polyrotaxanes for Treatment of Niemann-Pick Type C Disease." Scientific Reports 7, No. 1 (Sep. 2017): 46737. https://doi.org/10.1038/srep46737.

Comerford, Kevin B., Joseph D. Artiss, K.-L. Catherine Jen, and Sidika E. Karakas. "The Beneficial Effects α-Cyclodextrin on Blood Lipids and Weight Loss in Healthy Humans." Obesity 19, No. 6 (2011): 1200-1204. https://doi.org/10.1038/oby.2010.280.

(56) References Cited

OTHER PUBLICATIONS

Crumling, Mark A., Kelly A. King, and R. Keith Duncan. "Cyclodextrins and Iatrogenic Hearing Loss: New Drugs with Significant Risk." Frontiers in Cellular Neuroscience 11 (2017): 355. https://doi.org/10.3389/fncel.2017.00355.

Cyclo Therapeutics, Inc. "CTD Investor_Presentation." Sep. 2020.

Dai, Sheng, Andrés E. Dulcey, Xin Hu, Christopher A. Wassif, Forbes D. Porter, Christopher P. Austin, Daniel S. Ory, Juan Marugan, and Wei Zheng. "Methyl-β-Cyclodextrin Restores Impaired Autophagy Flux in Niemann-Pick C1-Deficient Cells through Activation of AMPK." Autophagy 13, No. 8 (Aug. 3, 2017): 1435-51. https://doi.org/10.1080/15548627.2017.1329081.

Davidson, Cristin D., Yonatan I. Fishman, István Puskás, Julianna Szemán, Tamás Sohajda, Leslie A. McCauliff, Jakub Sikora, et al. "Efficacy and Ototoxicity of Different Cyclodextrins in Niemann-Pick C Disease." Annals of Clinical and Translational Neurology 3, No. 5 (2016): 366-80. https://doi.org/10.1002/acn3.306.

Del Valle, E. M. Martin. "Cyclodextrins and Their Uses: a Review." Process Biochemistry 39, No. 9 (May 31, 2004): 1033-46. https://doi.org/10.1016/S0032-9592(03)00258-9.

Dienst, Erik van van, Bianca H. M. Snellink, Irma von Piekartz, Marcel H. B. Grote Gansey, Fokke Venema, Martinus C. Feiters, Roeland J. M. Nolte, Johan F. J. Engbersen, and David N. Reinhoudt. "Selective Functionalization and Flexible Coupling of Cyclodextrins at the Secondary Hydroxyl Face." The Journal of Organic Chemistry 60, No. 20 (Oct. 1995): 6537-45. https://doi.org/10.1021/jo00125a045.

Dodziuk, H. "Rigidity versus Flexibility. A Review of Experimental and Theoretical Studies Pertaining to the Cyclodextrin Nonrigidity." Journal of Molecular Structure 614, No. 1 (Sep. 2, 2002): 33-45. https://doi.org/10.1016/S0022-2860(02)00236-3.

European Medicines Agency. "Cyclodextrins Used as Excipients," Oct. 9, 2017.

F. Garrido, Pablo, Martín Calvelo, Rebeca Garcia-Fandiño, and Ángel Piñeiro. "Rings, Hexagons, Petals, and Dipolar Moment Sink-Sources: The Fanciful Behavior of Water around Cyclodextrin Complexes." Biomolecules 10, No. 3 (Mar. 10, 2020): 431. https://doi.org/10.3390/biom10030431.

FDA, U.S.F.D.U.S. "Inactive Ingredient Search for Approved Drug Products Betadex." https://www.accessdata.fda.gov/, May 14, 2020.

FDA, U.S.F.D.U.S. "Inactive Ingredient Search for Approved Drug Products Hydroxypropyl." https://www.accessdata.fda.gov/, May 14, 2020.

Feltes, McKenna, Sarah E. Gale, Samantha Moores, Daniel S. Ory, and Jean E. Schaffer. "Monitoring the Itinerary of Lysosomal Cholesterol in Niemann-Pick Type C1-Deficient Cells after Cyclodextrin Treatment." Journal of Lipid Research 61, No. 3 (Mar. 1, 2020): 403-12. https://doi.org/10.1194/jlr.RA119000571.

Frijlink, H. W., A. C. Eissens, N. R. Hefting, K. Poelstra, C. F. Lerk, and D. K. Meijer. "The Effect of Parenterally Administered Cyclodextrins on Cholesterol Levels in the Rat." Pharmaceutical Research 8, No. 1 (Jan. 1991): 9-16. https://doi.org/10.1023/a:1015861719134.

Frijlink, Henderik W., Jan Visser, Nanco R. Hefting, Roelof Oosting, Dirk K. F. Meijer, and Coenraad F. Lerk. "The Pharmacokinetics of β-Cyclodextrin and Hydroxypropyl-β-Cyclodextrin in the Rat." Pharmaceutical Research 7, No. 12 (Dec. 1, 1990): 1248-52. https://doi.org/10.1023/A:1015929720063.

Gale, Sarah E., Emily J. Westover, Nicole Dudley, Kathiresan Krishnan, Sean Merlin, David E. Scherrer, Xianlin Han, et al. "Side Chain Oxygenated Cholesterol Regulates Cellular Cholesterol Homeostasis through Direct Sterol-Membrane Interactions." The Journal of Biological Chemistry 284, No. 3 (Jan. 16, 2009): 1755-64. https://doi.org/10.1074/jbc.M807210200.

Gargiulo, Simona, Gabriella Testa, Paola Gamba, Erica Staurenghi, Giuseppe Poli, and Gabriella Leonarduzzi. "Oxysterols and 4-Hydroxy-2-Nonenal Contribute to Atherosclerotic Plaque Destabilization." Free Radical Biology and Medicine 111 (Oct. 2017): 140-50. https://doi.org/10.1016/j.freeradbiomed.2016.12.037.

Gaspar, Jason, Jacques Mathieu, and Pedro Alvarez. "2-Hydroxypropyl-Beta-Cyclodextrin (HPβCD) Reduces Age-Related Lipofuscin Accumulation through a Cholesterol-Associated Pathway." Scientific Reports 7, No. 1 (Dec. 2017): 2197. https://doi.org/10.1038/s41598-017-02387-8.

Gelissen, Ingrid C., Andrew J. Brown, Erin L. Mander, Leonard Kritharides, Roger T. Dean, and Wendy Jessup. "Sterol Efflux Is Impaired from Macrophage Foam Cells Selectively Enriched with 7-Ketocholesterol." Journal of Biological Chemistry 271, No. 30 (Jul. 26, 1996): 17852-60. https://doi.org/10.1074/jbc.271.30.17852.

Gould, Sarah, and Robert C. Scott. "2-Hydroxypropyl-Beta-Cyclodextrin (HP-Beta-CD): a Toxicology Review." Food and Chemical Toxicology: an International Journal Published for the British Industrial Biological Research Association 43, No. 10 (Oct. 2005): 1451-59. https://doi.org/10.1016/j.fct.2005.03.007.

Grard, S, C Elfakir, and M Dreux. "Analysis of Sulfobutyl Ether-b-Cyclodextrin Mixtures by Ion-Spray Mass Spectrometry and Liquid Chromatography—Ion-Spray Mass Spectrometry." J. Chromatogr. A, 2001, 9.

Grebe, Alena. "Targeting cholesterol crystals in atherosclerosis with cholesterol solubilizing 2-hydroxypropyl-β-cyclodextrin." Rheinischen Friedrich-Wilhelms-Universität Bonn, 2016.

Grunberger, George, K.-L. Catherine Jen, and Joseph D. Artiss. "The Benefits of Early Intervention in Obese Diabetic Patients with FBCxTM—a New Dietary Fibre." Diabetes/Metabolism Research and Reviews 23, No. 1 (2007): 56-62. https://doi.org/10.1002/dmrr.687.

Guo, Jiawei, Dandan Li, Hui Tao, Gang Li, Renfeng Liu, Yin Dou, Taotao Jin, et al. "Cyclodextrin-Derived Intrinsically Bioactive Nanoparticles for Treatment of Acute and Chronic Inflammatory Diseases." Advanced Materials 31, No. 46 (Nov. 2019): 1904607. https://doi.org/10.1002/adma.201904607.

Hamon, Florian, Claire Blaszkiewicz, Marie Buchotte, Estelle Banaszak-Léonard, Hervé Bricout, Sébastien Tilloy, Eric Monflier, et al. "Synthesis and Characterization of a New Photoinduced Switchable β-Cyclodextrin Dimer." Beilstein Journal of Organic Chemistry 10 (Dec. 4, 2014): 2874-85. https://doi.org/10.3762/bjoc.10.304.

Harada, Akira, Jun Li, and Mikiharu Kamachi. "Synthesis of a Tubular Polymer from Threaded Cyclodextrins." Nature 364, No. 6437 (Aug. 1993): 516-18. https://doi.org/10.1038/364516a0.

Harata, K., K. Uekama, M. Otagiri, and F. Hirayama. "Crystal Structures of Cyclodextrin Complexes with Chiral Molecules." Journal of Inclusion Phenomena 2, No. 3 (Sep. 1, 1984): 583-94. https://doi.org/10.1007/BF00662224.

Hayashi, Nobuyuki, Ronggang Chen, Masamitsu Hiraoka, Tomomi Ujihara, and Hidekazu Ikezaki. "Beta-Cyclodextrin/Surface Plasmon Resonance Detection System for Sensing Bitter-Astringent Taste Intensity of Green Tea Catechins." Journal of Agricultural and Food Chemistry 58, No. 14 (Jul. 28, 2010): 8351-56. https://doi.org/10.1021/jf1012693.

Hayashino, Yuji, Masatake Sugita, Hidetoshi Arima, Tetsumi Irie, Takeshi Kikuchi, and Fumio Hirata. "Predicting the Binding Mode of 2-Hydroxypropyl-β-Cyclodextrin to Cholesterol by Means of the MD Simulation and the 3D-RISM-KH Theory." The Journal of Physical Chemistry B 122, No. 21 (May 31, 2018): 5716-25. https://doi.org/10.1021/acs.jpcb.8b02098.

He, Yan, Ping Li, and Samuel H. Yalkowsky. "Solubilization of Fluasterone in Cosolvent/Cyclodextrin Combinations." International Journal of Pharmaceutics 264, No. 1-2 (Oct. 2, 2003): 25-34. https://doi.org/10.1016/s0378-5173(03)00389-2.

Hedges, et al.. "Use of Cyclodextrins for Encapsulation in the Use and Treatment of Food Products." In Encapsulation and Controlled Release of Food Ingredients, edited by Sara J. Risch and Gary A. Reineccius, 590:60-71. ACS Symposium Series. Washington, DC: American Chemical Society, 1995. https://doi.org/10.1021/bk-1995-0590.ch006.

Hoover, Randall K., Harry Alcorn, Laura Lawrence, Susan K. Paulson, Megan Quintas, David R. Luke, and Sue K. Cammarata. "Clinical Pharmacokinetics of Sulfobutylether-β-Cyclodextrin in Patients With Varying Degrees of Renal Impairment." The Journal of Clinical Pharmacology 58, No. 6 (Jun. 2018): 814-22. https://doi.org/10.1002/jcph.1077.

(56) References Cited

OTHER PUBLICATIONS

Iii, Robert O Williams, Vorapann Mahaguna, and Mongkol Sriwongjanya. "Characterization of an Inclusion Complex of Cholesterol and Hydroxypropyl-b-Cyclodextrin." European Journal of Pharmaceutics and Biopharmaceutics, 1998, 6.

Irie, Tetsumi, and Kaneto Uekama. "Pharmaceutical Applications of Cyclodextrins. III. Toxicological Issues and Safety Evaluation." Journal of Pharmaceutical Sciences 86, No. 2 (Feb. 1997): 147-62. https://doi.org/10.1021/js960213f.

Irie, et al. "Cyclodextrin-Induced Hemolysis and Shape Changes of Human Erythrocytes in Vitro." Journal of Pharmacobio-Dynamics 5, No. 9 (1982): 741-44. https://doi.org/10.1248/bpb1978.5.741.

Ishimaru, et al. "Synthesis of Secondary Face-to-Face Cyclodextrin Dimers Linked at Each 2-Position." Tetrahedron Letters 38, No. 21 (May 1997): 3743-44. https://doi.org/10.1016/S0040-4039(97)00742-9.

Isihimaru, Yoshihiro, Yasunori Kojo, Taich Masuda, Syunsuke Saito, Yu Yue, and Yu Fujisaki. "Design on Head-to-Tail Directly Linked Homogeneous and Heterogeneous Cyclodextrin Dimers and Their Evaluation of Hydrophobic Cavity." Tetrahedron Letters 55, No. 15 (Apr. 2014): 2438-41. https://doi.org/10.1016/j.tetlet.2014.02.128.

Jansook, et al. "Cyclodextrins: Structure, Physicochemical Properties and Pharmaceutical Applications." International Journal of Pharmaceutics 535, No. 1-2 (Jan. 2018): 272-84. https://doi.org/10.1016/j.ijpharm.2017.11.018.

Jansook, Phatsawee, Sergey V. Kurkov, and Thorsteinn Loftsson. "Cyclodextrins as Solubilizers: Formation of Complex Aggregates." Journal of Pharmaceutical Sciences 99, No. 2 (Feb. 2010): 719-29. https://doi.org/10.1002/jps.21861.

Ji, Jiecheng, Wanhua Wu, Wenting Liang, Guo Cheng, Ryohei Matsushita, Zhiqiang Yan, Xueqin Wei, et al. "An Ultimate Stereocontrol in Supramolecular Photochirogenesis. Photocyclodimerization of 2-Anthracenecarboxylate Mediated by Sulfur-Linked β-Cyclodextrin Dimers." Journal of the American Chemical Society, May 22, 2019, 39.

Jiang, et al. "Development and Validation of Sensitive LC-MS/MS Assays for Quantification of HP-β-CD in Human Plasma and CSF." Journal of Lipid Research 55, No. 7 (Jul. 2014): 1537-48. https://doi.org/10.1194/jlr.D050278.

Jiang, Tao, Dinesh K. Sukumaran, Sunil-Datta Soni, and David S. Lawrence. "The Synthesis and Characterization of a Pyridine-Linked Cyclodextrin Dimer." The Journal of Organic Chemistry 59, No. 18 (Sep. 1, 1994): 5149-55. https://doi.org/10.1021/jo00097a015.

Jong, Menno R. de, Patrick Berthault, Arie van Hoek, Antonie J.W.G. Visser, Jurriaan Huskens, and David N. Reinhoudt. "Complexation and Sensing Behavior of Dansyl-Appended Cyclodextrins and Cyclodextrin Dimers with Bile Salts." Supramolecular Chemistry 14, No. 2-3 (Mar. 2002): 143-51. https://doi.org/10.1080/10610270290026040.

Kang, Qing, Xiaobin Yao, Lifang Zhang, Zhihua Wu, and Yong Wang. "'One-Pot' Click Access to Triazole Bridged Cyclodextrin Chiral Phases for Differentiation of Clopidogrel Enantiomers." Analytical Methods 7, No. 15 (2015): 6432-36. https://doi.org/10.1039/C5AY01365H.

Kao, Mark L., Susan Stellar, Eric Solon, Alfred Lordi, Nicole Kasica, Gary Swain, Jessica H. Bagel, Brittney L. Gurda, and Charles H. Vite. "Pharmacokinetics and Distribution of 2-hydroxypropyl-β-cyclodextrin Following a Single Intrathecal Dose to Cats." Journal of Inherited Metabolic Disease 43, No. 3 (May 2020): 618-34. https://doi.org/10.1002/jimd.12189.

Keating, Gillian M. "Sugammadex: a Review of Neuromuscular Blockade Reversal." Drugs 76, No. 10 (Jul. 2016): 1041-52. https://doi.org/10.1007/s40265-016-0604-1.

Kerdpol, Khanittha, Jintawee Kicuntod, Peter Wolschann, Seiji Mori, Chompoonut Rungnim, Manaschai Kunaseth, Hisashi Okumura, Nawee Kungwan, and Thanyada Rungrotmongkol. "Cavity Closure of 2-Hydroxypropyl-β-Cyclodextrin: Replica Exchange Molecular Dynamics Simulations." Polymers 11, No. 1 (Jan. 16, 2019): 145. https://doi.org/10.3390/polym11010145.

Khan, Abdul Rauf, Peter Forgo, Keith J. Stine, and Valerian T. D'Souza. "Methods for Selective Modifications of Cyclodextrins." Chemical Reviews 98, No. 5 (Jul. 1998): 1977-96. https://doi.org/10.1021/cr970012b.

Kilsdonk, E. P., P. G. Yancey, G. W. Stoudt, F. W. Bangerter, W. J. Johnson, M. C. Phillips, and G. H. Rothblat. "Cellular Cholesterol Efflux Mediated by Cyclodextrins." The Journal of Biological Chemistry 270, No. 29 (Jul. 21, 1995): 17250-56. https://doi.org/10.1074/jbc.270.29.17250.

Kim, Heegon, Junhee Han, and Ji-Ho Park. "Cyclodextrin Polymer Improves Atherosclerosis Therapy and Reduces Ototoxicity." Journal of Controlled Release: Official Journal of the Controlled Release Society 319 (Mar. 10, 2020): 77-86. https://doi.org/10.1016/j.jconrel.2019.12.021.

Kim, Heegon, Sandeep Kumar, Dong-Won Kang, Hanjoong Jo, and Ji-Ho Park. "Affinity-Driven Design of Cargo-Switching Nanoparticles to Leverage a Cholesterol-Rich Microenvironment for Atherosclerosis Therapy." ACS Nano 14, No. 6 (Jun. 23, 2020): 6519-31. https://doi.org/10.1021/acsnano.9b08216.

Kiss, T., F. Fenyvesi, I. Bácskay, J. Váradi, É. Fenyvesi, R. Iványi, L. Szente, Á. Tósaki, and M. Vecsernyés. "Evaluation of the Cytotoxicity of β-Cyclodextrin Derivatives: Evidence for the Role of Cholesterol Extraction." European Journal of Pharmaceutical Sciences 40, No. 4 (Jul. 2010): 376-80. https://doi.org/10.1016/j.ejps.2010.04.014.

Kritharides, Leonard, Michele Kus, Andrew J. Brown, Wendy Jessup, and Roger T. Dean. "Hydroxypropyl-β-Cyclodextrin-Mediated Efflux of 7-Ketocholesterol from Macrophage Foam Cells." Journal of Biological Chemistry 271, No. 44 (Nov. 1, 1996): 27450-55. https://doi.org/10.1074/jbc.271.44.27450.

Kučáková, et al. "Molecular Structure Study of a Heptakis(2,3,6-Tri-O-Methyl)-β-Cyclodextrin Complex of Cholesterol." Steroids 155 (Mar. 1, 2020): 108555. https://doi.org/10.1016/j.steroids.2019.108555.

Kulkarni, et al. "Linear Cyclodextrin Polymer Prodrugs as Novel Therapeutics for Niemann-Pick Type C1 Disorder." Scientific Reports 8, No. 1 (Jun. 22, 2018): 1-13. https://doi.org/10.1038/s41598-018-27926-9.

Kurkov, Sergey V., Thorsteinn Loftsson, Martin Messner, and Donna Madden. "Parenteral Delivery of HPβCD: Effects on Drug-HSA Binding." AAPS PharmSciTech 11, No. 3 (Sep. 2010): 1152-58. https://doi.org/10.1208/s12249-010-9482-0.

Li Linlin, Duan Zunbin, Zhu Lijun, Xiang Yuzhi, Xia Daohong. "Progress in Study and Application of Supramolecular System Based on β-Cyclodextrin." Chinese Journal of Applied Chemistry 34, No. 2 (Feb. 2017): 123-38.

Li, Li, Song He, and Yu Liu. "Molecular Recognition of Bridged Bis(β-Cyclodextrin) s Linked by Phenylenediseleno Tether on the Primary or Secondary Side with Fluorescent Dyes." Chinese Journal of Chemistry 21, No. 7 (Aug. 26, 2010): 964-69. https://doi.org/10.1002/cjoc.20030210748.

Li, et al. "Analytical Characterization of Methy-β-Cyclodextrin for Pharmacological Activity to Reduce Lysosomal Cholesterol Accumulation in Niemann-Pick Disease Type C1 Cells." ASSAY and Drug Development Technologies 15, No. 4 (Jun. 2017): 154-66. https://doi.org/10.1089/adt.2017.774.

Liu, et al. "Cyclodextrin Overcomes the Transport Defect in Nearly Every Organ of NPC1 Mice Leading to Excretion of Sequestered Cholesterol as Bile Acid." Journal of Lipid Research 51, No. 5 (May 2010): 933-44. https://doi.org/10.1194/jlr.M000257.

Liu, Xiaopeng, Dalian Ding, Guang-Di Chen, Li Li, Haiyan Jiang, and Richard Salvi. "2-Hydroxypropyl-β-Cyclodextrin Ototoxicity in Adult Rats: Rapid Onset and Massive Destruction of Both Inner and Outer Hair Cells Above a Critical Dose." Neurotoxicity Research, Jun. 30, 2020. https://doi.org/10.1007/s12640-020-00252-7.

Liu, Y., C. C. You, and B. Li. "Synthesis and Molecular Recognition of Novel Oligo(Ethylenediamino) Bridged Bis(Beta-Cyclodextrin)s and Their Copper(II) Complexes: Enhanced Molecular Binding Ability and Selectivity by Multiple Recognition." Chemistry (Weinheim

(56) References Cited

OTHER PUBLICATIONS an Der Bergstrasse, Germany) 7, No. 6 (Mar. 16, 2001): 1281-88. https://doi.org/10.1002/1521-3765(20010316)7:6<1281::aid-chem1281>3.0.co;2-h.

Liu, et al. "Synthesis of I-Cystine Modified Cyclodextrin Monomers and Dimers with Primary-Side versus Secondary-Side and Their Molecular Binding Behaviours." Supramolecular Chemistry 20, No. 7 (Oct. 1, 2008): 609-17. https://doi.org/10.1080/10610270701543415.

Liu, Yu, and Yong Chen. "Cooperative Binding and Multiple Recognition by Bridged Bis(β-Cyclodextrin)s with Functional Linkers." Accounts of Chemical Research 39, No. 10 (Oct. 2006): 681-91. https://doi.org/10.1021/ar0502275.

Liu, Yu, Yun Song, Yong Chen, Xue-Qing Li, Fei Ding, and Rui-Qin Zhong. "Biquinolino-Modifiedβ-Cyclodextrin Dimers and Their Metal Complexes as Efficient Fluorescent Sensors for the Molecular Recognition of Steroids." Chemistry—A European Journal 10, No. 15 (Aug. 6, 2004): 3685-96. https://doi.org/10.1002/chem.200305724.

Loftsson, T, and D Duchene. "Cyclodextrins and Their Pharmaceutical Applications." International Journal of Pharmaceutics 329, No. 1-2 (Feb. 1, 2007): 1-11. https://doi.org/10.1016/j.ijpharm.2006.10.044.

Loftsson, Thorsteinn, and Marcus E. Brewster. "Pharmaceutical Applications of Cyclodextrins. 1. Drug Solubilization and Stabilization." Journal of Pharmaceutical Sciences 85, No. 10 (Oct. 1996): 1017-25. https://doi.org/10.1021/js950534b.

Loftsson, Thorsteinn, Audur Magnúsdóttir, Már Másson, and Jóhanna F. Sigurjónsdóttir. "Self-Association and Cyclodextrin Solubilization of Drugs." Journal of Pharmaceutical Sciences 91, No. 11 (Nov. 2002): 2307-16. https://doi.org/10.1002/jps.10226.

Loftsson, Thorsteinn, Már Másson, and Marcus E. Brewster. "Self-Association of Cyclodextrins and Cyclodextrin Complexes." Journal of Pharmaceutical Sciences 93, No. 5 (May 2004): 1091-99. https://doi.org/10.1002/jps.20047.

Loftsson, Thorsteinn, Maria D. Moya-Ortega, Carmen Alvarez-Lorenzo, and Angel Concheiro. "Pharmacokinetics of Cyclodextrins and Drugs after Oral and Parenteral Administration of Drug/Cyclodextrin Complexes." Journal of Pharmacy and Pharmacology 68, No. 5 (2016): 544-55. https://doi.org/10.1111/jphp.12427.

Lopez, Adam M, Sandi J Terpack, Kenneth S Posey, Benny Liu, Charina M Ramirez, and Stephen D Turley. "Systemic Administration of 2-Hydroxypropyl-β-Cyclodextrin to Symptomatic Npc1-Deficient Mice Slows Cholesterol Sequestration in the Major Organs and Improves Liver Function." Clinical and Experimental Pharmacology and Physiology 41, No. 10 (Oct. 2014): 780-87. https://doi.org/10.1111/1440-1681.12285.

López, Cesar A., Alex H. de Vries, and Siewert J. Marrink. "Molecular Mechanism of Cyclodextrin Mediated Cholesterol Extraction." Edited by Max Berkowitz. PLoS Computational Biology 7, No. 3 (Mar. 24, 2011): e1002020. https://doi.org/10.1371/journal.pcbi.1002020.

Lyons, Malcolm A, and Andrew J Brown. "7-Ketocholesterol." The International Journal of Biochemistry & Cell Biology 31, No. 3-4 (Mar. 1999): 369-75. https://doi.org/10.1016/S1357-2725(98)00123-X.

Machelart, Arnaud, Giuseppina Salzano, Xue Li, Aurore Demars, Anne-Sophie Debrie, Mario Menendez-Miranda, Elisabetta Pancani, et al. "Intrinsic Antibacterial Activity of Nanoparticles Made of β-Cyclodextrins Potentiates Their Effect as Drug Nanocarriers against Tuberculosis." ACS Nano 13, No. 4 (Apr. 23, 2019): 3992-4007. https://doi.org/10.1021/acsnano.8b07902.

Maeda, Yuki, Keiichi Motoyama, Rena Nishiyama, Taishi Higashi, Risako Onodera, Hideaki Nakamura, Toru Takeo, et al. "In Vivo Efficacy and Safety Evaluation of Lactosyl-β-Cyclodextrin as a Therapeutic Agent for Hepatomegaly in Niemann-Pick Type C Disease." Nanomaterials 9, No. 5 (May 25, 2019): 802. https://doi.org/10.3390/nano9050802.

Magnúsdóttir, A, M Másson, and T Loftsson. "Cyclodextrins" 44 (2002): 213-18.

Mahjoubin-Tehran, Maryam, Petri T. Kovanen, Suowen Xu, Tannaz Jamialahmadi, and Amirhossein Sahebkar. "Cyclodextrins: Potential Therapeutics against Atherosclerosis." Pharmacology & Therapeutics 214 (Oct. 1, 2020): 107620. https://doi.org/10.1016/j.pharmthera.2020.107620.

Makedonopoulou, null, and null Mavridis. "Structure of the Inclusion Complex of Beta-Cyclodextrin with 1, 12-Dodecanedioic Acid Using Synchrotron Radiation Data; a Detailed Dimeric Beta-Cyclodextrin Structure." Acta Crystallographica. Section B, Structural Science 56 (Pt 2) (Apr. 2000): 322-31. https://doi.org/10.1107/s0108768199014494.

Makieła, Damian, Iwona Janus-Zygmunt, Krzysztof Gorny, and Zygmunt Gburski. "Investigation of the Influence of β-Cyclodextrin on Cholesterol Lodgement—A Molecular Dynamics Simulation Study." Journal of Molecular Liquids 262 (Jul. 15, 2018): 451-59. https://doi.org/10.1016/j.molliq.2018.04.098.

Malanga, et al. "Back to the Future': A New Look at Hydroxypropyl Beta-Cyclodextrins." Journal of Pharmaceutical Sciences 105, No. 9 (Sep. 2016): 2921-31. https://doi.org/10.1016/j.xphs.2016.04.034.

Manor, Philip C., and Wolfram Saenger. "Topography of Cyclodextrin Inclusion Complexes. III. Crystal and Molecular Structure of Cyclohexaamylose Hexahydrate, the Water Dimer Inclusion Complex." Journal of the American Chemical Society 96, No. 11 (May 1974): 3630-39. https://doi.org/10.1021/ja00818a042.

Mao, Qiyue, and Hiroaki Kitagishi. "Optimized Synthesis of a Per-O-Methylated β-Cyclodextrin Dimer Linked at the Secondary Face by a Pyridine Ligand." Journal of Inclusion Phenomena and Macrocyclic Chemistry 93, No. 1-2 (Feb. 2019): 67-76. https://doi.org/10.1007/s10847-018-0839-4.

Martos-Maldonado, et al. "Secondary Face-to-Face 2-2' β-Cyclodextrin Dimers Linked with Fluorescent Rigid Spacer Arms: a Cyclodextrin-Based Ratiometric Sensor for Bile Salts." European Journal of Organic Chemistry 2012, No. 13 (May 2012): 2560-71. https://doi.org/10.1002/ejoc.201101598.

Matsuo, et al. "Effects of Cyclodextrin in Two Patients with Niemann-Pick Type C Disease." Molecular Genetics and Metabolism 108, No. 1 (Jan. 2013): 76-81. https://doi.org/10.1016/j.ymgme.2012.11.005.

Mendelsohn, Andrew R., and James W. Larrick. "Preclinical Reversal of Atherosclerosis by FDA-Approved Compound That Transforms Cholesterol into an Anti-Inflammatory 'Prodrug.'" Rejuvenation Research 19, No. 3 (Jun. 2016): 252-55. https://doi.org/10.1089/rej.2016.1849.

Merck and Co, Inc. "BRIDION® (Sugammadex) Injection Drug Label," Dec. 2015.

Messner, Martin, Sergey V. Kurkov, Phatsawee Jansook, and Thorsteinn Loftsson. "Self-Assembled Cyclodextrin Aggregates and Nanoparticles." International Journal of Pharmaceutics 387, No. 1-2 (Mar. 2010): 199-208. https://doi.org/10.1016/j.ijpharm.2009.11.035.

Michels, Jasper J., Jurriaan Huskens, and David N. Reinhoudt. "Noncovalent Binding of Sensitizers for Lanthanide(III) Luminescence in an EDTA-Bis(Beta-Cyclodextrin) Ligand." Journal of the American Chemical Society 124, No. 9 (Mar. 6, 2002): 2056-64. https://doi.org/10.1021/ja017025y.

Mixcoha, Edgar, José Campos-Terán, and Angel Piñeiro. "Surface Adsorption and Bulk Aggregation of Cyclodextrins by Computational Molecular Dynamics Simulations as a Function of Temperature: α-CD vs β-CD." The Journal of Physical Chemistry B 118, No. 25 (Jun. 26, 2014): 6999-7011. https://doi.org/10.1021/jp412533b.

Mocanu, Georgeta, Despina Vizitiu, and A. Carpov. "Cyclodextrin Polymers." Journal of Bioactive and Compatible Polymers 16, No. 4 (Jul. 2001): 315-42. https://doi.org/10.1106/JJUV-8F2K-JGYF-HNGF.

Moser, Joerg G., Irene Rose, Birgit Wagner, Tim Wieneke, and Anja Vervoorts. "Taxol Inclusion Complexes with a Cyclodextrin Dimer: Possibilities to Detoxify Chemotherapeutics and to Target Drugs Specifically to Tumors?" Journal of Inclusion Phenomena and Macrocyclic Chemistry 39, No. 1 (Feb. 1, 2001): 13-18. https://doi.org/10.1023/A:1008114826524.

Mourer, Maxime, Frédéric Hapiot, Eric Monflier, and Stéphane Menuel. "Click Chemistry as an Efficient Tool to Access β-Cyclodextrin Dimers." Tetrahedron 64, No. 30-31 (Jul. 2008): 7159-63. https://doi.org/10.1016/j.tet.2008.05.095.

(56) References Cited

OTHER PUBLICATIONS

Mulder, Alart, Amela Juković, Jurriaan Huskens, and David N. Reinhoudt. "Bis(Phenylthienyl) Ethene-Tethered β-Cyclodextrin Dimers as Photoswitchable Hosts." Organic & Biomolecular Chemistry 2, No. 12 (Jun. 7, 2004): 1748-55. https://doi.org/10.1039/B402146K.

Nelissen, Hubertus F. M., Martinus C. Feiters, and Roeland J. M. Nolte. "Synthesis and Self-Inclusion of Bipyridine-Spaced Cyclodextrin Dimers." The Journal of Organic Chemistry 67, No. 17 (Aug. 23, 2002): 5901-6. https://doi.org/10.1021/jo0256641.

Nishijo, Juziro, Shiho Moriyama, and Sachiko Shiota. "Interactions of Cholesterol with Cyclodextrins in Aqueous Solution." Chemical & Pharmaceutical Bulletin 51, No. 11 (2003): 1253-57. https://doi.org/10.1248/cpb.51.1253.

Okabe, Yuji, Hatsuo Yamamura, Ken-ichi Obe, Kazuko Ohta, Masao Kawai, and Kahee Fujita. "Synthesis of a 'Head-to-Tail' Type Cyclodextrin Dimer Linked by a Disulfide Bridge." Journal of the Chemical Society, Chemical Communications, No. 5 (Jan. 1, 1995): 581-82. https://doi.org/10.1039/C39950000581.

Ory, Daniel S, Elizabeth A Ottinger, Nicole Yanjanin Farhat, Kelly A King, Xuntian Jiang, Lisa Weissfeld, Elizabeth Berry-Kravis, et al. "Intrathecal 2-Hydroxypropyl-β-Cyclodextrin Decreases Neurological Disease Progression in Niemann-Pick Disease, Type C1: A Non-Randomised, Open-Label, Phase 1-2 Trial." The Lancet 390, No. 10104 (Oct. 2017): 1758-68. https://doi.org/10.1016/S0140-6736(17)31465-4.

Ozmen, Elif Yilmaz, Mehmet Sezgin, and Mustafa Yilmaz. "Synthesis and Characterization of Cyclodextrin-Based Polymers as a Support for Immobilization of Candida Rugosa Lipase." Journal of Molecular Catalysis B: Enzymatic 57, No. 1-4 (May 2009): 109-14. https://doi.org/10.1016/j.molcatb.2008.07.014.

Pilely, Katrine, Siril S. Bakke, Yaseelan Palarasah, Mikkel-Ole Skjoedt, Emil D. Bartels, Terje Espevik, and Peter Garred. "Alpha-Cyclodextrin Inhibits Cholesterol Crystal-Induced Complement-Mediated Inflammation: a Potential New Compound for Treatment of Atherosclerosis." Atherosclerosis 283 (2019): 35-42. https://doi.org/10.1016/j.atherosclerosis.2019.01.034.

Poli, Giuseppe, Fiorella Biasi, and Gabriella Leonarduzzi. "Oxysterols in the Pathogenesis of Major Chronic Diseases." Redox Biology 1, No. 1 (2013): 125-30. https://doi.org/10.1016/j.redox.2012.12.001.

Prakash, A.S., and P.J. Abbott. "Alpha-CYCLODEXTRIN (JECFA Food Additives Series 48)." Accessed Jan. 11, 2021. http://www.inchem.org/documents/jecfa/jecmono/v48je10.htm.

Puglisi, Antonino, and Yusuf Yagci. "Cyclodextrin-Based Macromolecular Systems as Cholesterol-Mopping Therapeutic Agents in Niemann-Pick Disease Type C." Macromolecular Rapid Communications 40, No. 1 (Jan. 2019): 1800557. https://doi.org/10.1002/marc.201800557.

Rajewski, Roger A., and Valentino J. Stella. "Pharmaceutical Applications of Cyclodextrins. 2. In Vivo Drug Delivery." Journal of Pharmaceutical Sciences 85, No. 11 (Nov. 1996): 1142-69. https://doi.org/10.1021/js960075u.

Ravishankar, Samyukta, and Sierin Lim. "Cyclodextrin Conjugated Ferritin Nanocages Reduce Intracellular Cholesterol Level in Foam Cells." Nano Research 12, No. 12 (Dec. 2019): 2925-32. https://doi.org/10.1007/s12274-019-2525-2.

Rekharsky, Mikhail, and Yoshihisa Inoue. "Chiral Recognition Thermodynamics of β-Cyclodextrin: The Thermodynamic Origin of Enantioselectivity and the Enthalpy—Entropy Compensation Effect." Journal of the American Chemical Society 122, No. 18 (May 1, 2000): 4418-35. https://doi.org/10.1021/ja9921118.

Ruebner, A., J. G. Moser, D. Kirsch, B. Spengler, S. Andrees, and S. Roehrs. "Synthesis of ?—Cyclodextrin Dimers as Carrier Systems for Photodynamic Therapy of Cancer." Journal of Inclusion Phenomena and Molecular Recognition in Chemistry 25, No. 1-3 (1996): 35-38. https://doi.org/10.1007/BF01041531.

Ruebner, A., Z. Yang, D. Leung, and R. Breslow. "A Cyclodextrin Dimer with a Photocleavable Linker as a Possible Carrier for the Photosensitizer in Photodynamic Tumor Therapy." Proceedings of the National Academy of Sciences of the United States of America 96, No. 26 (Dec. 21, 1999): 14692-93. https://doi.org/10.1073/pnas.96.26.14692.

Sá Couto, Andre, Alexey Ryzhakov, and Thorsteinn Loftsson. "2-Hydroxypropyl-β-Cyclodextrin Aggregates: Identification and Development of Analytical Techniques." Materials 11, No. 10 (Oct. 13, 2018): 1971. https://doi.org/10.3390/ma11101971.

Sadrerafi, Keivan, Ellen E. Moore, and Mark W. Lee. "Association Constant of β-Cyclodextrin with Carboranes, Adamantane, and Their Derivatives Using Displacement Binding Technique." Journal of Inclusion Phenomena and Macrocyclic Chemistry 83, No. 1 (Oct. 1, 2015): 159-66. https://doi.org/10.1007/s10847-015-0552-5.

Salehian, B, C Wang, G Alexander, T Davidson, V McDonald, N Berman, R E Dudley, F Ziel, and R S Swerdloff. "Pharmacokinetics, Bioefficacy, and Safety of Sublingual Testosterone Cyclodextrin in Hypogonadal Men: Comparison to Testosterone Enanthate—a Clinical Research Center Study." The Journal of Clinical Endocrinology & Metabolism 80, No. 12 (Dec. 1, 1995): 3567-75. https://doi.org/10.1210/jcem.80.12.8530600.

Santillan, G., J. S. M. Sarma, G. Pawlik, A. Rackl, A. Grenier, and R. J. Bing. "Toxicity, Pharmacokinetics, and Cholesterol-Inhibitory Effect of 7-Ketocholesterol." Atherosclerosis 35, No. 1 (Jan. 1, 1980): 1-10. https://doi.org/10.1016/0021-9150(80)90022-2.

Santos, Cecília I. A. V., Ana C. F. Ribeiro, and Miguel A. Esteso. "Drug Delivery Systems: Study of Inclusion Complex Formation between Methylxanthines and Cyclodextrins and Their Thermodynamic and Transport Properties." Biomolecules 9, No. 5 (May 20, 2019): 196. https://doi.org/10.3390/biom9050196.

Saokham, Phennapha, Chutimon Muankaew, Phatsawee Jansook, and Thorsteinn Loftsson. "Solubility of Cyclodextrins and Drug/Cyclodextrin Complexes." Molecules 23, No. 5 (May 11, 2018): 1161. https://doi.org/10.3390/molecules23051161.

Saybolt, Matthew, Saif Anwaruddin, Damir Hamamdzic, Thomas P. Schaer, and Robert Wilensky. "Cyclodextrins Affect Positive Arterial Wall Remodeling in Atherosclerotic Injury Model." Journal of the American College of Cardiology 67, No. 13 (Apr. 2016): 164. https://doi.org/10.1016/S0735-1097(16)30165-6.

Scantlebery, Angelique M. L., Peter Ochodnicky, Lotte Kors, Elena Rampanelli, Loes M. Butter, Chaima El Boumashouli, Nike Claessen, et al. "β-Cyclodextrin Counteracts Obesity in Western Diet-Fed Mice but Elicits a Nephrotoxic Effect." Scientific Reports 9, No. 1 (Nov. 27, 2019): 1-14. https://doi.org/10.1038/s41598-019-53890-z.

Schmid, Gerhard, Schmid. "Original Submission—Notice of GRAS Exemption for Beta-Cyclodextrin." Wacker Biochem Corp., Mar. 28, 2001.

Schönbeck, Christian, Peter Westh, and RenéHolm. "Complexation Thermodynamics of Modified Cyclodextrins: Extended Cavities and Distorted Structures." The Journal of Physical Chemistry B 118, No. 34 (Aug. 28, 2014): 10120-29. https://doi.org/10.1021/jp506001j.

School of Chemistry and Chemical Engineering, Southwest Petroleum University, Chengdu, 610500, PR, China, Changjun Zou, Lu Zhou, Yali Wang, and Lu Li. "Solubilization of Hydroxypropyl-β-Cyclodextrin on Cholesterol in Aqueous Solution." Journal of Applied Solution Chemistry and Modeling, Jun. 5, 2014, 48-52. https://doi.org/10.6000/1929-5030.2014.03.02.1.

Shuang, Yazhou, Yuqin Liao, Hui Wang, Yuanxing Wang, and Laisheng Li. "Preparation and evaluation of a triazole-bridged bis(β-cyclodextrin)-bonded chiral stationary phase for HPLC." Chirality 32, No. 2 (2020): 168-84. https://doi.org/10.1002/chir.23147.

Singhal, Ashutosh, Lajos Szente, James E. K. Hildreth, and Byeongwoon Song. "Hydroxypropyl-Beta and -Gamma Cyclodextrins Rescue Cholesterol Accumulation in Niemann—Pick C1 Mutant Cell via Lysosome-Associated Membrane Protein 1." Cell Death & Disease 9, No. 10 (Oct. 2018): 1019. https://doi.org/10.1038/s41419-018-1056-1.

Sohajda, Tamas. "Cyclodextrin News." Cyclodextrin News, Jul. 15, 2020. https://cyclodextrinnews.com/2020/07/15/cyclodextrin-dimers-to-treat-atherosclerotic-plaques-by-targeting-various-forms-of-cholesterol/.

Stella, Valentino J., and Quanren He. "Cyclodextrins." Toxicologic Pathology 36, No. 1 (Jan. 2008): 30-42. https://doi.org/10.1177/0192623307310945.

(56) References Cited

OTHER PUBLICATIONS

Sun, Li, and Julie A. Stenken. "The Effect of β-Cyclodextrin on Liquid Chromatography/Electrospray-Mass Spectrometry Analysis of Hydrophobic Drug Molecules." Journal of Chromatography A 1161, No. 1-2 (Aug. 2007): 261-68. https://doi.org/10.1016/j.chroma.2007.05.104.

Szejtli, J. "Dimethyl-β-Cyclodextrin as Parenteral Drug Carrier." Journal of Inclusion Phenomena 1, No. 2 (1983): 135-50. https://doi.org/10.1007/BF00656816.

Szejtli, J. "Highly Soluble β-Cyclodextrin Derivatives." Starch—Stärke 36, No. 12 (1984): 429-32. https://doi.org/10.1002/star.19840361207.

Szejtli, József. "Introduction and General Overview of Cyclodextrin Chemistry." Chemical Reviews 98, No. 5 (Jul. 1998): 1743-54. https://doi.org/10.1021/cr970022c.

Szente, Lajos, Ashutosh Singhal, Andras Domokos, and Byeongwoon Song. "Cyclodextrins: Assessing the Impact of Cavity Size, Occupancy, and Substitutions on Cytotoxicity and Cholesterol Homeostasis." Molecules 23, No. 5 (May 20, 2018): 1228. https://doi.org/10.3390/molecules23051228.

Takahashi, Satoe, Kazuaki Homma, Yingjie Zhou, Shinichi Nishimura, Chongwen Duan, Jessie Chen, Aisha Ahmad, Mary Ann Cheatham, and Jing Zheng. "Susceptibility of Outer Hair Cells to Cholesterol Chelator 2-Hydroxypropyl-β-Cyclodextrine Is Prestin-Dependent." Scientific Reports 6, No. 1 (Feb. 2016): 21973. https://doi.org/10.1038/srep21973.

Tanaka, Yuta, Yusei Yamada, Yoichi Ishitsuka, Muneaki Matsuo, Koki Shiraishi, Koki Wada, Yushiro Uchio, et al. "Efficacy of 2-Hydroxypropyl-β-Cyclodextrin in NiemannβPick Disease Type C Model Mice and Its Pharmacokinetic Analysis in a Patient with the Disease." Biological & Pharmaceutical Bulletin 38, No. 6 (2015): 844-51. https://doi.org/10.1248/bpb.b14-00726.

Tang, Bo, Hui-Ling Liang, Ke-Hua Xu, Zhen Mao, Xi-Feng Shi, and Zhen-Zhen Chen. "An Improved Synthesis of Disulfides Linked β-Cyclodextrin Dimer and Its Analytical Application for Dequalinium Chloride Determination by Spectrofluorimetry." Analytica Chimica Acta 554, No. 1-2 (Dec. 2005): 31-36. https://doi.org/10.1016/j.aca.2005.08.048.

Tang, Bo, Hui-Ling Liang, Li-Li Tong, and Ping Li. "Synthesis of Ethylenediamine Linked Beta-Cyclodextrin Dimer and Its Analytical Application for Tranilast Determination by Spectrofluorimetry." Bioorganic & Medicinal Chemistry 14, No. 11 (Jun. 1, 2006): 3947-52. https://doi.org/10.1016/j.bmc.2006.01.049.

Tang, Bo, Li Zhang, Jie Zhang, Zhen-Zhen Chen, and Yan Wang. "Synthesis of a Novel Host Molecule of Cross-Linking-Polymeric-Beta-Cyclodextrin-o-Vanillin Furfuralhydrazone and Spectrofluorimetric Analysis of Its Identifying Cadmium." Spectrochimica Acta. Part A, Molecular and Biomolecular Spectroscopy 60, No. 10 (Aug. 2004): 2425-31. https://doi.org/10.1016/j.saa.2003.12.018.

Tang, Hsiang-Yu, Chao-Hung Wang, Hung-Yao Ho, Pei-Ting Wu, Chun-Ling Hung, Cheng-Yu Huang, Pei-Ru Wu, Yung-Hsin Yeh, and Mei-Ling Cheng. "Lipidomics Reveals Accumulation of the Oxidized Cholesterol in Erythrocytes of Heart Failure Patients." Redox Biology 14 (2018): 499-508. https://doi.org/10.1016/j.redox.2017.10.020.

Tiwari, Vinod K., Bhuwan B. Mishra, Kunj B. Mishra, Nidhi Mishra, Anoop S. Singh, and Xi Chen. "Cu—Catalyzed Click Reaction in Carbohydrate Chemistry." Chemical Reviews 116, No. 5 (Mar. 9, 2016): 3086-3240. https://doi.org/10.1021/acs.chemrev.5b00408.

Trotta, Francesco, and Roberta Cavalli. "Characterization and Applications of New Hyper-Cross-Linked Cyclodextrins." Composite Interfaces 16, No. 1 (Jan. 2009): 39-48. https://doi.org/10.1163/156855408X379388.

Ueda, et al. "Synthesis of an α-Amylase Inhibitor: Highly Stereoselective Glycosidation and Regioselective Manipulations of Hydroxyl Groups in Carbohydrate Derivatives." Organic Process Research & Development 18, No. 12 (Dec. 19, 2014): 1728-39. https://doi.org/10.1021/op500306p.

Ueno, Akihiko, Iwao Suzuki, and Tetsuo Osa. "Association Dimers, Excimers, and Inclusion Complexes of Pyrene-Appended .Gamma.-Cyclodextrins." Journal of the American Chemical Society 111, No. 16 (Aug. 1989): 6391-97. https://doi.org/10.1021/ja00198a061.

Underdog Pharmaceuticals, Inc. "NPC-HPbCD Clinical Trials Search Results," Dec. 11, 2019. clinicaltrials.gov.

Vance, Jean E, and Kyle B Peake. "Function of the Niemann—Pick Type C Proteins and Their Bypass by Cyclodextrin:" Current Opinion in Lipidology 22, No. 3 (Jun. 2011): 204-9. https://doi.org/10.1097/MOL.0b013e3283453e69.

Vance, Jean E., and Barbara Karten. "Niemann—Pick C Disease and Mobilization of Lysosomal Cholesterol by Cyclodextrin." Journal of Lipid Research 55, No. 8 (Aug. 2014): 1609-21. https://doi.org/10.1194/jlr.R047837.

Váradi, Hermenean, Gesztelyi, Jeney, Balogh, Majoros, Malanga, et al. "Pharmacokinetic Properties of Fluorescently Labelled Hydroxypropyl-Beta-Cyclodextrin." Biomolecules 9, No. 10 (Sep. 20, 2019): 509. https://doi.org/10.3390/biom9100509.

Venema, Fokke, Alan E. Rowan, and Roeland J. M. Nolte. "Binding of Porphyrins in Cyclodextrin Dimers." Journal of the American Chemical Society 118, No. 1 (Jan. 1996): 257-58. https://doi.org/10.1021/ja952401y.

Venema, Fokke, Chantal M. Baselier, Erik van Dienst, Bianca H.M. Ruël, Martinus C. Feiters, Johan F.J. Engbersen, David N. Reinhoudt, and Roeland J.M. Nolte. "Synthesis and Binding Properties of Novel Cyclodextrin Dimers." Tetrahedron Letters 35, No. 11 (Mar. 1994): 1773-76. https://doi.org/10.1016/0040-4039(94)88343-2.

Vurgun, Nesrin, and Mark Nitz. "Highly Functionalized β-Cyclodextrins by Solid-Supported Synthesis." Chemistry—A European Journal 24, No. 17 (Mar. 20, 2018): 4459-67. https://doi.org/10.1002/chem.201800028.

Wang, He, Xinwei Zhang, Biao Yu, Xiaohuan Peng, Ying liu, Anbei Wang, Dazhong Zhao, Daxin Pang, Hongsheng OuYang, and Xiaochun Tang. "Cyclodextrin Ameliorates the Progression of Atherosclerosis via Increasing High-Density Lipoprotein Cholesterol Plasma Levels and Anti-Inflammatory Effects in Rabbits:" Journal of Cardiovascular Pharmacology 73, No. 5 (May 2019): 334-42. https://doi.org/10.1097/FJC.0000000000000660.

Wang, Min, Weiqing Long, Di Li, Duan Wang, Yuan Zhong, Di Mu, Jiayi Song, and Min Xia. "Plasma 7-Ketocholesterol Levels and the Risk of Incident Cardiovascular Events." Heart 103, No. 22 (Nov. 2017): 1788-94. https://doi.org/10.1136/heartjnl-2016-310914.

Wang, Yuquan, Lanlan Li, Weibo Zhao, Yin Dou, Huijie An, Hui Tao, Xiaoqiu Xu, et al. "Targeted Therapy of Atherosclerosis by a Broad-Spectrum Reactive Oxygen Species Scavenging Nanoparticle with Intrinsic Anti-Inflammatory Activity." ACS Nano 12, No. 9 (Sep. 25, 2018): 8943-60. https://doi.org/10.1021/acsnano.8b02037.

Ward, Sarah, Patricia O'Donnell, Steven Fernandez, and Charles H Vite. "2-Hydroxypropyl-β-Cyclodextrin Raises Hearing Threshold in Normal Cats and in Cats With Niemann—Pick Type C Disease." Pediatric Research 68, No. 1 (Jul. 2010): 52-56. https://doi.org/10.1203/PDR.0b013e3181df4623.

Benito, J., et al. "Chapter 13: Cyclodextrin Chemistry via Selective Protecting Group Manipulations," pp. 371-393, Protecting Groups Strategies and Applications in Carbohydrate Chemistry, published by WILEY-VCH, Edited by Sébastien Vidal, 2019. 25 sheets.

Zarrouk, Amira, Anne Vejux, John Mackrill, Yvonne O'Callaghan, Mohamed Hammami, Nora O'Brien, and Gérard Lizard. "Involvement of Oxysterols in Age-Related Diseases and Ageing Processes." Ageing Research Reviews 18 (Nov. 1, 2014): 148-62. https://doi.org/10.1016/j.arr.2014.09.006.

Zidovetzki, Raphael, and Irena Levitan. "Use of Cyclodextrins to Manipulate Plasma Membrane Cholesterol Content: Evidence, Misconceptions and Control Strategies." Biochimica et Biophysica Acta (BBA)—Biomembranes 1768, No. 6 (Jun. 2007): 1311-24. https://doi.org/10.1016/j.bbamem.2007.03.026.

Zimmer, Sebastian, Alena Grebe, Siril S. Bakke, Niklas Bode, Bente Halvorsen, Thomas Ulas, Mona Skjelland, et al. "Cyclodextrin Promotes Atherosclerosis Regression via Macrophage Reprogramming." Science Translational Medicine 8, No. 333 (Apr. 6, 2016): 333ra50-333ra50. https://doi.org/10.1126/scitranslmed.aad6100.

(56) References Cited

OTHER PUBLICATIONS

Pattarino et al. "Inclusion of methotrexate in alkyl-cyclodextrins: Effects of host substitutents on the stability of complexes." Journal of drug delivery science and technology. Jan. 1, 2005;15(6):465-8.
Loftsson et al. "Cyclodextrins in drug delivery." Expert opinion on drug delivery. Mar. 1, 2005;2(2):335-51.
De Jong et al. "Cyclodextrin dimers as receptor molecules for steroid sensors." Chemistry—A European Journal. Nov. 3, 2000;6(21):4034-40.
Casas-Solvas et al. "β-Cyclodextrin dimers linked through their secondary faces with rigid spacer arms as hosts for bile salts." Langmuir. Aug. 16, 2011;27(16):9729-37.
Michels et al. "Noncovalent binding of sensitizers for lanthanide (III) luminescence in an EDTA-bis (β-cyclodextrin) ligand." Journal of the American Chemical Society. Mar. 6, 2002;124(9):2056-64.
Potier, Jonathan, et al. "Limits of the inversion phenomenon in triazolyl-substituted β-cyclodextrin dimers." European Journal of Organic Chemistry 2014.7 (2014): 1547-1556.

FIG. 1C. βCD (DS0)
FIG. 1D. Hydroxypropylated βCD

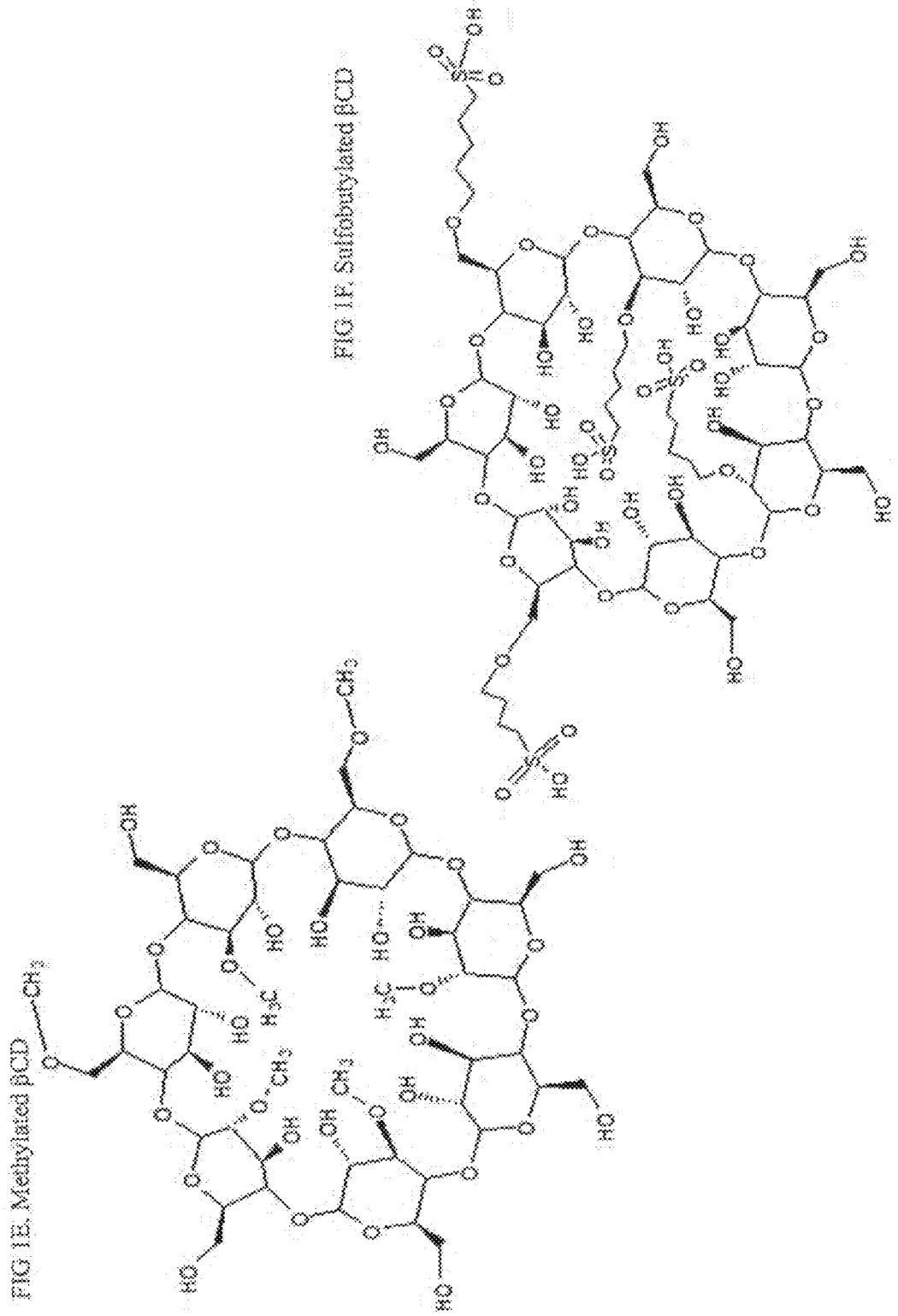

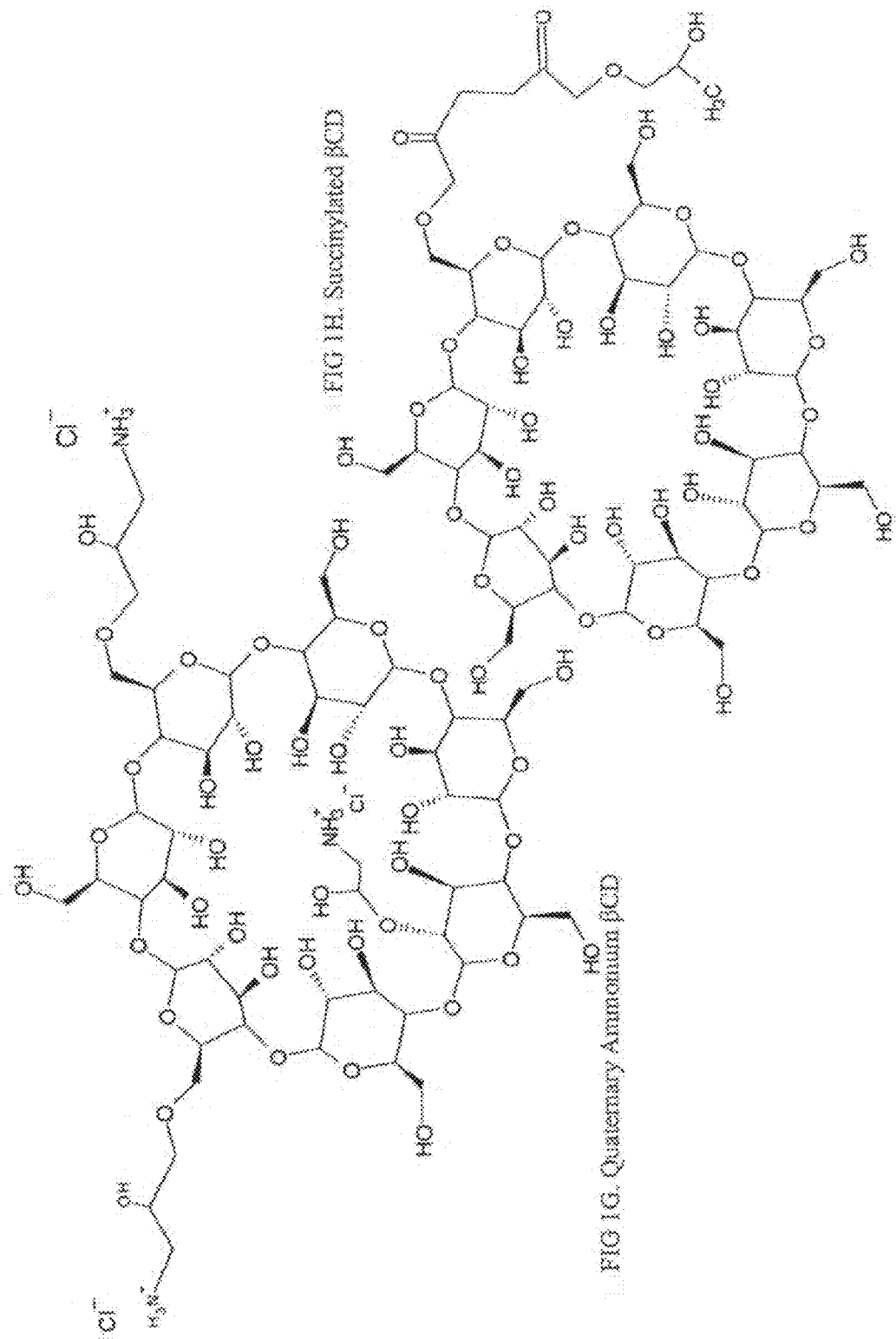
FIG. 1H. Succinylated βCD
FIG. 1G. Quaternary Ammonium βCD

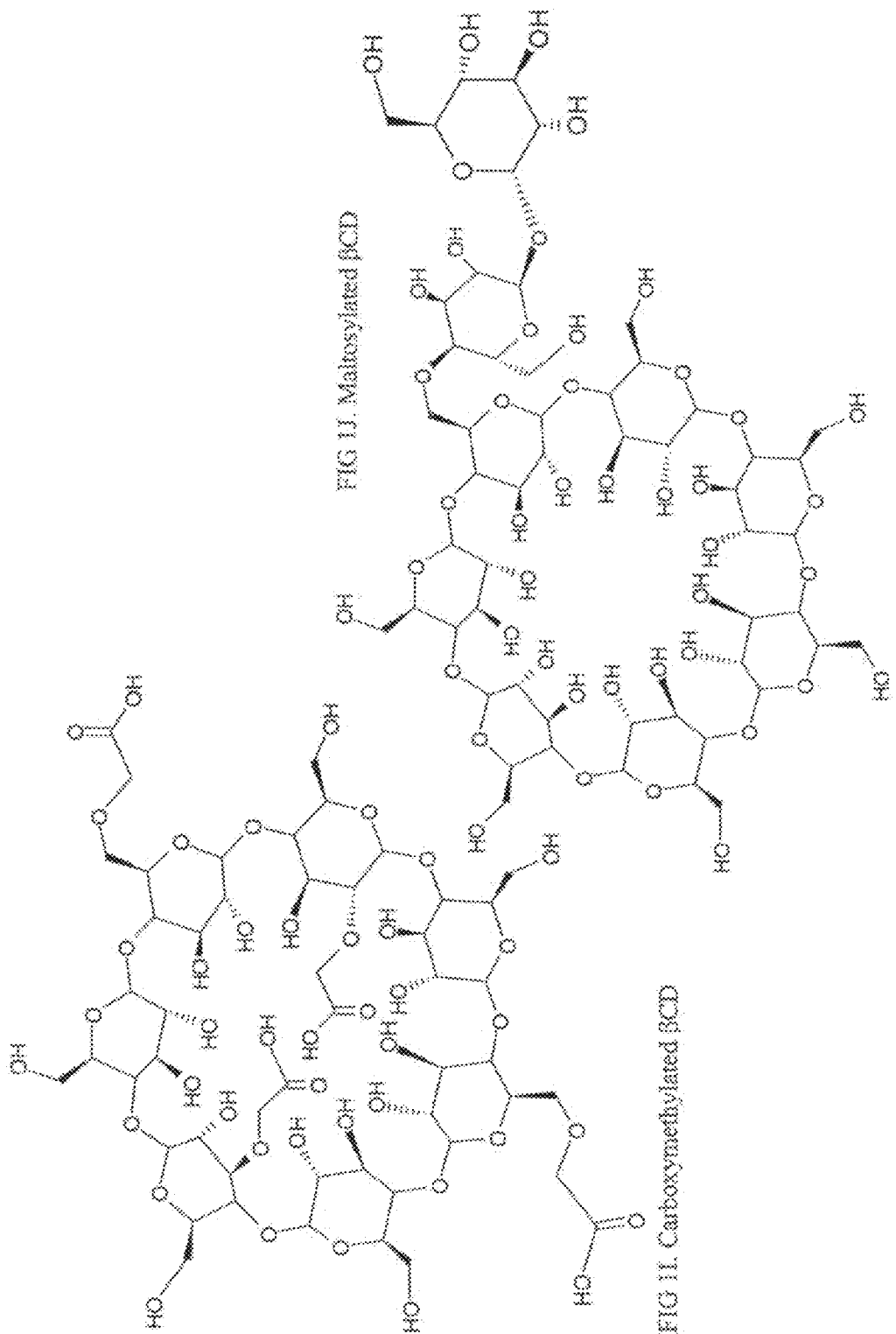

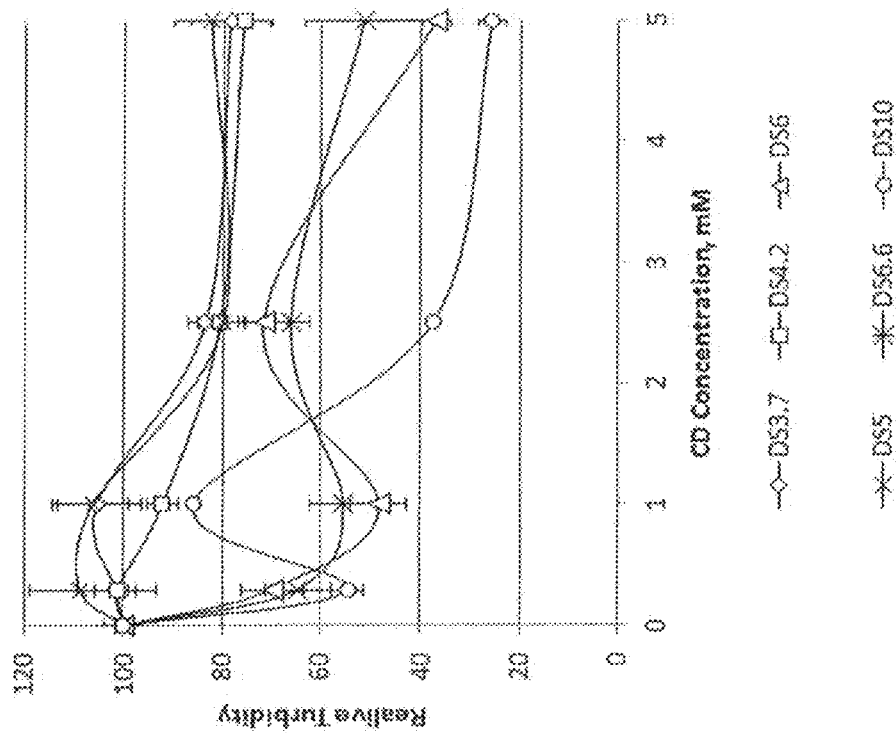
FIG. 2D. Cholesterol
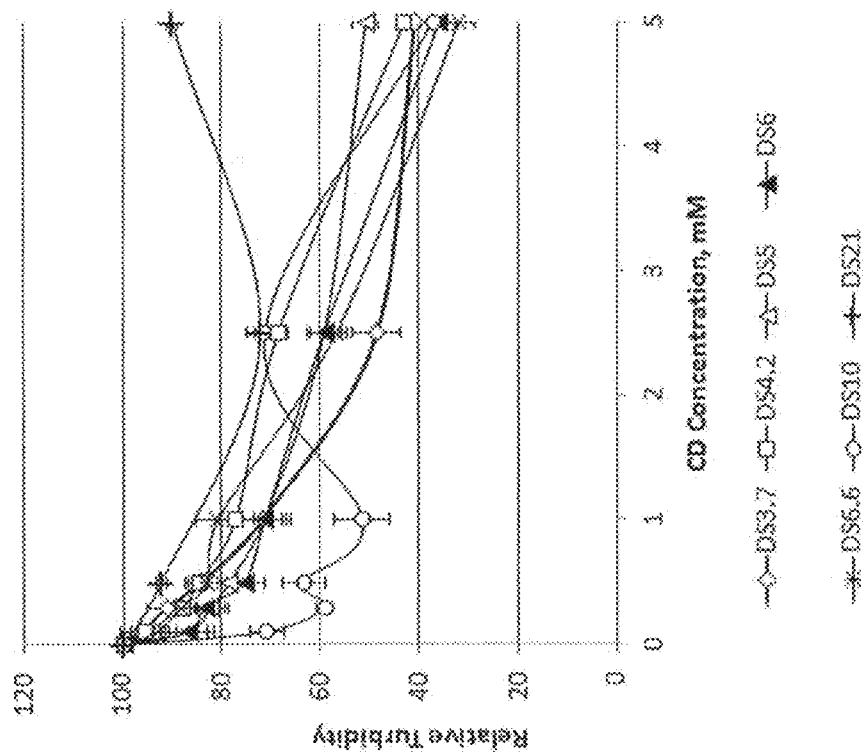
FIG. 2C. 7KC

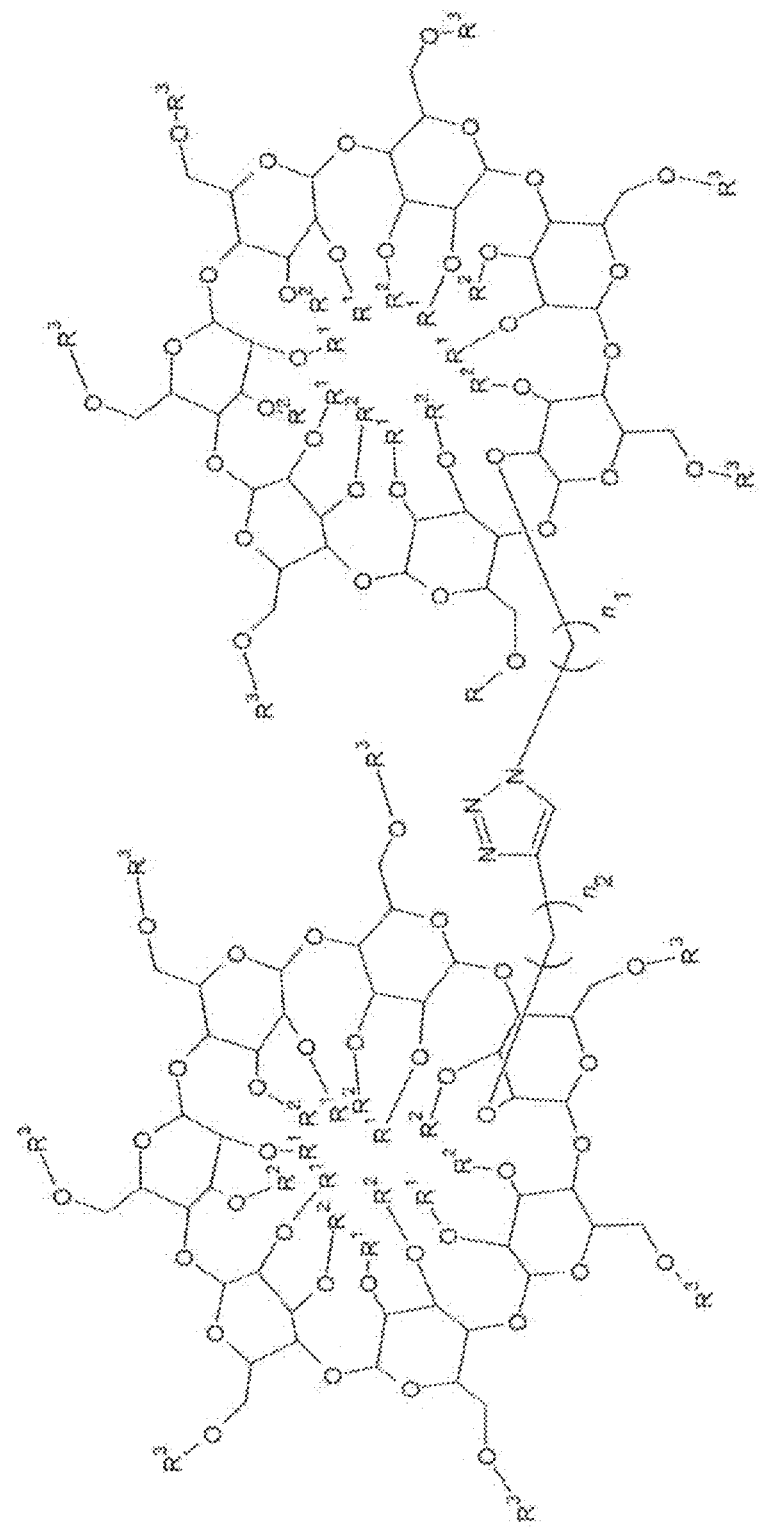
FIG. 3B. Formula I.

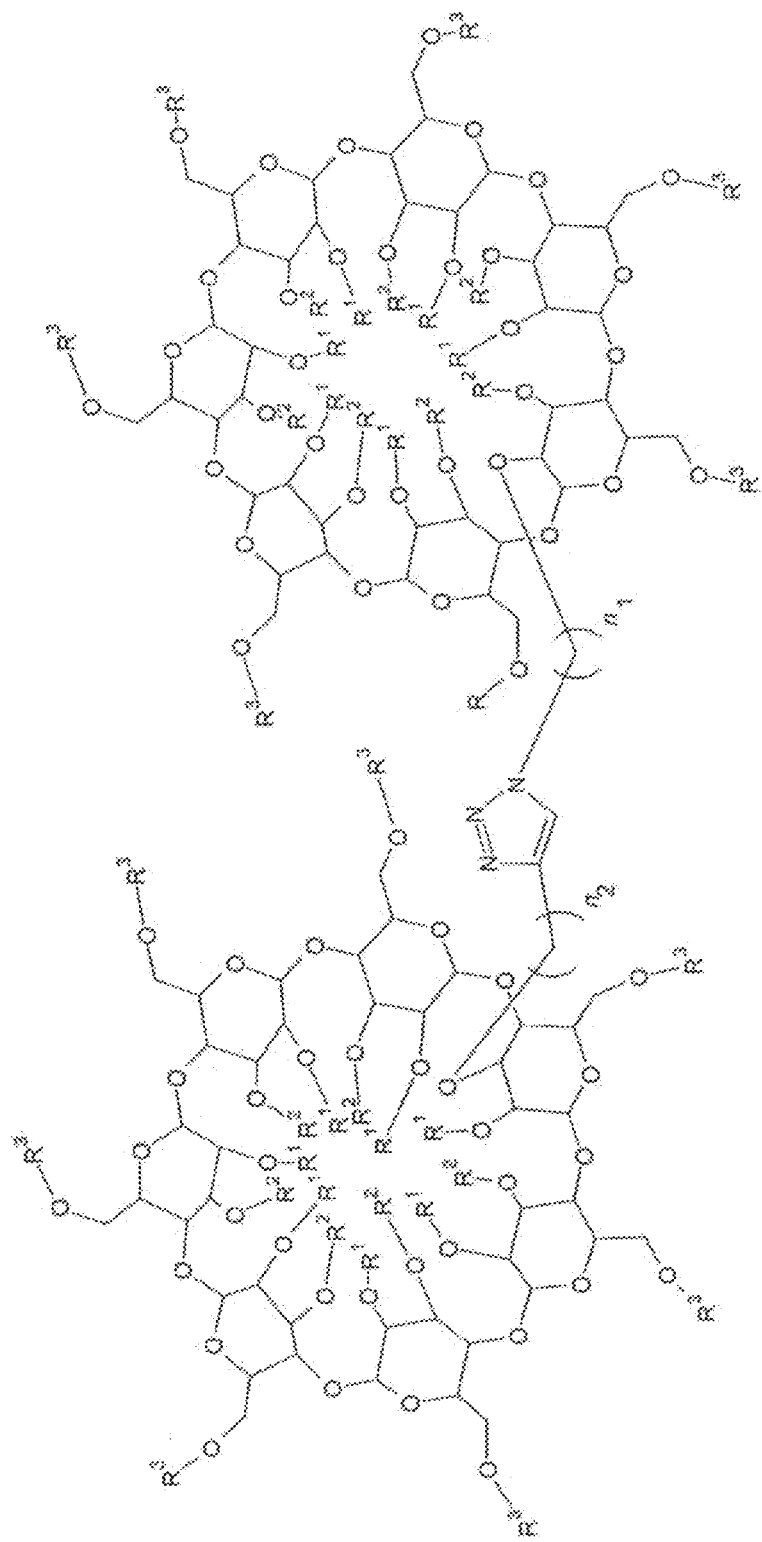
FIG. 3C. Formula II.

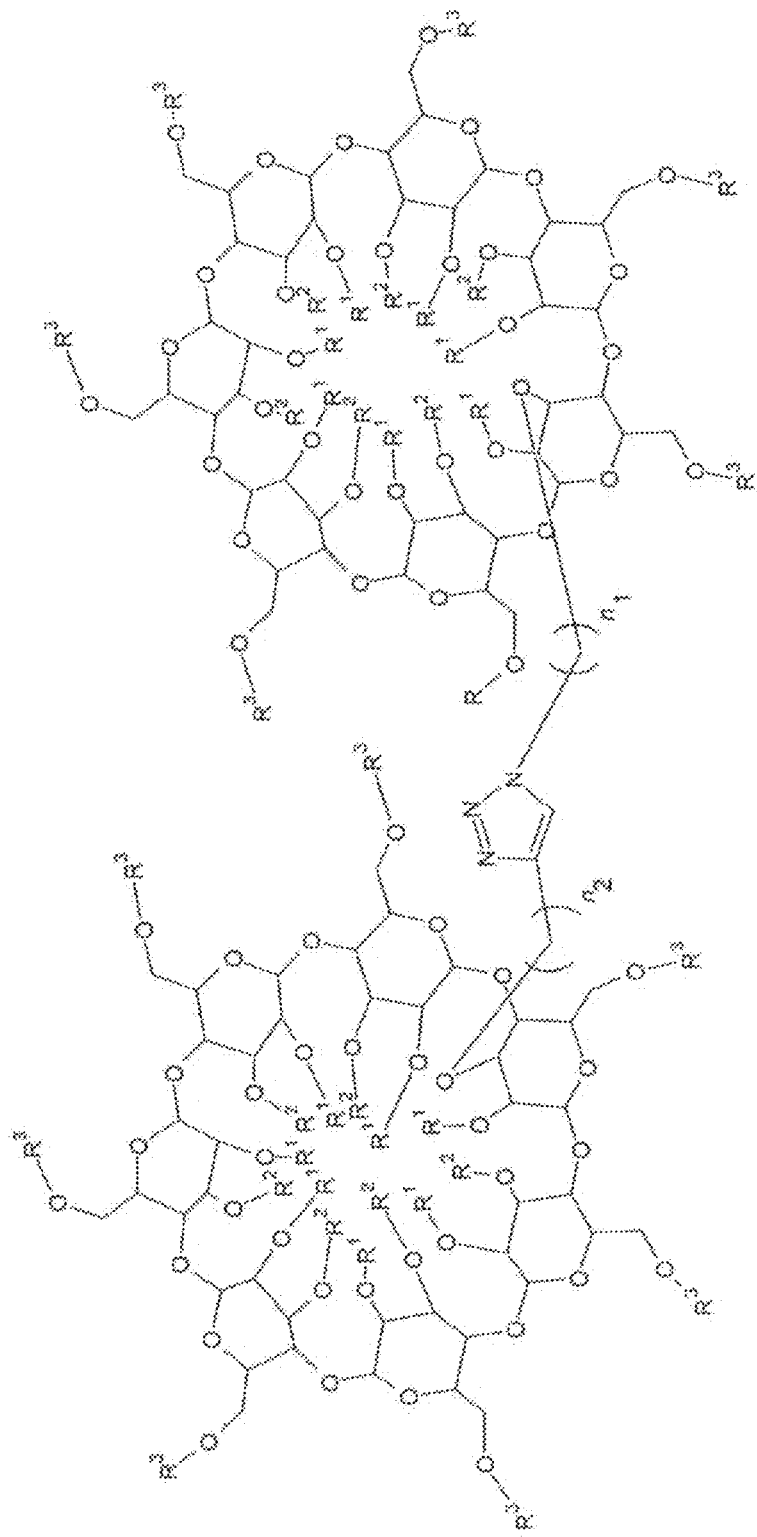
FIG. 3D. Formula III.

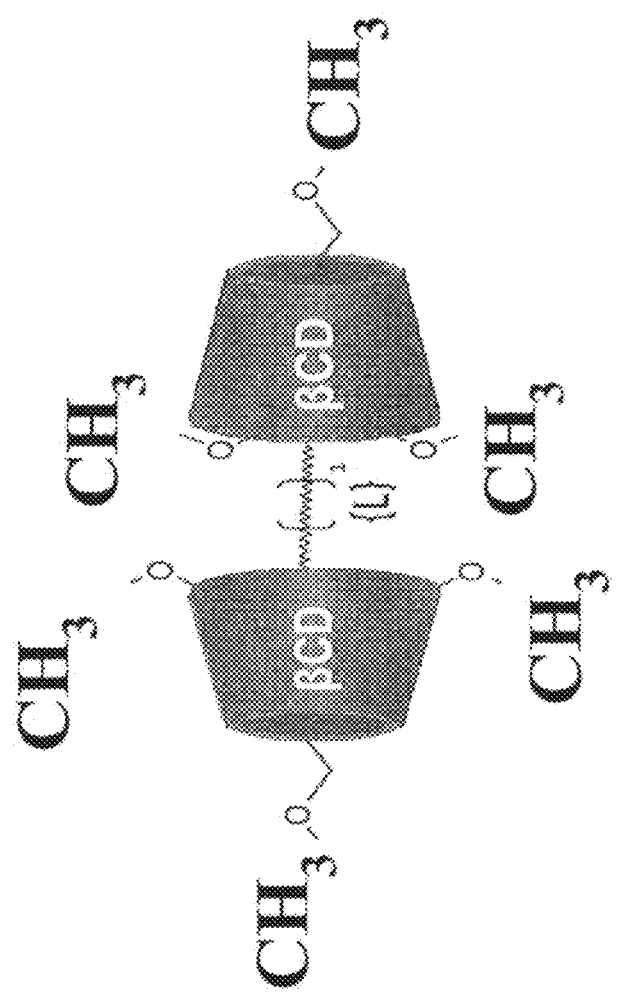
FIG. 3E. Formula IV.

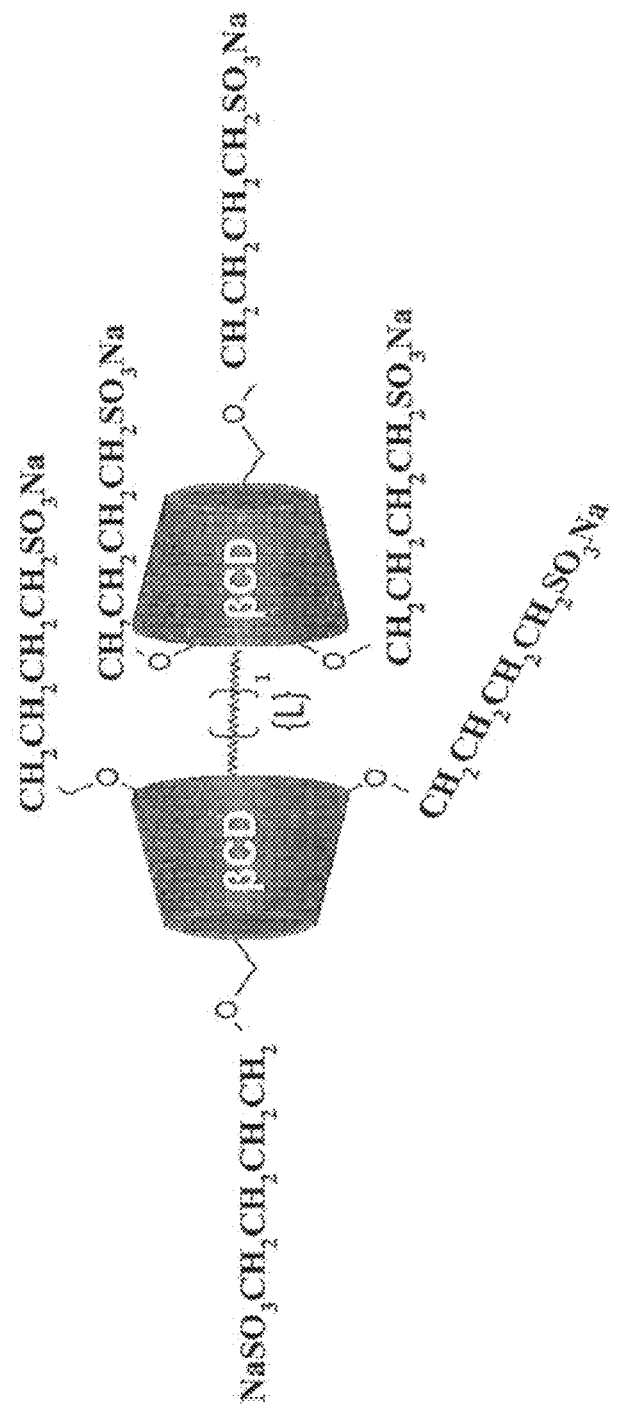
FIG. 3F. Formula V.

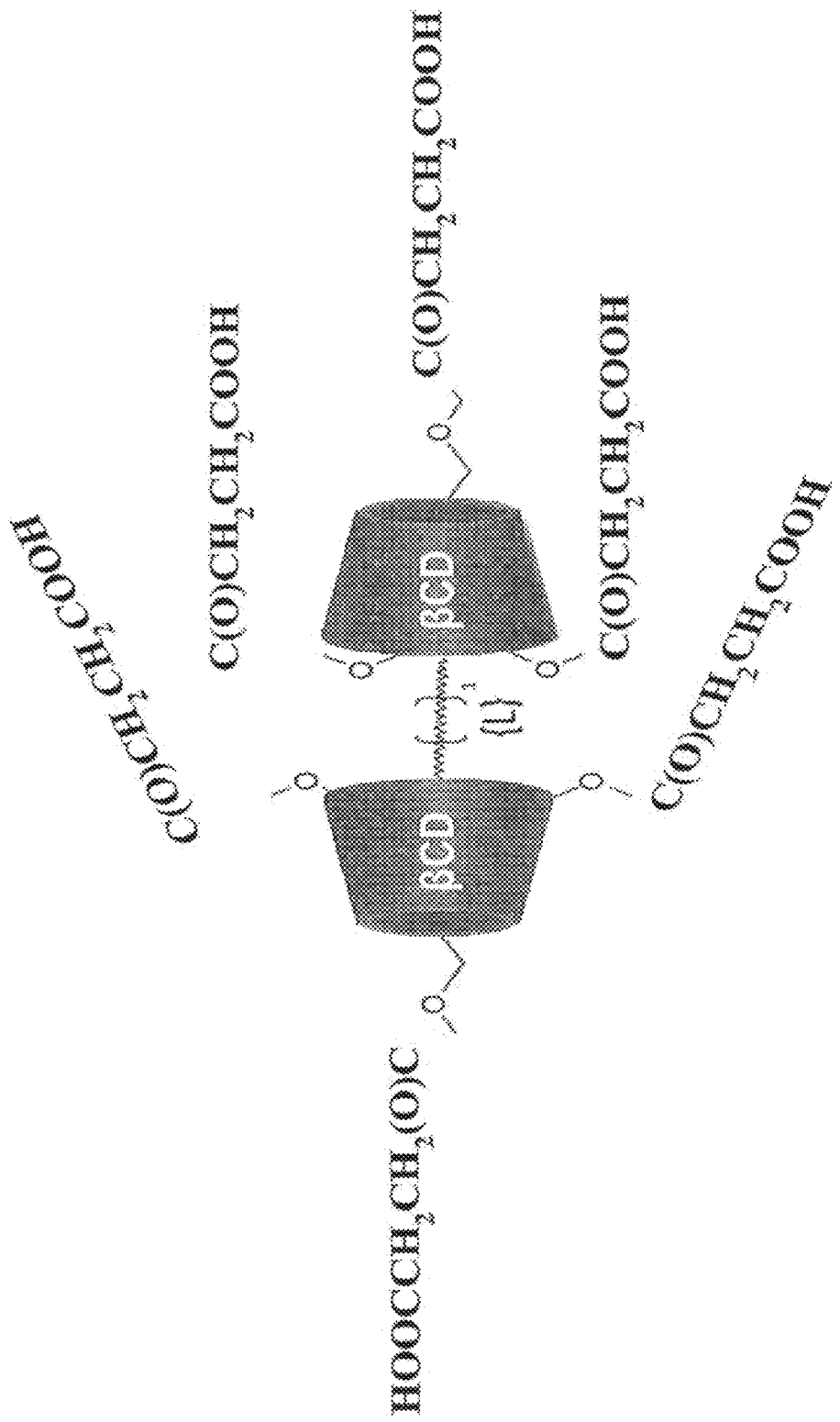
FIG. 3G. Formula VI.

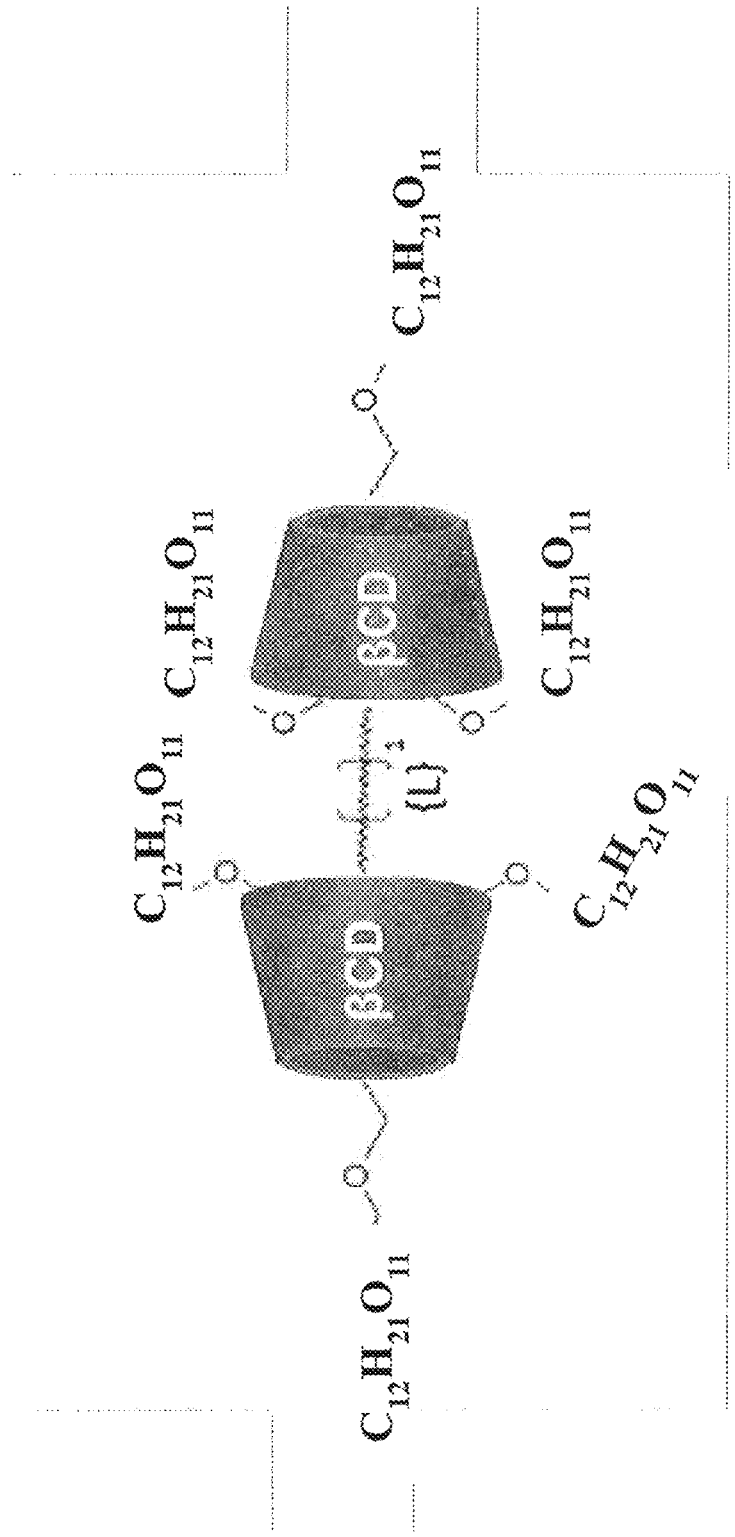
FIG. 3H. Formula VII.

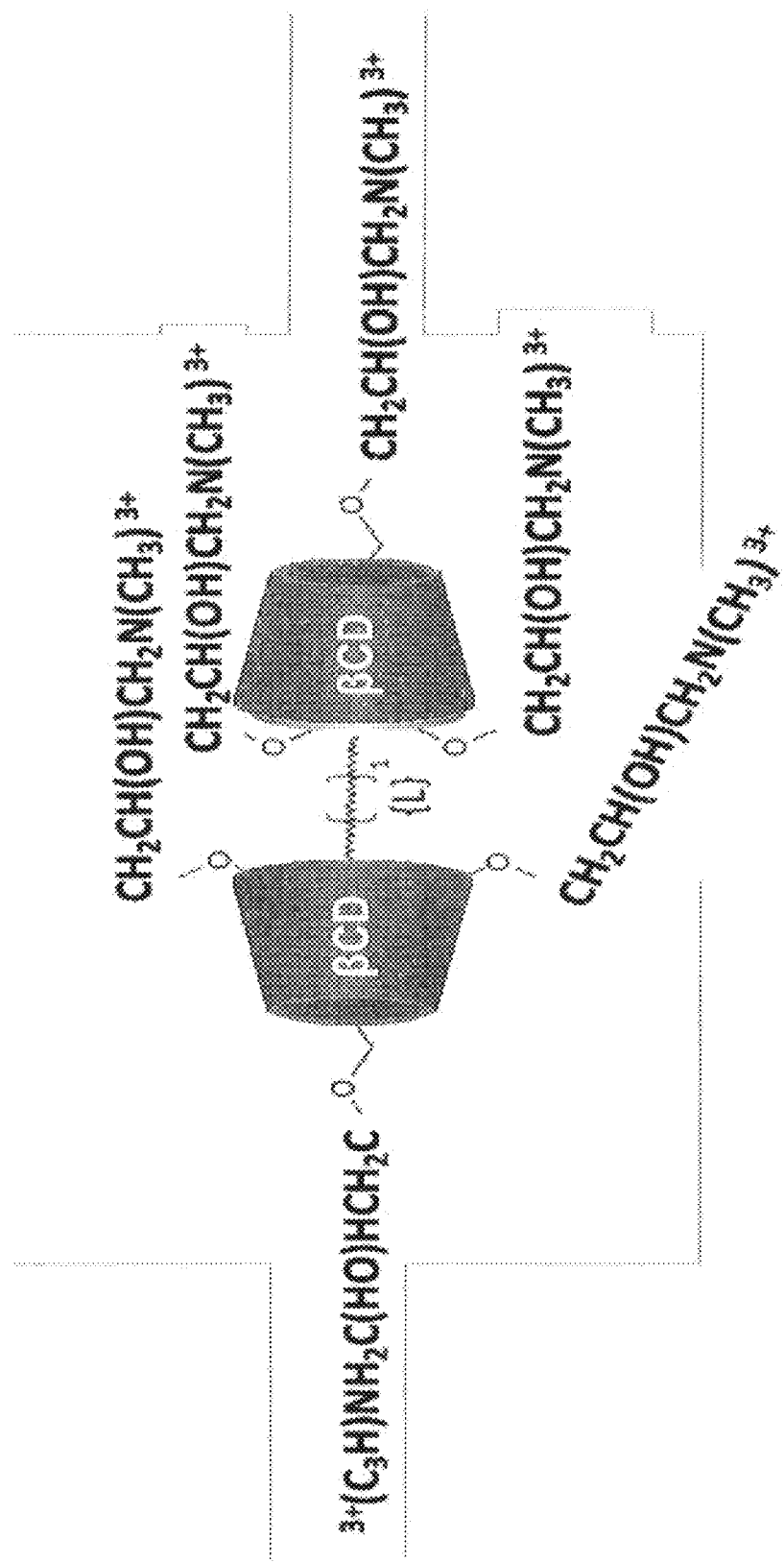
FIG. 31. Formula VIII.

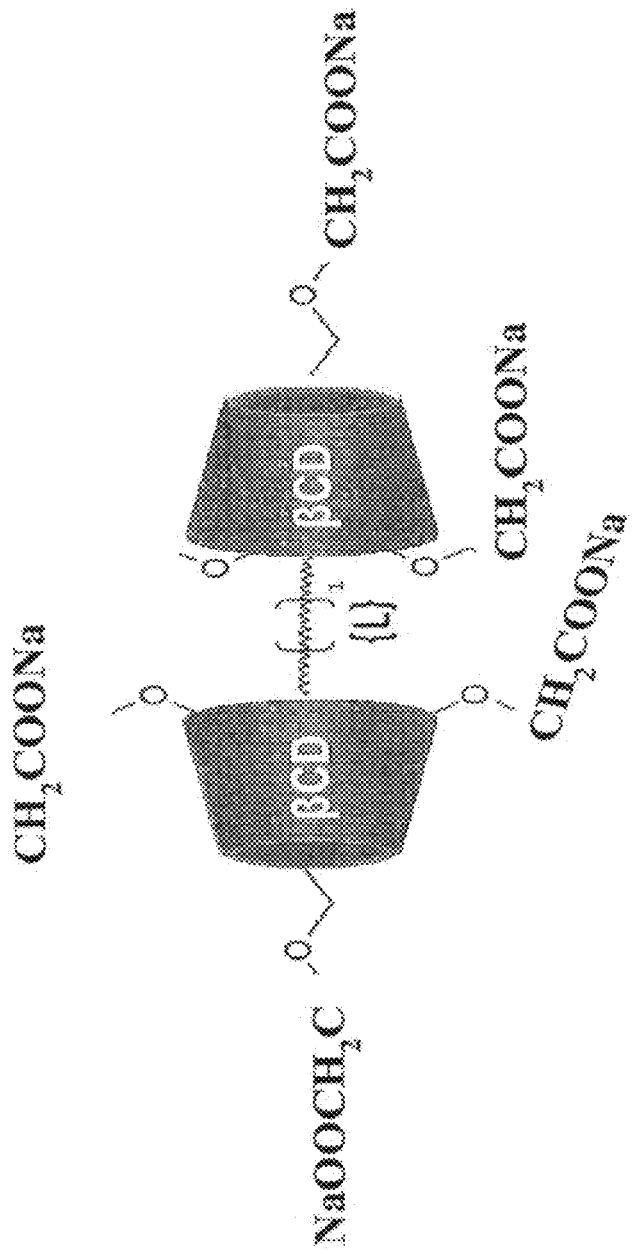
FIG. 3J. Formula IX.

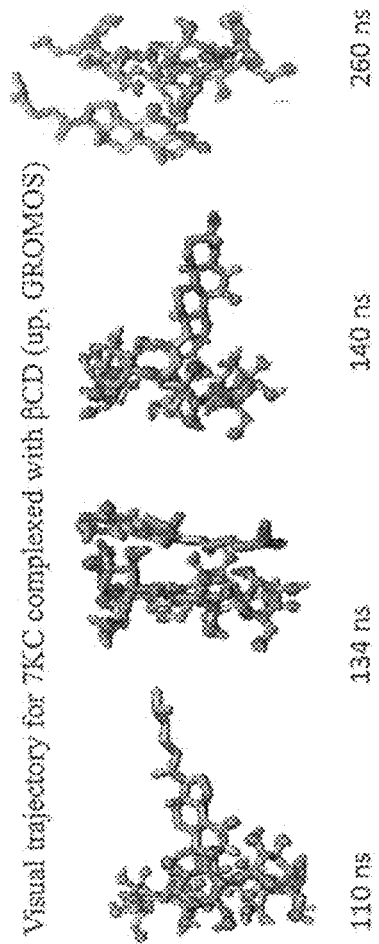
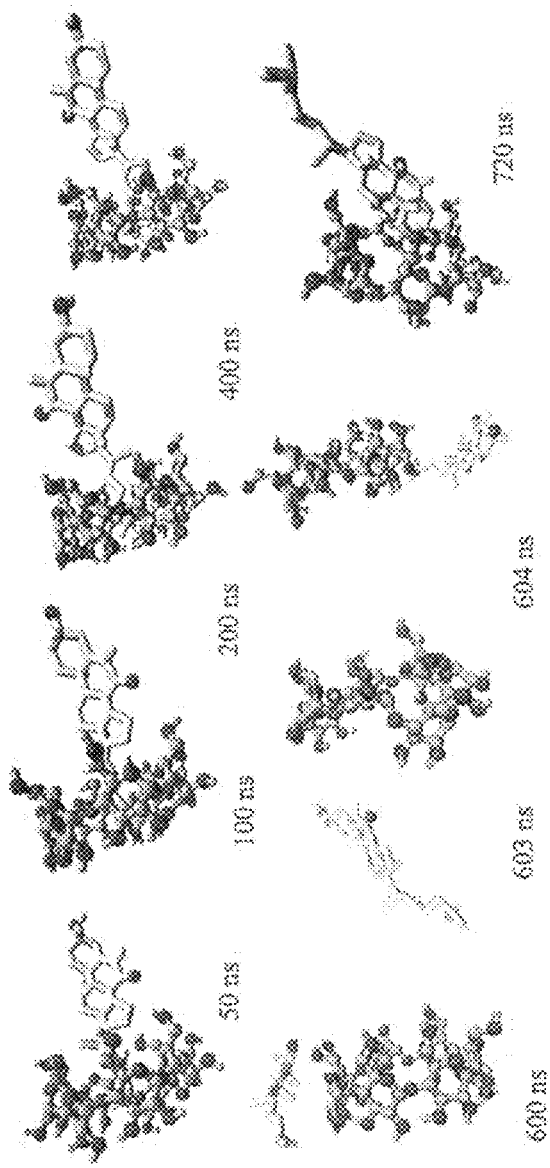
FIG. 4F

Visual trajectory for cholesterol complexed with βCD (up, GROMOS)

Visual trajectory for cholesterol complexed with βCD (down, GROMOS)

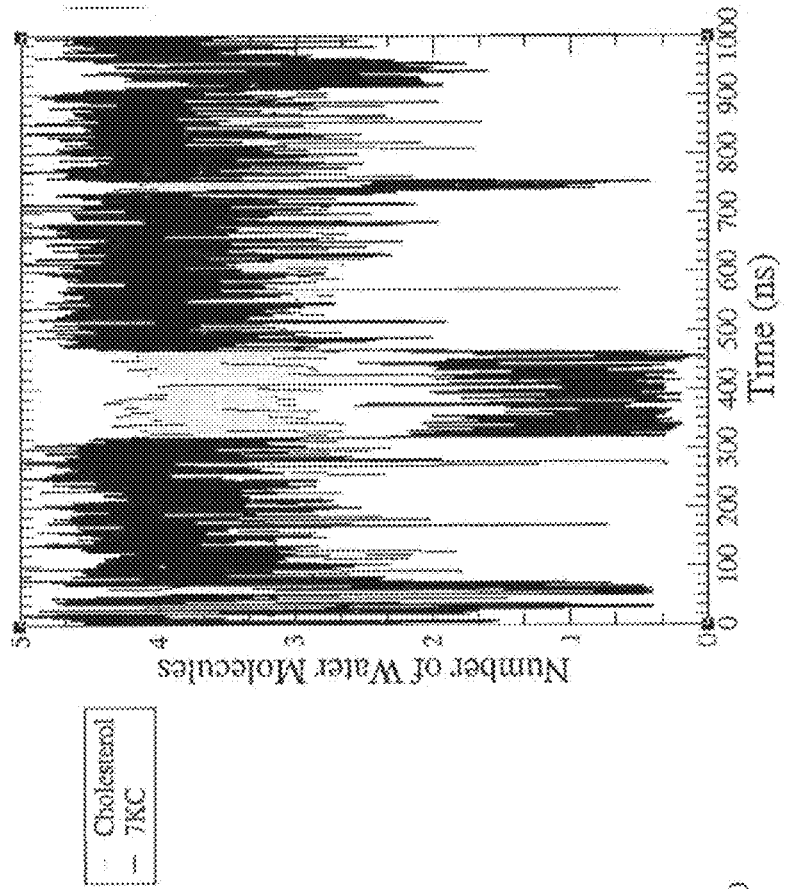
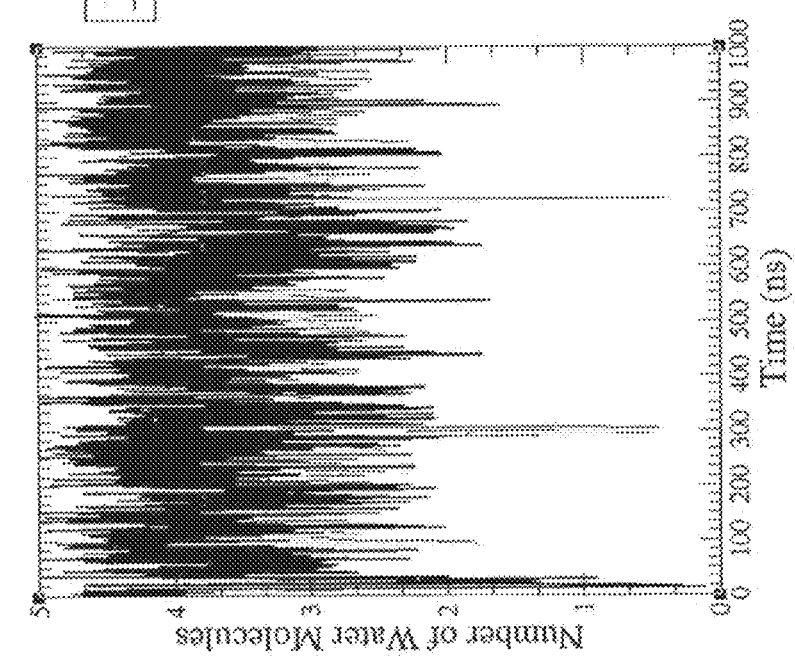
FIG. 4Q.

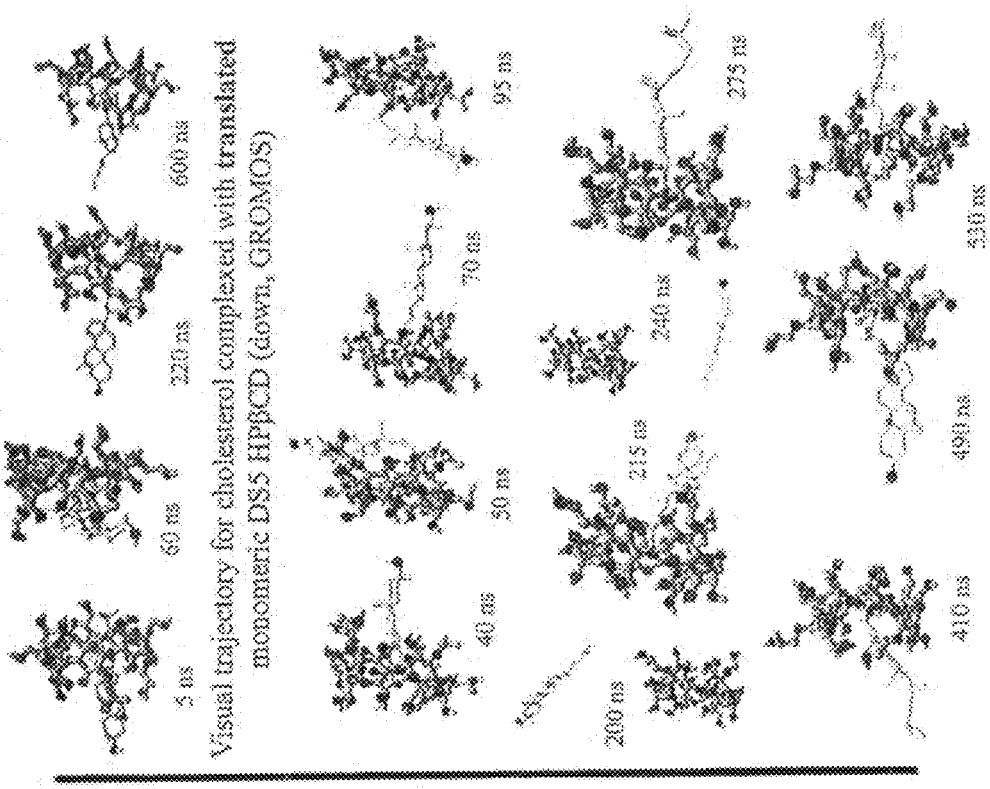
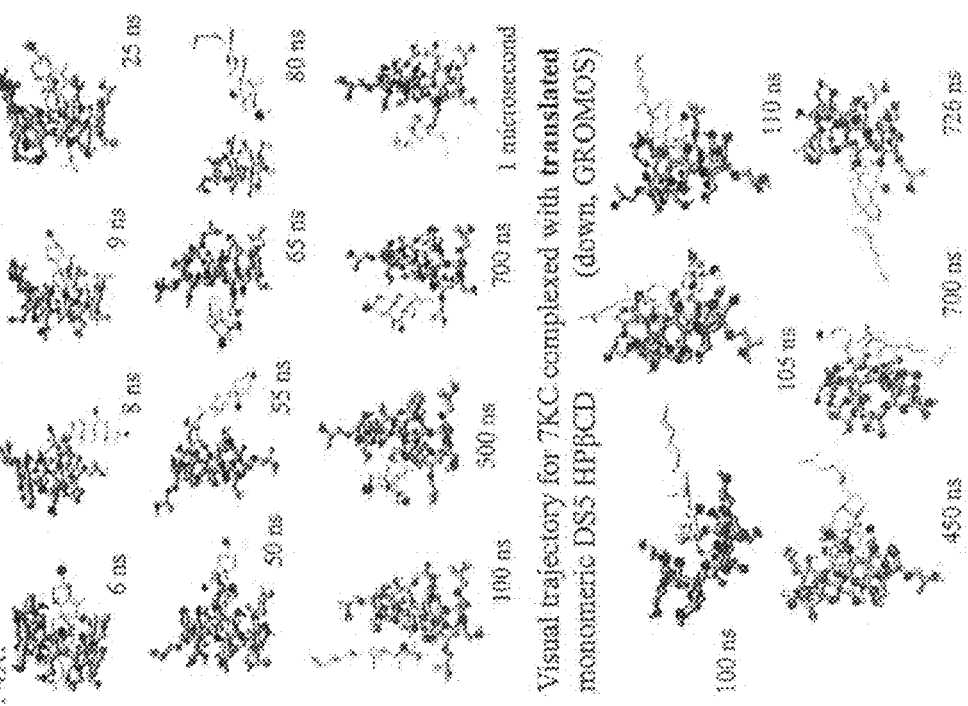
FIG. 4X

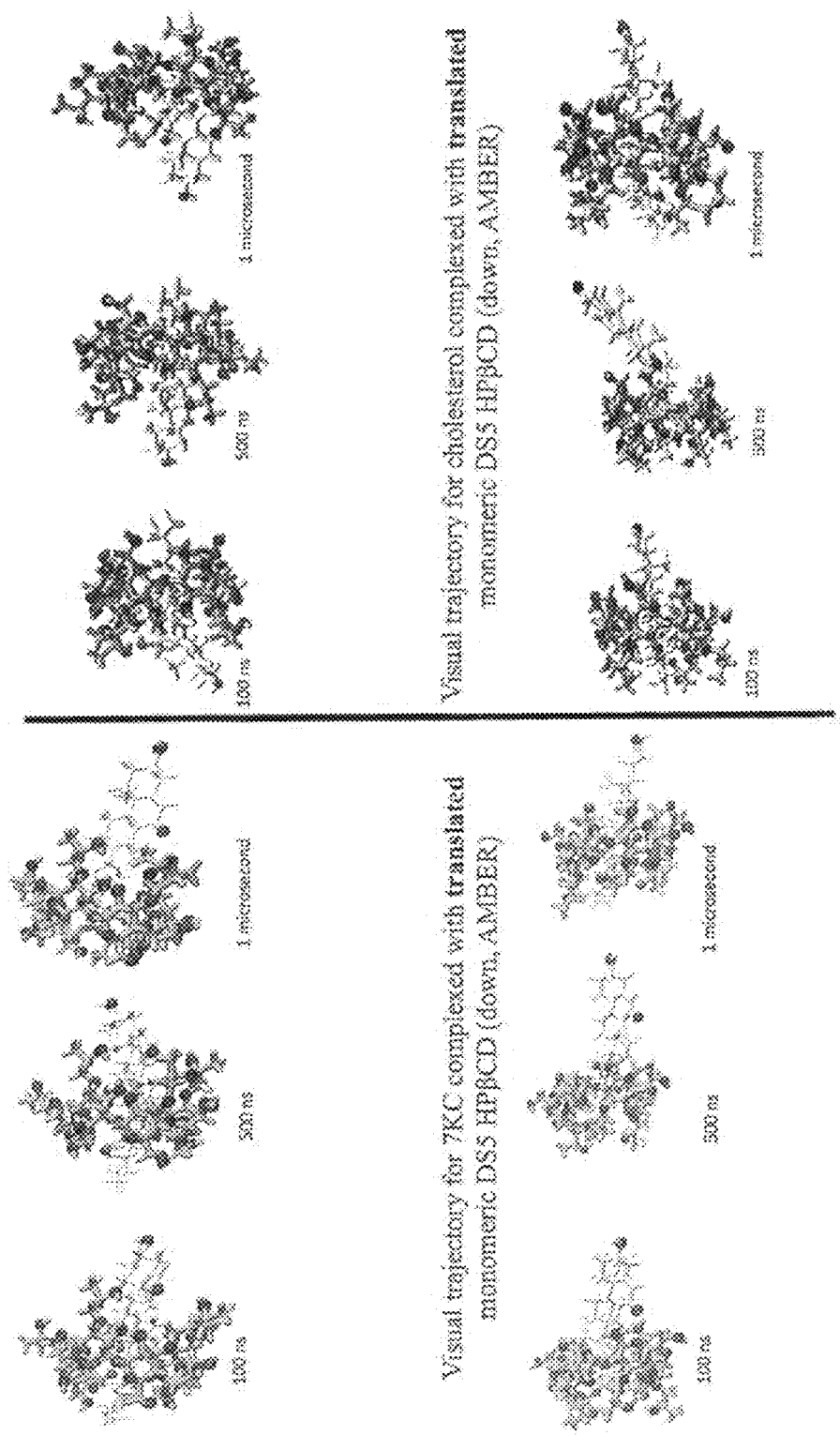

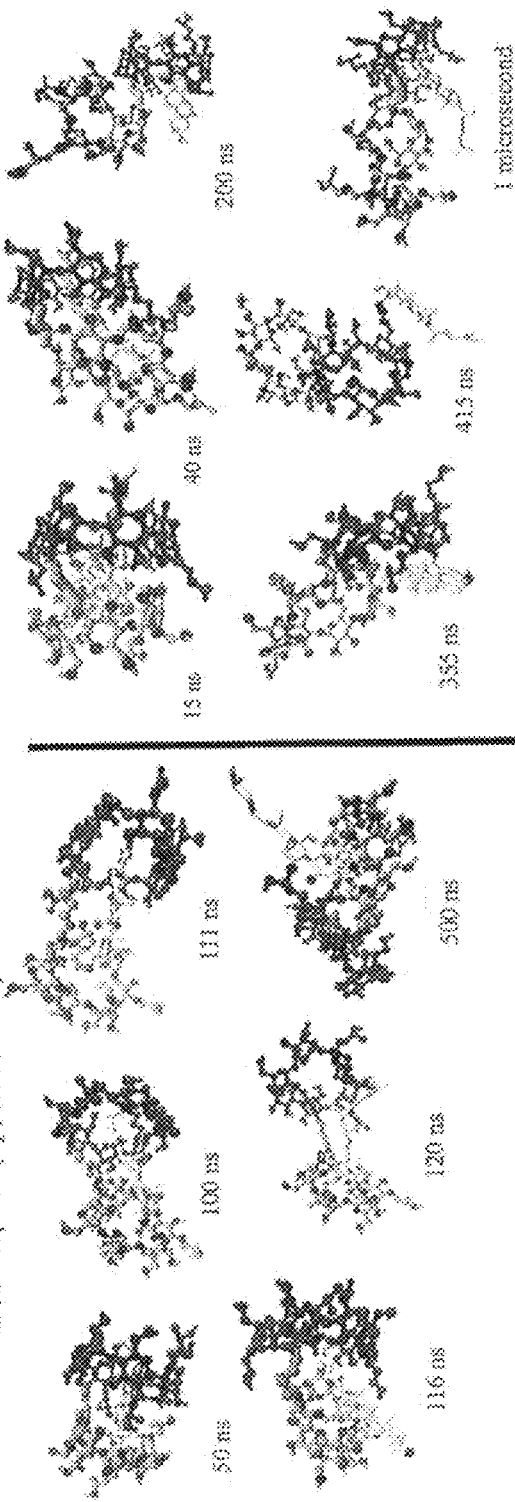
FIG. 43D.

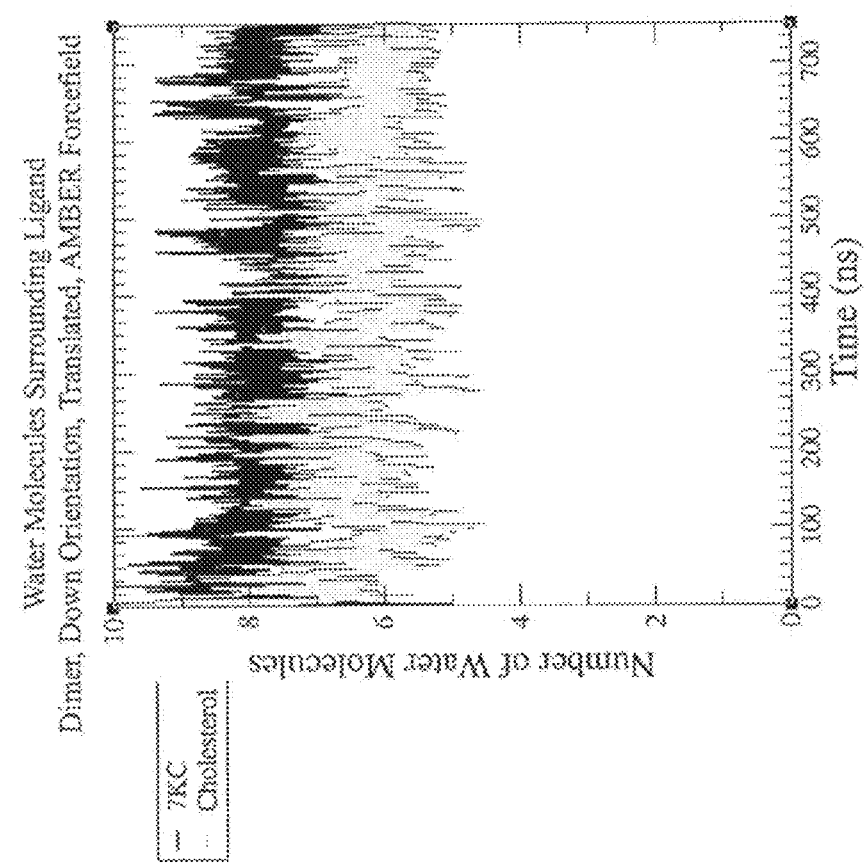
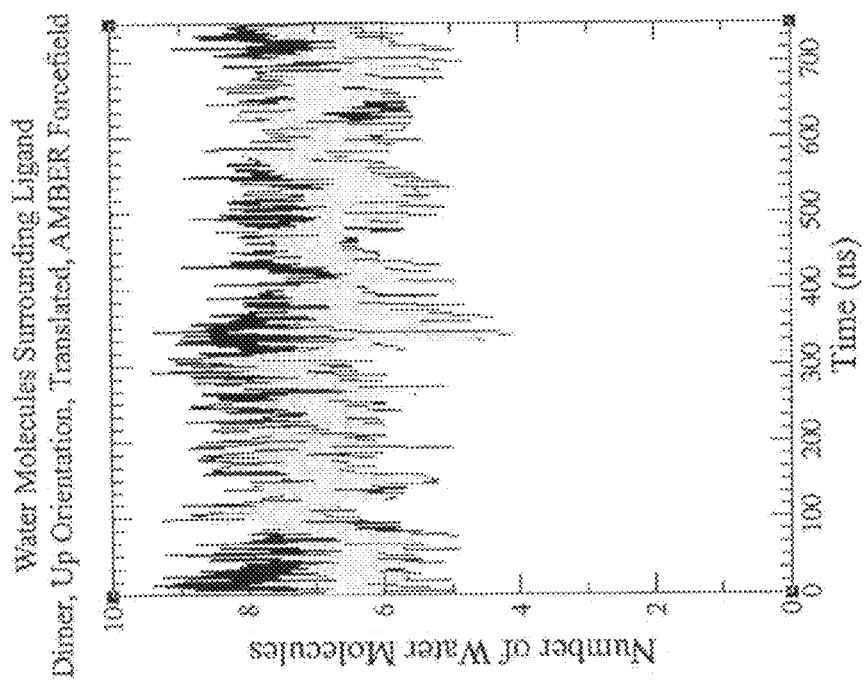
FIG. 4LL.

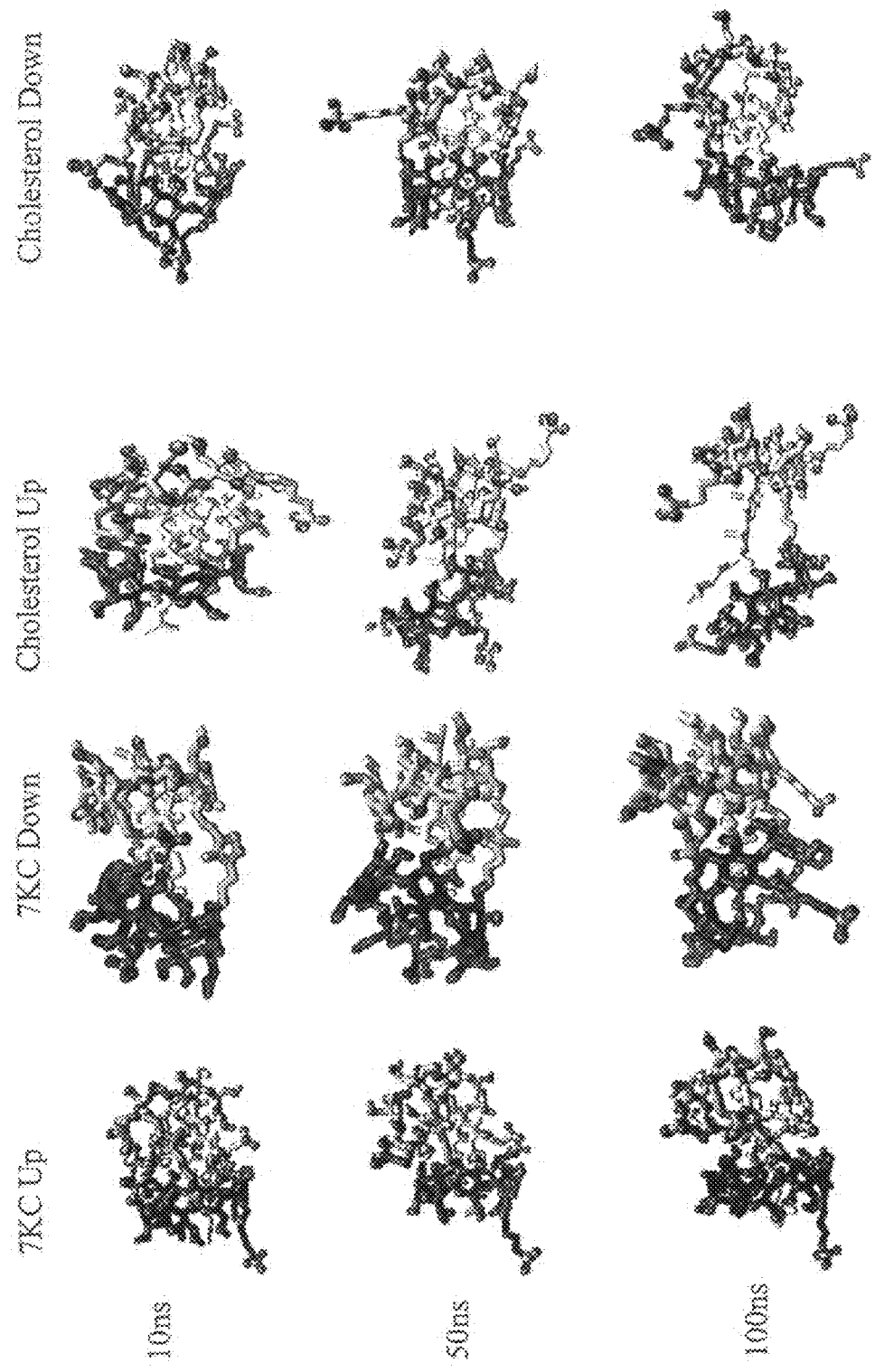

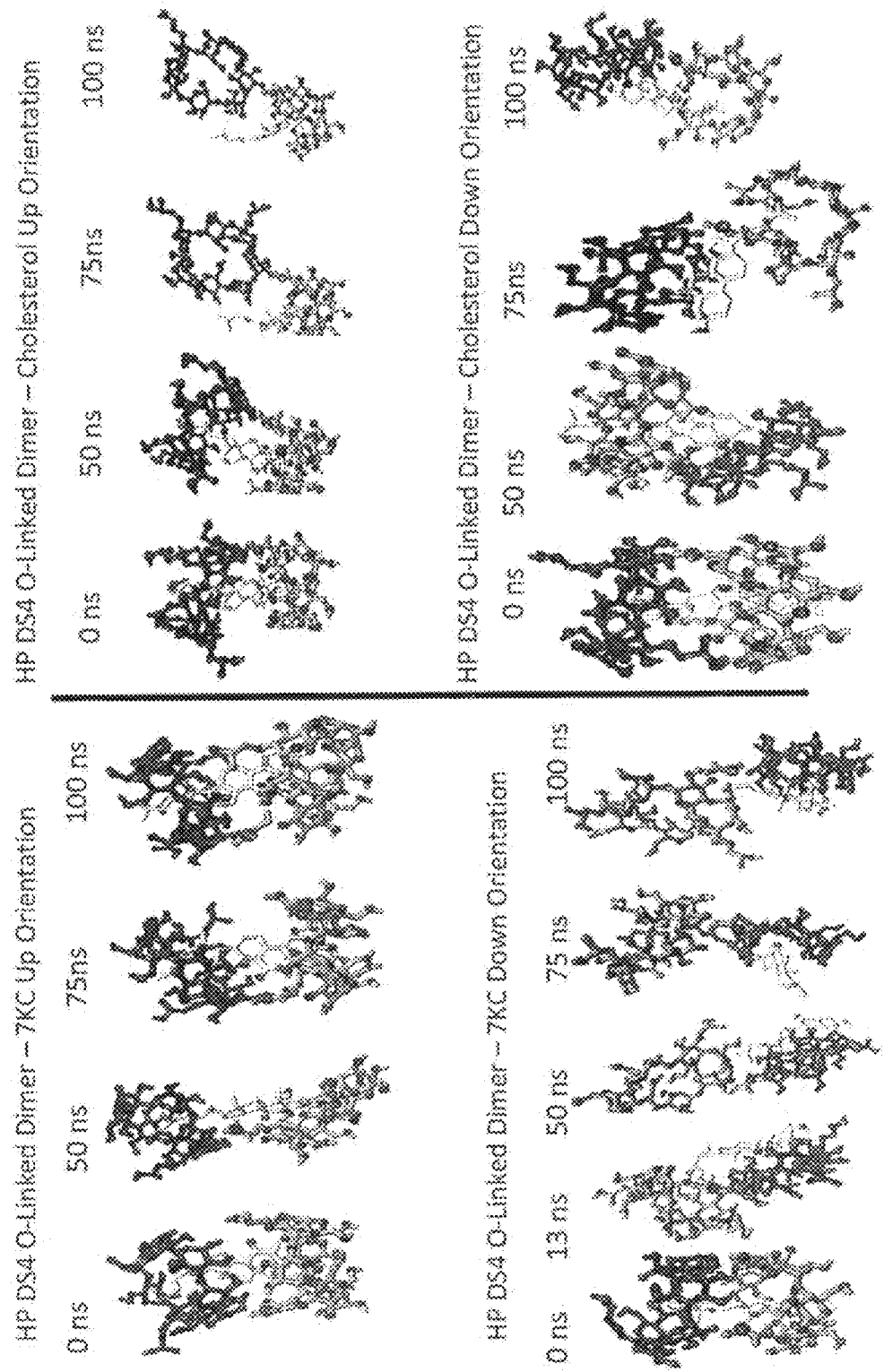

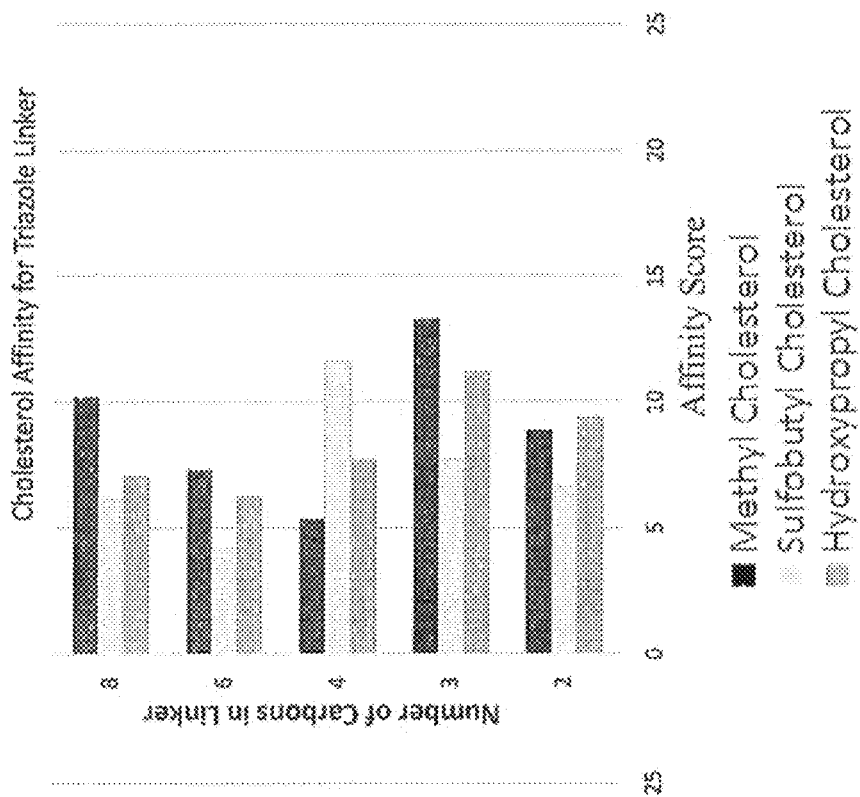
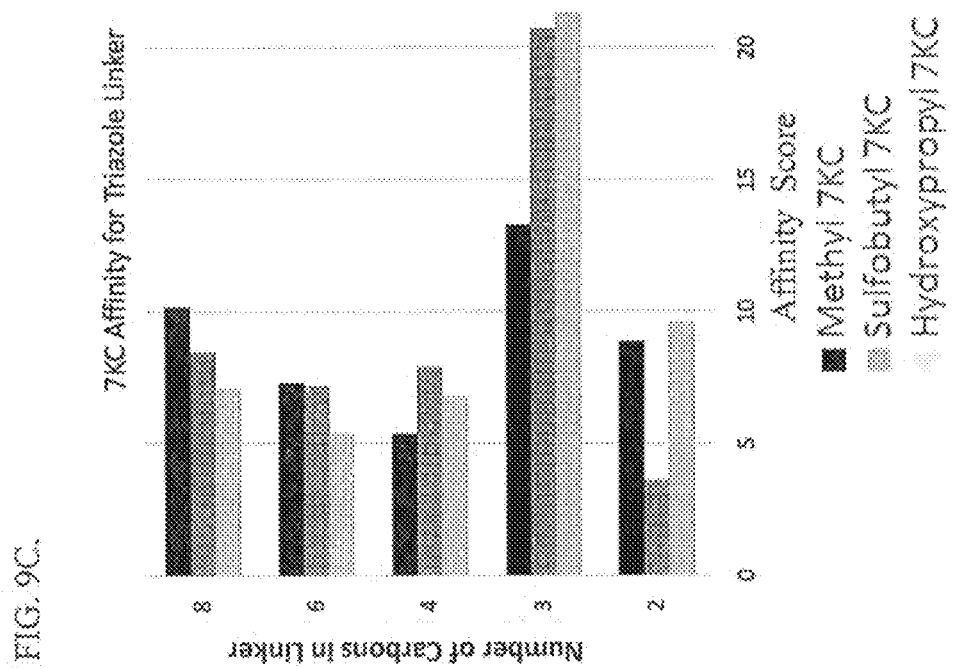
FIG. 9C.

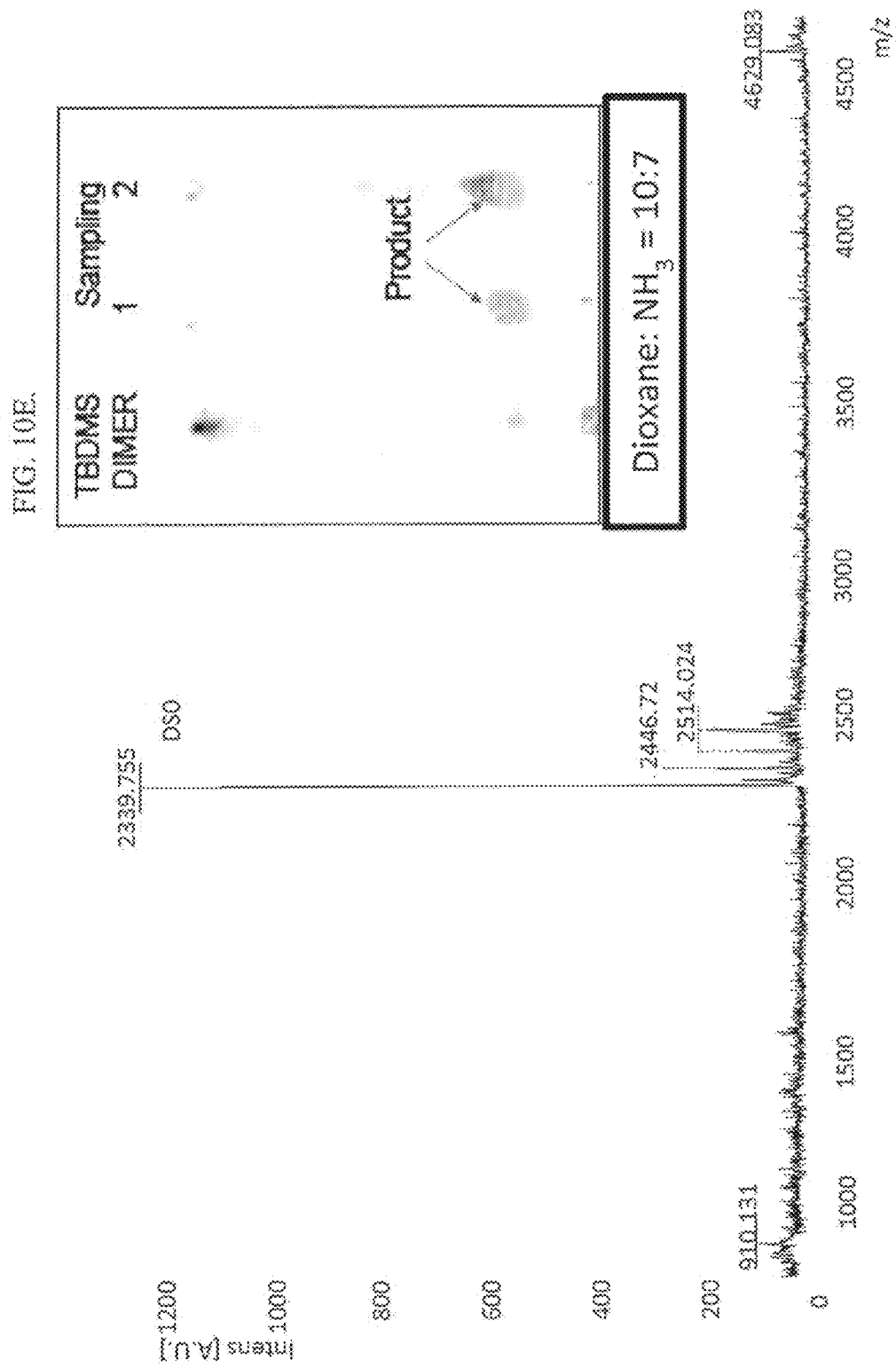

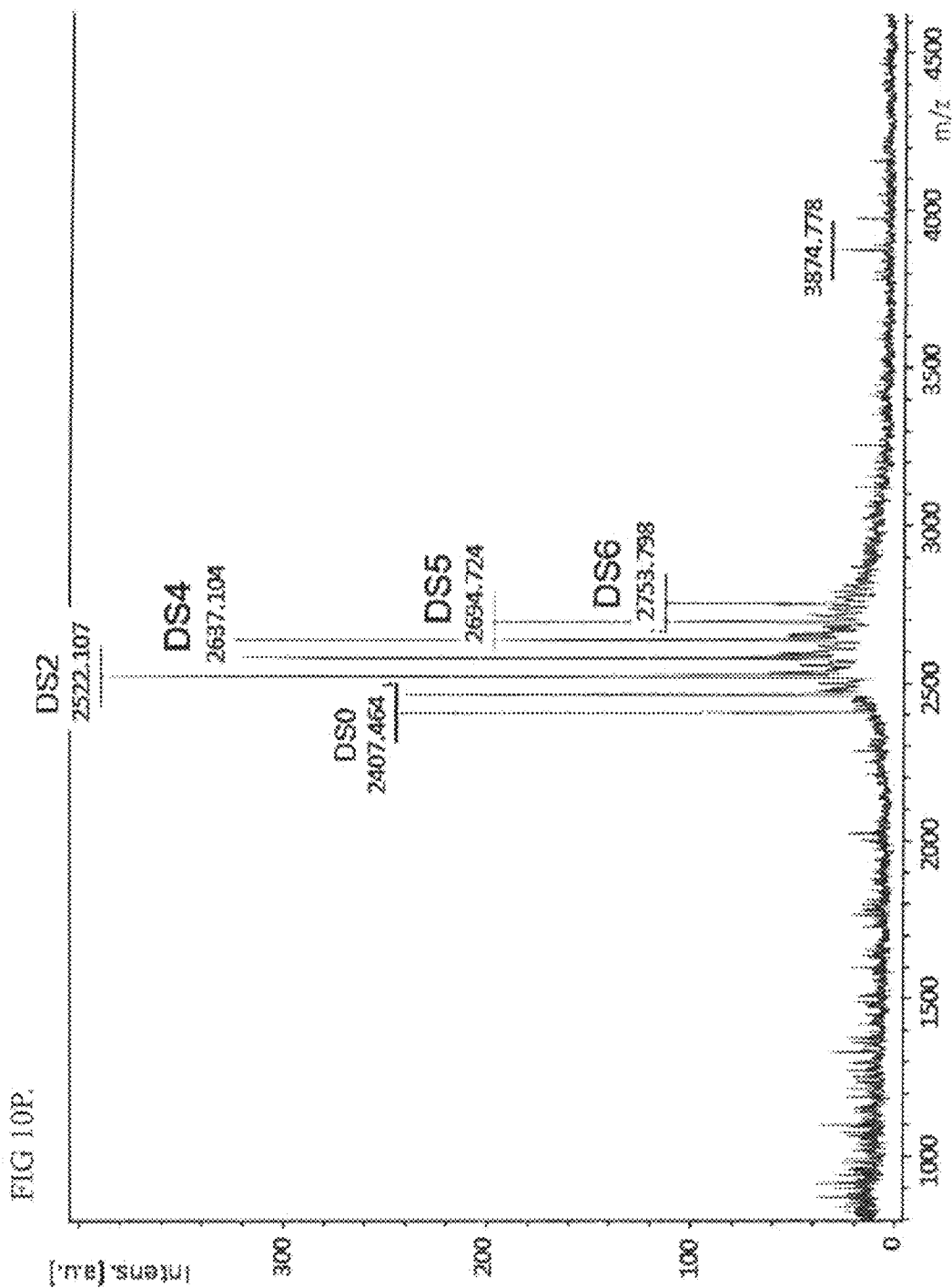

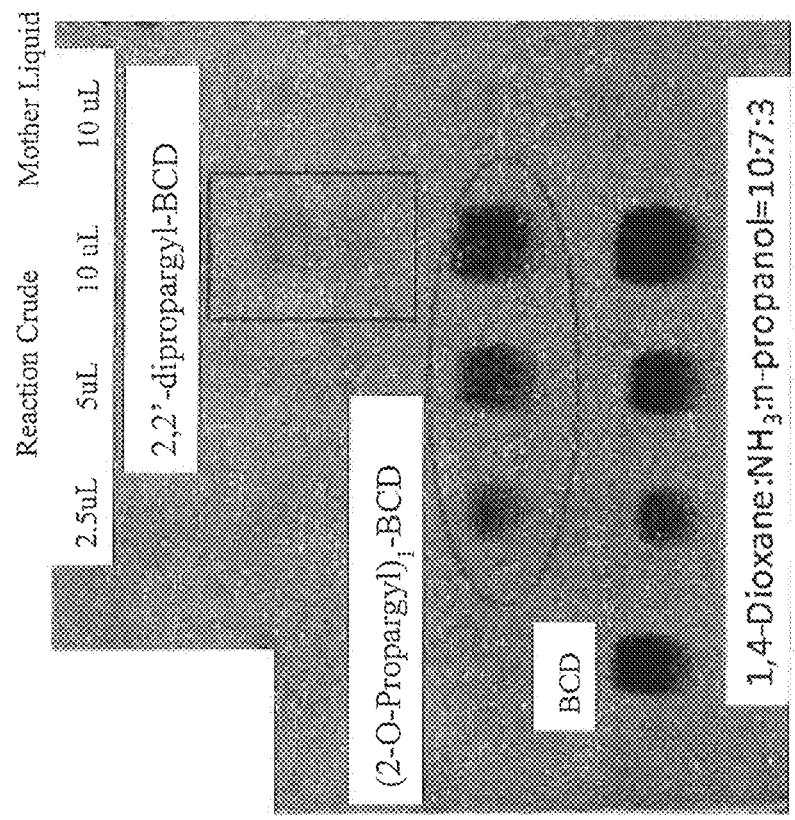
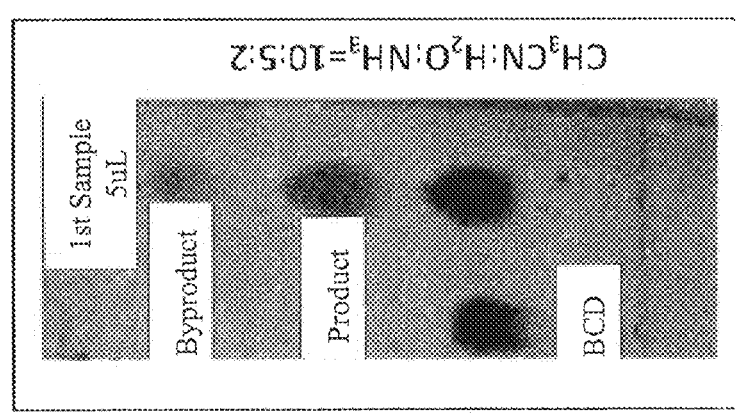
FIG. 10S.

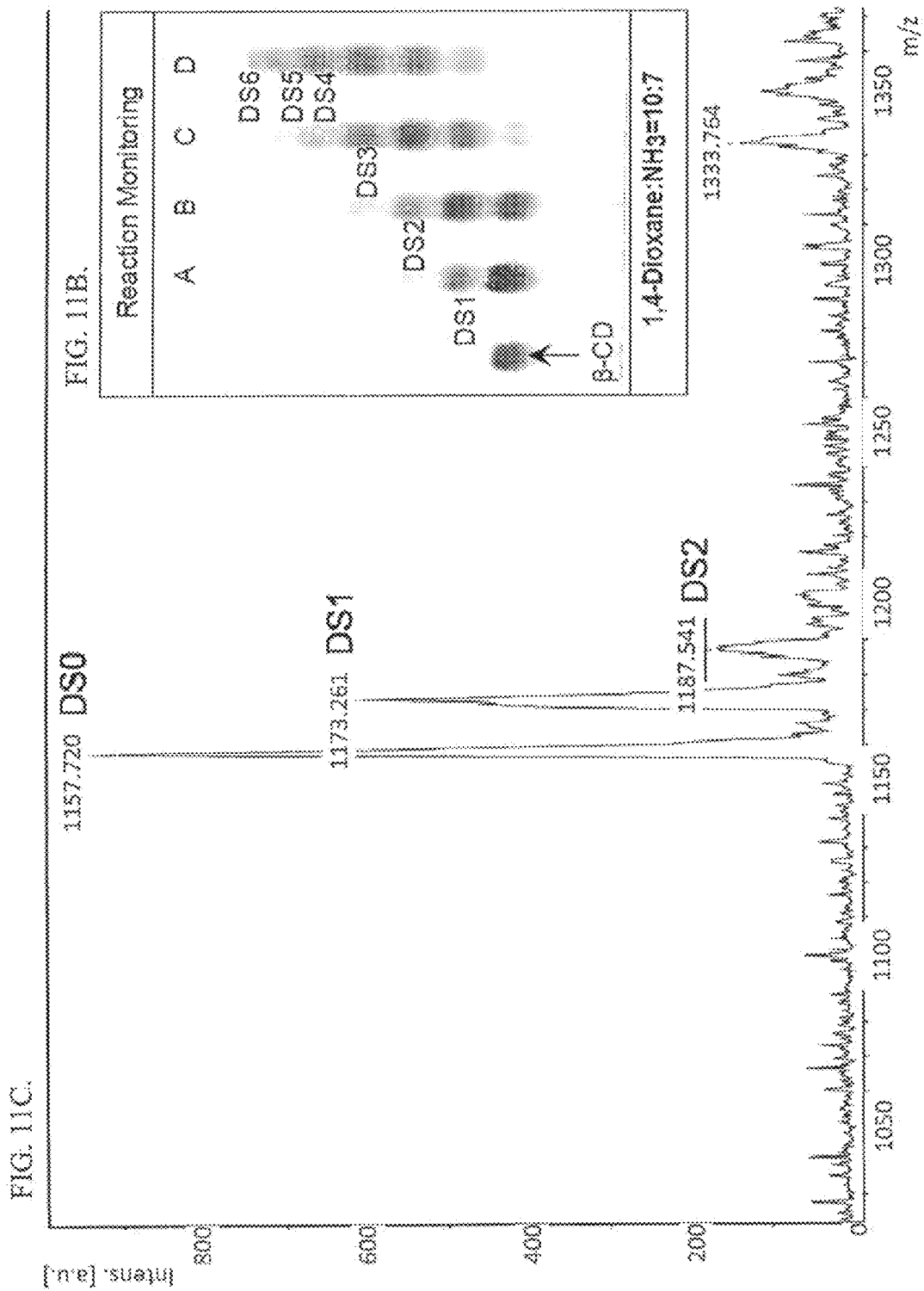

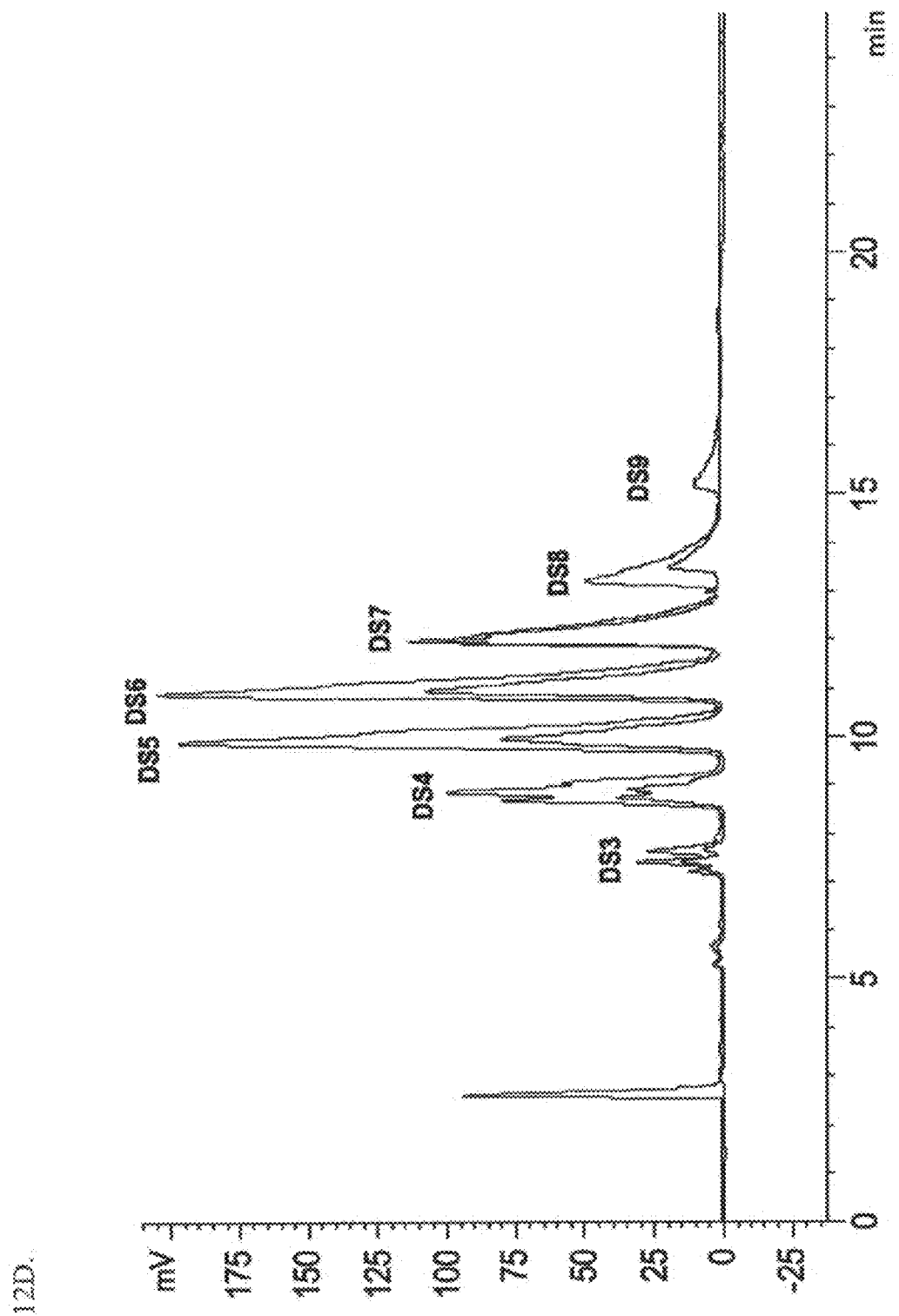

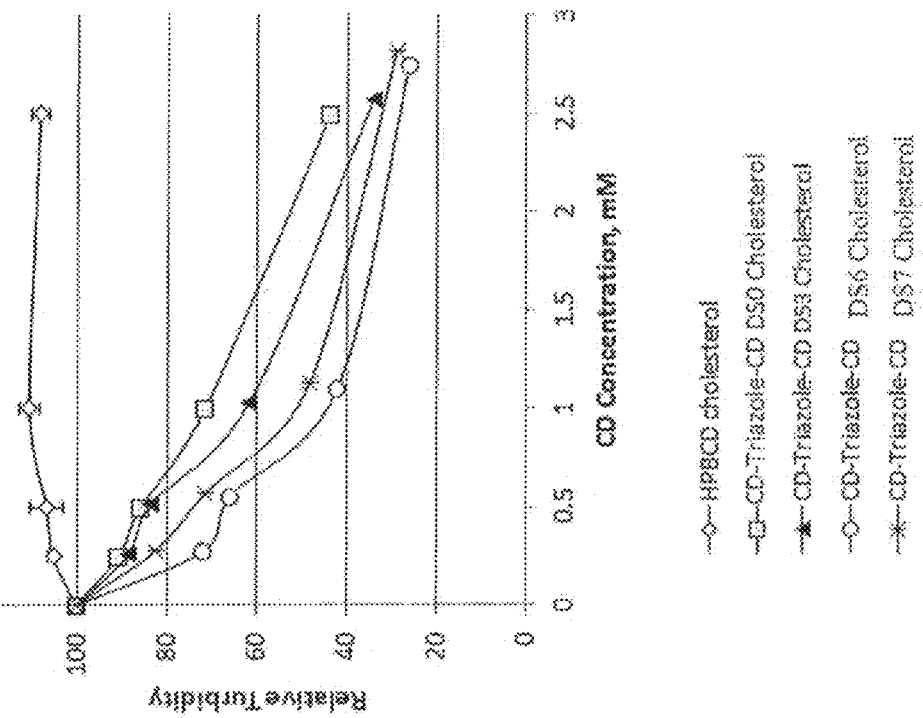
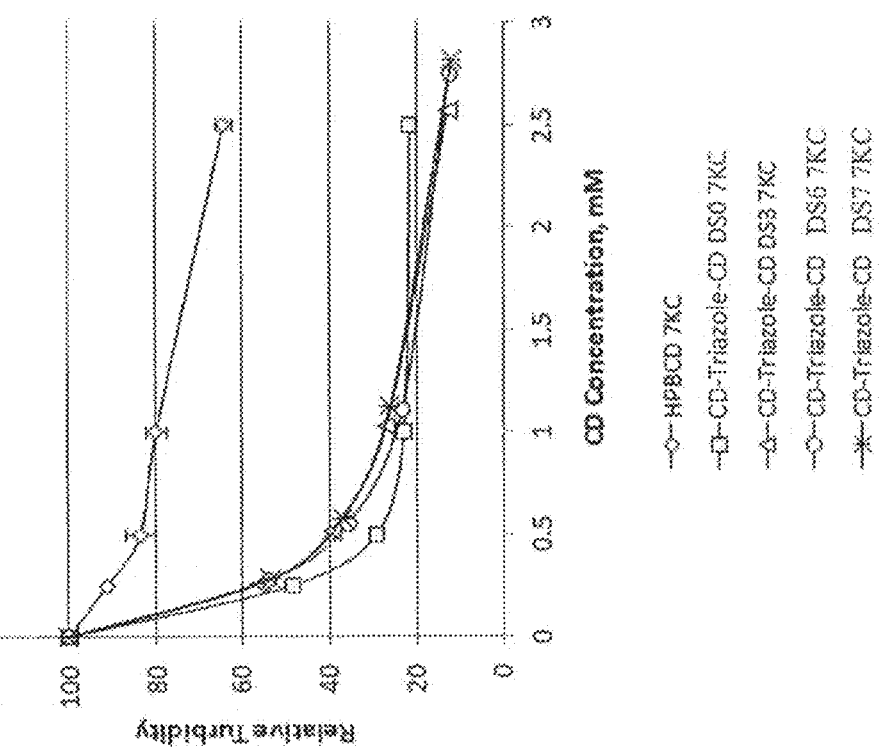
FIG. 16B.

CYCLODEXTRIN DIMERS, COMPOSITIONS THEREOF, AND USES THEREOF

CROSS-REFERENCE TO RELATED APPLICATIONS

This application is a divisional of U.S. application Ser. No. 16/733,945 filed Jan. 3, 2020, which claims the benefit of U.S. Provisional Application Ser. No. 62/787,869, filed Jan. 3, 2019, and U.S. Provisional Application Ser. No. 62/850,334, filed May 20, 2019, each of which is hereby incorporated by reference in its entirety.

BACKGROUND 7-ketocholesterol (7KC) is an oxysterol produced by the non-enzymatic reaction of oxygen radicals with cholesterol. 7KC can be formed in organisms or consumed in food, but it is potentially toxic and is thought to serve no useful purpose in humans and other eukaryotes. Like cholesterol, 7KC is found in atherosclerotic plaques. 7KC is the most abundant non-enzymatically produced oxysterol in atherosclerotic plaques and may contribute to the pathogenesis of atherosclerosis and other diseases of aging. 7KC also is believed to contribute to the pathogenesis of lysosomal storage diseases such as Niemann-Pick Type C (NPC).

Cyclodextrins (CDs) are cyclic oligosaccharide polymers comprised of 6 (αCD), 7 (βCD), or 8 (γCD) sugar rings (FIG. 1A). Alpha, beta, and gamma cyclodextrins are the most common forms, having many medical, industrial, consumer, and food related uses. Cyclodextrins have been used for a variety of applications, including as a food additive form of dietary fiber. Cyclodextrins have also been used in pharmaceutical compositions as an aerosolizing agent and as excipients for small hydrophobic drugs, typically in combination with an active pharmaceutical ingredient.

Hydroxypropyl-beta-cyclodextrin (HPβCD) is a beta cyclodextrin where some number of hydroxypropyl (HP) groups have been added to an O2, O3, or O6 oxygen (or to an atom substituted for said oxygen) on some or all of the seven glucose monomers composing βCD. Hydroxypropylation of cyclodextrin improves its solubility in water and its safety to the point where it can be used in humans for a variety of purposes, especially as excipients for active drugs; this has earned HPβCD GRAS (Generally-Recognized-as-Safe) list designation by the FDA. Most commercial HPβCDs have an average of between 4 and 9 HP substitutions, and all available products contain a mixture of substitution numbers and positions, usually reflected in the advertised average degree of substitution (DS).

Other CD substitutions include methyl, succinyl, sulfobutyl, maltosyl, carboxymethyl, and quaternary ammonium, among others, which can create CDs that are quite soluble in water and have low cytotoxicity, regardless of whether they are charged or neutral groups. Commercially available βCDs may have different degrees of substitution, which can vary from as little as ~1 up to fully substituted (21 substitutions) depending on the particular substituent and vendor.

BRIEF SUMMARY

The present disclosure describes the design and testing of various dimers of cyclodextrin (CD) including HPβCD dimers, methyl-βCD dimers, succinyl-βCD dimers, sulfobutyl-βCD dimers, and quaternary ammonium dimers, among others. It is demonstrated that certain dimers' affinity for 7KC and cholesterol are increased dramatically compared to monomeric CDs. The exemplified dimers are representative of a new class of linked and substituted cyclodextrin dimers having improved properties, including the ability to selectively interact with and solubilize sterols. Molecular modeling experiments, described below, show a predicted interaction mechanism. Moreover, working examples confirm the predicted ability of novel substituted cyclodextrin dimers to solubilize sterols, including selective solubilization of 7KC as compared to cholesterol.

In one aspect, the disclosure provides CD dimers of the structure CD-L-CD, wherein each CD is a beta cyclodextrin, L is linked to a C2 or C3 carbon of each CD monomer, and one or both of the CD monomers is substituted with at least one functional group, such as methyl, hydroxypropyl (HP), sulfobutyl (SB), succinyl (SUCC), quaternary ammonium (QA) such as —$CH_2CH(OH)CH_2N(CH_3)_3^+$, or a combination thereof. Typically, each CD monomer is made up of glucose monomers in the D-configuration. The CD dimers are substituted with functional groups, typically having a degree of substitution (DS) of between 1 and 28 wherein the degree of substitution refers to the total number of said functional group substitutions present on both CD subunits. Said substitutions may be present on either or both CD subunits. The linker length may be between 2-8 atoms long, such as 4-8 atoms long, on the shortest path through the linker connecting the two CD subunits of a cyclodextrin dimer. Said linker may comprise an alkyl (e.g., butyl) linker and/or a triazole linker, which is optionally substituted. Exemplary CD dimers are of the Formula I-IX (FIGS. 3B-3J, respectively). Optionally, said CD dimer is further substituted.

In another aspect, the disclosure provides βCD dimers of the structure CD-L-CD, wherein each CD is a beta cyclodextrin, L is linked to a C2 or C3 carbon of each CD monomer, and one or both of the CD monomers is substituted with at least one hydroxypropyl group. Typically, each CD monomer is made up of glucose monomers in the D-configuration. The βCD dimers are substituted with hydroxypropyl (HP), typically having a degree of substitution (DS) of between 1 and 40 wherein the degree of substitution refers to the total number of substitutions present on both CD subunits. Said substitutions may be present on either or both CD subunits. The linker length may be between 4-8 atoms long on the shortest path through the linker connecting the two CD subunits of a cyclodextrin dimer. Said linker may comprise an alkyl (e.g., butyl) linker and/or a triazole linker, which is optionally substituted. Exemplary βCD dimers are of the Formula I, II, or III (FIGS. 3B-3D, respectively). Optionally, said βCD dimer is further substituted.

7KC is believed to be involved in heart diseases, cystic fibrosis, liver damage and failure, and complications of hypercholesterolemia. When someone is affected by hypercholesterolemia, 7KC can diffuse through the membranes of cells where it affects receptors and enzymatic function; the increased rates of dementia in hypercholesterolemia have been associated with 7KC accumulation. In the liver, 7KC affects fenestration and porosity in the tissue, which increases with age. 7KC also promotes translocation of cytosolic NADPH oxidase components to the membrane in neutrophils (white blood cells) and enhances rapid reactive oxygen species production. Pathogenesis of other diseases of aging such as Age-Related Macular Degeneration (AMD—dry form), Alzheimer's disease, as well as lysosomal storage diseases such as Niemann-Pick Type C (NPC)

have also been tied to increased levels of 7KC. Oxysterols, including 7KC, are also involved in increasing free radical levels, which in turn affect lipid circulation in cystic fibrosis. The increase in free radicals caused by oxysterols like 7KC are believed to be involved in apoptosis, cytotoxicity, impairment of endothelial function, and regulation of enzymes involved in inflammation and in fatty acid metabolism.

7KC is formed from the non-enzymatic reaction of an oxygen radical with cholesterol, indicating that its formation may not be beneficial. Indeed, 7KC is believed to enhance the production of free radicals everywhere in the body, but heart and vascular tissue is of particular concern. Free radicals affect cells and enzymatic reactions that are important for cholesterol mediated tissue damage, which is especially important in these tissues; this is believed to enhance inflammation in the vasculature. By disrupting the function of cell and organelle membranes, 7KC is believed to cause dysfunction of mitochondria and lysosomes and is thought to be involved in increasing the frequency of formation of foam cells from macrophages in atherosclerotic plaques. The scavenging functions of these macrophages would be expected to help ameliorate the plaque, but instead they can become part of the plaque when they are congested with cholesterol and oxysterols.

Exemplary embodiments provide for the treatment of diseases associated with and/or exacerbated by 7KC accumulation, such as atherosclerosis, AMD, arteriosclerosis, coronary atherosclerosis due to calcified coronary lesion, heart failure (all stages), Alzheimer's disease, Amyotrophic lateral sclerosis, Parkinson's disease, Huntington's disease, vascular dementia, multiple sclerosis, Smith-Lemli-Opitz Syndrome, infantile neuronal ceroid Lipofuscinosis, Lysosomal acid lipase deficiency, Cerebrotendinous xanthomatosi, X-linked adrenoleukodystrophy, Sickle cell disease, Niemann-Pick Type A disease, Niemann-Pick Type B disease, Niemann-Pick Type C disease, Gaucher's disease, Stargardt's disease, idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia or dementia associated with hypercholesterolemia. Preferred cyclodextrin (e.g., HPβCD, MeβCD, SUCCβCD, QAβCD, or SBβCD) dimers are selective for 7KC (compared to cholesterol). Preferably, said CD dimer preferentially solubilizes 7KC, while minimizing or avoiding potentially deleterious or toxic effects that can result from excessive removal of cholesterol.

Exemplary embodiments of the invention provide for the use of cyclodextrin (e.g., HPβCD, MeβCD, SUCCβCD, QAβCD, or SBβCD) dimers for the solubilization and/or removal of 7KC, which may be performed in vitro or in vivo.

In exemplary embodiments, said cyclodextrin (e.g., HPβCD, MeβCD, SUCCβCD, QAβCD, or SBβCD) dimer, exhibits greater binding affinity and/or solubilization of 7KC than cholesterol. The specificity for 7KC over cholesterol is most evident at sub-saturating concentrations, whereas at higher concentrations the solubilization of both sterols can approach 100%. This specificity allows for use of such cyclodextrin dimers in order to preferentially solubilize and remove 7KC.

In exemplary embodiments, the disclosure provides a cyclodextrin dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

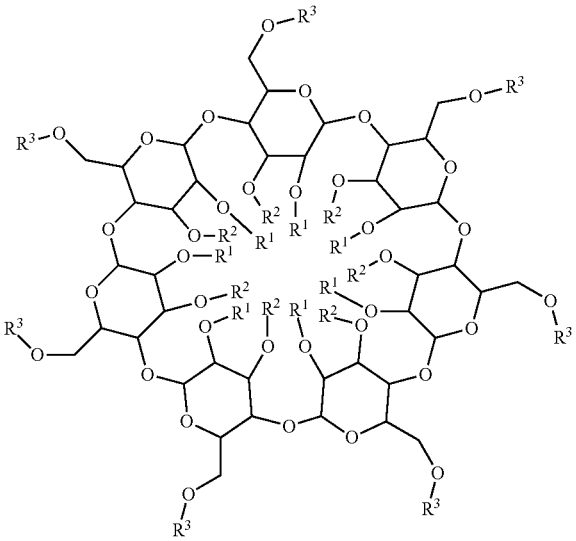

(Formula X)

wherein L has a length of no more than 8 atoms on the shortest path through the linker connecting the two CD subunits of the dimer, wherein said no more than 8 atoms are preferably each C, N, O, or S;

and the CDs are substituted with between 1 and 40 groups, such as between 1 and 28 groups, optionally between 2 and 15 or between 4 and 20 groups. Said number of substitutions refers to the total number of $R^1$, $R^2$, and/or $R^3$ groups that are not H. Said CDs may have one or more additional substitutions.

Said $R^1$, $R^2$, and $R^3$ may each be independently selected from H, methyl, hydroxypropyl, sulfobutyl, succinyl, quaternary ammonium such as —$CH_2CH(OH)CH_2N(CH_3)_3^+$, alkyl, lower alkyl, alkylene, alkenyl, alkynyl, alkoxy, alkoxyalkyl, alkoxyalkoxyalkyl, alkylcarbonyloxyalkyl, alkylcarbonyl, alkyl sulfonyl, alkylsulfonylalkyl, alkylamino, alkoxyamino, alkylsulfanyl, amino, alkylamino, dialkylamino, alkylaminoalkyl, dialkylaminoalkyl, aminoalkyl, aminoalkoxy, alkylsulfonylamido, aminocarbonyloxyalkyl, aminosulfonyl, ammonium, ammonia, alkylaminosulfonyl, dialkylaminosulfonyl, alkynylalkoxy, aryl, arylalkyl, aryl sulfonyl, aryloxy, aralkyloxy, azido, bromo, chloro, cyanoalkyl, cycloalkyl, cycloalkenyl, cycloalkylalkyl, cycloalkylene, cycloalkylalkylene, deoxy, glucosyl, heteroalkyl, heteroaryl, heteroarylalkyl, heteroarylsulfonyl, heteroaryloxy, heteroaralkyloxy, heterocyclylalkoxy, halogen, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, iodo, ureido, carbamate, carboxy, sulfate, sulfuryl, sulfonamido, nitro, nitrite, cyano, phosphate, phosphoryl, phenoxy, acetyl group, fatty acid such as palmitoyl group, monosaccharide, or disaccharide. In exemplary embodiments, said substitutions are preferably maltosyl groups or carboxymethyl groups.

In exemplary embodiments, said $R^1$, $R^2$, and/or $R^3$ groups may be each independently selected from H, methyl, hydroxypropyl, sulfobutyl, succinyl, maltosyl, carboxymethyl, quaternary ammonium (such as —$CH_2CH(OH)CH_2N(CH_3)_3^+$), glucosyl, palmitoyl, phosphate, phosphoryl, amino, azido, sulfate, sulfuryl, alkyl, ethyl, propyl, isopropyl, butyl, isobutyl, bromo, chloro, wherein between 1 and 40, such as between 1 and 28 or optionally between 2 and 15 or between 4 and 20 of said $R^2$, and $R^3$ groups are not H.

In exemplary embodiments, said R', $R^2$, and $R^3$ groups may be each independently selected from H, methyl, hydroxypropyl, sulfobutyl, succinyl, maltosyl, carboxymethyl, quaternary ammonium such as —$CH_2CH(OH)CH_2N(CH_3)_3^+$, wherein between 1 and 40 such as between 1 and 28 of said $R^2$, and $R^3$ groups are not H, optionally between 2 and 15 or between 4 and 20 of said $R^2$, and $R^3$ groups are not H. Said $R^1$, $R^2$, and $R^3$ groups may comprise one or more maltosyl or carboxymethyl groups.

In further exemplary embodiments, the disclosure provides a CD dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

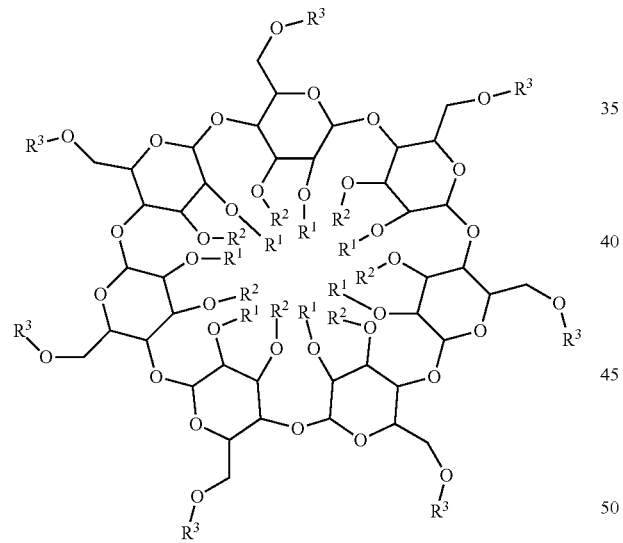

(Formula X)

wherein L has a length of no more than 8 atoms on the shortest path through the linker connecting the two CD subunits of the dimer, wherein said no more than 8 atoms are preferably each C, N, O, or S;

the CDs are hydroxypropyl (HP) substituted with between 1 and 28 HP groups, optionally between 2 and 15 or between 4 and 20 HP groups, preferably between 2 and 5 HP groups, and optionally said CDs have one or more additional substitutions. Said CD may comprise between 2 and 4 HP groups, or may comprise 2 HP groups, 3 HP groups, 4 HP groups, or 5 HP groups.

In further exemplary embodiments, the disclosure provides a CD dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

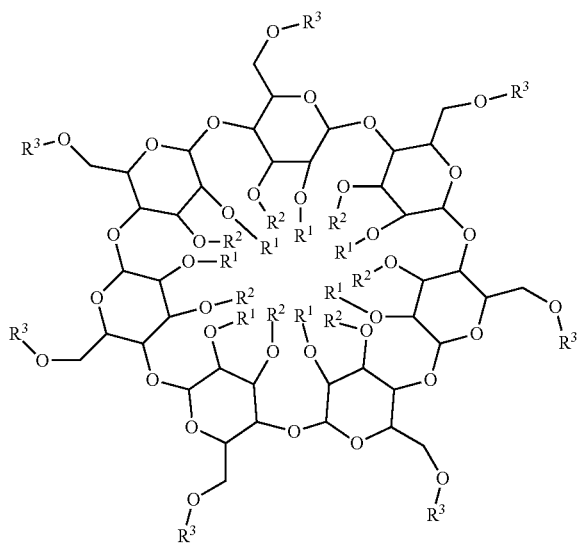

(Formula X)

wherein L has a length of no more than 8 atoms on the shortest path through the linker connecting the two CD subunits of the dimer, wherein said no more than 8 atoms are preferably each C, N, O, or S;

the CDs are methyl (Me) substituted with between 1 and 40 Me groups, optionally between 1 and 28 Me groups, optionally between 2 and 15 Me groups or between 4 and 20 Me groups, preferably between 2 and 10 Me groups, and optionally said CDs have one or more additional substitutions. Without intent to be limited by theory, it is believed that the methyl groups are particularly well-suited for substitution on such a CD dimer at high numbers of substituents because the size of the methyl groups is particularly small and thus does not interfere with the entry of guests (such as 7KC or cholesterol) into the CD dimer binding cavity. Additionally, it is envisioned that one or more methyl substitutions may be added to any cyclodextrin dimer of the present disclosure, including at higher numbers than specified in the general formulae herein, e.g., up to 40 total substituents that are not hydrogen when including both the non-methyl substituents and added methyl substituents.

In further exemplary embodiments, the disclosure provides a CD dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

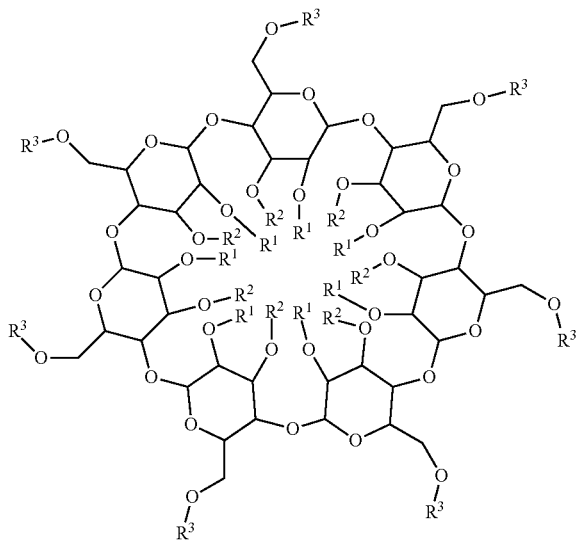

(Formula X)

wherein L has a length of no more than 8 atoms on the shortest path through the linker connecting the two CD subunits of the dimer, wherein said no more than 8 atoms are preferably each C, N, O, or S;

the CDs are sulfobutyl substituted with between 1 and 28 sulfobutyl groups, such as between 1 and 14 sulfobutyl groups, optionally between 2 and 10 sulfobutyl groups, preferably between 2 and 5 sulfobutyl groups, and optionally said CDs have one or more additional substitutions. Said CDs may have between 2 and 4 sulfobutyl groups, or may have 2 sulfobutyl groups, 3 sulfobutyl groups, 4 sulfobutyl groups, or 5 sulfobutyl groups.

In further exemplary embodiments, the disclosure provides a CD dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

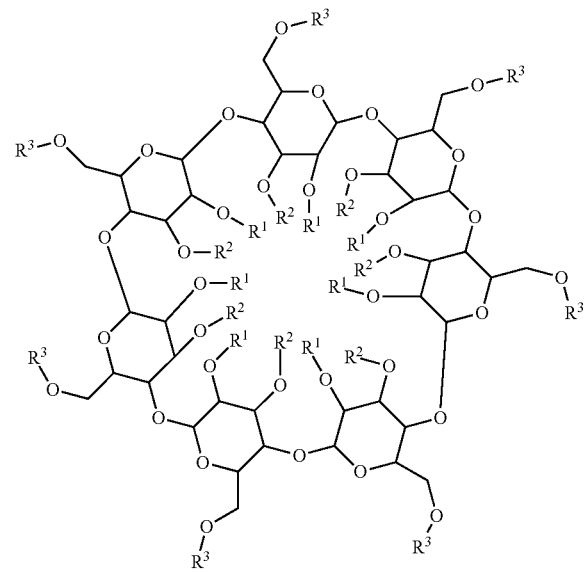

(Formula X)

wherein L has a length of no more than 8 atoms on the shortest path through the linker connecting the two CD subunits of the dimer, wherein said no more than 8 atoms are preferably each C, N, O, or S;

the CDs are succinyl substituted with between 1 and 28 succinyl groups, optionally between 2 and 15 succinyl groups or between 4 and 20 succinyl groups, preferably between 2 and 5 succinyl groups, and optionally said CDs have one or more additional substitutions. Said CD may comprise between 2 and 4 succinyl groups, or may comprise 2 succinyl groups, 3 succinyl groups, or 4 succinyl groups, or 5 succinyl groups.

In further exemplary embodiments, the disclosure provides a CD dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

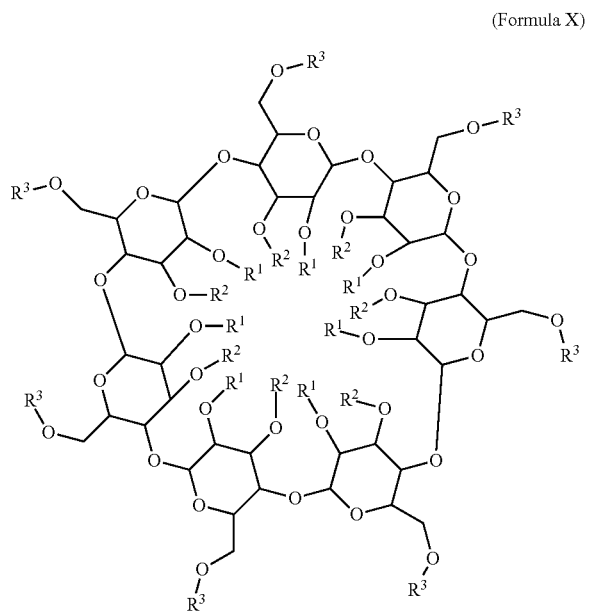

(Formula X)

wherein L has a length of no more than 8 atoms on the shortest path through the linker connecting the two CD subunits of the dimer, wherein said no more than 8 atoms are preferably each C, N, O, or S;

the CDs are substituted with between 1 and 28 quaternary ammonium groups, optionally between 2 and 15 quaternary ammonium groups or between 4 and 20 quaternary ammonium groups, preferably between 2 and 5 quaternary ammonium groups, wherein said quaternary ammonium groups comprise —$CH_2CH(OH)CH_2N(CH_3)_3^+$, such as —$CH_2CH(OH)CH_2N(CH_3)_3Cl$, and optionally said CDs have one or more additional substitutions. Said CD may comprise between 2 and 4 quaternary ammonium groups, or may comprise 2 quaternary ammonium groups, 3 quaternary ammonium groups, or 4 quaternary ammonium groups, or 5 quaternary ammonium groups. It is to be understood that any pharmaceutically acceptable salt of said quaternary ammonium is included in the scope of the present disclosure.

L may have the structure:

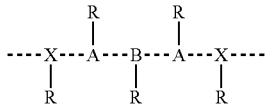

wherein each R is independently selected from H, X, SH, NH, $NH_2$, or OH, or may be absent;

the linkage of each CD to the linker is independently through an O, S, or N linked to a C2 or a C3 carbon thereof, or through an acetal attachment through two adjacent oxygens of the CD;

each X is a substituted or unsubstituted alkane, alkene, or alkyne;

each A is independently selected from a single, double, or triple covalent bond, S, N, NH, O, or a substituted or unsubstituted alkane, alkene, or alkyne; and B is a substituted or unsubstituted 5 or 6 membered ring, S, N, NH, NR, O, or absent.

The length of said linker may be between 2 and 7, between 3 and 6, between 4 and 7, between 4 and 6, between 4 and 5, or 4, or between 2 and 3.

Said linker may be an unsubstituted alkyl, such as unsubstituted butyl.

Said linker may be a substituted or unsubstituted butyl linker.

Said linker may comprise a triazole.

Said linker may comprise the structure:

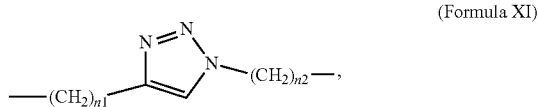

(Formula XI)

wherein n1 and n2 are each between 1 and 8 or 1 and 4, preferably wherein n1 is 1 and n2 is 3.

In exemplary embodiments, said linker L may be linked to an O2 position of each CD monomer when said linker comprises a triazole, e.g., having the structure Formula XI, wherein n1 and n2 may each be between 0 and 8, such as each between 1 and 4; preferably, the total length of said linker may be 8 or less, such as 8, 7, 6, 5, 4, 3, or any numerical range therein; and in a preferred embodiment, n1 is 1 and n2 is 3.

In exemplary embodiments, said linker L may be linked to an O2 position of each CD monomer, an O2 position of one CD monomer and an O3 position of the other CD monomer, or an O3 position of both CD monomers, when said linker comprises substituted or unsubstituted alkyl, preferably having a length of no more than 8 atoms, such as between 2 and 7, between 2 and 6, or between 4 and 7 or between 4 and 6 or between 4 and 5, or a length of 8, 7, 6, 5, 4, 3, or 2, or any numerical range therein; wherein preferably said linker is substituted or unsubstituted butyl, more preferably unsubstituted butyl.

Said linker may comprise a single attachment point to each CD monomer. Said linker may comprise a single attachment point to one CD monomer and multiple (two or more) attachment points to the other CD monomer. Said linker may comprise multiple attachment points (two or more each) to each CD monomer. Said linker may comprise any of the linkers depicted in FIG. 8D. It is to be understood that the depicted linkers include oxygen atoms at each end which form part of the cyclodextrins to which they are linked; such oxygen atoms are not considered to be part of the linker for purposes of determining its length. Also, in the case of linkers that connect to one or both cyclodextrin monomers in multiple locations, the linkages shown at the left connect to one monomer, and the linkages shown at the right connect to the other monomer.

In exemplary embodiments, the disclosure provides a CD dimer having the structure:

CD-L-CD wherein L is linked to the large (secondary) face of each CD molecule through a C2 carbon (in place of an $R^1$) and/or C3 carbon (in place of an $R^2$) of each CD subunit;

wherein CD has the structure of Formula X:

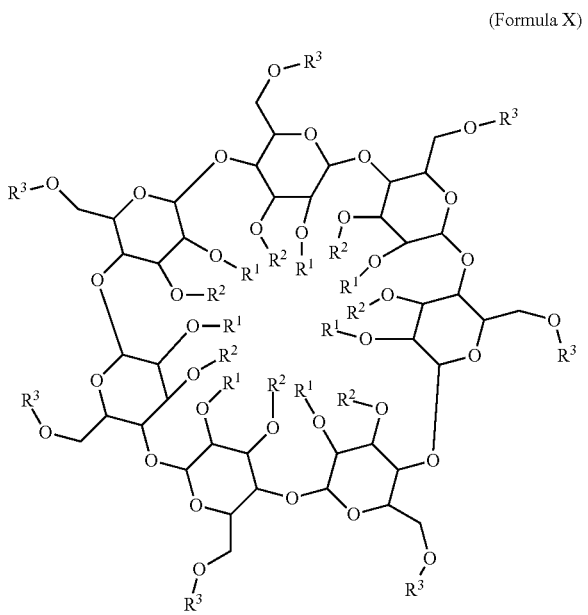

(Formula X)

wherein L is a triazole and has a length of no more than 8 atoms, wherein said no more than 8 atoms are preferably each C, N, O, or S;

the CDs substituted with between 0 and 28 groups, optionally 0 groups, or optionally said CDs have one or more substitutions.

Said linker may comprise the structure:

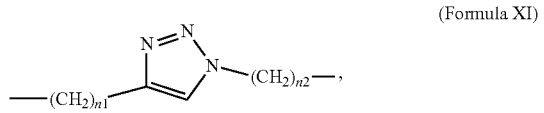

(Formula XI)

wherein n1 and n2 are each between 1 and 8 or 1 and 4, preferably wherein n1 is 1 and n2 is 3.

The length of said linker may be between 3 and 7, between 3 and 6, between 4 and 7, between 4 and 6, or between 5 and 6.

The length of said linker may be between 4 and 5.

Said cyclodextrin may be further substituted with (a) at least one methyl, hydroxypropyl, sulfobutyl, or succinyl group, and/or (b) at least one alkyl, lower alkyl, alkylene, alkenyl, alkynyl, alkoxy, alkoxyalkyl, alkoxyalkoxyalkyl, alkylcarbonyloxyalkyl, alkylcarbonyl, alkyl sulfonyl, alkylsulfonylalkyl, alkylamino, alkoxyamino, alkylsulfanyl, amino, alkylamino, dialkylamino, alkylaminoalkyl, dialkylaminoalkyl, aminoalkyl, aminoalkoxy, alkylsulfonylamido, aminocarbonyloxyalkyl, aminosulfonyl, alkylaminosulfonyl, dialkylaminosulfonyl, alkynylalkoxy, aryl, arylalkyl, aryl sulfonyl, aryloxy, aralkyloxy, cyanoalkyl, cycloalkyl, cycloalkenyl, cycloalkylalkyl, cycloalkylene, cycloalkylalkylene, heteroalkyl, heteroaryl, heteroarylalkyl, heteroarylsulfonyl, heteroaryloxy, heteroaralkyloxy, heterocyclylalkoxy, halogen, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carbamate, carboxy, sulfonamido, nitro, cyano, phenoxy, acetyl group ammonium, ammonia, azido, bromo, chloro, deoxy, glucosyl, iodo, sulfate, sulfuryl, nitrite, phosphate, phosphoryl, fatty acid such as palmitoyl group, monosaccharide, or disaccharide and/or (c) at least one methyl, hydroxypropyl, sulfobutyl, succinyl, maltosyl, carboxymethyl, quaternary ammonium (such as —$CH_2CH(OH)CH_2N(CH_3)_3^+$), glucosyl, palmitoyl, phosphate, phosphoryl, amino, azido, sulfate, sulfuryl, alkyl, ethyl, propyl, isopropyl, butyl, isobutyl, bromo, or chloro group.

The cyclodextrin dimer may have the structure according to any one of Formulae I-IX (FIGS. 3B-3J, respectively).

Each $R^1$, each $R^2$, and each $R^3$ may be independently selected from (a) methyl, H, hydroxypropyl, sulfobutyl ether, succinyl, succinyl-hydroxypropyl, quaternary ammonium, carboxymethyl, carboxymethyl-hydroxypropyl, hydroxyethyl, maltosyl, acetyl, carboxyethyl, sulfated, sulfopropyl, sodium phosphate, or glucosyl; and/or (b) hydrogen, alkyl, lower alkyl, alkylene, alkenyl, alkynyl, alkoxy, alkoxyalkyl, alkoxyalkoxyalkyl, alkylcarbonyloxyalkyl, alkylcarbonyl, alkyl sulfonyl, alkylsulfonylalkyl, alkylamino, alkoxyamino, alkylsulfanyl, amino, alkylamino, dialkylamino, alkylaminoalkyl, dialkylaminoalkyl, aminoalkyl, aminoalkoxy, alkylsulfonylamido, aminocarbonyloxyalkyl, aminosulfonyl, alkylaminosulfonyl, dialkylaminosulfonyl, alkynylalkoxy, aryl, arylalkyl, aryl sulfonyl, aryloxy, aralkyloxy, cyanoalkyl, cycloalkyl, cycloalkenyl, cycloalkylalkyl, cycloalkylene, cycloalkylalkylene, heteroalkyl, heteroaryl, heteroarylalkyl, heteroarylsulfonyl, heteroaryloxy, heteroaralkyloxy, heterocyclylalkoxy, halogen, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carbamate, carboxy, sulfonamido, nitro, cyano, phenoxy, or acetyl group.

L may be linked to a C2 carbon of each CD monomer, to a C3 carbon of each CD monomer, or to a C2 carbon of one CD monomer and a C3 of the other CD monomer. In the case of a linker having multiple attachment points to a single CD monomer, those may be linked to C2, C3, or a combination of C2 and C3 carbons of that monomer; a particular arrangement may be favored based on the reactions utilized in the formation thereof, the purification steps, and/or based on the structure of the linker.

Said cyclodextrin dimer may exhibit greater affinity for 7KC than cholesterol. Said greater affinity may be determined using the turbidity test disclosed herein.

Said cyclodextrin dimer may exhibit at least 1.1-fold, 1.5-fold, 2-fold, 3-fold, 4-fold, 5-fold, or 10-fold, stronger affinity for 7KC than cholesterol. Said cyclodextrin dimer may exhibit at least a 5%, 10%, 15%, 20%, 25%, 30%, 35%, 40%, 45%, or 50%, or greater, reduction in relative turbidity of 7KC than of cholesterol in the turbidity test.

In exemplary embodiments, the disclosure provides a composition comprising a mixture of cyclodextrin dimers as disclosed herein, wherein optionally the average degree of substitution may be between 2 and 10, such as between 2 and 8, such as between 3 and 7, or between 2 and 5. Said composition may comprise a mixture of CD dimers having a degree of substitution with hydroxypropyl, sulfobutyl, succinyl, or quaternary ammonium groups of between 2 and 5, such as about 2, about 3, about 4, or about 5 of said substituent. Said composition may comprise a mixture of CD dimers having a degree of substitution with methyl groups of between 2 and 10. Said degree of substitution may be measured by NMR. Said degree of substitution may be measured by mass spectrometry, such as MALDI.

In exemplary embodiments, the disclosure provides a composition comprising a mixture of cyclodextrin dimers as disclosed herein, e.g., according to Formulae I-III (FIGS. 3B-3D, respectively).

In exemplary embodiments, the disclosure provides a pharmaceutical composition comprising a cyclodextrin dimer or a composition thereof as disclosed herein and a pharmaceutically acceptable carrier. Said cyclodextrin dimer may be the only active ingredient in said composition. Said pharmaceutical composition may consist of or consist essentially of said cyclodextrin dimer and said pharmaceutically acceptable carrier.

In exemplary embodiments, the disclosure provides a therapeutic method comprising administration of an effective amount of a cyclodextrin dimer or composition thereof as disclosed herein to a subject in need thereof. The subject in need thereof may be suffering from harmful or toxic effects of 7KC.

In exemplary embodiments, the disclosure provides a method for reducing the amount of 7KC in a subject in need thereof comprising administration of an effective amount of a cyclodextrin dimer as disclosed herein to a subject in need thereof.

Said cyclodextrin dimer may be administered to said patient via parenteral (e.g., subcutaneous, intramuscular, or intravenous), topical, transdermal, oral, sublingual, or buccal administration, preferably, intravenously.

Said method may comprise administering to said patient between about 1 mg and 10 g, such as between 10 mg and 1 g, between 50 mg and 200 mg, or 100 mg of said cyclodextrin dimer. In exemplary embodiments, between 1 and 10 g of cyclodextrin dimer may be administered, such as about 2 g, about 3 g, about 4 g, or about 5 g. In exemplary embodiments, between 50 mg and 5 g of cyclodextrin dimer may be administered, such as between 100 mg and 2.5 g, between 100 mg and 2 g, between 250 mg and 2.5 g, e.g., about 1 g.

Said method may prevent, treat, and/or ameliorate the symptoms of one or more of atherosclerosis, arteriosclerosis, coronary atherosclerosis due to calcified coronary lesion, heart failure (all stages), Alzheimer's disease, Amyotrophic lateral sclerosis, Parkinson's disease, Huntington's disease, vascular dementia, multiple sclerosis, Smith-Lemli-Opitz Syndrome, infantile neuronal ceroid Lipofuscinosis, Lysosomal acid lipase deficiency, Cerebrotendinous xanthomatosi, X-linked adrenoleukodystrophy, Sickle cell disease, Niemann-Pick Type A disease, Niemann-Pick Type B disease, Niemann-Pick Type C disease, Gaucher's disease, Stargardt's disease, age-related Macular degeneration (dry type), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia, preferably, atherosclerosis.

Said method may further comprise administering a second therapy to said patient, wherein said second therapy may be administered concurrently or sequentially in either order.

Said second therapy may comprise one or more of an anti-cholesterol drug, such as a fibrate or statin, anti-platelet drug, anti-hypertension drug, or dietary supplement. Said statin may comprise ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), or ZOCOR® (simvastatin).

Said second therapy may comprise an anti-cholesterol drug and an anti-hypertension drug.

In exemplary embodiments, the disclosure provides a method of purification of oxysterols, comprising: contacting a composition comprising oxysterols with a cyclodextrin dimer as disclosed herein, thereby solubilizing said oxysterols in said cyclodextrin dimer; and recovering said cyclodextrin dimer and solubilized oxysterols. Said oxysterols comprise or consist of 7KC. Said method may further comprise measuring the concentration of 7KC in said solubilized oxysterols, thereby determining the relative concentration of 7KC in the composition. Said composition may comprise a patient sample. Said method may be used for the determination of 7KC concentration in a patient sample, which may be used in diagnosis and/or treatment planning.

In exemplary embodiments, the disclosure provides an in vitro method of removing oxysterols from a sample, comprising: contacting a sample comprising oxysterols with a cyclodextrin dimer as disclosed herein, thereby solubilizing said oxysterols in said cyclodextrin dimer; and separating said sample from said cyclodextrin dimer and solubilized sterols.

In exemplary embodiments, the disclosure provides a method of producing a reduced cholesterol product, comprising: contacting a product comprising cholesterol with a cyclodextrin dimer as disclosed herein, thereby solubilizing said cholesterols in said cyclodextrin dimer; and removing said cyclodextrin dimer and solubilized cholesterol from said product. Said product may be a food product, e.g., meat and/or dairy.

In another aspect, the disclosure provides a method of making a cyclodextrin dimer as described herein, such as a cyclodextrin dimer comprising an unsubstituted or substituted alkyl linker, comprising: (a) reacting β-cyclodextrin that is protected on the primary side with a dialkylating agent, thereby producing a primary-protected βCD dimer linked through the secondary face, and optionally purifying said primary protected βCD dimer; (b) deprotecting said primary protected βCD dimer, thereby producing a deprotected βCD dimer, and optionally purifying said deprotected βCD dimer; and (c) hydroxypropylating said deprotected βCD, thereby producing a cyclodextrin dimer, and optionally purifying said cyclodextrin dimer. Said β-cyclodextrin that is protected on the primary side may comprise heptakis (6-O-tert-butyldimethylsilyl)-O-cyclodextrin. Said dialkylating agent may comprise a dibromoalkane, optionally 1,4 dibromobutane. Step (a) may be performed in anhydrous conditions and/or with sodium hydride as a base. Said purification in step (a) may comprise direct phase chromatography with isocratic elution. Step (b) may be performed in tetrahydrofuran (THF) with tetrabutylammonium fluoride. Said purification in step (b) may comprise direct phase chromatography with isocratic elution. Step (c) may comprise reacting said deprotected βCD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium linking reagent such as glycidyltrimethylammonium chloride.

Step (c) may be performed in aqueous conditions, optionally comprising sodium hydroxide as a base. Step (c) may comprise one or more of ion exchange resin treatment, charcoal clarification and dialysis.

In another aspect, the disclosure provides a method of making a cyclodextrin dimer as described herein, such as a cyclodextrin dimer comprising a triazole linker, comprising: (a) reacting a 2-O-(n-azidoalkyl)-βCD and a 2-O-(n-alkyne)-βCD, thereby forming a βCD-triazole-βCD dimer having the structure βCD-alk1-triazole-alk2-βCD, and optionally (b) purifying said βCD-triazole-βCD dimer. Step (a) may be performed with a copper (I) catalyst, optionally of about 15 mM copper (I). Step (a) may be carried out in an aqueous solution. The aqueous solution may comprise dimethylformamide (DMF), optionally about 50% DMF (v/v). Step (b) may comprise chromatography. Said method may further comprise, prior to step (a) producing said 2-O-(n-azidoalkyl)-βCD by a method comprising: (1) reacting n-azido-1-bromo-alkane with a β-cyclodextrin, optionally with a catalytic amount of lithium iodide, thereby producing said 2-O-(n-azidoalkyl)-βCD; and (2) optionally purifying said 2-O-(n-azidoalkyl)-βCD. Step (2) may comprise chromatography. Said method may further comprise, prior to step (a) producing 2-O-(n-alkyne)-βCD by a method comprising: (i) reacting n-bromo-1-alkyne with a β-cyclodextrin, optionally with a catalytic amount of lithium iodide, thereby producing said 2-O-(n-alkyne)-βCD and (ii) optionally purifying said 2-O-(n-alkyne)-βCD. Step (2) may comprise silica gel chromatography. Step (1) may be carried out in dry DMSO. The reaction in step (1) may comprise lithium hydride. Said βCD-triazole-βCD dimer may comprise the structure:

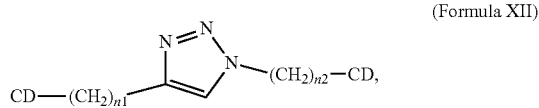

(Formula XII)

wherein n1 may be between 1 and 8 and/or n2 may be between 1 and 8, optionally n1 may be 1, 2, 3, or 4 and/or n2 may be 1, 2, 3, or 4, preferably wherein n1 is 1 and n2 is 3. The length of said triazole linker may be between 5 and 8. Said method may further comprise hydroxypropylating said βCD-triazole-βCD dimer, thereby producing a cyclodextrin dimer, and optionally purifying said cyclodextrin dimer. Step (c) may comprise reacting said βCD-triazole-βCD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium linking reagent such as glycidyltrimethylammonium chloride.

Step (c) may be performed in aqueous conditions, optionally comprising sodium hydroxide as a base. Said purification in step (c) may comprise one or more of ion exchange resin treatment, charcoal clarification, membrane filtration, and dialysis.

Embodiments of the invention provide compositions and methods for the treatment or prevention of atherosclerosis. 7KC is the most abundant non-enzymatically produced oxysterol in atherosclerotic plaques and is believed to contribute to the pathogenesis of atherosclerosis. Treatment with the CD (such as HPβCD or another CD of the present disclosure) dimers of this invention is expected to be beneficial for the prevention and/or reversal of atherosclerotic plaque formation.

Embodiments of the invention provide compositions and methods for the treatment or prevention of diseases and conditions in which 7KC has been implicated. These include, but are not limited to diseases of aging such as atherosclerosis, AMD, arteriosclerosis, coronary atherosclerosis due to calcified coronary lesion, heart failure (all stages), Alzheimer's disease, Parkinson's disease, vascular dementia, chronic obstructive pulmonary disease, non-alcoholic fatty liver disease, and/or hypercholesterolemia or dementia associated with hypercholesterolemia. Other sporadic and/or congenital diseases in which 7KC accumulation is also implicated include Huntington's disease, multiple sclerosis, Smith-Lemli-Opitz Syndrome, infantile neuronal ceroid lipofuscinosis, lysosomal acid lipase deficiency, Amyotrophic lateral sclerosis, cerebrotendinous xanthomatosi, X-linked adrenoleukodystrophy, sickle cell anemia, Niemann-Pick Type A disease, Niemann-Pick Type B disease, Niemann-Pick Type C disease, Gaucher's disease, Stargardt's disease, idiopathic pulmonary fibrosis, cystic fibrosis, liver damage, liver failure, non-alcoholic steatohepatitis, ulcerative colitis, Crohn's disease, and other irritable bowel syndromes.

In another exemplary embodiment, the disclosure provides a cyclodextrin dimer composition having a degree of substitution of between 1 and 40, such as between 1 and 28 or between 4 and 20, preferably between 2 and 15, with a substituent selected from methyl, hydroxypropyl, sulfobutyl, succinyl, quaternary ammonium such as —CH$_2$CH(OH)CH$_2$N(CH$_3$)$_3^+$, alkyl, lower alkyl, alkylene, alkenyl, alkynyl, alkoxy, alkoxyalkyl, alkoxyalkoxyalkyl, alkylcarbonyloxyalkyl, alkylcarbonyl, alkyl sulfonyl, alkylsulfonylalkyl, alkylamino, alkoxyamino, alkylsulfanyl, amino, alkylamino, dialkylamino, alkylaminoalkyl, dialkylaminoalkyl, aminoalkyl, aminoalkoxy, alkylsulfonylamido, aminocarbonyloxyalkyl, aminosulfonyl, ammonium, ammonia, alkylaminosulfonyl, dialkylaminosulfonyl, alkynylalkoxy, aryl, arylalkyl, arylsulfonyl, aryloxy, aralkyloxy, azido, bromo, chloro, cyanoalkyl, cycloalkyl, cycloalkenyl, cycloalkylalkyl, cycloalkylene, cycloalkylalkylene, deoxy, glucosyl, heteroalkyl, heteroaryl, heteroarylalkyl, heteroarylsulfonyl, heteroaryloxy, heteroaralkyloxy, heterocyclylalkoxy, halogen, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, iodo, ureido, carbamate, carboxy, sulfate, sulfuryl, sulfonamido, nitro, nitrite, cyano, phosphate, phosphoryl, phenoxy, acetyl group, fatty acid such as palmitoyl group, monosaccharide, or disaccharide, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said substituent may be carboxymethyl or maltosyl. Said substituent is preferably methyl, hydroxypropyl, sulfobutyl, succinyl, quaternary ammonium (such as —CH$_2$CH(OH)CH$_2$N(CH$_3$)$_3^+$). Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, with a substituent selected from methyl, hydroxypropyl, sulfobutyl, succinyl, maltosyl, carboxymethyl, quaternary ammonium (such as —CH$_2$CH(OH)CH$_2$N(CH$_3$)$_3^+$), glucosyl, palmitoyl, phosphate, phosphoryl, amino, azido, sulfate, sulfuryl, alkyl, ethyl, propyl, isopropyl, butyl, isobutyl, bromo, or chloro, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, with a substituent selected from methyl, hydroxypropyl, sulfobutyl, succinyl, maltosyl, carboxymethyl, or quaternary ammonium such as —CH$_2$CH(OH)CH$_2$N(CH$_3$)$_3^+$, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, more preferably between 2 and 5, and even more preferably between 2 and 4, with a hydroxypropyl substituent, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, more preferably between 2 and 10, with a methyl substituent, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, more preferably between 2 and 5, and even more preferably between 2 and 4, with a sulfobutyl substituent, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, more preferably between 2 and 5, and even more preferably between 2 and 4, with a succinyl substituent, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 1 and 40, such as between 1 and 28 or between 4 and 20, preferably between 2 and 15, more preferably between 2 and 5, and even more preferably between 2 and 4, with a quaternary ammonium substituent, preferably —CH$_2$CH(OH)CH$_2$N(CH$_3$)$_3^+$, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X having said substituent at one or more of R1, R2, and/or R3, wherein L has a length of no more than 8 atoms, wherein said no more than 8 atoms are preferably each C, N, O, or S. Said degree of substitution may be determined by NMR. Said degree of substitution may be determined by mass spectrometry, such as MALDI.

In another exemplary embodiment, the disclosure provides a cyclodextrin dimer composition having a degree of substitution of between 0 and 40, the composition comprising a cyclodextrin dimer of the structure CD-L-CD, wherein L is linked to the large (secondary) face of each CD molecule through a C2 carbon (in place of an R1) and/or C3 carbon (in place of an R2) of each CD subunit; wherein each CD has the structure of Formula X optionally substituted with one or more substituents, wherein L has a length of no more than 8 atoms, wherein said no more than 8 atoms are preferably each C, N, O, or S. Said cyclodextrin dimer composition may be used in the synthesis of a cyclodextrin dimer composition substituted with one or more substituents. Said degree of substitution may be determined by NMR. Said degree of substitution may be determined by mass spectrometry, such as MALDI.

Said linker L may have the structure:

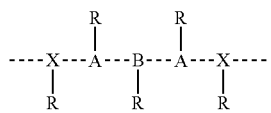

wherein each R is independently selected from H, X, SH, NH, NH$_2$, or OH, or is absent;
the linkage of each CD to the linker is independently through an O, S, or N linked to a C2 or a C3 carbon thereof, or through an acetal attachment through two adjacent oxygens of the CD;
each X is a substituted or unsubstituted alkane, alkene, or alkyne;
each A is independently selected from a single, double, or triple covalent bond, S, N, NH, O, or a substituted or unsubstituted alkane, alkene, or alkyne; and
B is a substituted or unsubstituted 5 or 6 membered ring, S, N, NH, NR, O, or absent.

The length of said linker may be between 2 and 7. The length of said linker may be between 3 and 6. The length of said linker may be 2 or 3. The length of said linker may be between 4 and 7. The length of said linker may be between 4 and 6. The length of said linker may be between 4 and 5. The length of said linker may be 4.

Said linker may be a substituted or unsubstituted alkyl, such as an unsubstituted alkyl, e.g., unsubstituted butyl. Said linker may comprise a triazole.

Said linker may comprise the structure:

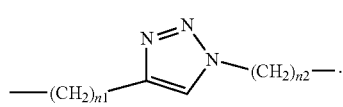
(Formula XI)

n1 and n2 may each be between 0 and 8, such as each between 1 and 4. Preferably, the total length of said linker may be 8 or less, such as 8, 7, 6, 5, 4 or any numerical range therein. In a preferred embodiment, n1 is 1 and n2 is 3.

In exemplary embodiments, said linker L may be linked to an O2 position of each CD monomer when said linker comprises a triazole, e.g., having the structure Formula XI, wherein n1 and n2 may each be between 0 and 8, such as each between 1 and 4; preferably, the total length of said linker may be 8 or less, such as 8, 7, 6, 5, 4 or any numerical range therein; and in a preferred embodiment, n1 is 1 and n2 is 3.

In exemplary embodiments, said linker L may be linked to an O2 position of each CD monomer, an O2 position of one CD monomer and an O3 position of the other CD monomer, or an O3 position of both CD monomers, when said linker comprises substituted or unsubstituted alkyl, preferably having a length of no more than 8 atoms, such as between 2 and 7, between 2 and 6, or between 4 and 7 or between 4 and 6 or between 4 and 5 or a length of 8, 7, 6, 5, 4, 3, or 2, or any numerical range therein; wherein preferably said linker is substituted or unsubstituted butyl, more preferably unsubstituted butyl.

Said linker may comprise any of the linkers depicted in FIG. 8D, wherein the depicted oxygen atoms at each end of each linker form part of the cyclodextrin monomers to which the linker is linked.

Said cyclodextrin dimer composition may comprise further substitution of said cyclodextrin dimer with (a) at least one methyl, hydroxypropyl, sulfobutyl, succinyl, or quaternary ammonium group such as —CH$_2$CH(OH)CH$_2$N(CH$_3$)$_3$$^+$, and/or (b) at least one alkyl, lower alkyl, alkylene, alkenyl, alkynyl, alkoxy, alkoxyalkyl, alkoxyalkoxyalkyl, alkylcarbonyloxyalkyl, alkylcarbonyl, alkyl sulfonyl, alkylsulfonylalkyl, alkylamino, alkoxyamino, alkylsulfanyl, amino, alkylamino, dialkylamino, alkylaminoalkyl, dialkylaminoalkyl, aminoalkyl, aminoalkoxy, alkylsulfonylamido, aminocarbonyloxyalkyl, aminosulfonyl, alkylaminosulfonyl, dialkylaminosulfonyl, alkynylalkoxy, aryl, arylalkyl, aryl sulfonyl, aryloxy, aralkyloxy, cyanoalkyl, cycloalkyl, cycloalkenyl, cycloalkylalkyl, cycloalkylene, cycloalkylalkylene, heteroalkyl, heteroaryl, heteroarylalkyl, heteroarylsulfonyl, heteroaryloxy, heteroaralkyloxy, heterocyclylalkoxy, halogen, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carbamate, carboxy, sulfonamido, nitro, cyano, phenoxy, acetyl group, ammonium, ammonia, azido, bromo, chloro, deoxy, glucosyl, iodo, sulfate, sulfuryl, nitrite, phosphate, phosphoryl, fatty acid such as palmitoyl group, monosaccharide, or disaccharide and/or (c) at least one methyl, hydroxypropyl, sulfobutyl, succinyl, maltosyl, carboxymethyl, quaternary ammonium (such as —CH$_2$CH(OH)CH$_2$N(CH$_3$)$_3$$^+$), glucosyl, palmitoyl, phosphate, phosphoryl, amino, azido, sulfate, sulfuryl, alkyl, ethyl, propyl, isopropyl, butyl, isobutyl, bromo, chloro group.

Said cyclodextrin dimer composition may comprise a cyclodextrin dimer having the structure according to any one of Formulae I-IX (FIGS. 3B-3J, respectively).

Each R1, each R2, and each R3 not otherwise specified may be independently selected from (a) methyl, H, hydroxypropyl, sulfobutyl ether, succinyl, succinyl-hydroxypropyl, quaternary ammonium such as —CH$_2$CH(OH)CH$_2$N(CH$_3$)$_3$$^+$, carboxymethyl, carboxymethyl-hydroxypropyl, hydroxyethyl, maltosyl, acetyl, carboxyethyl, sulfated, sulfopropyl, sodium phosphate, or glucosyl; and/or (b) hydrogen, alkyl, lower alkyl, alkylene, alkenyl, alkynyl, alkoxy, alkoxyalkyl, alkoxyalkoxyalkyl, alkylcarbonyloxyalkyl, alkylcarbonyl, alkylsulfonyl, alkylsulfonylalkyl, alkylamino, alkoxyamino, alkylsulfanyl, amino, alkylamino, dialkylamino, alkylaminoalkyl, dialkylaminoalkyl, aminoalkyl, aminoalkoxy, alkylsulfonylamido, aminocarbonyloxyalkyl, aminosulfonyl, alkylaminosulfonyl, dialkylaminosulfonyl, alkynylalkoxy, aryl, arylalkyl, arylsulfonyl, aryloxy, aralkyloxy, cyanoalkyl, cycloalkyl, cycloalkenyl, cycloalkylalkyl, cycloalkylene, cycloalkylalkylene, heteroalkyl, heteroaryl, heteroarylalkyl, heteroarylsulfonyl, heteroaryloxy, heteroaralkyloxy, heterocyclylalkoxy, halogen, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carbamate, carboxy, sulfonamido, nitro, cyano, phenoxy, or acetyl group.

Said linker L may be linked to a C2 carbon of each CD monomer. Said linker L may be linked to a C3 carbon of each CD monomer. Said linker L may be linked to a C2 carbon of one CD monomer and a C3 of the other CD monomer.

Said cyclodextrin dimer composition may exhibit greater affinity for 7KC than cholesterol, wherein optionally said greater affinity is determined by a turbidity test.

Said cyclodextrin dimer composition may exhibit at least 1.1-fold, 1.5-fold, 2-fold, 3-fold, 4-fold, 5-fold, or 10-fold, stronger affinity for 7KC than cholesterol. Said cyclodextrin dimer may exhibit at least a 5%, 10%, 15%, 20%, 25%, 30%, 35%, 40%, 45%, or 50%, or greater, reduction in relative turbidity of 7KC than of cholesterol in the turbidity test.

Said degree of substitution may be 2. Said degree of substitution may be 3. Said degree of substitution may be 4. Said degree of substitution may be 5. Said degree of substitution may be 6. Said degree of substitution may be 7. Said degree of substitution may be 8. Said degree of substitution may be 9. Said degree of substitution may be 10.

Said cyclodextrin dimer composition may comprise a mixture of cyclodextrin dimer molecules individually having different numbers of substituents and/or different linker attachment points, wherein the average degree of substitution of the composition is as specified.

In another aspect, the disclosure provides a pharmaceutical composition comprising a cyclodextrin dimer composition as disclosed herein and a pharmaceutically acceptable carrier. Said pharmaceutical composition may be suitable for administration to a subject, e.g., parenteral (e.g., subcutaneous, intramuscular, or intravenous), topical, transdermal, oral, sublingual, or buccal administration, preferably intravenous or subcutaneous administration, more preferably intravenous administration. Said cyclodextrin dimer composition may be the only active ingredient in said composition. Said pharmaceutical composition may consist of or consist essentially of said cyclodextrin dimer and said pharmaceutically acceptable carrier.

In another aspect, the disclosure provides a therapeutic method comprising administration of an effective amount of a cyclodextrin dimer composition as disclosed herein to a subject in need thereof. Said subject may be suffering from harmful or toxic effects of 7KC or a condition associated with harmful or toxic effects of 7KC.

In another aspect, the disclosure provides a method for reducing the amount of 7KC in a subject in need thereof comprising administration of an effective amount of a cyclodextrin dimer composition as disclosed herein or pharmaceutical composition comprising a cyclodextrin dimer composition as disclosed herein to said subject.

Said cyclodextrin dimer composition may be administered to said subject via parenteral (e.g., subcutaneous, intramuscular, or intravenous), topical, transdermal, oral, sublingual, or buccal administration, preferably intravenous administration.

Said method may comprise administering to said subject (a) between about 1 mg and 20 g, such as between 10 mg and 1 g, between 50 mg and 200 mg, or 100 mg of said cyclodextrin dimer composition to said subject, or (b) between 1 and 10 g of said cyclodextrin dimer composition, such as about 2 g, about 3 g, about 4 g, or about 5 g, or (c) between 50 mg and 5 g of said cyclodextrin dimer composition, such as between 100 mg and 2.5 g, between 100 mg and 2 g, between 250 mg and 2.5 g.

Said method may be used to prevent, treat, or ameliorate the symptoms of one or more of atherosclerosis/coronary artery disease, arteriosclerosis, coronary atherosclerosis due to calcified coronary lesion, heart failure (all stages), Alzheimer's disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosi, X-linked adrenoleukodystrophy, sickle cell disease, Niemann-Pick Type A disease, Niemann-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy. Said method may comprise administering a second therapy to said subject, wherein said second therapy is administered concurrently or sequentially in either order.

Said method may be for the prevention, treatment, or ameliorating the symptoms of atherosclerosis. Said cyclodextrin dimer composition may be administered in combination with another therapy for the treatment or prevention of atherosclerosis, such as an anti-cholesterol drug, anti-hypertension drug, anti-platelet drug, dietary supplement, or surgical or behavioral intervention, including but not limited to those described herein. Said anti-cholesterol drug, may comprise a fibrate or statin, anti-platelet drug, anti-hypertension drug, or dietary supplement. Said statin may comprise ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), or ZOCOR® (simvastatin).

Said method may be for the prevention, treatment, or ameliorating the symptoms of dry age-related macular degeneration. Said method may be for the prevention, treatment, or ameliorating the symptoms of Stargardt's disease. Said cyclodextrin dimer composition may be administered in combination with another therapy for the treatment or prevention of dry AMD or Stargardt's Disease, such as LBS-008 (Belite Bio) (a nonretinoid antagonist of retinol binding protein 4), AREDS supplement formula comprising vitamins C and E, beta-carotene, zinc, and copper, AREDS2 supplement formula comprising a supplement formula that has vitamins C and E, zinc, copper, lutein, zeaxanthin, and omega-3 fatty acids, or combinations thereof.

Said method may be for the prevention, treatment, or ameliorating the symptoms of Niemann-Pick Disease. Said cyclodextrin dimer composition may be administered in combination with another therapy for the treatment or prevention of Niemann-Pick Disease, such as one or more of miglustat (ZAVESCA®), HPβCD (TRAPPSOL CYCLO, VTS-270), and physical therapy.

Said method may be for the prevention, treatment, or ameliorating the symptoms of Alzheimer's Disease. Said cyclodextrin dimer composition may be administered in combination with another therapy for the treatment or prevention of Alzheimer's Disease, such as cholinesterase inhibitors (ARICEPT®, EXELON®, RAZADYNE®) and memantine (NAMENDA®) or a combination thereof.

Said method may be for the prevention, treatment, or ameliorating the symptoms of heart failure. Said cyclodextrin dimer composition may be administered in combination with another therapy for the treatment or prevention of heart failure, such as one or more aldosterone antagonists, ACE inhibitors, ARBs (angiotensin II receptor blockers), ARNIs (angiotensin receptor-neprilysin inhibitors), beta-blockers, blood vessel dilators, calcium channel blockers, digoxin, diuretics, heart pump medications, potassium, magnesium, selective sinus node inhibitors, or combinations thereof.

In another aspect, the disclosure provides a method of making a cyclodextrin dimer composition as described herein, such as a cyclodextrin dimer composition comprising an unsubstituted or substituted alkyl linker, comprising: (a) reacting β-cyclodextrin that is protected on the primary side with a dialkylating agent, thereby producing a primary-protected βCD dimer linked through the secondary face, and optionally purifying said primary protected βCD dimer; (b) deprotecting said primary protected βCD dimer, thereby producing a deprotected βCD dimer, and optionally purifying said deprotected βCD dimer; and (c) hydroxypropylating said deprotected βCD, thereby producing a cyclodextrin dimer composition, and optionally purifying said cyclodextrin dimer composition. Said β-cyclodextrin that is protected on the primary side may comprise heptakis(6-O-tert-butyldimethylsilyl)-β-cyclodextrin. Said dialkylating agent may comprise a dibromoalkane, optionally 1,4 dibromobutane. Step (a) may be performed in anhydrous conditions and/or with sodium hydride as a base. Said purification in step (a) may comprise direct phase chromatography with isocratic elution. Step (b) may be performed in tetrahydrofuran (THF) with tetrabutylammonium fluoride. Said purification in step (b) may comprise direct phase chromatography with isocratic elution. Step (c) may comprise reacting said deprotected βCD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium linking reagent such as glycidyltrimethylammonium chloride. Said cyclodextrin dimer composition may be a cyclodextrin dimer composition as disclosed herein. Said cyclodextrin dimer composition may have a degree of substitution with a substituent of between 1 and 40, such as between 1 and 28 or between 4 and 20, preferably between 2 and 15, more preferably between 2 and 5 or between 2 and 10.

Step (c) may be performed in aqueous conditions, optionally comprising sodium hydroxide as a base. Step (c) may comprise one or more of ion exchange resin treatment, charcoal clarification and dialysis.

In another aspect, the disclosure provides a method of making a cyclodextrin dimer composition as described herein, such as a cyclodextrin dimer composition comprising a triazole linker, comprising: (a) reacting a 2-O-(n-azidoalkyl)-βCD and a 2-O-(n-alkyne)-βCD, thereby forming a βCD-triazole-βCD dimer having the structure βCD-alk1-triazole-alk2-βCD, and optionally (b) purifying said βCD-triazole-βCD dimer. Step (a) may be performed with a copper (I) catalyst, optionally of about 15 mM copper (I). Step (a) may be carried out in an aqueous solution. The aqueous solution may comprise dimethylformamide (DMF), optionally about 50% DMF (v/v). Step (b) may comprise chromatography. Said method may further comprise, prior to step (a) producing said 2-O-(n-azidoalkyl)-βCD by a method comprising: (1) reacting n-azido-1-bromo-alkane with a β-cyclodextrin, optionally with a catalytic amount of lithium iodide, thereby producing said 2-O-(n-azidoalkyl)-βCD; and (2) optionally purifying said 2-O-(n-azidoalkyl)-βCD. Step (2) may comprise chromatography. Said method may further comprise, prior to step (a) producing 2-O-(n-alkyne)-βCD by a method comprising: (i) reacting n-bromo-1-alkyne with a β-cyclodextrin, optionally with a catalytic amount of lithium iodide, thereby producing said 2—O-(n-alkyne)-βCD and (ii) optionally purifying said 2-O-(n-alkyne)-βCD. Step (2) may comprise silica gel chromatography. Step (1) may be carried out in dry DMSO. The reaction in step (1) may comprise lithium hydride. Said βCD-triazole-βCD dimer composition may comprise the structure:

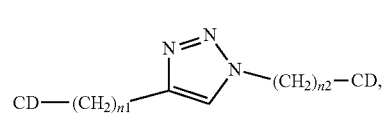

(Formula XII)

wherein n1 may be between 1 and 8 and/or n2 may be between 1 and 8, optionally n1 may be 1, 2, 3, or 4 and/or n2 may be 1, 2, 3, or 4, preferably wherein n1 is 1 and n2 is 3. The length of said triazole linker may be between 5 and 8. Said method may further comprise hydroxypropylating said βCD-triazole-βCD dimer composition, thereby producing a cyclodextrin dimer composition, and optionally purifying said cyclodextrin dimer composition. Step (c) may comprise reacting said βCD-triazole-βCD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium linking reagent such as glycidyltrimethylammonium chloride. Said cyclodextrin dimer composition may be a cyclodextrin dimer composition as disclosed herein. Said cyclodextrin dimer composition may have a degree of substitution with a substituent of between 1 and 40, such as between 1 and 28 or between 4 and 20, preferably between 2 and 15, more preferably between 2 and 5 or between 2 and 10.

Step (c) may be performed in aqueous conditions, optionally comprising sodium hydroxide as a base. Said purification in step (c) may comprise one or more of ion exchange resin treatment, charcoal clarification, membrane filtration, and dialysis.

In another aspect, the disclosure provides a pharmaceutical composition comprising said CD (such as HPβCD or another CD of the present disclosure) dimer.

In another aspect, the disclosure provides pharmaceutical compositions comprising a cyclodextrin dimer as disclosed herein and a hydrophobic drug. Said hydrophobic drug may comprise a hormone or sterol, such as estrogen, an estrogen analog, etc. Said cyclodextrin dimer may be present in an amount effective to solubilize said hydrophobic drug.

The phrase "pharmaceutically acceptable" is used herein to refer to those compounds, materials, compositions, and/or dosage forms that are, within the scope of sound medical judgment, suitable for entering a living organism or living biological tissue, preferably without significant toxicity, irritation, or allergic response. The present invention includes methods which comprise administering a cyclodextrin dimer to a patient, wherein the cyclodextrin dimer is contained within a pharmaceutical composition. The pharmaceutical compositions of the invention are formulated with pharmaceutically acceptable carriers, excipients, and other agents that provide suitable transfer, delivery, tolerance, and the like. A multitude of appropriate formulations can be found in the formulary known to pharmaceutical chemists, such as Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also (Powell [et al.], *J. Pharm. Sci. Technol.*, 52:238-311, (1998)).

The phrase "pharmaceutically acceptable carrier," as used herein, generally refers to a pharmaceutically acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body. Each carrier must be "acceptable" in the sense of being compatible with other ingredients of the formulation and not injurious to the patient. Examples of suitable aqueous and non-aqueous carriers that may be employed in the pharmaceutical compositions of the invention include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

Other examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition. Some examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Pharmaceutical formulations of the present invention may be prepared by any of the methods known in the pharmaceutical arts. The amount of active ingredient (i.e., CD dimer such as HPβCD dimer or another CD dimer of the present disclosure) that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. The amount of active compound may be in the range of about 0.1 to 99.9 percent, more typically, about 80 to 99.9 percent, and more typically, about 99 percent. The amount of active compound may be in the range of about 0.1 to 99 percent, more typically, about 5 to 70 percent, and more typically, about 10 to 30 percent. In an exemplary embodiment, the dosage form is provided for intravenous administration in an aqueous solution having a concentration of between 0.5% and 0.001%, such as between 0.12% and 0.0105%, e.g., about 0.01% (W/V). In an exemplary embodiment, the dosage form is provided for intravenous administration in an aqueous solution having a concentration of between 2.5% and 0.25%, such as between 2% and 0.5%, e.g., about 1% (W/V). In an exemplary embodiment, the dosage form provides for intravenous administration of up to 500 mLs of a 1% solution (W/V), resulting in a dosage of up to 5 grams.

In exemplary embodiments, the cyclodextrin dimer may be administered to a patient in an amount of between 1 mg and 10 g, such as between 10 mg and 1 g, between 100 mg and 500 mg. In exemplary embodiments, about 400 mg of cyclodextrin dimer may be administered. In exemplary embodiments, between 1 and 10 g of cyclodextrin dimer may be administered, such as about 2 g, about 3 g, about 4 g, or about 5 g. In exemplary embodiments, between 50 mg and 5 g of cyclodextrin dimer may be administered, such as between 100 mg and 2.5 g, between 100 mg and 2 g, between 250 mg and 2.5 g, e.g., about 1 g.

Exemplary embodiments provide a single dosage form, which may comprise the foregoing amount of cyclodextrin dimer, which may be packaged for individual administration, optionally further comprising a pharmaceutically acceptable carrier or excipient. The total amount of said cyclodextrin dimer in said single dosage form may be as provided above, e.g., between 1 mg and 10 g, such as between 10 mg and 1 g, between 100 mg and 500 mg, between 1 and 10 g of cyclodextrin dimer, between 50 mg and 5 g, between 100 mg and 2.5 g, between 100 mg and 2 g, between 250 mg and 2.5 g, such as about 1 g, 2 g, about 3 g, about 4 g, or about 5 g.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. The active compound may also be administered as a bolus, electuary, or paste.

Methods of preparing these formulations or compositions generally include the step of admixing a compound of the present invention with the carrier, and optionally, one or more auxiliary agents. In the case of a solid dosage form (e.g., capsules, tablets, pills, powders, granules, trouches, and the like), the active compound can be admixed with a finely divided solid carrier, and typically, shaped, such as by pelletizing, tableting, granulating, powderizing, or coating. Generally, the solid carrier may include, for example, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more auxiliary ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent.

The tablets, and other solid dosage forms of the active agent, such as capsules, pills and granules, may optionally be scored or prepared with coatings and shells, such as enteric coatings and other coatings well known in the pharmaceutical-formulating art. The dosage form may also be formulated so as to provide slow or controlled release of the active ingredient therein using, for example, hydroxypropyl methyl cellulose in varying proportions to provide the desired release profile, other polymer matrices, liposomes and/or microspheres. The dosage form may alternatively be formulated for rapid release, e.g., freeze-dried.

Generally, the dosage form is required to be sterile. For this purpose, the dosage form may be sterilized by, for example, filtration through a bacteria-retaining filter, or by incorporating sterilizing agents in the form of sterile solid compositions which can be dissolved in sterile water, or some other sterile injectable medium immediately before use. The pharmaceutical compositions may also contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms are typically a pharmaceutically acceptable emulsion, microemulsion, solution, suspension, syrup, or elixir of the active agent. In addition to the active ingredient, the liquid dosage form may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Dosage forms specifically intended for topical or transdermal administration can be in the form of, for example, a powder, spray, ointment, paste, cream, lotion, gel, solution, or patch. Ophthalmic formulations, such as eye ointments, powders, solutions, and the like, are also contemplated herein. The active compound may be mixed under sterile conditions with a pharmaceutically acceptable carrier, and with any preservatives, buffers, or propellants that may be required. The topical or transdermal dosage form may contain, in addition to an active compound of this invention, one or more excipients, such as those selected from animal and vegetable fats, oils, waxes, paraffins, starch, tragacanth, cellulose derivatives, polyethylene glycols, silicones, bentonites, silicic acid, talc and zinc oxide, and mixtures thereof. Sprays may also contain customary propellants, such as chlorofluorohydrocarbons and volatile unsubstituted hydrocarbons, such as butane and propane.

For purposes of this invention, transdermal patches may provide the advantage of permitting controlled delivery of a compound of the present invention into the body. Such dosage forms can be made by dissolving or dispersing the compound in a suitable medium. Absorption enhancers can also be included to increase the flux of the compound across the skin. The rate of such flux can be controlled by either providing a rate-controlling membrane or dispersing the compound in a polymer matrix or gel.

Pharmaceutical compositions of this invention suitable for parenteral administration generally include one or more compounds of the invention in combination with one or more pharmaceutically acceptable sterile isotonic aqueous or nonaqueous solutions, dispersions, suspensions or emulsions, or sterile powders that may be reconstituted into sterile injectable solutions or dispersions prior to use, which may contain sugars, alcohols, antioxidants, buffers, bacteriostats, or solutes that render the formulation isotonic with the blood of the intended recipient.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms can be made by forming microencapsule matrices of the active compound in a biodegradable polymer, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions that are compatible with body tissue.

The pharmaceutical composition may also be in the form of a microemulsion. In the form of a microemulsion, bioavailability of the active agent may be improved. Reference is made to (Dorunoo [et al.], *Drug Development and Industrial Pharmacy*, 17(12):1685-1713 (1991)) and (Sheen [et al.], *J. Pharm. Sci.*, 80(7):712-714, (1991)), the contents of which are herein incorporated by reference in their entirety.

The pharmaceutical composition may also contain micelles formed from a compound of the present invention and at least one amphiphilic carrier, in which the micelles have an average diameter of less than about 100 nm. In some embodiments, the micelles have an average diameter less than about 50 nm, or an average diameter less than about 30 nm, or an average diameter less than about 20 nm.

While any suitable amphiphilic carrier is considered herein, the amphiphilic carrier is generally one that has been granted Generally-Recognized-as-Safe (GRAS) status, and that can both solubilize the compound of the present invention and microemulsify it at a later stage when the solution comes into a contact with a complex water phase (such as one found in the living biological tissue). Usually, amphiphilic ingredients that satisfy these requirements have HLB (hydrophilic to lipophilic balance) values of 2-20, and their structures contain straight chain aliphatic radicals in the range of C-6 to C-20. Some examples of amphiphilic agents include polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series). Commercially available amphiphilic carriers are particularly contemplated, including the Gelucire®-series, Labrafil®, Labrasol®, or Lauroglycol®, PEG-mono-oleate, PEG-di-oleate, PEG-mono-laurate and di-laurate, Lecithin, Polysorbate 80.

The CD (such as HPβCD or another CD of the present disclosure) dimer may be administered by any suitable means. Preferred routes of administration include parenteral (e.g., subcutaneous, intramuscular, or intravenous), topical, transdermal, oral, sublingual, or buccal. Said administration may be ocular (e.g., in the form of an eyedrop), intravitreous, retro-orbital, subretinal, subscleral, which may be preferred in case of ocular disorders, such as AMD.

The CD (such as HPβCD or another CD of the present disclosure) dimer may be administered to a subject, or may be used in vitro, e.g., applied to a cell or tissue that have been removed from an animal. Said cell or tissue may then be introduced into a subject, whether the subject from which it was removed or another individual, preferably of the same species.

The subject (i.e., patient) receiving the treatment is typically an animal, generally a mammal, preferably a human. The subject may be a non-human animal, which includes all vertebrates, e.g., mammals and non-mammals, such as non-human primates, sheep, dogs, cats, cows, horses, chickens, amphibians, and reptiles. In some embodiments, the subject is livestock, such as cattle, swine, sheep, poultry, and horses, or companion animals, such as dogs and cats. The subject may be genetically male or female. The subject may be any age, such as elderly (generally, at least or above 60, 70, or 80 years of age), elderly-to-adult transition age subjects, adults, adult-to-pre-adult transition age subjects, and pre-adults, including adolescents (e.g., 13 and up to 16, 17, 18, or 19 years of age), children (generally, under 13 or before the onset of puberty), and infants. The subject can also be of any ethnic population or genotype. Some examples of human ethnic populations include Caucasians, Asians, Hispanics, Africans, African Americans, Native Americans, Semites, and Pacific Islanders. The methods of the invention may be more appropriate for some ethnic populations, such as Caucasians, especially northern European populations, and Asian populations.

The present disclosure includes further substitutions of the dimeric CDs (such as HPβCDs or another CD of the present disclosure) described herein. Chemical modification may be performed before or after dimerization. Chemical modification of cyclodextrins can be made directly on the native beta cyclodextrin rings by reacting a chemical reagent (nucleophile or electrophile) with a properly functionalized cyclodextrin (Adair-Kirk [et al.], *Nat. Med.*, 14(10):1024-5, (2008)); (Khan, [et al.], *Chem. Rev.*, 98(5):1977-1996, (1998)). To date, more than 1,500 cyclodextrin derivatives have been made by chemical modification of native cyclodextrins. Cyclodextrins can also be prepared by de novo synthesis, starting with glucopyranose-linked oligopyranosides. Such a synthesis can be accomplished by using various chemical reagents or biological enzymes, such as cyclodextrin transglycosylase. An overview of chemically modified cyclodextrins as drug carriers in drug delivery systems is described, for example, in (Stella, [et al.], *Toxicol. Pathol.*, 36(1):30-42, (2008)), the disclosure of which is herein incorporated by reference in its entirety. U.S. Pat. Nos. 3,453,259 and 3,459,731 describe electroneutral cyclodextrins, the disclosures of which are herein incorporated by reference in its entirety. Other derivatives include cyclodextrins with cationic properties, as disclosed in U.S. Pat. No. 3,453,257; insoluble crosslinked cyclodextrins, as disclosed in U.S. Pat. No. 3,420,788; and cyclodextrins with anionic properties, as disclosed in U.S. Pat. No. 3,426,011, the disclosures of which are all hereby incorporated by reference in their entirety. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin, as disclosed, for example, in U.S. Pat. No. 3,426,011. Sulfoalkyl ether cyclodextrin derivatives have also been described, e.g., in U.S. Pat. No. 5,134,127, the disclosure of which is hereby incorporated by reference in its entirety. In some embodiments, the cyclic oligosaccharide can have two or more of the monosaccharide units replaced by triazole rings, which can be synthetized by the Azide-alkyne Huisgen cycloaddition reaction ((Bodine, [et al.], *J. Am. Chem. Soc.*, 126(6):1638-9, (2004)).

The dimeric cyclodextrins of the disclosure are joined by a linker. Methods that may be used to join the CD subunits to a linker are described in the working examples. Additional methods of joining CD subunits to a linker are known in the art. (Georgeta [et al.], *J. Bioact. Compat. Pol.*, 16:39-48. (2001)), (Liu [et al.], *Acc. Chem. Res.*, 39:681-691. (2006)), (Ozmen [et al.], *J. Mol. Catal. B-Enzym.*, 57:109-114. (2009)), (Trotta [et al.], *Compos. Interface*, 16:39-48. (2009)), each of which is hereby incorporated by reference in its entirety. For example, a linker group containing a portion reactive to a hydroxyl group (e.g., a carboxyl group, which may be activated by a carbodiimide) can be reacted with the cyclodextrin to form a covalent bond thereto. In another example, one or more hydroxyl groups of the cyclodextrin can be activated by known methods (e.g., tosylation) to react with a reactive group (e.g., amino group) on the linker.

In general, the linker initially contains two reactive portions that react with and bond to each CD monomer. In one embodiment, a linker is first attached to a cyclodextrin to produce a linker-cyclodextrin compound that is isolated, and then the remaining reactive portion of the linker in the linker-cyclodextrin compound is subsequently reacted with a second cyclodextrin. The second reactive portion of the linker may be protected during reaction of the first reactive group, though protection may not be employed where the first and second reactive portions of the linker react with the two molecules differently. A linker may be reacted with both molecules simultaneously to link them together. In other embodiments, the linker can have additional reactive groups in order to link to other molecules.

Numerous linkers are known in the art. Such linkers can be used for linking any of a variety of groups together when the groups possess, or have been functionalized to possess, groups that can react and link with the reactive linker. Some groups capable of reacting with double-reactive linkers include amino, thiol, hydroxyl, carboxyl, ester, and alkyl halide groups. For example, amino-amino coupling reagents can be employed to link a cyclic oligosaccharide with a polysaccharide (or, for example, any of these groups with a fluorophore or with each other) when each of the groups to be linked possess at least one amino group. Some examples of amino-amino coupling reagents include diisocyanates, alkyl dihalides, dialdehydes, disuccinimidyl suberate (DSS), disuccinimidyl tartrate (DST), and disulfosuccinimidyl tartrate (sulfo-DST), all of which are commercially available. In other embodiments, amino-thiol coupling agents can be employed to link a thiol group of one molecule with an amino group of another molecule. Some examples of amino-thiol coupling reagents include succinimidyl 4-(N-maleimidomethyl)-cyclohexane-1-carboxylate (SMCC), and sulfo-succinimidyl 4-(N-maleimidomethyl)-cyclohexane-1-carboxylate (sulfo-SMCC). In yet other embodiments, thiol-thiol coupling agents can be employed to link groups bearing at least one thiol group.

In some embodiments, the linker is as small as a single atom (e.g., an —O—, —CH2—, or —NH— linkage), or two or three atoms in length (e.g., an amido, ureido, carbamate, ester, carbonate, sulfone, ethylene, or trimethylene linkage). In other embodiments, the linker provides more freedom of movement by being at least four, five, six, seven, or eight atom lengths, and up to, for example, 10, 12, 14, 16, 18, 20, 22, 24, 26, 28, or 30 atom lengths. Preferred linker lengths are between 2 and 12 atoms, or between 4 and 8 atoms. In exemplary embodiments, the linker is C4 alkyl, which may be unsubstituted. In exemplary embodiments, the linker comprises a triazole.

Atherosclerosis

Exemplary cyclodextrin dimers described herein are useful to prevent or treat disease such as atherosclerosis. The combination of the cyclodextrin dimer and one or more active agents, such as those described herein (e.g., antihyperlipidemic agents such as statins) are useful in treating any atherosclerosis, as well as the signs, symptoms or complications of atherosclerosis. Atherosclerosis (also known as arteriosclerotic vascular disease or ASVD and known as coronary artery disease or CAD) is a condition in which an artery wall thickens as a result of the accumulation of fatty materials such as cholesterol. Atherosclerosis is a chronic disease that can remain asymptomatic for decades. It is a syndrome affecting arterial blood vessels, a chronic inflammatory response in the walls of arteries, thought to be caused largely by the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

The pathobiology of atherosclerotic lesions is complicated but generally, stable atherosclerotic plaques, which tend to be asymptomatic, are rich in extracellular matrix and smooth muscle cells, while unstable plaques are rich in macrophages and foam cells and the extracellular matrix separating the lesion from the arterial lumen (also known as the fibrous cap) is usually weak and prone to rupture. Ruptures of the fibrous cap expose thrombogenic material, such as collagen to the circulation and eventually induce thrombus formation in the lumen. Upon formation, intraluminal thrombi can occlude arteries outright (e.g., coronary occlusion), but more often they detach, move into the circulation and can eventually occlude smaller downstream branches causing thromboembolism (e.g., stroke is often caused by thrombus formation in the carotid arteries). Apart from thromboembolism, chronically expanding atherosclerotic lesions can cause complete closure of the lumen. Chronically expanding lesions are often asymptomatic until lumen stenosis is so severe that blood supply to downstream tissue(s) is insufficient, resulting in ischemia.

These complications of advanced atherosclerosis are chronic, slowly progressive and cumulative. In some instances, soft plaques suddenly rupture, causing the formation of a thrombus that will rapidly slow or stop blood flow, leading to death of the tissues fed by the artery (infarction). Coronary thrombosis of a coronary artery is also a common complication which can lead to myocardial infarction. Blockage of an artery to the brain may result in stroke. In advanced atherosclerotic disease, claudication from insufficient blood supply to the legs, typically caused by a combination of both stenosis and aneurysmal segments narrowed with clots, may occur.

Atherosclerosis can affect the entire artery tree, but larger, high-pressure vessels such as the coronary, renal, femoral, cerebral, and carotid arteries are typically at greater risk.

Signs, symptoms and complications of atherosclerosis include, but are not limited to increased plasma total cholesterol, VLDL-C, LDL-C, free cholesterol, cholesterol ester, triglycerides, phospholipids and the presence of lesions (e.g., plaques) in arteries, as discussed above. In some instances, increased cholesterol (e.g., total cholesterol, free cholesterol and cholesterol esters) can be seen in one or more of plasma, aortic tissue and aortic plaques.

Certain individuals may be predisposed to atherosclerosis. Accordingly, the present disclosure relates to methods of administering the subject cyclodextrin dimers alone, or in combination with one or more additional therapeutic agents (e.g., antihyperlipidemic agents, such as statins), to prevent atherosclerosis, or the signs, symptoms or complications thereof. In some embodiments a subject predisposed to atherosclerosis may exhibit one or more of the following characteristics: advanced age, a family history of heart disease, a biological condition, high blood cholesterol. In some embodiments, the biological condition comprises high levels of low-density lipoprotein cholesterol (LDL-C) in the blood, low levels of high-density lipoprotein cholesterol (HDL-C) in the blood, hypertension, insulin resistance, diabetes, excess body weight, obesity, sleep apnea, contributing lifestyle choice(s) and/or contributing behavioral habit(s). In some embodiments, the behavioral habit comprises smoking and/or alcohol use. In some embodiments, the lifestyle choice comprises an inactive lifestyle and/or a high stress level.

Exemplary embodiments provide for the administration of a cyclodextrin dimer of the present disclosure, optionally in combination with one or more additional agents, to a patient having atherosclerosis. The patient may exhibit one or more signs or symptoms of atherosclerosis. Atherosclerosis may be diagnosed based on one or more of Doppler ultrasound, ankle-brachial index, electrocardiogram, stress test, angiogram (optionally with cardiac catheterization), computerized tomography (CT), magnetic resonance angiography (MRA), or other methods of imaging arteries or measuring blood flow.

Exemplary embodiments provide for the administration of a combination of therapies comprising a cyclodextrin dimer of the present disclosure and one or more additional therapies. These combination therapies for treatment of atherosclerosis may include a cyclodextrin dimer of the present disclosure and another therapy for the treatment or prevention of atherosclerosis, such as an anti-cholesterol drug, anti-hypertension drug, anti-platelet drug, dietary supplement, or surgical or behavioral intervention, including but not limited to those described below. Additional combination therapies include a CD dimer of the present disclosure and another therapy for the treatment of heart failure, such as one or more aldosterone antagonists, ACE inhibitors, ARBs (angiotensin II receptor blockers), ARNIs (angiotensin receptor-neprilysin inhibitors), beta-blockers, blood vessel dilators, calcium channel blockers, digoxin, diuretics, heart pump medications, potassium, magnesium, selective sinus node inhibitors, or combinations thereof. Combination therapies for the treatment of the dry form of age-related macular degeneration (AMD) or Stargardt's disease include a CD dimer of the present disclosure and another therapy for the treatment of AMD, such as, LBS-008 (Belite Bio) (a nonretinoid antagonist of retinol binding protein 4), AREDS supplement formula comprising vitamins C and E, beta-carotene, zinc, and copper, AREDS2 supplement formula comprising a supplement formula that has vitamins C and E, zinc, copper, lutein, zeaxanthin, and omega-3 fatty acids, or combinations thereof. Combination therapies for treatment of Alzheimer's disease include a CD dimer of the present disclosure and one or more cholinesterase inhibitors (ARICEPT®, EXELON®, RAZADYNE®) and memantine (NAMENDA®) or a combination thereof. Combination therapies for Niemann-Pick Disease include a CD dimer of the present disclosure and one or more of miglustat (ZAVESCA®), HPβCD (TRAPPSOL CYCLO, VTS-270), and physical therapy. The combination therapies may be administered simultaneously, essentially simultaneously, or sequentially, in either order. Combination therapies may be co-administered in a single formulation, or separately, optionally in a dosage kit or pack containing each medication in the combination, e.g., in a convenient pre-measured format in which one or more single doses of each drug in the combination is provided. The combination therapy may exhibit a synergistic effect, wherein the effects of the combined therapies exceed the effects of the individual treatments alone. While combination therapies in general include administration of an effective amount of the CD dimer and the combined therapy, the combination therapies may allow for effective treatment with a lower dosage of the CD and/or the combined therapy, which advantageously may decrease side-effects associated with the regular (non-combination) dosage.

Combination therapies may include therapies for the treatment or prevention of diseases or conditions related to atherosclerosis, such as coronary artery disease, angina pectoralis, heart attack, cerebrovascular disease, transient ischemic attack, and/or peripheral artery disease. Combination therapies may include therapies for the treatment or prevention of conditions that may contribute to atherosclerosis formation and/or a worse prognosis, such as hypertension, hypercholesterolemia, hyperglycemia, and diabetes.

In exemplary embodiments, a cyclodextrin dimer of the present invention is co-administered with an anti-cholesterol drug, such as a fibrate or statin, e.g., ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and/or ZOCOR® (simvastatin). The anti-cholesterol drug may be administered in an amount effective to prevent or treat hypercholesterolemia.

In exemplary embodiments, a cyclodextrin dimer of the present invention is co-administered with an anti-platelet drug, e.g., aspirin.

In exemplary embodiments, a cyclodextrin dimer of the present invention is co-administered with an anti-hypertension drug. Exemplary anti-hypertension drugs include beta blockers, Angiotensin-converting enzyme (ACE) inhibitors, calcium channel blockers, and/or diuretics.

In exemplary embodiments, a cyclodextrin dimer of the present invention is co-administered with a dietary supplement, such as one or more of alpha-linolenic acid (ALA), barley, beta-sitosterol, black tea, blond psyllium, calcium, cocoa, cod liver oil, coenzyme Q10, fish oil, folic acid, garlic, green tea, niacin, oat bran, omega-3 fatty acids (such as eicosapentaenoic acid (EPA) and/or docosahexaenoic acid (DHA)), sitostanol, and/or vitamin C.

Exemplary combination therapies also include intervention in patient behavior and/or lifestyle, including counseling and/or supporting smoking cessation, exercise, and a healthy diet, such as a diet low in low density lipoprotein (LDL) and optionally elevated in high density lipoprotein (HDL).

Exemplary combination therapies also include surgical intervention, such as angioplasty, stenting, or both.

The methods of the present invention are useful for treating or preventing atherosclerosis in human subjects. In some instances, the patient is otherwise healthy except for exhibiting atherosclerosis. For example, the patient may not exhibit any other risk factor of cardiovascular, thrombotic or other diseases or disorders at the time of treatment. In other instances, however, the patient is selected on the basis of being diagnosed with, or at risk of developing, a disease or disorder that is caused by or correlated with atherosclerosis. For example, at the time of, or prior to administration of the pharmaceutical composition of the present invention, the patient may be diagnosed with or identified as being at risk of developing a cardiovascular disease or disorder, such as, e.g., coronary artery disease, acute myocardial infarction, asymptomatic carotid atherosclerosis, stroke, peripheral artery occlusive disease, etc. The cardiovascular disease or disorder, in some instances, is hypercholesterolemia.

In other instances, at the time of, or prior to administration of the pharmaceutical composition of the present invention, the patient may be diagnosed with or identified as being at risk of developing atherosclerosis.

In yet other instances, the patient who is to be treated with the methods of the present invention is selected on the basis of one or more factors selected from the group consisting of age (e.g., older than 40, 45, 50, 55, 60, 65, 70, 75, or 80 years), race, gender (male or female), exercise habits (e.g., regular exerciser, non-exerciser), other preexisting medical conditions (e.g., type-II diabetes, high blood pressure, etc.), and current medication status (e.g., currently taking statins, such as e.g., cerivastatin, atorvastatin, simvastatin, pitavastatin, rosuvastatin, fluvastatin, lovastatin, pravastatin, etc., beta blockers, niacin, etc.).

BRIEF DESCRIPTION OF THE SEVERAL VIEWS OF THE DRAWINGS

In the drawings that follow, the following abbreviations are used: Me or ME or me or met: methyl; SB: sulfobutyl; QA=quaternary ammonium, e.g., $-CH_2CH(OH)CH_2N(CH_3)_3^+$, such as $-CH_2CH(OH)CH_2N(CH_3)_3Cl$; SUCC: succinyl; DMSO: dimethylsulfoxide.

FIGS. 1B-1J. Structure of substituted CDs.

FIG. 1B. where $R^1$, $R^2$ and $R^3$ are substitutive groups,

FIG. 1C. βCD (DS0), i.e., each $R^1$, $R^2$ and $R^3$ is hydrogen,

FIG. 1D. Hydroxypropyl BCD (DS4),

FIG. 1E. Methyl βCD (DS 6),

FIG. 1F. sulfobutyl BCD (DS4),

FIG. 1G. quaternary ammonium (DS 3),

FIG. 1H. succinyl (DS 1),

FIG. 1I. carboxymethyl (DS 4), and

FIG. 1J. maltosyl (DS 1) groups are substituted on the C2, C3, or C6 position of BCD.

FIG. 2B depicts the results for 7-ketocholesterol (7KC (X with line)), 4-beta hydroxycholesterol (4-BOH (square)), 25-hydroxycholesterol (25OH (triangle)), cholesterol epoxide (diamond), and 27-hydroxycholesterol (27OH (circle)).

FIG. 2C. Solubilization of 7KC by various forms of hydroxypropyl-beta cyclodextrin monomers assessed by relative turbidity. DS=average number of hydroxypropyl substitutions per molecule.

FIG. 2D. Solubilization of cholesterol by various forms of hydroxypropyl-beta cyclodextrin monomers assessed by relative turbidity. DS=average number of hydroxypropyl substitutions per molecule.

FIG. 3B. Formula I. C2-C2 cyclodextrin dimer with triazole linker.

FIG. 3C. Formula II. C2-C3 cyclodextrin dimer with triazole linker.

FIG. 3D. Formula III. C3-C3 cyclodextrin dimer with triazole linker.

FIG. 3E. Formula IV. Secondary face-linked methyl substituted BCD with a linker L.

FIG. 3F. Formula V. Secondary face-linked sulfobutyl substituted BCD with a linker L. A sodium salt is depicted though other salts are also embraced within the compounds of the present disclosure.

FIG. 3G. Formula VI. Secondary face-linked succinyl substituted BCD with a linker L.

FIG. 3H. Formula VII. Secondary face-linked maltosyl substituted BCD with a linker L.

FIG. 3I. Formula VIII. Secondary face-linked quaternary ammonium substituted BCD with a linker L.

FIG. 3J. Formula IX. Secondary face-linked carboxymethyl substituted BCD with a linker L. A sodium salt is depicted though other salts are also embraced within the compounds of the present disclosure.

FIG. 4I. Visual trajectory for 7KC and cholesterol complexed with native DS0 βCD (AMBER forcefield) in both orientations. Abbreviation used: "ms": microsecond.

FIG. 4U. Visual trajectory for 7KC and cholesterol complexed with HPβCD DS5 (AMBER forcefield) in both orientations.

FIG. 4X. Visual trajectory for 7KC and cholesterol complexed with monomeric HPβCD DS5, translated, (GROMOS forcefield) in both orientations.

FIG. 4AA. Visual trajectory for 7KC and cholesterol complexed with monomeric DS5 HPβCD, translated, (AMBER forcefield) in both orientations.

FIG. 4BB. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between butyl-dimerized HPβCD DS5 and cholesterol or 7KC, up and down ligand orientations in the GROMOS forcefield.

FIG. 4CC. Solubilization of 7KC and cholesterol by butyl-dimerized HPβCD DS5 in the GROMOS forcefield.

FIG. 4DD. Visual trajectory for 7KC and cholesterol complexed with butyl-dimerized DS5 HPβCD (GROMOS forcefield) in both orientations.

FIG. 4EE. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for butyl-dimerized HPβCD DS5, up and down ligand orientations in the AMBER forcefield.

FIG. 4FF. Solubilization of ligand by butyl-dimerized HPβCD DS5 in the AMBER forcefield.

FIG. 4GG. Visual trajectory for 7KC and cholesterol complexed with butyl-dimerized HPβCD DS5 (AMBER forcefield) in both orientations.

FIG. 4HH. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for dimerized DS5 hydroxypropyl beta cyclodextrin, up and down ligand orientations, translated, in the GROMOS forcefield.

FIG. 4II. Solubilization of 7KC and cholesterol by butyl-dimerized DS5 HPβCD, translated, in the GROMOS forcefield.

FIG. 4JJ. Visual trajectory for 7KC and cholesterol complexed with butyl-dimerized DS5 HPβCD, translated, (GROMOS forcefield) in both orientations.

FIG. 4KK. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for butyl-dimerized DS5 hydroxypropyl beta cyclodextrin, up and down ligand orientations, translated, in the AMBER forcefield.

FIG. 4LL. Solubilization of 7KC and cholesterol by butyl-dimerized DS5 HPβCD, translated, in the AMBER forcefield.

FIG. 4MM. Visual trajectory for 7KC and cholesterol complexed with butyl-dimerized DS5 HPβCD, translated, (AMBER forcefield) in both orientations.

FIG. 4NN. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for unsubstituted (DS0) butyl-dimerized beta cyclodextrin, up and down ligand orientations in the GROMOS forcefield.

FIG. 4OO. Visual trajectory for 7KC and cholesterol complexed with unsubstituted (DS0) butyl-dimerized βCD (AMBER forcefield) in both orientations.

FIG. 4PP. MD analysis of triazole-linked DS0 cyclodextrin. The angle between a vector perpendicular to the plane formed by the O4 atoms of CD and the main axis of the ligand and Lennard-Jones and Coulombic energy of interaction between the cyclodextrin and the ligand for unsubstituted (DS0) dimerized beta cyclodextrin, up and down ligand orientations in the GROMOS forcefield.

FIG. 4QQ. Visual trajectory for 7KC and cholesterol complexed with triazole-dimerized, DS0 βCD in both orientations.

FIG. 4RR. MD analysis of triazole-linked DS4 HPβCD. The angle between a vector perpendicular to the plane formed by the O4 atoms of CD and the main axis of the ligand and Lennard-Jones and Coulombic energy of interaction between the cyclodextrin and the ligand for translated dimerized DS4 hydroxypropyl beta cyclodextrin, up and down ligand orientations in the GROMOS forcefield.

FIG. 4SS. Visual trajectory for 100 ns of interaction between a triazole-linked DS4 hydroxypropyl βCD dimer and 7KC/cholesterol in both orientations.

FIG. 6E. Visual trajectories of triazole-linked DS4 sulfobutyl βCD dimer and 7KC/cholesterol in both up and down orientations.

FIG. 8I. Visual trajectories of nitrogen-linked DS4 hydroxypropyl BCD dimer and 7KC/cholesterol in both orientations (Linker O).

FIG. 9C. Sterol affinity for various lengths of triazole linkers with hydroxypropyl, methyl, and sulfobutyl substitutions (DS4); as modeled by molecular docking. Order of bars as in FIG. 9B.

FIG. 10P. MALDI spectrum of synthetic large-face triazole-linked beta-cyclodextrin HP(βCD-Triazole-βCD) DS-3. Some peaks are not labeled due to crowding but exhibit the expected molecular weight.

Figure 10A:
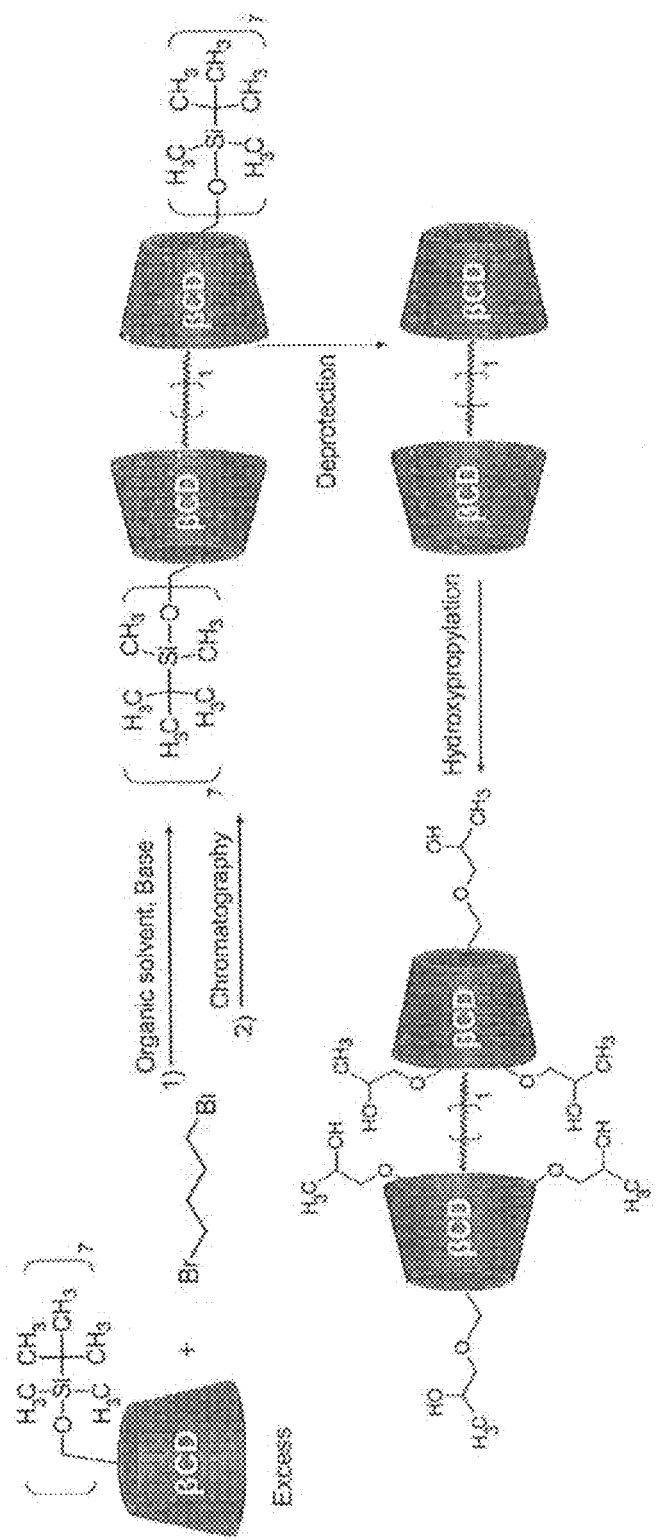
FIG. 10A. Synthetic strategy for hydroxypropylated-dimer connected with one linker unit based on 1,4-dibromobutane (resulting in a butyl linked HPβCD dimer).
Figure 10B:
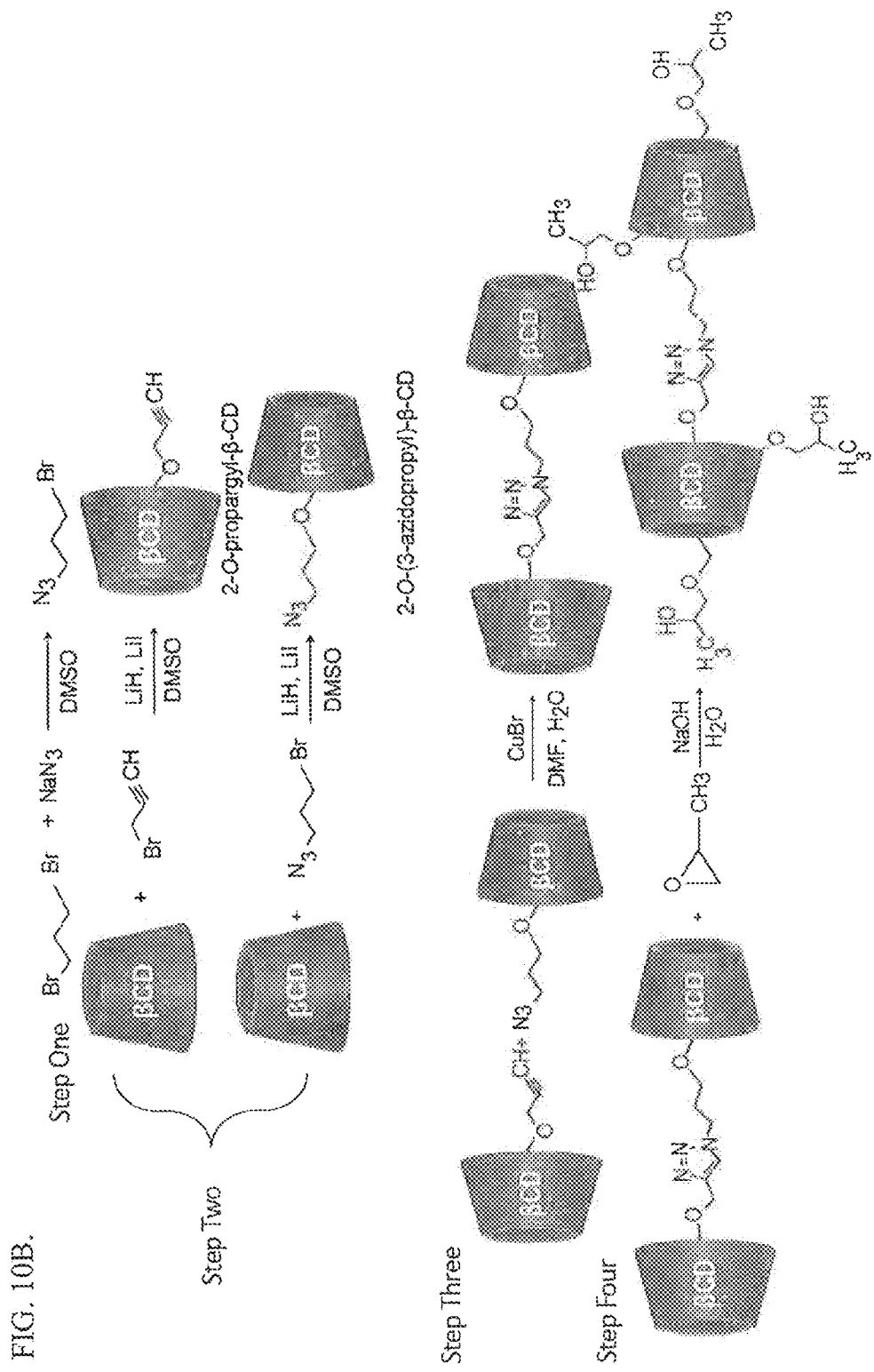
FIG. 10B. Synthetic strategy for hydroxypropylated-dimer connected with one linker unit based on 3-azido-1-bromo-propane (resulting in a triazole linked HPβCD dimer).
Figure 10C:
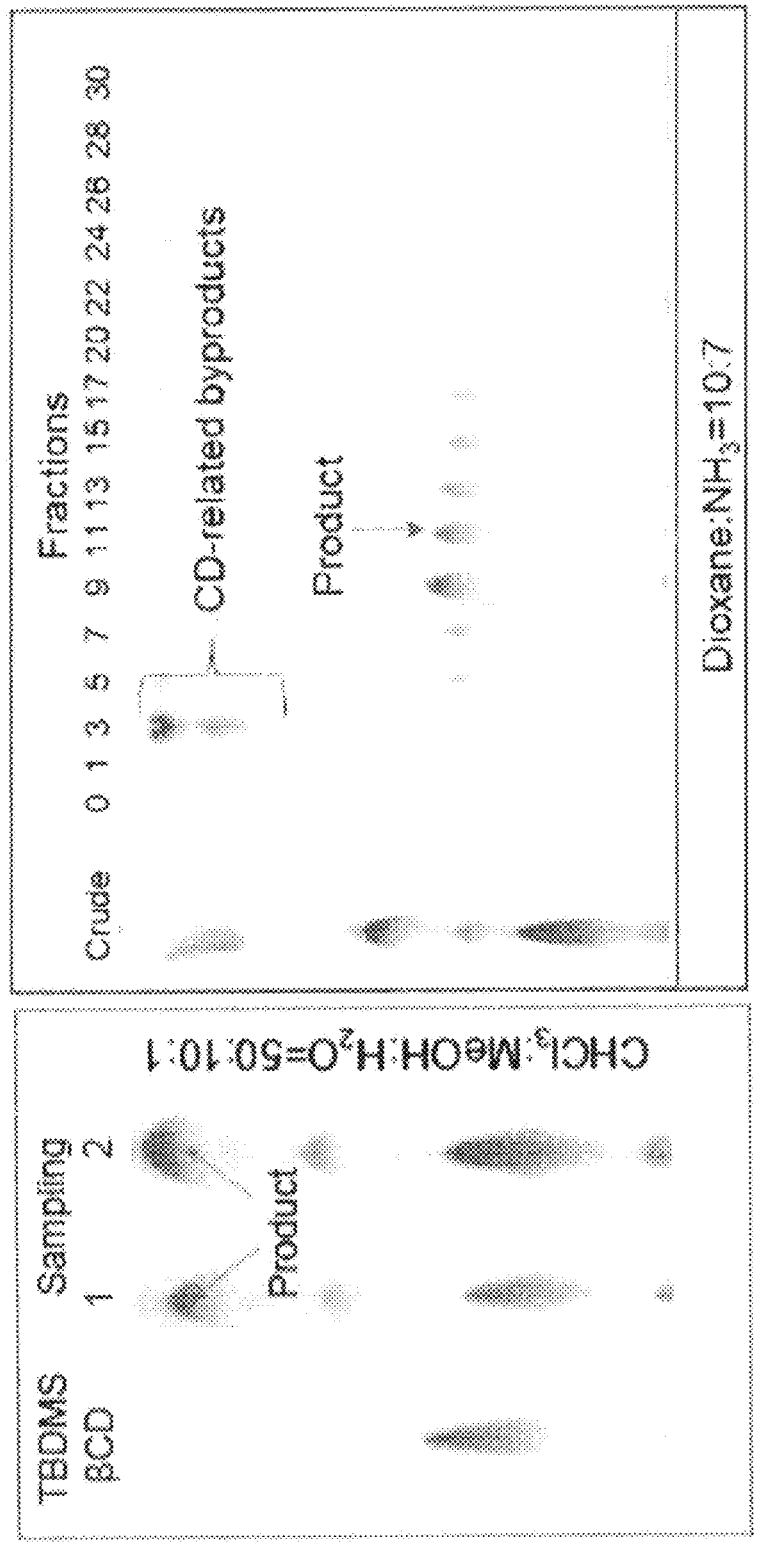
FIG. 10C. TLC analysis used for evaluating the reaction proceeding and the conversion rate.
Figure 10D:
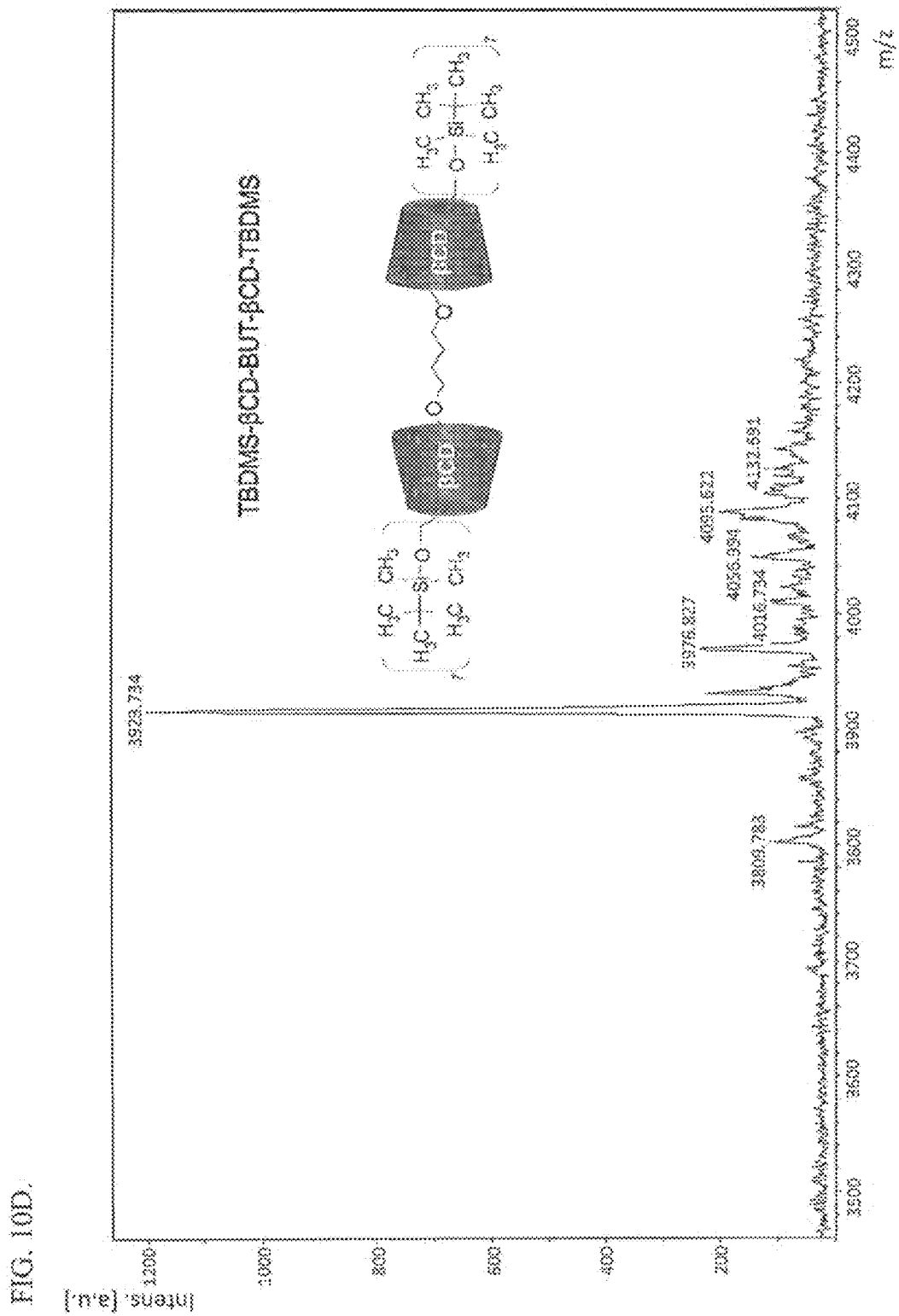
FIG. 10D. MALDI spectrum of TBDMS-βCD-BUT-βCD-TBDMS.
Figure 10G:
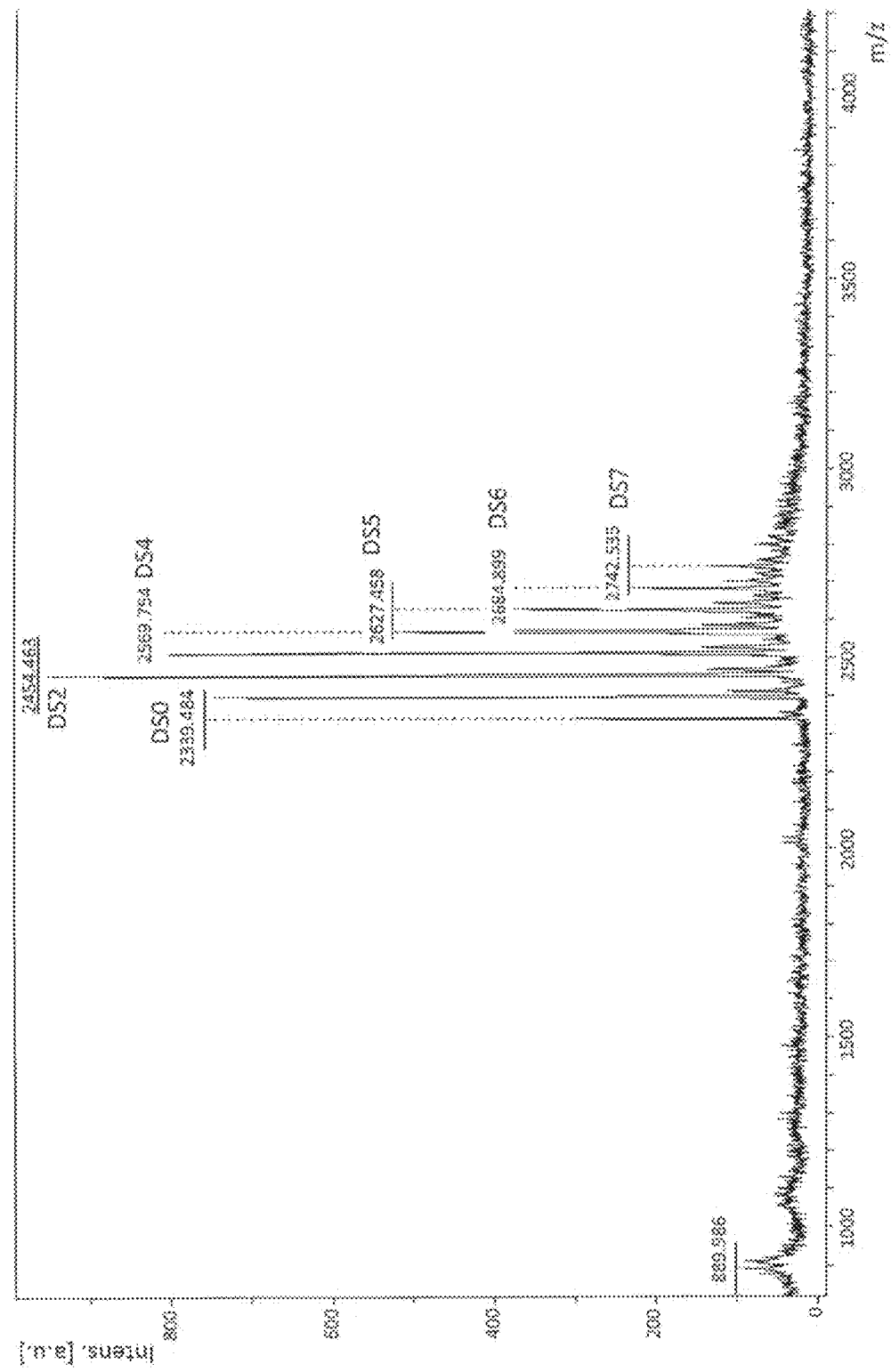
FIG. 10G. MALDI spectrum of synthetic large-face butyl-linked hydroxy-propyl beta-cyclodextrin HP(βCD-BUT-βCD), DS-3. Some peaks are not labeled due to crowding but exhibit the expected molecular weight.
Figure 10H:
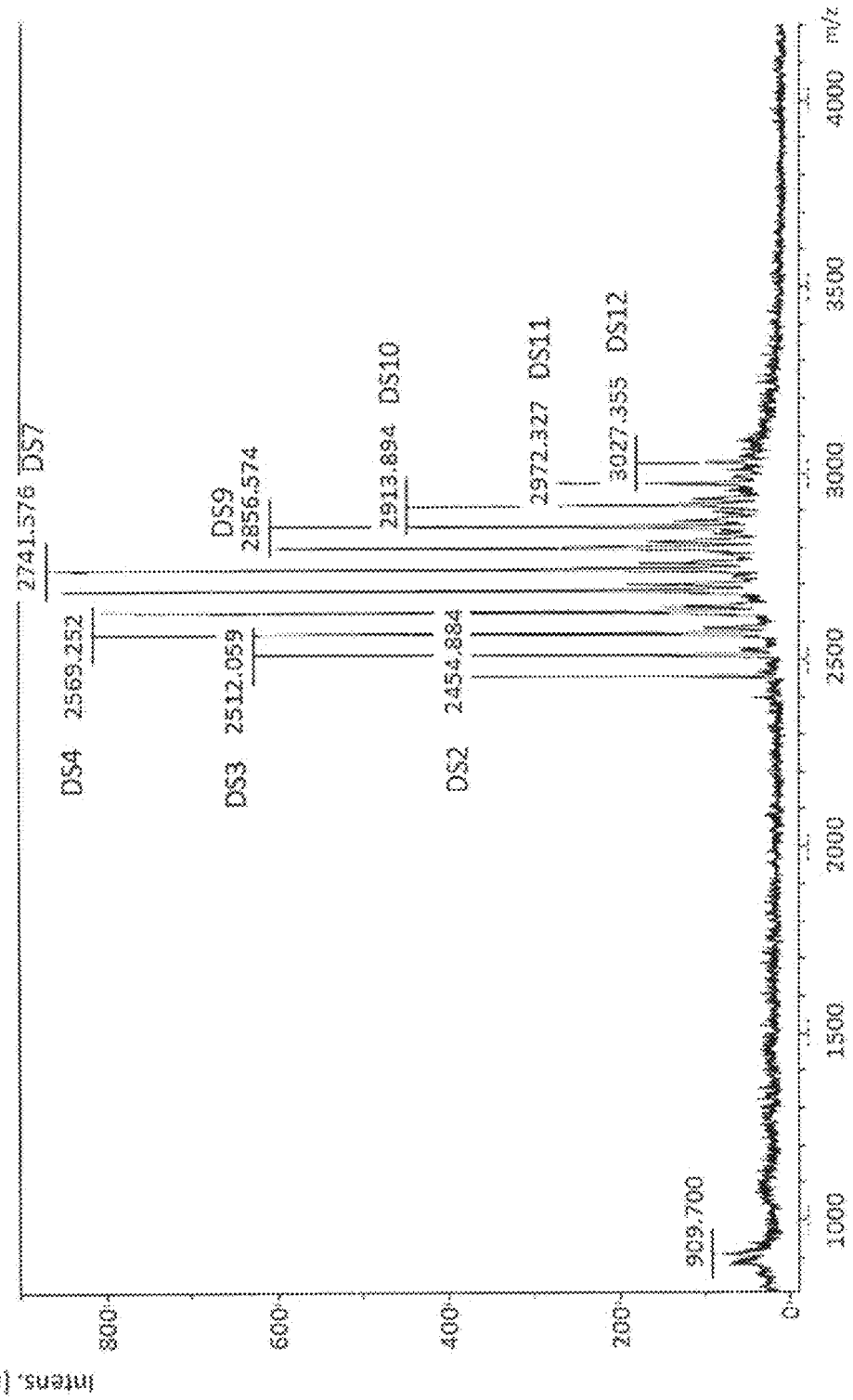
FIG. 10H. MALDI spectrum of synthetic large-face butyl-linked hydroxy-propyl beta-cyclodextrin HP(βCD-BUT-βCD), DS-6. Some peaks are not labeled due to crowding but exhibit the expected molecular weight.
Figure 101L:
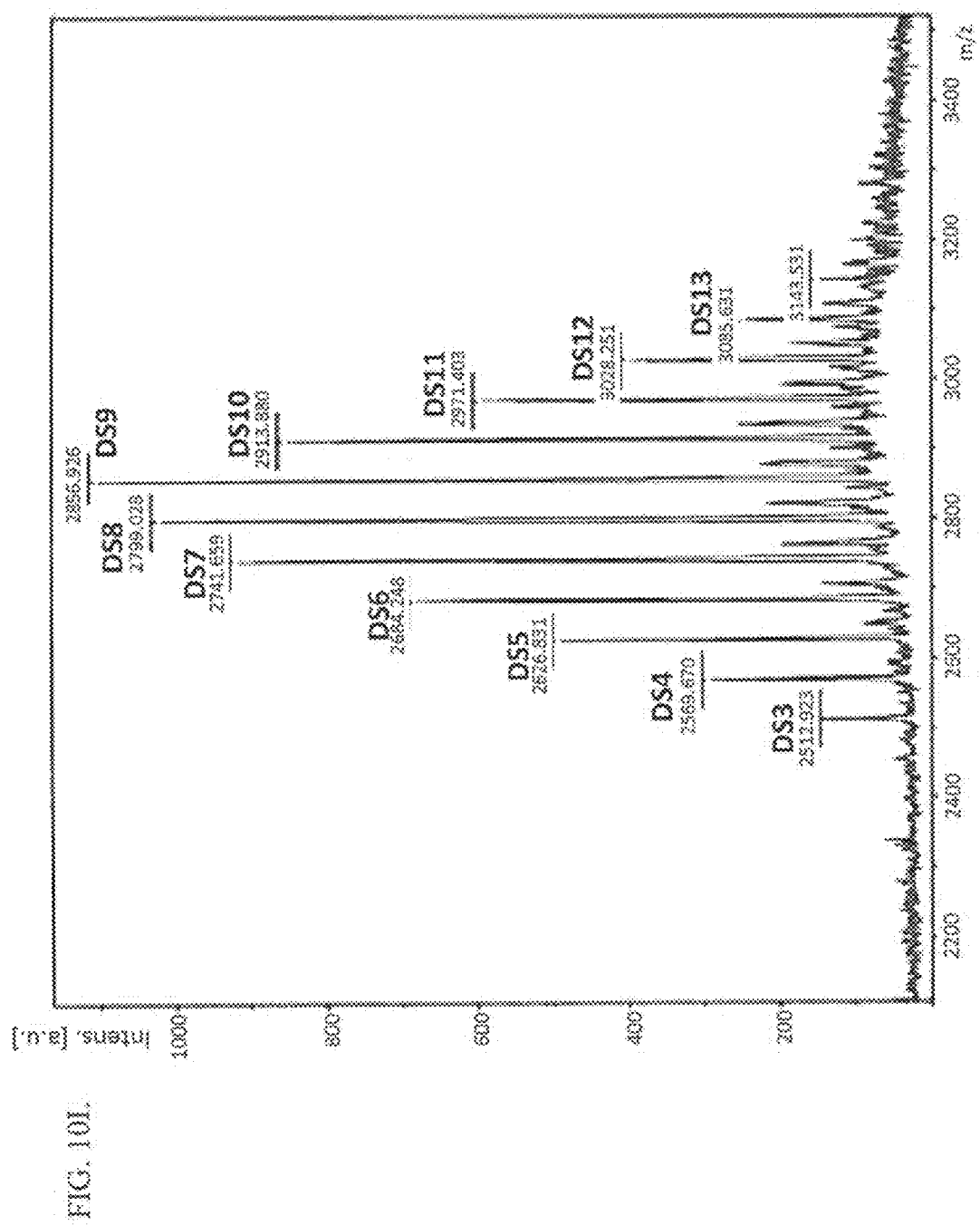
Figure 103:
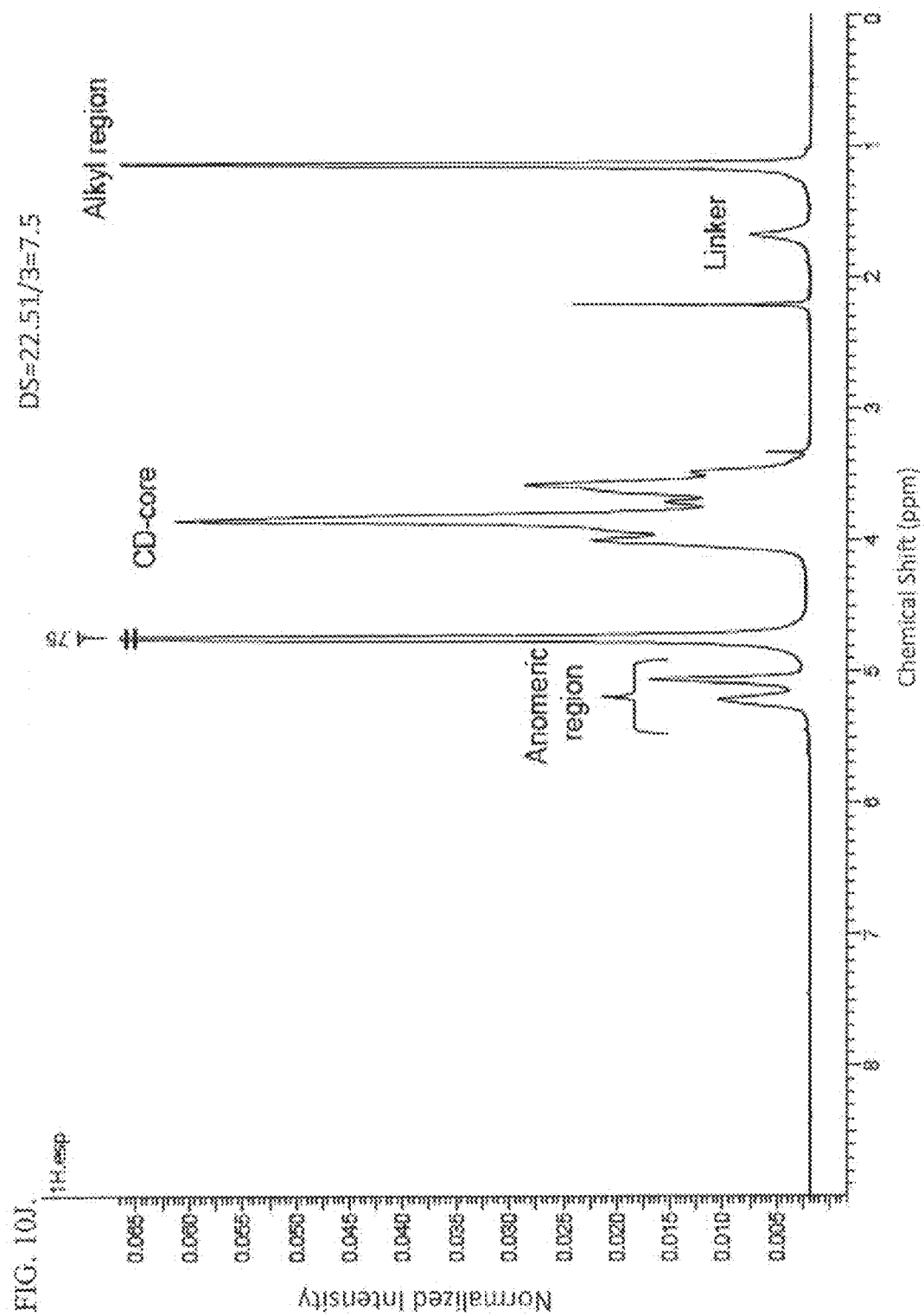
Figure 10K:
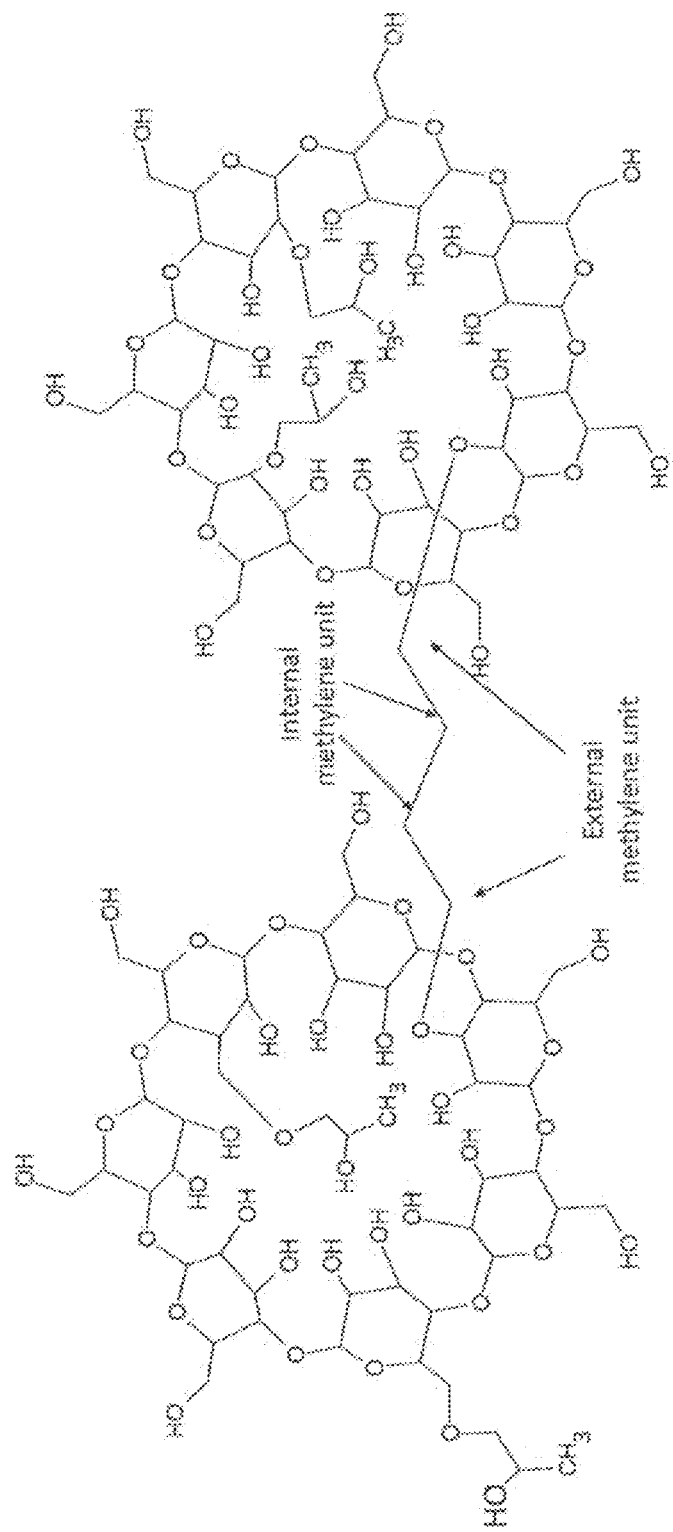
FIG. 10K. Structure of one expected isomer of HP(βCD-BUT-βCD) DS8 with nomenclature of the linker.
Figure 10L:
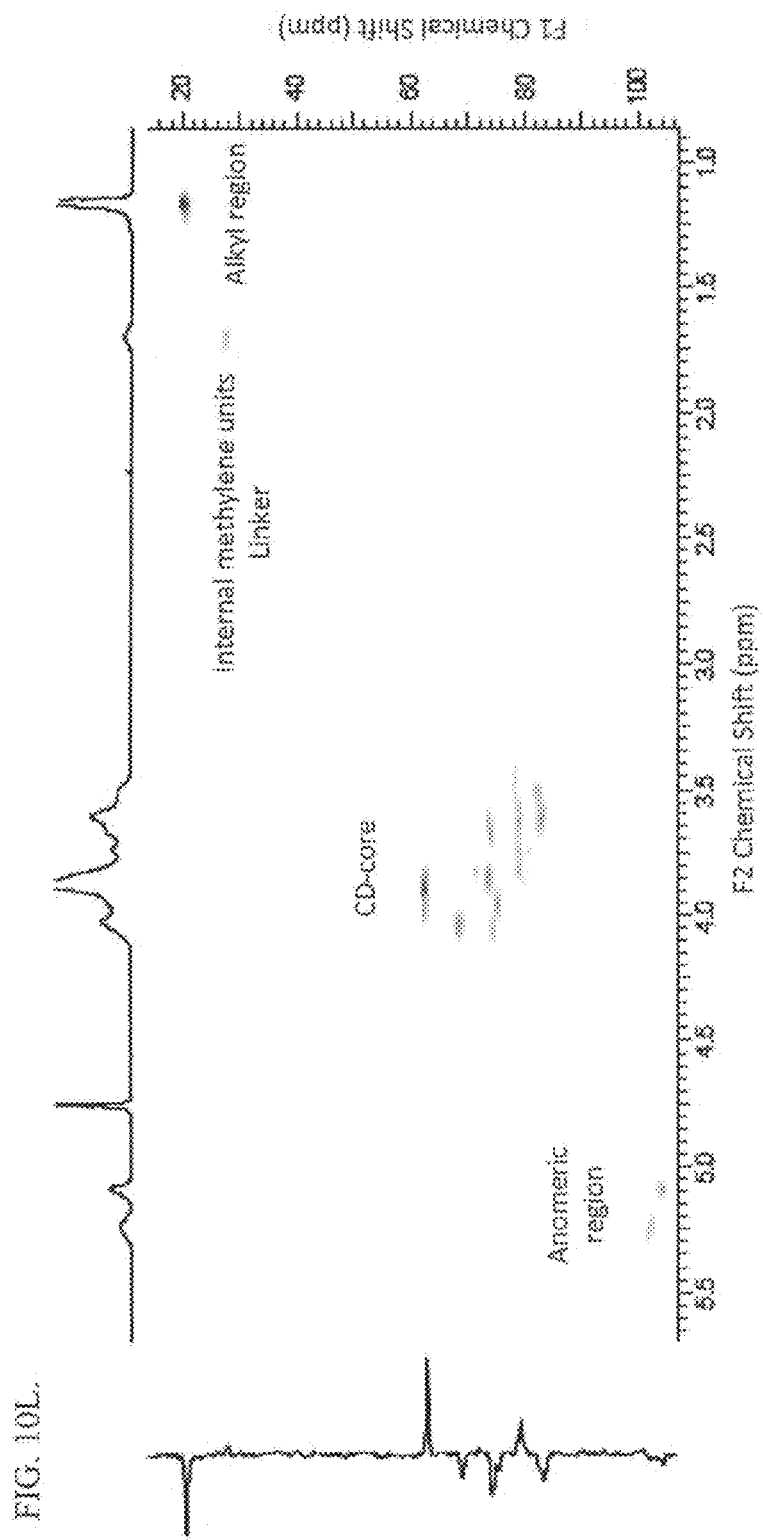
FIG. 10L. DEPT-edited HSQC spectrum of HP(βCD-BUT-βCD) (D2O, 298 K).
Figure 10M:
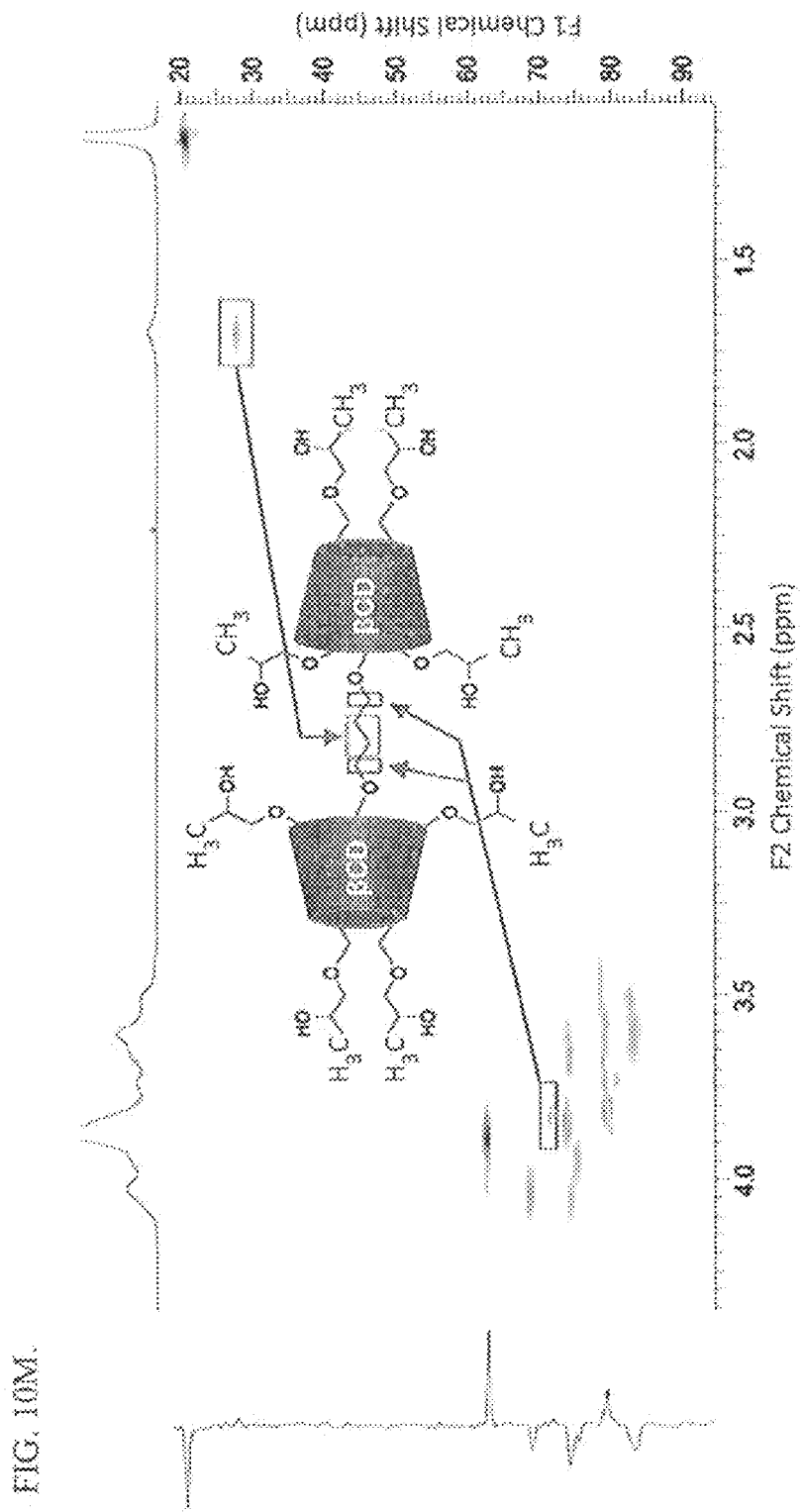
FIG. 10M. DEPT-edited HSQC spectrum of HP(βCD-BUT-βCD) with assignment of the linker frequencies determined by heat mapping (D2O, 298 K).
Figure 10N:
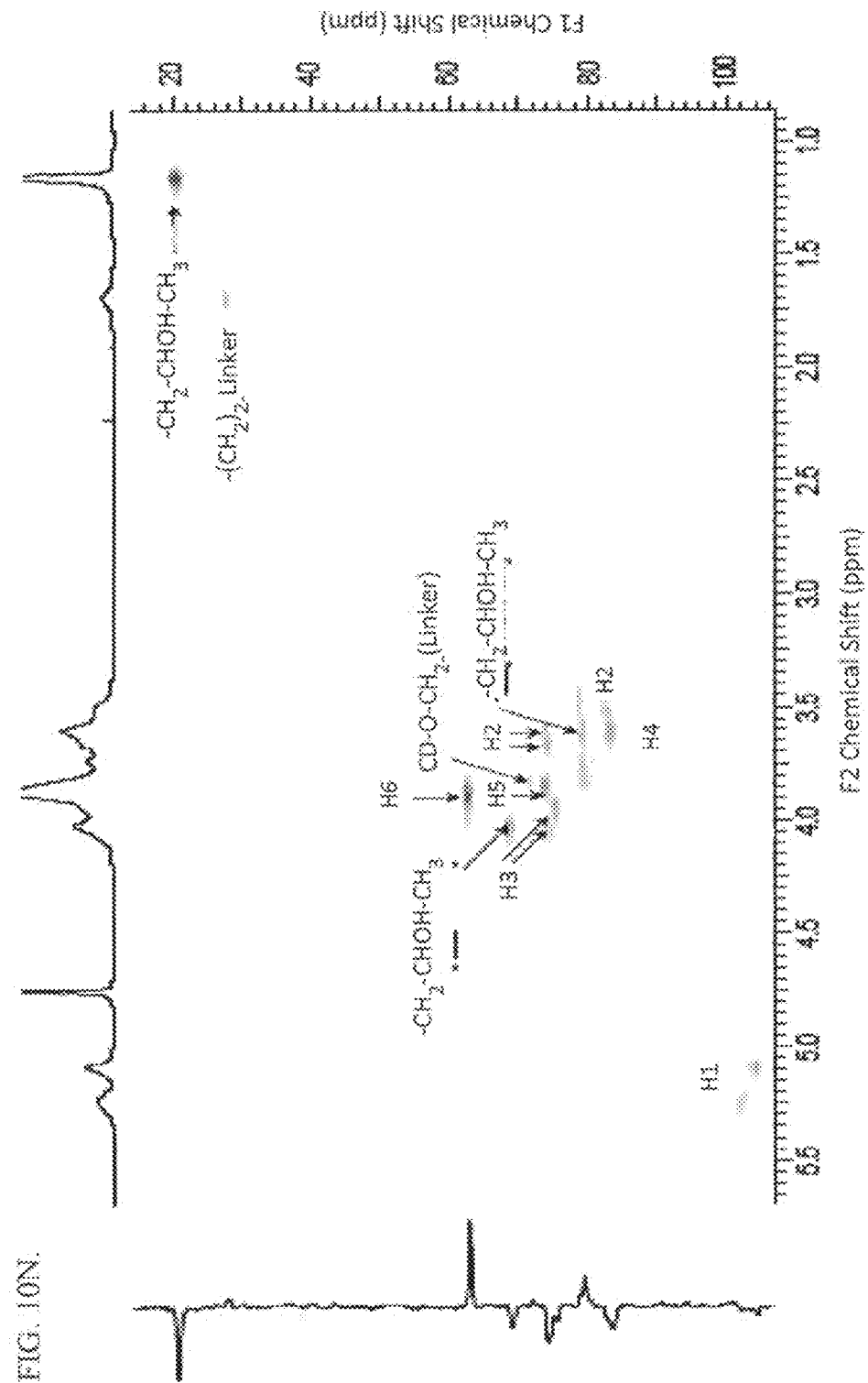
FIG. 10N. DEPT-edited HSQC spectrum of HP(βCD-BUT-βCD) with full assignment (D2O, 298 K).
Figure 100:
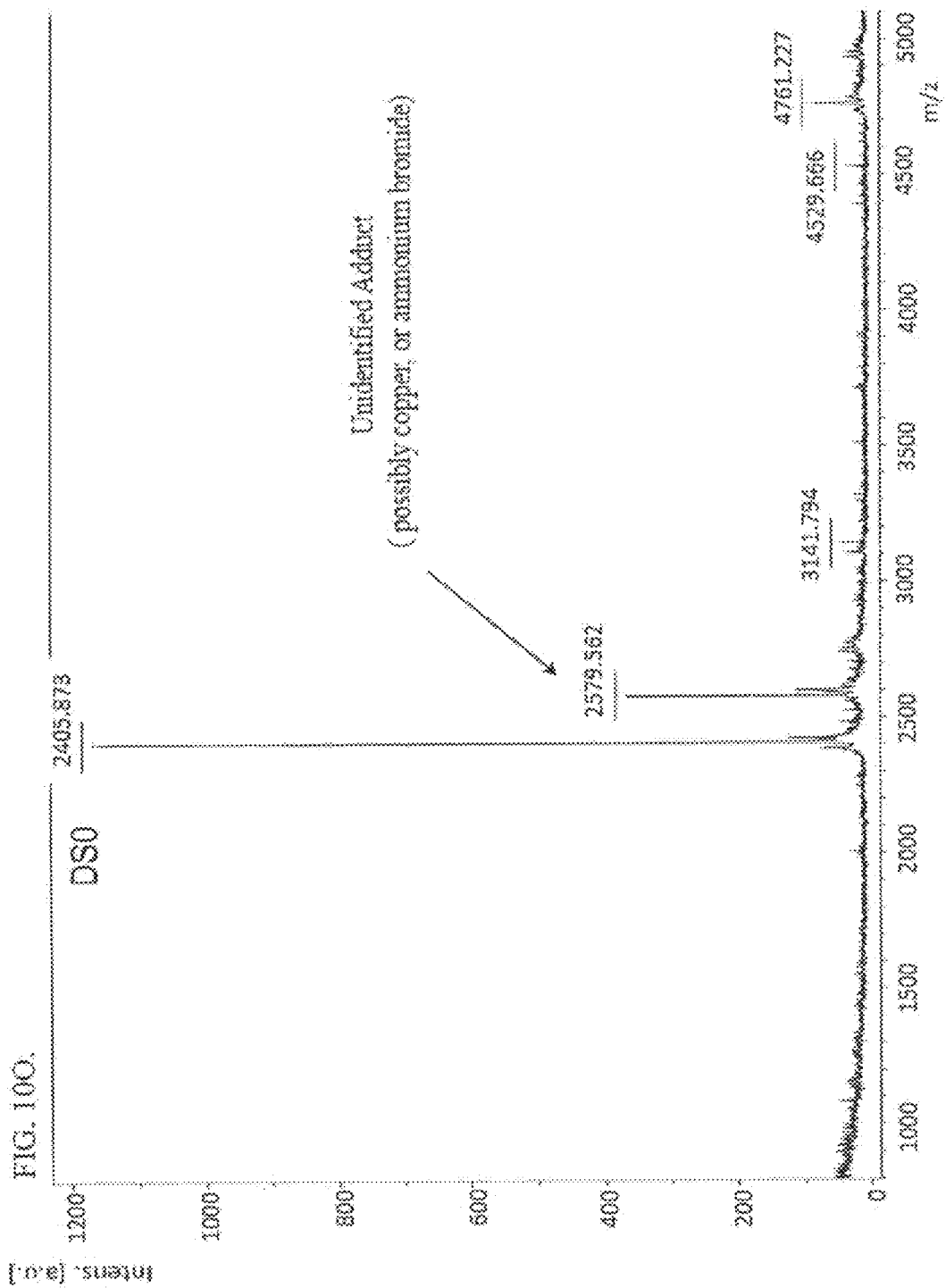
Figure 10Q:
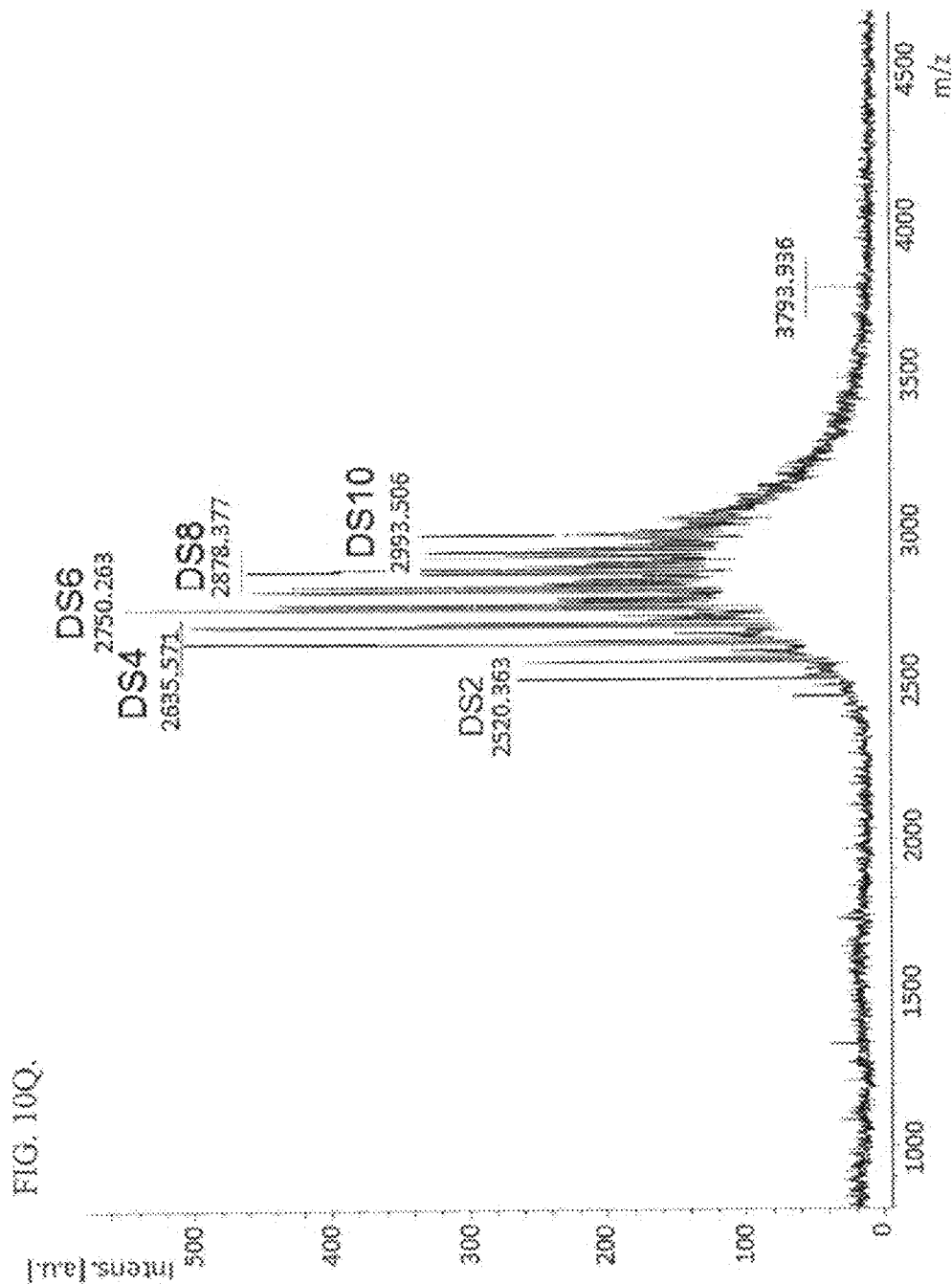
FIG. 10E. TLC analysis used for evaluating the reaction proceeding and the conversion rate.
FIG. 10F. MALDI spectrum of synthetic large-face butyl-linked beta-cyclodextrin (βCD-BUT-βCD) DS=0.
FIG. 10I. MALDI spectrum of synthetic large-face butyl-linked hydroxy-propyl beta-cyclodextrin HP(βCD-BUT-βCD), DS-8.
FIG. 10J. $^1$H-NMR spectrum of HP(βCD-BUT-βCD) (D2O, 298 K) with signals labeled.
FIG. 10O. MALDI spectrum of synthetic large-face triazole-linked beta-cyclodextrin (βCD-(Triazole)1-BCD, DS=0).

FIG. 10Q. MALDI spectrum of synthetic large-face triazole-linked beta-cyclodextrin HP(βCD-Triazole-βCD) DS-7. Some peaks are not labeled due to crowding but exhibit the expected molecular weight.

Figure 10R:
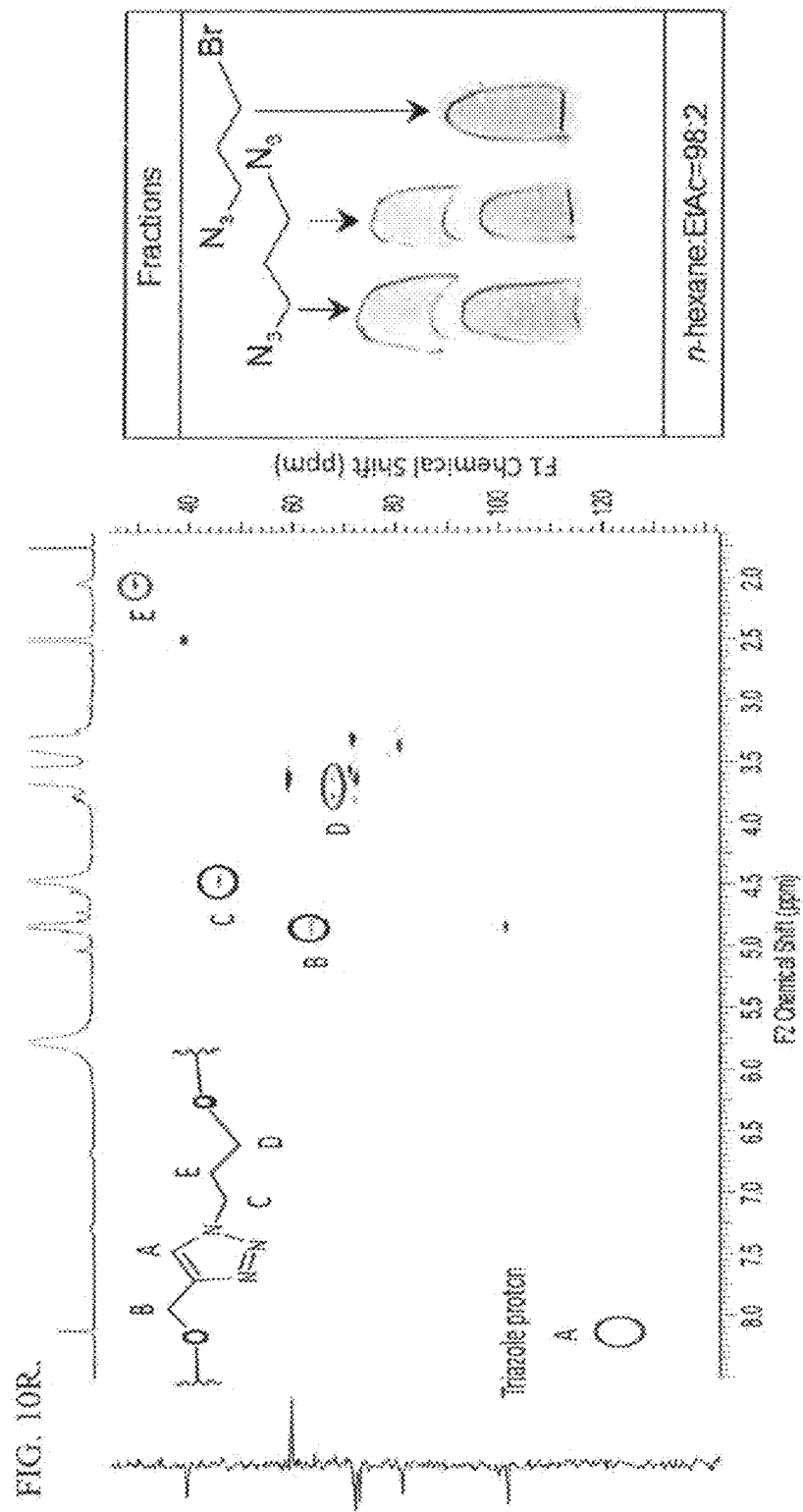

FIG. 10R. DEPT-edited HSQC spectrum of HP(βCD-triazole-βCD) with linker assignment (D2O, 298 K). DS-7 (left) and TLC with linker fractions (right).

FIG. 10S. TLC plates showing reaction monitoring with spots assignment.

Figure 10T:
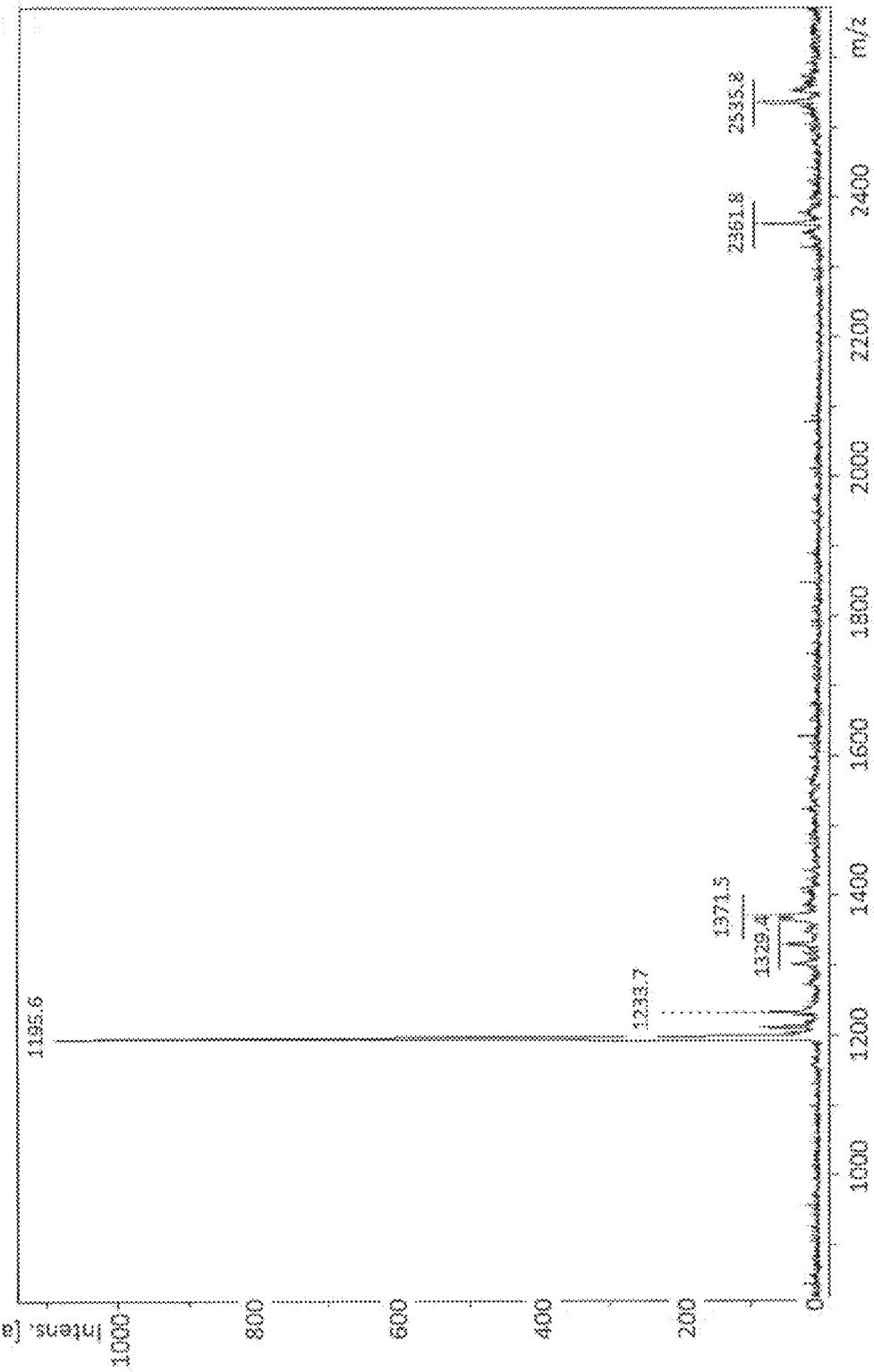

FIG. 10T. MALDI spectrum of 2-O-propargyl-β-CD.

Figure 10U:
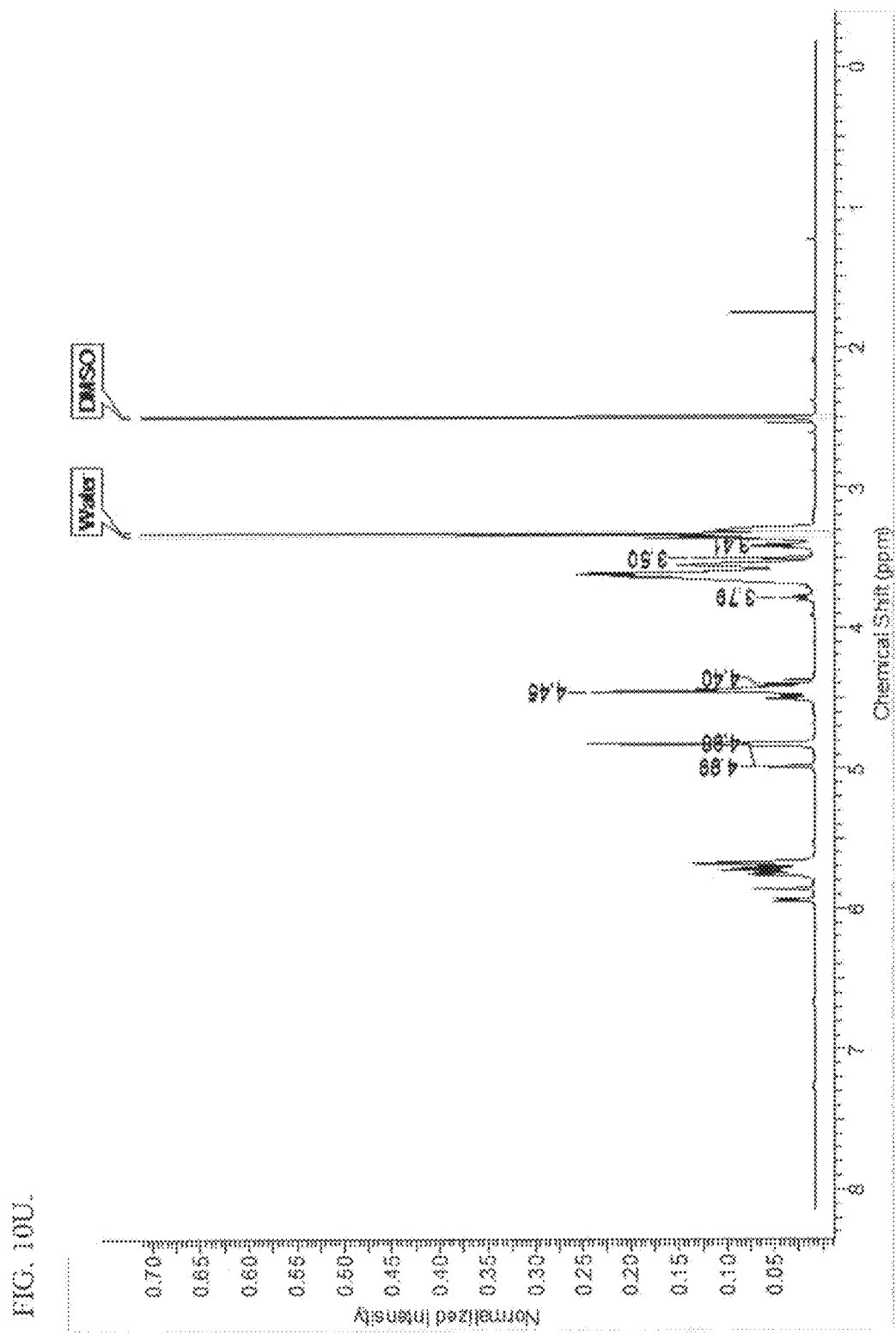

FIG. 10U. $^1$H-NMR spectrum of 2-O-propargyl-β-CD with partial peak-picking (DMSO-d$_6$, 298 K).

Figure 10V:
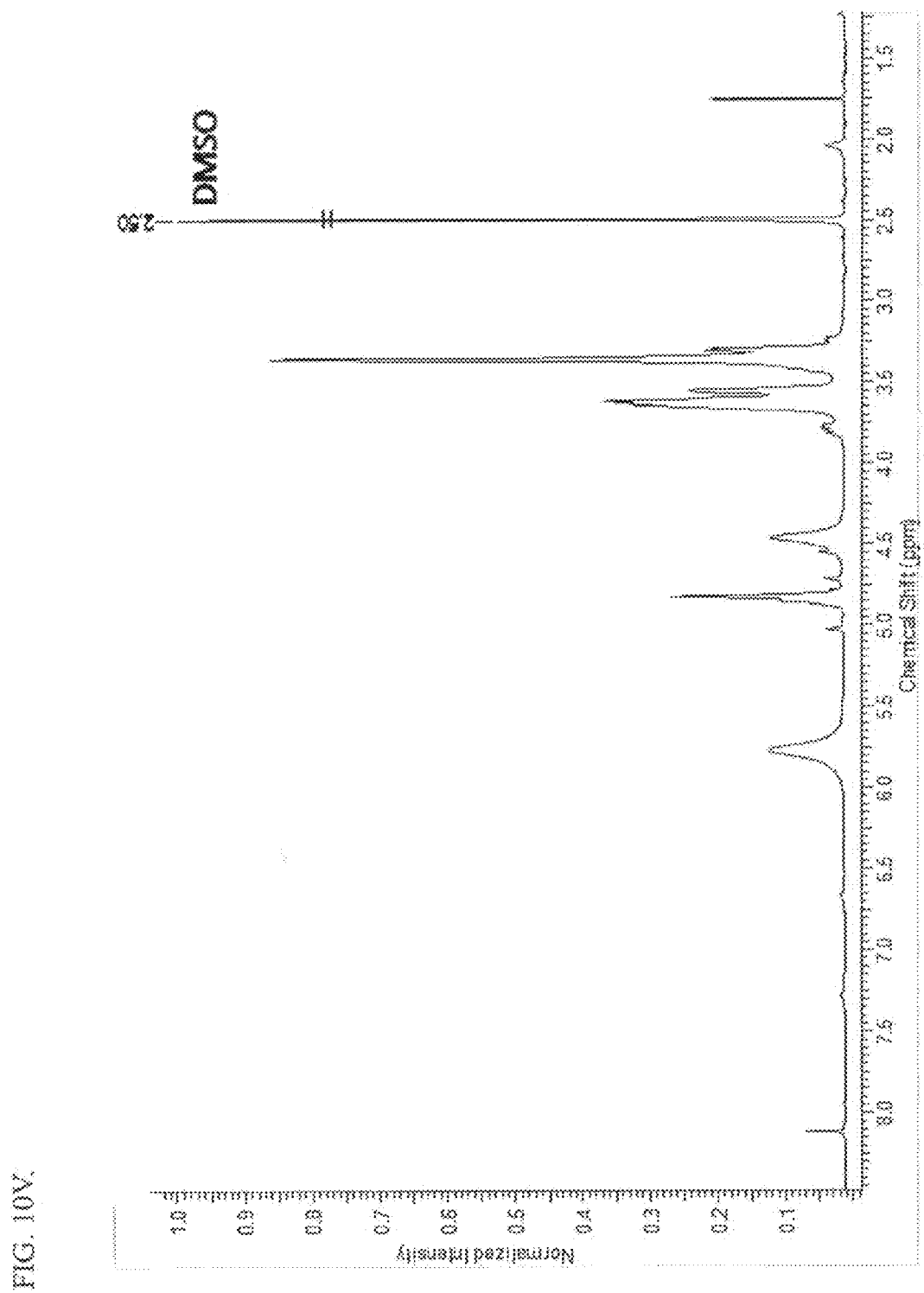

FIG. 10V. $^1$H-NMR spectrum of BCD-(TRIAZOLE)$_1$-BCD DIMER (D$_2$O, 298 K).

Figure 10W:
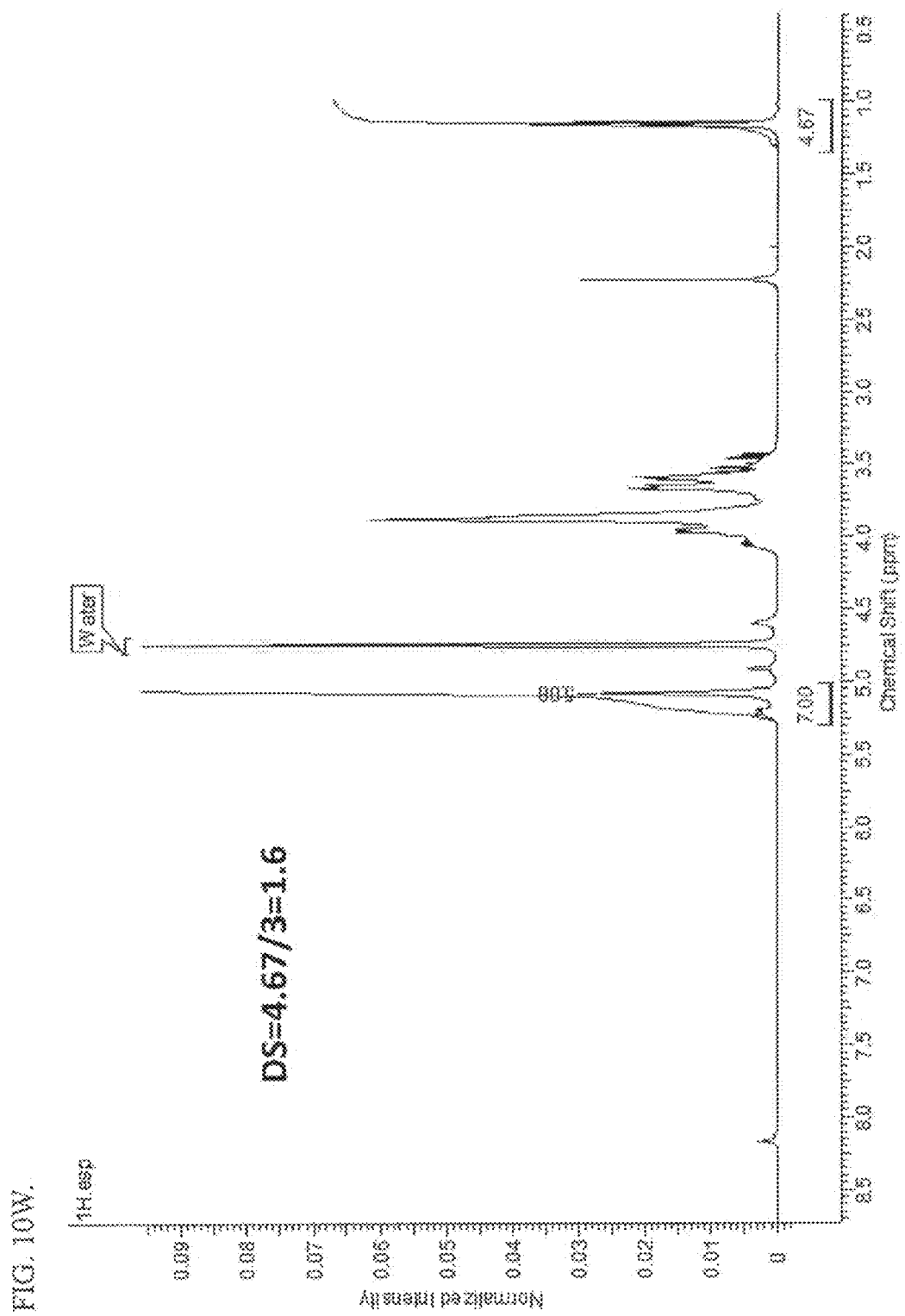

FIG. 10W. $^1$H-NMR spectrum of HP(βCD-TRIAZOLE-βCD) (D2O, 298 K) with signals labeled. Corresponds to the molecule labeled CD-Triazole-CD DS3 in FIG. 16B and elsewhere.

Figure 10X:
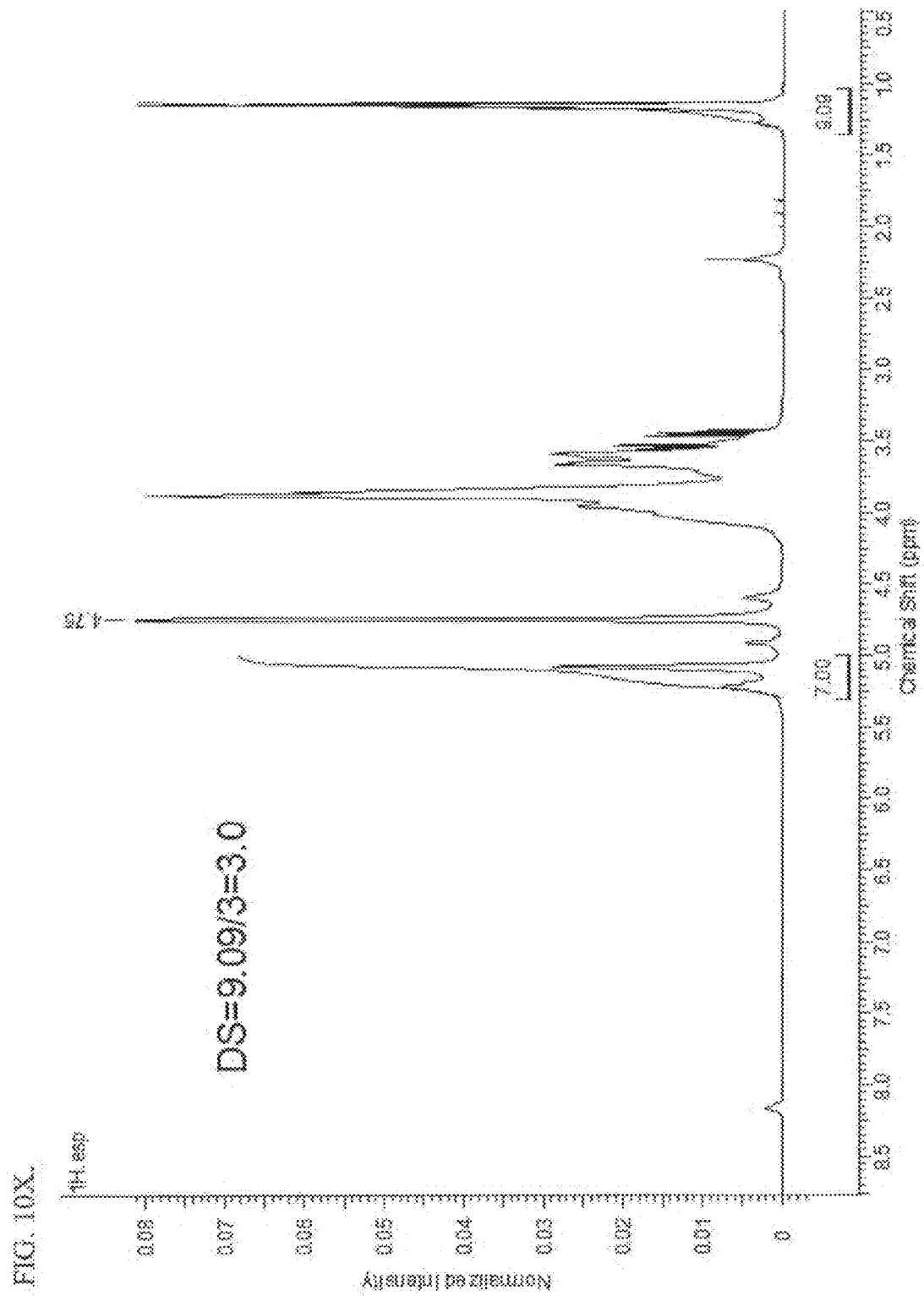

FIG. 10X. $^1$H-NMR spectrum of HP(βCD-TRIAZOLE-βCD) (D2O, 298 K) with signals labeled. Corresponds to the molecule labeled CD-Triazole-CD DS6 in FIG. 16B.

Figure 10Y:
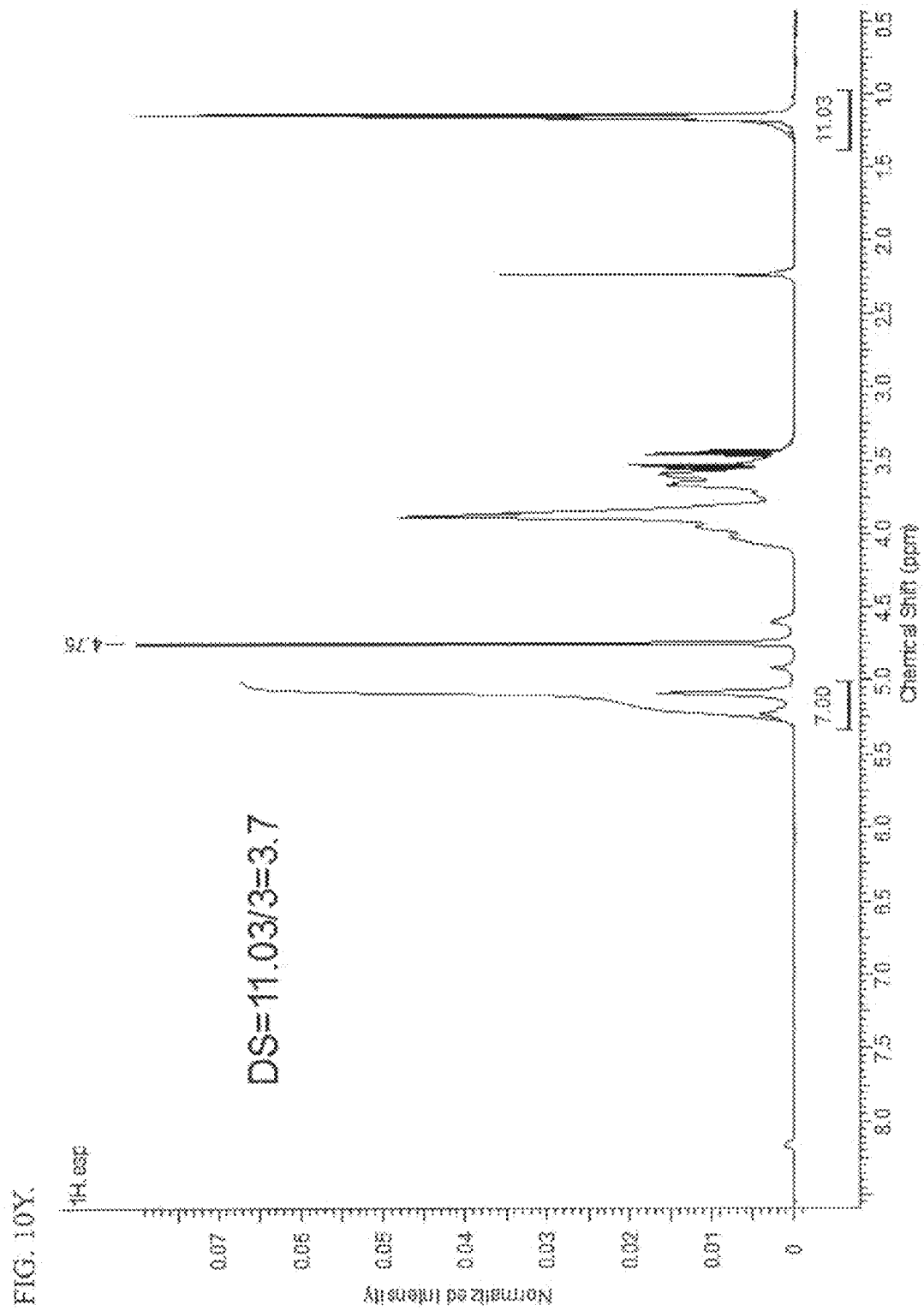

FIG. 10Y. $^1$H-NMR spectrum of HP(βCD-TRIAZOLE-βCD) (D2O, 298 K) with signals labeled. Corresponds to the molecule labeled CD-Triazole-CD DS7 in FIG. 16B.

Figure 11A:
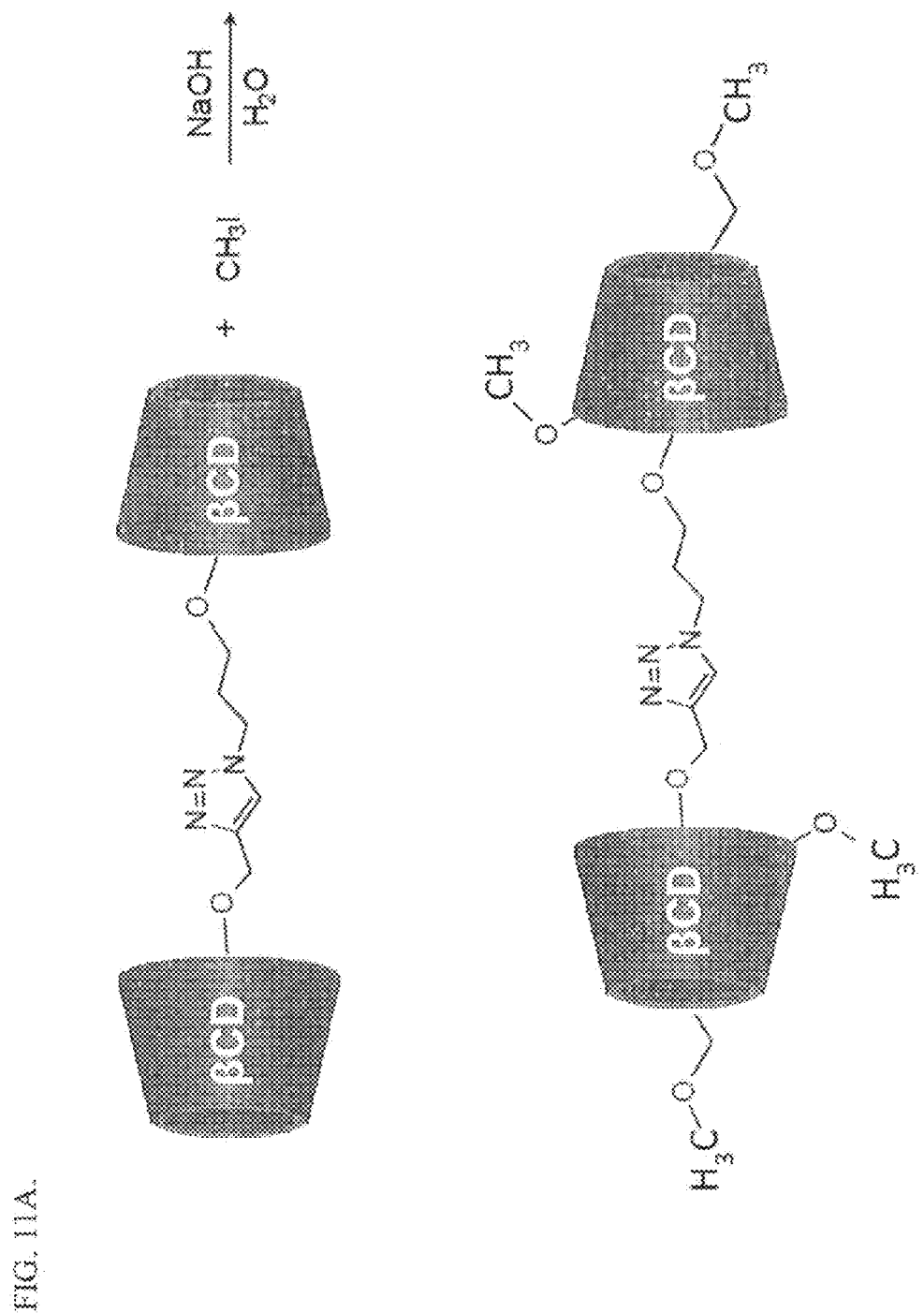

FIG. 11A. Synthetic scheme for methylated βCD dimer.

FIG. 11B. TLC analysis used for evaluating reaction process and conversion rate.

FIG. 11C. MALDI spectrum of final compound obtained with reaction in (A).

Figure 11D:
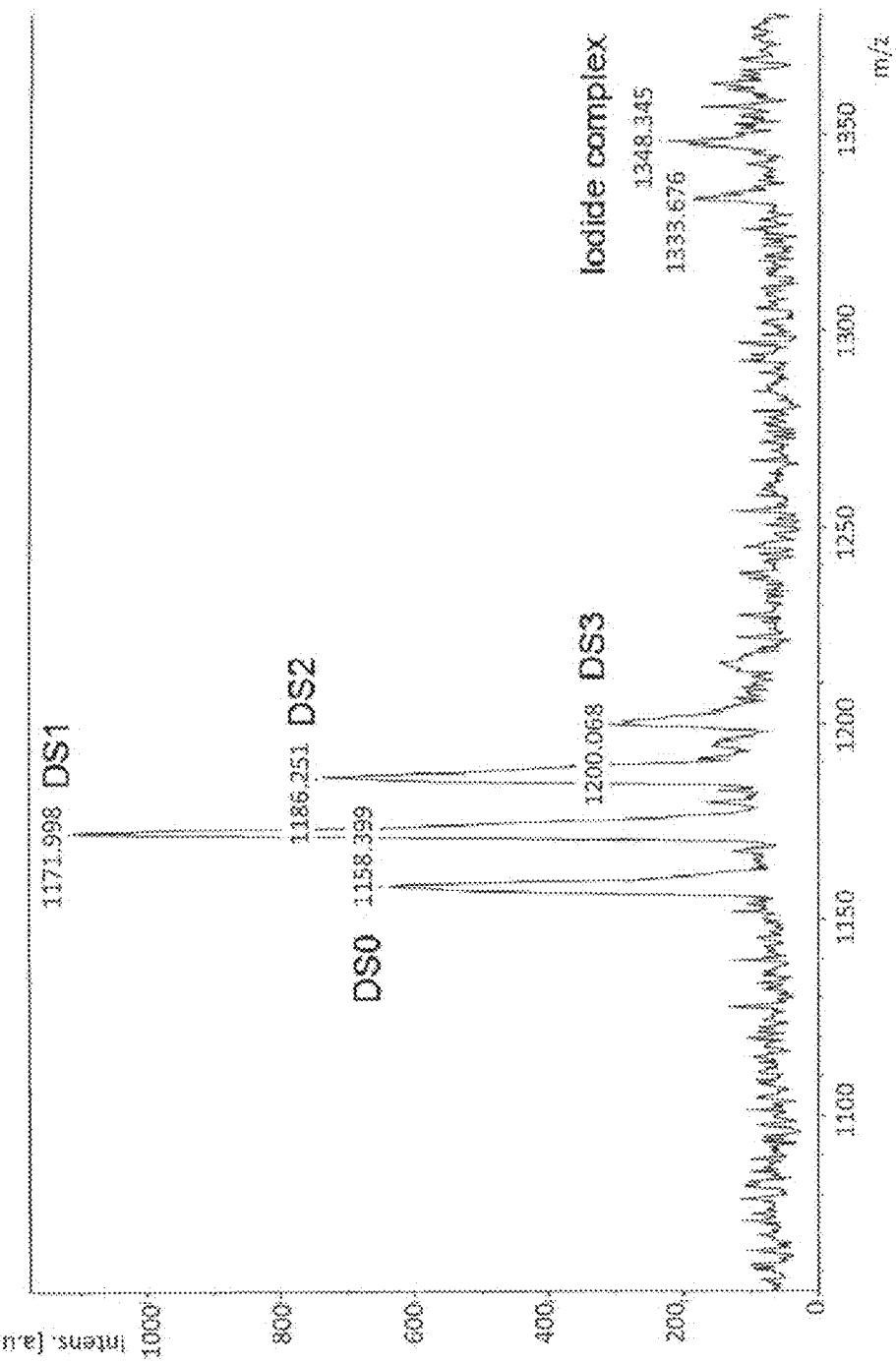

FIG. 11D. MALDI spectrum of final compound obtained with reaction in (B).

Figure 11E:
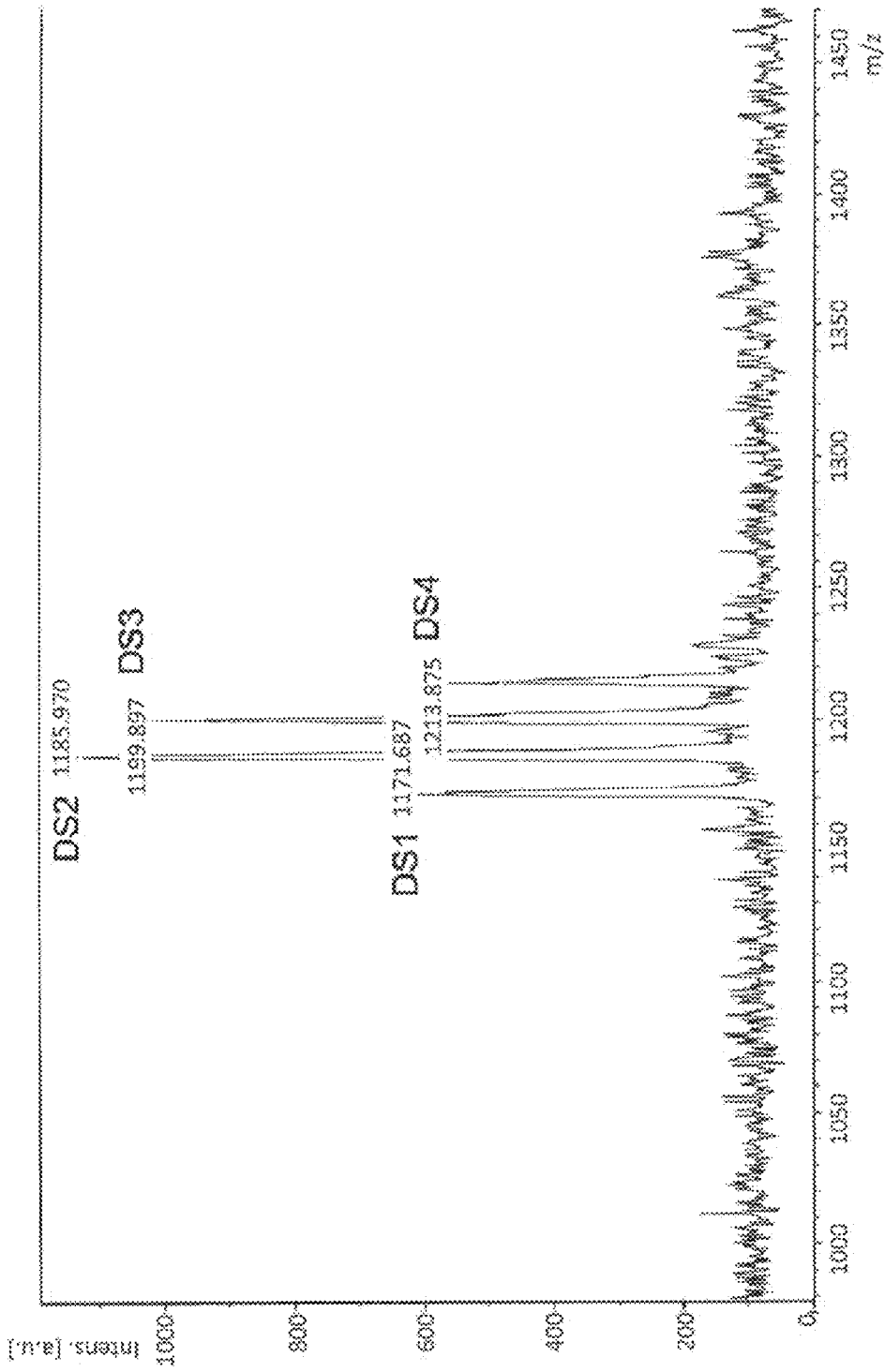

FIG. 11E. MALDI spectrum of final compound obtained with reaction in (C).

Figure 11F:
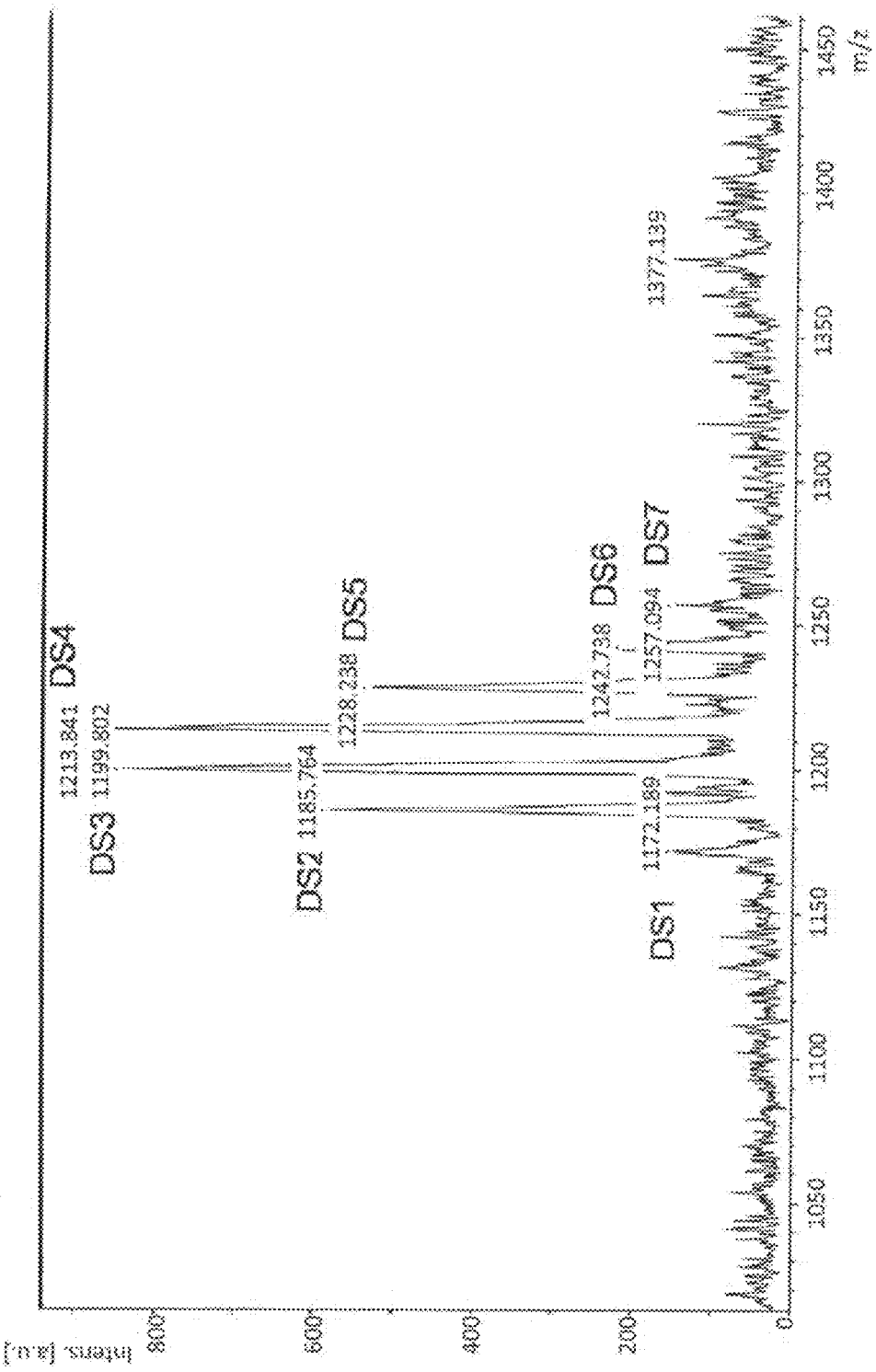

FIG. 11F. MALDI spectrum of final compound obtained with reaction in (D).

Figure 11G:
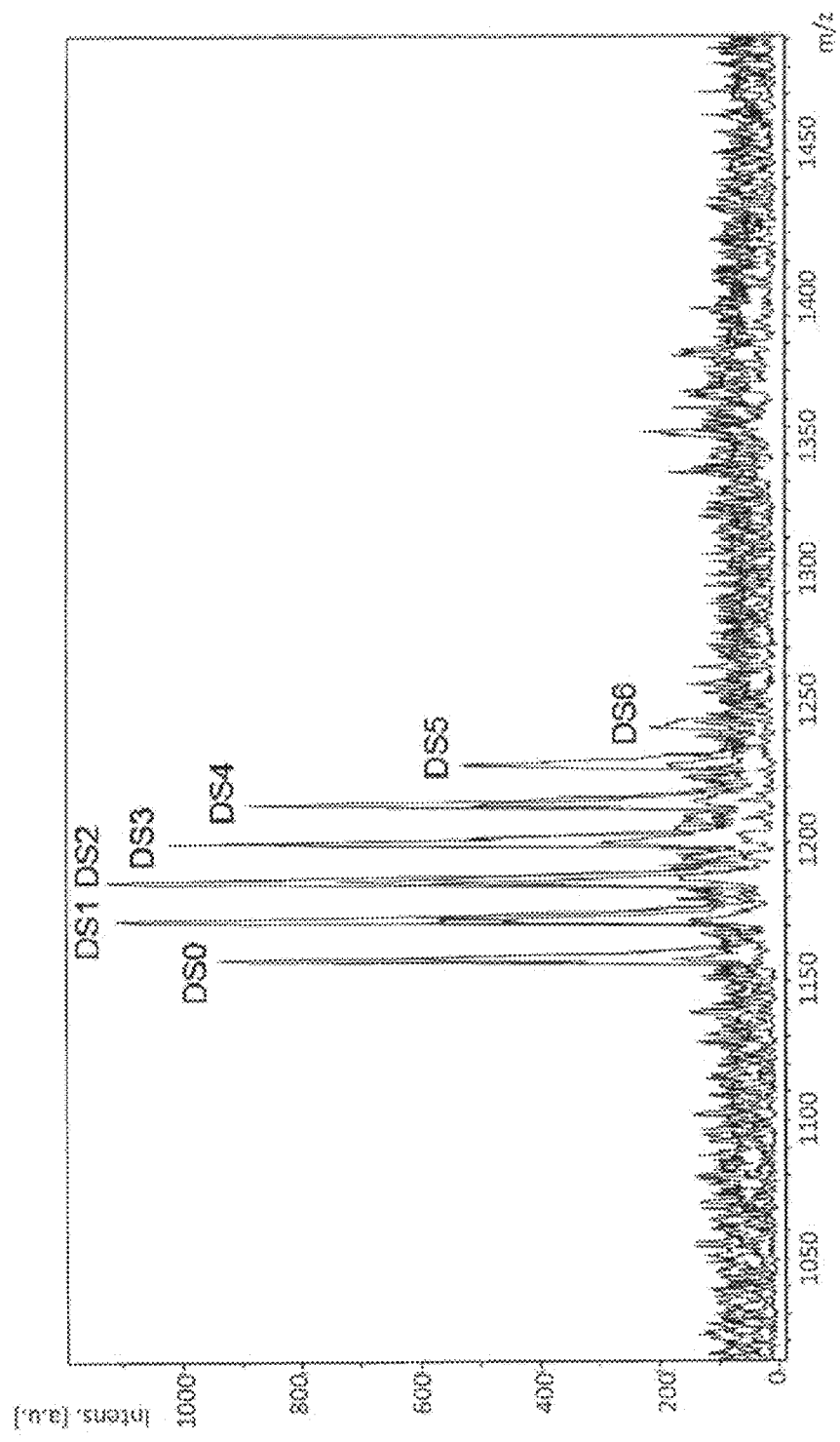

FIG. 11G. Superimposed MALDI spectra of reaction trails. Reaction A (DS0), reaction B (DS1), reaction C (DS2), and reaction D (DS4, 5, 6).

Figure 11H:
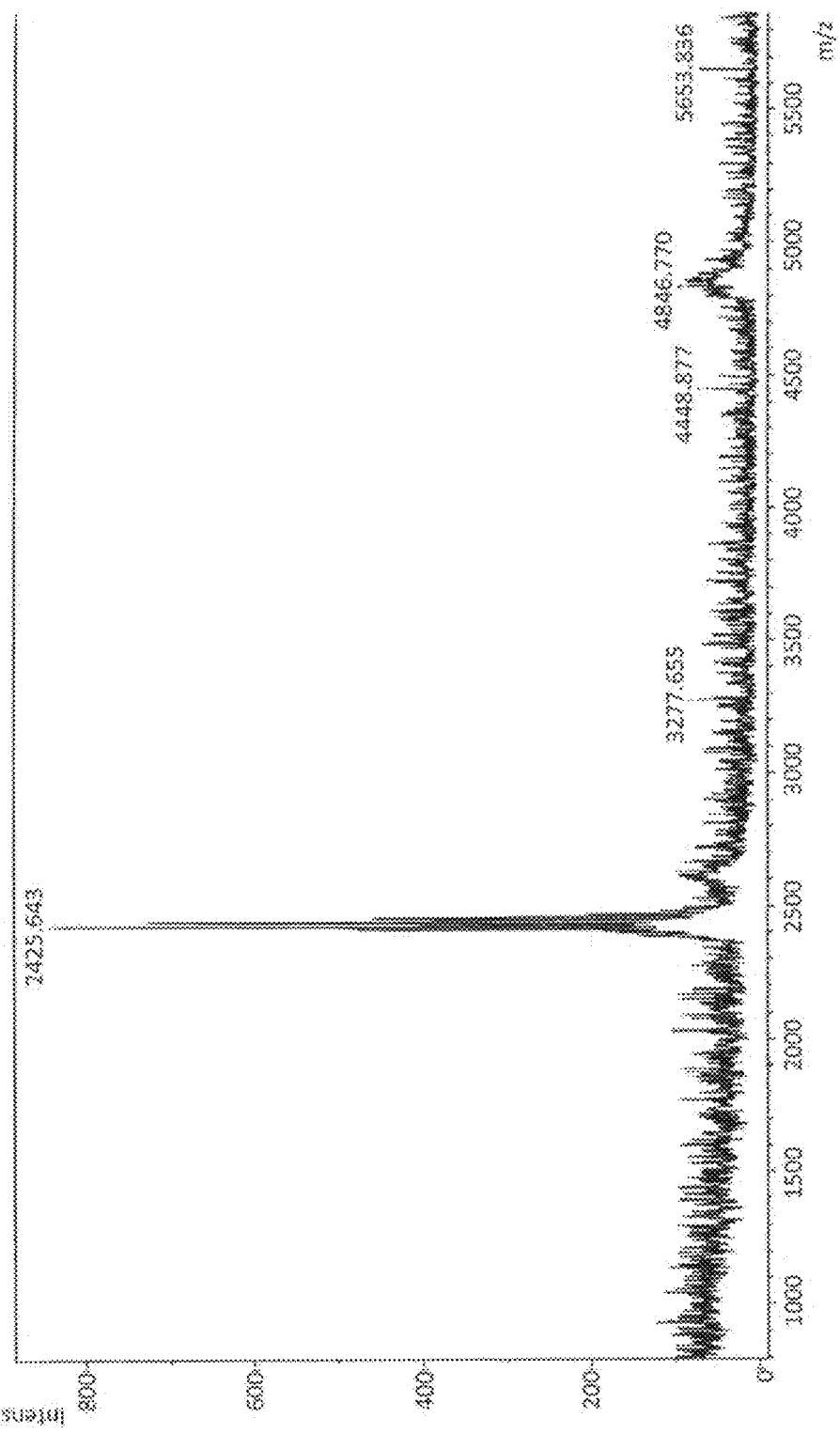
Figure 111:
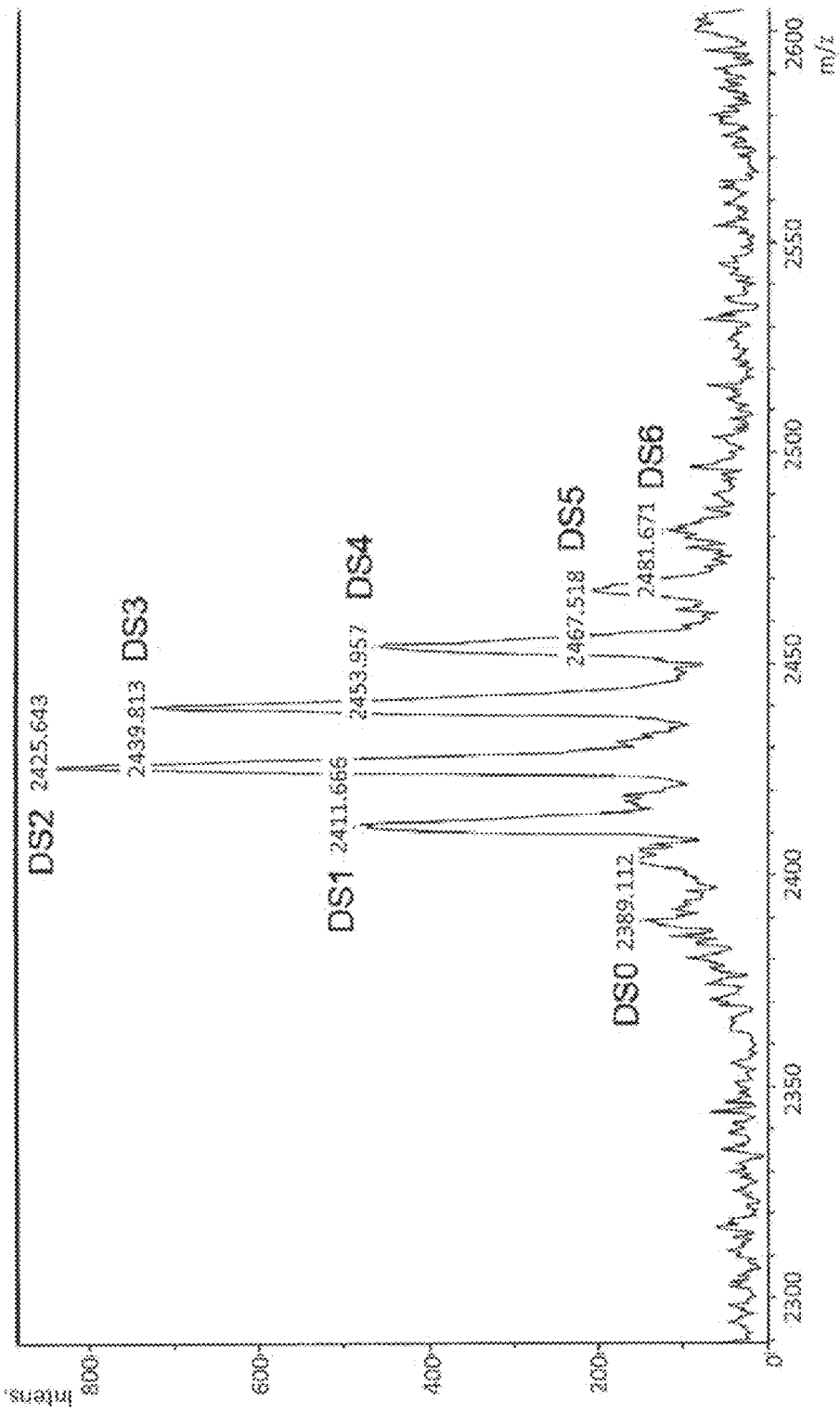

FIG. 11H. MALDI spectrum of Me-(βCD-TRIAZOLE-βCD) dimer.

FIG. 11I. Enlargement of MALDI spectrum of Me-(βCD-TRIAZOLE-βCD) dimer.

Figure 11J:
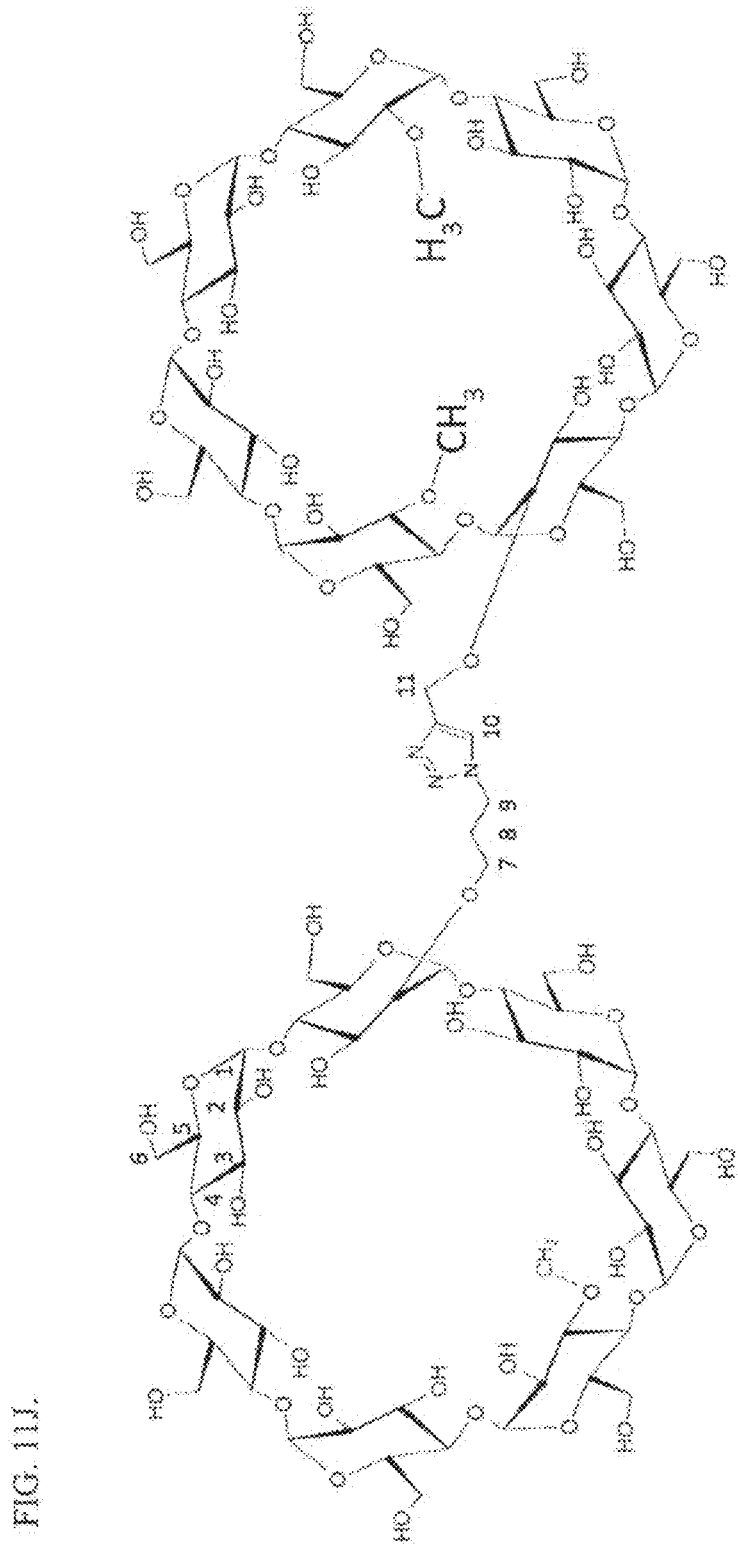

FIG. 11J. Structure of one possible isomer of Me-(βCD-TRIAZOLE-βCD) dimer with atom numbering.

Figure 11K:
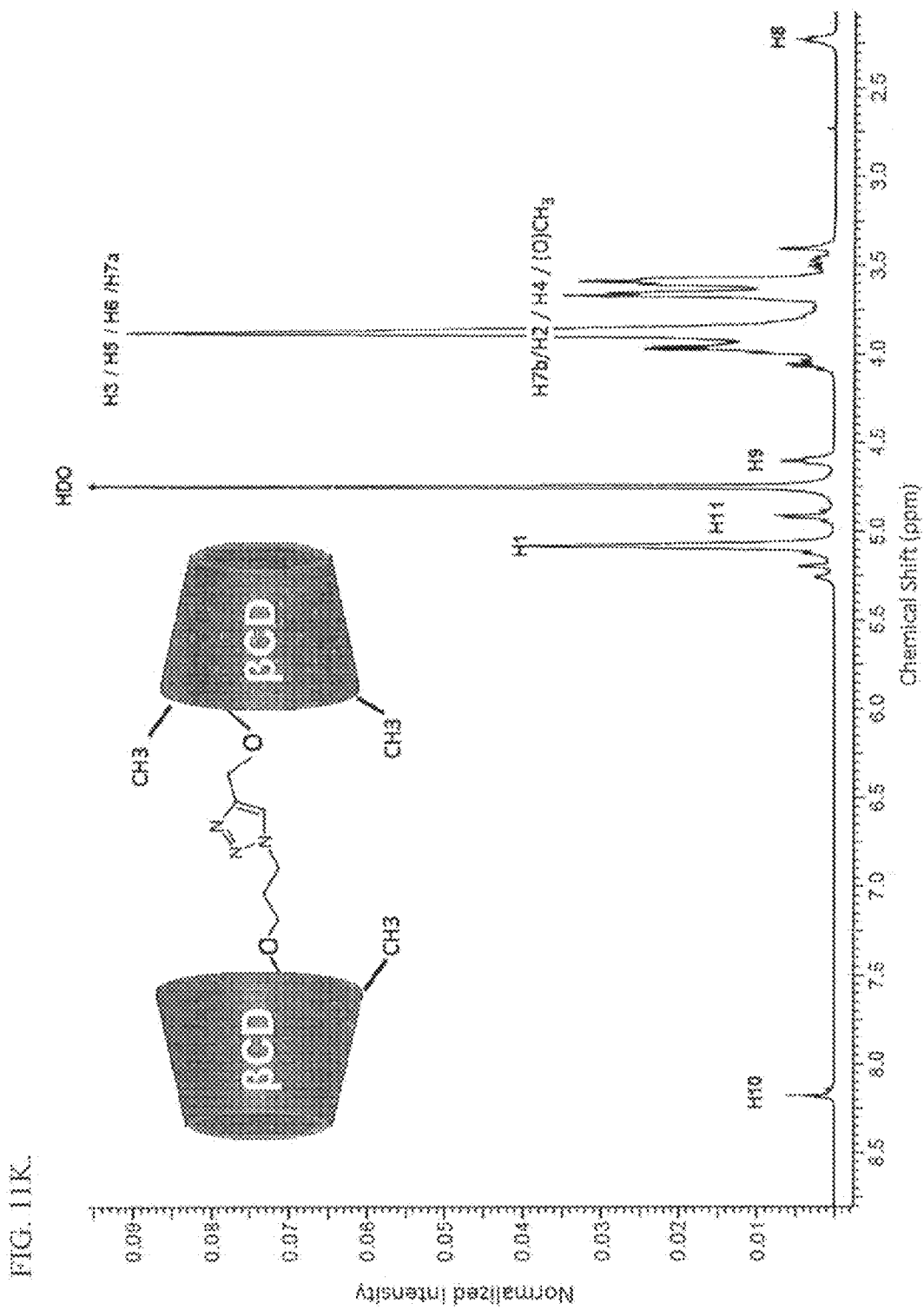

FIG. 11K. HNMR spectrum of Me-(βCD-TRIAZOLE-βCD) dimer with full assignment of the frequencies.

Figure 11L:
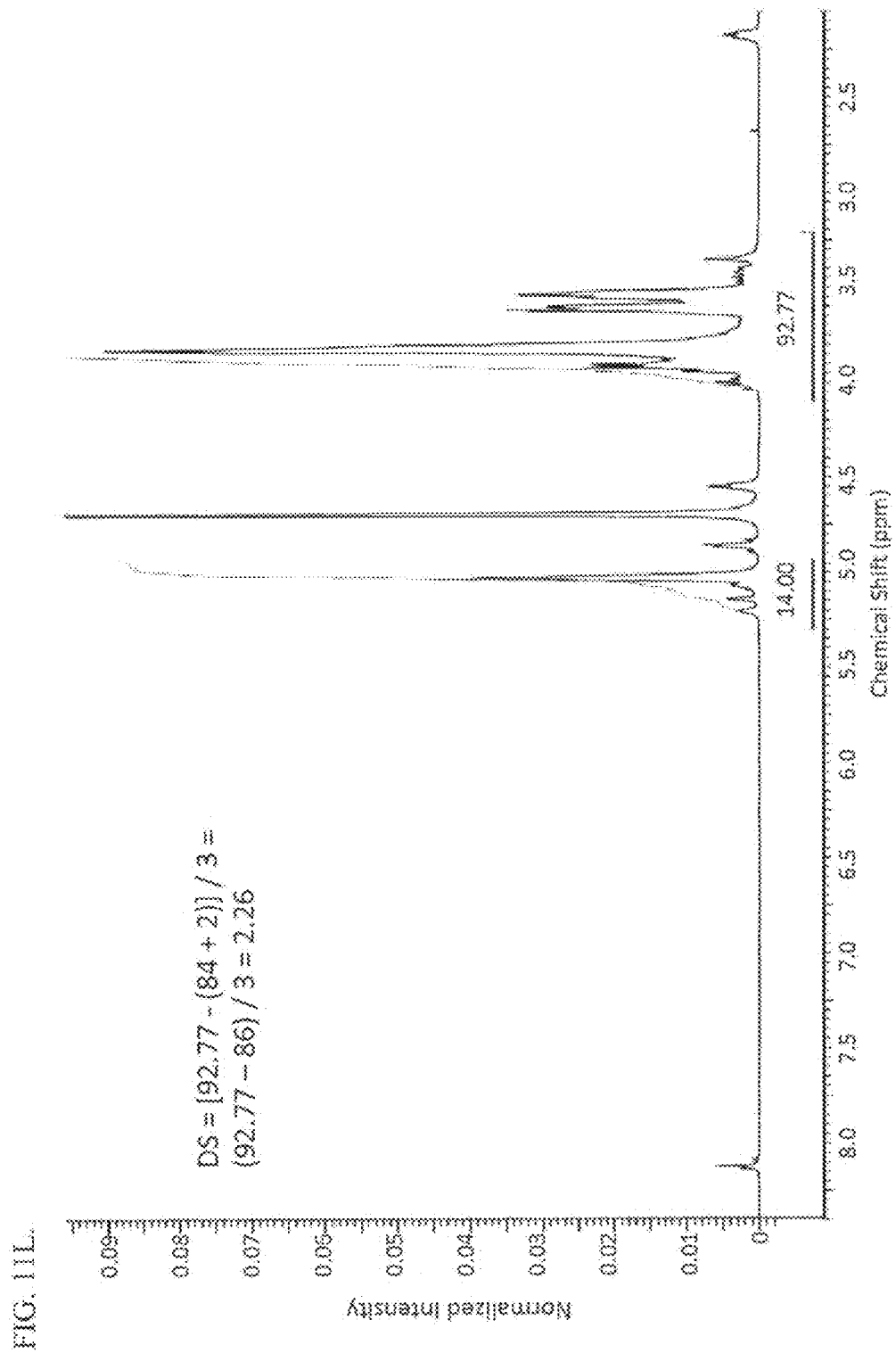

FIG. 11L. HNMR spectrum of Me-(βCD-TRIAZOLE-βCD) dimer with integration.

Figure 11M:
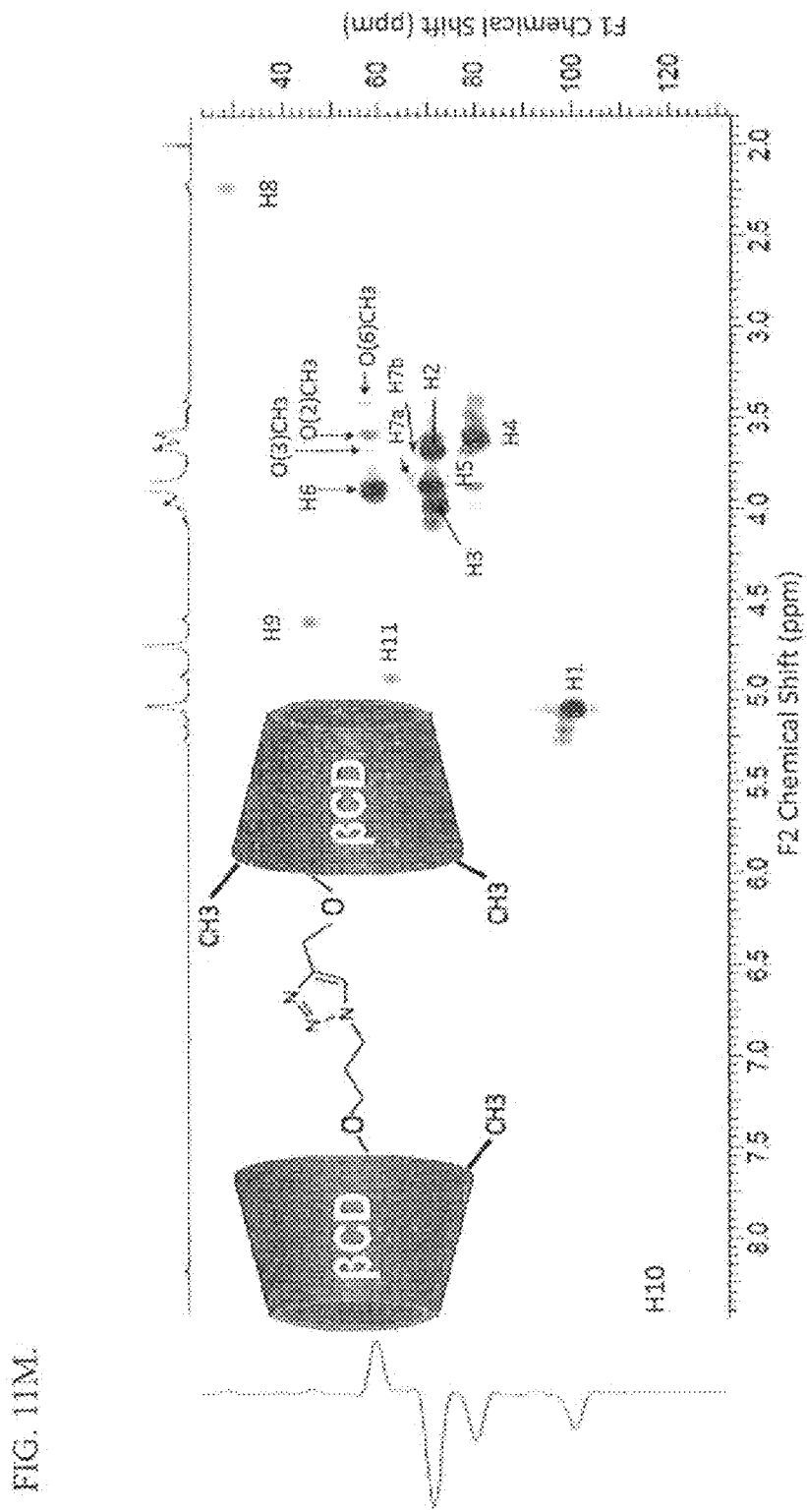

FIG. 11M. DEPT-edited HSQC spectrum of Me-(βCD-TRIAZOLE-βCD) dimer with full assignment.

Figure 11N:
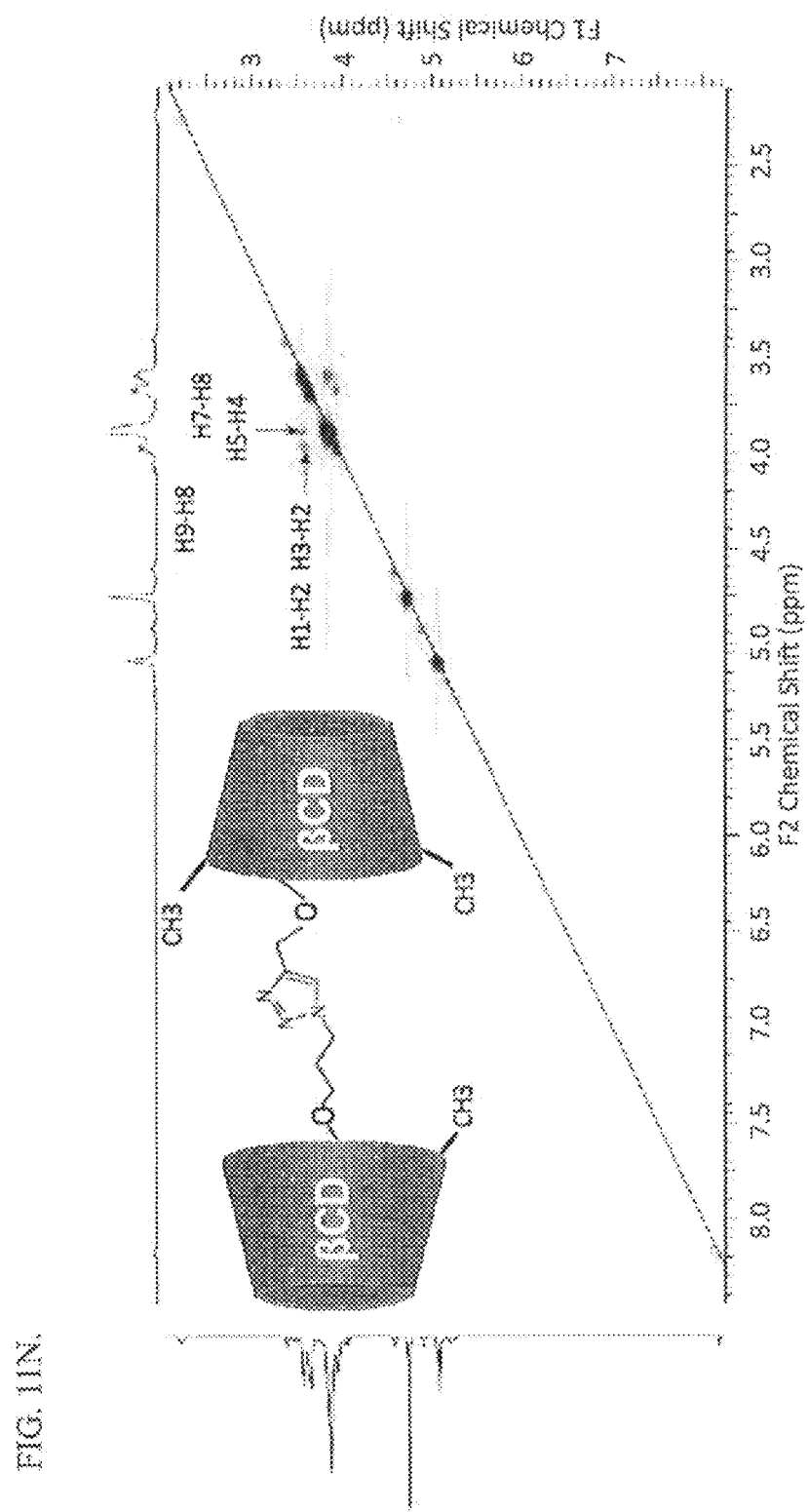

FIG. 11N. COSY-NMR spectrum of Me-(βCD-TRIAZOLE-βCD) dimer with assignment.

Figure 12B:
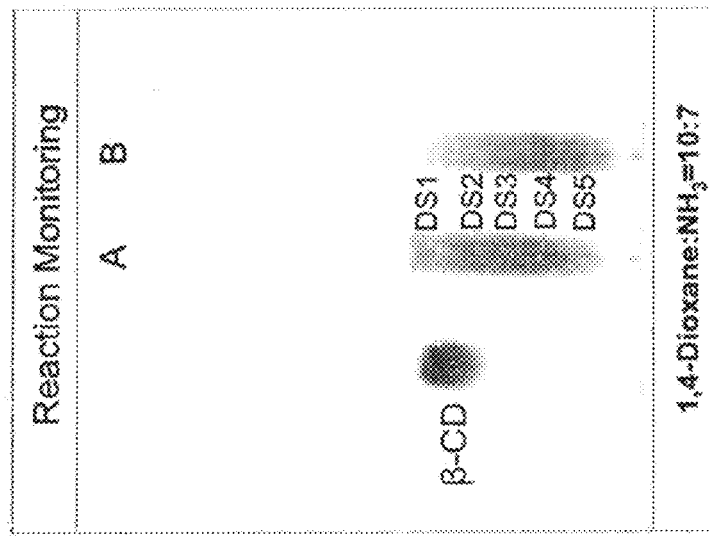
Figure 12A:
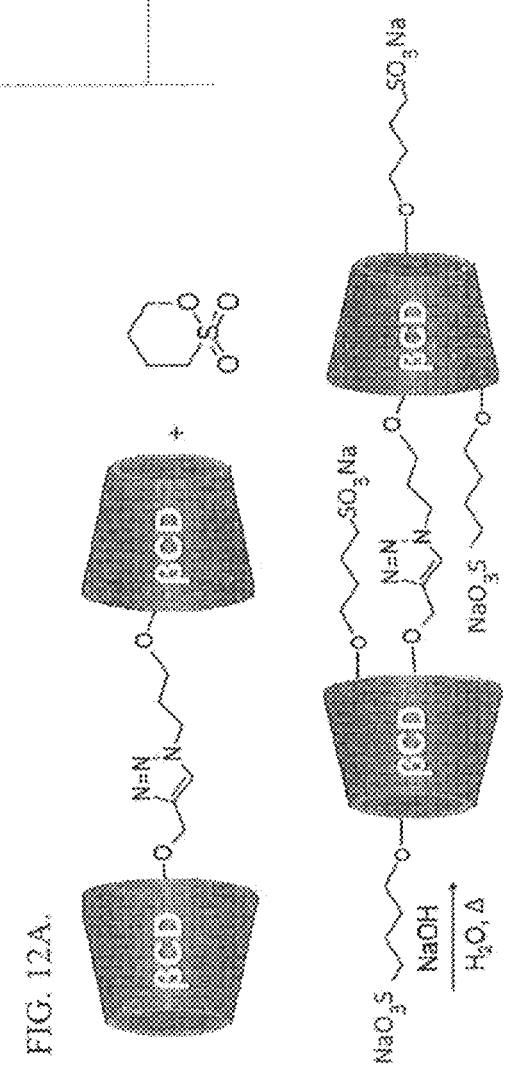

FIG. 12A. Synthetic scheme for sulfobutylated βCD dimer.

FIG. 12B. TLC analysis used for evaluating the SB-βCD trial reactions proceeding and the conversion rate.

Figure 12C:
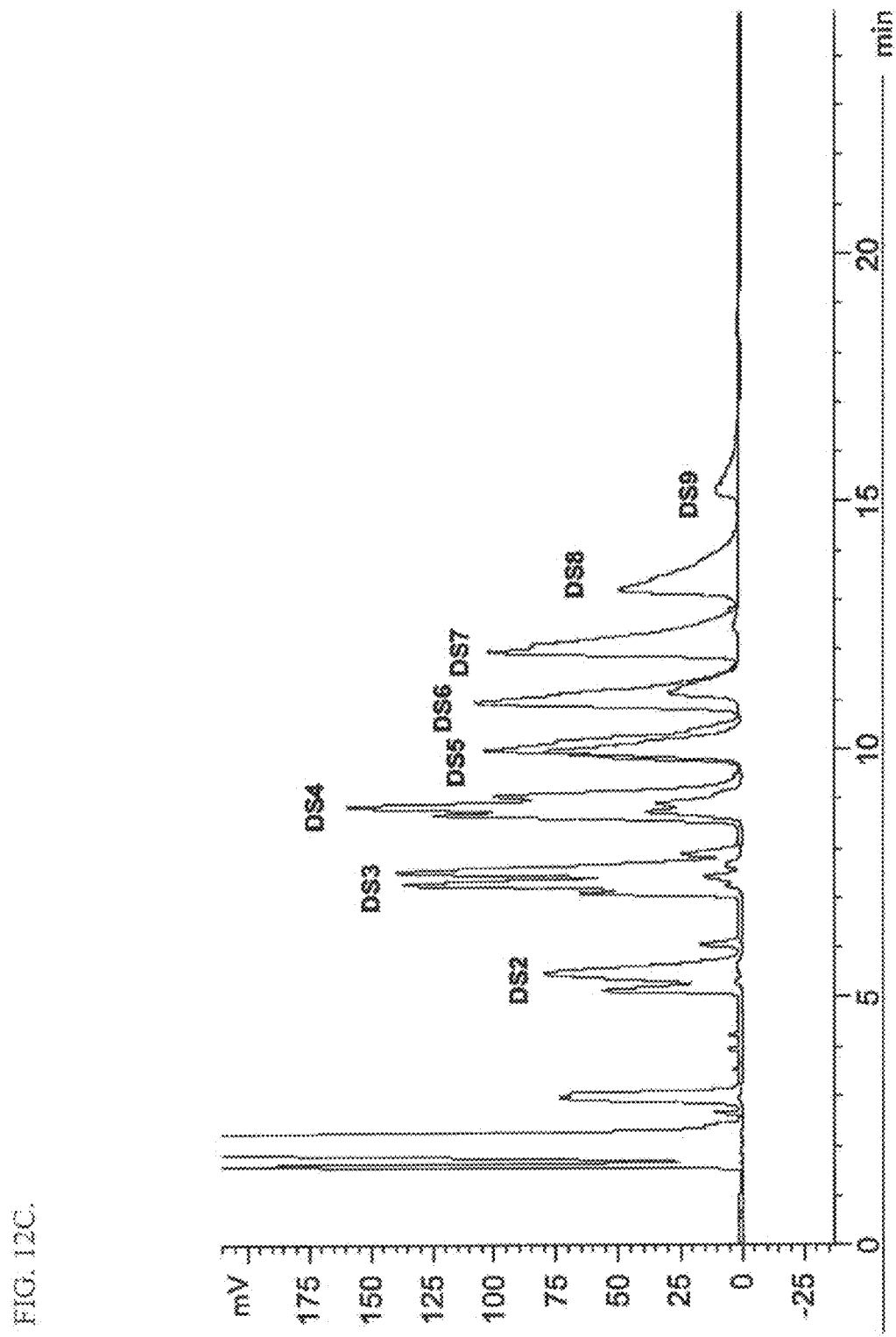

FIG. 12C. Overlaid fingerprint chromatogram analysis used for evaluating the DS of SB-βCD trial reaction A.

FIG. 12D. Overlaid fingerprint chromatogram analysis used for evaluating the DS of SB-βCD trial reaction B.

Figure 12E:
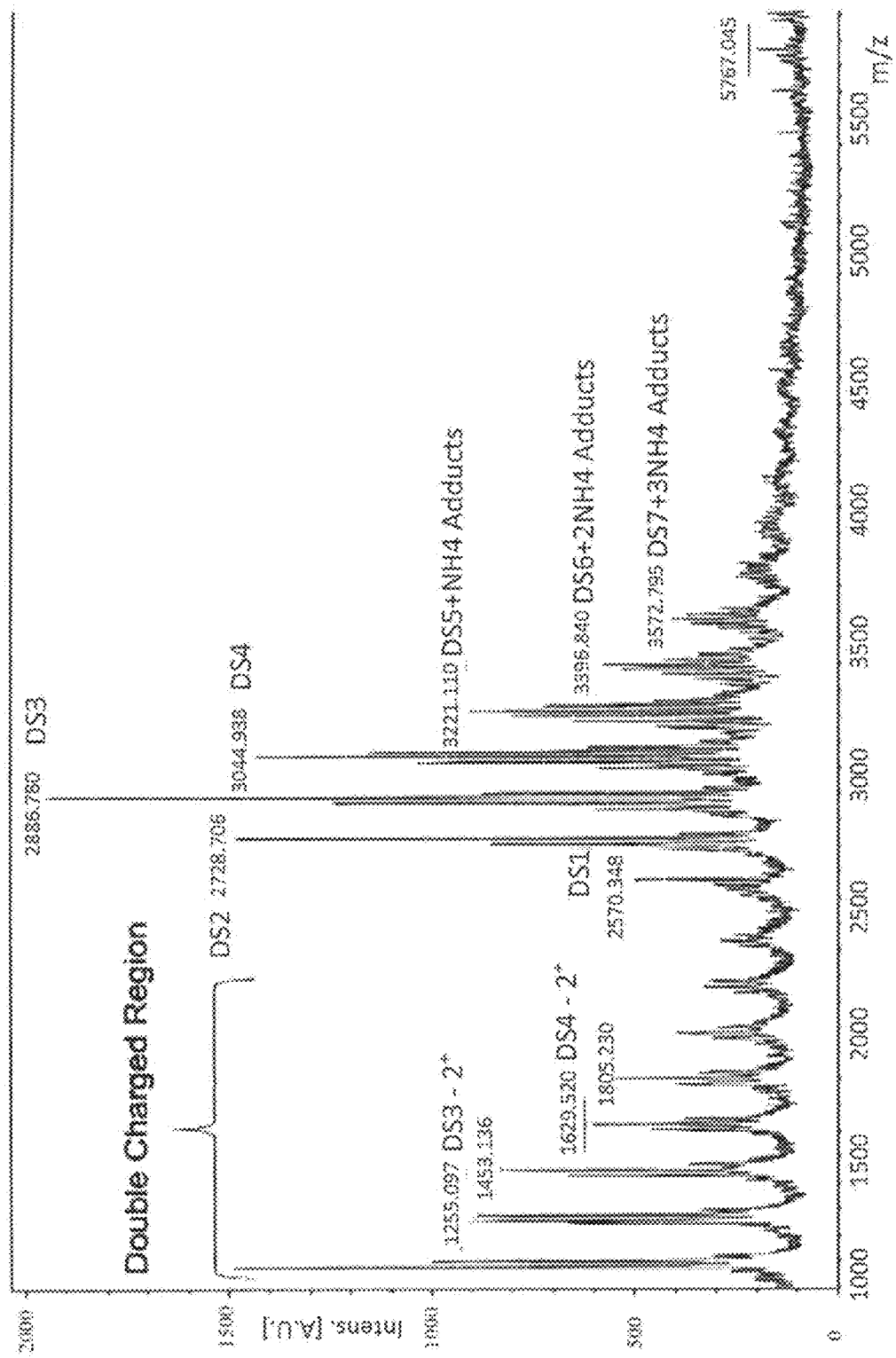

FIG. 12E. MALDI for SB-βCD dimer (Low DS).

Figure 12F:
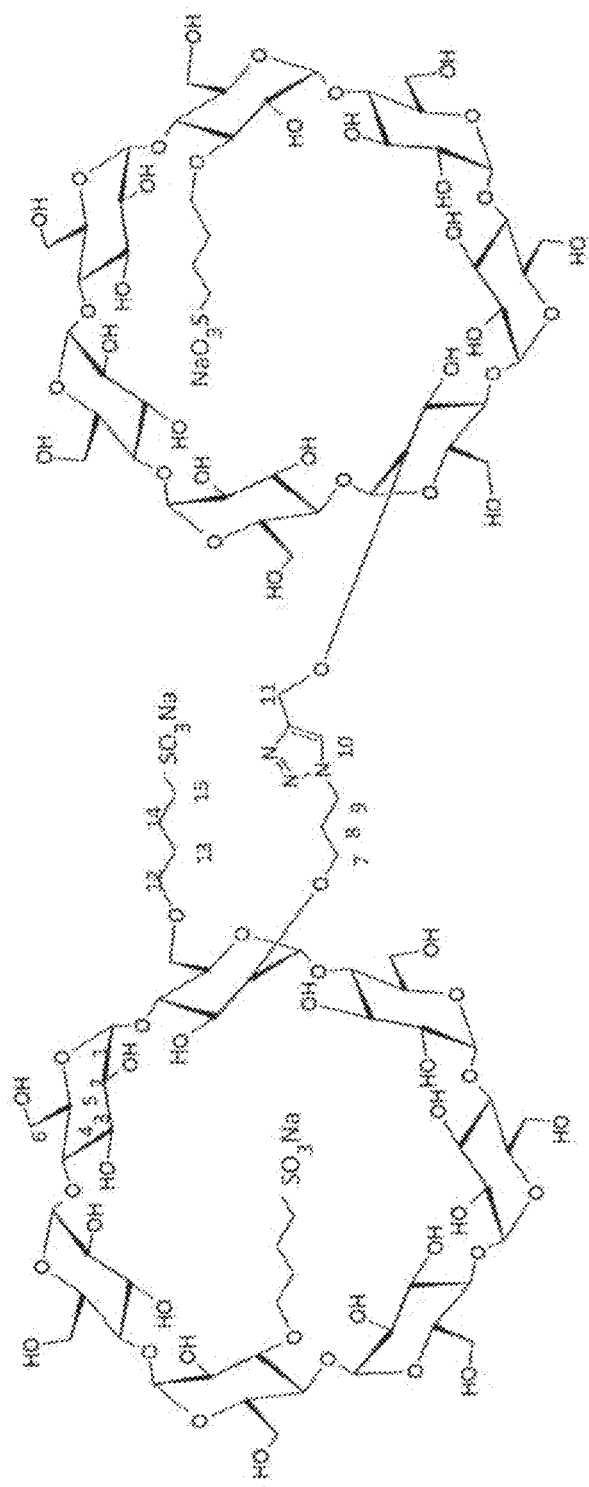

FIG. 12F. One possible isomer of SB-βCD dimer with atom numbering.

Figure 12G:
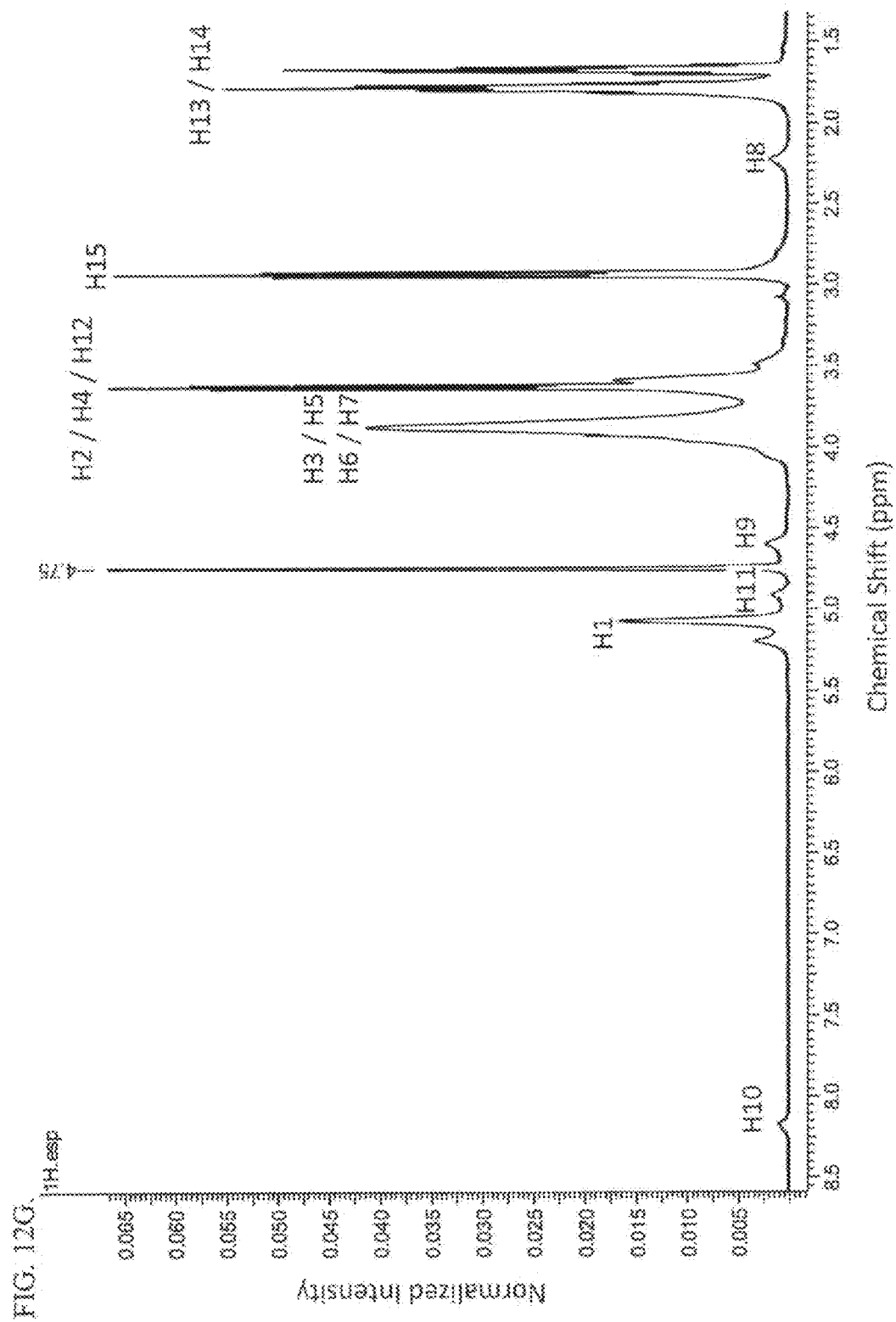

FIG. 12G. HNMR spectrum of sulfobutylated dimer (Low DS) with full assignment (D20; 298K).

Figure 12H:
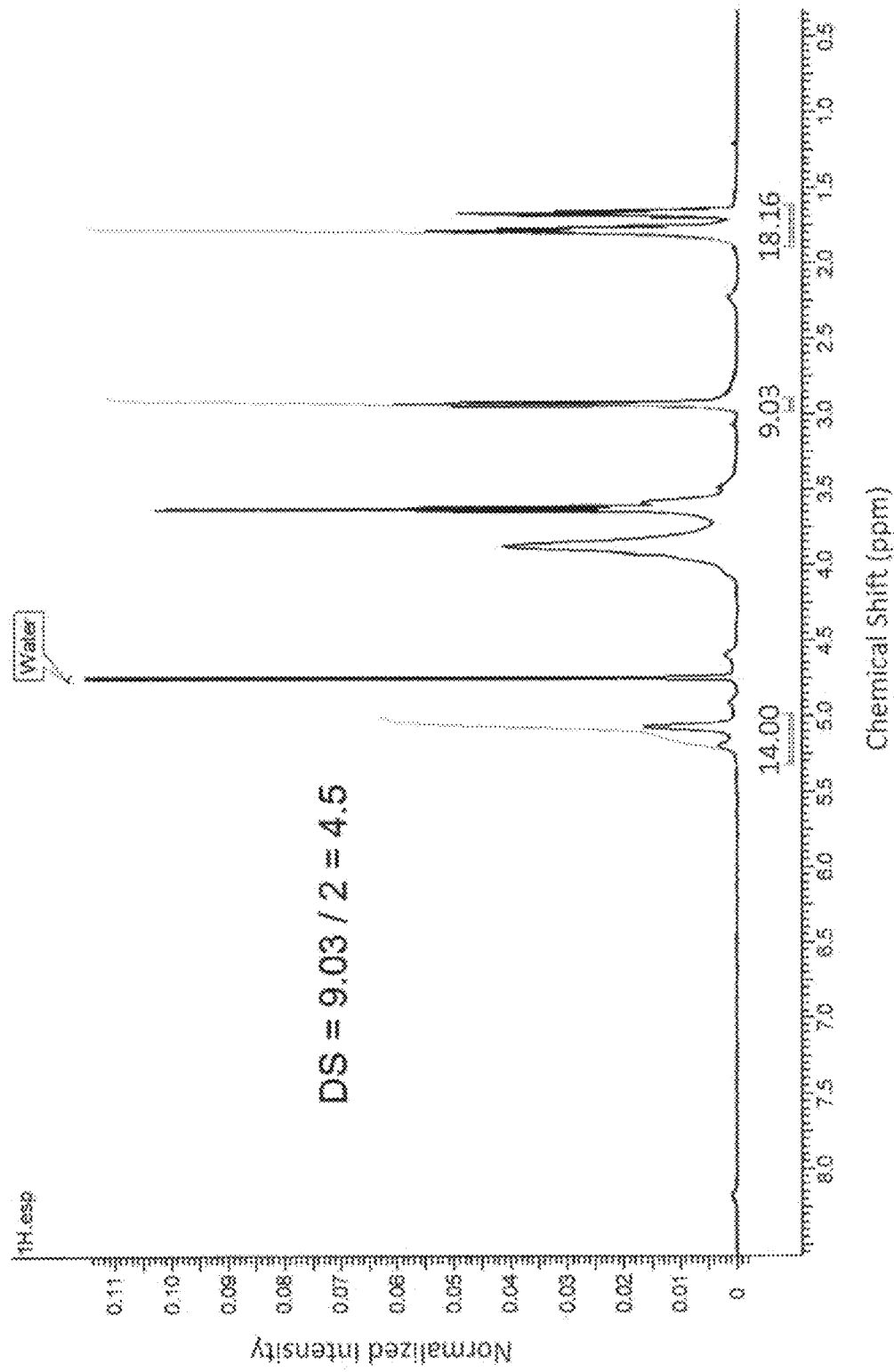

FIG. 12H. HNMR spectrum of sulfobutylated dimer (Low DS) with integration (D20; 298K). The DS value calculation based on the NMR is illustrated.

Figure 12I:
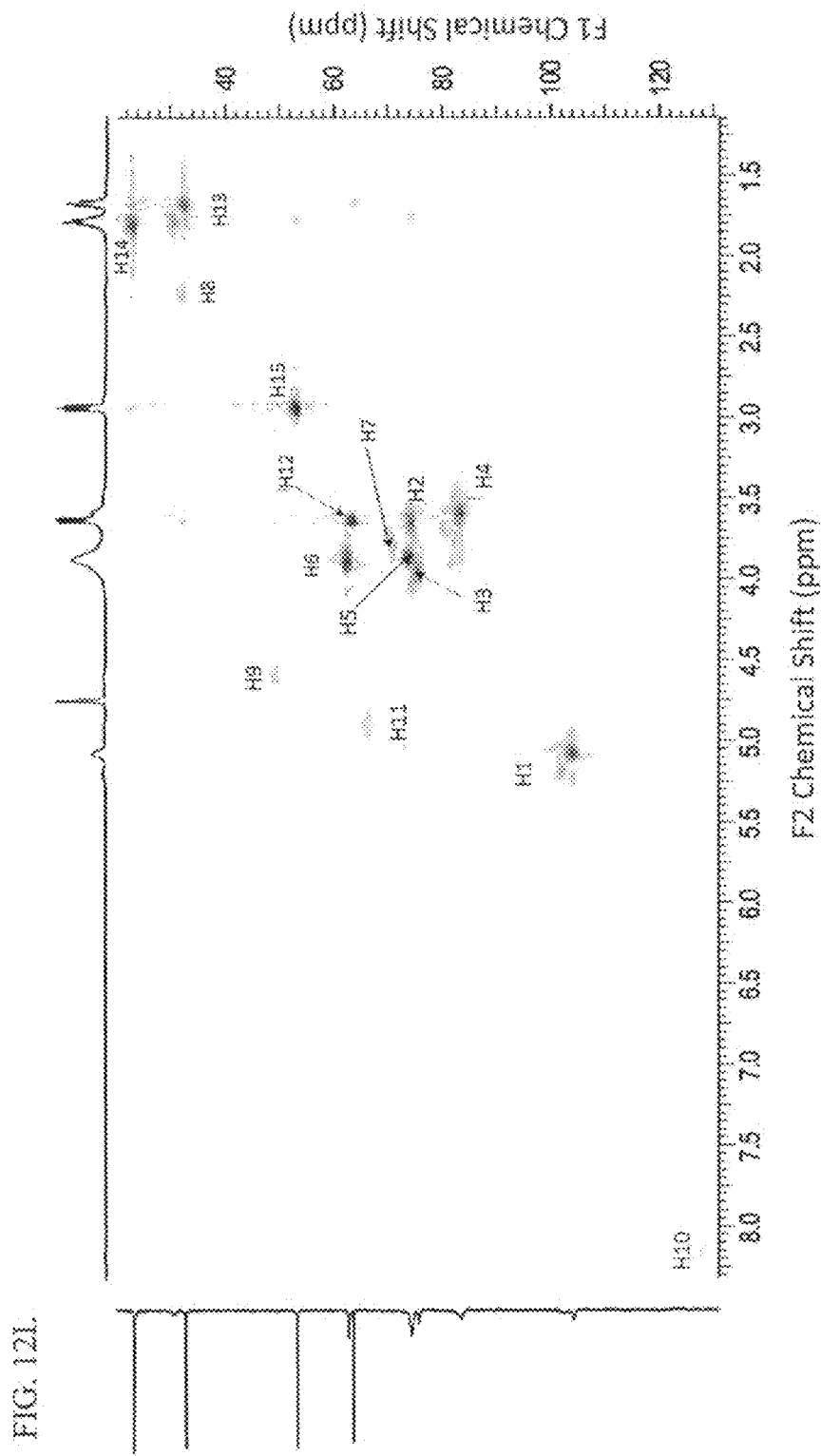
Figure 12I:
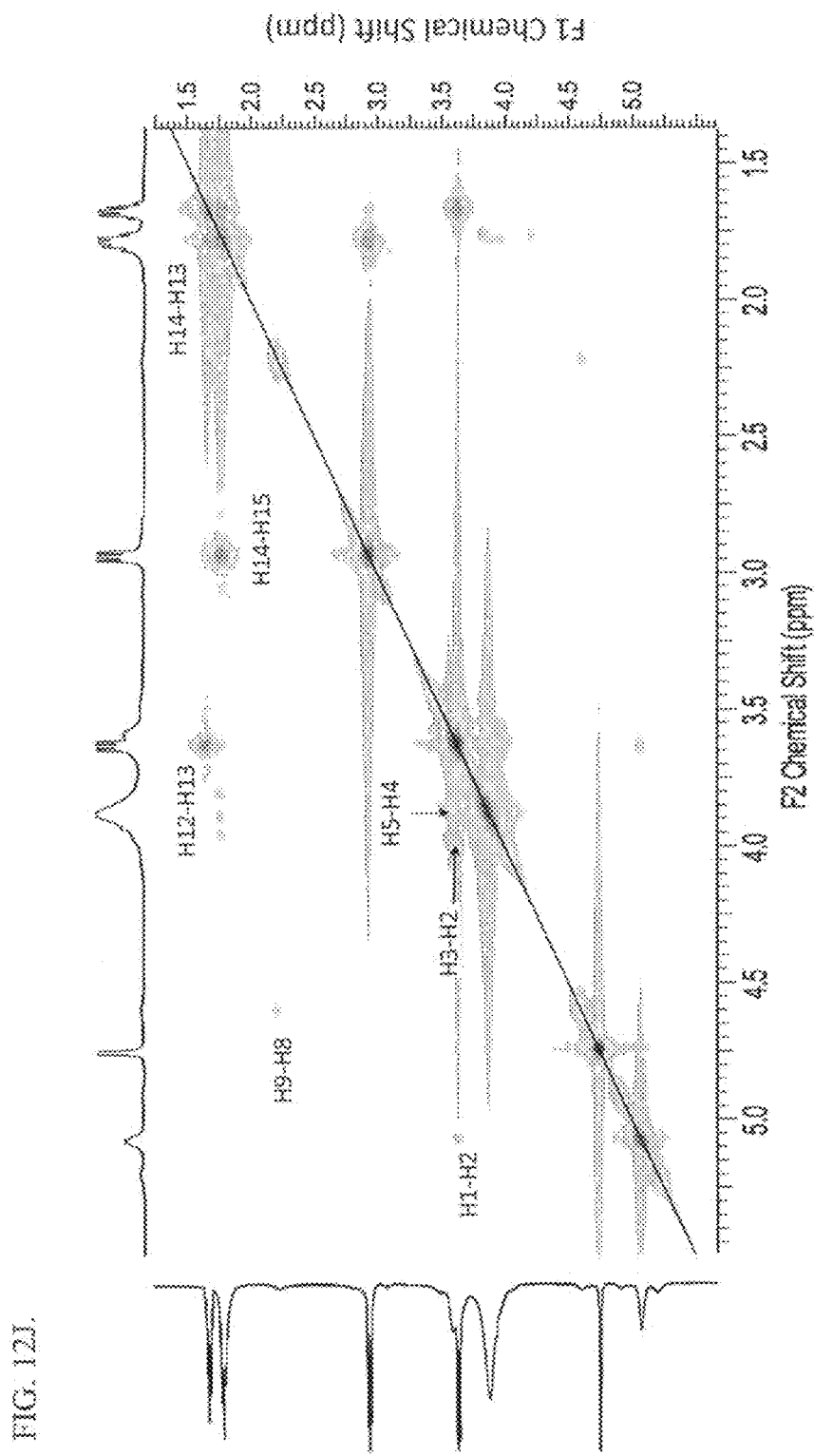

FIG. 12I. DEPT-edited HSQC spectrum of SB-dimer (Low DS) with full assignment (D2O, 298K).

FIG. 12J. COSY spectrum of SB-dimer (Low DS) with full assignment (D2O, 298K).

Figure 12K:
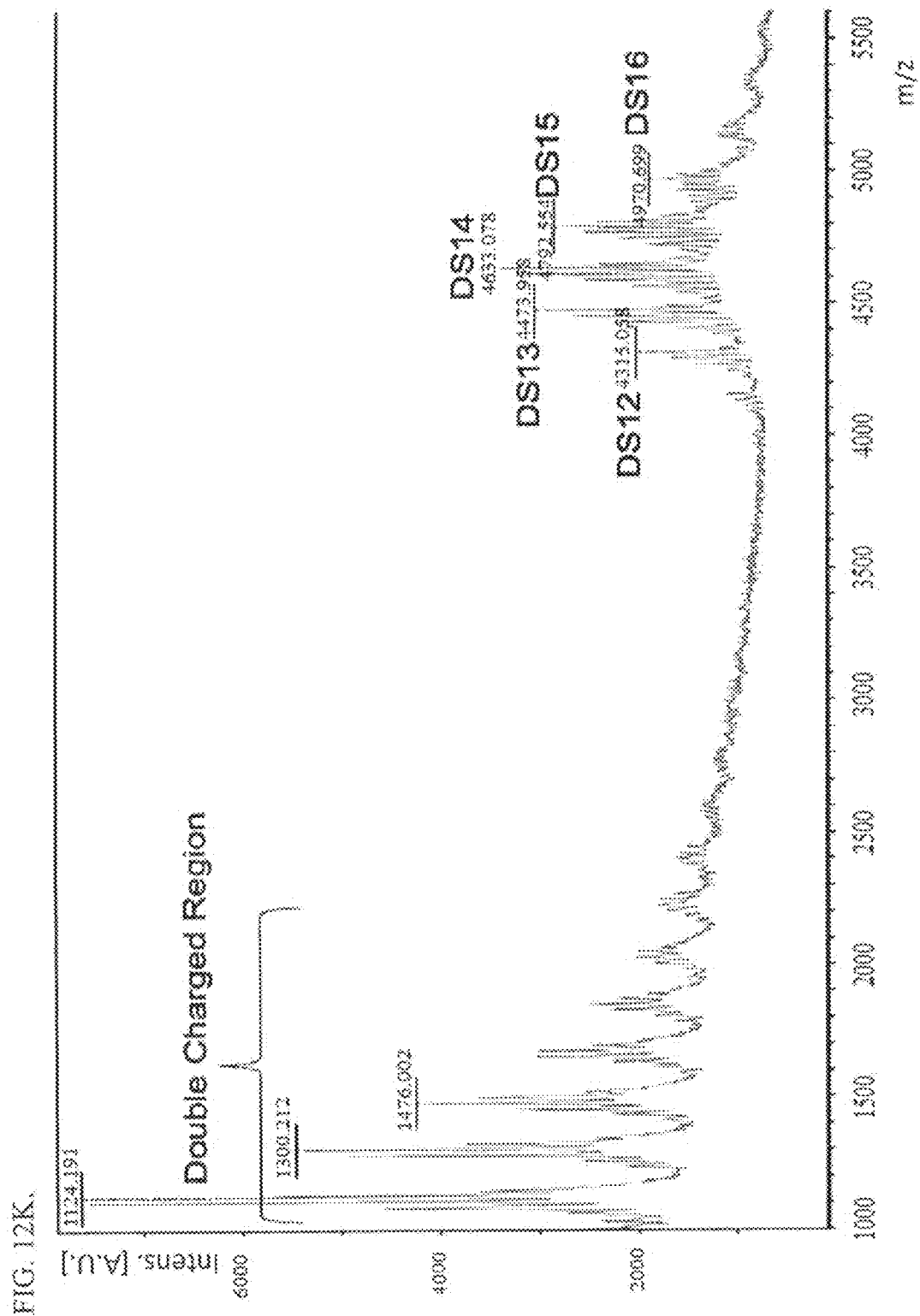

FIG. 12K. MALDI spectrum of SB-dimer (High DS).

Figure 12L:
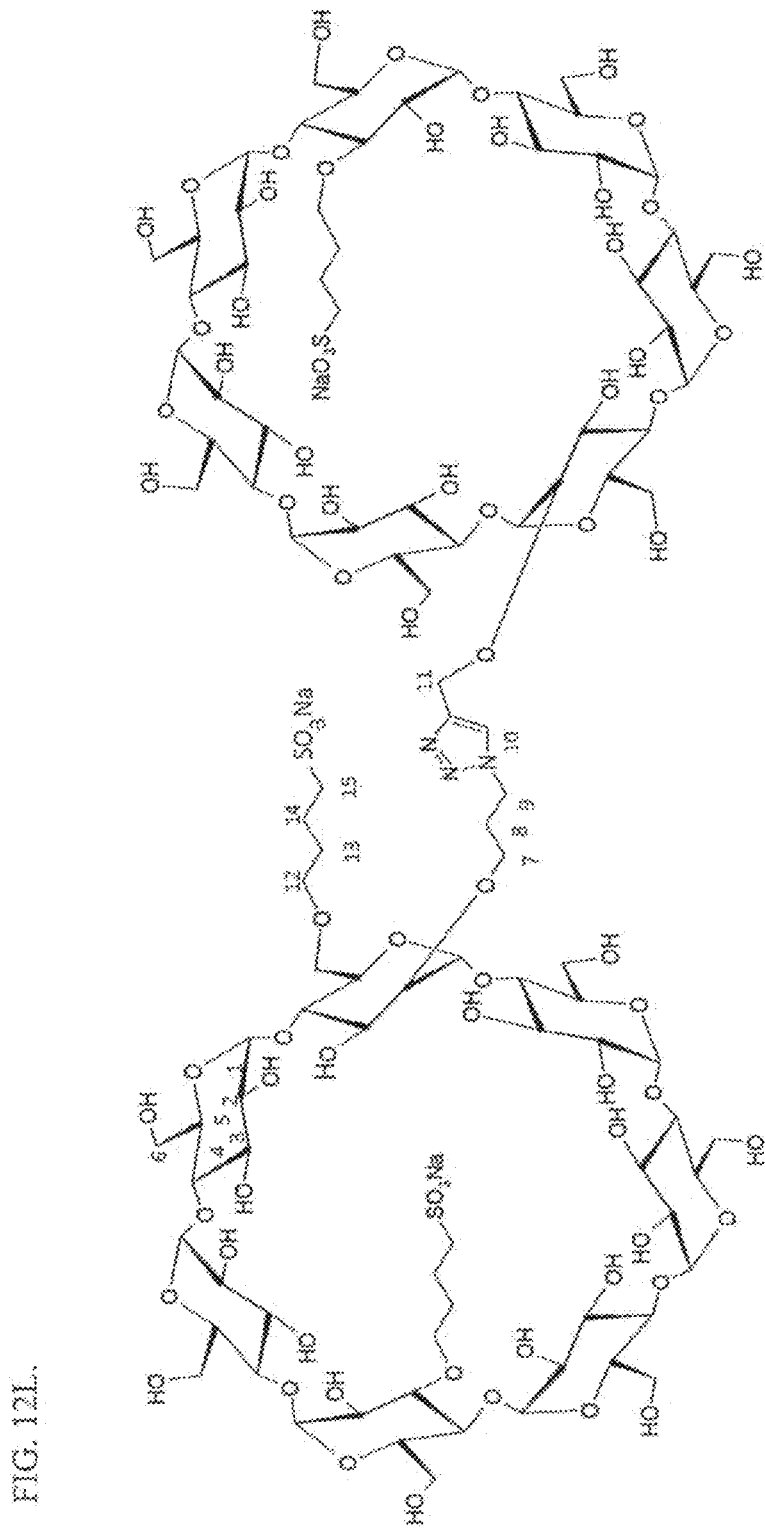

FIG. 12L. Structure of one possible isomer of SB-dimer (DS3) with atom numbering.

Figure 12M:
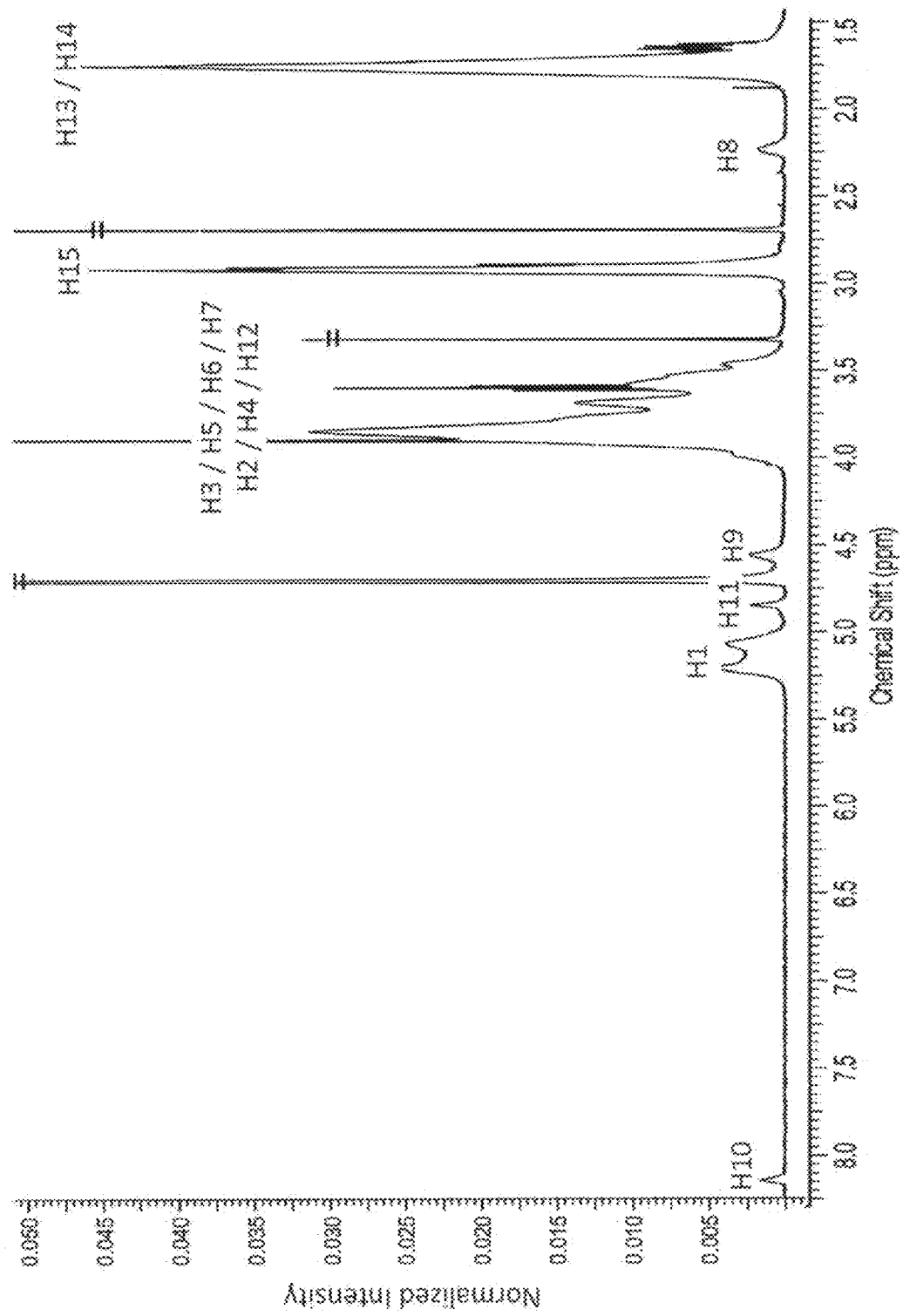

FIG. 12M. HNMR spectrum of SB-dimer (High DS) with full assignment (D20, 298K).

Figure 12N:
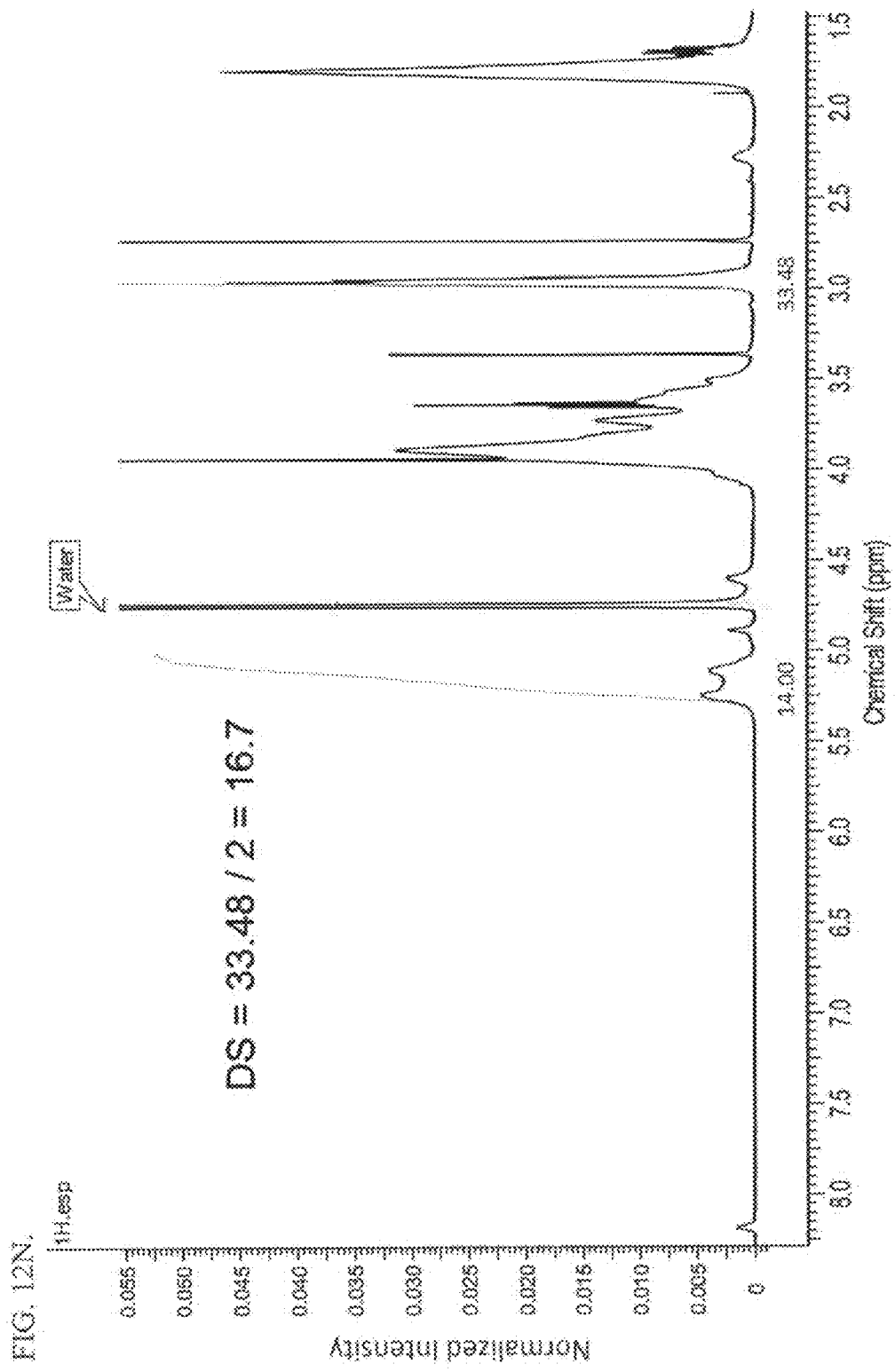
Figure 120:
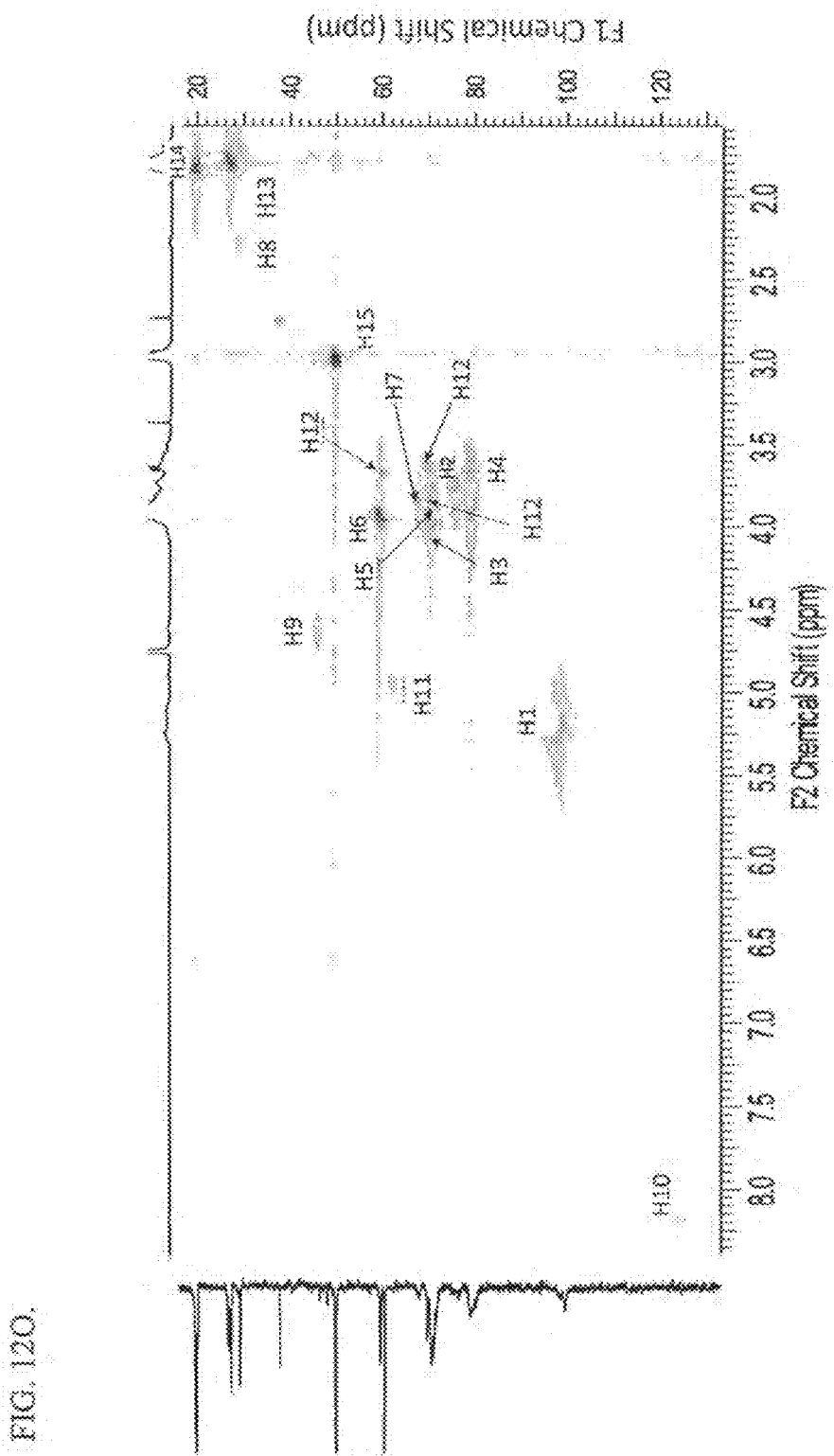

FIG. 12N. HNMR spectrum of SB-dimer (High DS) with integration (D20, 298K). The DS value calculation based on the NMR is illustrated.

FIG. 12O. Dept-edited HSQC spectrum of SB-dimer (High DS) with full assignment (D20, 298K).

Figure 12P:
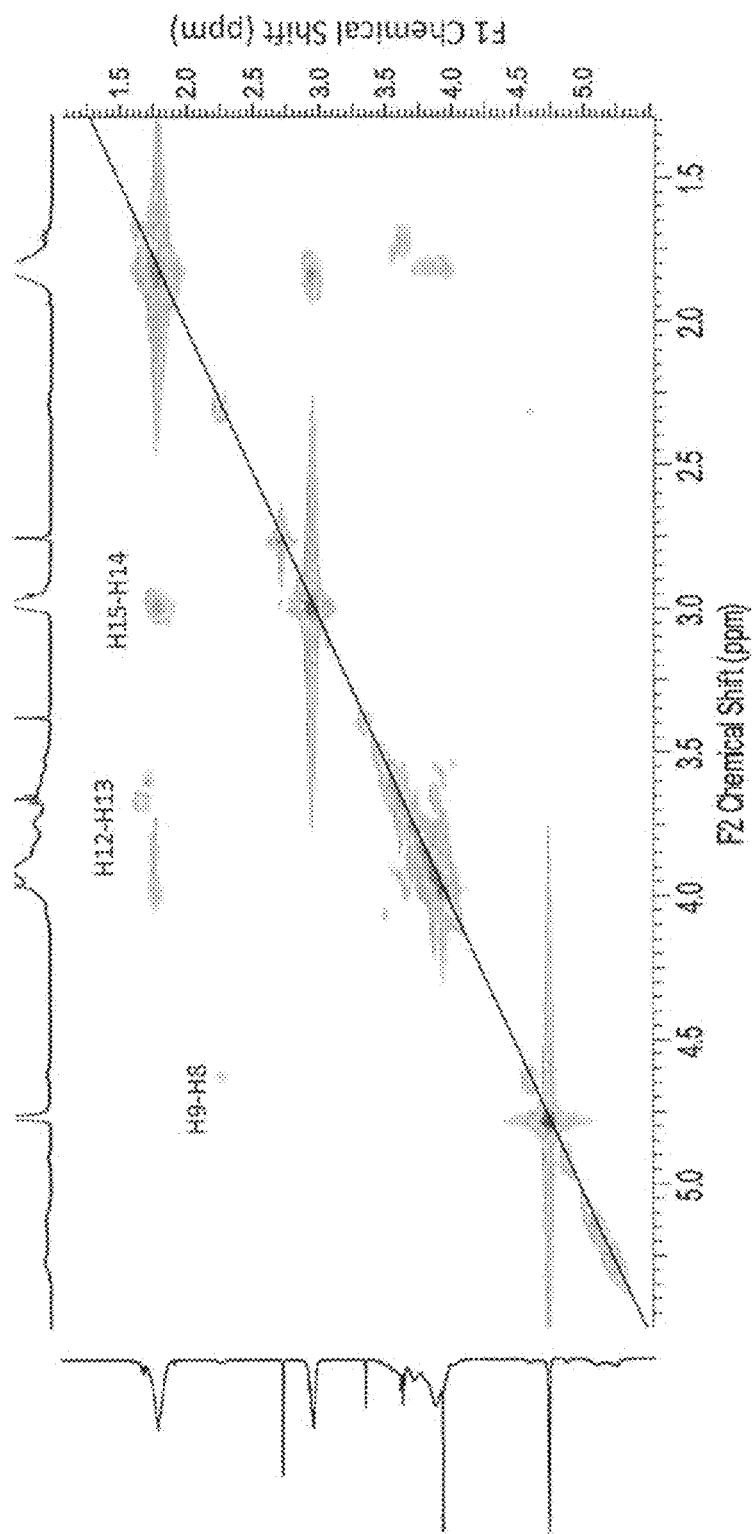

FIG. 12P. COSY spectrum of SB-dimer (High DS) with full assignment (D20, 298K).

Figure 13A:
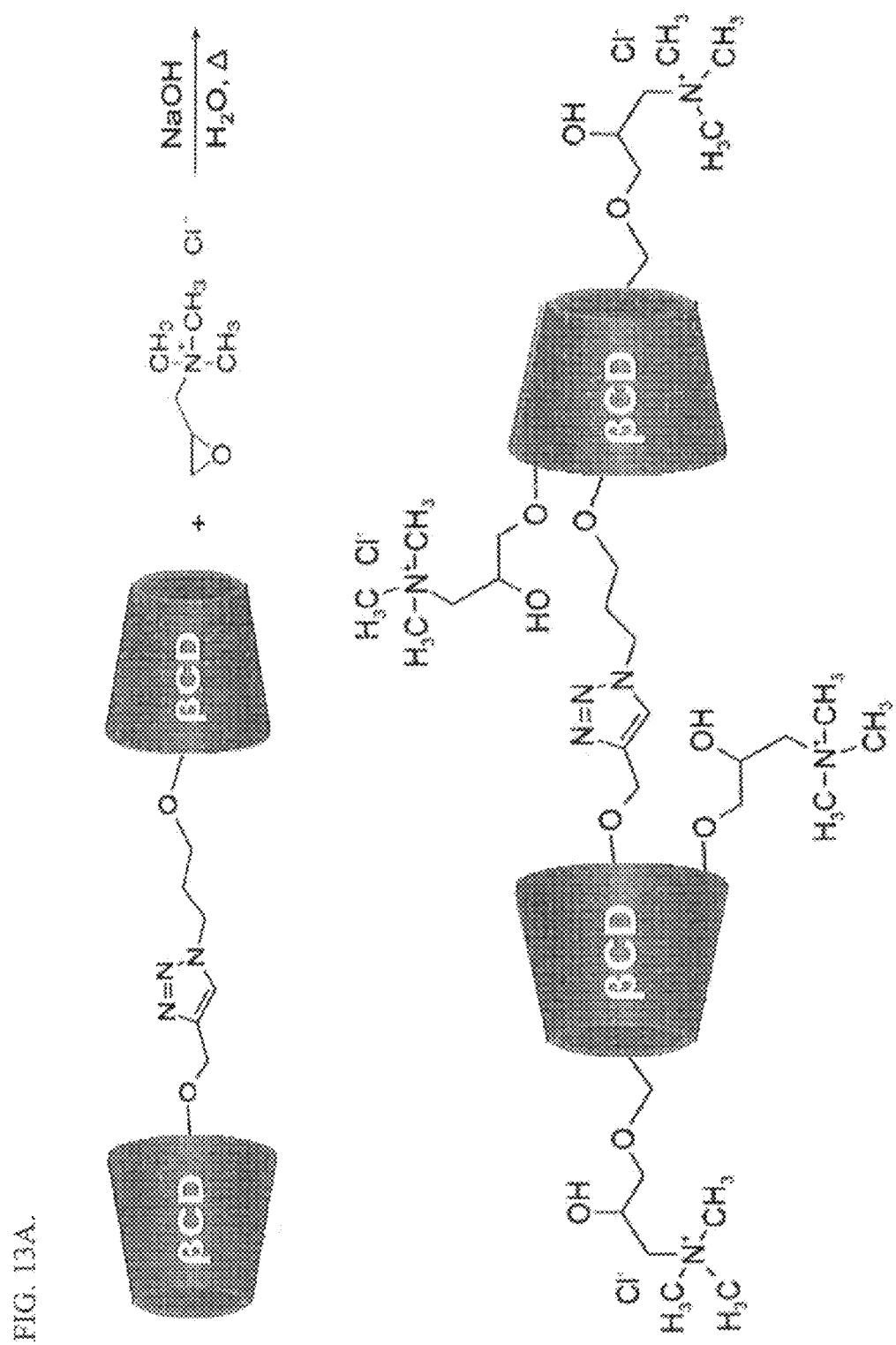

FIG. 13A. Synthetic scheme for quaternary ammonium β-cyclodextrin dimer.

Figure 13B:
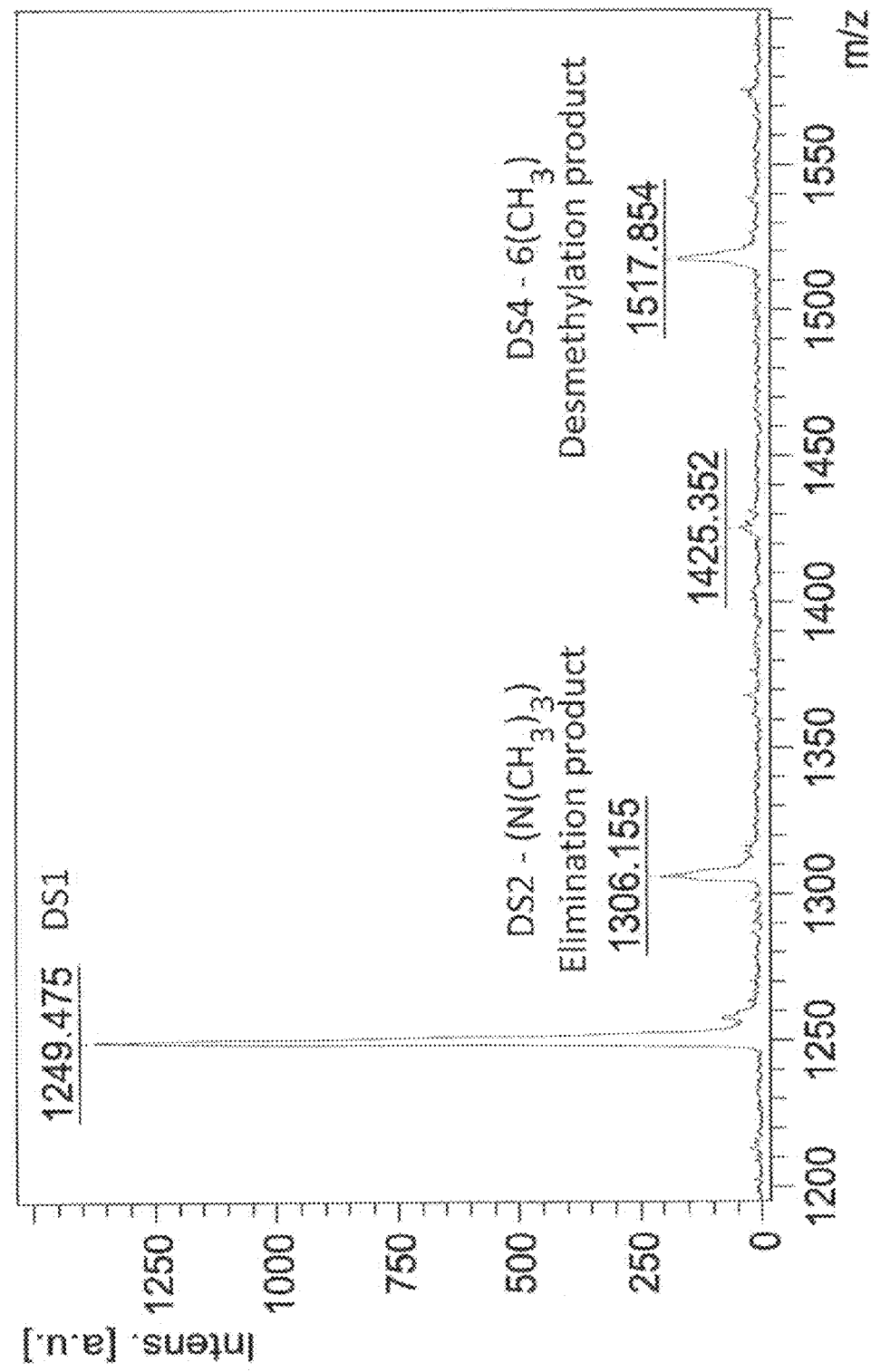

FIG. 13B. MALDI spectrum of quaternary ammonium β-cyclodextrin dimer reaction A.

Figure 13C:
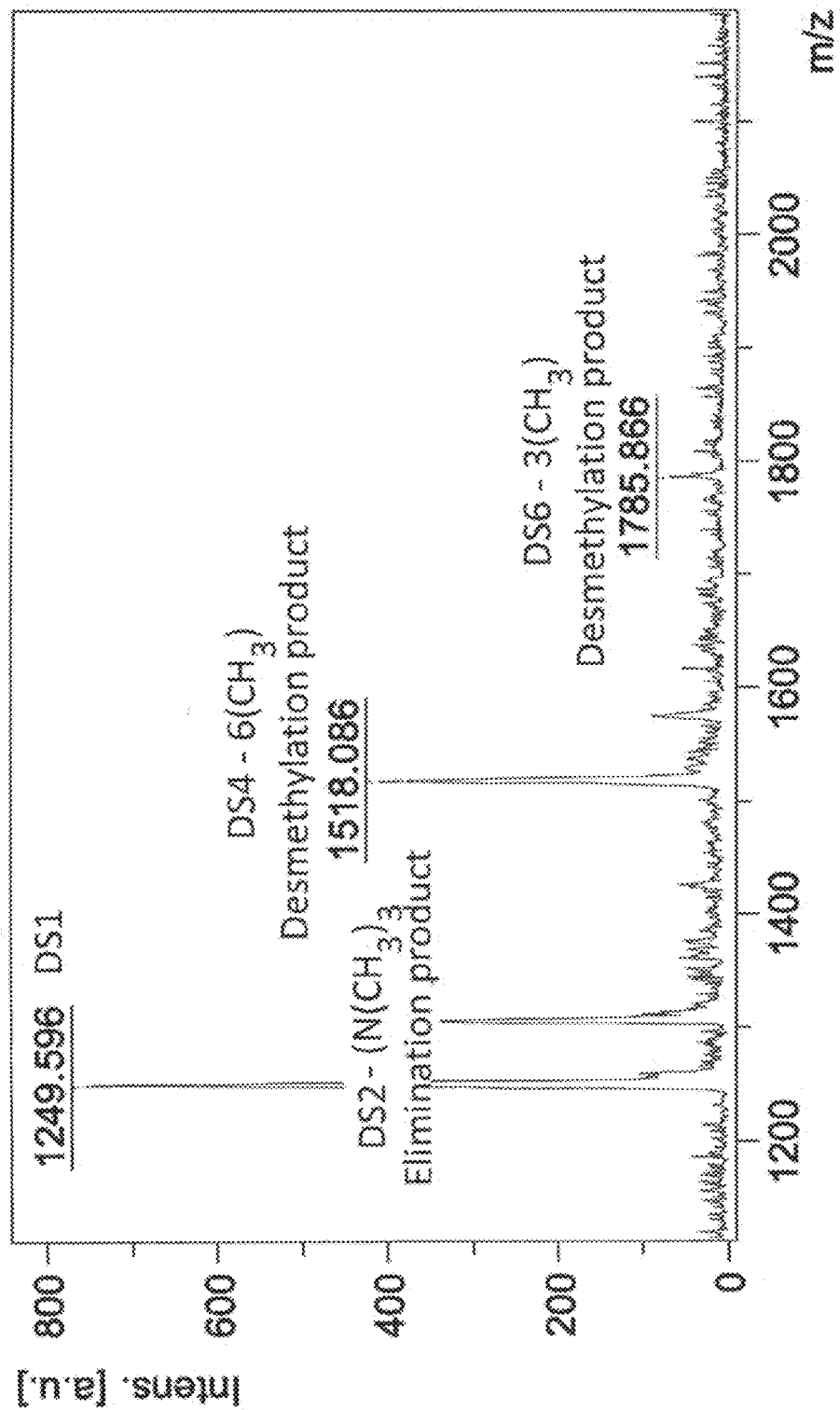

FIG. 13C. MALDI spectrum of quaternary ammonium β-cyclodextrin dimer reaction B.

Figure 13D:
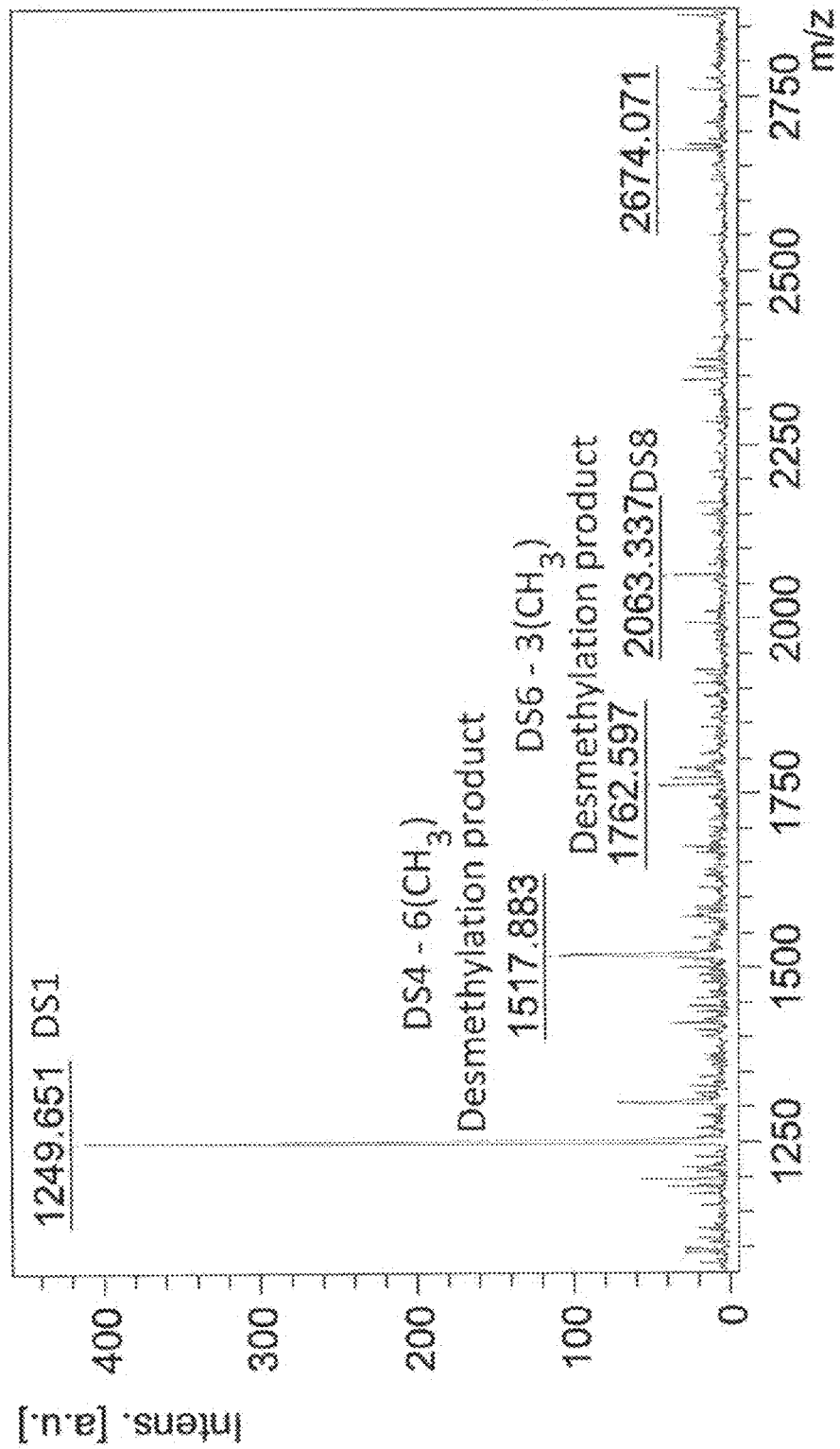

FIG. 13D. MALDI spectrum of quaternary ammonium β-cyclodextrin dimer reaction C.

Figure 13E:
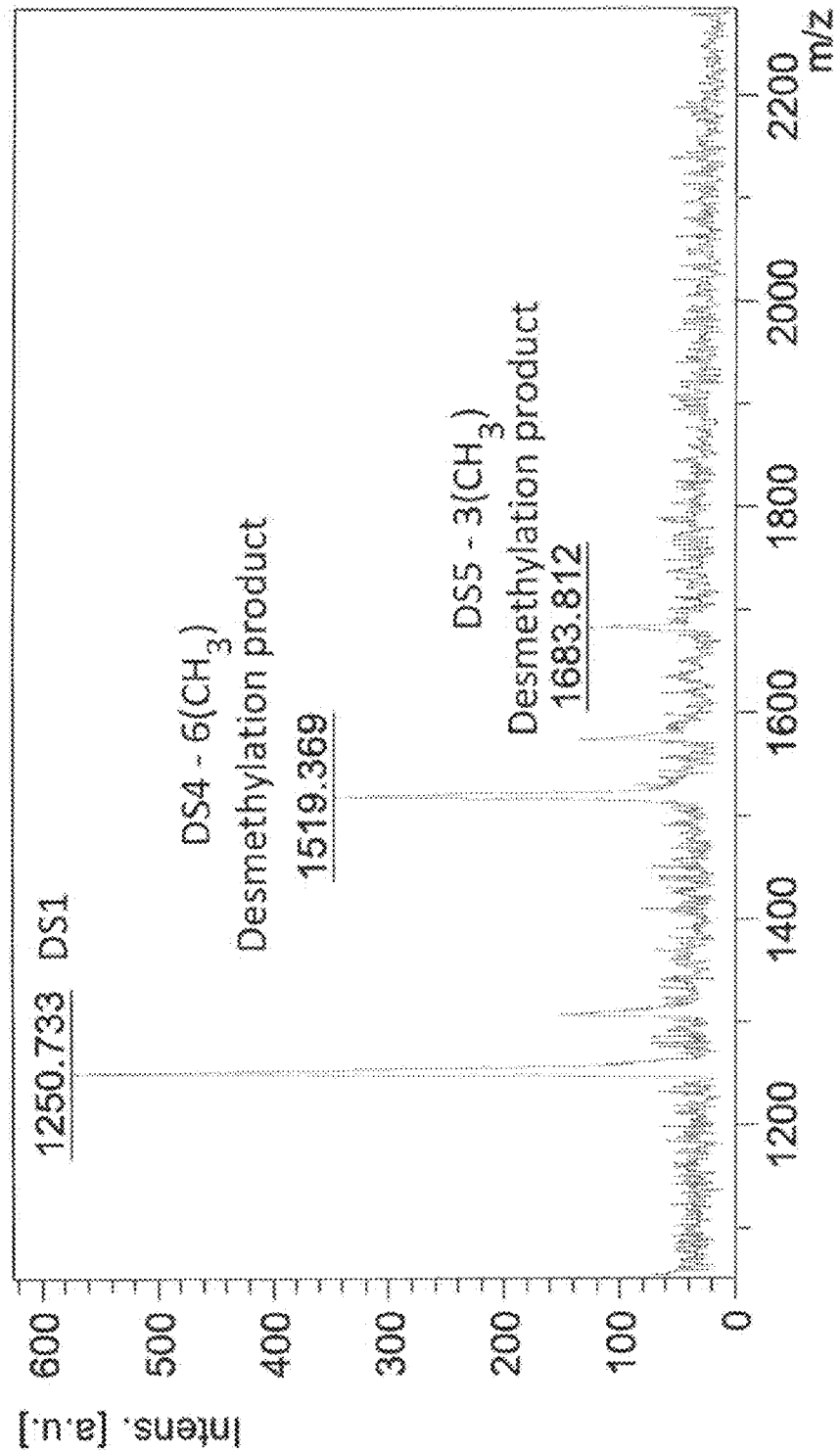

FIG. 13E. MALDI spectrum of quaternary ammonium β-cyclodextrin dimer reaction D.

Figure 13F:
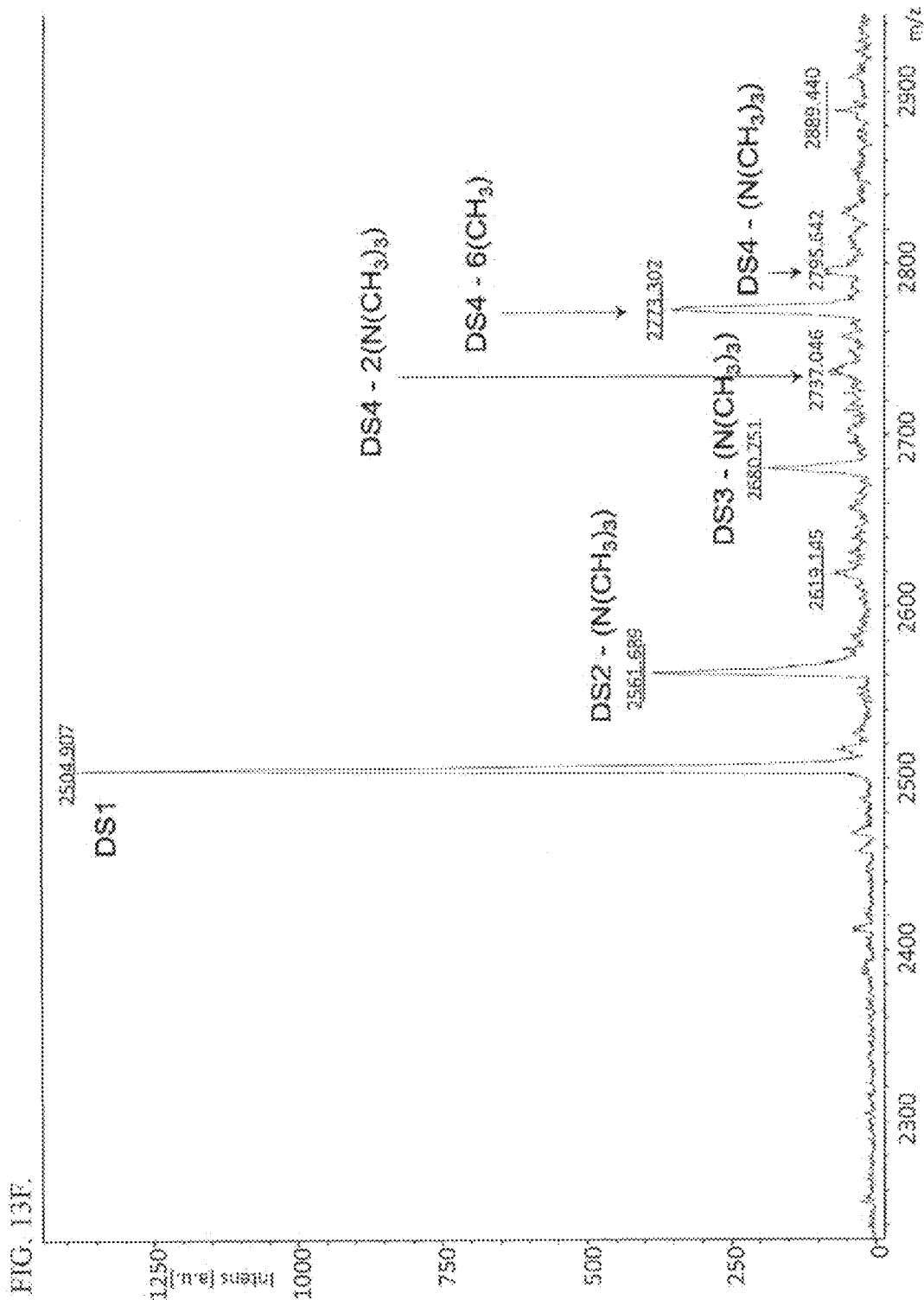

FIG. 13F. MALDI spectrum of quaternary ammonium β-cyclodextrin dimer.

Figure 13G:
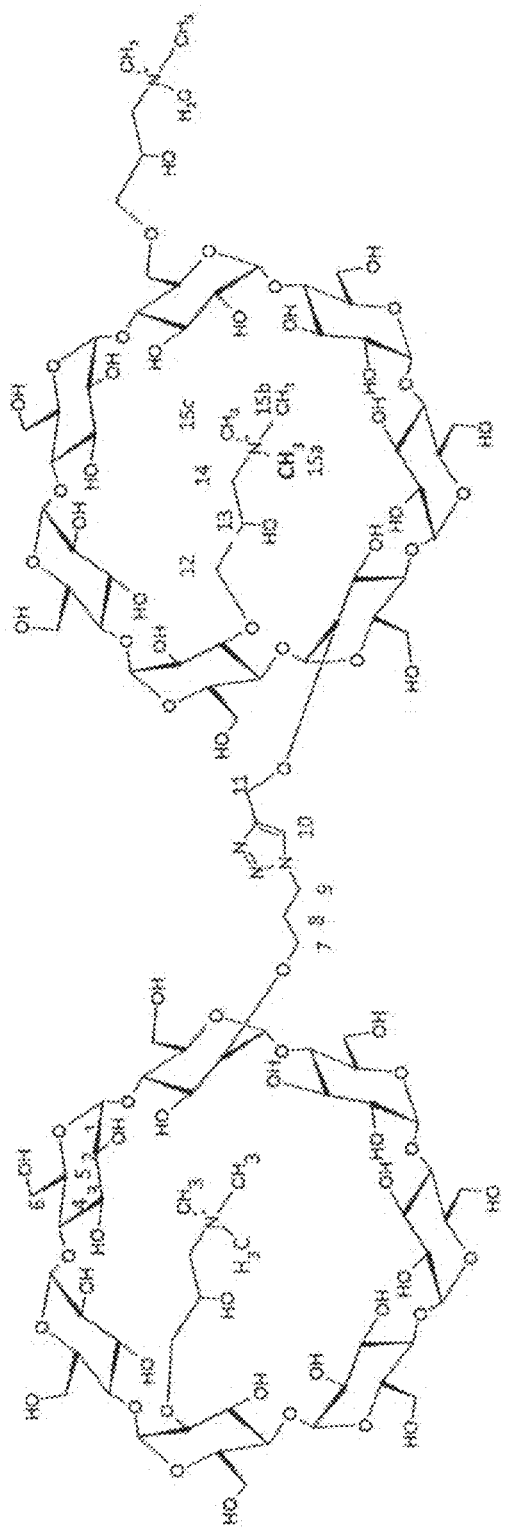

FIG. 13G. Structure of one possible QA-dimer isomer (DS3) with atom numbering.

Figure 13H:
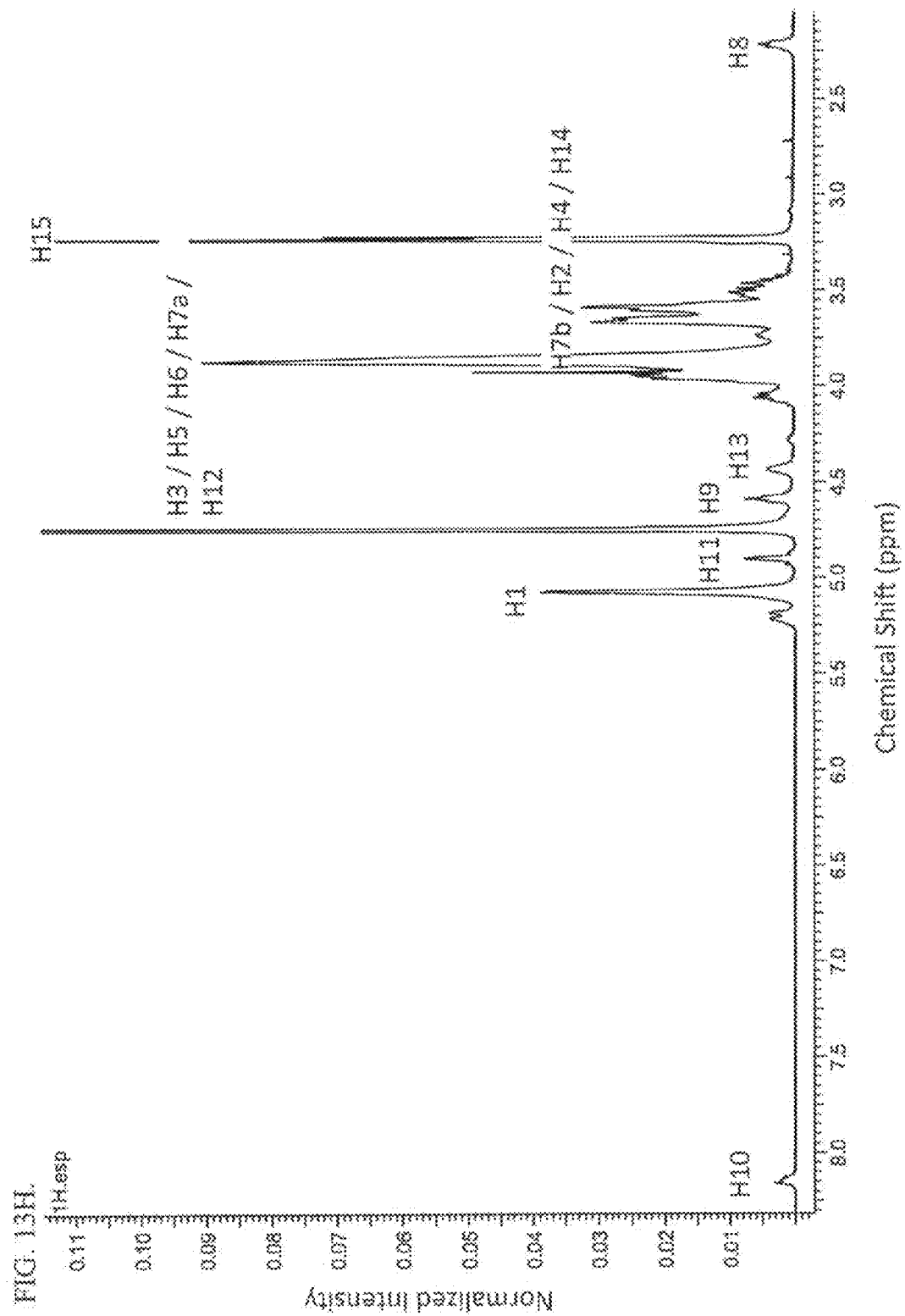

FIG. 13H. HNMR spectrum of QA-dimer with full assignment (D20, 298K).

Figure 13I:
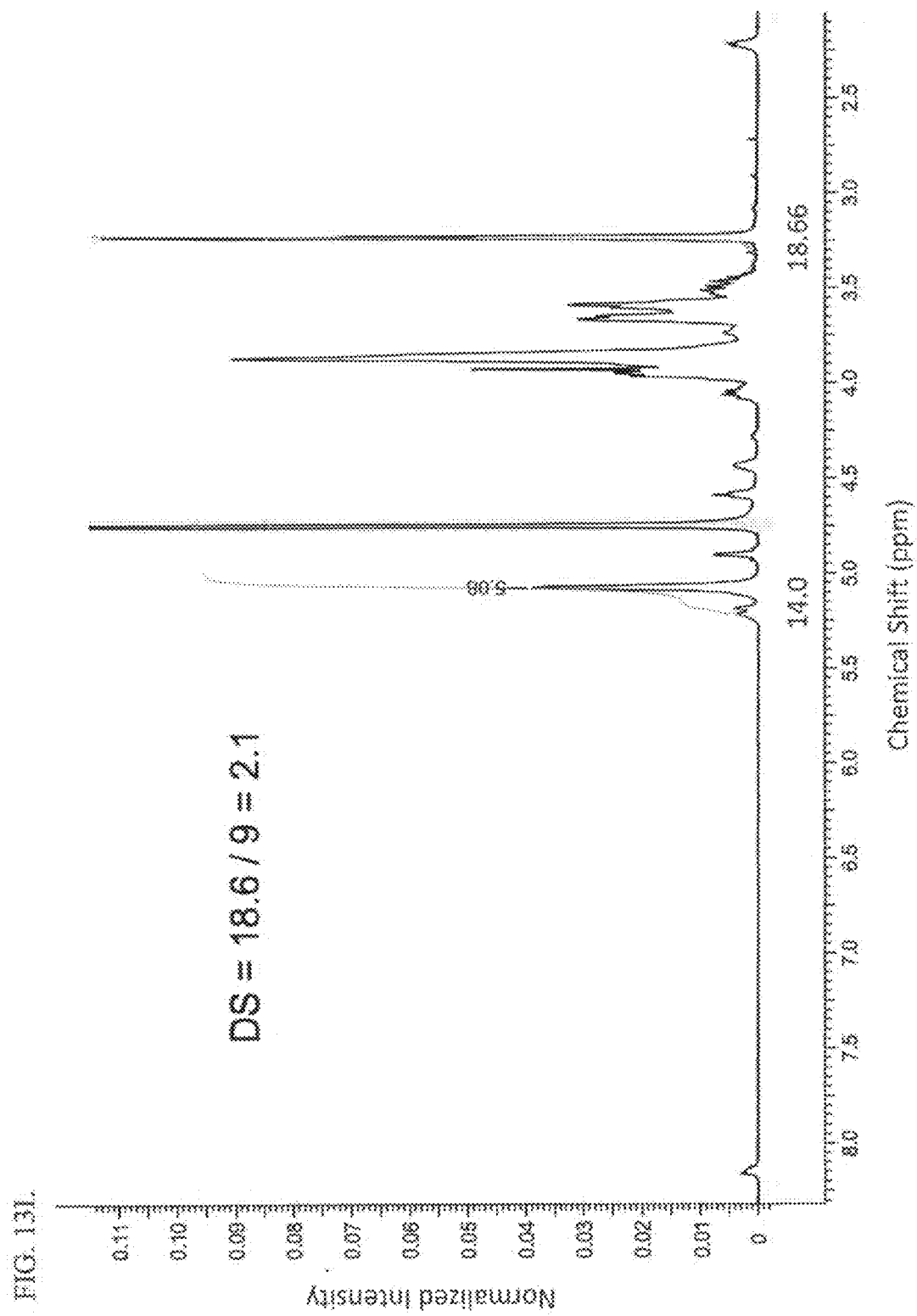

FIG. 13I. HNMR spectrum of QA-dimer with integration (D20, 298K). The DS value calculation based on the NMR is illustrated.

Figure 13J:
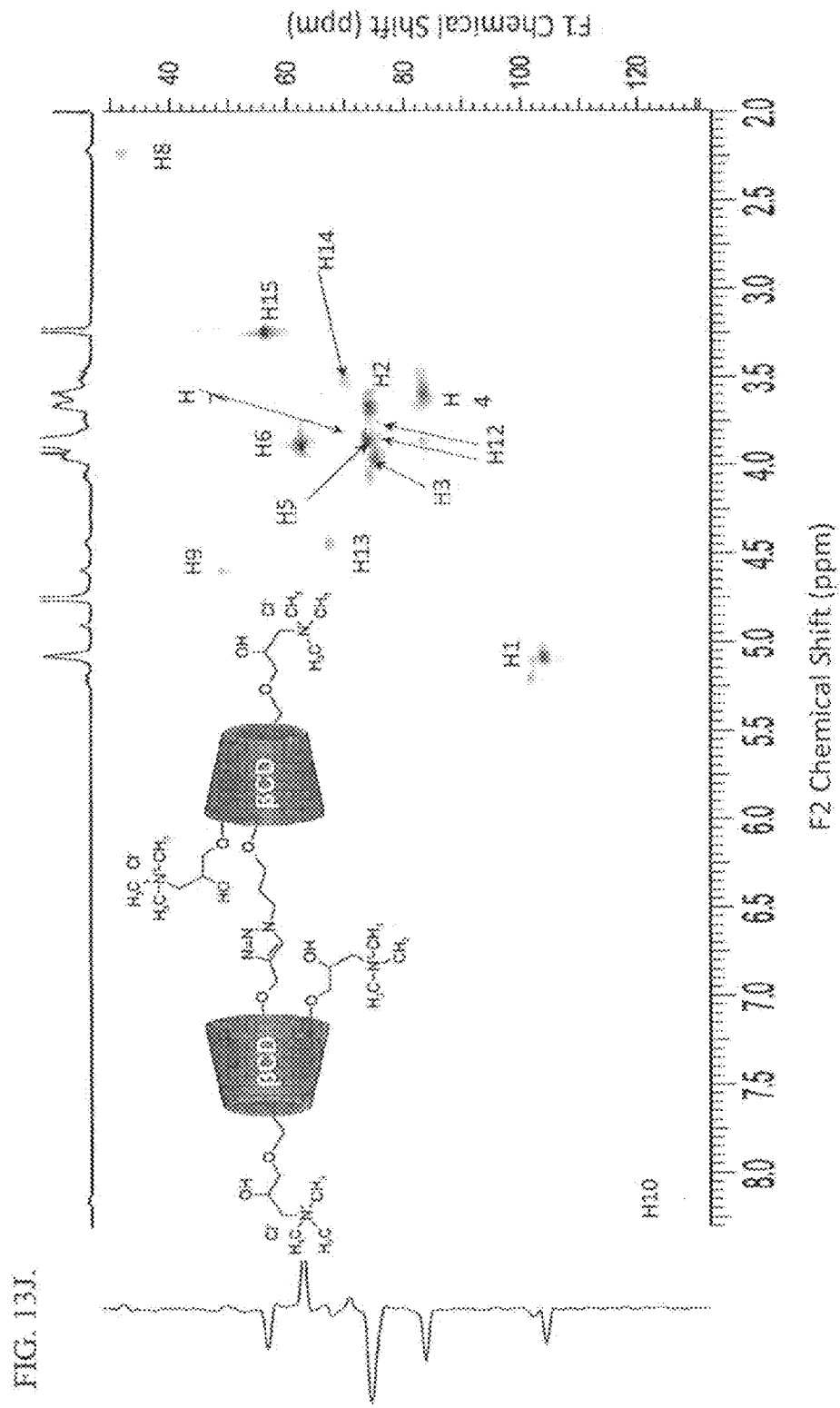

FIG. 13J. DEPT-edited HSQC spectrum of QA-dimer with full assignment (D20, 298K).

Figure 13K:
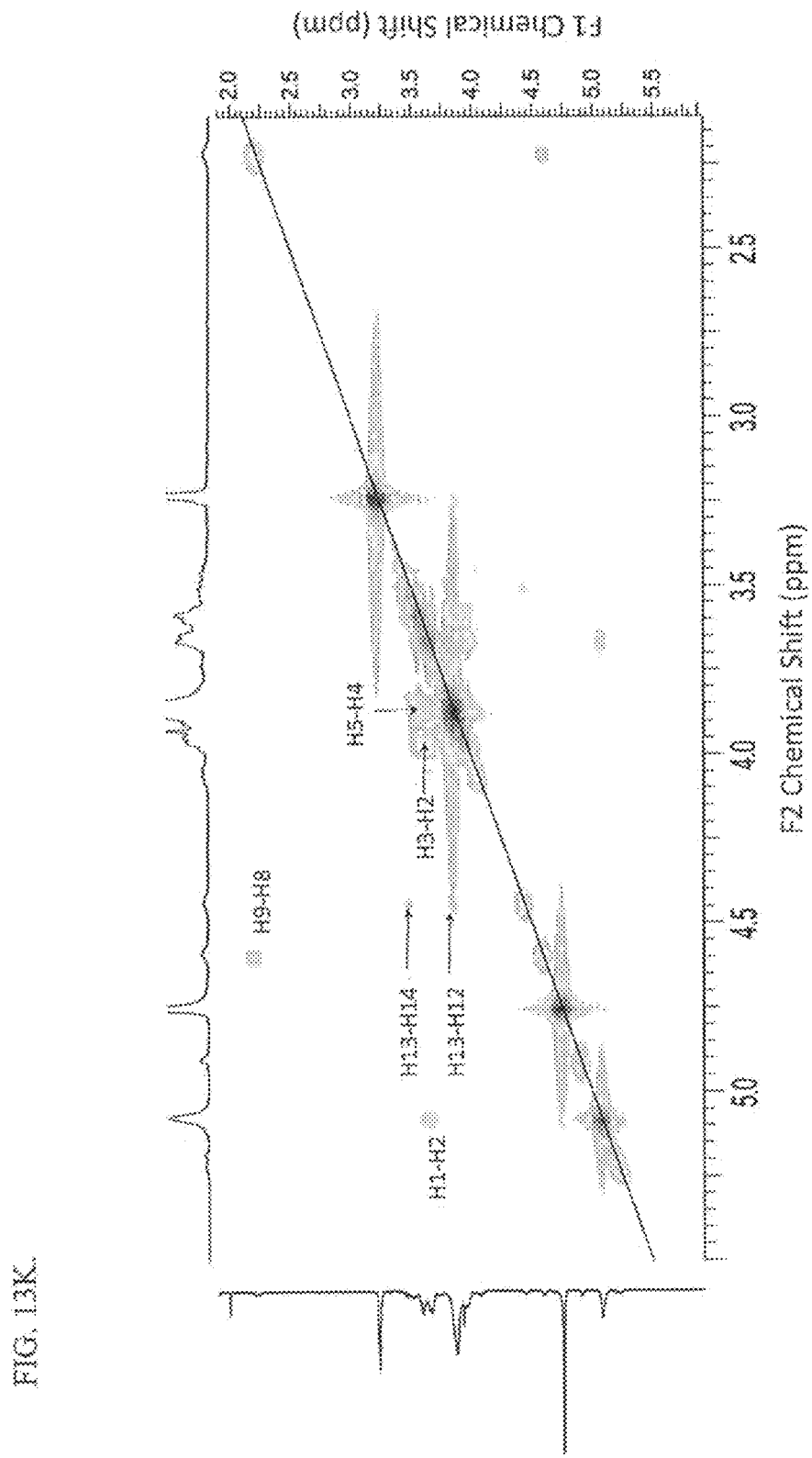

FIG. 13K. COSY spectrum of QA-dimer with partial assignment (D20, 298K).

Figure 14A:
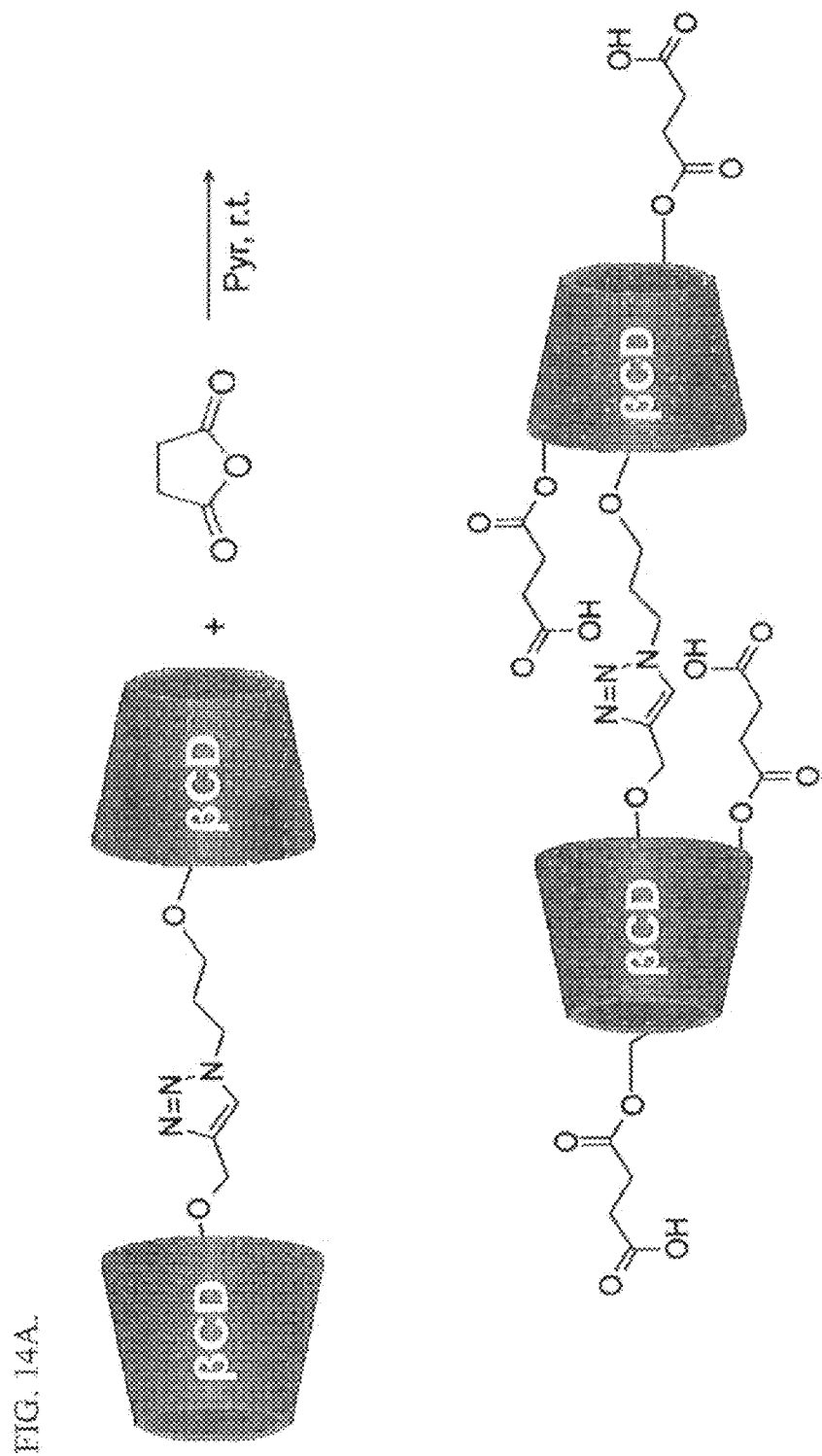

FIG. 14A. Synthetic scheme for succinylated dimer.

Figure 14B:
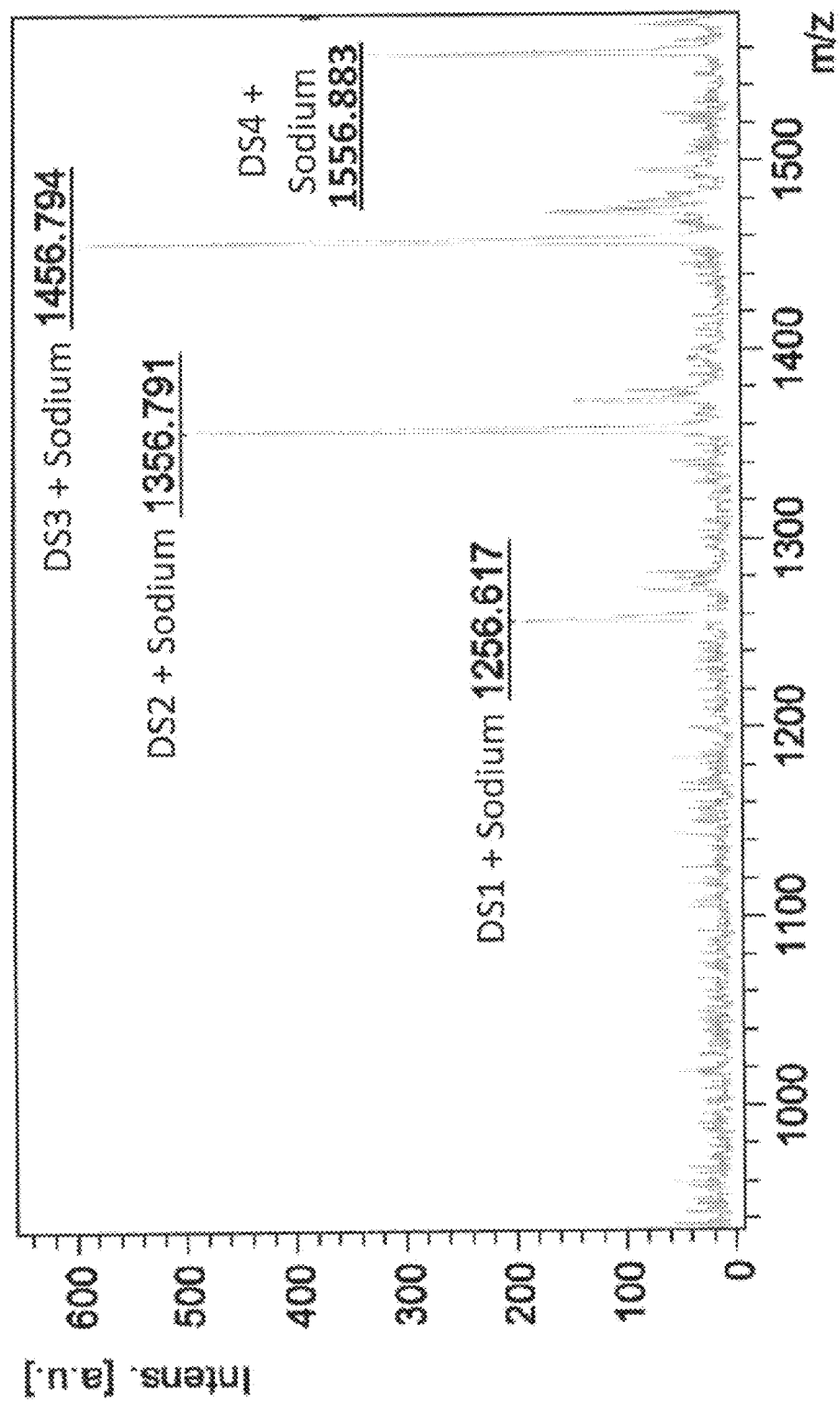

FIG. 14B. MALDI for succinylated dimer reaction A.

Figure 14C:
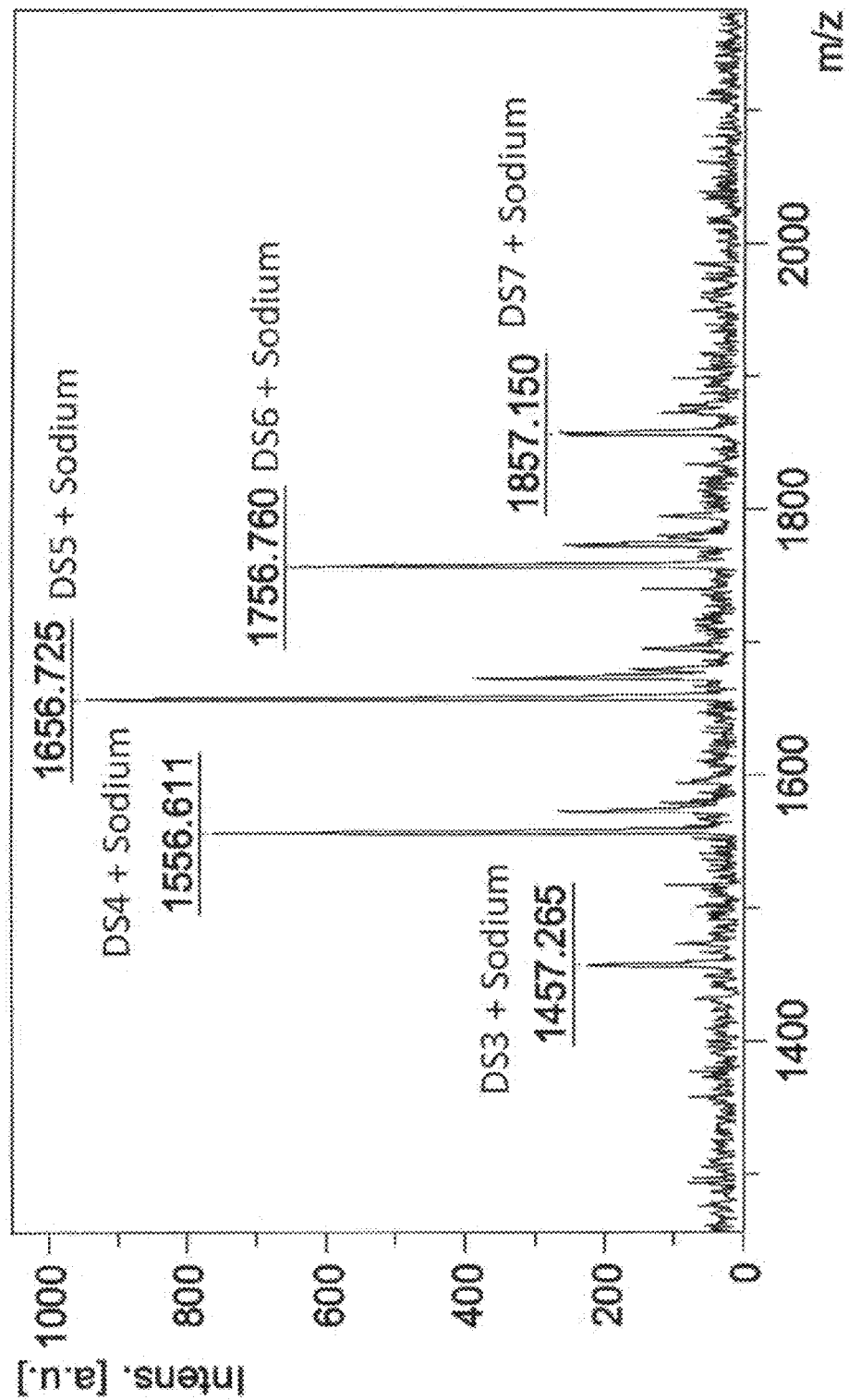

FIG. 14C. MALDI for succinylated dimer reaction B.

Figure 14D:
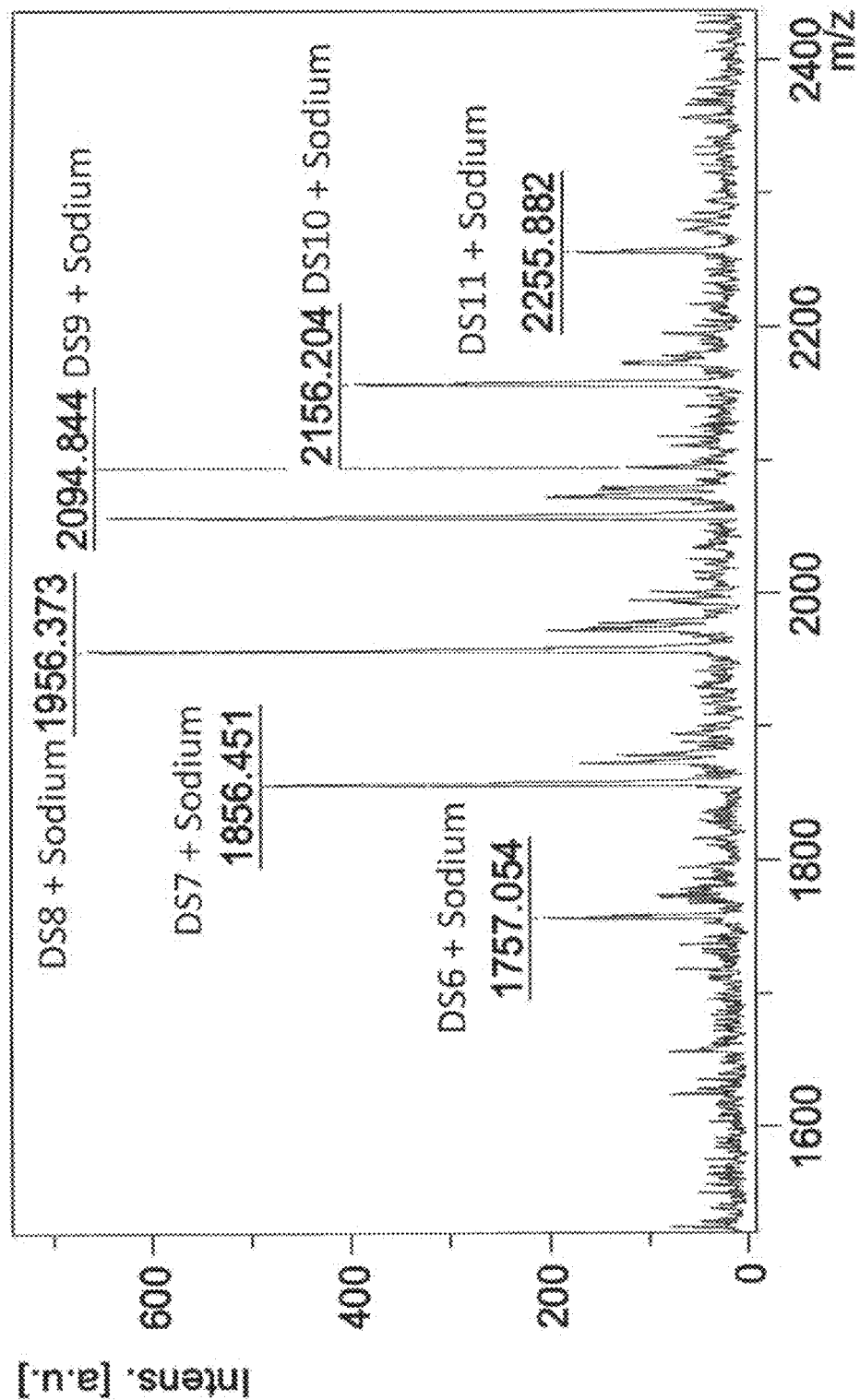

FIG. 14D. MALDI for succinylated dimer reaction C.

Figure 14E:
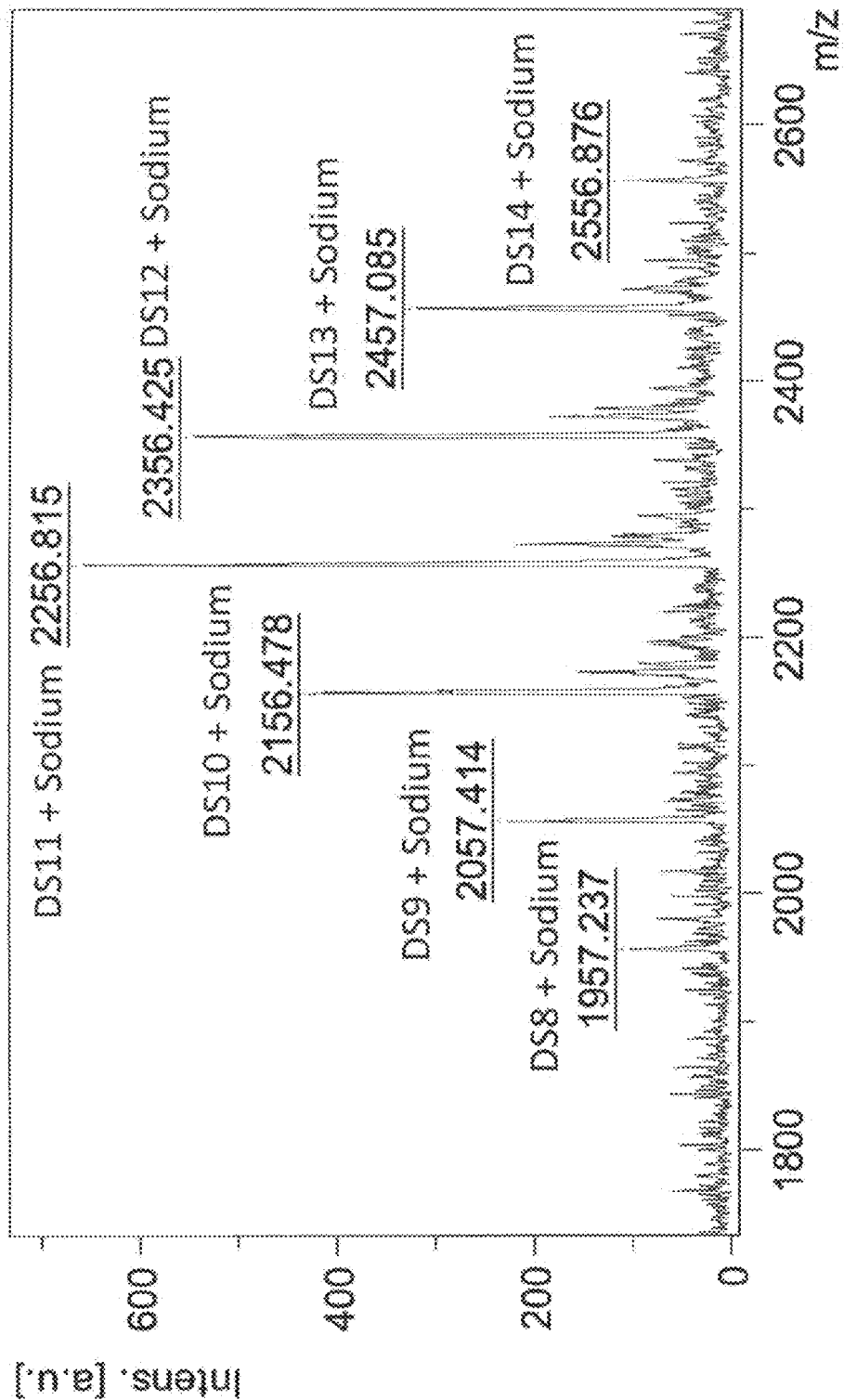

FIG. 14E. MALDI for succinylated dimer reaction D.

Figure 14F:
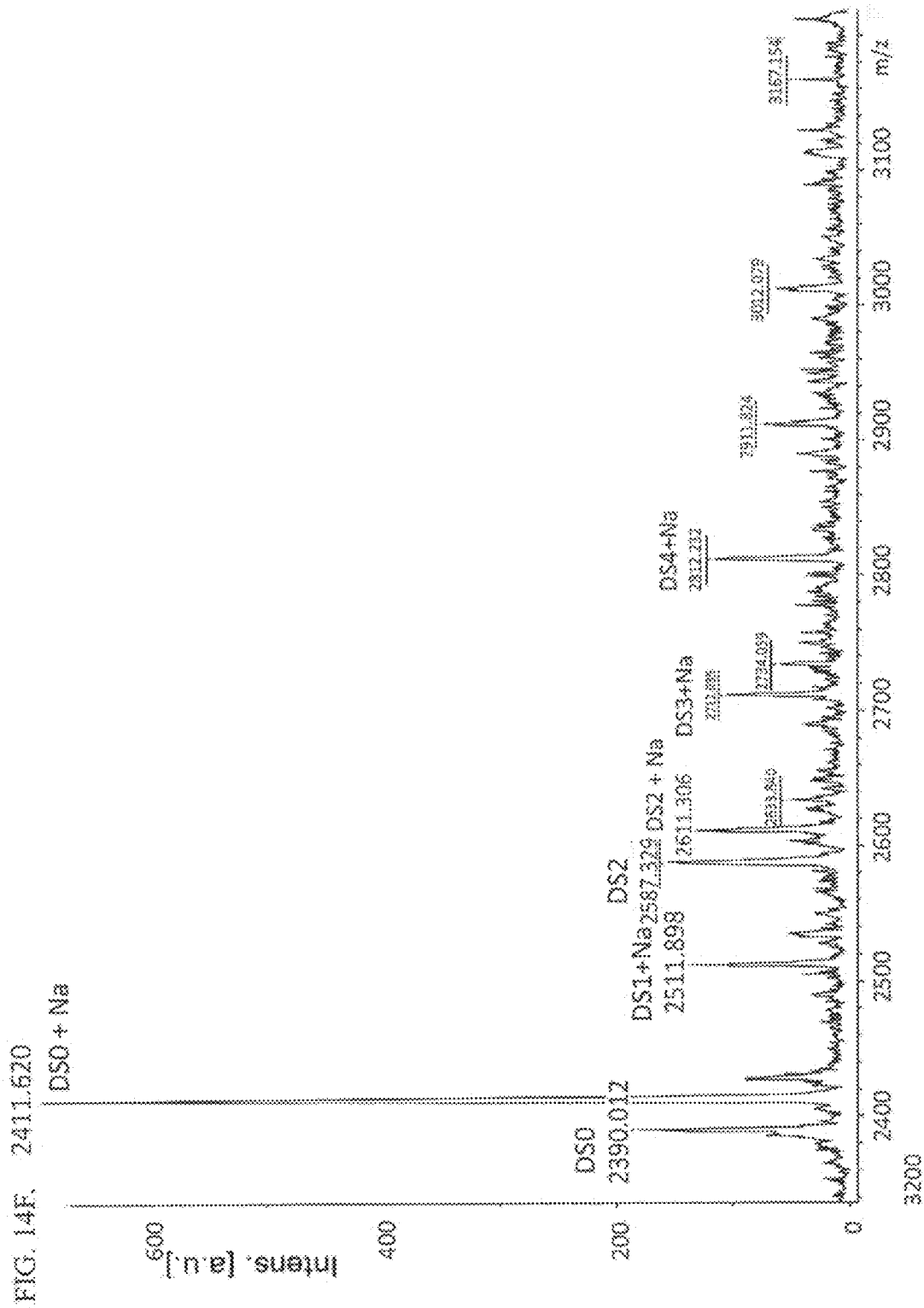

FIG. 14F. MALDI for succinylated dimer.

Figure 14G:
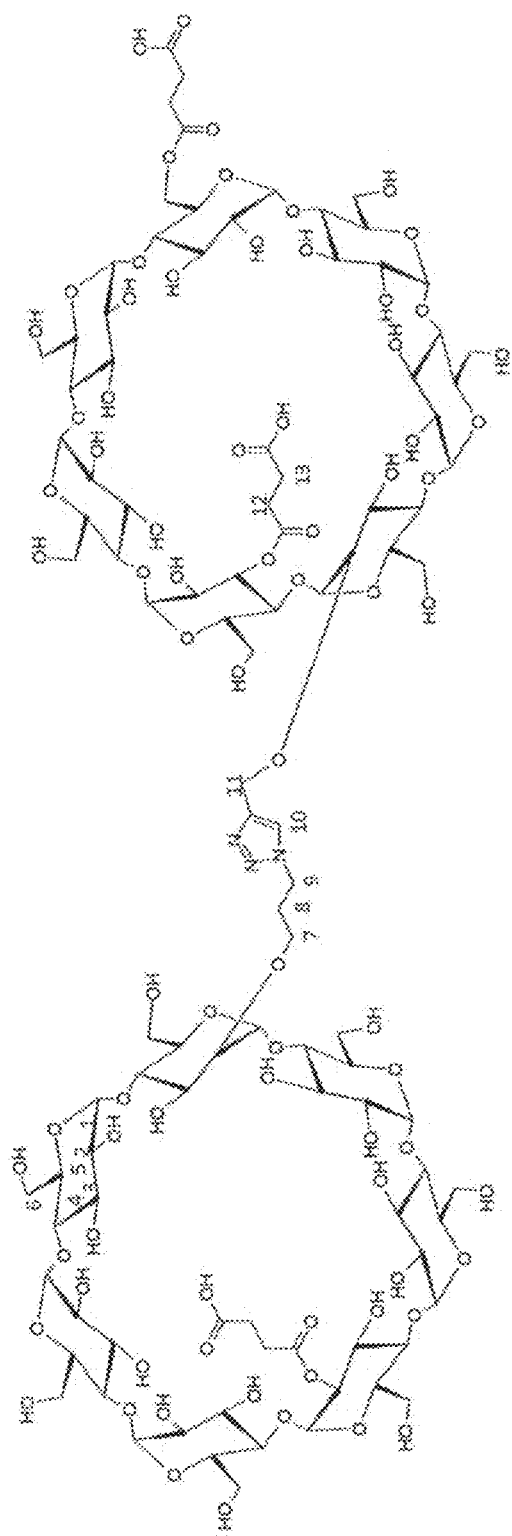

FIG. 14G. Structure of one possible SUCC-dimer isomer (DS3) with atom numbering.

Figure 14H:
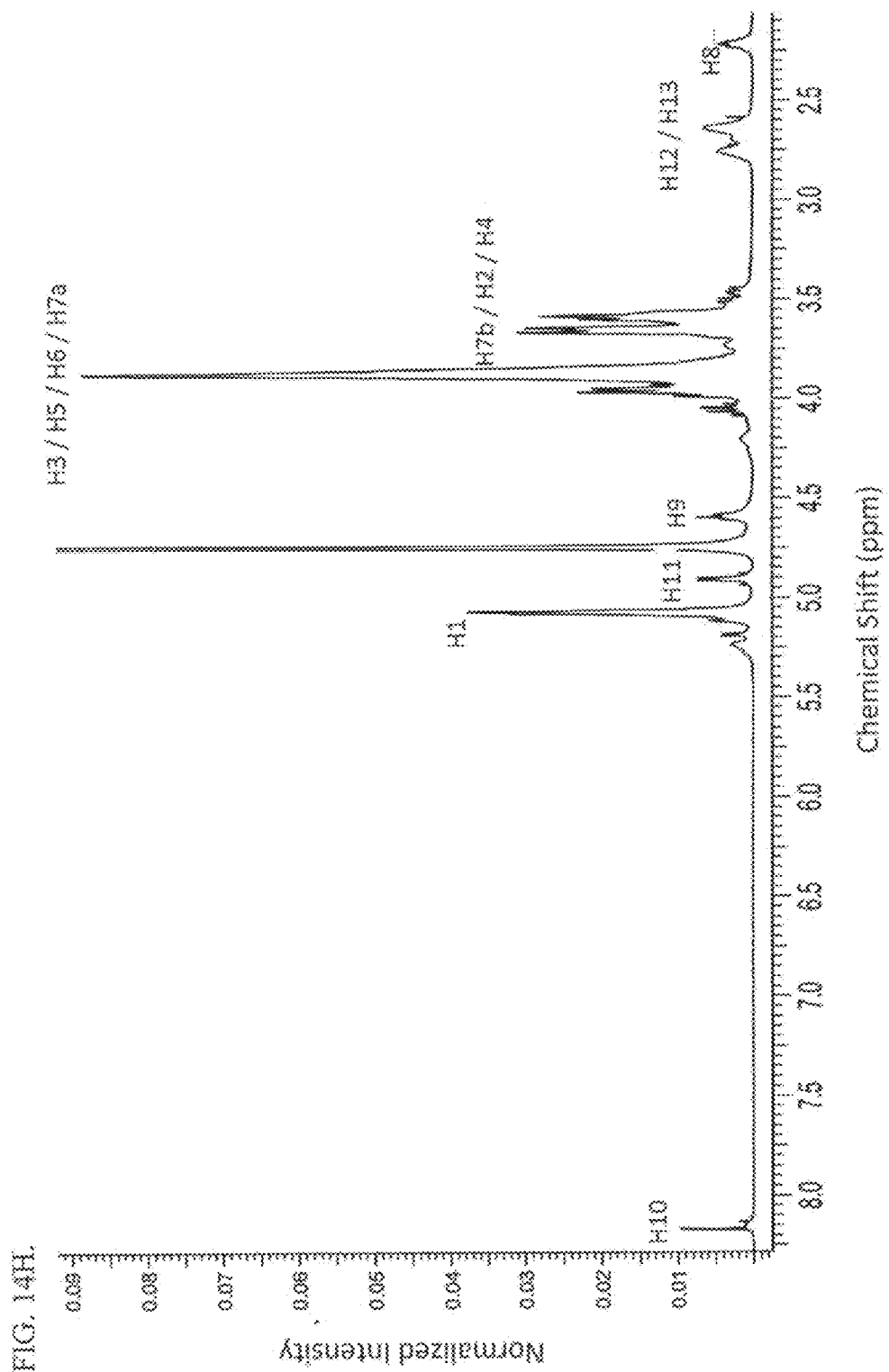
Figure 14L:
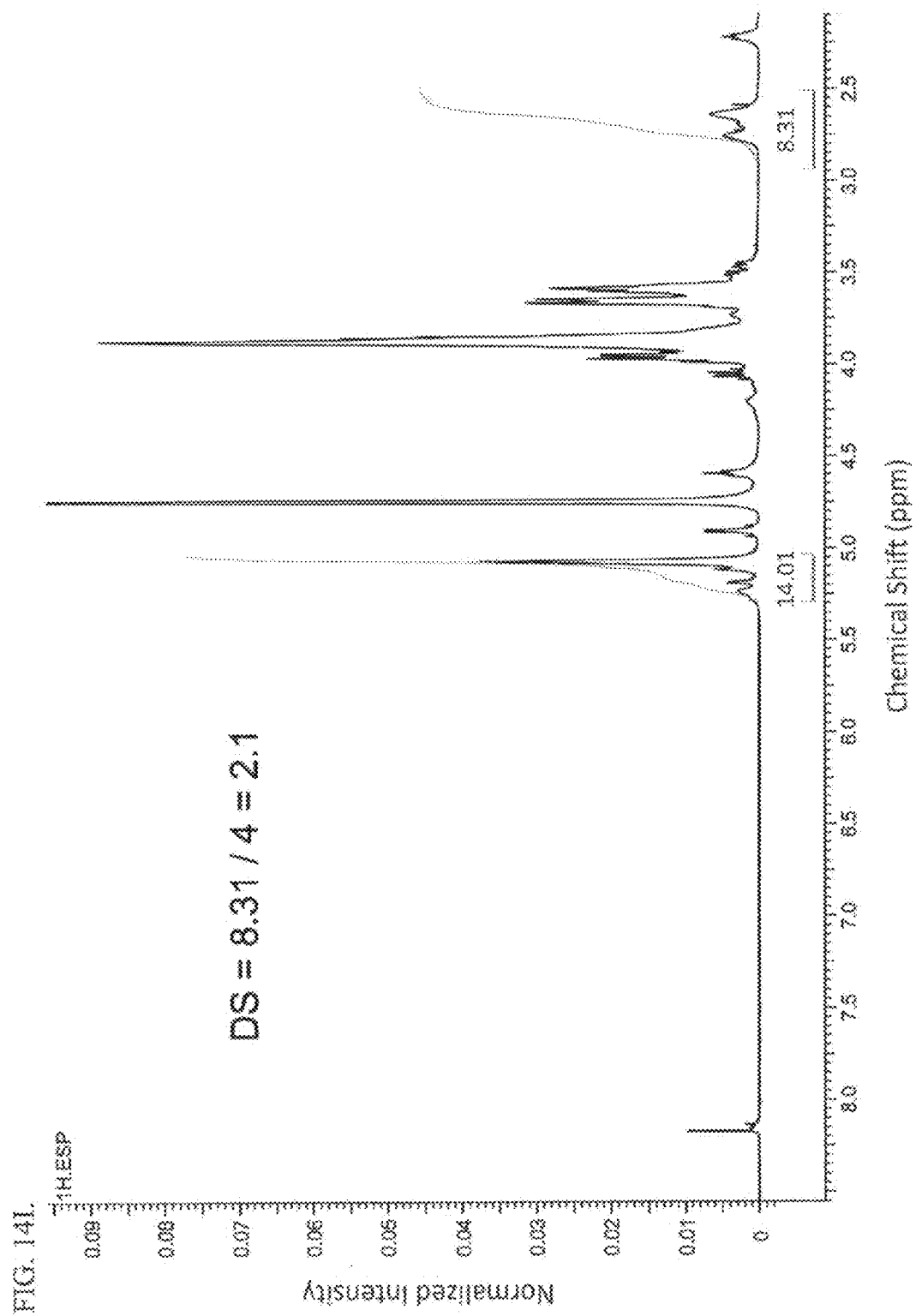

FIG. 14H. HNMR spectrum of succinylated dimer with full assignment (D20, 298K).

FIG. 14I. HNMR spectrum of succinylated dimer with integration (D20, 298K). The DS value calculation based on the NMR is illustrated.

Figure 14J:
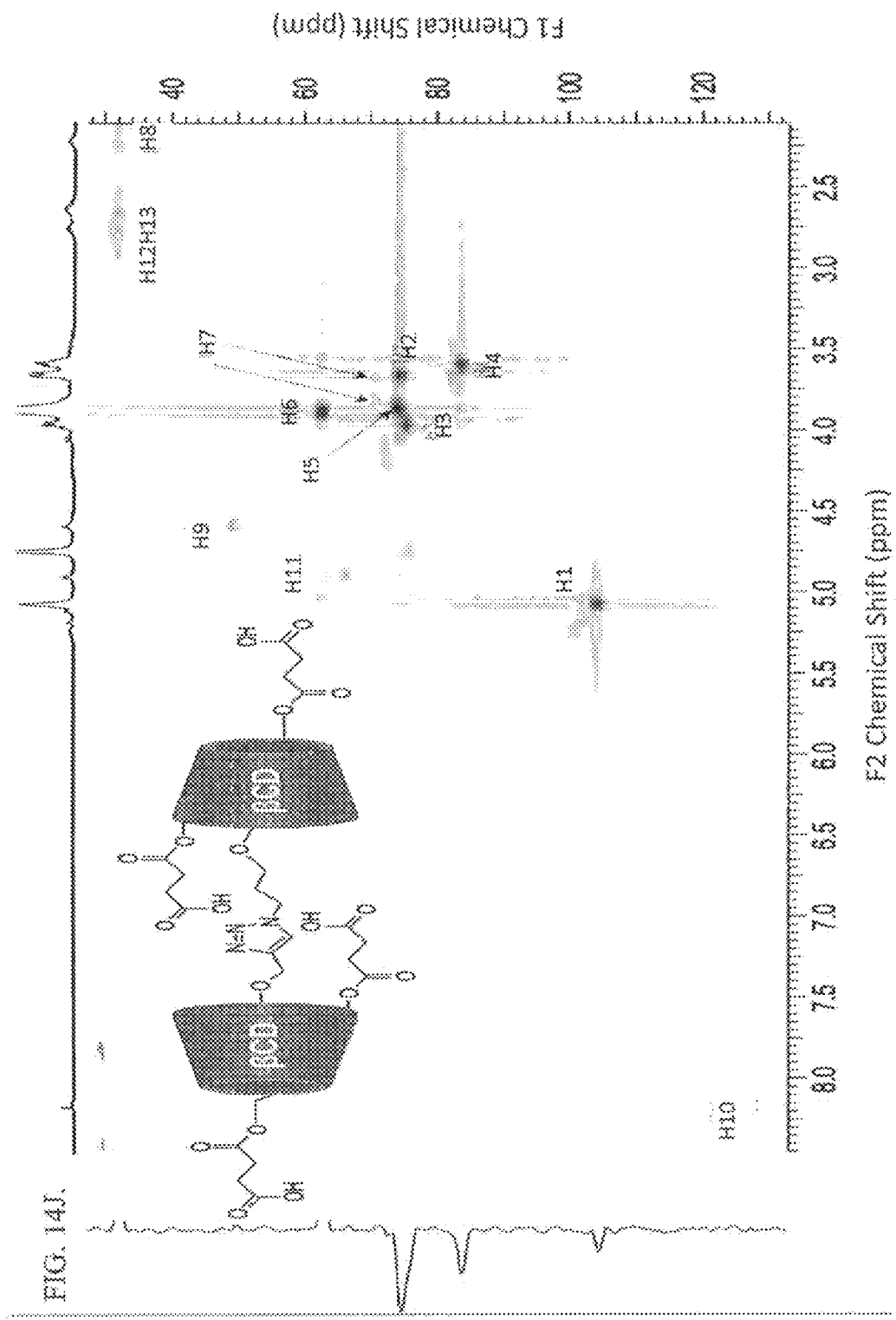

FIG. 14J. DEPT-edited HSQC spectrum of succinylated dimer with full assignment (D20, 298K).

Figure 14K:
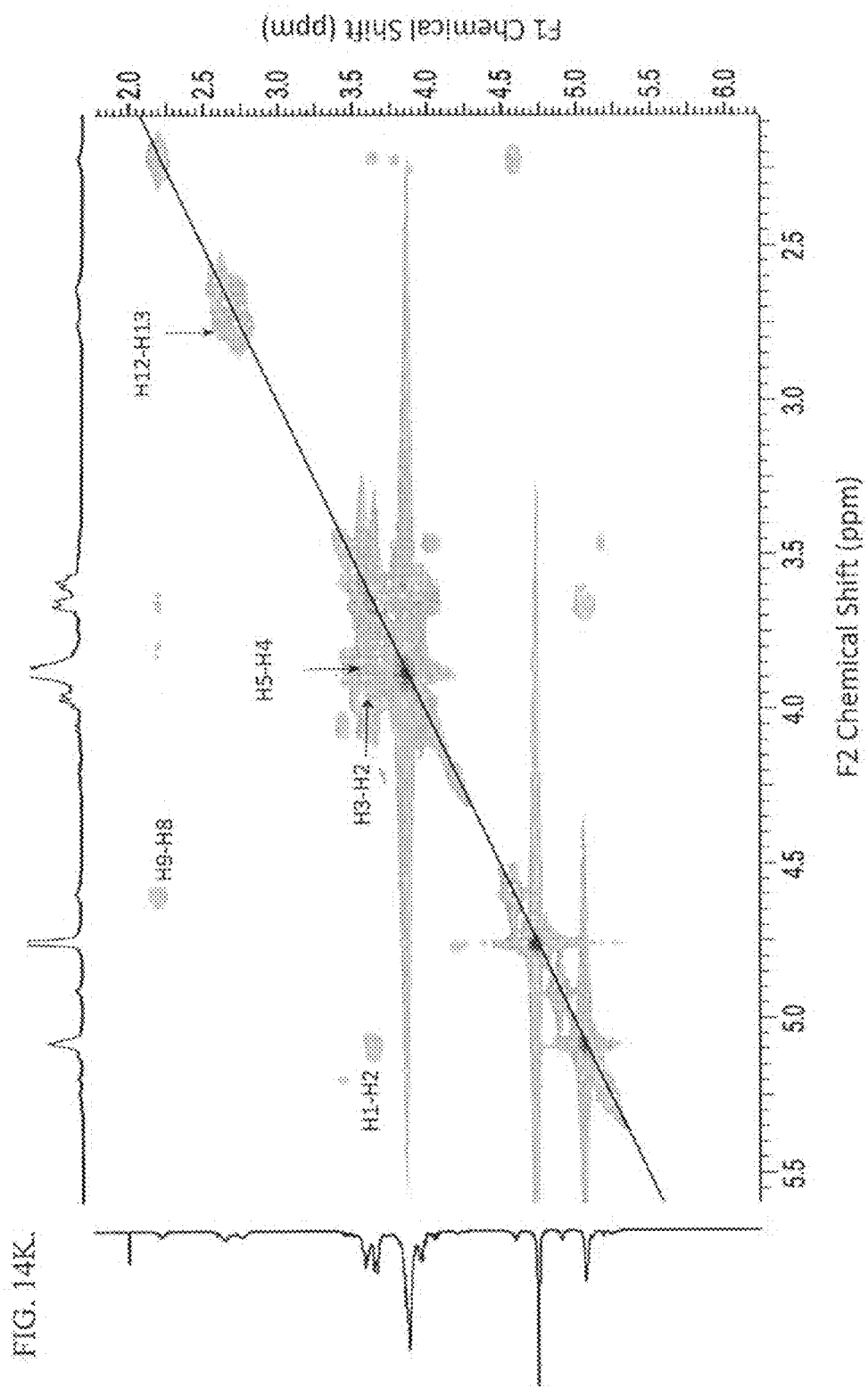

FIG. 14K. COSY spectrum of succinylated dimer with partial assignment (D20, 298K).

Figure 15B:
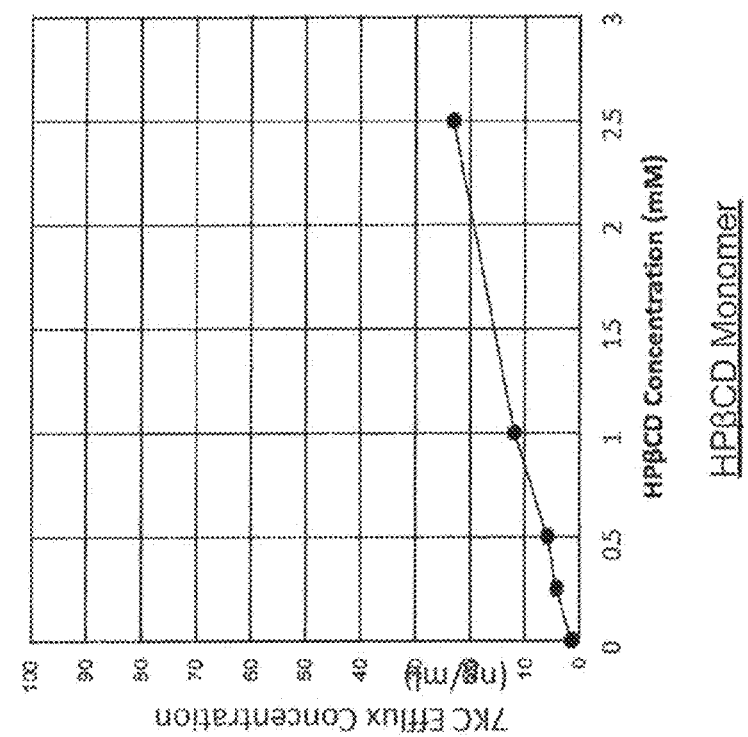
Figure 15A:
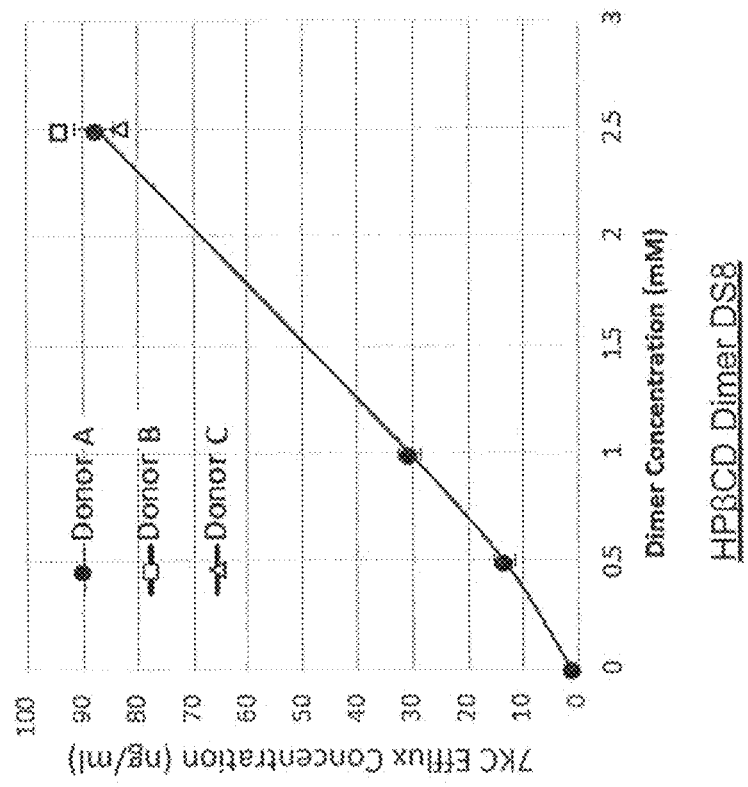

FIG. 15A. 7KC blood cell efflux concentration after incubation with DS8 HPβCD dimer.

FIG. 15B. 7KC blood cell efflux concentration after incubation with HPβCD monomer.

Figure 15C:
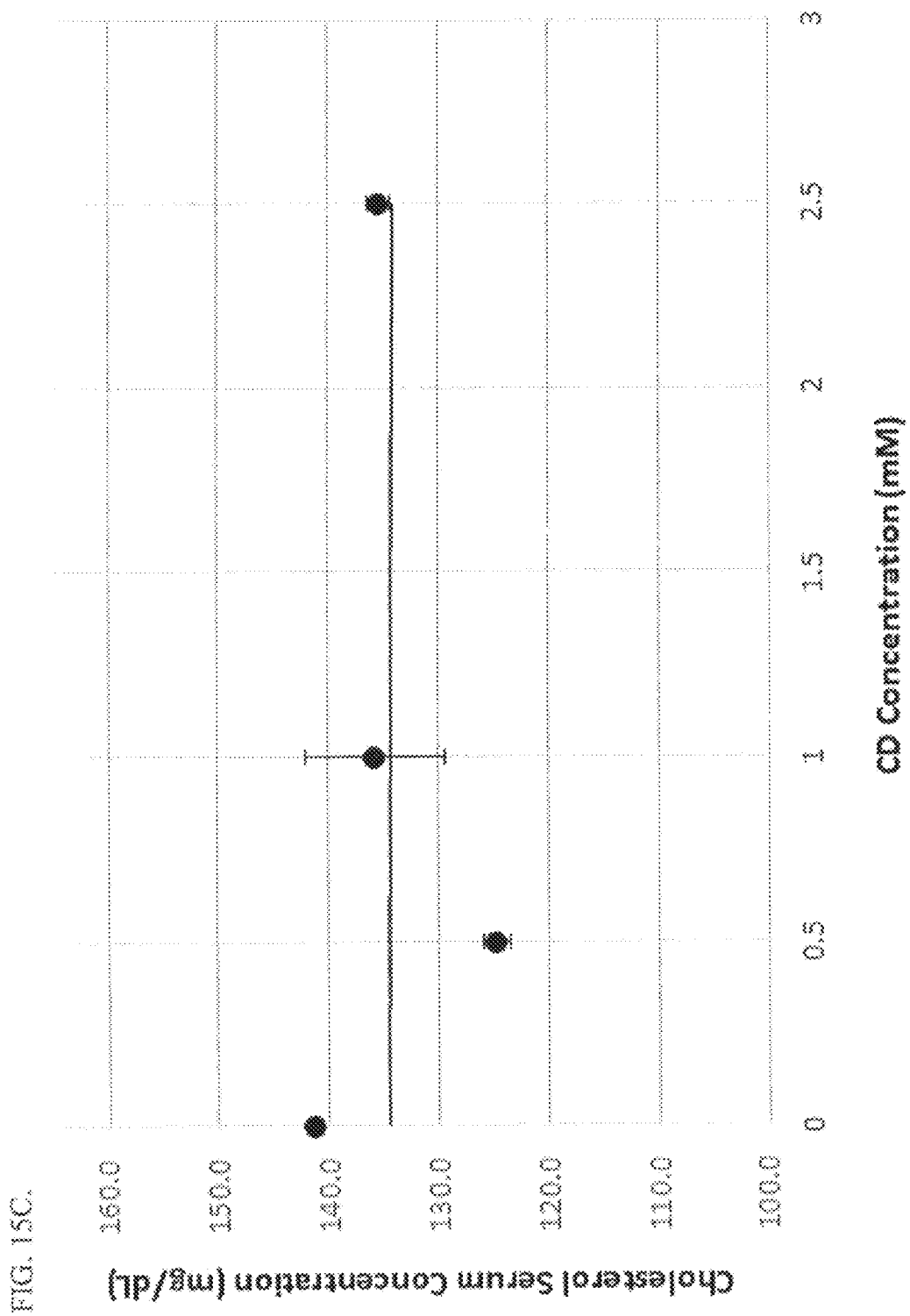

FIG. 15C. Plasma cholesterol is not perturbed by incubation with the HPβCD dimer. Blood plasma cholesterol was measured by mass spectrometry to determine the efflux of cholesterol from blood cells caused by incubation with the HPβCD dimer.

Figure 15D:
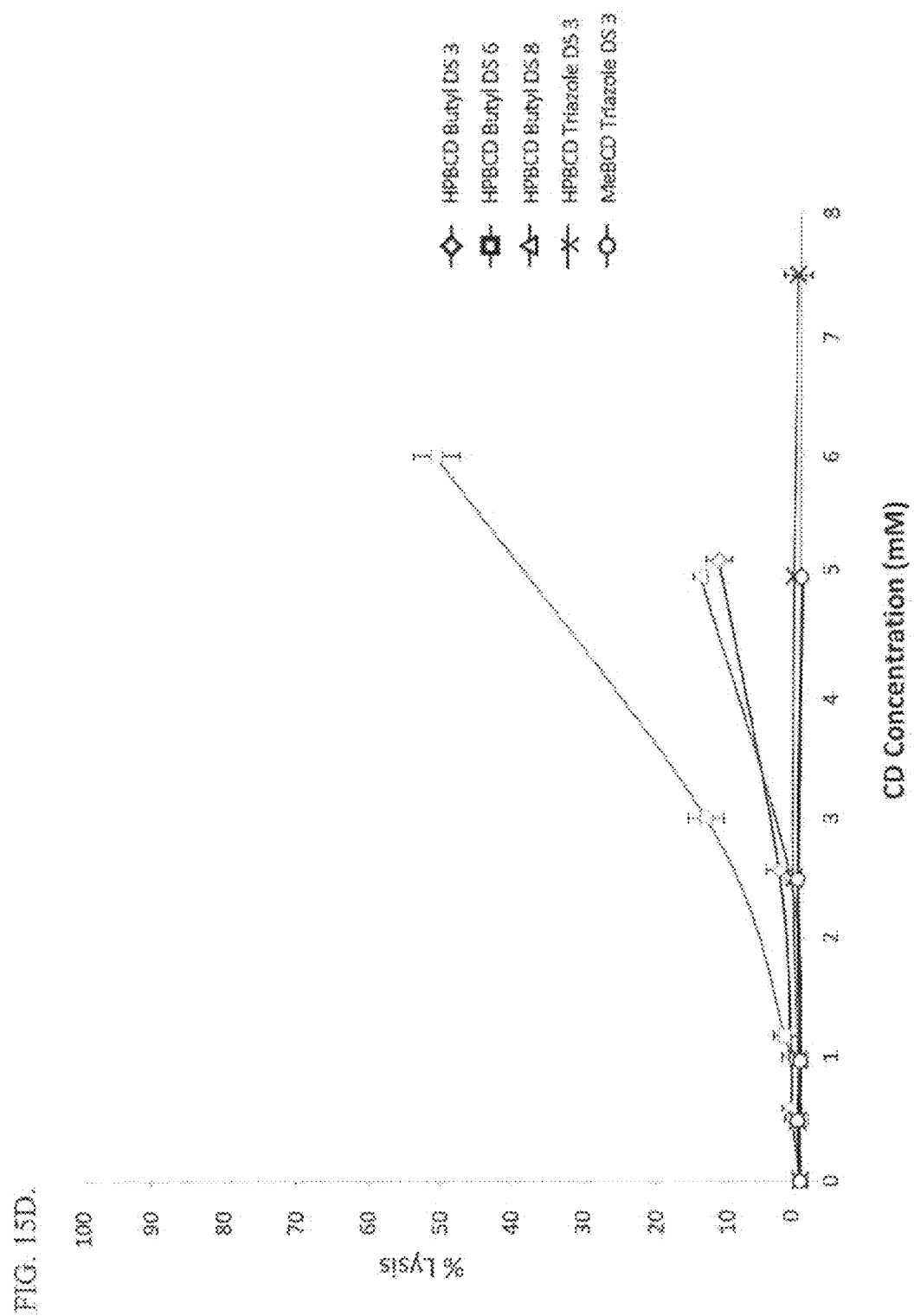

FIG. 15D. Hemolysis assay as a measure of potential cellular toxicity of various butyl- and triazole-linked HPβCD and methyl dimers.

Figure 15E:
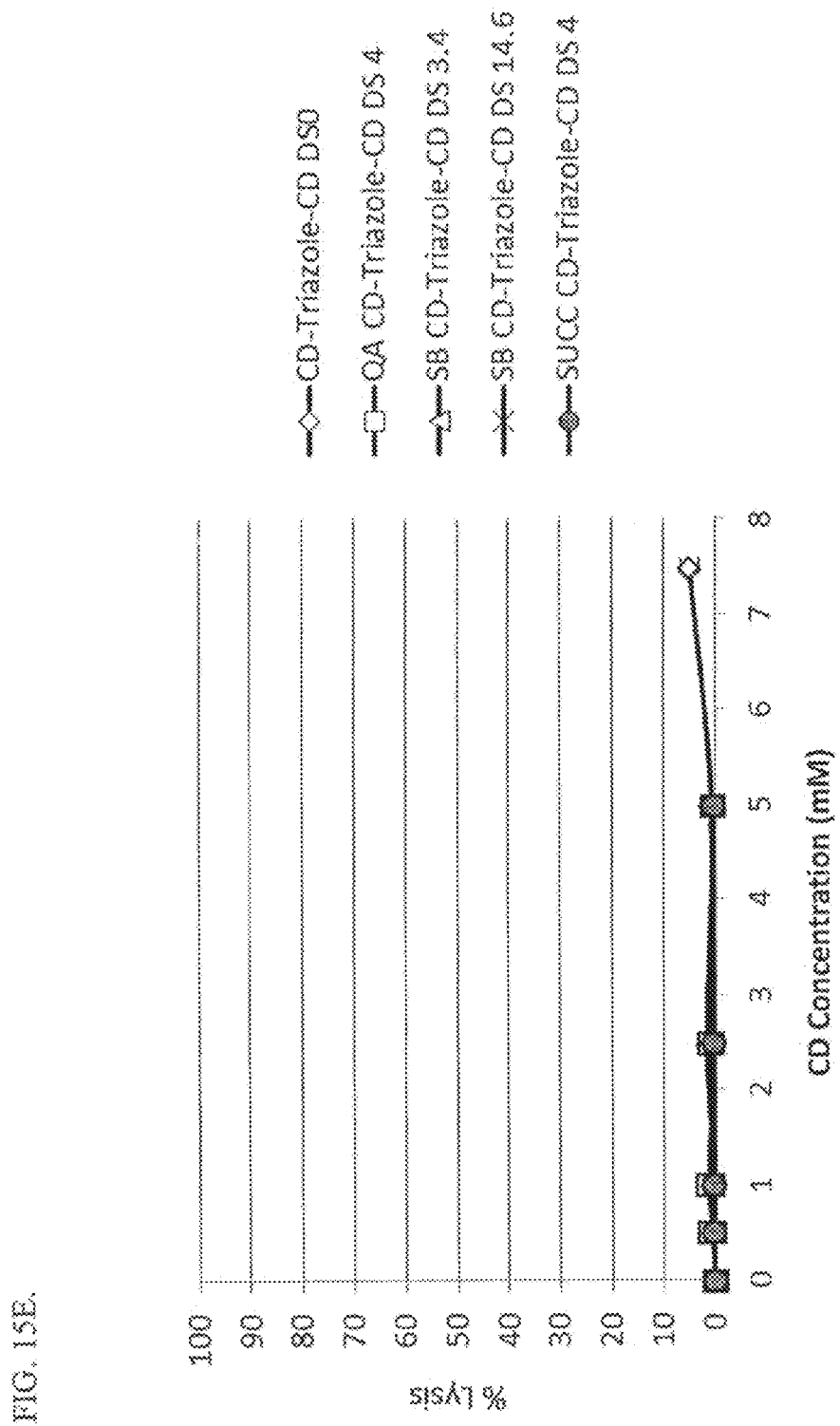

FIG. 15E. Hemolysis assay as a measure of potential cellular toxicity of various triazole-linked βCD dimers: unsubstituted βCD, SBβCD (low and high DS), QAβCD, and succinylated βCD dimers.

Figure 16A:
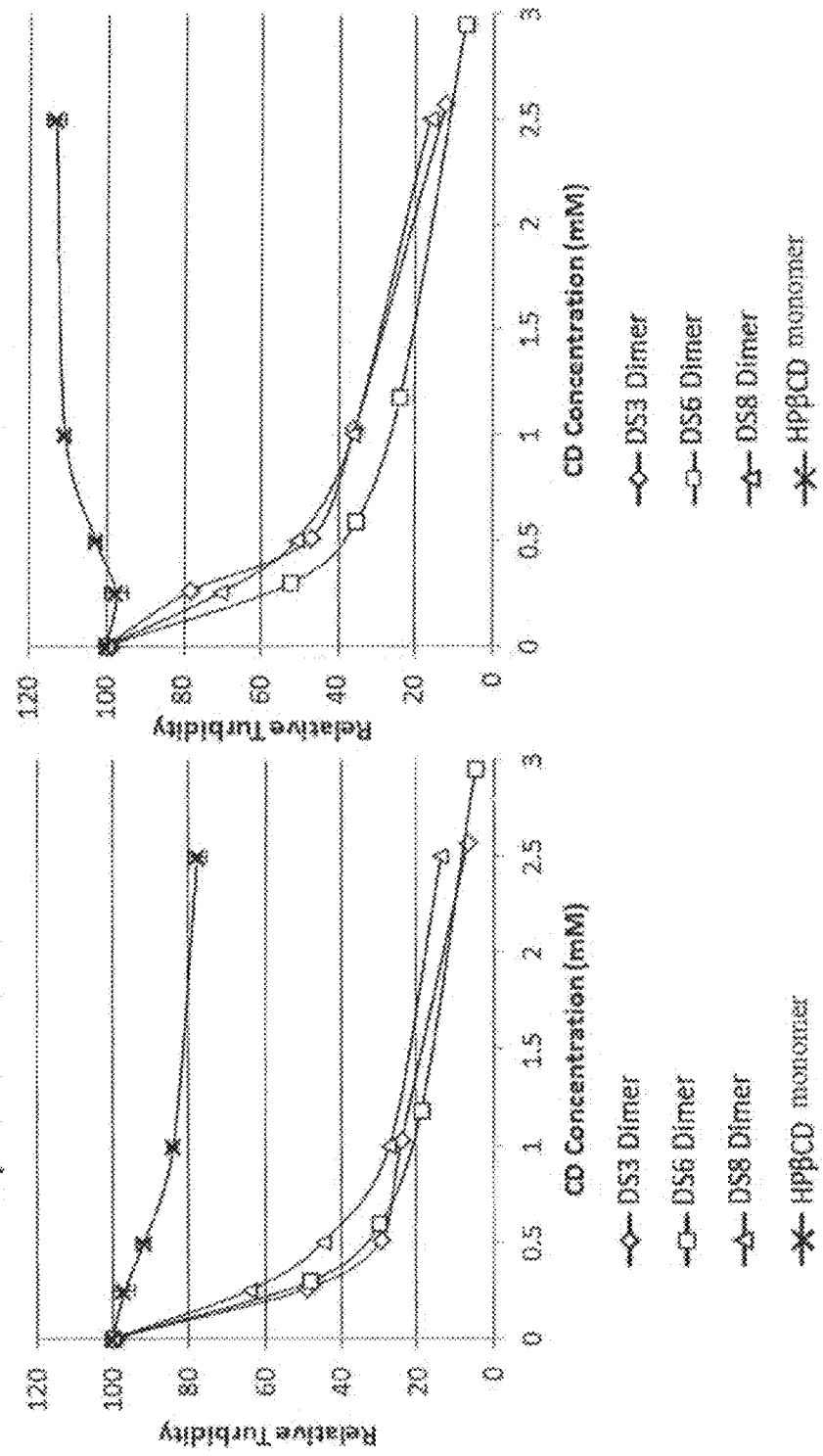

FIG. 16A. Butyl-linked HPβCD dimers are vastly superior to monomeric HPβCD at solubilizing 7KC and cholesterol. Dimers with ~3, ~6, and ~8 degrees of substitution were tested.

FIG. 16B. Triazole-linked HPβCD dimers are vastly superior to monomeric HPβCD at solubilizing 7KC and cholesterol. Dimers with 0, ~3, ~5, and ~6 degree of substitution were tested. HPBCD indicates monomeric HPβCD, while CD-triazole-CD denotes triazole-linked dimers with the indicated degree of substitution.

Figure 16C:
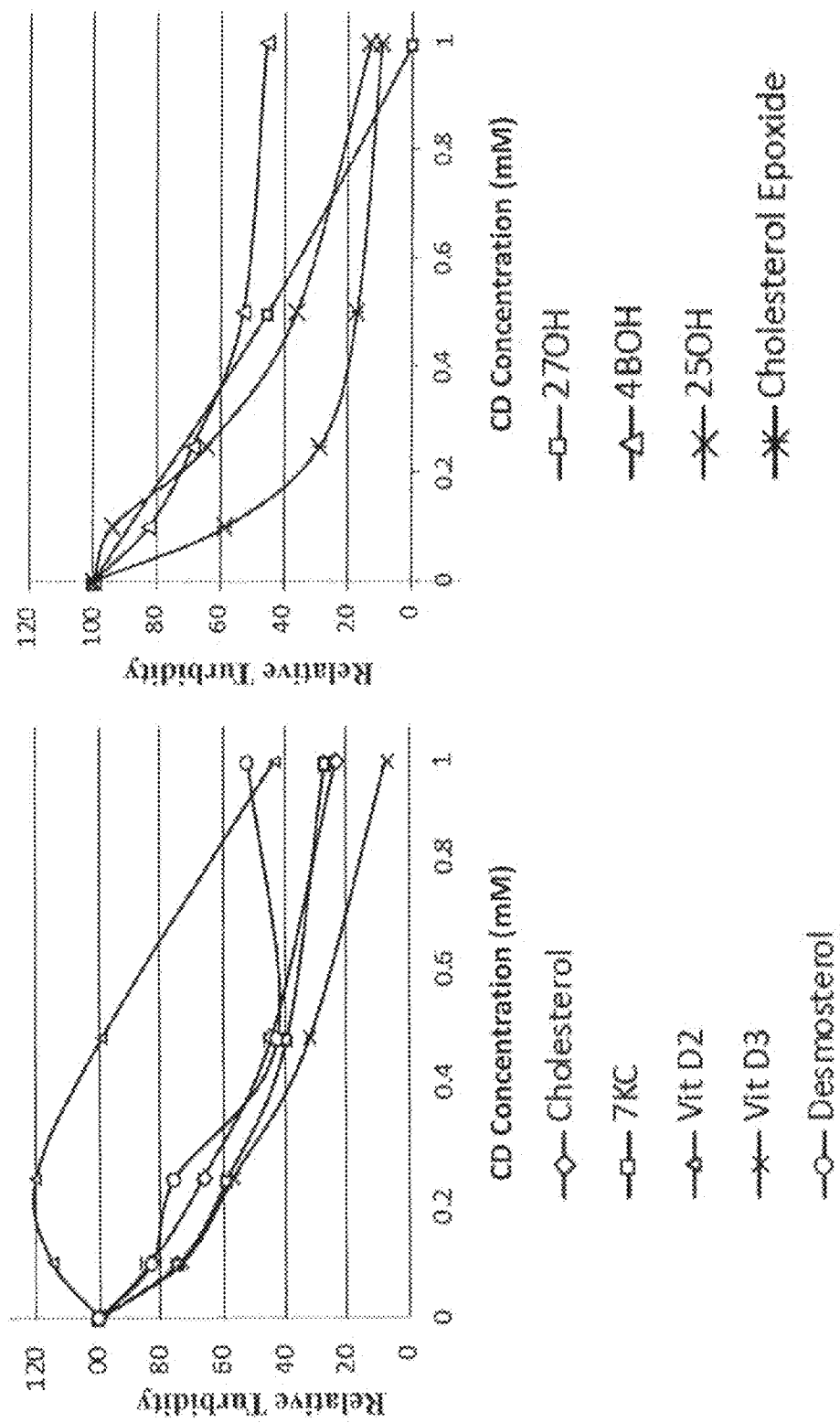

FIG. 16C. Butyl-linked HPβCD dimer (DS-8) solubilization of various cholesterol derivatives and oxysterols. Results are depicted for cholesterol, 7-ketocholesterol (7KC), vitamin D2, vitamin D3, desmosterol, 27-hydroxycholesterol (27OH), 4-beta hydroxycholesterol (4BOH), 25-hydroxycholesterol (25OH), and cholesterol epoxide.

Figure 16D:
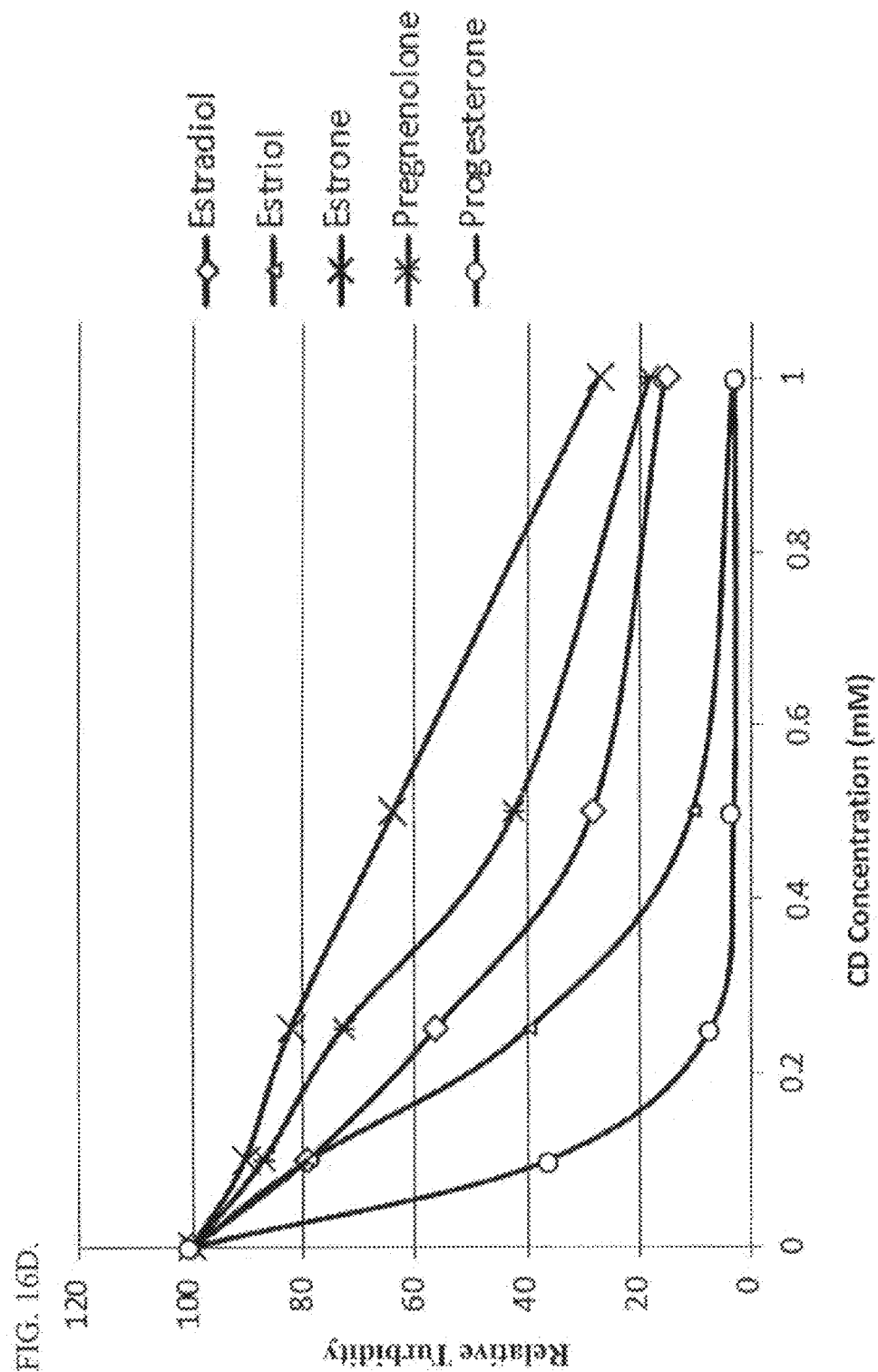

FIG. 16D. Compound solubilization by butyl-linked HPBCD dimer (DS-8). Sterol hormones tested were estradiol, estriol, estrone, pregnenolone, and progesterone.

Figure 16E:
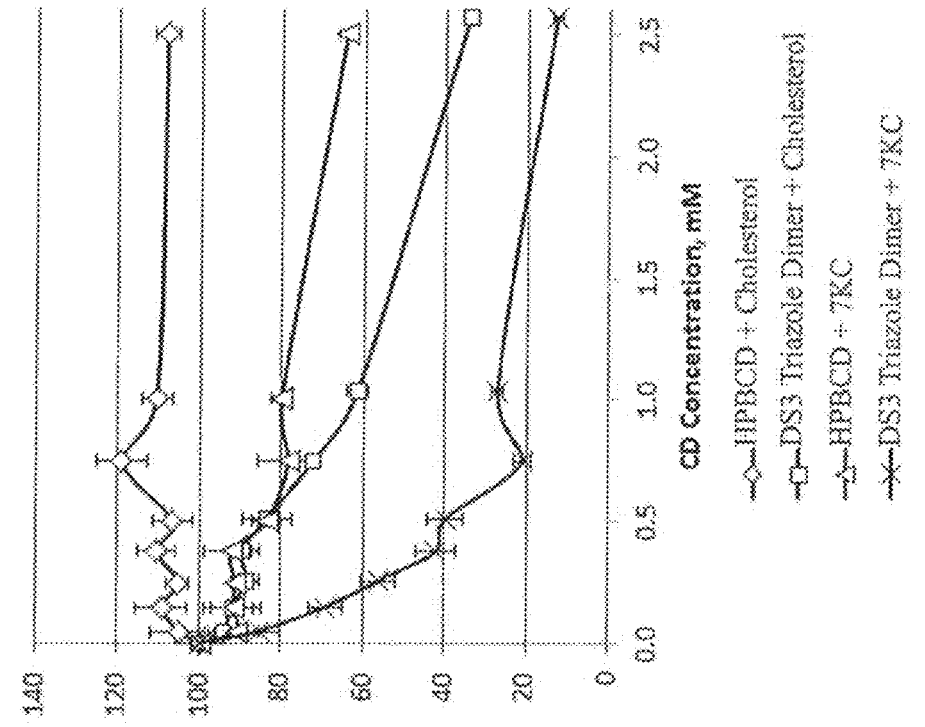

FIG. 16E. Butyl-linked HPβCD dimer (DS-3) ("DS3 butyl dimer") has affinity and specificity for 7KC. HPBCD indicates monomeric HPβCD.

Figure 16F:
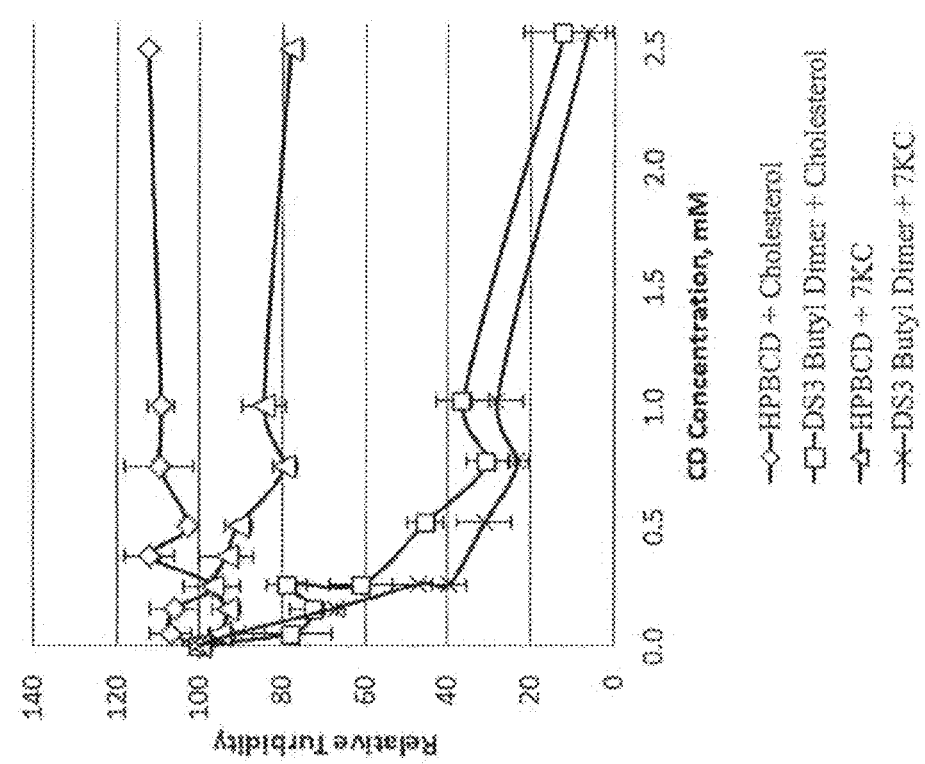

FIG. 16F. Triazole-linked HPβCD dimer (DS-3) has affinity and specificity for 7KC.

Figure 16G:
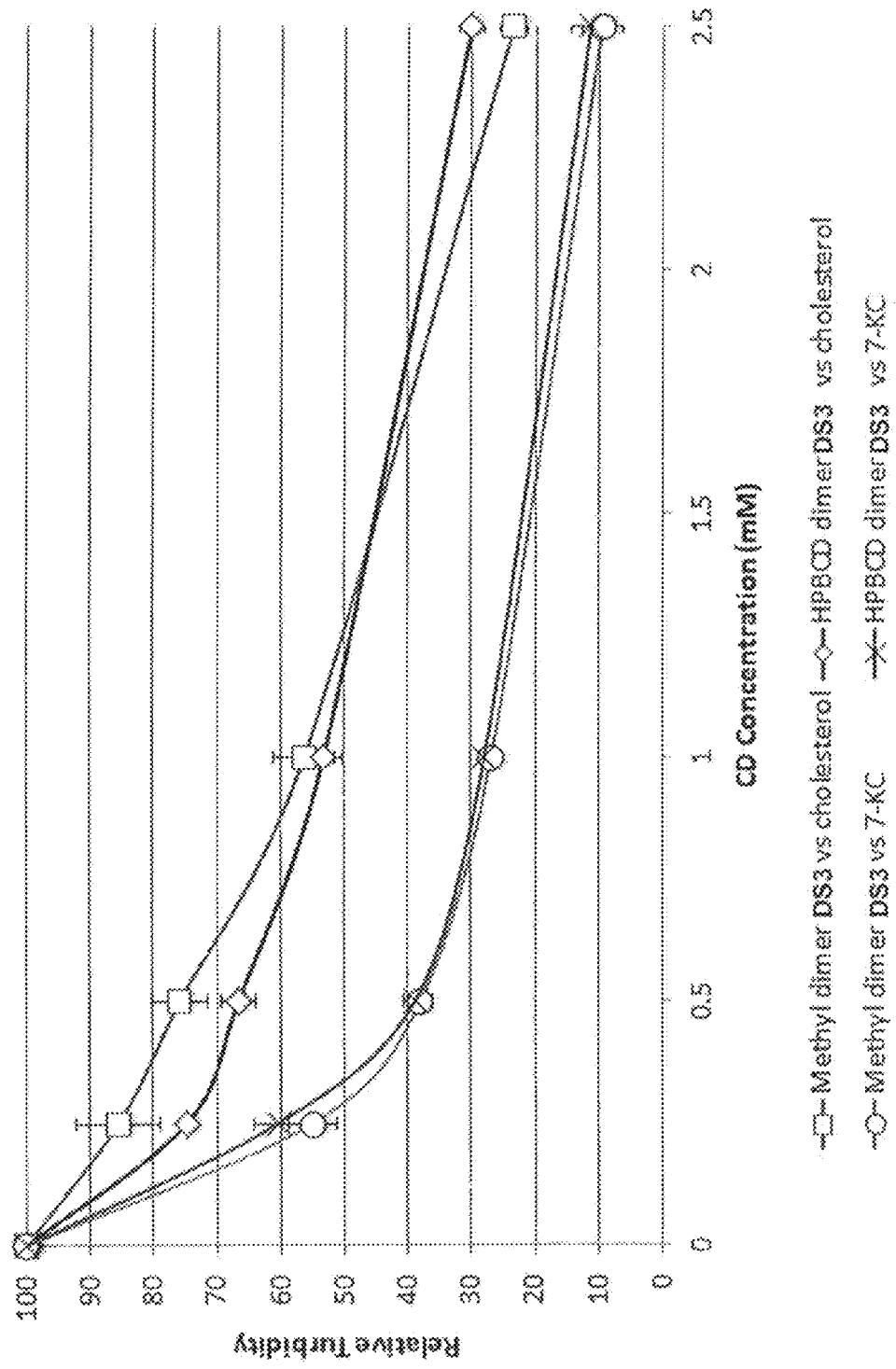

FIG. 16G. Triazole-linked MeβC dimer (DS-3) ("methyl dimer DS3") is effective similarly to HPβCD dimer (DS-3) ("HPBCD dimer DS3") at solubilizing 7KC and cholesterol.

Figure 16H:
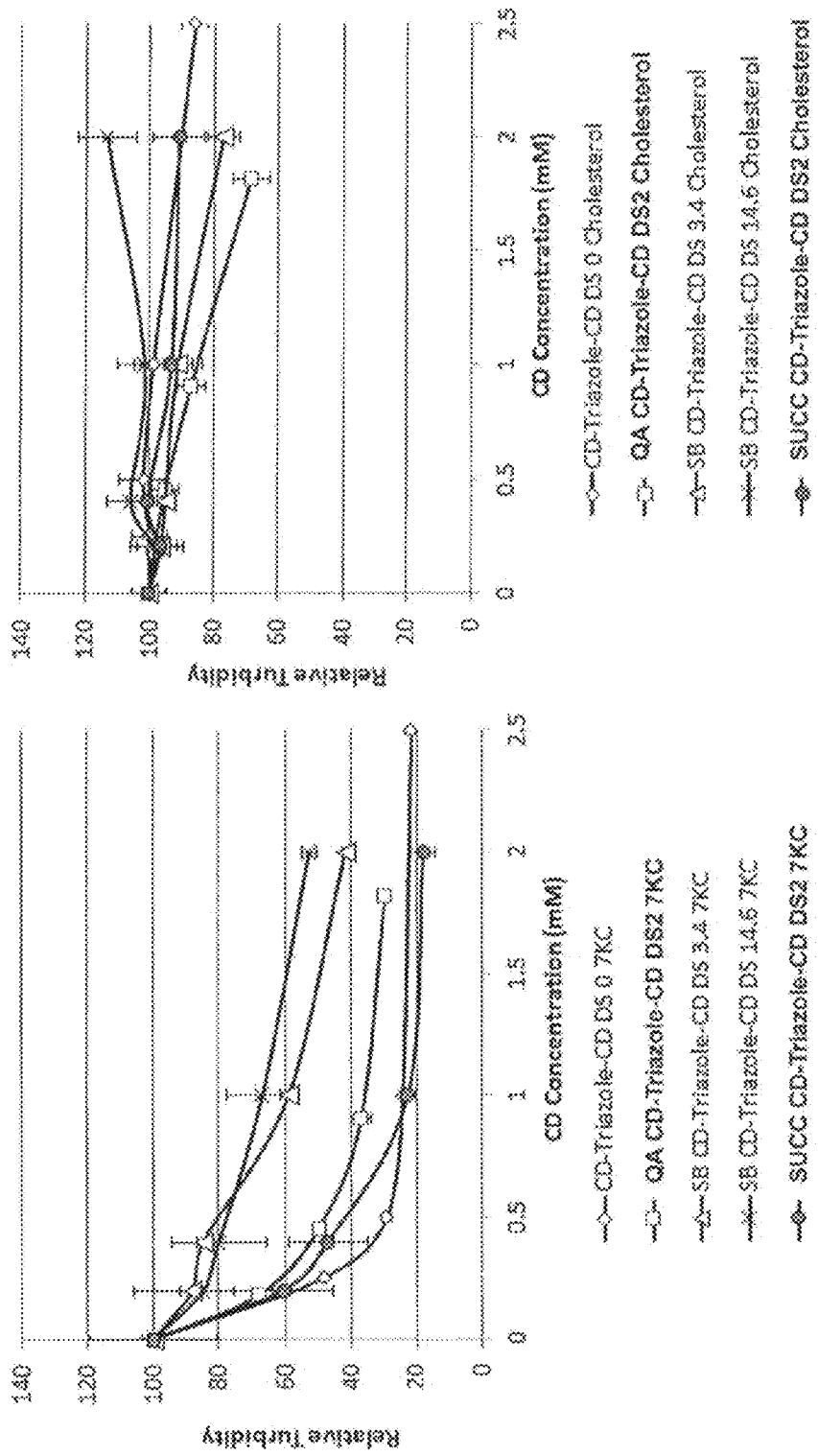

FIG. 16H. Triazole-linked unsubstituted βCD ("CD-triazole-CD DS 0"), triazole-linked SBβCD dimer (DS-3.4) ("SB CD-Triazole-CD DS 3.4"), triazole-linked QaβCD dimer (DS~2) (QA CD-Triazole-CD DS 2"), and triazole-linked succinylated βCD dimer (DS~2) ("SUCC CD-Triazole-CD DS 2") all have specificity for 7KC over cholesterol in vitro. Triazole-linked SBβCD dimer (DS~14.6) ("SB CD-Triazole-CD DS 14.6) had less affinity for both cholesterol and 7KC.

DEFINITIONS

Unless otherwise stated, the following terms used in this Application, including the specification and claims, have the definitions given herein.

As used in the specification and the appended claims, the singular forms "a", "an", and "the" include plural referents unless the context clearly dictates otherwise.

Figure 3A:
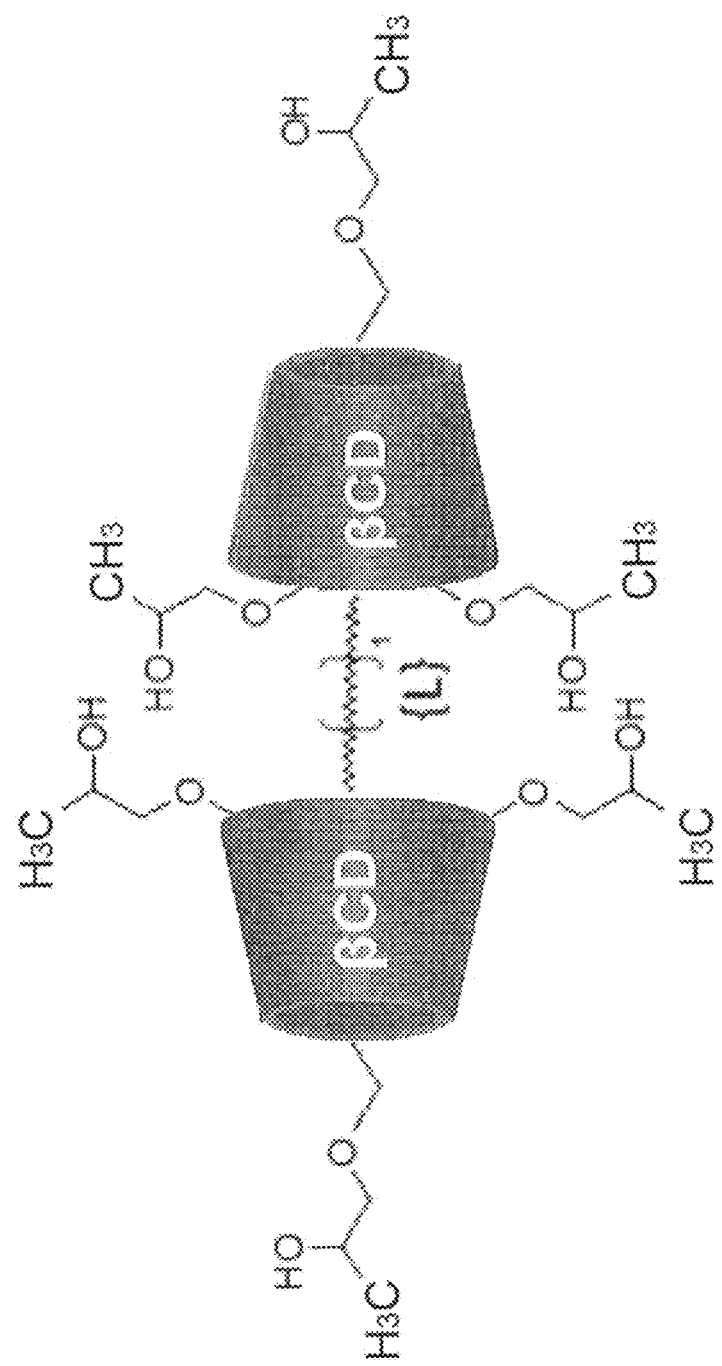
FIG. 3A. Structure of a HPβCD dimer of the disclosure. The beta cyclodextrin monomers are linked through the large (secondary) face, i.e., the linker is linked to a C2 or C3 carbon of each CD subunit. The HP substitutions are linked to C2, C3, and/or C6 carbons (typically in combination).

Linker length. As used herein, the length of a linker or interchangeably "linker length" refers to the number atoms of the linker on the shortest path through the linker connecting the two CD subunits of a cyclodextrin dimer. For clarity, the length of the linker does not include the oxygen atoms of each CD subunit (or other atom that may be substituted for said oxygen) to which the linker is attached. For example, in FIG. 3B, the linker length is 3+n1+n2, reflecting the shortest path through the triazole ring. In case of a linker attached to one or both of the cyclodextrin monomers at multiple points, the linker length is the shortest path that connects two cyclodextrins from among all possible paths which may start and end at different locations in each cyclodextrin.

Head-to-head cyclodextrin dimer. As used herein, the term "head-to-head cyclodextrin dimer" refers to a CD dimer wherein two CD monomers linked through the large (secondary) face of the cyclodextrin, typically attached via C2 and/or C3 carbons of each CD monomer.

Tail-to-tail cyclodextrin dimer. As used herein the term "tail-to-tail cyclodextrin dimer" refers to a CD dimer wherein two CD monomers are attached on the small (primary) face of the cyclodextrin molecule, typically attached via the C6 carbons of each CD monomer.

Head-to-tail cyclodextrin dimer. As used herein, the term "head-to-tail cyclodextrin dimer" refers to a CD dimer wherein two CD monomers attached at opposite ends, i.e., one monomer attached from the small (primary) face, typically through a C6 carbon, and the other attached from the large (secondary) face, typically via a C2 and/or C3 carbon.

Degree of substitution (DS). As used herein, the "degree of substitution" or "DS" refers to the number of a given subgroup bound to the monomer or dimer. For instance, MeβCD DS3 refers to a βCD having, on average, 3 methyl R groups attached to O2, O3, or O6 of the CD, while HPβCD DS3 indicates the monomer or dimer has, on average, 3 hydroxypropyl groups attached to O2, O3, or O6 of the CD. When referring to a CD dimer, unless indicated otherwise, the DS is used to refer to the total average substitution of both constituent monomers, including all substituents (e.g., in the case of mixed substituents such as mixed hydroxypropyl and methyl substituents, all are counted). Terminology such as "degree of substitution with substituent X" and the like refer to the average number of that substituent X per CD dimer, i.e., not including other substituents that may be present. The DS may be measured by mass spectrometry (e.g., matrix assisted laser desorption/ionization, "MALDI") or by NMR. MALDI is preferred in for cyclodextrin derivatives containing substituents that give a more typical Gaussian distribution of ions in the mass spectrum, e.g., as exhibited for methyl, hydroxypropyl, and sulfobutyl substituents in FIGS. 10G-10I, 10P-10Q, 11C-11G, 11I, 12E, and 12K. Average DS as determined by MALDI is calculated by averaging the peak heights of the peaks corresponding to each DS species of the CD in question. In other instances a less regular pattern of ion peaks may be present, e.g., due to the formation of various adducts, fragmentation, elimination products, etc. Other mass spectrometric techniques may be utilized to potentially circumvent these issues. Alternatively, NMR may be used to determine the DS value, which was preferred for succinyl and quaternary ammonium groups given the more complex MS spectra observed by MALDI. The calculation of the average degree of substitution (DS) is then accomplished by identifying a peak that corresponds to protons from the core dimer and first scaling the measured values such that the peak area corresponds to the known number of such protons in the structure. A signal corresponding to protons in the substituent group is then examined and scaled appropriate in order to yield the average degree of substitution. In the simpler case, a clearly resolved peak corresponding to substituent protons is identified, and having already been scaled as described previously, is then divided by the number of protons represented in that peak in order to yield the average number of substituents. For example, in the case of hydroxypropyl substituents, a peak identified as corresponding to 14 protons in the core structure (the anomeric region of the glucopyranose) was identified and signalized normalized to 14, then the peak corresponding to the 3 protons of the methyl substituent was identified, and finally the area of that peak was divided by 3 in order to yield the average number of hydroxypropyl groups present per molecule. In other instances, substituent peaks and cyclodextrin core peaks may be in close proximity or overlapping. In this case, the number of contributing protons from the cyclodextrin core structure is identified and then subtracted from the peak area (the peak area having already been scaled to an integrated area of 1 per proton), and then the remaining area is divided by the number of contributing protons in order to yield the average degree of substitution. For example, in the case of a methyl substituent (illustrated in FIGS. 11K-11L), a cluster of peaks was identified corresponding to the three methyl hydrogens of the substituent, and additionally a group of 86 protons of the core cyclodextrin dimer structure. As in the hydroxypropyl substituent example, a peak identified as corresponding to 14 protons in the core structure (the anomeric region of the glucopyranose) was identified and the signalized normalized to 14; the area of the peak containing the methyl hydrogens and core cyclodextrin hydrogens was determined to be 92.77, leaving 6.77 after subtracting the signal from the 86 protons of the core cyclodextrin structure; and after dividing by the 3 protons of each methyl group, the average degree of substitution was estimated to be 2.26. For HP and ME substituted CDs integration is divided by 3, for QA the integration is divided by 9, for SB the integration is divided by 2, and for SUCC the integration is divided by 4. The foregoing calculation is straightforwardly adapted to other substituent types based on the identification of peaks corresponding to protons in the substituent structure. DS calculations using NMR are illustrated in FIGS. 10X-Y, 11L, 12H, 12N, 13I, and 14I. A CD composition, such as a CD dimer composition (defined below) may comprise a mixture of individual molecules substituted with differing numbers of substituents, in which case the DS value is expressed as the average (median) number of substitutions. Fractional DS values reflect the case where the median value may be between whole number substitutions. Unless indicated otherwise, a whole number DS value indicates a CD composition having that DS number when rounded to the nearest whole number. For example, DS4 refers to a DS value of at least 3.5 and less than 4.5.

Average degree of substitution with hydroxypropyl groups. As used herein, the term "average degree of substitution with hydroxypropyl groups" refers to the degree of substitution, as defined above, disregarding any substituent other than a hydroxypropyl group. Likewise, references to the average degree of substitution with a specified substituent refers to the average degree of substitution as defined above disregarding other substituent types.

Hydroxypropyl (HP or Hp) substituted cyclodextrin (CD). As used herein, the term "hydroxypropyl substituted cyclodextrin" or "HP substituted CD" refers to a cyclodextrin that is linked to a hydroxypropyl group, i.e., —CH2-CH(OH)—CH3. Typically, the HP groups are linked to the oxygen atoms linked to the C2, C3, and/or C6 carbons of the CD (most commonly having a mixture of those attachment sites).

Hydroxypropyl beta cyclodextrin, abbreviated as HPβCD, HPBCD, HPβCD, HPBCD, HP-BCD, HP-BCD, HP-βCD, HP-βCD, 2-HPβCD, and similar terms, refers to a beta cyclodextrin that is substituted with one or more hydroxypropyl groups, i.e., —CH2-CH(OH)—CH3, typically linked to the oxygen atoms linked to the C2, C3, and/or C6 carbons of the CD (most commonly having a mixture of those attachment sites).

Hydroxypropyl beta cyclodextrin dimers, abbreviated as HP(CD-L-CD) or HP(CD-L-CD) or HP(βCD-L-βCD) or HP(βCD-L-βCD)HP and similar terms, refers to covalently linked hydroxypropyl beta cyclodextrin dimers with the linker L. A particular average number of substitutions may be present, e.g., DS4 indicating 4 HP groups present on average. Additional substitutions may be present, as further described herein.

Similar conventions are used for other substituted cyclodextrins and cyclodextrin dimers such as methyl (Me), quaternary ammonium (QA), succinyl (SUCC), sulfobutyl (SB) and the like. Such that, for example MeβCD refers to methyl beta cyclodextrin. Similarly methyl beta cyclodextrin dimers are sometimes abbreviated as Me(CD-L-CD) or Me(CD-L-CD) or Me(βCD-L-βCD) or Me(βCD-L-βCD)Me and similar terms, which refer to covalently linked methyl beta cyclodextrin dimers with the linker L. A particular average number of substitutions may be present, e.g., DS4 indicating 4 Me groups present on average. Additional substitutions may be present, as further described herein.

Cyclodextrin dimer composition. As used herein, the term "cyclodextrin dimer composition" or "CD dimer composition" refers to a mixture of cyclodextrin dimers, e.g., CD dimers substituted with varying numbers of the same substituent. Typically, a CD dimer composition is characterized by having a specified degree of substitution with a specified substituent. A CD dimer composition can result from of a synthesis process wherein the substituent is added to the CD dimers in a stochastic manner due to the mostly symmetrical nature of the CD molecule, such that individual CD molecules will vary in the number and position of substituents. Additionally, a CD dimer composition may comprise a mixture of individual molecules having differing sites of linker attachment (e.g., O2 to O2, O2 to O3, O3 to O2, or O3 to O3), or alternatively the site of linker attachment may be uniform (e.g., only O2 to O2, only O2 to O3, only O3 to O2, or only O3 to O3). The degree of substitution of the CD dimer composition may be determined by NMR and/or mass spectrometry, e.g., as described above.

The term "specifically binds," or the like, means that a molecule, e.g., a cyclodextrin dimer of the present disclosure, forms a complex with a binding partner, e.g., a cholesterol (such as an oxysterol, e.g., 7KC) that is relatively stable under physiologic conditions. Methods for determining whether a molecule specifically binds to a binding partner are well known in the art and include, for example, equilibrium dialysis, surface plasmon resonance, and the like. In exemplary embodiments, a cyclodextrin dimer of the present disclosure binds to a cholesterol, oxysterol, or 7KC with a $K_D$ of between about 5 µM and about 100 µM, between about 10 µM and about 90 µM, between about 20 µM and about 80 µM, between about 30 µM and about 70 µM, between about 40 µM and about 60 µM, between about 0.5 µM and about 50 µM, between about 1 µM and about 40 µM, between about 2 µM and about 30 µM, between about 3 µM and about 20 µM, between about 4 µM and about 10 µM, less than about 1000 µM, less than about 500 µM, less than about 300 µM, less than about 200 µM, less than about 100 µM, less than about 90 µM, less than about 80 µM, less than about 70 µM, less than about 60 µM, less than about 50 µM, less than about 40 µM, less than about 30 µM, less than about 20 µM, less than about 10 µM, less than about 5 µM, less than about 4 µM, less than about 3 µM, less than about 2 µM, less than about 1 µM or less than about 0.5 µM.

Greater affinity for 7KC than cholesterol. As used herein, the term "greater affinity for 7KC than cholesterol" refers to a compound (e.g., a cyclodextrin) having a greater ability to solubilize 7KC than cholesterol. Greater affinity can be also be predicted by molecular docking, predicted by molecular dynamic simulation, or measured by calorimetry. In exemplary embodiments, the cyclodextrin dimer has a binding affinity for 7KC that, compared to its binding affinity for cholesterol, is at least 1.5-fold, at least 2-fold, at least 3-fold, at least 4-fold, at least 5-fold, at least 8-fold, at least 10-fold, at least 15-fold, at least 20-fold, at least 30-fold, or at least 50-fold stronger, which optionally may be determined by comparing concentrations at which 50% of 7KC in a suspension becomes solubilized, e.g., using the procedures described in the working examples herein. In exemplary embodiments, the cyclodextrin dimer has a binding affinity for 7-KC that, compared to its binding affinity for cholesterol, is at least 1.1-fold, 1.5-fold, 2-fold, 3-fold, 4-fold, 5-fold, or 10-fold stronger, which optionally may be determined by dividing the computed or measured binding affinity ($K_D$) for cholesterol by the computed binding affinity for 7KC.

Greater affinity for one compound than another, e.g., greater affinity for 7KC than cholesterol, may be determined using a "turbidity test" performed on an aqueous suspension containing 3% ethanol, 300 uM sterol, in PBS and 1 mM of the cyclodextrin to be tested. This single concentration of cyclodextrin is used in order to standardize the test results. To perform the test, the samples are incubated for 30 mins at 37 C, and then absorbance at 350 nm is measured, e.g., using a spectrophotometer plate reader. Relative turbidity is determined by dividing the measured turbidity in the presence of the cyclodextrin to the baseline turbidity without the cyclodextrin. A given cyclodextrin has greater affinity for 7KC than cholesterol if the relative turbidity of the 7KC suspension is lower than the relative turbidity of the cholesterol solution.

Hydrophobic drug. As used herein, the term "hydrophobic drug" refers to a drug that is not soluble in water absent some detergent or other solvent. Hydrophobic drugs include, but are not limited to, hormones such as estrogen, progesterone, and testosterone. The cyclodextrin dimers of the present disclosure may be used as an excipient for hydrophobic drugs. Additional exemplary hydrophobic drugs include dexamethorphan HBr (DXM), diphenhydramine HCl (DPH), lidocaine HCl (LDC), Heprin, Bendroflumethiazide, acyclovir, Revaprazan, curcumin, and testosterone propionate (IP), to name a few. The cyclodextrin dimer may be present in an amount sufficient to increase the solubility of the molecule and/or aid in better drug delivery. The molecular ratio of the drug to cyclodextrin may be 1:1 ratio or more than 1:1.

Amount effective to solubilize said hydrophobic drug. As used herein, the phrase "amount effective to solubilize said hydrophobic drug" refers to the concentration of a substance (e.g., a cyclodextrin dimer) that is able to solubilize a hydrophobic drug, typically in an aqueous composition such as phosphate buffered saline (PBS) or water. The solubilization can be determined by spectrophotometry or other means known in the art. Solubilization may be determined at room temperature, physiological temperature (37 degrees C.) or another appropriate temperature (e.g., between 0 and 4 degrees C.).

"Alkyl" means the monovalent linear or branched saturated hydrocarbon moiety, consisting solely of carbon and hydrogen atoms, having from one to twelve carbon atoms.

"Lower alkyl" refers to an alkyl group of one to six carbon atoms, i.e. C3 alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear or branched saturated divalent hydrocarbon radical of one to twelve carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenyl" means a linear monovalent hydrocarbon radical of two to twelve carbon atoms or a branched monovalent hydrocarbon radical of three to twelve carbon atoms, containing at least one double bond. Examples of alkenyl groups include, but are not limited to, ethenyl (vinyl, —CH═CH2), 1-propenyl (—CH═CH—CH3), 2-propenyl (allyl, —CH—CH═CH2) moieties include, but are not limited to, methoxy, ethoxy, iso-propoxy, and the like.

"Alkoxyalkyl" means a moiety of the formula Ra-O—Rb-, where Ra is alkyl and Rb is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxyalkyl" means a group of the formula —R—O—R'—O—R" wherein R and R' each are alkylene and R" is alkyl as defined herein.

"Alkylcarbonyloxyalkyl" means a group of the formula —R—O—C(O)—R' wherein R is alkylene and R' is alkyl as defined herein.

"Alkylcarbonyl" means a moiety of the formula —R'—R", where R' is —C(═O)— and R" is alkyl as defined herein.

"Alkylsulfonyl" means a moiety of the formula —R'—R", where R' is —SO2- and R" is alkyl as defined herein.

"Alkylsulfonylalkyl" means a moiety of the formula —R'—R"—R" where R' is alkyl, R" is —SO2- and R" is alkyl as defined herein.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkali metal ion" means a monovalent ion of a group I metal such as lithium, sodium, potassium, rubidium or cesium, preferably sodium or potassium.

"Alkaline earth metal ion" means a divalent ion of a group II metal such as beryllium, magnesium, calcium, strontium or barium, preferably magnesium or calcium.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like.

"Aminoalkoxy" means a group —OR—R1 wherein R' is amino and R is alkylene as defined herein.

"Alkylsulfonylamido" means a moiety of the formula —NR'SO2-R wherein R is alkyl and R' is hydrogen or alkyl.

"Aminocarbonyloxyalkyl" or "carbamylalkyl" means a groups —R—O—C(═O)—R' wherein R' is amino and R is alkylene as defined herein.

"Aminosulfonyl" means a group —SO2-NR'R" wherein R' and R" each independently is hydrogen or alkyl. "Aminosulfonyl" as used herein thus encompasses "alkylaminosulfonyl" and "dialkylaminosulfonyl".

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenyl sulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-RaRb where Ra is an alkylene group and Rb is an aryl group as defined herein; e.g., phenylalkyls such as benzyl, phenylethyl, 3-(3-chlorophenyl)-2-methylpentyl, and the like are examples of arylalkyl.

"Arylsulfonyl" means a group of the formula —SO2-R wherein R is aryl as defined herein.

"Aryloxy" means a group of the formula —O—R wherein R is aryl as defined herein.

"Aralkyloxy" or "Arylalkyloxy" means a group of the formula —O—R—R" wherein R is alkylene and R' is aryl as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkenyl" means a monovalent unsaturated carbocyclic moiety consisting of mono- or bicyclic rings containing at least one double bond. Cycloalkenyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkenyl moieties include, but are not limited to, cyclopropenyl, cyclobutenyl, cyclopentenyl, cyclohexenyl, cycloheptenyl.

"Cycloalkylalkyl" means a moiety of the formula —R'—R", where R' is alkylene and R" is cycloalkyl as defined herein.

"Cycloalkylene" means a divalent saturated carbocyclic radical consisting of mono- or bicyclic rings. Cycloalkylene can optionally be substituted with one or more substituents, wherein each substituent is independently hydroxy, alkyl, alkoxy, halo, haloalkyl, amino, monoalkylamino, or dialkylamino, unless otherwise specifically indicated.

"Cycloalkylalkylene" means a moiety of the formula —R'—R"—, where R' is alkylene and R" is cycloalkylene as defined herein.

"Heteroalkyl" means an alkyl radical as defined herein wherein one, two or three hydrogen atoms have been replaced with a substituent independently selected from the group consisting of —ORa, —NRbRc, and —S(O)nRd (where n is an integer from 0 to 2), wherein the point of attachment of the heteroalkyl radical is through a carbon atom, wherein Ra is hydrogen, acyl, alkyl, cycloalkyl, or cycloalkylalkyl; Rb and Rc are independently of each other hydrogen, acyl, alkyl, cycloalkyl, or cycloalkylalkyl; and when n is 0, Rd is hydrogen, alkyl, cycloalkyl, or cycloalkylalkyl, and when n is 1 or 2, Rd is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, wherein the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" or "heteroaralkyl" means a group of the formula —R—R' wherein R is alkylene and R' is heteroaryl as defined herein.

"Heteroarylsulfonyl" means a group of the formula —SO2-R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

"Heterocyclylalkoxy means a group of the formula —O—R—R' wherein R is alkylene and R' is heterocyclyl as defined herein.

The terms "halo", "halogen" and "halide", which may be used interchangeably, refer to a substituent fluoro, chloro, bromo, or iodo. In some embodiments, halo refers to a fluoro substituent.

"Haloalkyl" means alkyl as defined herein in which one or more hydrogen has been replaced with same or different halogen. In some embodiments, haloalkyl is a fluoroalkyl; in some embodiments, the haloalkyl is a perfluoroalkyl. Exemplary haloalkyls include —CH2Cl, —CH2CF3, —CH2CCl3, perfluoroalkyl (e.g., —CF3), and the like.

"Haloalkoxy" means a moiety of the formula —OR, wherein R is a haloalkyl moiety as defined herein. In some embodiments, haloalkoxy is a fluoroalkoxy; in some embodiments, the haloalkoxyl is a perfluoroalkoxy. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydroisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxy-propyl, 2-hydroxy-1-hydroxymethylethyl, 2,3-dihydroxybutyl, 3,4-dihydroxybutyl and 2-(hydroxymethyl)-3-hydroxypropyl.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxyl-5-methyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Hydroxycycloalkyl" means a cycloalkyl moiety as defined herein wherein one, two, or three hydrogen atoms in the cycloalkyl radical have been replaced with a hydroxy substituent. Representative examples include, but are not limited to, 2-, 3-, or 4-hydroxy-cyclohexyl, and the like.

"Urea" or "ureido" means a group of the formula —NR'—C(O)—NR"R'" wherein R, R" and R'" each independently is hydrogen or alkyl.

"Carbamate" means a group of the formula —O—C(O)—NR'R" wherein R' and R" each independently is hydrogen or alkyl.

"Carboxy" means a group of the formula —C(O)OH.

"Sulfonamido" means a group of the formula —SO2-NR'R" wherein R', R" and R" each independently is hydrogen or alkyl.

"Nitro" means —NO2.

"Cyano" means —CN.

"Phenoxy" means a phenyl ring that is substituted with at least one —OH group.

"Acetyl" means —C(=O)—CH3.

"Cn-m-" is used as a prefix before a functional group wherein 'n' and 'm' are recited as integer values (i.e., 0, 1, 2, 12), for example C1-12-alkyl or C5-12-heteroaryl. The prefix denotes the number, or range of numbers, of carbon atoms present in the functional group. In the case of ring systems, the prefix denotes the number of ring atoms, or range of the number of ring atoms, whether the ring atoms are carbon atoms or heteroatoms. In the case of functional groups made up a ring portion and a non-ring portion (i.e. "arylalkyl" is made up of an aryl portion and an alkyl portion) the prefix is used to denote how many carbon atoms and ring atoms are present in total. For example, with arylalkyl, "C7-arylalkyl" may be used to denote "phenyl-CH2-". In the case of some functional groups zero carbon atoms may be present, for example C0-aminosulfonyl (i.e. —SO2-NH2, with both potential R groups as hydrogen) the '0' indicates that no carbon atoms are present.

"Peptide" means an amide derived from two or more amino acids by combination of the amino group of one acid with the carboxyl group. "Monopeptide" means a single amino acid, "dipeptide" means an amide compound comprising two amino acids, "tripeptide" means an amide compound comprising three amino acids, and so on. The C-terminus of a "peptide" may be joined to another moiety via an ester functionality.

"Optionally substituted", when used in association with "aryl", phenyl", "heteroaryl" "cyclohexyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl), —(CR'R")n-COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")n-CONRaRb (where n is an integer from 0 to 5, R' and R" are independently hydrogen or alkyl, and Ra and Rb are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including, e.g., benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tertbutanol, dioxane, pyridine, and the like. Unless specified to the contrary, the solvents used in the reactions of the present disclosure are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalene-sulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, trimethylamine, tromethamine, and the like. Acceptable inorganic bases include aluminum hydroxide, calcium hydroxide, potassium hydroxide, sodium carbonate and sodium hydroxide. The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium. All references to pharmaceutically acceptable salts include solvent addition forms (solvates) or crystal forms (polymorphs) as defined herein, of the same acid addition salt. In general, when a particular salt is included in a structure or formula herein, it is understood that other pharmaceutically acceptable salts may be substituted within the scope of the present disclosure, e.g., in the case of the quaternary ammonium salt of formula VIII, chloride or another negative ion or combination of ions may be included, and similarly in the carboxymethyl sodium salt of formula IX another positive ion may be substituted for the depicted sodium.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of the present disclosure rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The person skilled in the art will know how to choose a group for the ease of removal and for the ability to withstand the following reactions.

"Subject" means mammals and non-mammals. Mammals means any member of the Mammalia class including, but not limited to, humans; non-human primates such as chimpanzees and other apes and monkey species; farm animals such as cows, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to affect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes: (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

Any open valency appearing on a carbon, oxygen, sulfur or nitrogen atom in the structures herein indicates the presence of a hydrogen atom.

EXAMPLES

Example 1. Solubilization of Compounds by HPβCD

Figure 1A:
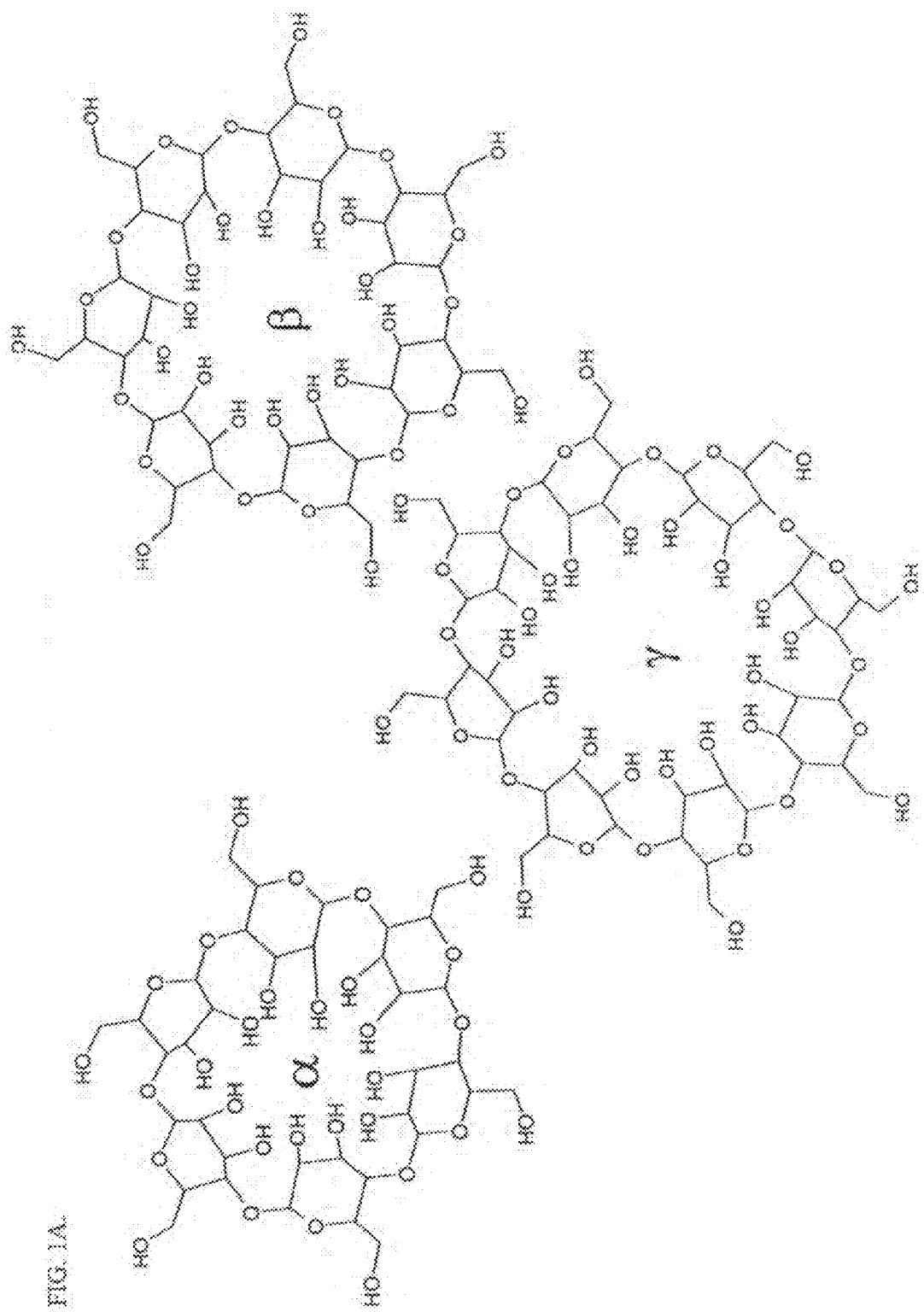
FIG. 1A. Structure of cyclodextrins (CDs), cyclic oligosaccharide polymers comprised of 6 (αCD), 7 (βCD), or 8 (γCD) sugar rings (left to right). All the sugar rings in all CDs are D-glucose molecules.
Figure 1B:
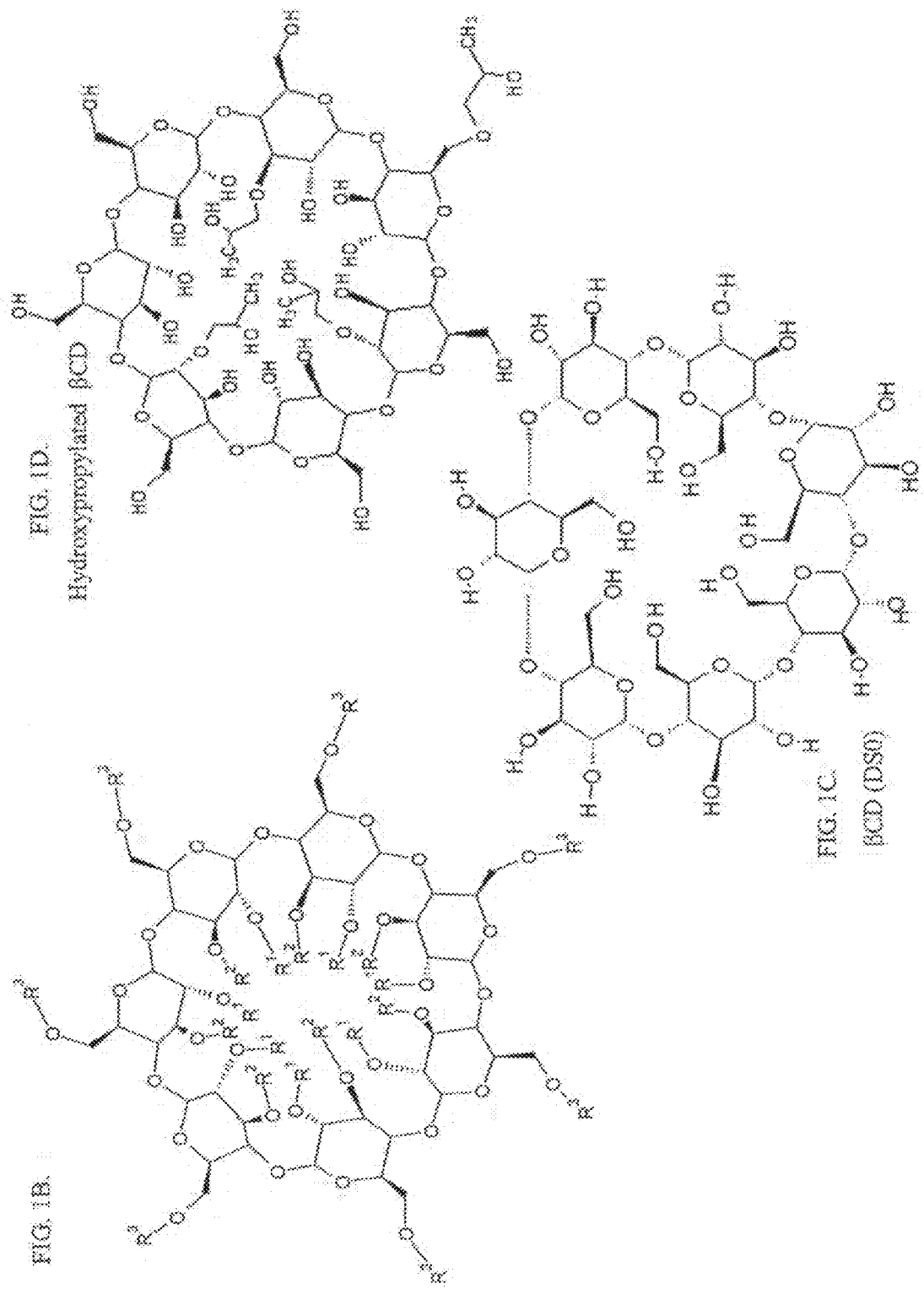
Figure 2A:
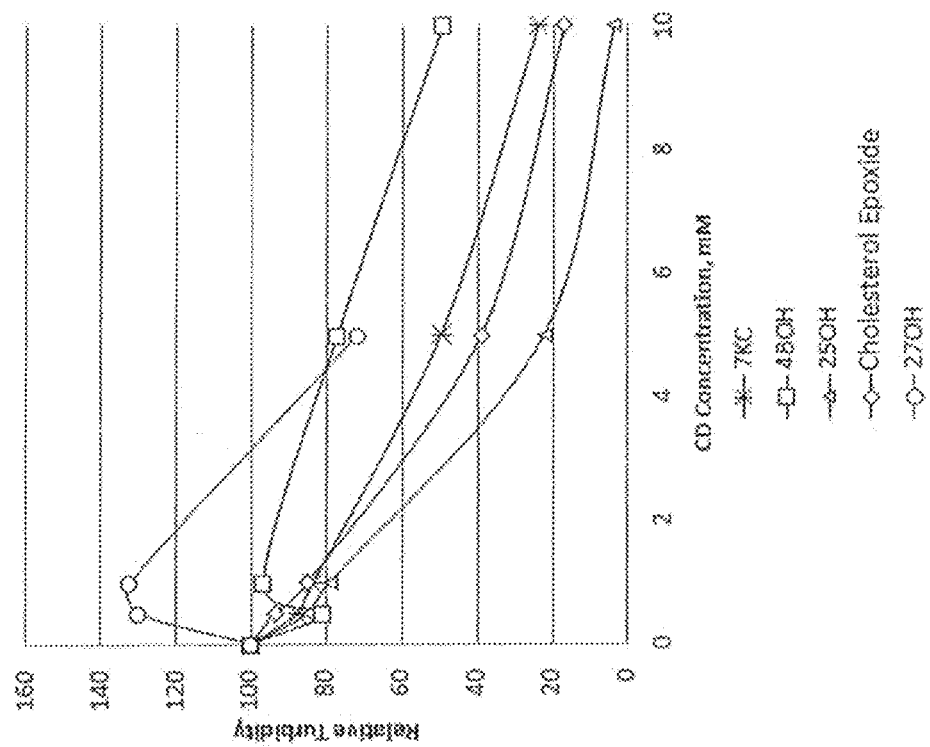
FIG. 2A. Solubilization of various cholesterol derivatives by HPβCD (DS 4.5) monomers assessed by relative turbidity, where 100 is defined as the absorbance of an aqueous suspension containing 300 uM of the sterol tested in PBS. Shown in FIG. 2A are results for cholesterol (diamond), 7KC (square), vitamin D2 (triangle), vitamin D3 (X), and desmosterol (+). In this figure and the figures that follow, the data points are connected by a smooth curve in order to assist with visualization of the results.
Figure 2B:
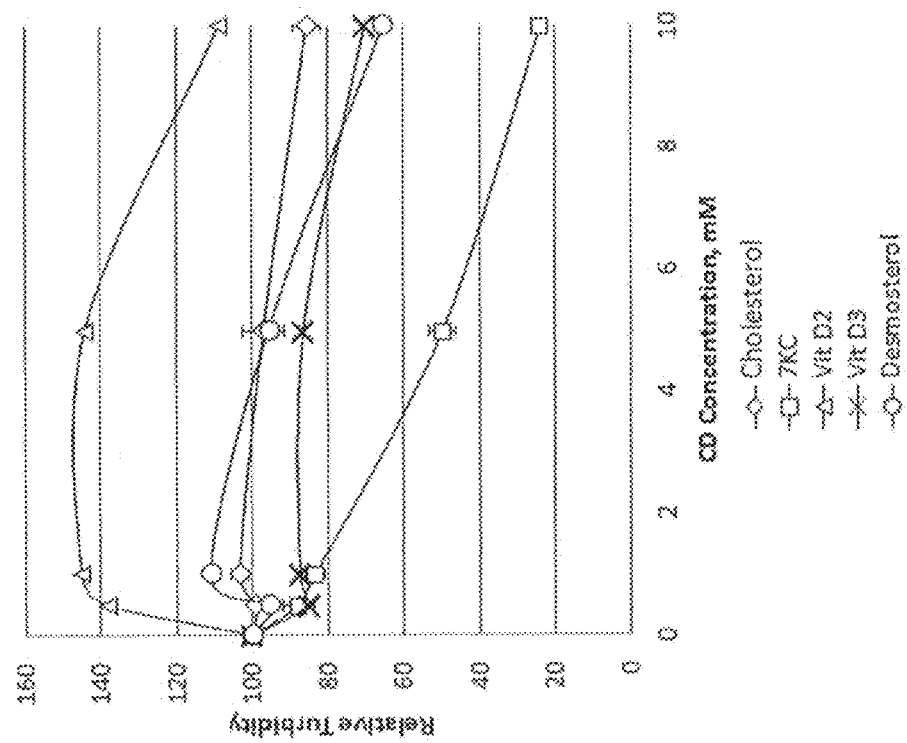
FIG. 2B. Solubilization of various sterols by hydroxypropyl-beta cyclodextrin (DS 4.5) monomers assessed by relative turbidity, where 100 is defined as the absorbance of an aqueous suspension containing 300 uM of the sterol tested in PBS.

Example 1 is a demonstration of the ability of HPβCD (DS 4.5) monomers to solubilize various sterols, vitamins, oxysterols, and steroid hormones (FIGS. 2A-B). Lower turbidity indicates greater ability to solubilize a given sterol. FIG. 2A-B shows solubilization of various sterols and sterol derivatives by HPβCD (DS 4.5) monomers assessed by relative turbidity.

Figure 2E:
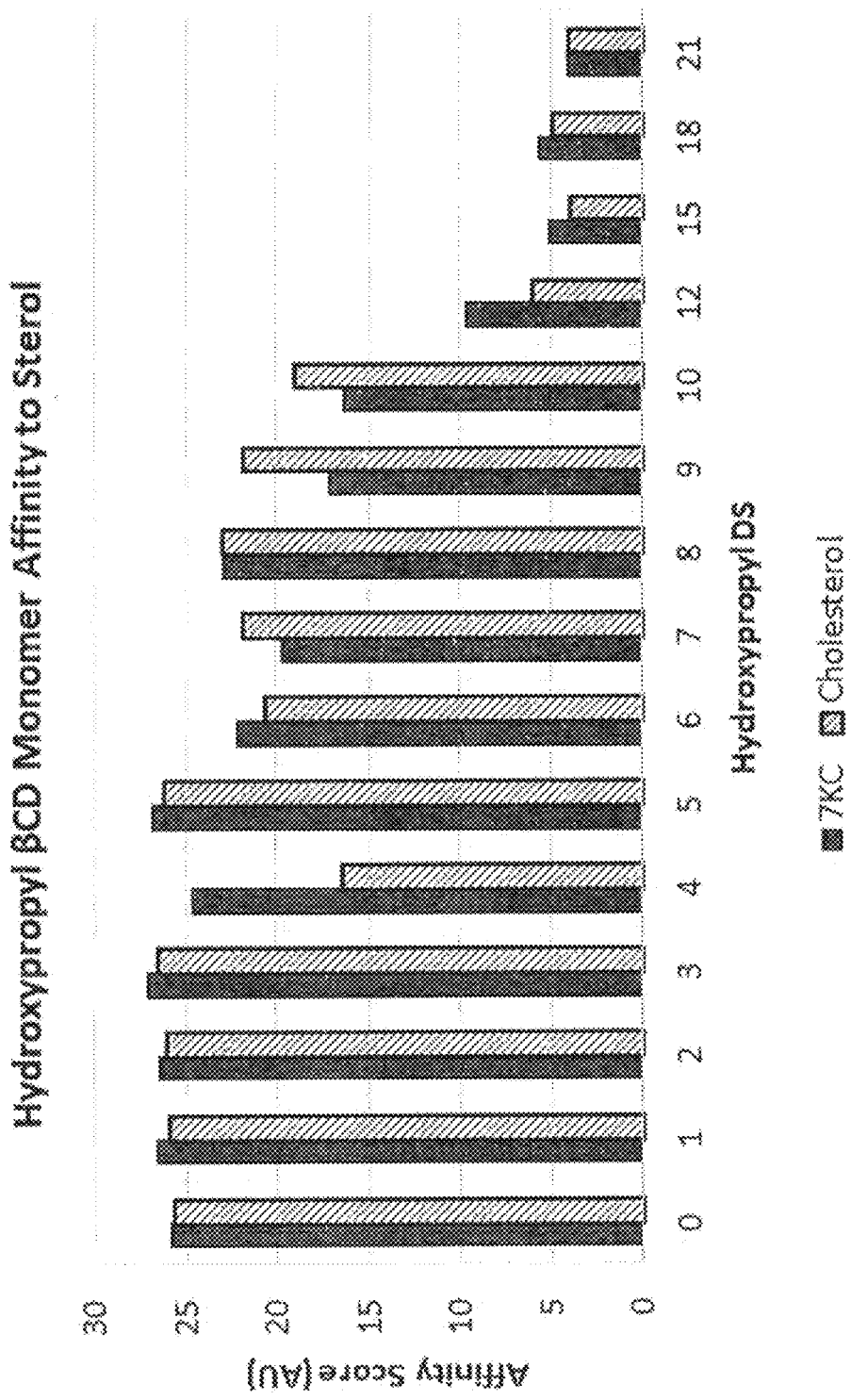
FIG. 2E. Predicted relative affinities of HPβCD molecules calculated by molecular docking. DS indicates the number of hydroxypropyl substitutions per molecule.
Figures 2F, 2G:
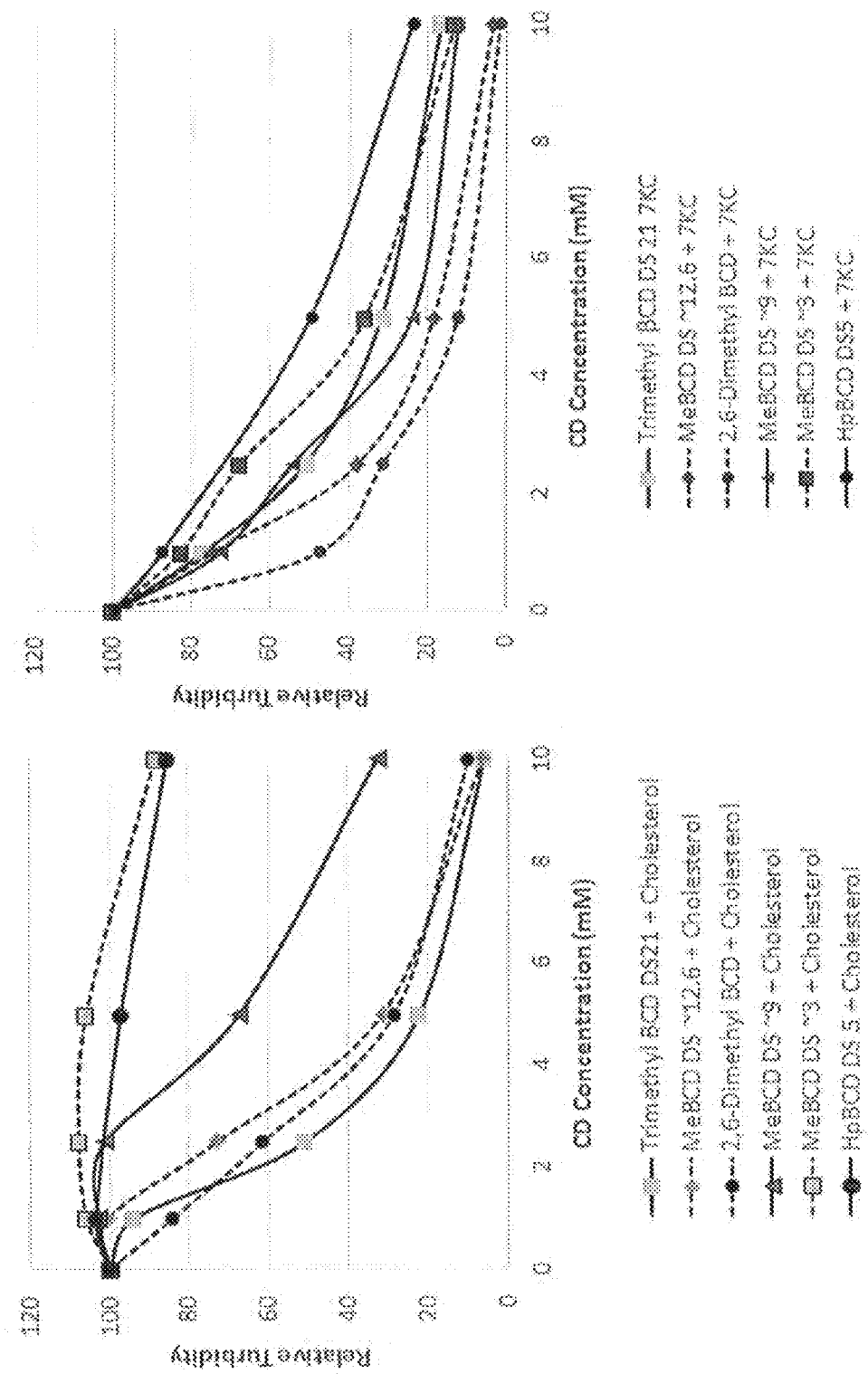
FIG. 2F. MeβCDs of various degrees of substitution solubilization of cholesterol in vitro as assessed by relative turbidity.
FIG. 2G. MeβCDs of various degrees of substitution solubilization of 7KC in vitro as assessed by relative turbidity.
Figure 2I:
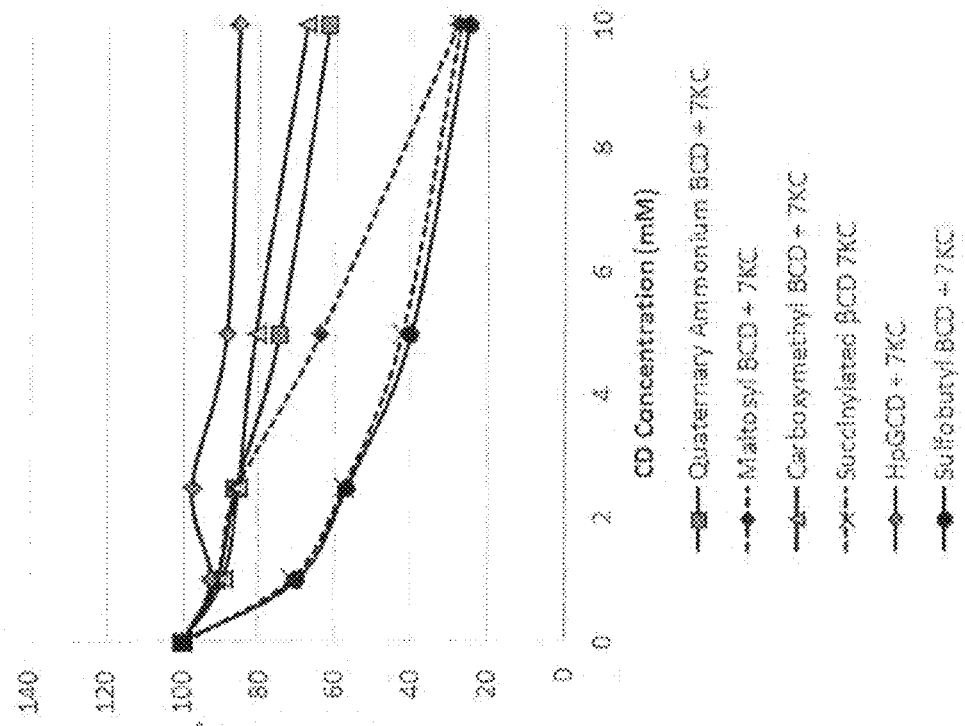
FIG. 2I. Various monomeric βCDs solubilization of 7KC in vitro as assessed by relative turbidity.
Figure 2H:
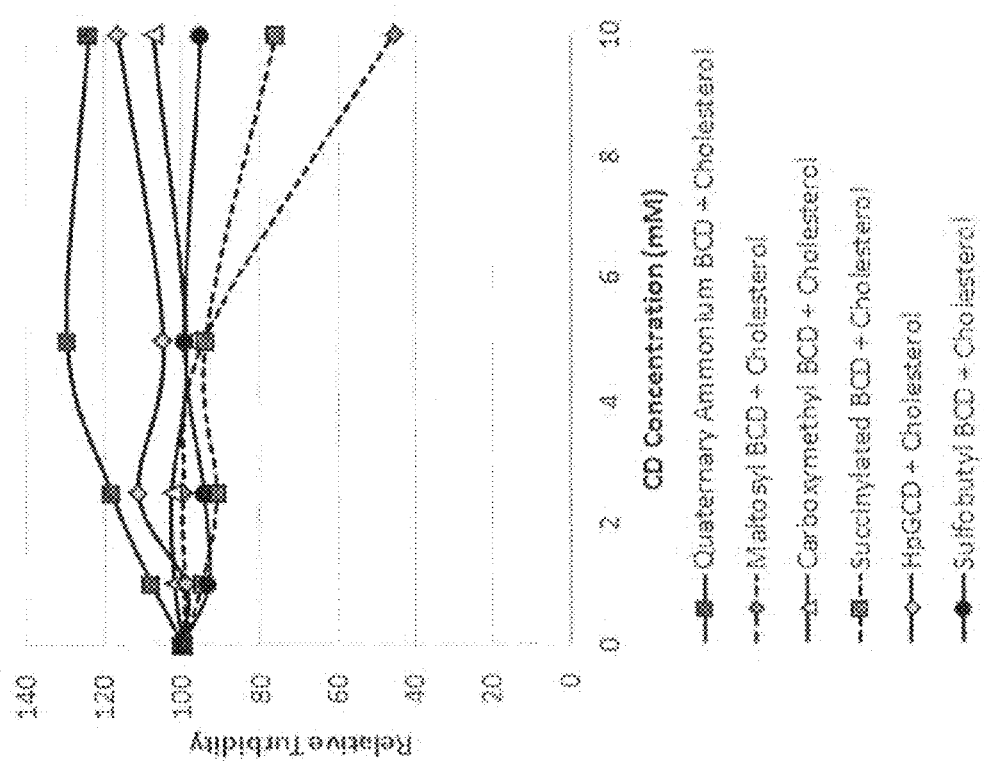
FIG. 2H. Various monomeric βCDs solubilization of cholesterol in vitro as assessed by relative turbidity.

We also tested variations on HPβCD by testing a range of the number of hydroxypropyl groups on the HPβCD. We tested a range from 3.7 to 21 (maximum possible number of substitutions). While the data was noisy, the ability to solubilize 7KC and cholesterol decreased with greater degrees of substitution (FIGS. 2C-2D). This was strongly supported by molecular docking of a wide range of substitutions on monomeric HPβCDs (FIG. 2E). Monomers and sterols were designed in PyMOL based on known chemical characteristics. The most probable placement of each hydroxypropyl group was used and the top 20 conformations were considered in determining the affinity score for each pair. A conformation was included in the calculation if any atom of the sterol passed the plane formed by the O4 oxygens of the cyclodextrin. Lower DS HPβCDs showed a preference for solubilizing 7KC over cholesterol suggesting that they have specificity for 7KC. Without intent to be limited by theory, a potential explanation is the availability of the maximum number of hydroxyl groups for hydrogen bonding with the keto group at the 7 position on 7KC, however, this theory is not required in order to practice the invention.

Example 2. Computational Modeling of Cyclodextrin Monomer and Dimer Interactions with Cholesterol and 7KC Overview This example describes molecular modeling and computational simulations performed to investigate the mechanisms by which CDs bind to sterols, predict relative binding ability of cyclodextrin dimers for cholesterol and 7KC, and identify cyclodextrin dimers that are predicted to have higher affinity for 7KC than for cholesterol. Presumably, a configuration in which the sterol is fully enclosed by the CD or CD dimer shields the hydrophobic sterol from the hydrophilic solvent, thus allowing the sterol to go into solution.

For initial docking analysis (FIG. 2E [monomers], 4B [dimers]), the computer modeling program PyMOL (the PyMOL Molecular Graphics System, Version 2.0 Schrödinger, LLC.) was used to build the HPβCD monomers and dimers of various substitution level and then the extension AutoDock Vina (Trott [et al.], *J. Comput. Chem.*, 31(2):455-61. (2010)), developed at the Scripps Research Institute (La Jolla, CA, USA), was used to model interactions between these hypothetical CD molecules and 7KC or cholesterol. Autodock Vina is a molecular docking software with significant accuracy and speed improvements over the previous Autodock 4. This software predicts noncovalent binding between molecules to predict energetically favorable conformations as well as binding affinity using a scoring-function to approximate the standard chemical potentials of the system. It was generally found that hydroxypropyl dimers and monomers of DS~2-6 show the best specificity for 7KC.

Molecular dynamics simulations using GROMACS 2018 (University of Groningen, Groningen, Netherlands; Bekker [et al.], *World Scientific* (1993); and Berendsen [et al.], *Comp. Phys. Comm.*, 91:43-56. (1995), among others) were carried out in addition to docking simulations with AutoDock Vina for three derivatives of beta-cyclodextrin binding either 7KC or cholesterol: native monomeric (DS0) beta-cyclodextrin (βCD), monomeric hydroxypropyl-beta-cyclodextrin (DS 5, HPβCD), and dimerized DS5 hydroxypropyl-beta-cyclodextrin where the two HPβCD monomers are linked via a butyl chain through an O2 oxygen of the DS2 monomer to an O3 oxygen of the DS3 monomer, resulting in a total DS of 5. Both of these ligands are asymmetrical, so simulations were done for both orientations of the ligand, up and down. These simulations were then repeated in the AMBER forcefield and in a translated position to establish which position/forcefield yields the most informative data for these novel molecules (initial MD analysis, FIG. 4D-MM). It was determined that the GROMOS forcefield in the initial position was the most effective at capturing the interactions of CD dimers with sterols, and so this forcefield and position were used for subsequent, abbreviated MD simulations of other CD dimers (subsequent MD analyses, FIG. 4NN-SS; 5B-C; 6B-7B).

Generally, it was found that the addition of hydroxypropyl groups results in less stable complexes, but also conveyed some specificity for 7KC over cholesterol than seen in native, unsubstituted βCD. This was seen because 7KC can form and reform a somewhat stable complex in both up and down orientations while cholesterol is less able to form a stable complex, potentially because it does not appear to be as fully encapsulated by βCD as 7KC, particularly in the 'down' orientation. Dimerization of βCD conveyed significantly more affinity for sterol targets such as 7KC and cholesterol. This is made clear by the formation of stable dimer complexes with strong energy of interaction for all ligands and orientations, where the ligand is nestled inside the hydrophobic core of the CD dimer, allowing the ligand to be solubilized in an aqueous solution.

To further analyze the effects of small modifications on βCD dimers, additional docking and molecular dynamics simulations were conducted for various linkers and degrees of substitution of HPβCD (FIG. 8). We extended this analysis to include other selected types of substitutions and other selected linkers (FIG. 9) and found that, among those tested, in general DS at ~2-6 showed the best specificity for 7KC for a wide range of substitution and linker types.

Based on this extended computational analysis, we believe that the dimerization of βCD is paramount in forming strong, soluble complexes with sterols regardless of the type or position of substitution or linker used. A broad range of dimerized βCD molecules have been tested and indicate that much higher affinity to sterols is maintained for many types of substitutions and linkers, even if they are chemically quite different from each other, over the monomeric form of βCD.

Computational Methods

Initial Docking Simulations

We have developed a method of using AutoDock Vina to more quickly and easily make predictions in-silico of cyclodextrin binding to various sterols without analyzing the entire trajectory, which is very time consuming and computationally expensive. Adapting this technique to cyclodextrin systems has allowed us to perform hundreds of docking simulations with many different cyclodextrins that we have designed. This type of computational modeling has shown us likely interactions between different cyclodextrins and different sterols, yielding both spatial information and binding affinity data.

Figure 4A:
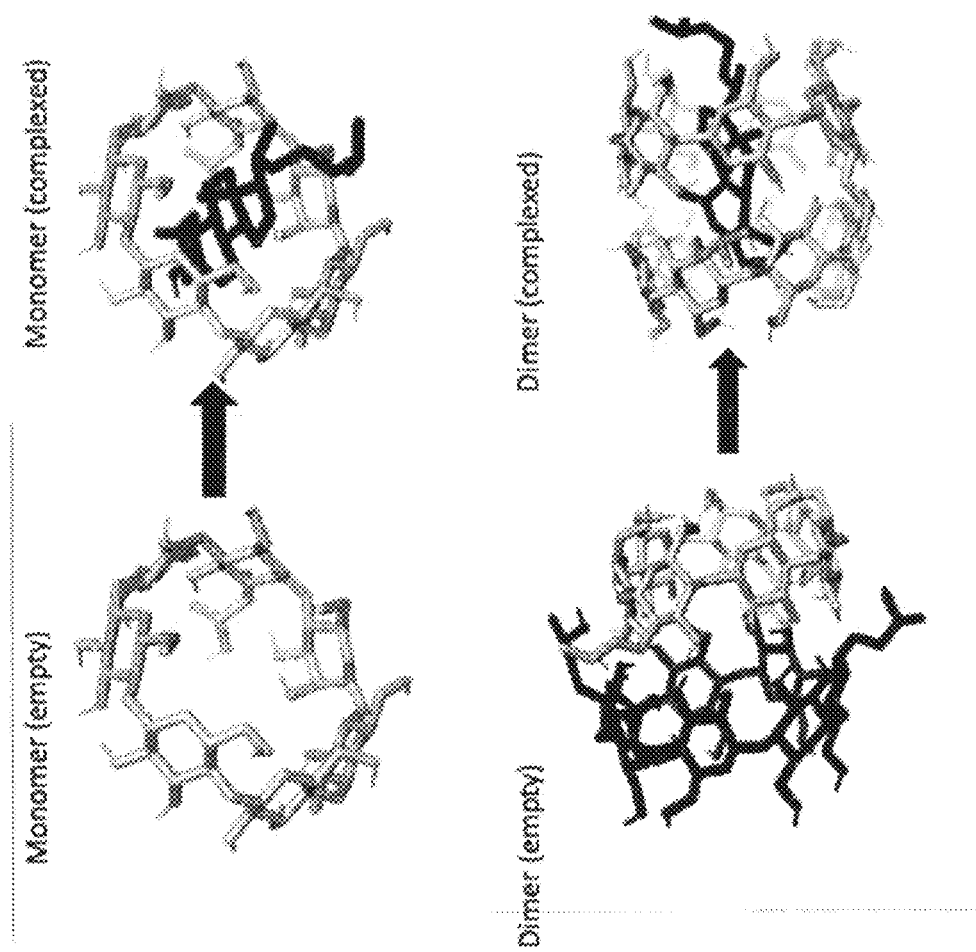
FIG. 4A. Structural model of HPβCD monomer to sterol association (top) or HPβCD butyl-linked dimer to sterol association (bottom). This is shown as an illustration of a monomer-sterol and dimer-sterol host-guest interaction.

These conformational predictions can be modeled for multiple different sterols and/or derivatives of CD so that potential mechanistic features may be revealed. We have several preliminary theories of binding which we hope to test using computational techniques. We have developed different models for HPβCD to test our theories of binding:

Monomer-Sterol association: We tested monomer-to-sterol affinity for comparison to dimer association in order to help determine whether the sterol is more likely to bind a monomer or dimer of HPβCD, and whether the monomers exhibit specificity for 7KC or cholesterol (FIG. 4A).

Linked Dimer-Sterol: To eliminate the need for multiple steps as well as test new potential molecules, two monomers were covalently linked with multiple types of linkers and associated with sterol to investigate affinity and specificity for these pre-linked dimers (FIG. 4A).

In order to make the outputs of these files comparable to one another, a scoring system for complexation with sterol was developed in which the most-favorable affinity was adjusted based on whether the dimer was head-to-head (where applicable) and whether the sterol was actually within the barrel of the HPβCD cavity. This number of "complexed conformations" (out of up to twenty configurations) was then added to the absolute value of the most-favorable affinity; i.e., an association resulting in 15/20 configurations which complex with the sterol (head-to-head and/or sterol inside the cavity of CD) and a best affinity of −10 kJ/mol would give a score of 25 (|−10|+15=25). For this computation, the ligand was considered in the complex if any atom on the ligand crossed the plane formed by the O4 atoms of CD, no matter the angle or extent of insertion into the cavity. The resulting value is referred to as the "affinity score."

Figure 5A:
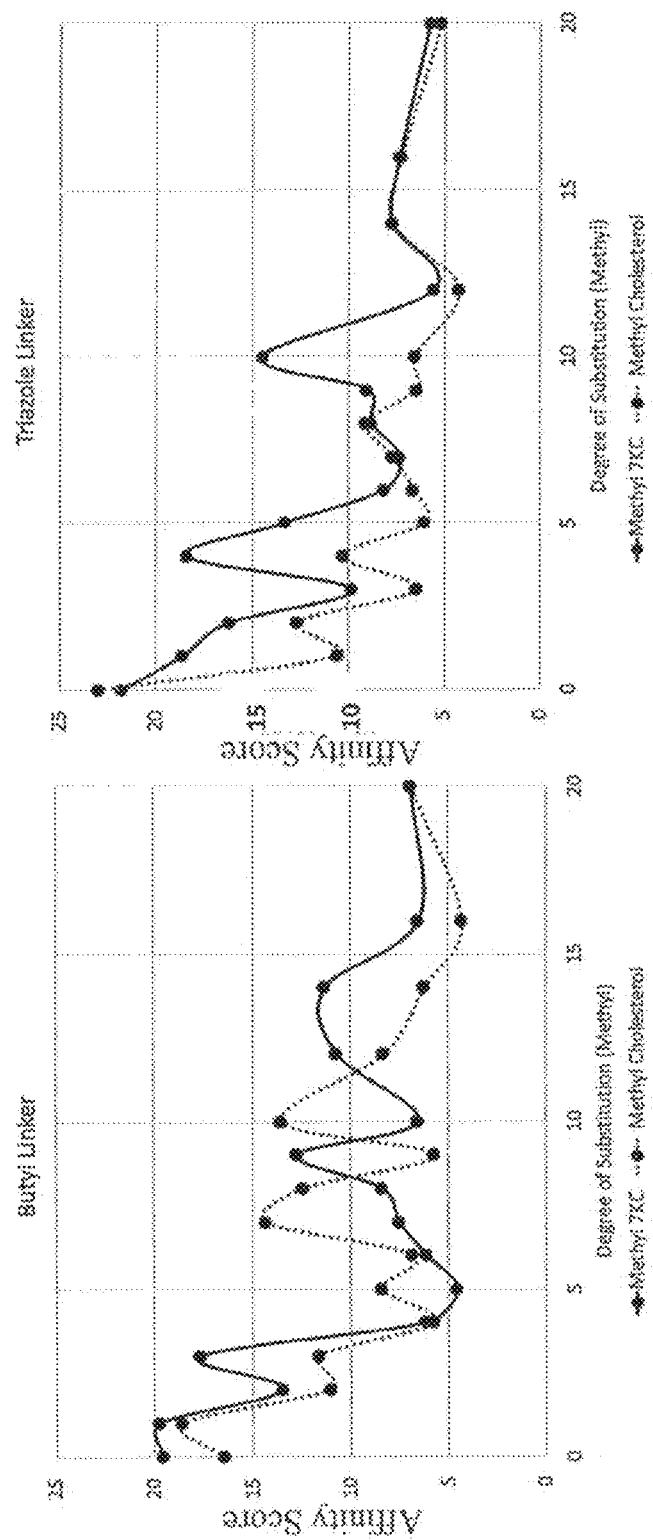
FIG. 5A. Predicted relative affinities of a wide range of possible dimerized MeβCD molecules by molecular docking. Butyl (left) and triazole (right) linked dimers' affinity for sterol. Docking calculations were performed on linked MeβCD dimers of various degrees of methylation. Cholesterol (dotted line) vs 7KC (solid line).
Figure 6A:
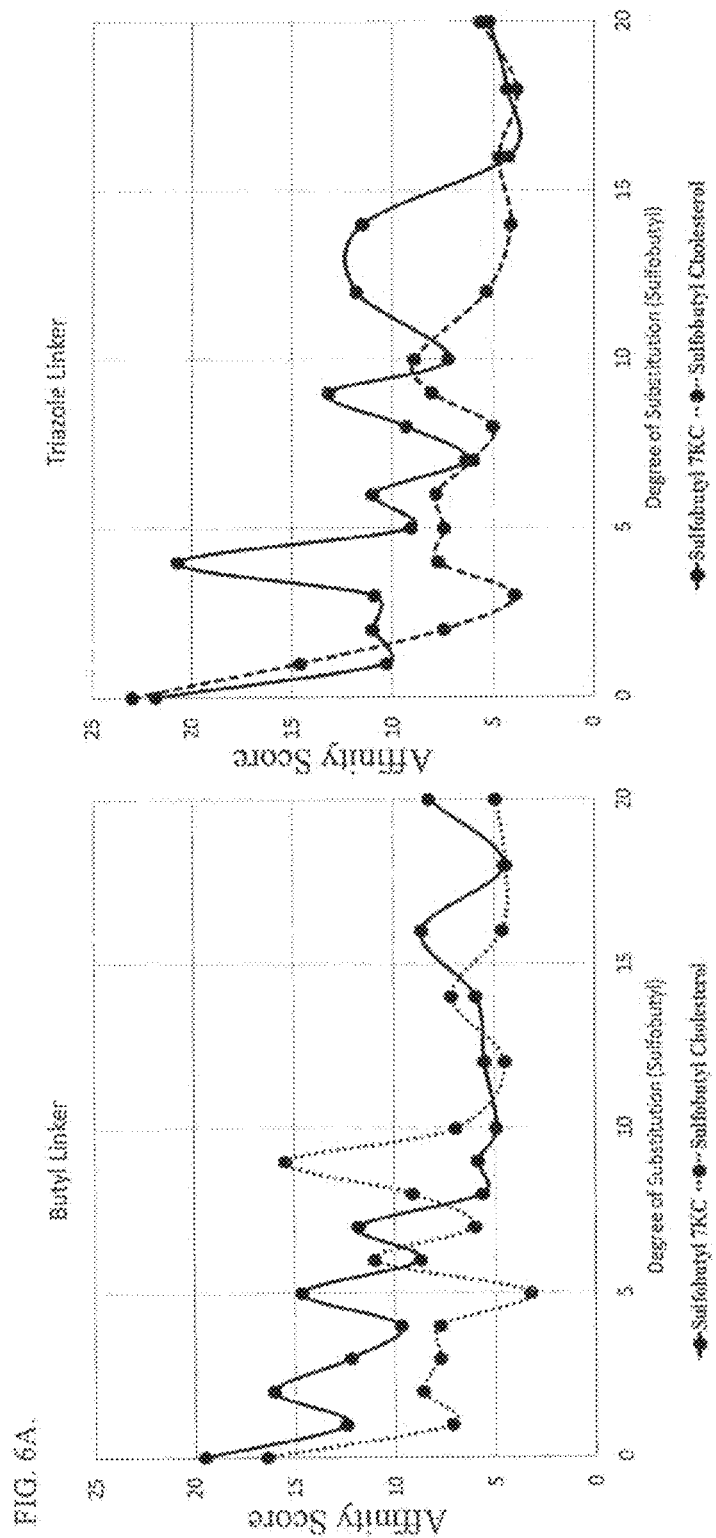
FIG. 6A. Predicted relative affinities of a wide range of possible dimerized sulfobutylated βCD molecules by molecular docking. Butyl and triazole linked dimers affinity for sterol. Docking calculations were performed on linked SBβCD dimers of various degrees of sulfobutylation. Cholesterol (dotted line) vs 7KC (solid line).
Figure 6B:
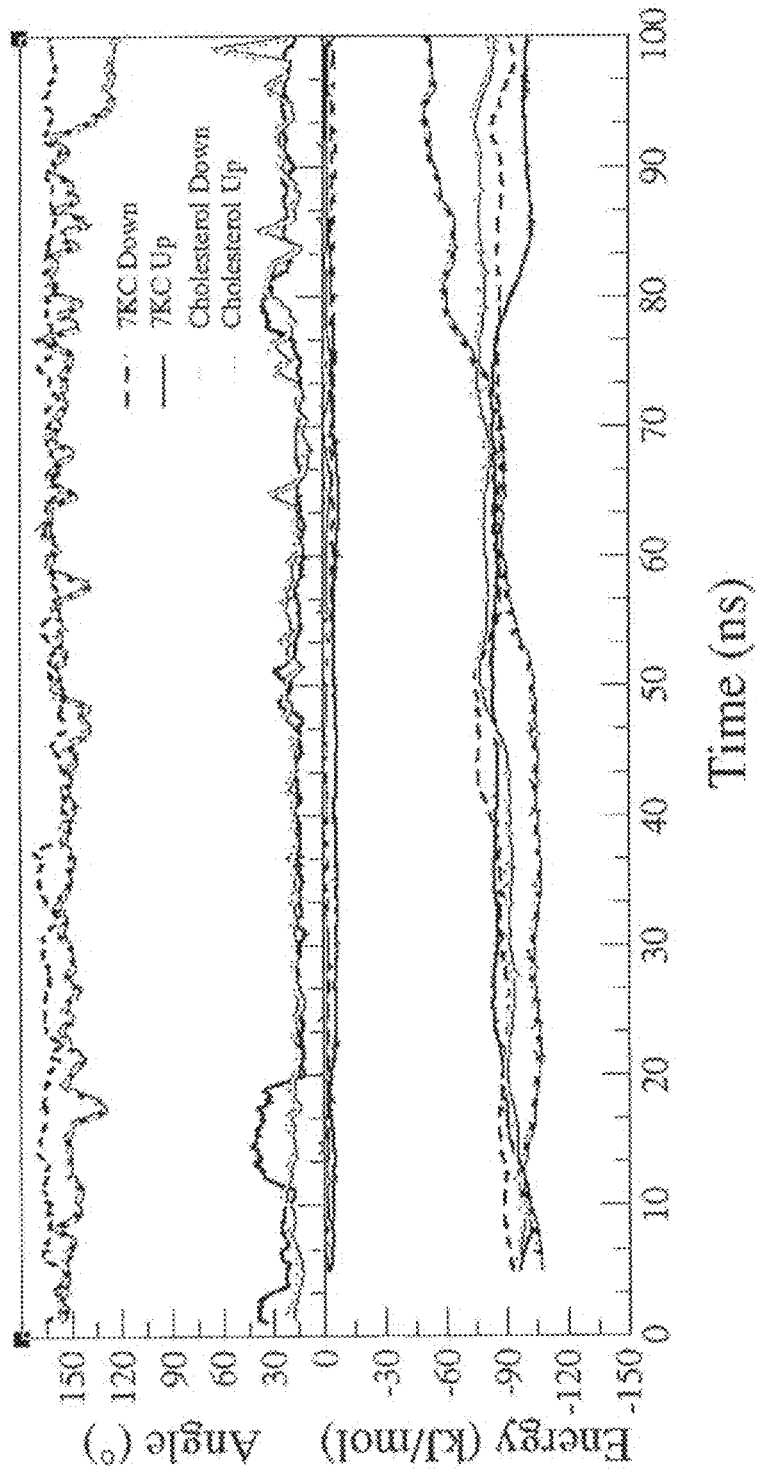
FIG. 6B. MD simulation describing 100 ns of interaction between a butyl-linked DS4 sulfobutyl βCD dimer and 7KC/cholesterol in both up and down orientations. Legend as in FIG. 5B.
Figure 6C:
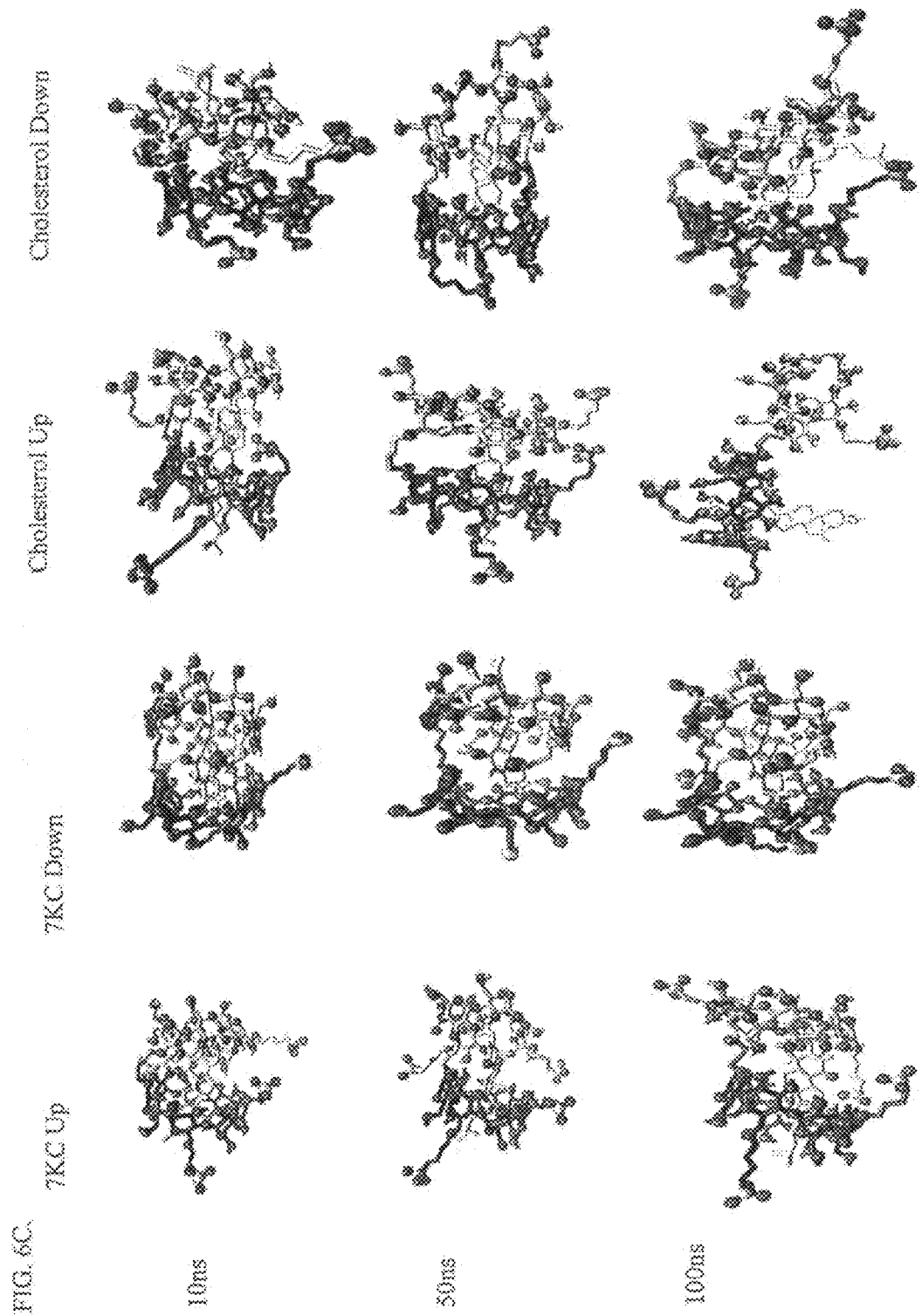
FIG. 6C. Visual trajectories of butyl-linked DS4 sulfobutyl βCD dimer and 7KC/cholesterol in both up and down orientations.
Figure 6D:
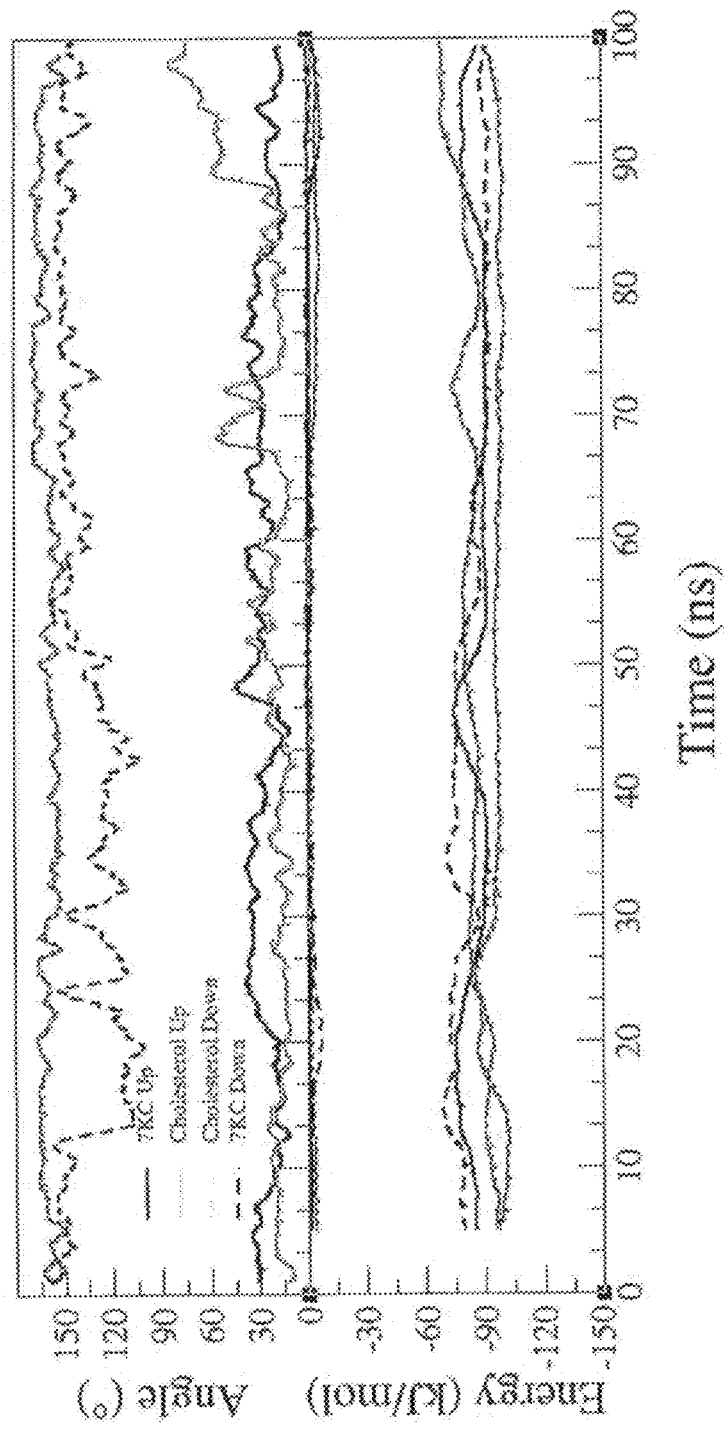
FIG. 6D. MD simulation describing 100 ns of interaction between a triazole-linked DS4 sulfobutyl βCD dimer and 7KC/cholesterol in both up and down orientations. Legend as in FIG. 5B.

We then extended this docking analysis to include various different types of substitutions (including those with charged groups) and linkers to determine if 7KC specificity is affected by these factors. Sulfobutyl and methyl substitutions with triazole and butyl linkers were tested at a full DS range of 0-20 and showed a similar pattern to hydroxypropyl, where the DS with highest 7KC specificity was approximately 4 (FIGS. 5A and 6A). Therefore, other cyclodextrins like quaternary ammonium and carboxymethylated were only tested at low DS (~4).

Figure 4B:
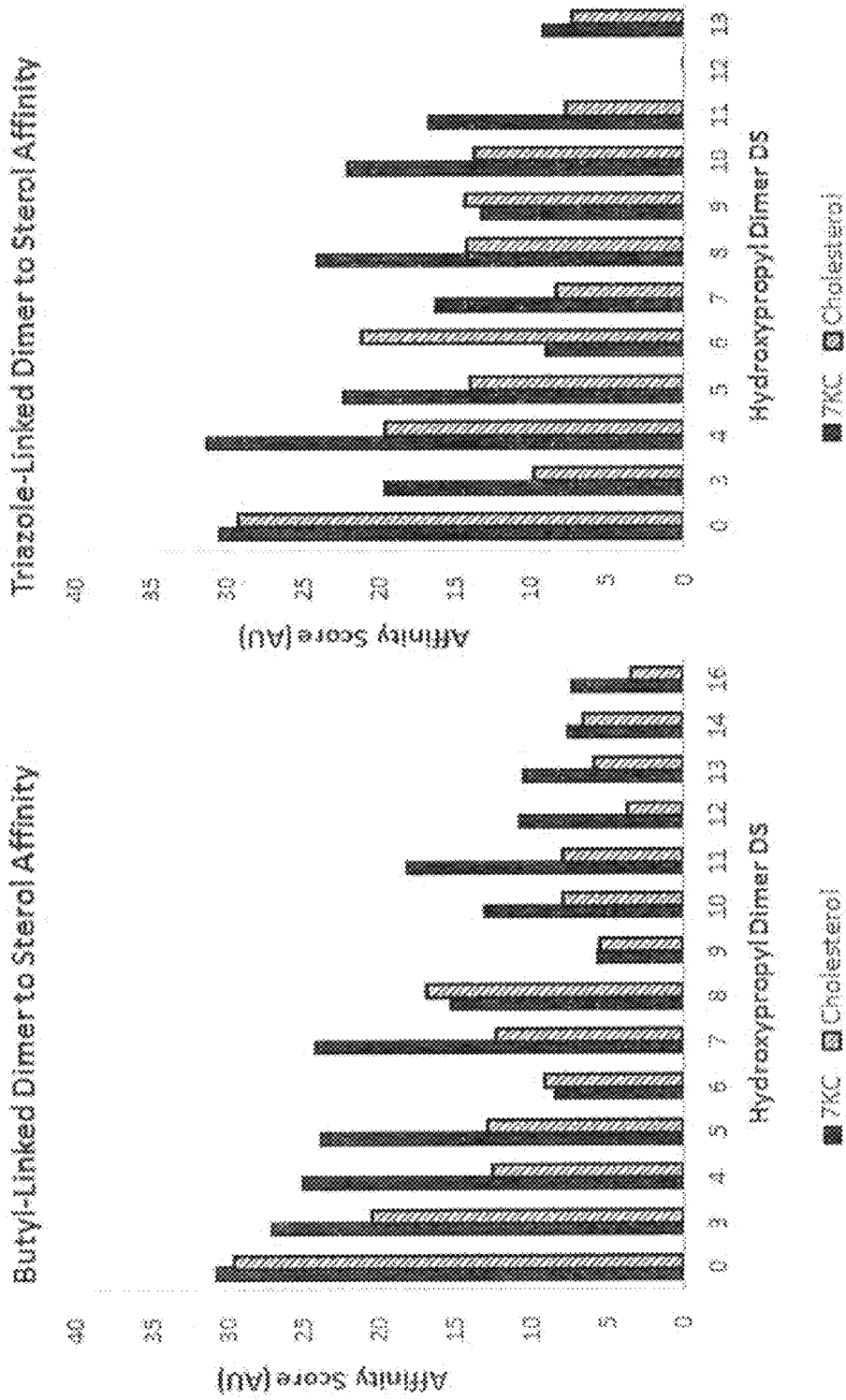
FIG. 4B. Butyl and triazole linked dimers predicted relative affinities for cholesterol and 7KC. Docking calculations were performed on linked HPβCD dimers of various degrees of hydroxypropylation.
Figure 4C:
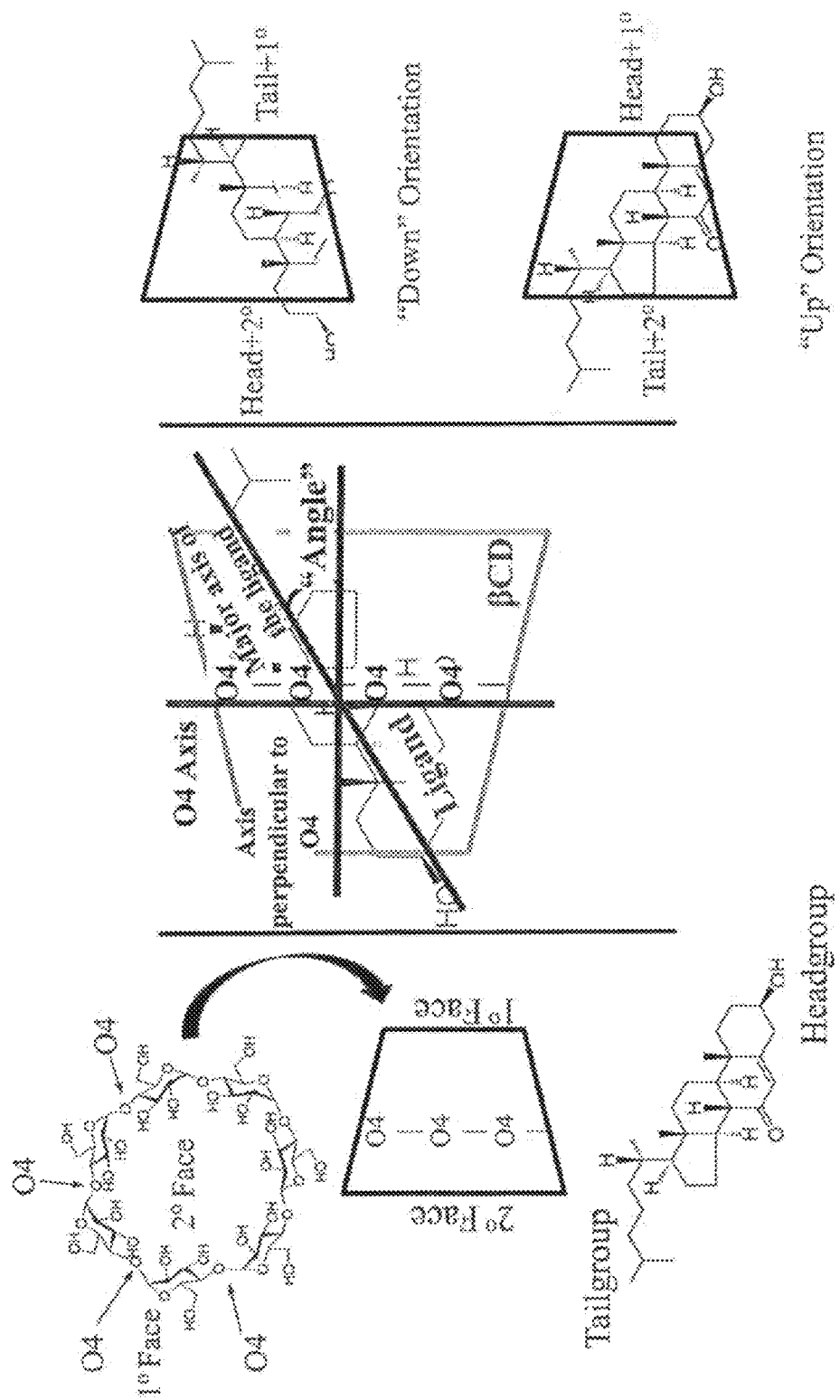
FIG. 4C. Description of measurements used for molecular dynamics simulations. The nomenclature of cyclodextrins and sterols is included to define the O4 atoms of CD (marked with arrows), the secondary and primary faces of CD, and the head and tailgroups of sterols. The angle between the O4 plane and the ligand indicates how well nested the ligand is inside the CD cavity. 30 degrees corresponds to the solubilized "up" configuration (head of sterol associated with the secondary face of CD, tail with primary) while 150 degrees corresponds to the solubilized "down" configuration (tail of sterol associated with the secondary face of CD, head with the primary face).
Figure 4D:
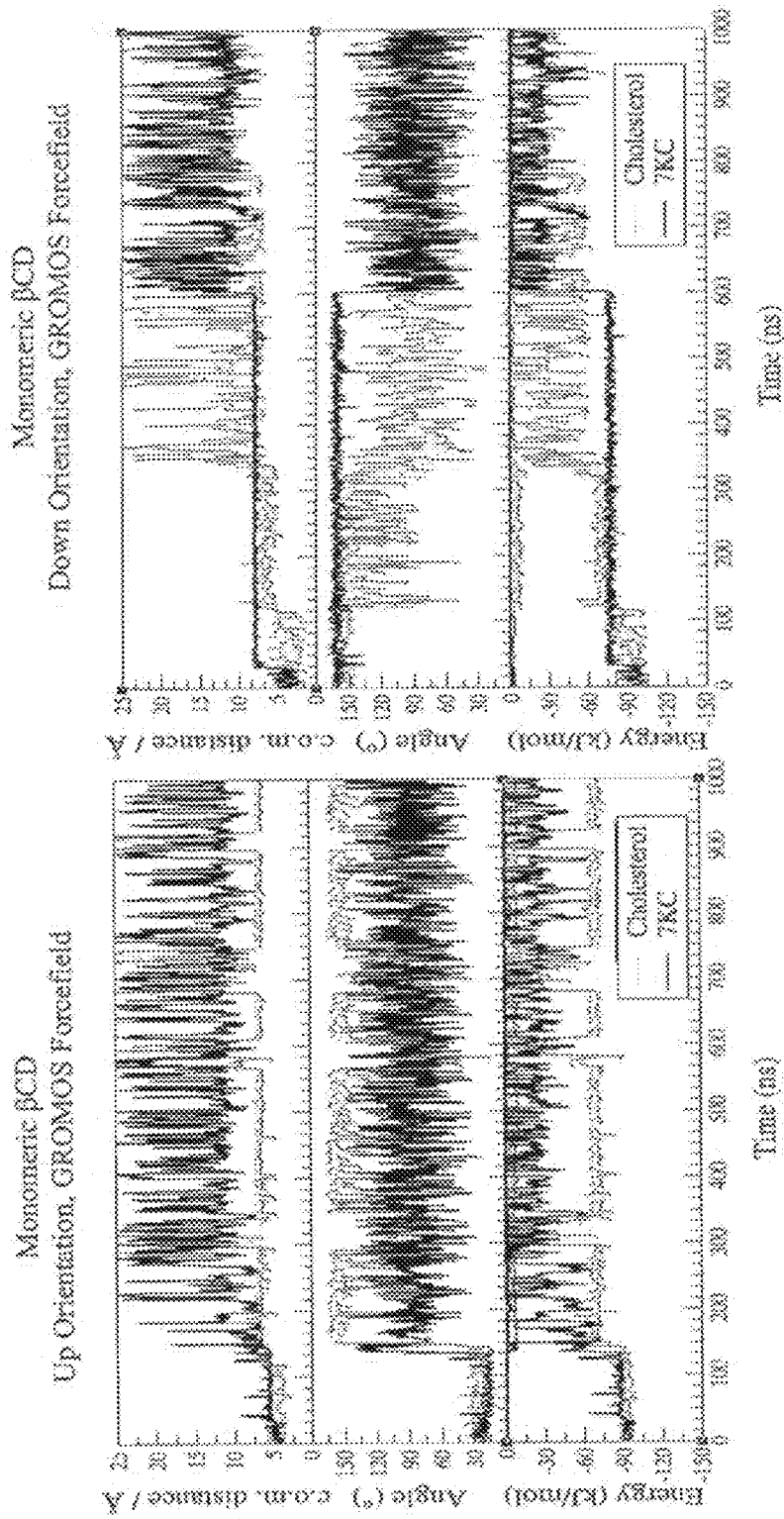
FIG. 4D. MD simulation of DS0 βCD: Distance between the center of mass of all O4 oxygens and the center of mass of the ligand (top); the angle between a vector perpendicular to the plane formed by the O4 atoms of CD and the main axis of the ligand (middle); Lennard-Jones and Coulombic energy of interaction between the cyclodextrin and the ligand (bottom) for native (i.e., unsubstituted) monomeric beta CD, up and down ligand orientations in the GROMOS forcefield. In the graphs included between FIGS. 4D and 4LL, the light-colored lines graph the results for cholesterol while the darker lines are for 7KC.
Figure 4E:
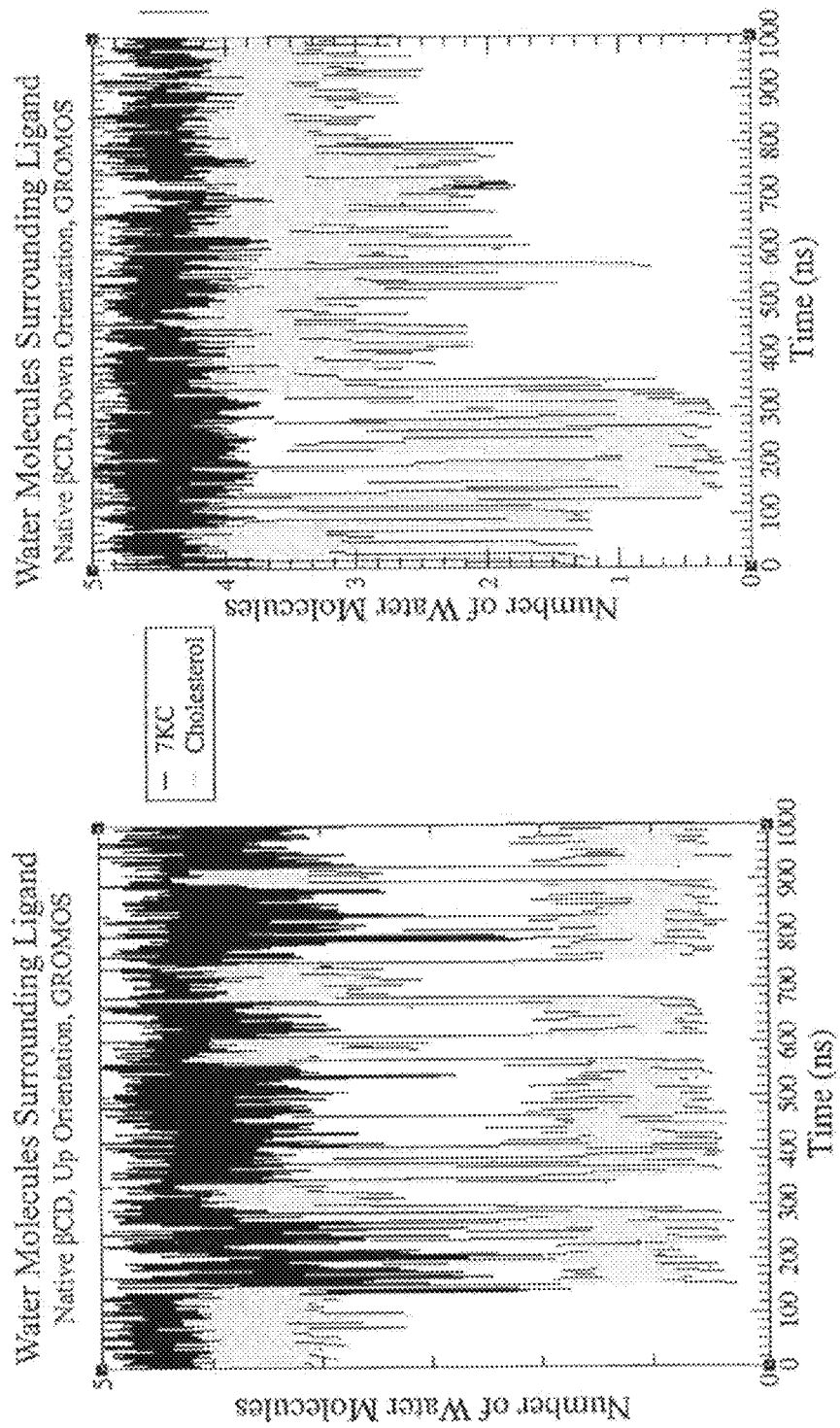
FIG. 4E. Solubilization of ligand by native DS0 monomeric βCD in the GROMOS forcefield.

Initial Molecular Dynamics Simulations (FIG. 4D-MM)

This initial set of simulations were performed using GROMACS 2018 (University of Groningen, Groningen, Netherlands) in both GROMOS 54a7 and AMBER 99SB forcefields, resulting in two repetitions of these simulations to help determine the consistency of the interactions observed. These two repetitions for each of the three CD molecules and each orientation of the ligand were then repeated with a different initial structure where the ligand is shifted to determine the dependence of these calculations on the initial structure as well as the forcefield. The resulting 48 hydroxypropyl dimer trajectories were then analyzed using GROMACS tools.

Molecular dynamics, unlike docking, allows simulated molecules to interact in a time-dependent way, rather than simply snapshots of energetically favorable conformations as provided by docking. The simulations were extended to one microsecond (an extremely long time for MD simulations) for each of the initial three CD-sterol complexes, allowing sufficient time for the complex to stabilize. Then, the output was analyzed to determine the distance between the center of mass of all O4 atoms (the center of the CD cavity for both dimers and monomers) and the center of mass of the ligand, the angle between a vector perpendicular to the plane formed by the O4 atoms of CD and the main axis of the ligand (see FIG. 4C), and both Lennard-Jones and Coulombic energies of interaction between the cyclodextrin and the ligand.

In this way, the distance indicates the proximity of the ligand to the cyclodextrin, the angle indicates how well nested the ligand is inside the CD cavity, and the energy of interaction represents how strongly the two molecules interact (more negative interaction energy designates a stronger interaction). FIG. 4C indicates how the "angle" measurement is useful to determine how well shielded the ligand is from surrounding water molecules: zero or 180 degrees indicates that the ligand is perfectly perpendicular to the plane of the cyclodextrin while 90 degrees would indicate that the ligand is parallel to the CD plane and therefore not complexed within the cavity. For these simulations, we chose 30 degrees to correspond to the starting, complexed "up" configuration (head of sterol associated with the secondary face of CD, tail with primary, the entire ligand inserted into the cavity of CD) and 150 degrees to be the initial complexed "down" configuration (tail of sterol associated with the secondary face of CD, head with the primary face, the entire ligand inserted into the cavity of CD). Note that for the dimers, the plane of only one CD monomer is considered in the angle between CD and ligand, but if the dimer is perfectly formed, then this plane would mirror the sister monomer's plane.

The number of water molecules within 3 Å of the ligand was determined over time to determine how well the CD shields the ligand from surrounding solvent. Presumably, more water molecules around the ligand would indicate that it is not sufficiently shielded from surrounding water and is therefore not in solution. All of these simulations were extended to 1 microsecond (1000 ns), which should be sufficiently long to accurately describe the interaction between CD and sterol.

This long initial analysis provides evidence that the simulations properly capture the interactions of CD monomers and dimers with sterol ligands, and thus can be expanded to other CD monomers and dimers without necessitating such laborious methods.

Figure 4F:
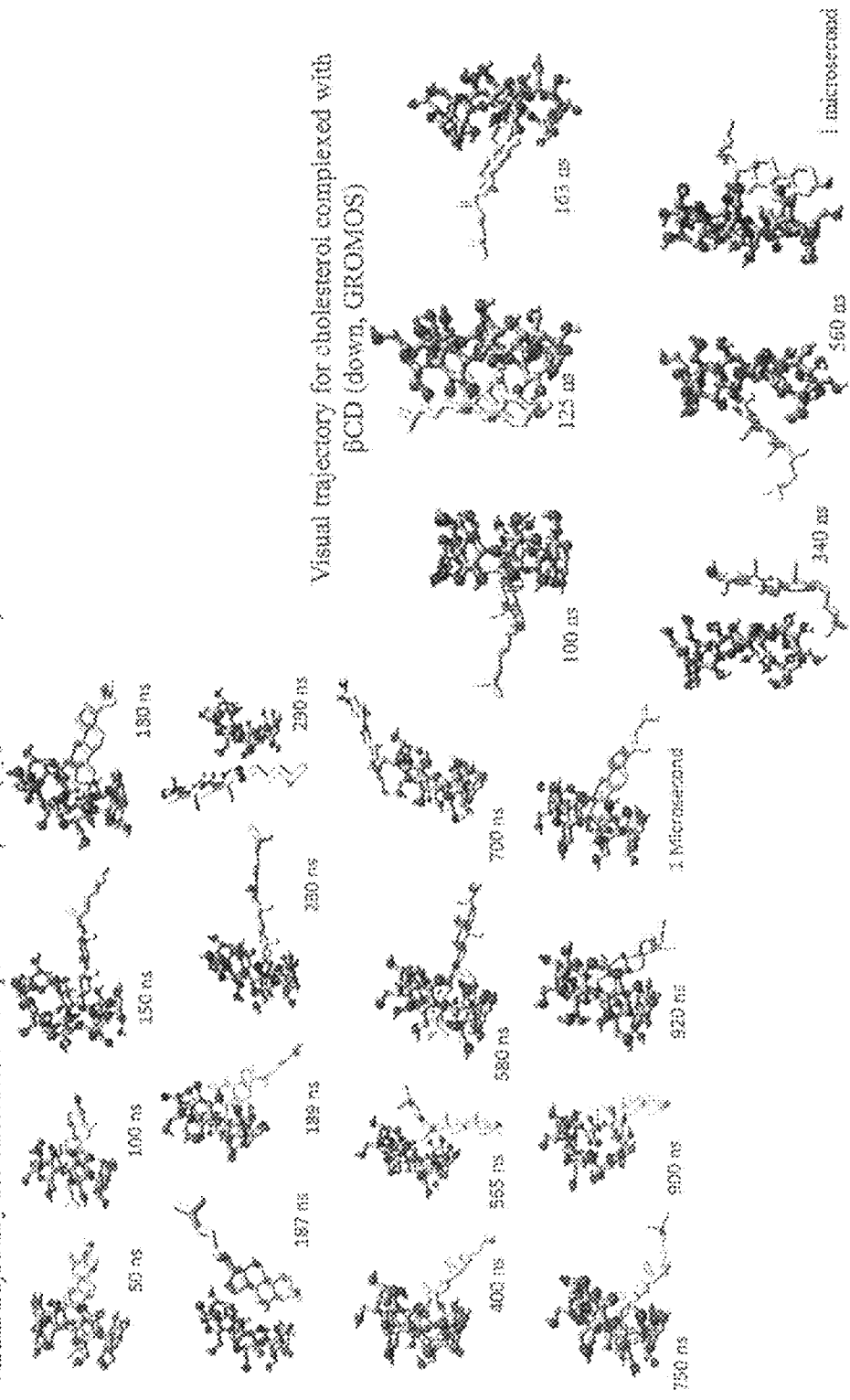
FIG. 4F. Visual trajectory for 7KC and cholesterol complexed with native DS0 βCD (GROMOS forcefield) in both orientations.
Figure 4G:
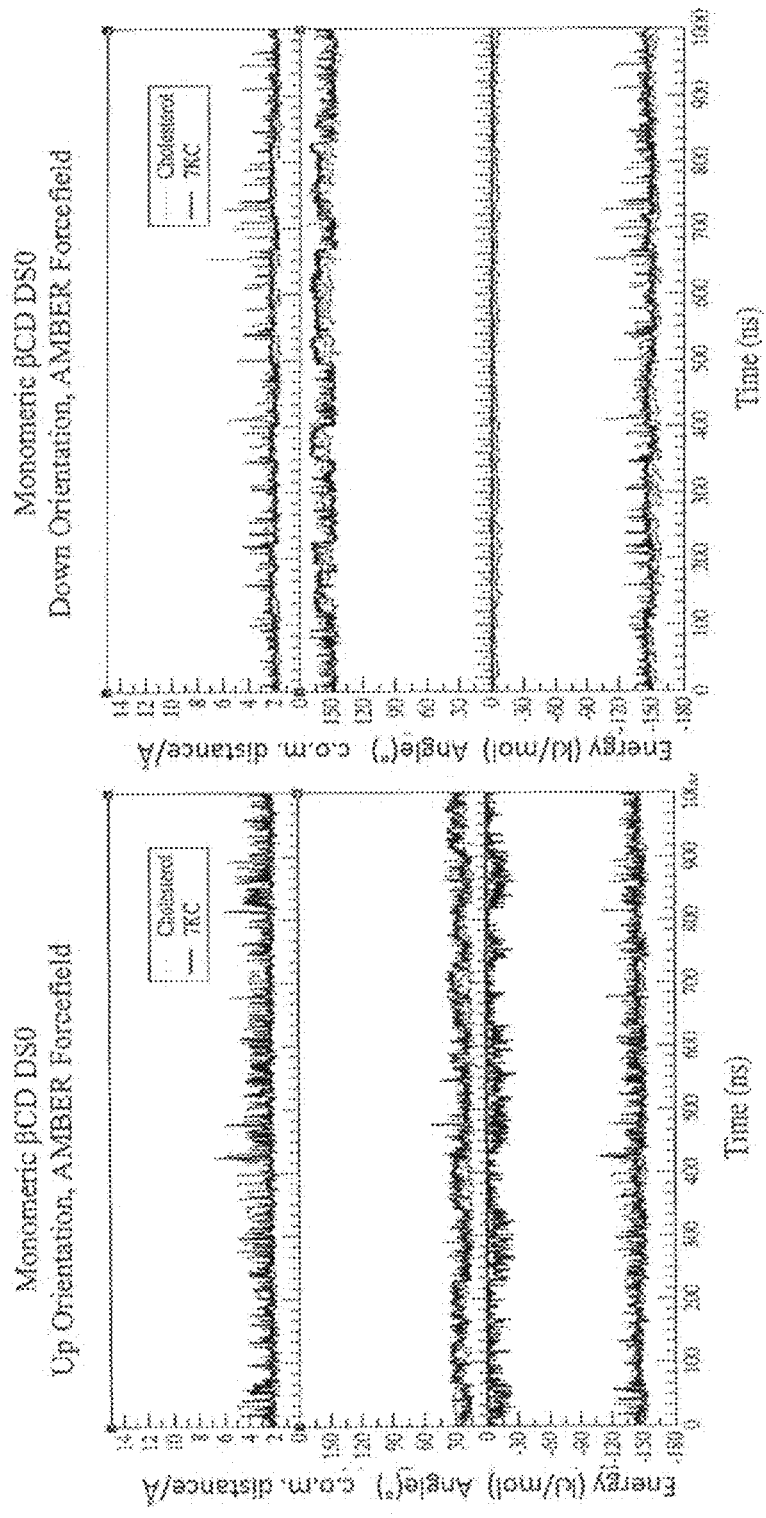
FIG. 4G. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for native monomeric DS0 beta cyclodextrin, up and down ligand orientations in the AMBER forcefield.
Figure 4H:
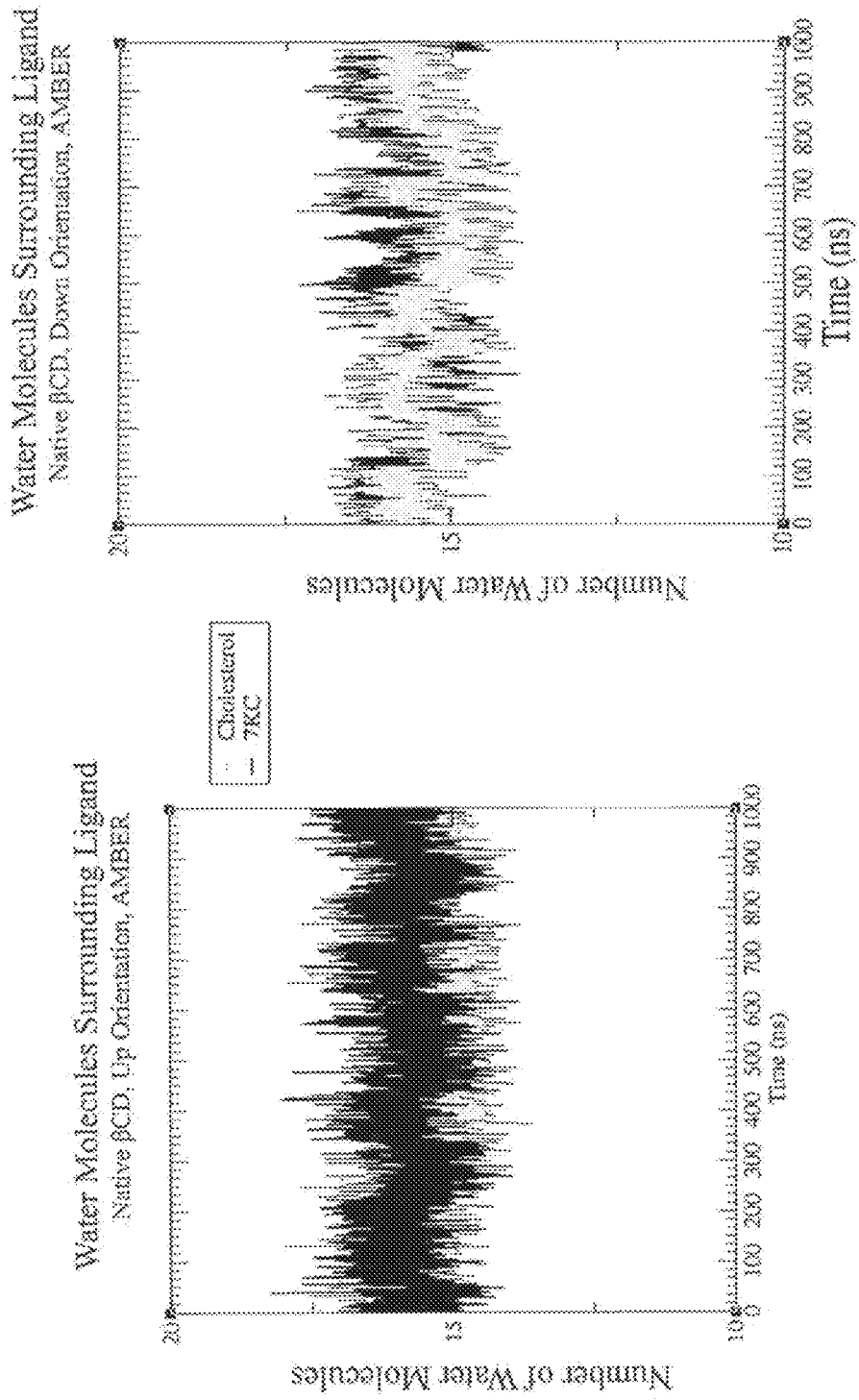
FIG. 4H. Solubilization of ligand by native DS0 monomeric βCD in the AMBER forcefield.
Figure 41:
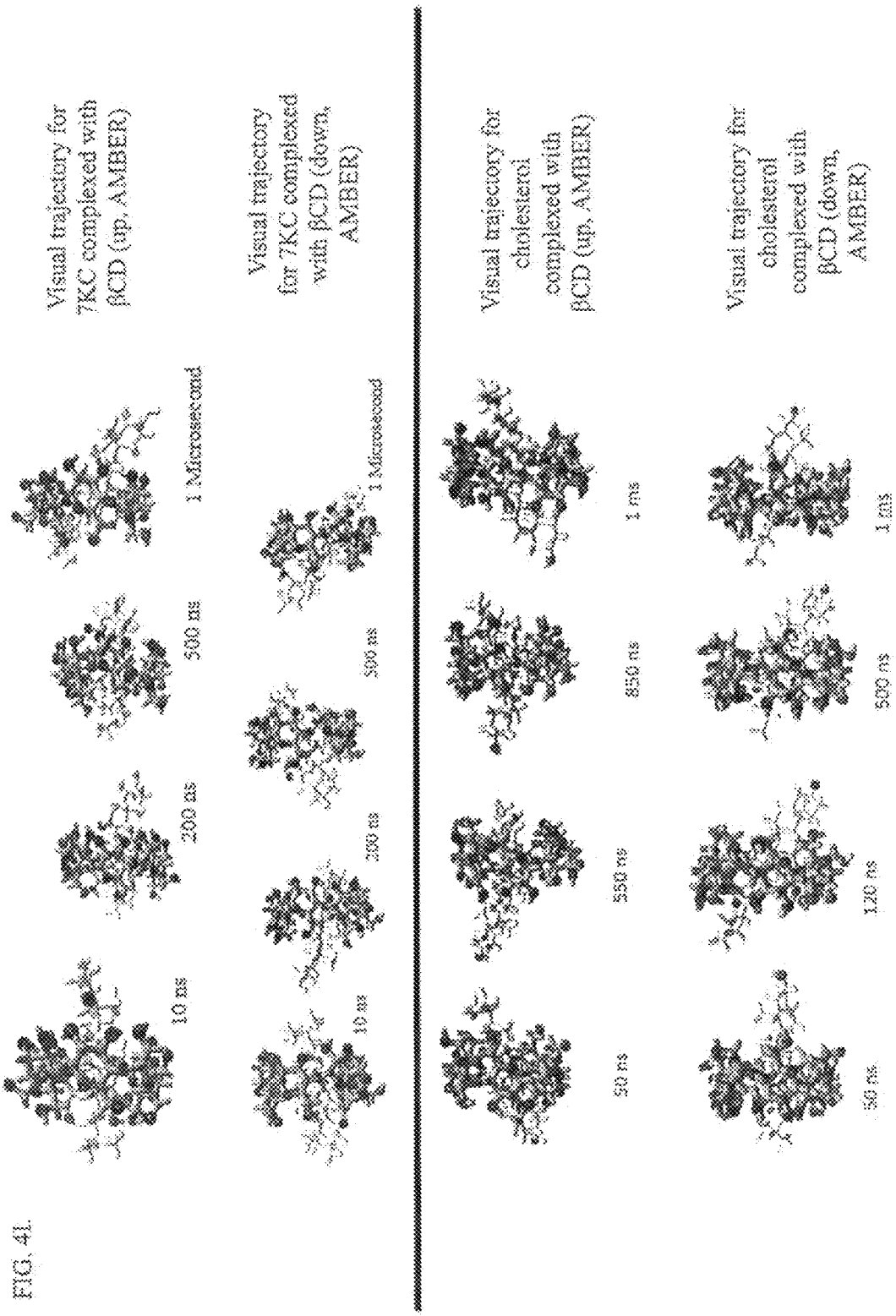
Figure 41:
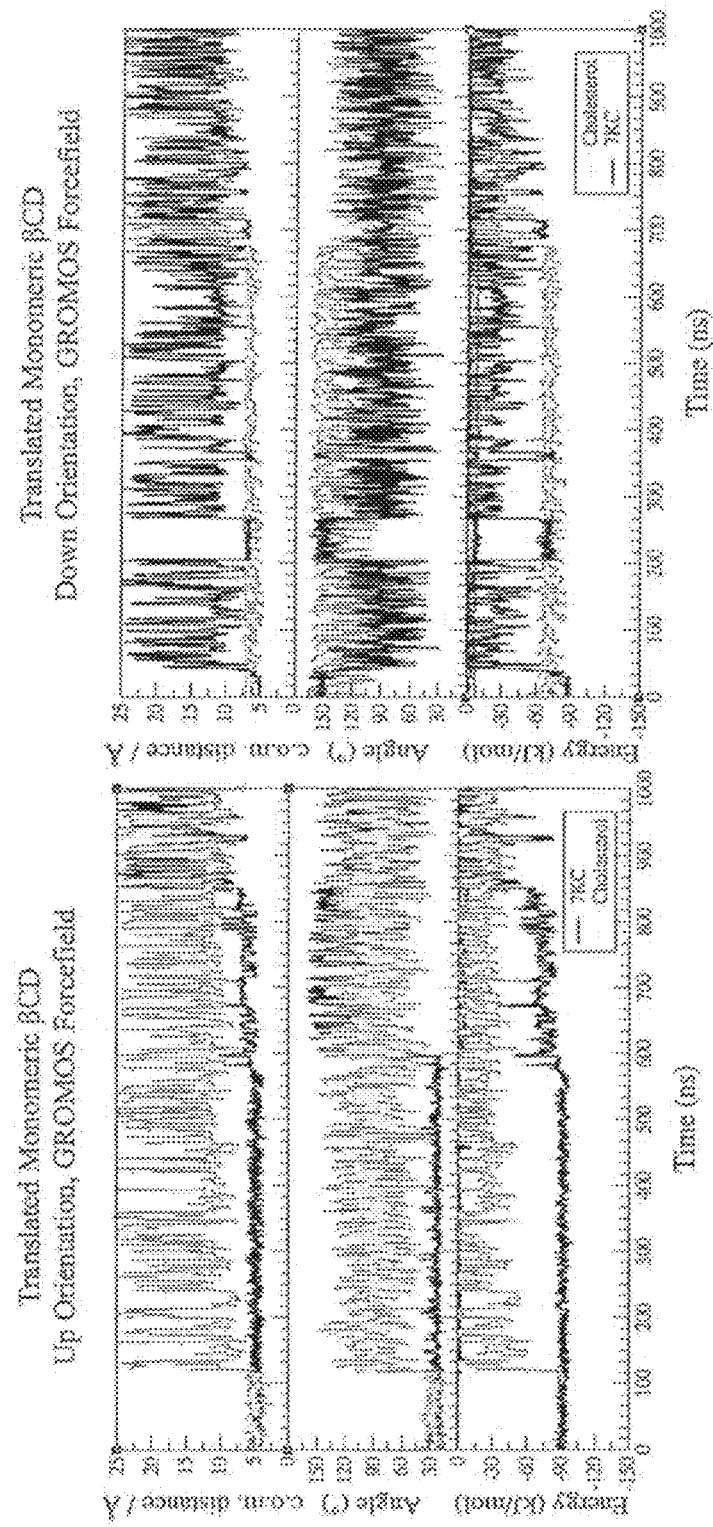
Figure 4K:
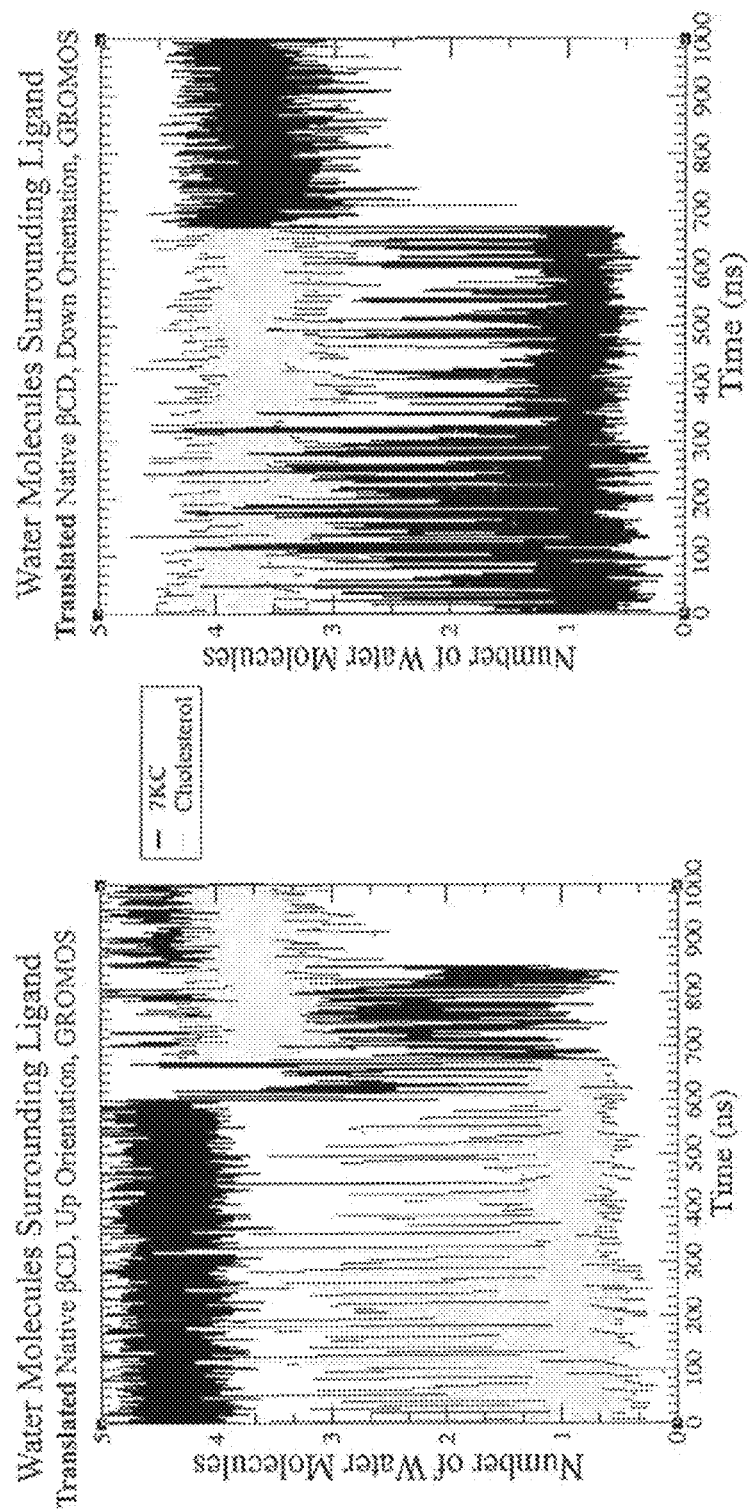
FIG. 4K. Solubilization of ligand by translated monomeric βCD in the GROMOS forcefield.
Figure 4L:
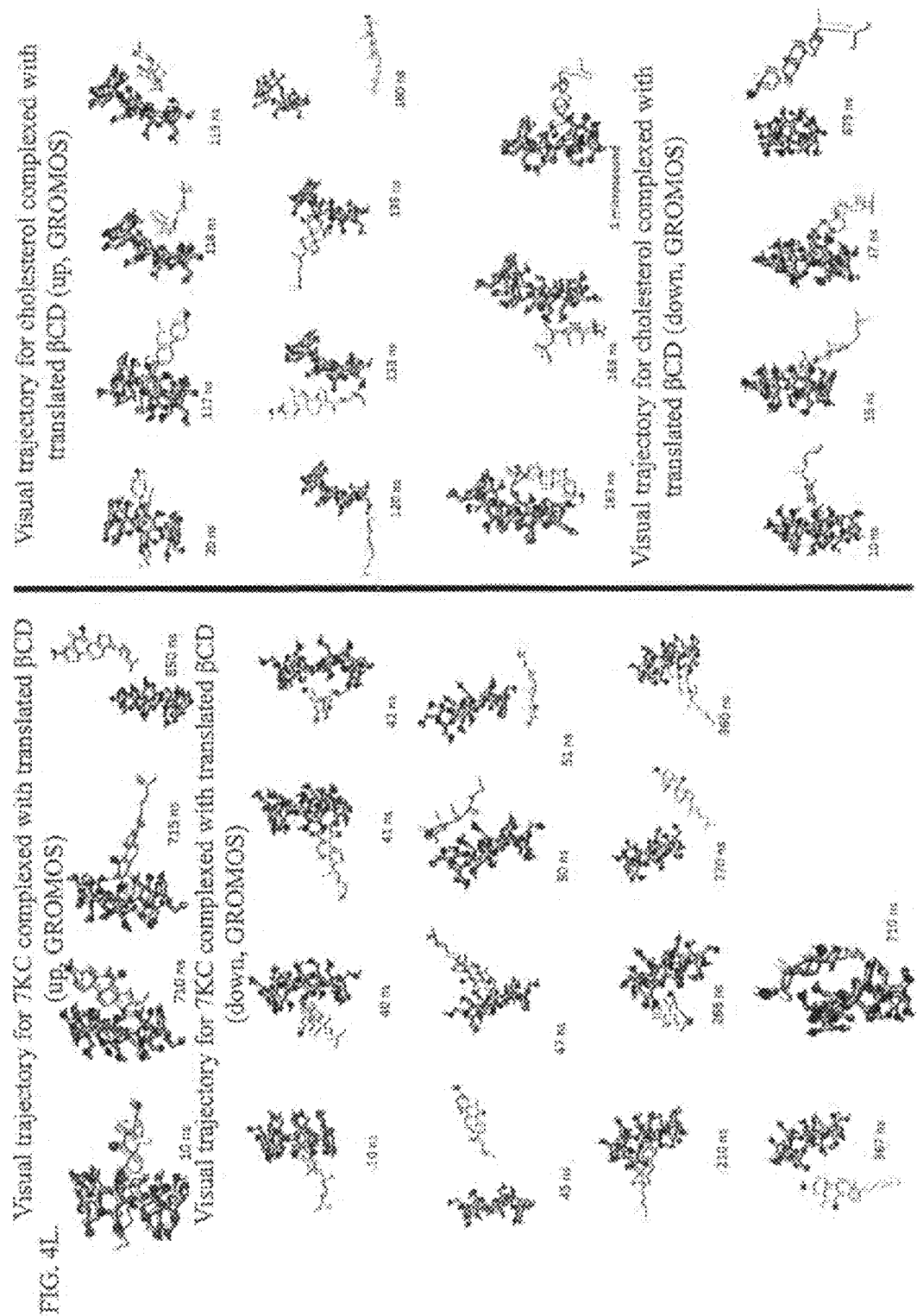
FIG. 4L. Visual trajectory for 7KC and cholesterol complexed with translated native (DS0) βCD in the GROMOS forcefield.
Figure 4M:
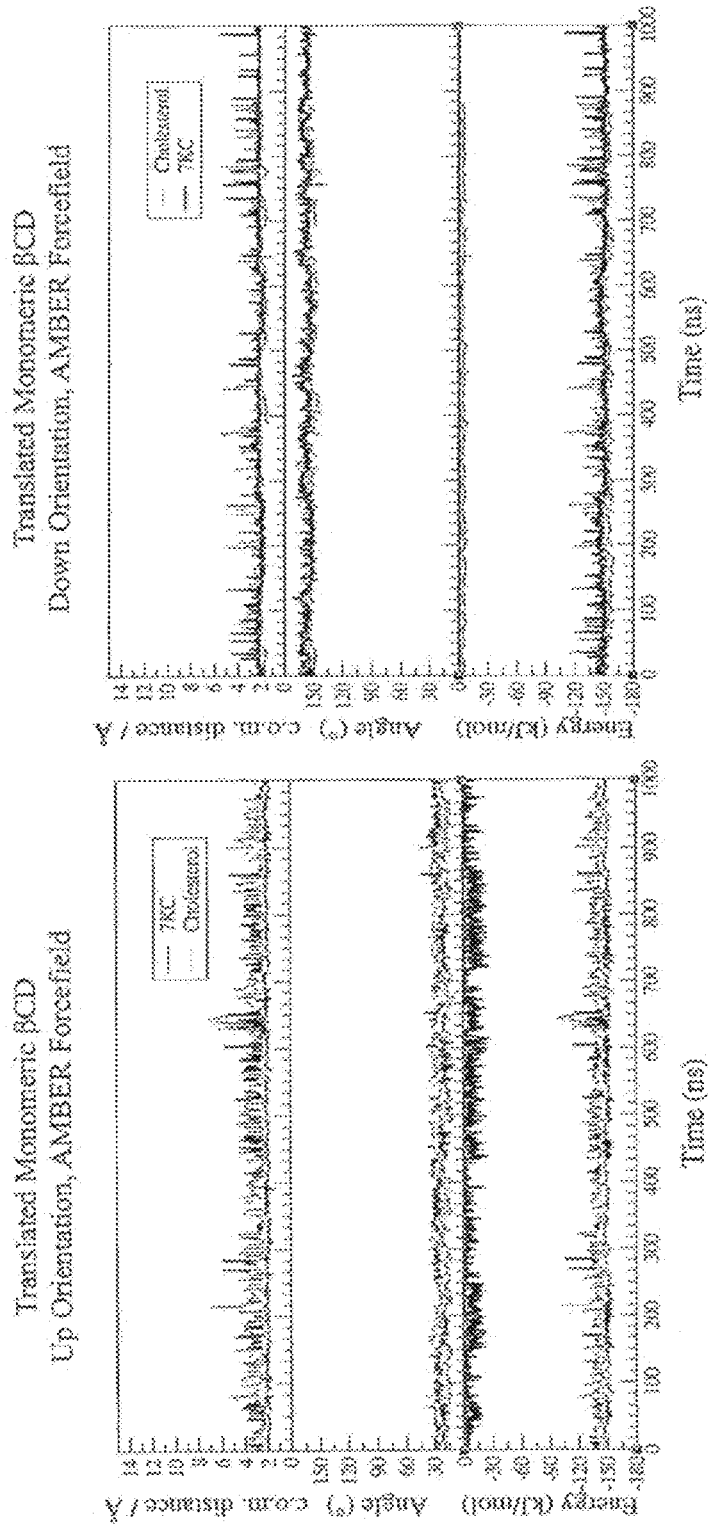
FIG. 4M. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for translated native monomeric beta cyclodextrin (DS0), up and down ligand orientations in the AMBER forcefield.
Figure 4N:
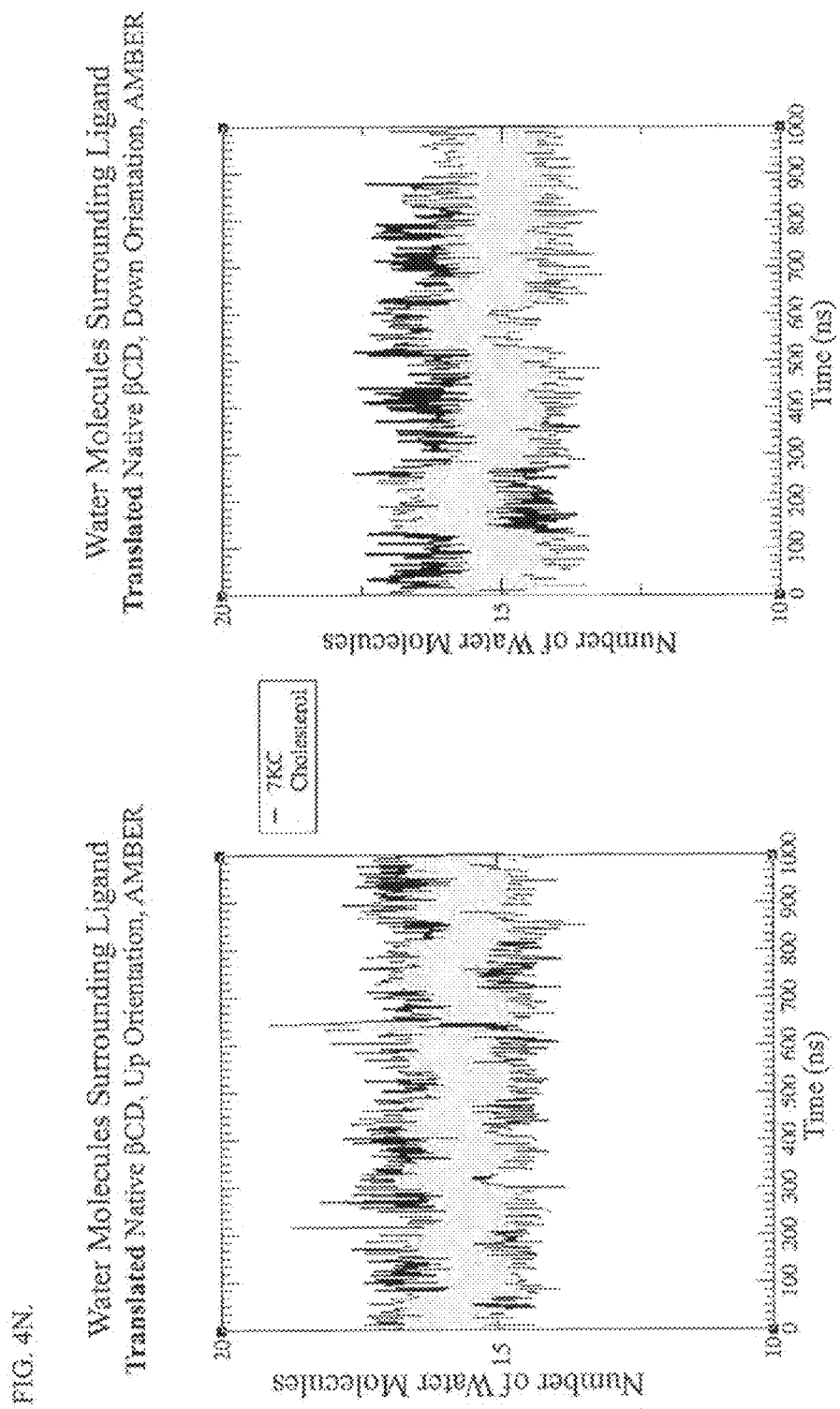
FIG. 4N. Solubilization of ligand by translated monomeric βCD in the AMBER forcefield.

Additional Molecular Dynamics Simulations (FIGS. 4NN-SS, 5B-C, 6B-C, 7A-B, 8H-I)

Figure 4O:
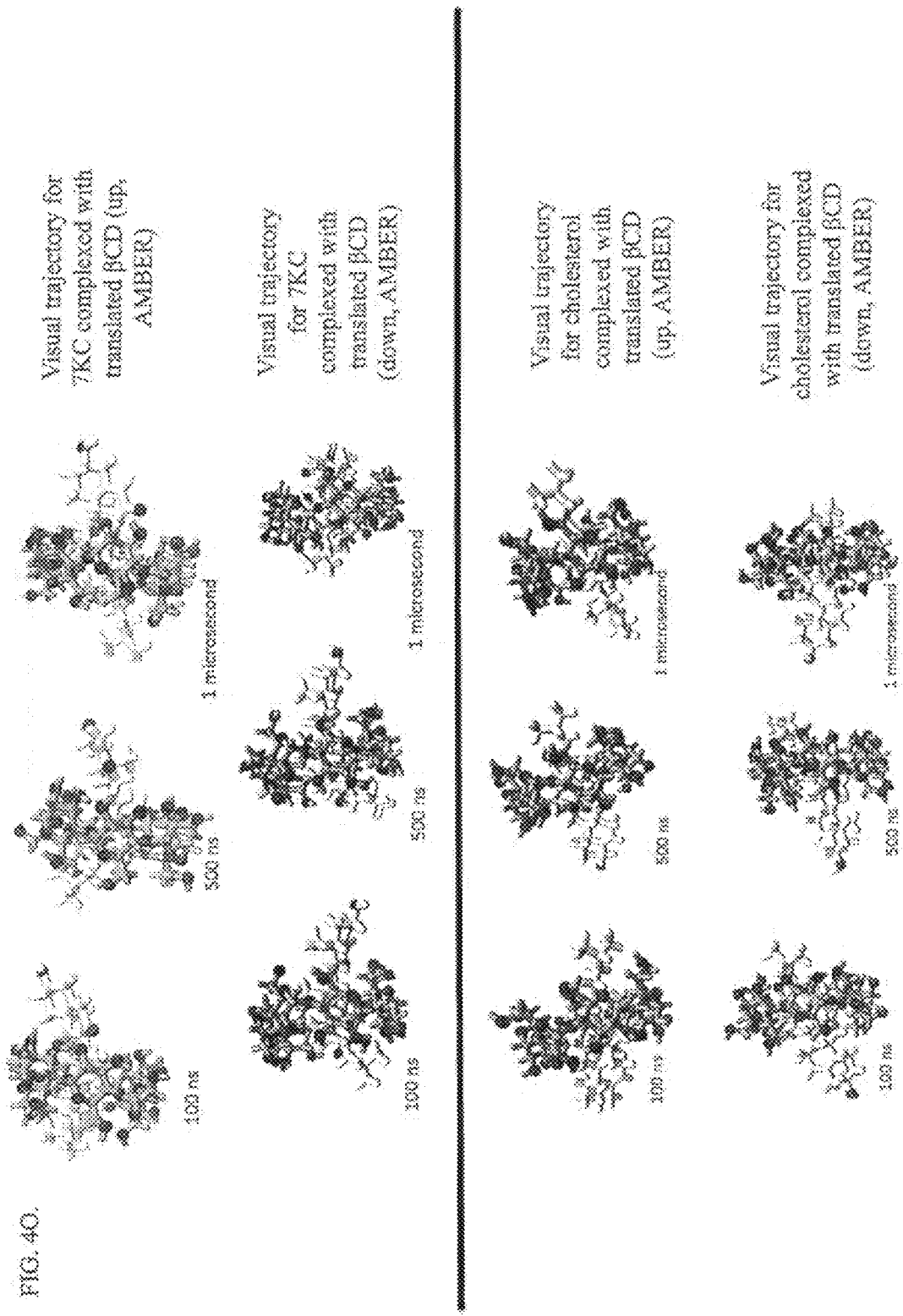
FIG. 4O. Visual trajectory for 7KC and cholesterol complexed with native DS0 βCD (AMBER forcefield) in both orientations.

Based on the initial HPβCD simulations, it was concluded that the GROMOS forcefield in the non-translated position produced the best and most dynamic results for these complexes. This long, initial analysis was important for establishing a precedent for modeling these novel molecules so that shorter, more targeted simulations could be conducted for other types of dimers. Thus, an extension of the molecular dynamics analysis was conducted with various types of linkers and substitutions which showed promise. First, docking calculations were done for a range of DS for methyl (FIG. 5A) and sulfobutyl (FIG. 6A) βCD dimers. This demonstrated that low DS (~4) showed the most promising results in terms of dimers with the best 7KC specificity. Therefore, additional MD simulations were conducted for DS4 βCD dimers with triazole and butyl linkers (FIGS. 4RR-SS, 5B-C, 6B-C, 7A-B). We also conducted simulations for DS0 βCD dimers (FIG. 4NN-QQ). These simulations were conducted for 100 ns and analyzed for only angle and energy of interaction to assess for major differences or similarities between these molecular interactions and those with the butyl-linked hydroxypropyl dimer.

Additional Docking Simulations

After the initial simulations proved similarly promising for a feasible range of substitutions and linkers, a screen of many more linkers, substitutions, and even substitution positions was conducted using the same docking techniques described above. This analysis serves to show that the effectiveness of these molecules is largely (if not fully) conveyed by the actual dimerization of βCD, regardless of linker or substitution type.

Computational Results and Conclusions

Docking:

We first examined whether HPβCD could bind cholesterol and 7KC as a monomer (FIG. 2E), then we examined whether HPβCD could bind cholesterol and 7KC as a dimer (FIG. 4B).

We found that HPβCD monomers (FIG. 2E) have a high affinity for both cholesterol and 7KC at low degree of substitution (DS) but seem to have a decreasing affinity for both sterols as the DS increases. This is likely due to crowding from the hydroxypropyl groups which does not allow the sterol to enter the core of the monomer. Additionally, fewer hydroxyl groups on the inside surface of the CD are available to hydrogen bond to the carbonyl group on 7KC. The best specificity (but not the best affinity) is seen as a spike at DS4, with preference for 7KC extending from DS2 to DS6 and switching to cholesterol for DS7 and above. After DS10, there is little to no affinity observed in these models.

The butyl-linked dimers showed higher affinities for sterols as compared with monomeric CDs, with the best affinity/specificity for 7KC at dimerized DS10 and DS4 (FIG. 4B). However, this specificity appears to be present only in dimers of specific DS for these calculations, and the change between different DS shown in these calculations is significant. Triazole-linked dimers show better specificity overall, except at DS6, with similar affinity to the butyl-linked dimer. It is hypothesized that this specificity is due to additional hydrogen bonding to 7KC between the hydrogen-bond donating nitrogen and the hydrogen-bond accepting ketone of 7KC.

Initial Molecular Dynamics Analysis:

FIGS. 4D-O support the hypothesis that native (unsubstituted, DS0), monomeric βCD is able to complex with both 7KC and cholesterol in the up and down orientations, although 7KC maintains a more stable complex than cholesterol in the down orientation and vice versa in the up orientation. Cholesterol exhibits less variation throughout the up-oriented trajectory, showing how cholesterol leaves and reassociates with CD in the up orientation multiple times (note the large angle change at about 150 ns where cholesterol rotates around to associate in the opposite orientation) (FIG. 4D). This angle change indicates that the down orientation is significantly more stable, so much so that cholesterol leaves the cavity and rotates 180 degrees before reassociating, and that the overall affinity for cholesterol is very high as it is able to complete this large movement in the simulation.

7KC, on the other hand, does not reassociate once the complex breaks in either orientation, but the down orientation is significantly more stable for more than half the trajectory, supporting the hypothesis that the down orientation is favored for 7KC. This indicates that both 7KC and cholesterol favor the down orientation, where the headgroup is associated with the primary face and the tail is associated with the secondary face, but only cholesterol is able to actually leave and reassociate with CD in this favorable conformation. This could explain why native CD is extremely good at solubilizing cholesterol and its derivatives but does not show specificity for 7KC. This slight preference for cholesterol by native, monomeric βCD is expected and consistent with published experimental results (Zidovetzki [et al.], Biochim. Biophys. Acta., 1768(6): 1311-1324. (2007)) and is further bolstered by the number of water molecules surrounding the ligand (FIG. 4E); cholesterol sees much less water than 7KC, especially in the 'up' orientation.

The AMBER forcefield (FIG. 4G-4I) showed significantly stronger interactions between native βCD and sterols. Both ligands in both orientations remain inside the cyclodextrin ring for the entirety of the trajectory, with little preference for 7KC or cholesterol observed. The AMBER forcefield shows stronger, longer interactions between the two molecules than the GROMOS forcefield, and solubilization of sterol by native βCD in the AMBER forcefield appears to be nearly identical between the two ligands in both up and down orientations. Despite this strong, stable interaction, the AMBER forcefield may not completely capture the interactions between βCD and sterols as the complex simply does not break. Some movement is necessary to fully elucidate the interactions happening, but this is good evidence that a strong complex is indeed formed between these two molecules.

Even when the ligand was translated more deeply inside the CD cavity (FIG. 4J-O) the native complex was still effectively formed in both forcefields, although again less consistently for GROMOS than for AMBER. The GROMOS forcefield showed a significant preference for the 'up' orientation for 7KC and the 'down' orientation for cholesterol, however only AMBER showed strong interactions between both ligands and CD. This indicates that 7KC and cholesterol interact similarly and strongly with native βCD, which is consistent with experimental data, but the orientation of the ligand does appear to make a difference in the complexation observed. The nuances of these trajectories are detailed below.

Figure 4P:
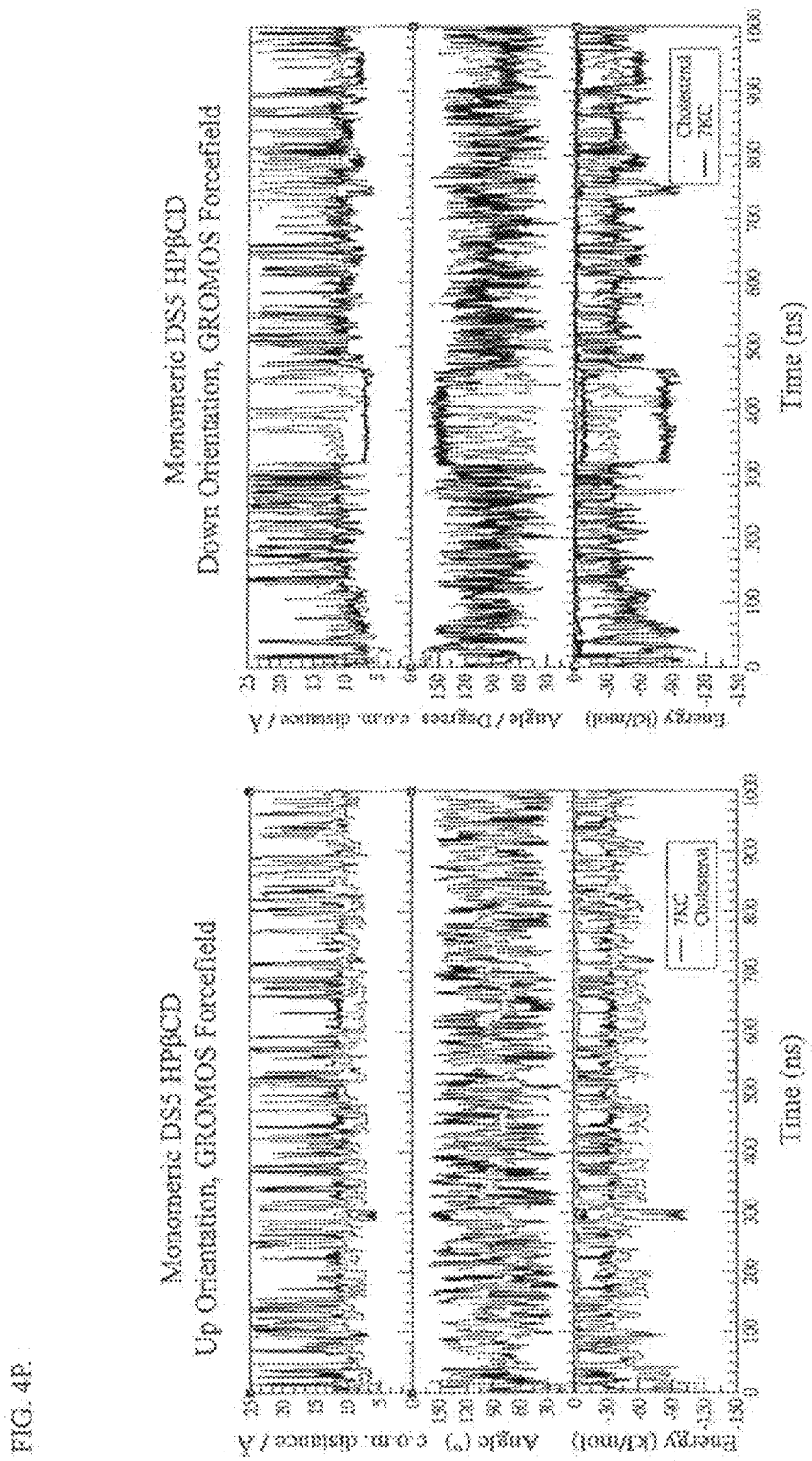
FIG. 4P. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for native DS0 monomeric beta cyclodextrin, up and down ligand orientations in the GROMOS forcefield.
Figure 4R:
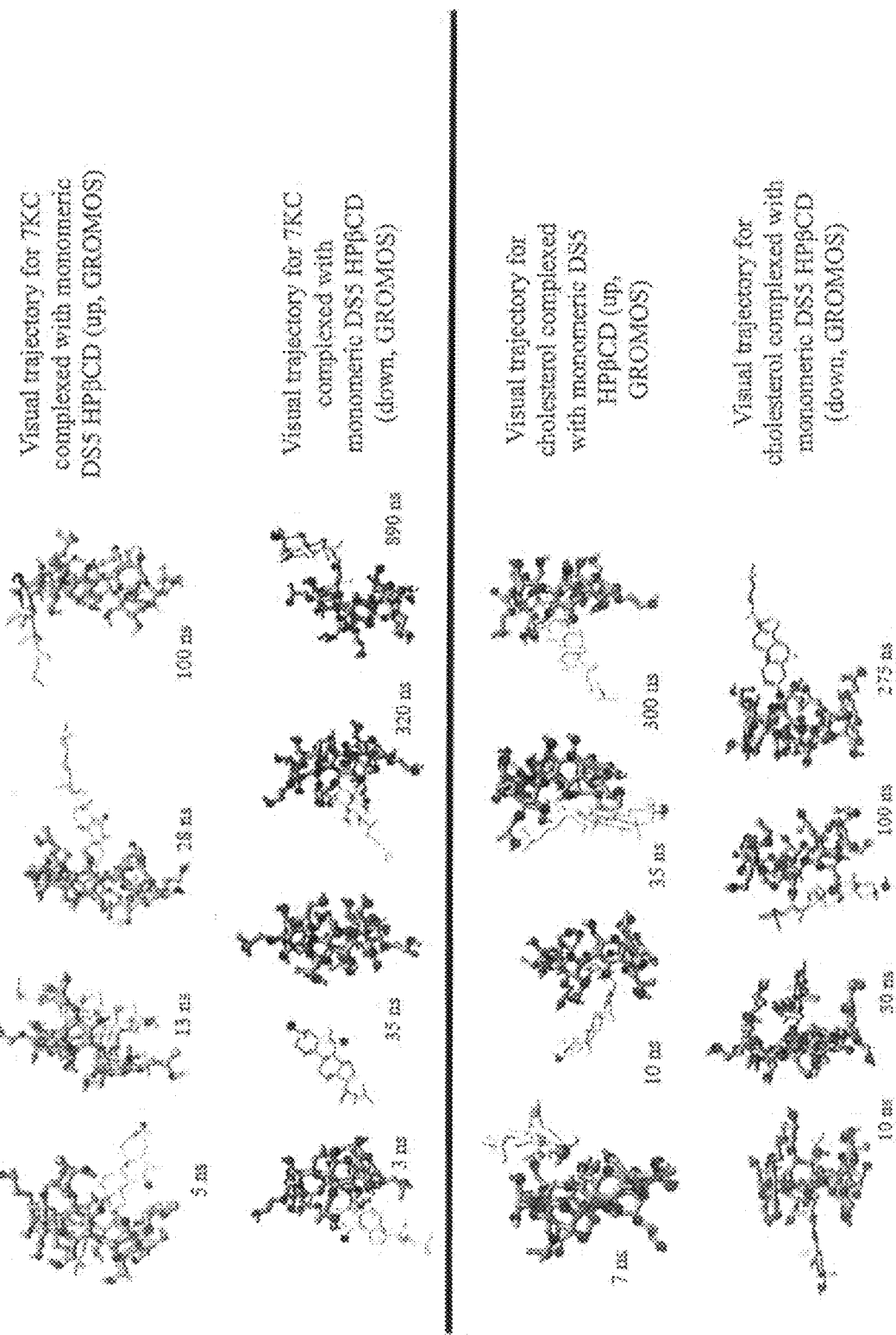
FIG. 4R. Visual trajectory for 7KC and cholesterol complexed with native monomeric βCD (GROMOS forcefield) in both orientations.
Figure 4S:
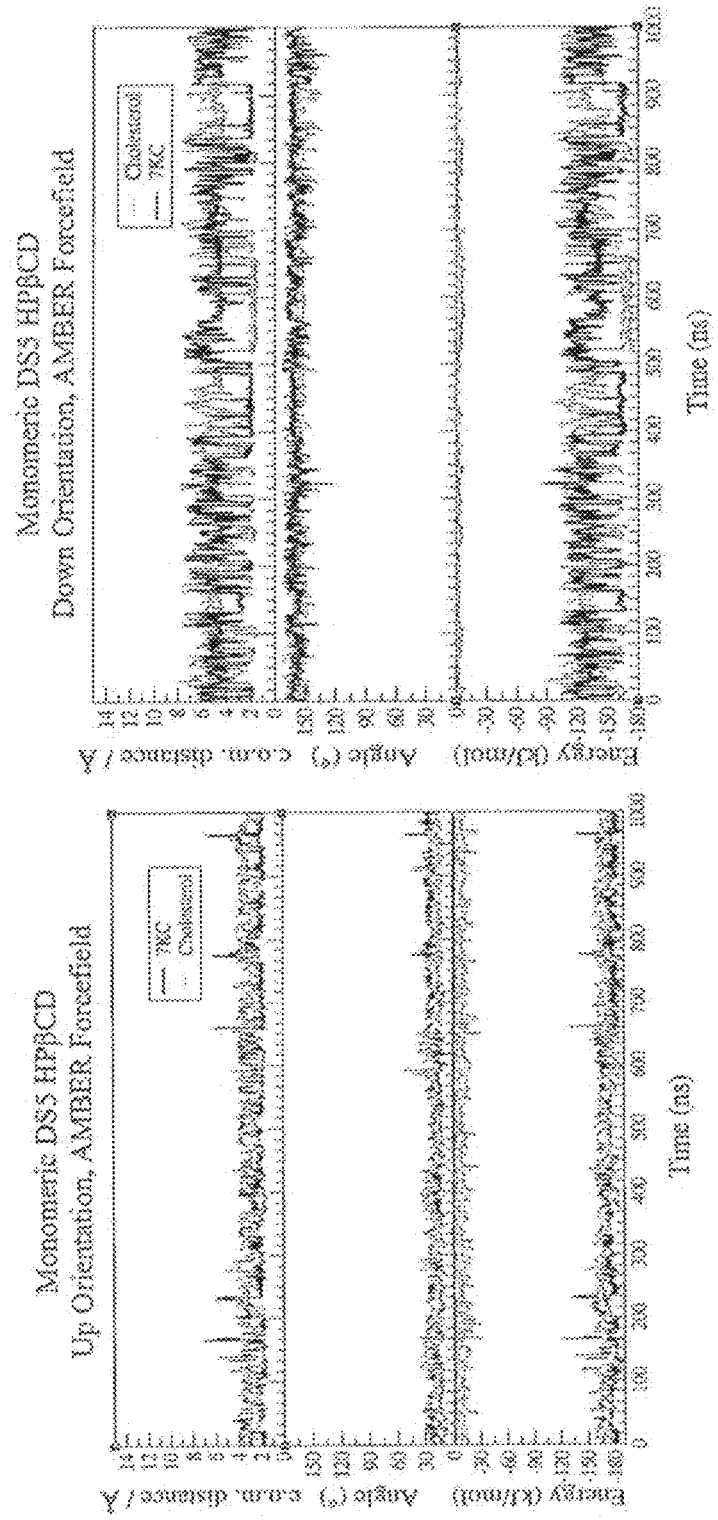
FIG. 4S. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between HPβCD DS5 and cholesterol or 7KC for the up and down ligand orientations in the AMBER forcefield.

Monomeric DS5 HPβCD (FIG. 4P-AA) shows less consistent interaction between CD and sterol in the GROMOS forcefield than native CD, but also appeared to favor the down orientation for 7KC as seen in FIG. 4P. The AMBER forcefield (FIG. 4S, Y) once again showed stronger, more consistent interactions, but the stable complex formed was still the same in both forcefields. Overall, we can see that the addition of hydroxypropyl groups to cyclodextrin monomers makes the formation of a complex less likely for both ligands in both forcefields, but 7KC is more consistently able to form and reform a stable complex than cholesterol. Cholesterol appears to form a complex with HPβCD less readily with more water molecules able to access cholesterol than 7KC in general for both forcefields, indicating a preference for 7KC by HPβCD. This is clear in FIG. 4R, as the 7KC complex forms and reforms in the 'down' orientation while cholesterol does not complex as well. This visual trajectory also shows how the 'up' orientation is strongly favored by 7KC, but still forms a complex in the 'down' orientation at about 500 ns.

Figure 4T:
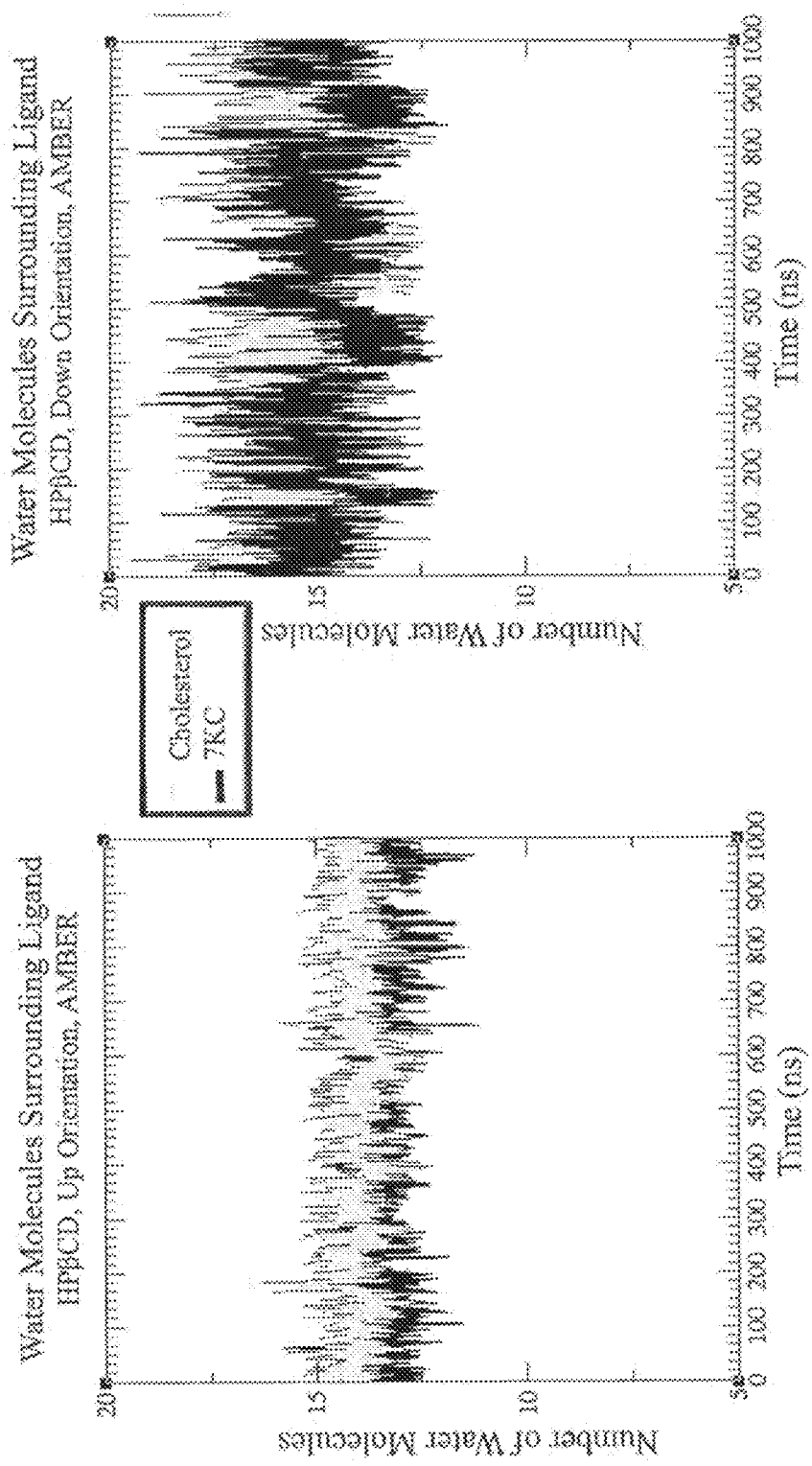
FIG. 4T. Solubilization of ligand by HPβCD DS5 in the AMBER forcefield.
Figure 4L:
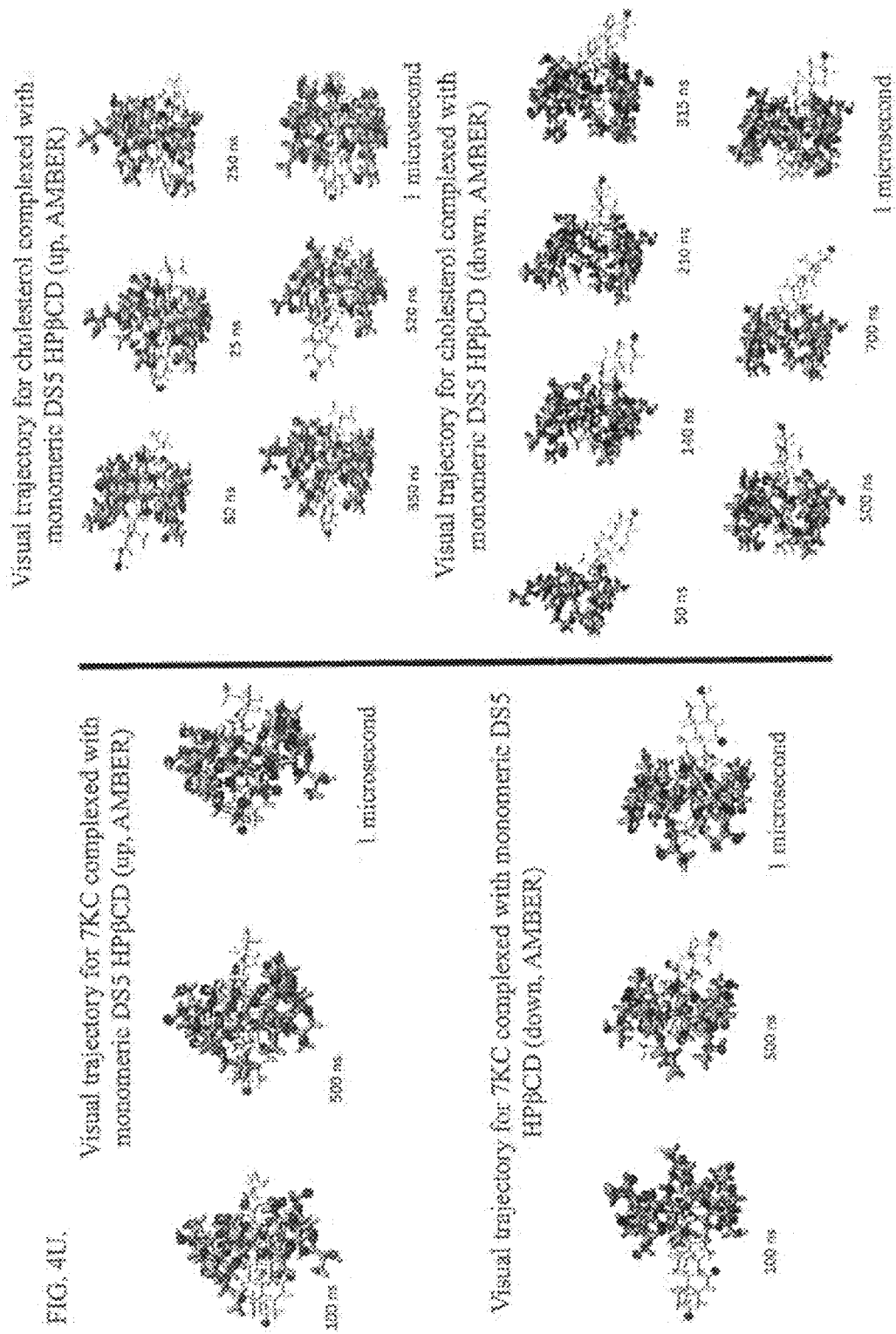
Figure 4V:
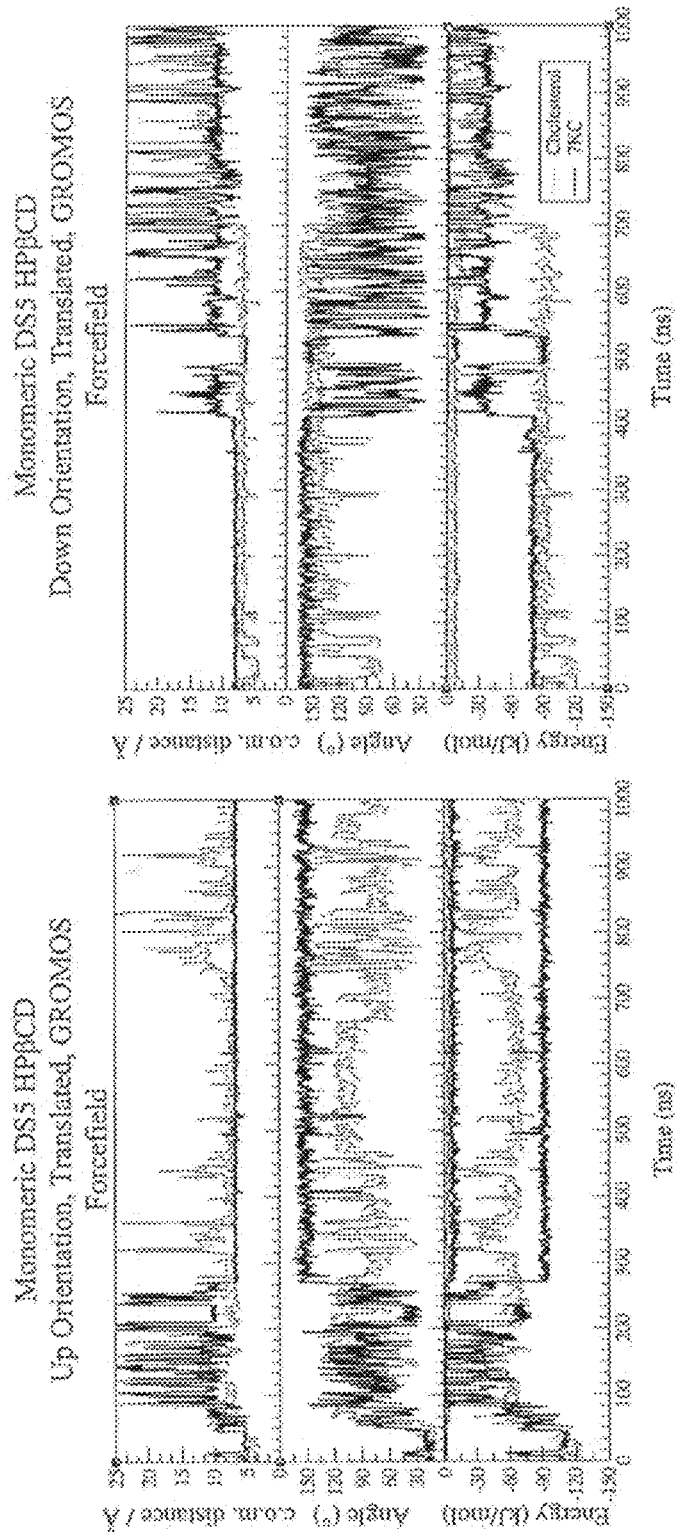
FIG. 4V. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between HPβCD DS5 and cholesterol or 7KC, up and down ligand orientations, translated, in the GROMOS forcefield.
Figure 4W:
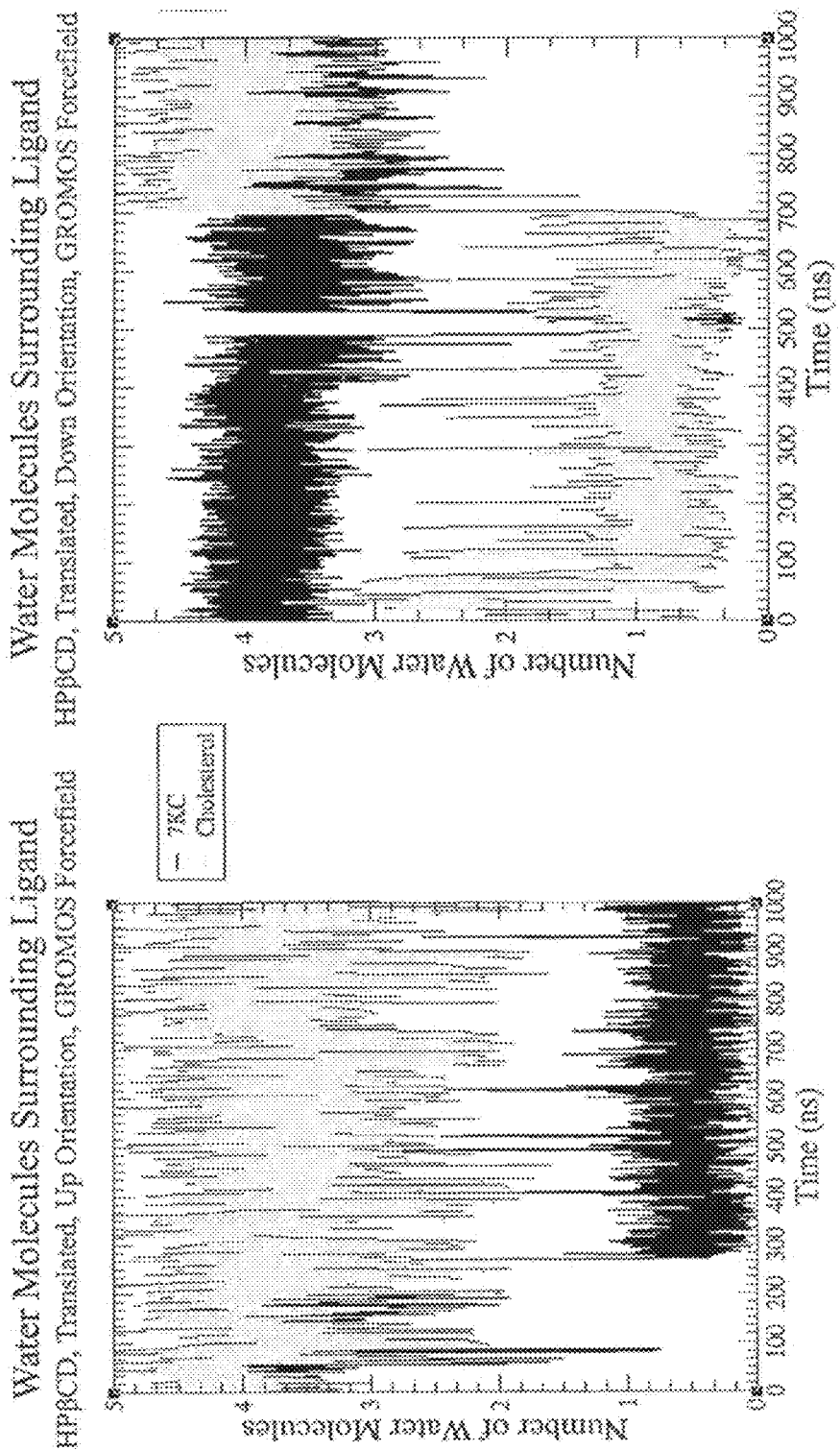
FIG. 4W. Solubilization of ligand by monomeric HPβCD, translated, in the GROMOS forcefield.
Figure 4Y:
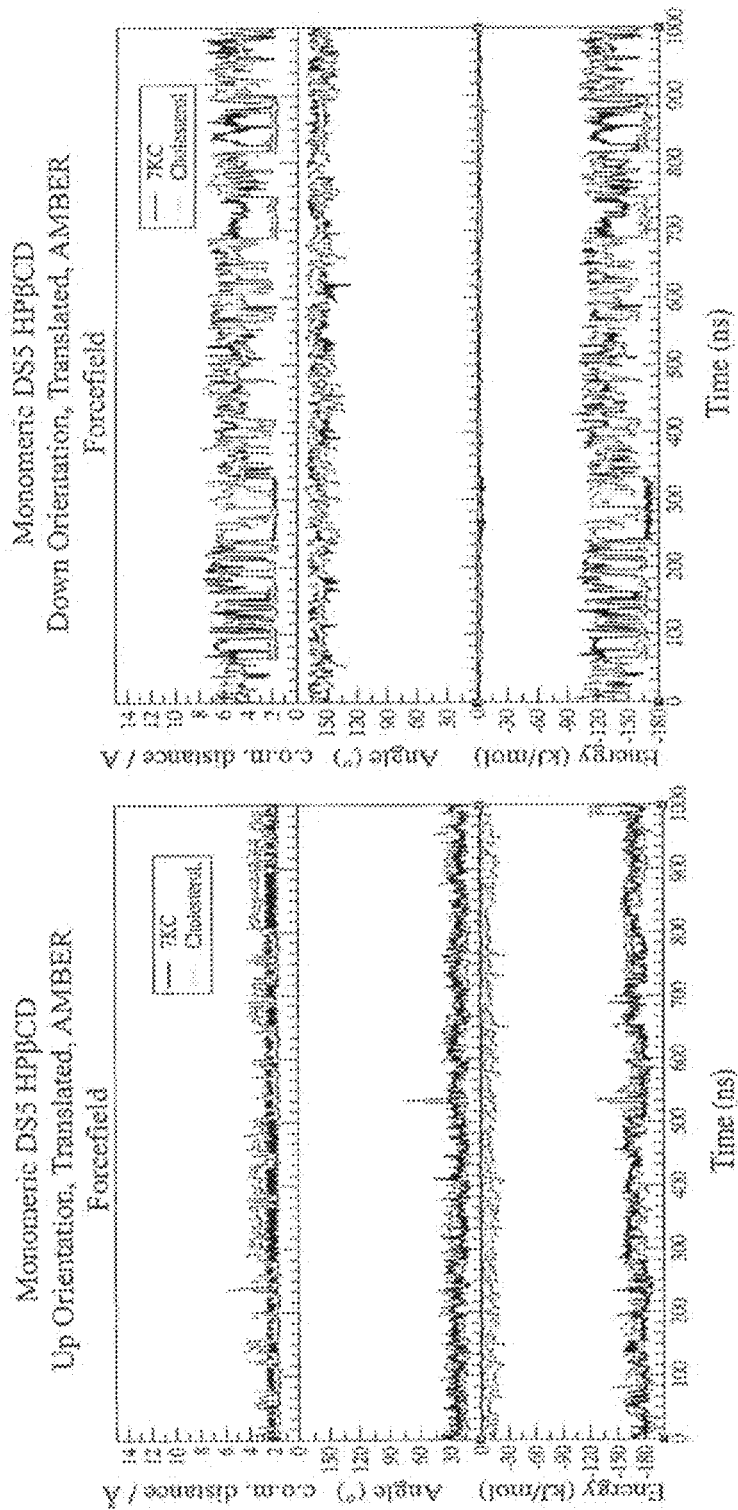
FIG. 4Y. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between HPβCD DS5 and cholesterol or 7KC, up and down ligand orientations, translated, in the AMBER forcefield.
Figure 4Z:
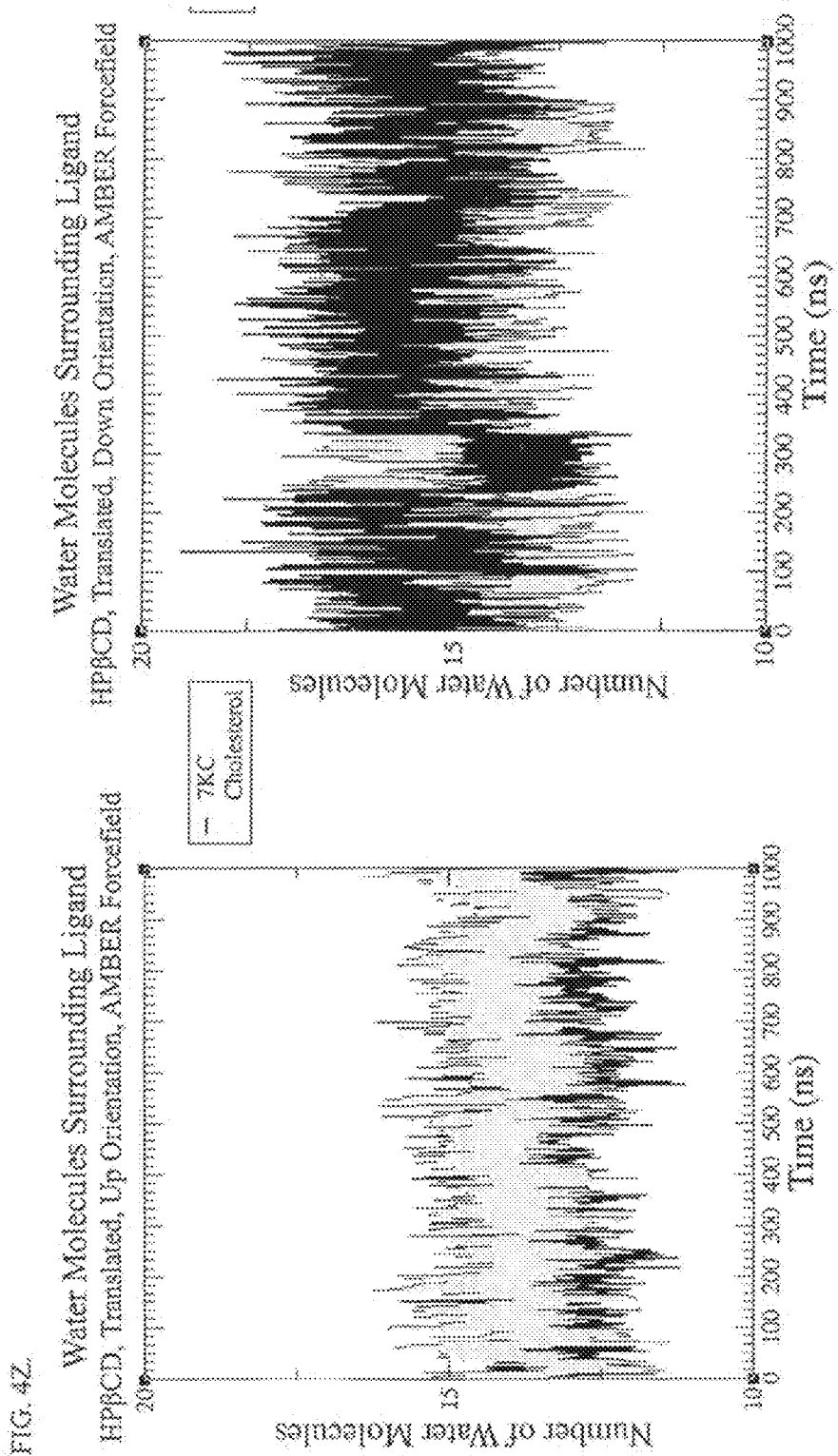
FIG. 4Z. Solubilization of ligand by monomeric HPβCD DS5, translated, in the AMBER forcefield.
Figure 4B:
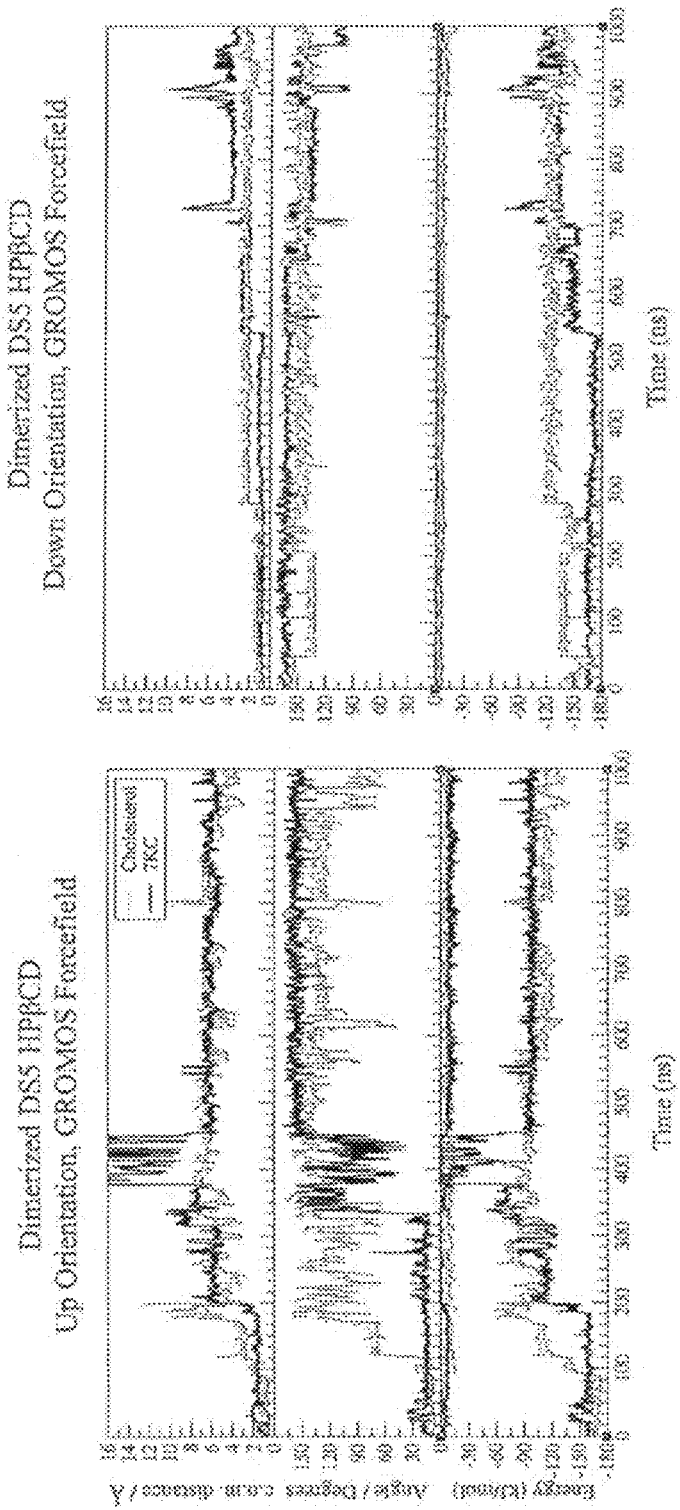
Figure 4C:
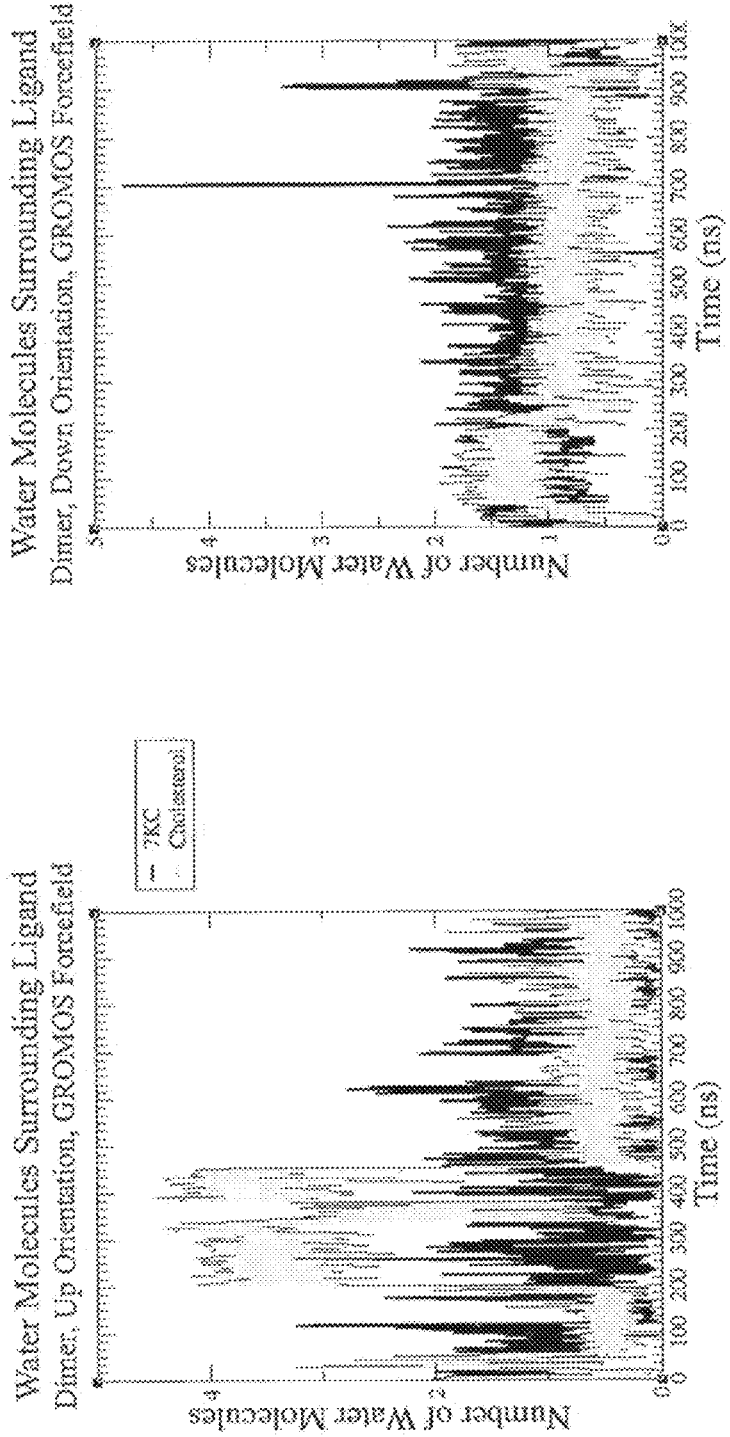
Figure 4E:
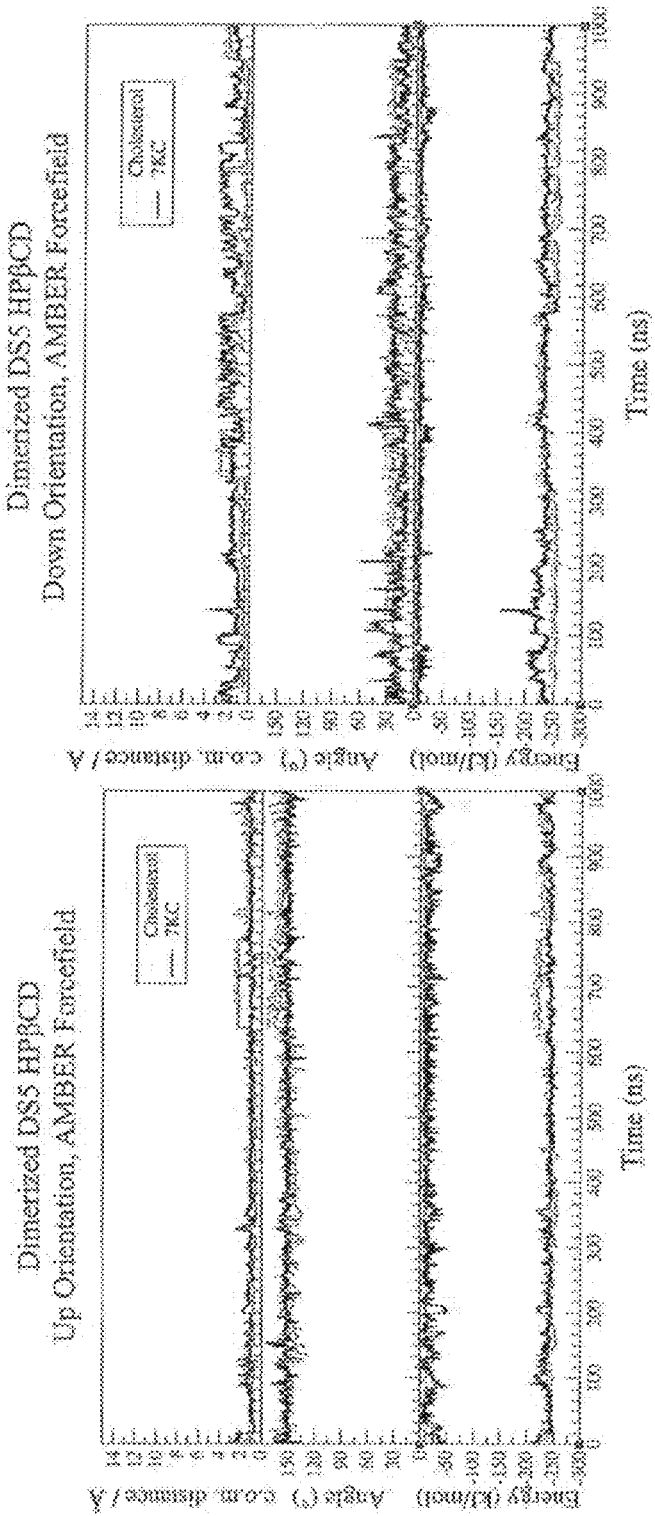
Figure 4F:
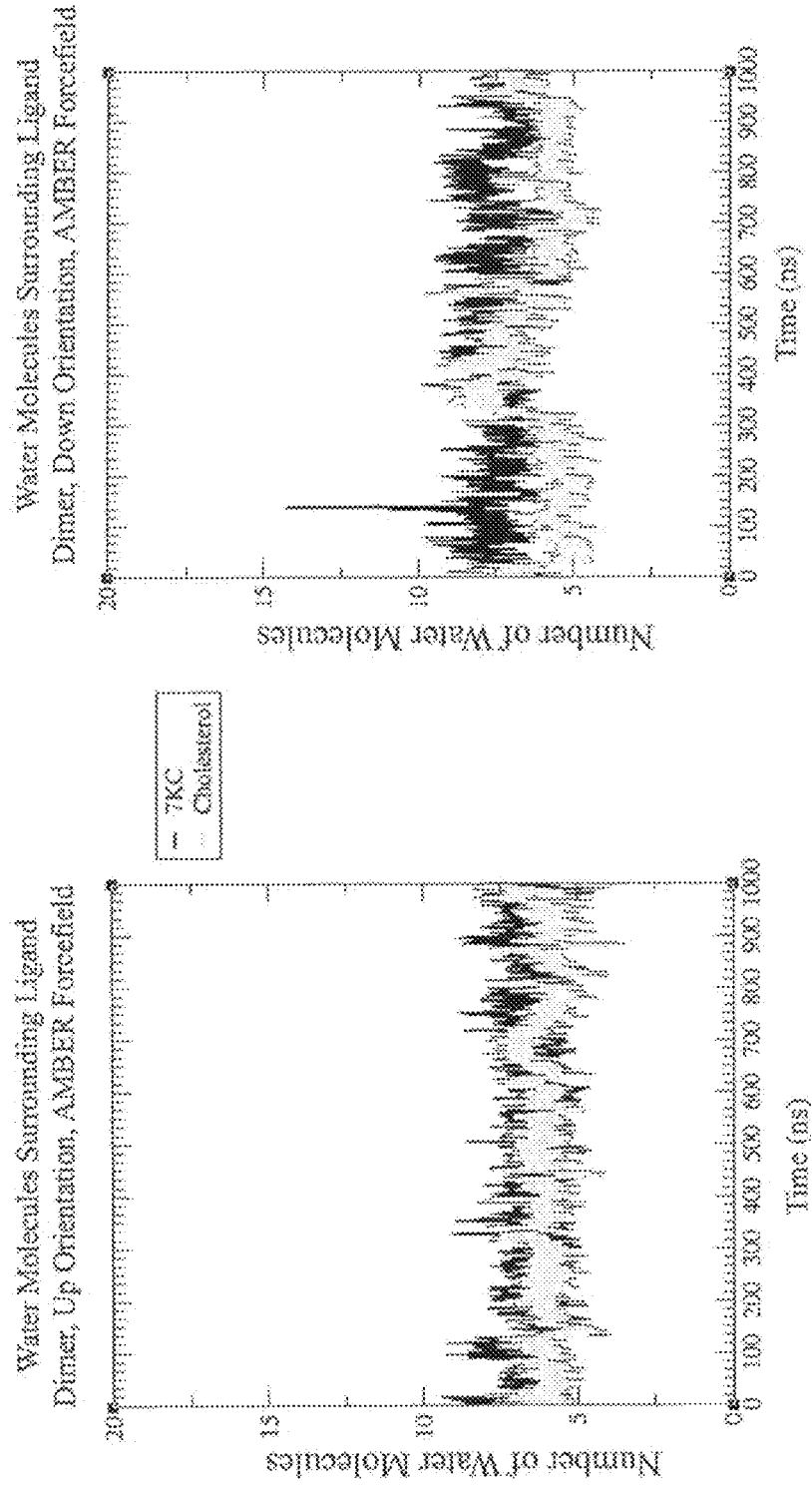
Figure 4G:
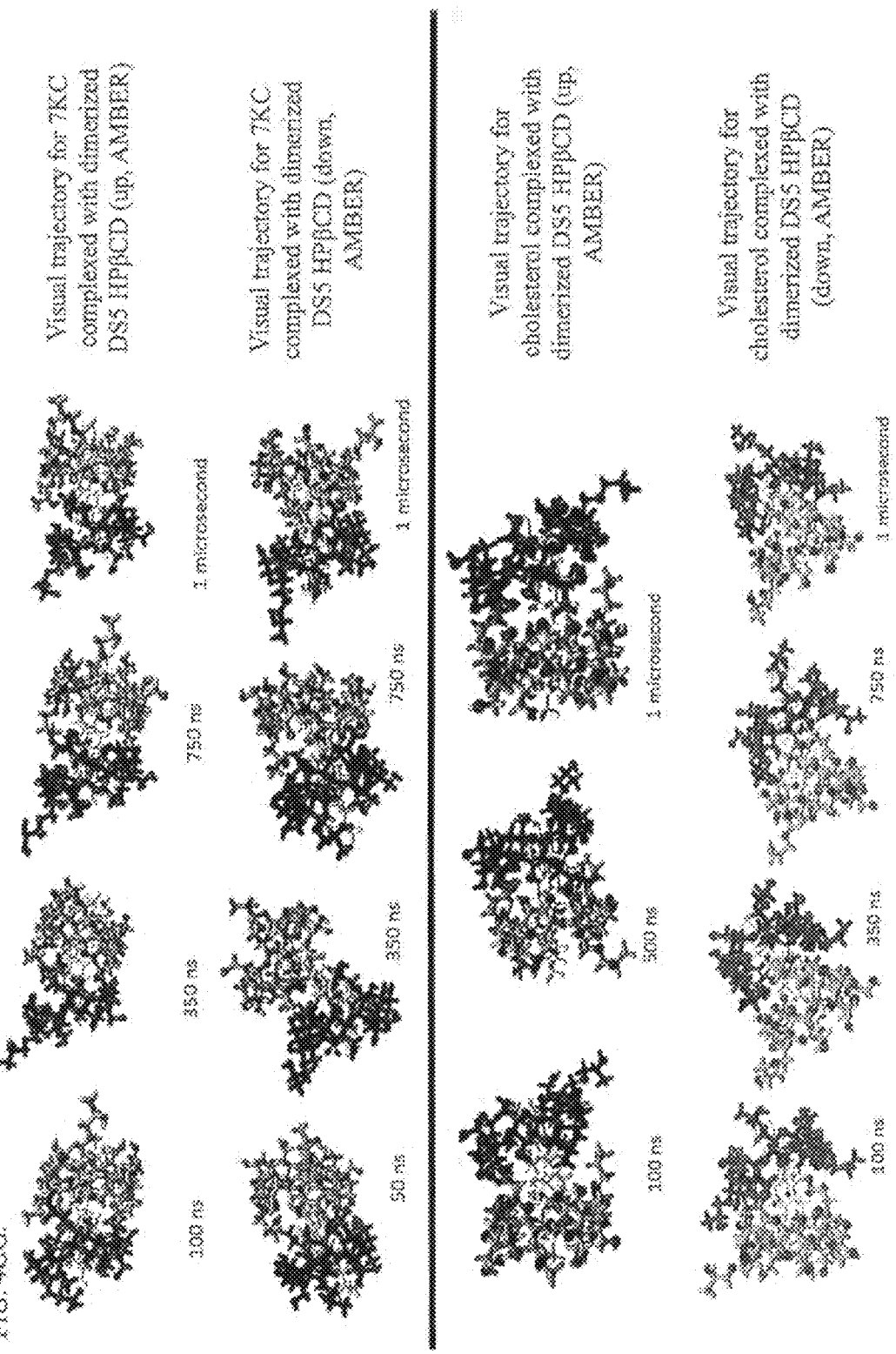
Figure 41H:
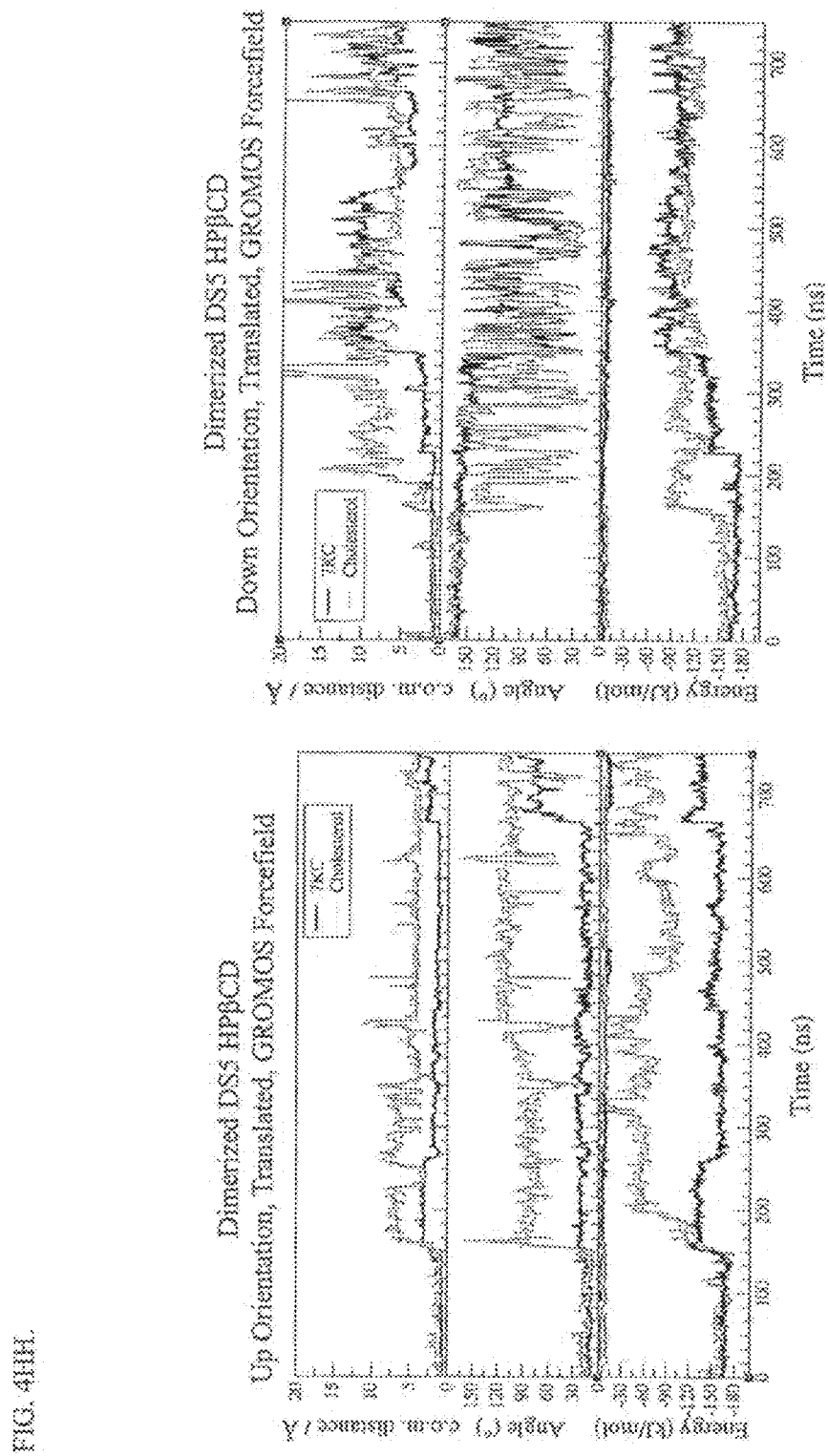
Figure 41L:
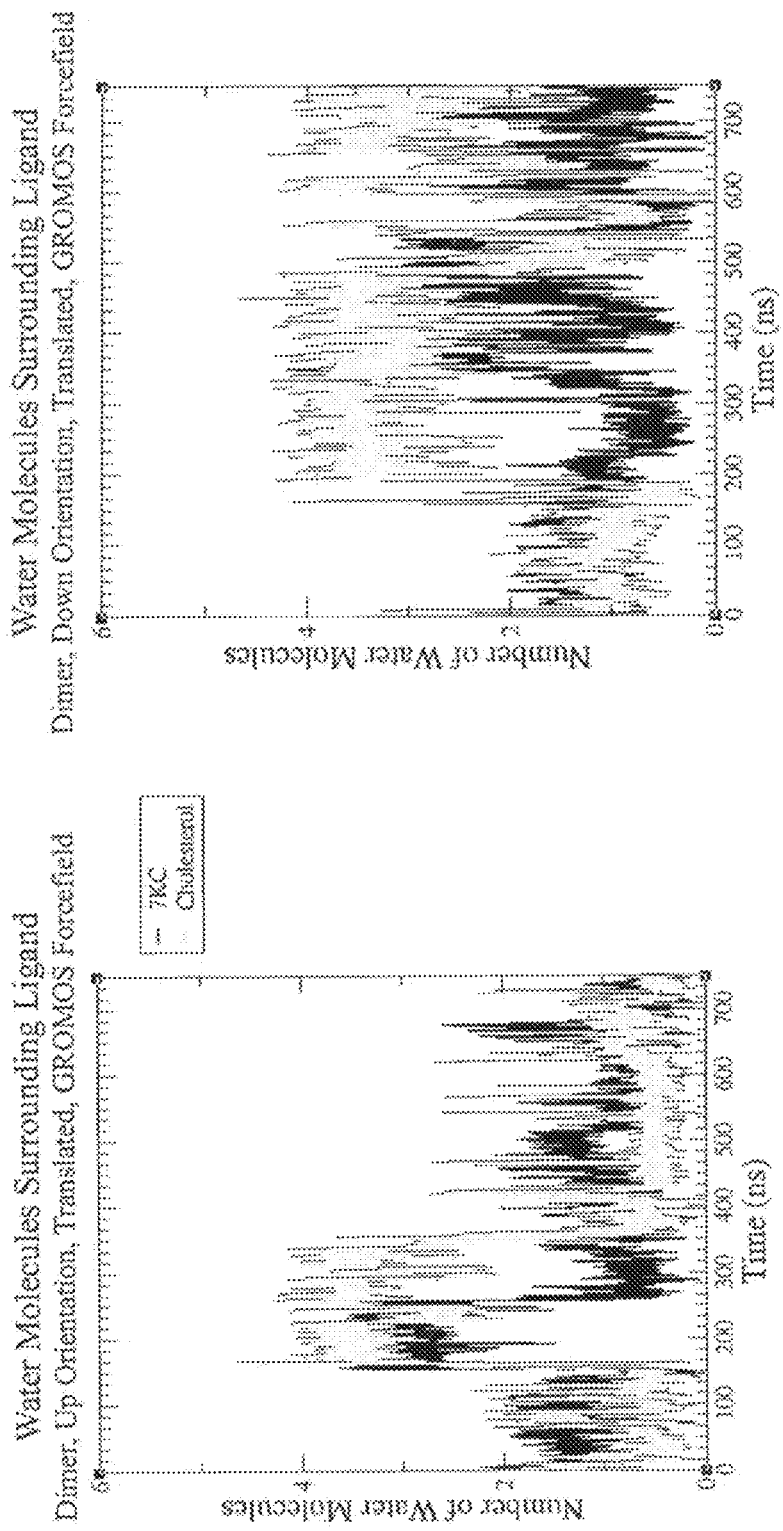

When the ligand is translated, HPβCD was able to complex with both sterols more effectively as the initial position of the ligand was more deeply embedded in the cavity of CD. For this translated trajectory in GROMOS (FIG. 4V), the preference for 7KC over cholesterol is much more obvious than in the previous simulation, as 7KC is able to form stable complexes in both orientations while cholesterol can only form a stable complex in the 'down' orientation. Moreover, 7KC in the up orientation begins outside the cavity and is able to associate with the cavity and form a very stable complex within 300 ns. The AMBER forcefield again showed significantly stronger interactions between HPβCD and the sterols, but still formed the same stable complex and favored the up orientation for both ligands, and with slightly less water surrounding 7KC in general throughout the trajectory (see FIG. 4T). This is presumably because the 'down' orientation shows the headgroup of the sterol protruding out of the cavity more than in the 'up' orientation. This is consistent with our experimental data (FIG. 2) as HPβCD monomers have been shown to have some specificity for 7KC while still forming stable, apparently solubilized complexes with both 7KC and cholesterol. All of these simulations are detailed below.

Our novel, butyl-linked DS5 hydroxypropyl β-cyclodextrin dimer was then modeled with 7KC and cholesterol in the GROMOS and AMBER forcefields as seen in FIGS. 4BB-MM. The contrast between the plots of these trajectories and those for monomeric HPβCD and native βCD provide clear evidence that the dimerized version consistently binds sterols significantly more reliably than its monomeric counterpart, hydroxypropylated or not. This is consistent with our experimental data (FIG. 16). The angle, distance, and energy as well as water molecules surrounding the ligand are all much more stable and in an apparently more solubilized configuration than in the monomeric simulations. The GROMOS forcefield showed less than five angstroms between the center of mass of the ligand and the CD when the complex was fully formed in the down orientation (FIG. 4BB) while monomers in the GROMOS forcefield consistently showed upwards of 5-10 angstroms between the molecules when the complex was formed. The AMBER forcefield also showed very strong interactions between sterol and dimerized CD, with energies of interaction approaching −300 kJ/mol in the down orientation as compared to monomers at about −150 kJ/mol (FIG. 4BB). This indicates that the dimer forms a very strong, stable complex with both ligands, especially in the down orientation and particularly when compared to monomeric βCD.

The AMBER forcefield results (FIG. 4EE, KK) support the findings from the GROMOS forcefield simulations that dimerization of HPβCD creates stronger, more stable interactions between CD and sterol with a very small distance between the two molecules and a very large interaction energy. Dimerized CD also consistently shows less than five water molecules surrounding the ligand, especially in the down orientation, while monomeric CD showed upwards of ten water molecules surrounding the ligand (FIG. 4CC). Although this is sometimes reached for monomers with 7KC and cholesterol, the overall presence of water around the sterol has been significantly reduced by dimerization. Dimerization of HPβCD also conveyed some specificity for 7KC, which is evident in that 7KC always stayed associated to at least one of the two linked CDs for the entire trajectory, no matter the forcefield or translation, while cholesterol commonly disassociated from both monomers for at least part of the trajectory and even created a distorted head-to-tail dimer configuration in which cholesterol was not able to be fully enclosed by the dimer. These trajectories are detailed in the following section.

These simulations provide strong evidence that dimerization of HPβCD promotes complexation with sterols by the formation of an encapsulating complex that shields the hydrophobic sterol from surrounding water molecules. The data implicates that the dimerized HPβCD has much greater sterol affinity overall than the monomer and that it has preference for 7KC as 7KC is associated with at least one CD for significantly longer than cholesterol. We are able to conclude from this methodology that, although strong complex formation in the AMBER forcefield is good evidence for the legitimacy of our complex formation and stability, more valuable information can be gleaned from the GROMOS forcefield. This is because GROMOS forcefield, unlike AMBER, shows dynamic interaction between the molecules rather than just one incredibly (possibly unrealistically) stable complex.

The details of the 48 trajectories of hydroxypropyl-beta cyclodextrin dimers, each one microsecond-long are described below.

Detailed Description of Initial Molecular Dynamics Trajectories (FIG. 4):

Native Monomeric βCD and 7KC, Up Orientation, GROMOS Forcefield:

7KC begins with the headgroup inserted into the CD cavity and the tail extending out of the secondary face in FIG. 4F. At 134 ns, the complex breaks and 7KC moves towards the secondary face, rotating out of the cavity. It then remains associated with the secondary face, moving the headgroup in and out of the cavity, until the complex completely disassociates at 150 ns and 7KC moves around the box, re-associating with the primary face. 7KC continues to associate and disassociate from the primary face, but it does not re-enter the cavity for the remainder of the trajectory.

Native Monomeric βCD and Cholesterol, Up Orientation, GROMOS Forcefield:

FIG. 4F shows that cholesterol (up) begins with the tail inserted into the CD cavity and the headgroup extending out of secondary face. The complex breaks at about 150 ns, visible by a large change in the 'Angle' for cholesterol, as cholesterol leaves cavity and rotates outwards, parallel to cyclodextrin, then re-associates in the opposite direction, with the tail extending out of secondary face. Cholesterol then reinserts headgroup and cycles between inserting headgroup and becoming parallel with CD for about 200 ns, visible as changes in Angle, Energy, and Distance for cholesterol (up) in FIG. 4D. At about 300 ns, the complex fully breaks (corresponding to spikes for cholesterol in FIG. 4D) and cholesterol moves around the CD molecule randomly. The two molecules reassociate briefly at 310 ns for about one nanosecond where cholesterol lays parallel to the primary face of CD. Cholesterol then resumes random motion until it reassociates to the secondary face at 330 ns for about two more nanoseconds with the cholesterol tail loosely inserting into the CD cavity. The cholesterol then flips at about 400 ns to associate the headgroup with the CD cavity, this configuration remains relatively stable with the headgroup associating and disassociating regularly until the complex breaks again at about 560 ns. At this point, the cholesterol briefly randomly moves around the CD, then associates the tail with the secondary CD face. By 580 ns, the tail of cholesterol is snugly inserted into the CD molecule with the headgroup extending from the secondary CD face. The complex then breaks again at 582 ns until 610 ns where it reforms again with the headgroup inserted from the secondary face. The complex again breaks at about 680 ns and reforms at 750 ns, then breaks again at 880 ns, reforms at 920 ns, and continues to break and reform (but always associated as seen at 920 ns) approximately every 10 ns until the end of the trajectory. The fact that cholesterol fully leaves the cavity of CD and then re-associates within the simulation time indicates that the program was able to associate the two molecules on its own, not by any outside circumstance. This provides strong evidence that this interaction is legitimate, re-occurring, and captured effectively by the simulation.

Native Monomeric βCD and 7KC, Down Orientation, GROMOS Forcefield:

7KC begins with the tail inserted into the CD cavity and the headgroup extending out of primary face in FIG. 4F. This complex remains in this conformation with the 7KC moving and tilting back and forth in the cavity. Not until 600 ns does the complex break, at which point 7KC quickly leaves the cavity and rotates to the secondary face. 7KC proceeds to float around the simulation box, periodically and briefly associating with CD in a conformation similar to that at 720 ns. Overall, the complex remains disassociated until the end of the simulation. Despite this disassociation, the complex is stable for 600 ns which shows that once the 7KC is within the cavity of CD, it is held there by interactive forces. This trajectory can be quantified in FIG. 4D as the plot for 7KC (up) remains relatively flat until about 600 ns, which is where the complex breaks and assumes random motion.

Native Monomeric βCD and Cholesterol, Down Orientation, GROMOS Forcefield:

In FIG. 4F, cholesterol in the down position begins with the headgroup inside the CD cavity and the tail extending out of the secondary face. This remains stable until about 125 ns where cholesterol rotates out of the cavity, but cholesterol continues to periodically insert the headgroup into the cavity of CD from the secondary face for the next 200 ns. At about 340 ns, the complex breaks entirely and cholesterol flies around the simulation box until reassociating with the secondary face in the same manner as before at about 560 ns. Cholesterol then disassociates about 30 ns later and reassociates parallel with the primary face. Cholesterol then oscillates between associating in this way with the primary face and floating randomly for the remainder of the trajectory.

Native Monomeric βCD and 7KC, Up Orientation, AMBER Forcefield:

The interactions seen in the AMBER forcefield in FIG. 4I support strong solubilization of sterol by native monomeric βCD. Both ligands in both orientations remain inside the cyclodextrin ring for the entirety of the trajectory, with little preference for 7KC or cholesterol seen. 7KC (up) begins with center of the molecule inside the CD cavity and with the headgroup extending slightly out of the secondary face while the tail group extends slightly out of the primary face. 7KC remains snugly fit inside the CD cavity for the entire trajectories, with slight rocking back and forth, visible in FIG. 4G as slight variations in an overall flat line, indicating a stable conformation has been formed and does not break. This is also consistent with experimental data, although the AMBER forcefield shows stronger, longer interactions between the two molecules than the GROMOS forcefield.

Native Monomeric βCD and Cholesterol, Up Orientation, AMBER Forcefield:

Cholesterol (up) begins with center of the molecule inside the CD cavity and with the headgroup extending slightly out of the secondary face while the tail group extends slightly out of the primary face in FIG. 4I. This complex remains stable for the entire trajectory; cholesterol never leaves the cavity or changes orientation, it simply rocks back and forth inside the cavity. These small variations in position correspond to small bumps in FIG. 4G, particularly the angle section.

Native Monomeric βCD and 7KC, Down Orientation, AMBER Forcefield:

7KC (down) in FIG. 4I begins with center of the molecule inside the CD cavity and with the headgroup extending slightly out of the primary face while the tail group extends slightly out of the secondary face. This complex remains stable for the entire trajectory; 7KC never leaves the cavity or changes orientation, it simply rocks back and forth inside the cavity. These small variations in position correspond to small bumps in FIG. 4G, particularly the angle section.

Native Monomeric βCD and Cholesterol, Down Orientation, AMBER Forcefield:

FIG. 4I shows cholesterol (down) beginning with center of the molecule inside the CD cavity and with the headgroup extending slightly out of the primary face while the tail group extends slightly out of the secondary face. This complex remains stable for the entire trajectory; cholesterol never leaves the cavity or changes orientation, it simply rocks back and forth inside the cavity. These small variations in position correspond to small bumps in FIG. 4G, particularly the angle section.

Figure 7A:
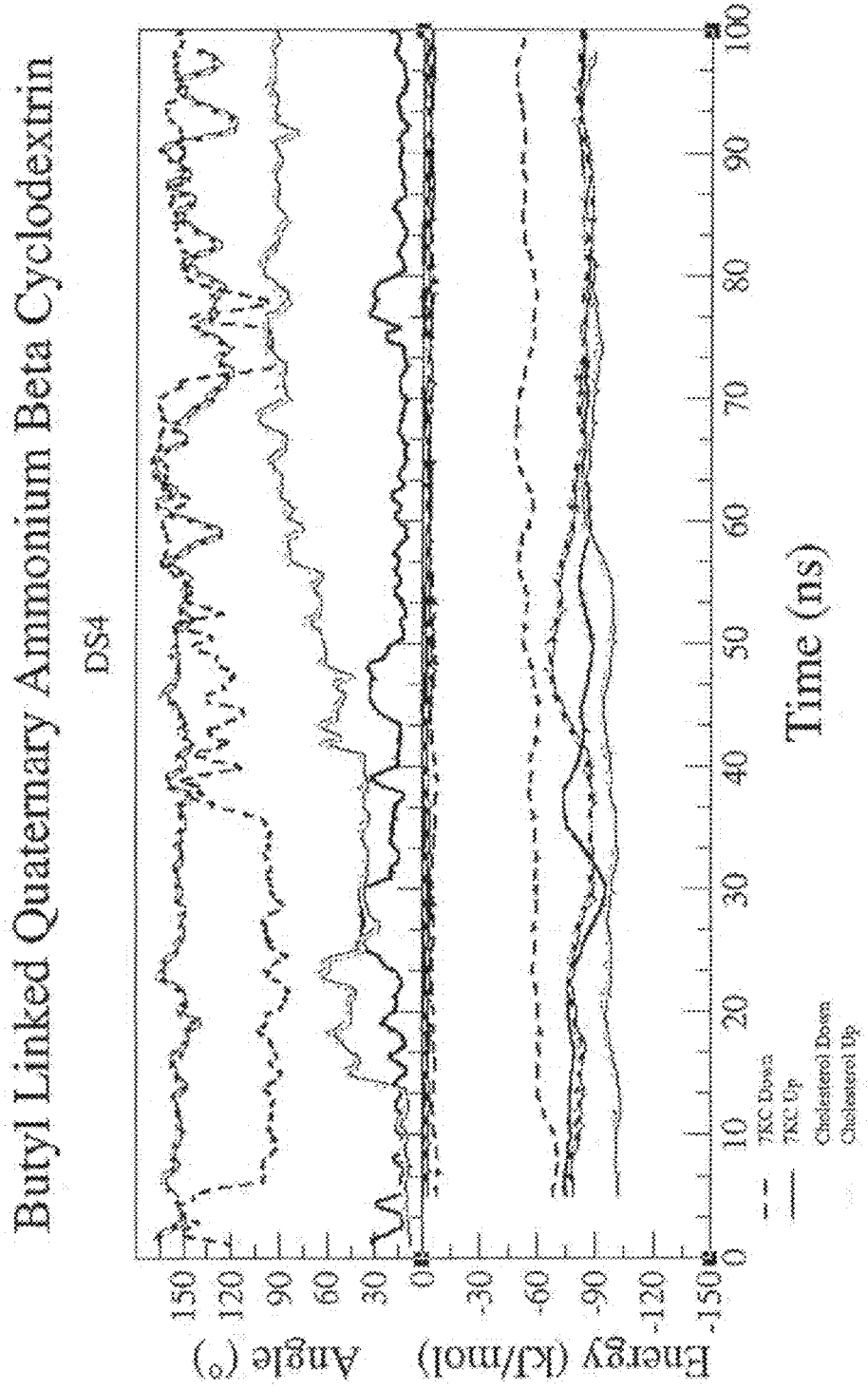
FIG. 7A. MD simulation describing 100 ns of interaction between a butyl-linked DS4 quaternary ammonium βCD dimer and 7KC/cholesterol in both up and down orientations. Legend as in FIG. 5B.
Figure 7B:
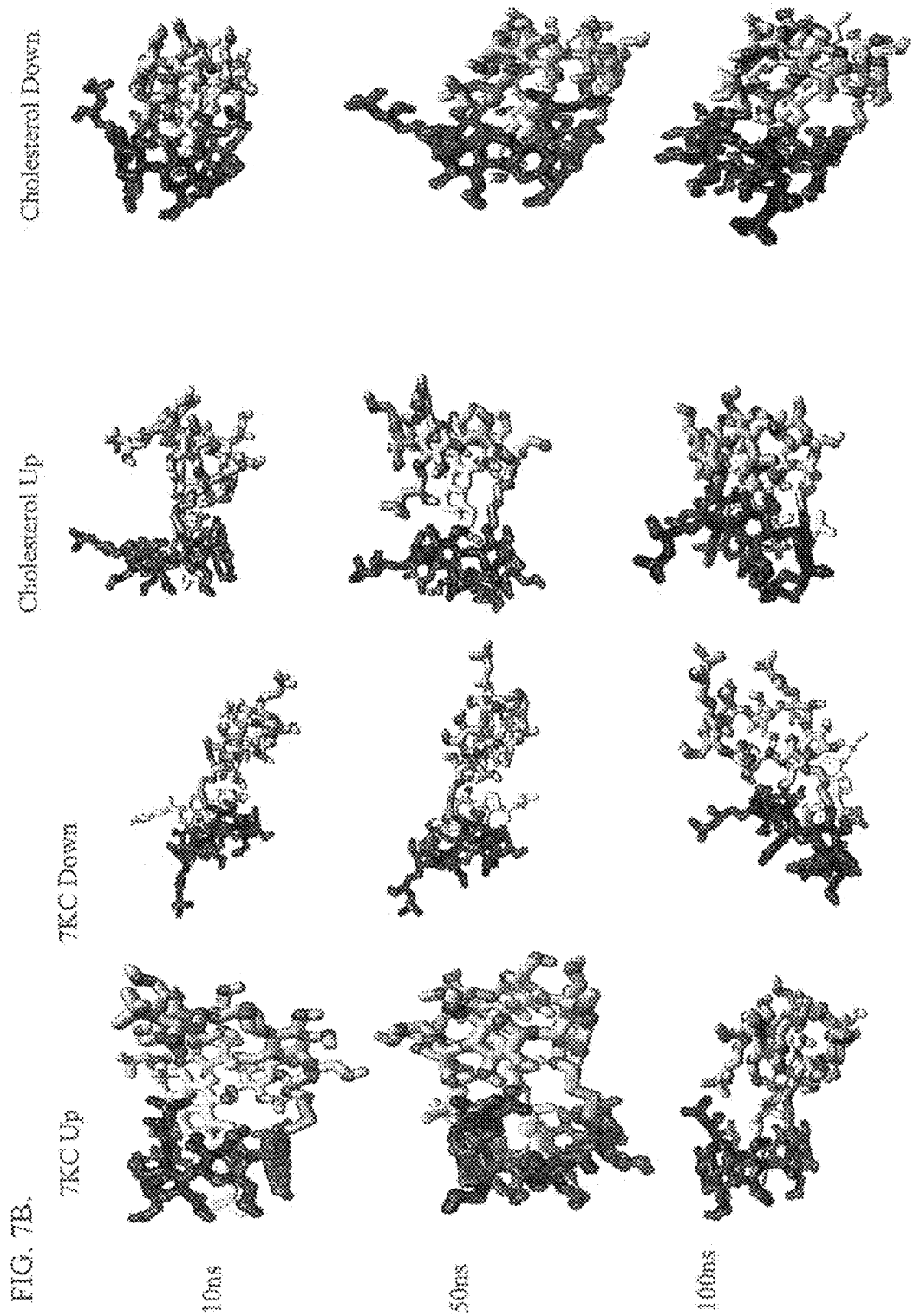
FIG. 7B. Visual trajectories of butyl-linked DS4 quaternary ammonium βCD dimer and 7KC/cholesterol in both up and down orientations.
Figure 7C:
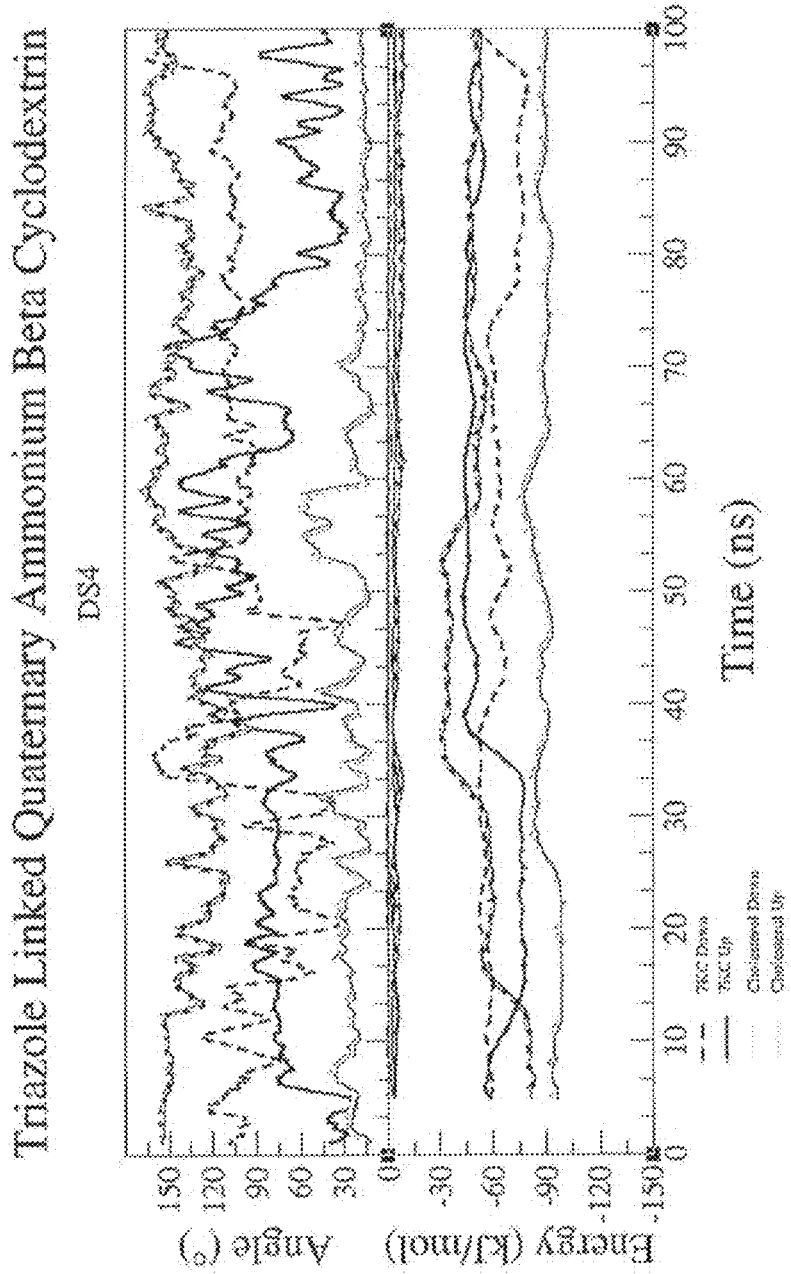
FIG. 7C. MD simulation describing 100 ns of interaction between a triazole-linked DS4 quaternary ammonium βCD dimer and 7KC/cholesterol in both up and down orientations. Legend as in FIG. 5B.
Figure 7D:
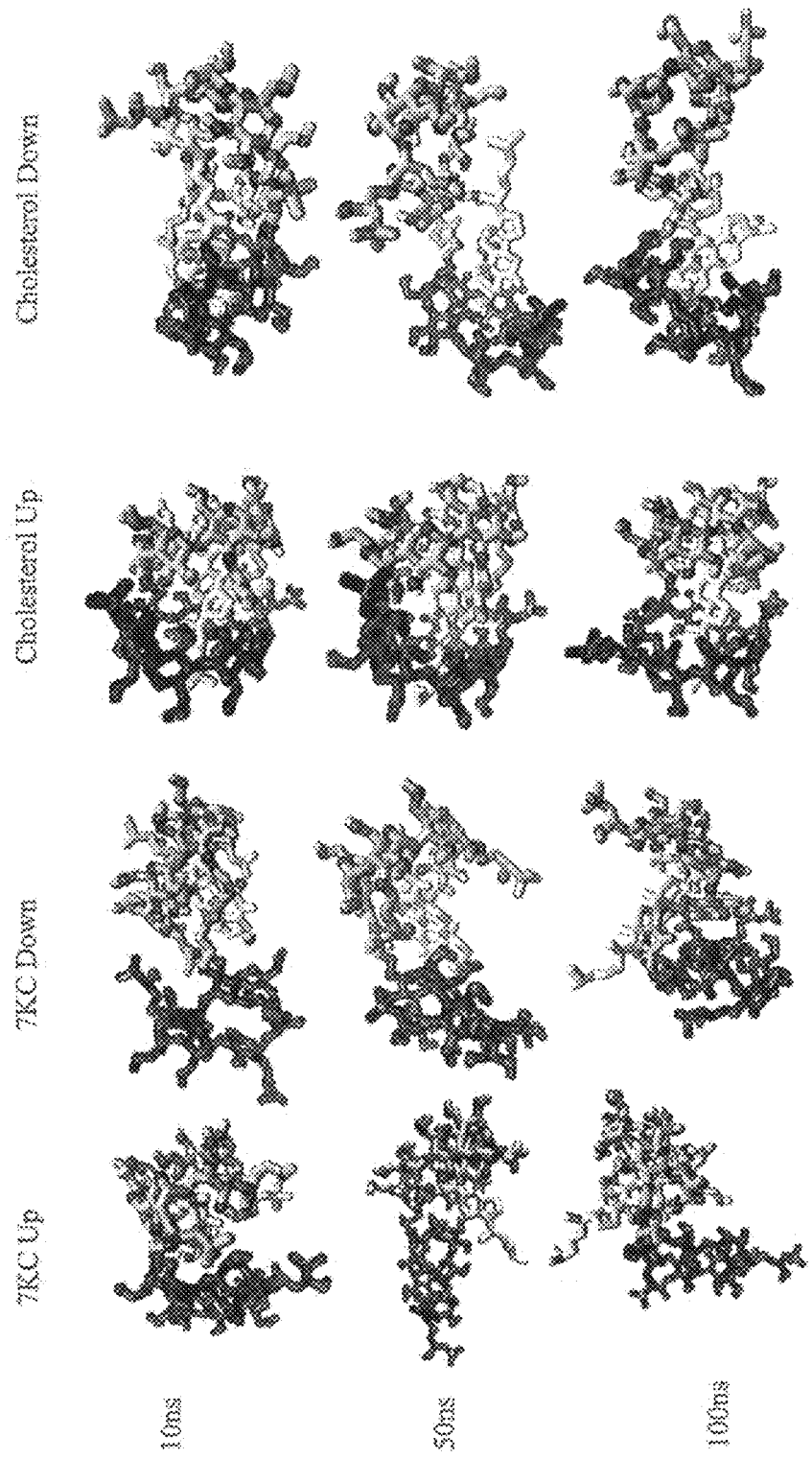
FIG. 7D. Visual trajectories of triazole-linked DS4 quaternary ammonium βCD dimers and 7KC/cholesterol in both up and down orientations. Legend as in FIG. 5B.

Translated Native Monomeric βCD and 7KC, Up Orientation, GROMOS Forcefield:

In FIG. 4L, 7KC begins with center of the molecule inside the CD cavity and with the headgroup extending slightly out of the secondary face while the tail group extends slightly out of the primary face. The complex stays stable until about 710 ns when 7KC moves out of the secondary face and rotates to associate parallel to the secondary face. 7KC then entirely rotates to insert the headgroup so that the headgroup extends towards the primary face and the tail extends out of the secondary face at 715 ns. 7KC then associates and disassociates the headgroup from the CD cavity several times until the complex entirely breaks at about 850 ns. The complex remains disassociated for the remainder of the trajectory.

Translated Native Monomeric βCD and Cholesterol, Up Orientation, GROMOS Forcefield:

FIG. 4L shows that cholesterol begins associated with the CD, the headgroup extending out of the secondary face while the tail extends from the primary face. The complex disassociates at ~120 ns when cholesterol moves to primary CD face, inserts the headgroup and rotates in and out of cavity on primary side until completely disassociating again at about 160 ns. At about 163 ns cholesterol reassociates with the secondary face until rotating back to the primary face 5 ns later. Cholesterol then switches between secondary or primary face association and random movement until the complex somewhat reforms at the very end of the trajectory for the last three nanoseconds. This continuous formation and deformation of the complex in silico indicates that it has a strong tendency to form in reality.

Translated Native Monomeric βCD and 7KC, Down Orientation, GROMOS Forcefield:

FIG. 4L shows 7KC beginning in the down position, the headgroup extending out of the primary face. At 40 ns 7KC backs out of the cavity and associates parallel with the secondary face, reinserts headgroup 2 ns later, then backs out again. The complex breaks completely at 45 ns, at which point 7KC floats around simulation box and associates again with the primary face at 47 ns, briefly inserts headgroup and then rotates back to parallel with the face until the complex breaks again at 51 ns. The complex reforms at 210 ns with the headgroup inserted from the secondary face and the tail extending outwards, like the initial conformation, and this complex remains stable until 268 ns when 7KC again backs out of CD and associates parallel with the secondary face. The complex breaks entirely again but briefly reforms at 360 ns. After this, 7KC occasionally associates parallel to one of the two faces in a conformation like the one at 710 ns but does not re-enter the cavity of CD. This trajectory is somewhat ambiguous because 7KC is only associated with the cavity for 100 ns, but this complex is still formed freely in the simulation which indicates that it is likely to form in reality, even though the interactive forces appear to be less consistent.

Translated Native Monomeric βCD and Cholesterol, Down Orientation, GROMOS Forcefield:

In FIG. 4L, cholesterol begins with the headgroup associated with the primary side and the tail extending out of the secondary face. Cholesterol sways side to side in the cavity until the complex breaks at about 15 ns. Cholesterol reinserts the headgroup at 17 ns and continues to rotate between being parallel with the secondary face of the CD and inserting (always the headgroup) into the cavity from the secondary side until the complex truly disassociates at about 675 ns. This indicates strong interaction and tendency for cholesterol to form an apparently stable complex with native βCD, but the complex does not reassociate once cholesterol has entirely disassociated from the secondary face of the CD at 675 ns.

Translated Native Monomeric βCD and 7KC, Up Orientation, AMBER Forcefield:

In FIG. 4O, 7KC begins with the headgroup extending out of the secondary face and the tail extending out of the primary face. This complex remains stable for the entire trajectory, but 7KC does exhibit a more extreme bending than seen in the down orientation—7KC remains bent around the ring of CD for significant portions of the trajectory.

Translated Native Monomeric βCD and Cholesterol, Up Orientation, AMBER Forcefield:

FIG. 4O shows how cholesterol begins with the headgroup extending out of the secondary face and the tail extending out of the primary face. This complex remains stable for the entire trajectory. Cholesterol does notably move substantially back and forth in the cavity, but the angle inside the cavity remains relatively constant.

Translated Native Monomeric βCD and 7KC, Down Orientation, AMBER Forcefield:

7KC begins with the headgroup extending out of the primary face and the tail extending out of the secondary face as seen in FIG. 4O. This complex remains stable for the entire trajectory, and 7KC does not flex significantly inside the cavity of CD, as evident in the level and steady graphs in FIG. 4M.

Translated Native Monomeric βCD and Cholesterol, Down Orientation, AMBER Forcefield:

FIG. 4O shows how cholesterol begins with the headgroup extending out of the primary face and the tail extending out of the secondary face. This complex remains stable for the entire trajectory, and cholesterol does not flex significantly inside the cavity of the CD, as evident in the level and steady graphs in FIG. 4M.

Monomeric Hydroxypropyl βCD and 7KC, Up Orientation, GROMOS Forcefield:

7KC in the up position (FIG. 4R) begins with the tail inside the cavity of HPβCD and the head extending out of the secondary face. At about 13 ns, 7KC rotates out of the secondary face and associates parallel to the face. At 28 ns, the headgroup of 7KC reassociates with the cavity but then rotates back out multiple times, 7KC remains associated parallel with the secondary face until about 47 ns when the complex fully breaks. 7KC then rotates between associating parallel to one of the faces or moving randomly around the box until the remainder of the trajectory. A stable complex is not formed.

Monomeric Hydroxypropyl βCD and Cholesterol, Up Orientation, GROMOS Forcefield:

Cholesterol begins with the tail inserted into the CD cavity and the headgroup extending out of the secondary face in FIG. 4R. This complex stays stable until about 3 ns when cholesterol rotates out of the secondary face, becoming parallel to CD, then around to the primary face by 7 ns. Cholesterol then moves randomly around the simulation box, occasionally associating parallel to either the primary or secondary face, but it is never able to stabilize inside the cavity, except for briefly at about 300 ns. This lack of strong association is clear by the intense variation in FIG. 4P and is supported by experimental evidence.

Monomeric Hydroxypropyl βCD and 7KC, Down Orientation, GROMOS Forcefield:

FIG. 4R shows that 7KC begins somewhat outside of the monomer cavity, and initially flies randomly around the simulation box. By 29 ns, 7KC has associated the headgroup within the cavity of HPβCD, the tail extending from the secondary face. This remains stable until 35 ns when the complex entirely disassociates. The complex remains disassociated until 320 ns when it reforms, again with the headgroup inside the cavity and the tail extending out of the secondary face. The complex remains associated until about 470 ns when it disassociates again until the end of the trajectory.

Monomeric Hydroxypropyl βCD and Cholesterol, Down Orientation, GROMOS Forcefield:

FIG. 4R shows cholesterol in the down position begins with the tail inserted into the cavity and the head extending out of the primary face. This complex remains stable until about 300 ns when cholesterol rotates out of the secondary face and associates parallel to CD, then the complex fully breaks and disassociates from CD. Cholesterol then moves around CD, sometimes associating parallel to the secondary face, and eventually associates with the primary face at about 100 ns. Cholesterol then continues random motion around CD, sometimes associating with either face or rotating as if to enter the cavity, similar to the conformation at 275 ns, but cholesterol never fully re-enters the cavity for any significant amount of time. These trajectories suggest a preference for the up orientation, where the only stable complexes formed were 7KC-up, which formed independently in the simulation after entirely disassociating, and for cholesterol-down which remained stable from the initial conformation. This suggests a strong preference for 7KC in the up orientation with some interaction with cholesterol in the down orientation.

Monomeric Hydroxypropyl βCD and 7KC, Up Orientation, AMBER Forcefield:

7KC (up) begins with center of the molecule inside the CD cavity and with the headgroup extending slightly out of the secondary face while the tail group extends slightly out of the primary face. FIG. 4U shows how 7KC remains in the cavity of HPβCD for the entire trajectory, bobbing up and down slightly but never extending either end far out of the cavity. This complex does not break.

Monomeric Hydroxypropyl βCD and Cholesterol, Up Orientation, AMBER Forcefield:

The AMBER forcefield shows much more consistent interactions and much more stable complexes than the GROMOS forcefield for both native and HPβCD. In FIG. 4U, cholesterol (up) begins with center of the molecule inside the CD cavity and with the headgroup extending slightly out of the secondary face while the tail group extends slightly out of the primary face. This complex remains stable for the entire trajectory; cholesterol never leaves the cavity or changes orientation, it simply rocks back and forth inside the cavity. The most favorable conformation occurs from 500-700 ns, as visible in FIG. 4S, but cholesterol and CD remain complexed for the whole trajectory. These small variations in position correspond to small bumps in FIG. 4S, particularly in the angle section.

Monomeric Hydroxypropyl βCD and 7KC, Down Orientation, AMBER Forcefield:

7KC (down) begins with center of the molecule inside the CD cavity and with the headgroup extending slightly out of the primary face while the tail group extends slightly out of the secondary face. FIG. 4U shows how the head of 7KC is more extended from the cavity than in the up orientation, but that the complex stays intact for the entirety of the trajectory. This preference for the up orientation is visible in FIG. 4S as the plots for "up" are much less varied than the plots for "down", although both are still significantly less varied than HPβCD in GROMOS.

Monomeric Hydroxypropyl βCD and Cholesterol, Down Orientation, AMBER Forcefield:

FIG. 4U shows cholesterol (down) begins inside the CD cavity and with the headgroup extending out of the primary face while the tail group extends slightly out of the secondary face. Notably, the headgroup of cholesterol at times extends significantly further out of the cavity than for the up orientation, but still this complex remains stable for the entire trajectory. Cholesterol never fully leaves the cavity or changes orientation. These small variations in position correspond to small bumps in FIG. 4S, particularly the angle section. There is noticeably more lateral movement through the cavity of CD and less radial rocking than for other complexes.

Translated Monomeric Hydroxypropyl βCD and 7KC, Up Orientation, GROMOS Forcefield:

FIG. 4X shows 7KC, translated in the up orientation, begins with the tail inserted into the CD cavity and the headgroup extending out of the secondary face. 7KC rotates out of the cavity at about 105 ns, then 7KC oscillates approximately every 5-10 ns between inserting the headgroup into the CD and being parallel to CD, appearing to spend more time in the conformation where the headgroup is within the cavity. At about 415 ns, the structure settles with the headgroup inserted until it breaks again and fully disassociates at 700 ns. The complex then remains disassociated for the remainder of the trajectory, except for one brief reassociation at 726 ns, when the headgroup of 7KC inserts itself into the large face of CD. The interaction energy here is briefly comparable to that at 400 ns, where the complex is formed. Because the complex appears to be able to readily form and break, it is likely that this interaction is real, strong, and captured by the simulation.

Translated Monomeric Hydroxypropyl βCD and Cholesterol, Up Orientation, GROMOS Forcefield:

Cholesterol begins with the headgroup inserted into the cavity and the tail extending out of the primary face. This complex is stable for 60 ns, until the cholesterol rotates out of the secondary face and associates parallel to the CD. Cholesterol then leaves CD entirely and moves randomly around the simulation box until reassociating the tail with the cavity of CD at about 215 ns, the headgroup again extending from the secondary face. This stays stable for about 30 ns, until cholesterol again leaves CD and then quickly reassociates the headgroup in the cavity of CD at 280 ns, this time with the headgroup in the cavity and the tail extending from the secondary face. This complex remains stable for the rest of the trajectory. This indicates that the complex formed at the end of the trajectory is very stable and likely to form as seen in FIG. 4X.

Translated Monomeric Hydroxypropyl βCD and 7KC, Down Orientation, GROMOS Forcefield:

7KC, translated in the down orientation, begins with the headgroup inserted into the CD cavity and the tail extending out of the secondary face. 7KC rotates out of the cavity at about 105 ns, then 7KC oscillates approximately every 5-10 ns between inserting the headgroup into the CD and being parallel to CD, appearing to spend more time in the conformation where the headgroup is within the cavity. At about 415 ns, the structure settles with the headgroup inserted until it breaks again and fully disassociates at 700 ns. The complex then remains disassociated for the remainder of the trajectory as seen in FIG. 4X.

Translated Monomeric Hydroxypropyl βCD and Cholesterol, Down Orientation, GROMOS Forcefield:

In the down orientation of translated cholesterol for HPβCD, cholesterol begins with the tail inserted into the CD cavity and the headgroup extending out of the primary face. The complex breaks at 50 ns but cholesterol remains associated with the primary face, with the tail periodically entering and leaving the cavity before fully disassociating at 88 ns. The cholesterol molecule then associates with the secondary side of CD before resuming random motion about the simulation box. The trajectory cycles between association with one of the two faces and random motion until 215 ns when the tail of cholesterol re-enters the cavity from the primary side for the next 25 ns. Cholesterol then resumes random motion about CD. At 275 nanoseconds the headgroup of cholesterol enters the cavity from the primary face and remains there until the complex fully dissociates at about 410 ns. At this point cholesterol moves randomly about the simulation box until about 490 ns when cholesterol rotates to the secondary face and inserts the headgroup into the cavity. The complex remains in this conformation until about 530 ns when cholesterol moves out of the cavity, rotates, and inserts its tail group back into the cavity from the secondary face. By 540 ns, cholesterol has resumed random motion. Cholesterol never reinserts into the cavity but does commonly associate closely with either face of the CD. Because cholesterol never forms a stable complex with HPβCD for any significant amount of time, the interaction between HPβCD and cholesterol appears to be transient and not as strong as the interactions between HPβCD and 7KC, even in a translated position as evident in FIG. 4X.

Translated Monomeric Hydroxypropyl βCD and 7KC, Up Orientation, AMBER Forcefield:

FIG. 4AA shows that 7KC begins with the headgroup extending out of the primary face and the tail facing out of the secondary face, the center of 7KC nestled in the cavity of CD. This complex remains stable for the entire trajectory, and 7KC does not flex significantly inside the cavity of CD, as evident in the level and steady graphs in FIG. 4Y.

Translated Monomeric Hydroxypropyl βCD and Cholesterol, Up Orientation, AMBER Forcefield:

FIG. 4AA shows that cholesterol begins with the headgroup extending out of the primary face and the tail facing out of the secondary face, the center of cholesterol nestled in the cavity of CD. This complex remains stable for the entire trajectory, and cholesterol does not flex or move about significantly inside the cavity of CD, as evident in the level and steady graphs in FIG. 4Y.

Translated Monomeric Hydroxypropyl βCD and 7KC, Down Orientation, AMBER Forcefield:

FIG. 4AA shows that 7KC begins with the headgroup extending significantly out of the primary face and the tail facing out towards the secondary face, but the tail is entirely within the cavity. This complex remains stable for the entire trajectory, and 7KC does not flex significantly inside the cavity of CD, as evident in the level and steady graphs in FIG. 4Y. 7KC does exhibit more lateral movement in this orientation than in the up orientation.

Translated Monomeric Hydroxypropyl βCD and Cholesterol, Down Orientation, AMBER Forcefield:

FIG. 4AA shows that cholesterol begins with the headgroup extending out of the primary face and the tail facing out of the secondary face, the center of cholesterol nestled in the cavity of CD. This complex remains stable for the entire trajectory, but cholesterol does move significantly inside the cavity, often with only the tail associated and the headgroup extending out of CD. This can be seen in FIG. 4Y as the down orientation is more varied than the up orientation, especially in distance.

Dimerized Hydroxypropyl βCD and 7KC, Up Orientation, GROMOS Forcefield:

In FIG. 4DD, 7KC begins inside the dimer, nicely caged. The dimer begins to stretch at about 100 ns, but 7KC remains in the barrel inside the two CDs despite this stretching. At 111 ns, the headgroup disassociates from its monomer (in this discussion the term "monomer" refers to a CD subunit, notwithstanding that it is part of a covalently linked dimer) while the tail stays associated with the cavity of the other monomer. 5 ns later, the headgroup of 7KC proceeds to interact with the large face (not the cavity) of one monomer while the tail stays anchored in the other. At 120 ns, the tail releases its monomer and the headgroup inserts itself into the cavity of the other monomer. This configuration remains stable, with the sterol-associated monomer swinging around the empty monomer, until the end of the trajectory.

Dimerized Hydroxypropyl βCD and Cholesterol, Up Orientation, GROMOS Forcefield:

The cholesterol (up) trajectory begins with cholesterol encased in the dimer. The dimer begins to flex at about 22 ns, but cholesterol moves with it and remains inside the dimer cavity. At about 200 ns, the monomer associated with the headgroup of cholesterol breaks off and disassociates from the dimer, but the cholesterol remains associated with one of the monomers (headgroup aligned with secondary face, tail aligned with primary). This configuration remains until the cholesterol fully disassociates from the cavity and rotates towards the secondary face at 355 ns. Cholesterol then remains between the two monomers, occasionally associating the headgroup loosely with one monomer, until it completely leaves and floats about the simulation box. The cholesterol continues to interact with one CD monomer intermittently, but the dimer-cholesterol complex never fully reforms as seen in FIG. 4DD.

Dimerized Hydroxypropyl βCD and 7KC, Down Orientation, GROMOS Forcefield:

7KC in the down position, shown in FIG. 4DD, begins caged inside the dimer. The dimer does not begin to deform until about 600 ns when one monomer stretches away from the other, 7KC remaining between the two. At about 820 ns, 7KC disassociates the tail from one of the monomers, the headgroup remaining in the cavity of the other monomer. This configuration remains stable, with the sterol-associated monomer swinging around the empty monomer, until the end of the trajectory.

Dimerized Hydroxypropyl βCD and Cholesterol, Down Orientation, GROMOS Forcefield:

Cholesterol in the down position (FIG. 4DD) begins inside the dimer cage. At about 50 ns, the complex begins to stretch and contort, but cholesterol stays anchored inside the dimer for the entirety of the trajectory. This is clear in FIG. 4BB as the plot for cholesterol angle is very level and stable for the entire trajectory. This is the only complex in the GROMOS forcefield analysis that stays intact for the whole trajectory. FIG. 4BB shows the molecular dynamics analysis for our novel, butyl-linked hydroxypropyl DS5 β-cyclodextrin dimer forming very stable complexes with 7KC and cholesterol. The contrast between these graphs and those for monomeric HPβCD provide clear evidence that the dimerized version consistently binds sterols significantly more reliably than its monomeric counterpart. For the down orientation, energy, angle, and distance all stay very consistent with minimal variation showing that there is a stable, apparently solubilized complex for both 7KC and cholesterol which does not change significantly over time. The same can be seen for the up orientation, but with somewhat more variation, particularly for cholesterol. This suggests that 7KC is most effectively bound in the down orientation, with strong preference for this orientation as seen by the angle reversal at about 350 ns for the up orientation; this is where 7KC leaves the dimer and reassociates in the down orientation. Cholesterol does this as well, but it is a less stable complex than that formed with 7KC, showing that cholesterol does not have the same ability to form the more stable, down complex from the less stable, up complex while 7KC appears to be able to do so.

Dimerized Hydroxypropyl βCD and 7KC, Up Orientation, AMBER Forcefield:

FIG. 4GG details how 7KC remains nestled inside the cavity formed by the two monomers for the whole trajectory. The complex flexes somewhat and 7KC moves slightly inside the cavity, but the 7KC remains complexed with the CD dimer for the whole trajectory.

Dimerized Hydroxypropyl βCD and Cholesterol, Up Orientation, AMBER Forcefield:

In FIG. 4GG, cholesterol remains nestled between the two monomers for the entirety of the trajectory. The monomers stay associated with each other and the cholesterol—the complex flexes but never breaks.

Dimerized Hydroxypropyl βCD and 7KC, Down Orientation, AMBER Forcefield:

FIG. 4GG shows that 7KC remains nestled inside the cavity formed by the two monomers for the whole trajectory. The complex flexes somewhat and 7KC moves slightly inside the cavity, but the 7KC remains complexed with the CD dimer for the whole trajectory.

Dimerized Hydroxypropyl βCD and Cholesterol, Down Orientation, AMBER Forcefield:

FIG. 4GG shows how cholesterol remains nestled inside the cavity formed by the two monomers for the whole trajectory. The complex flexes somewhat and cholesterol moves slightly inside the cavity, but the cholesterol remains complexed with the CD dimer for the whole trajectory.

Figure 4J:
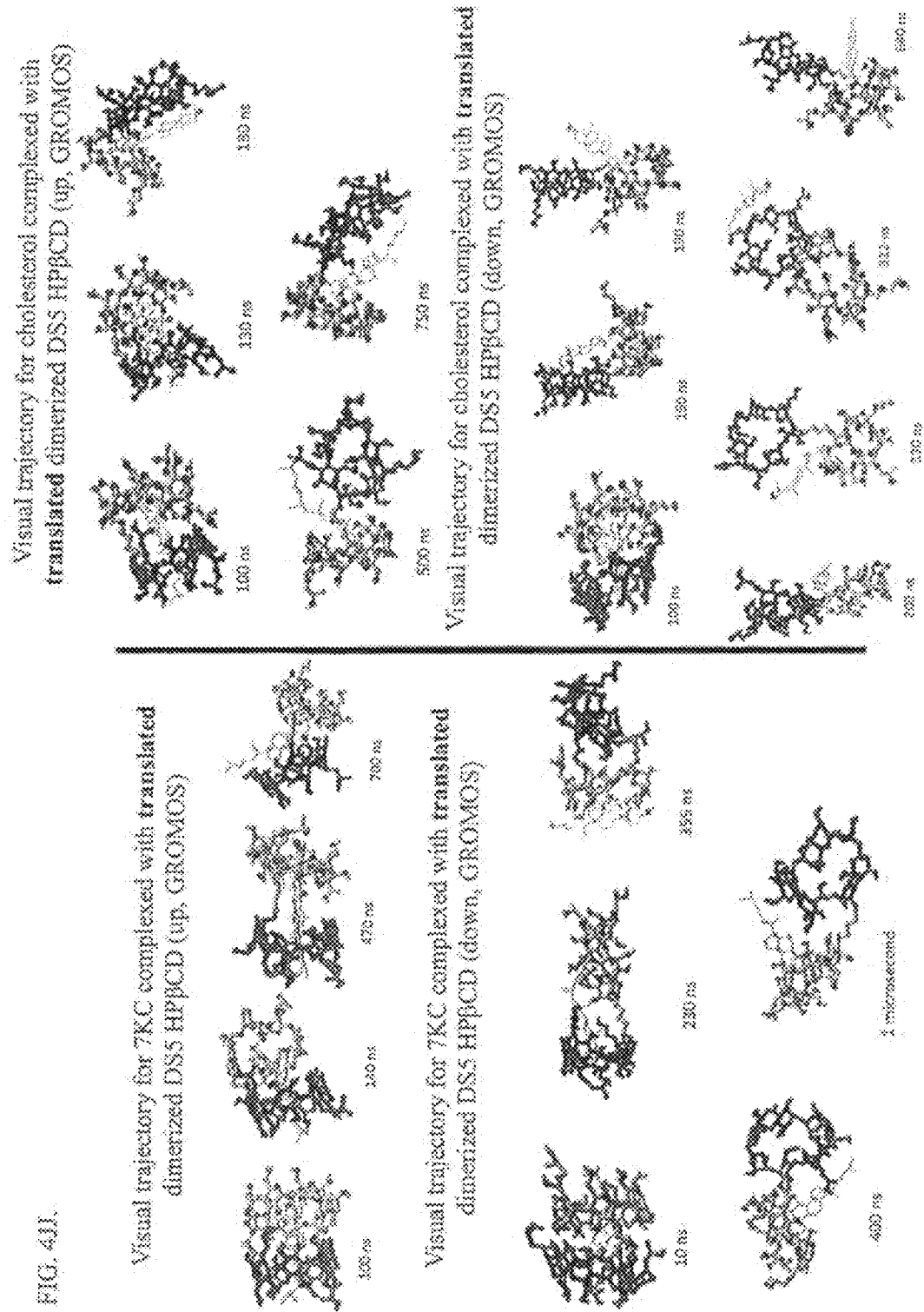
FIG. 4J. Distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the cyclodextrin and the ligand for translated native monomeric beta cyclodextrin (DS0), up and down ligand orientations in the GROMOS forcefield.
Figure 4K:
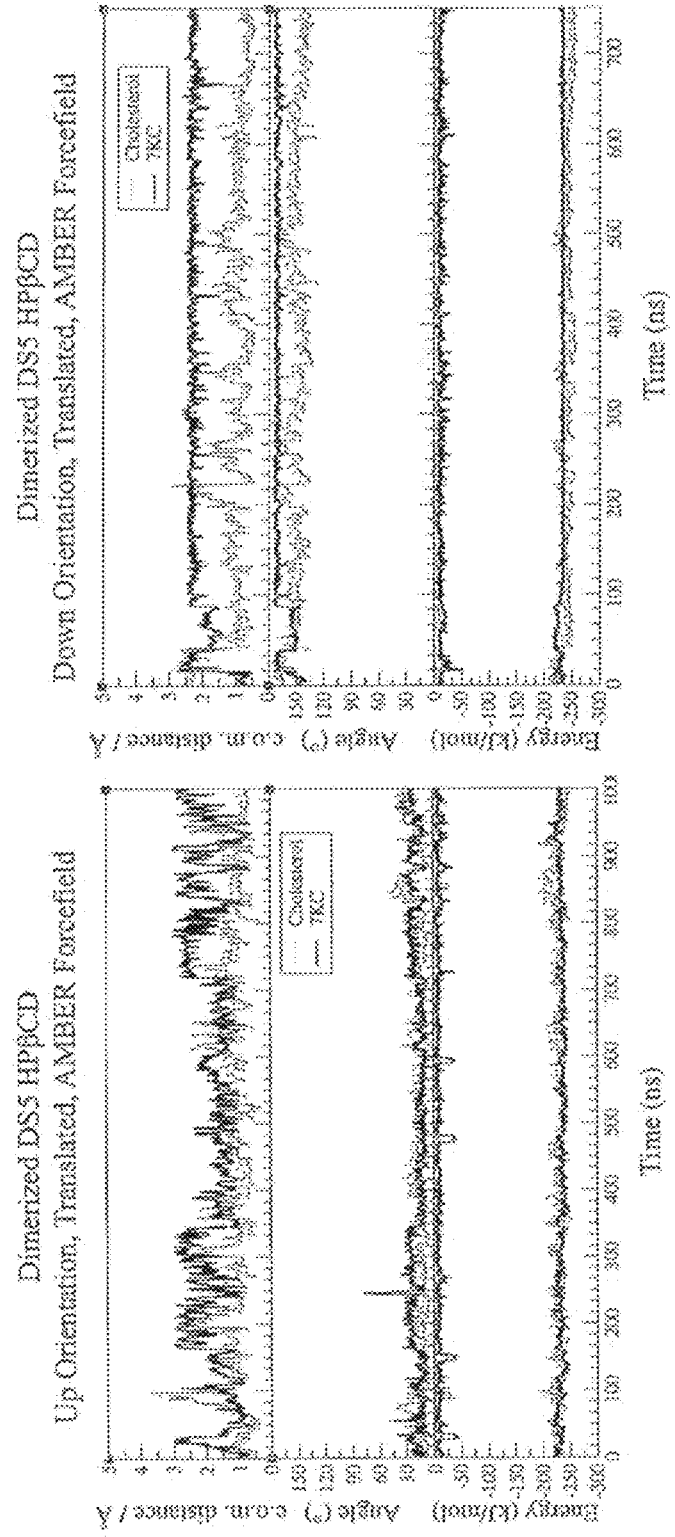
Figure 4M:
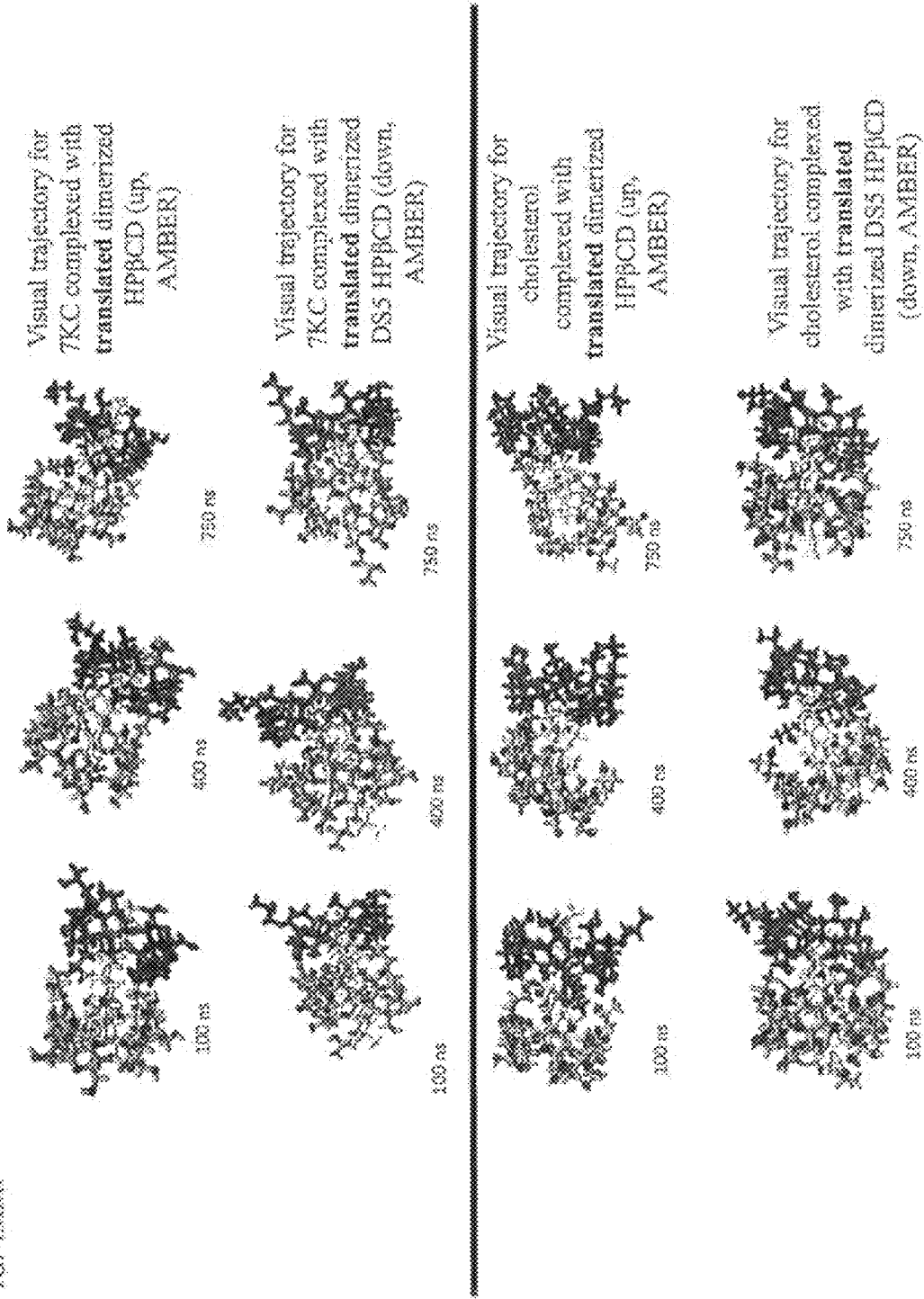
Figure 4N:
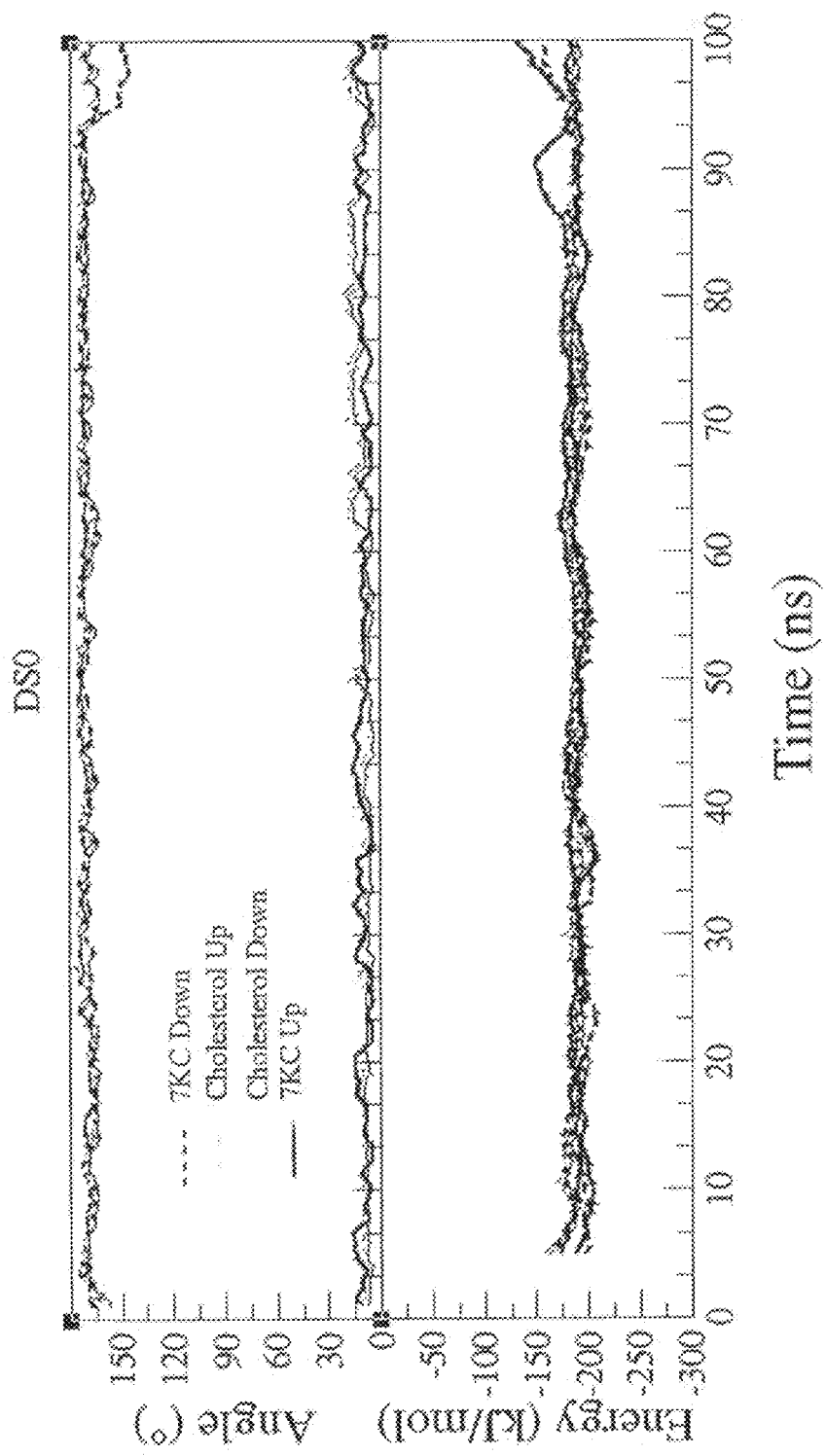
Figure 40O:
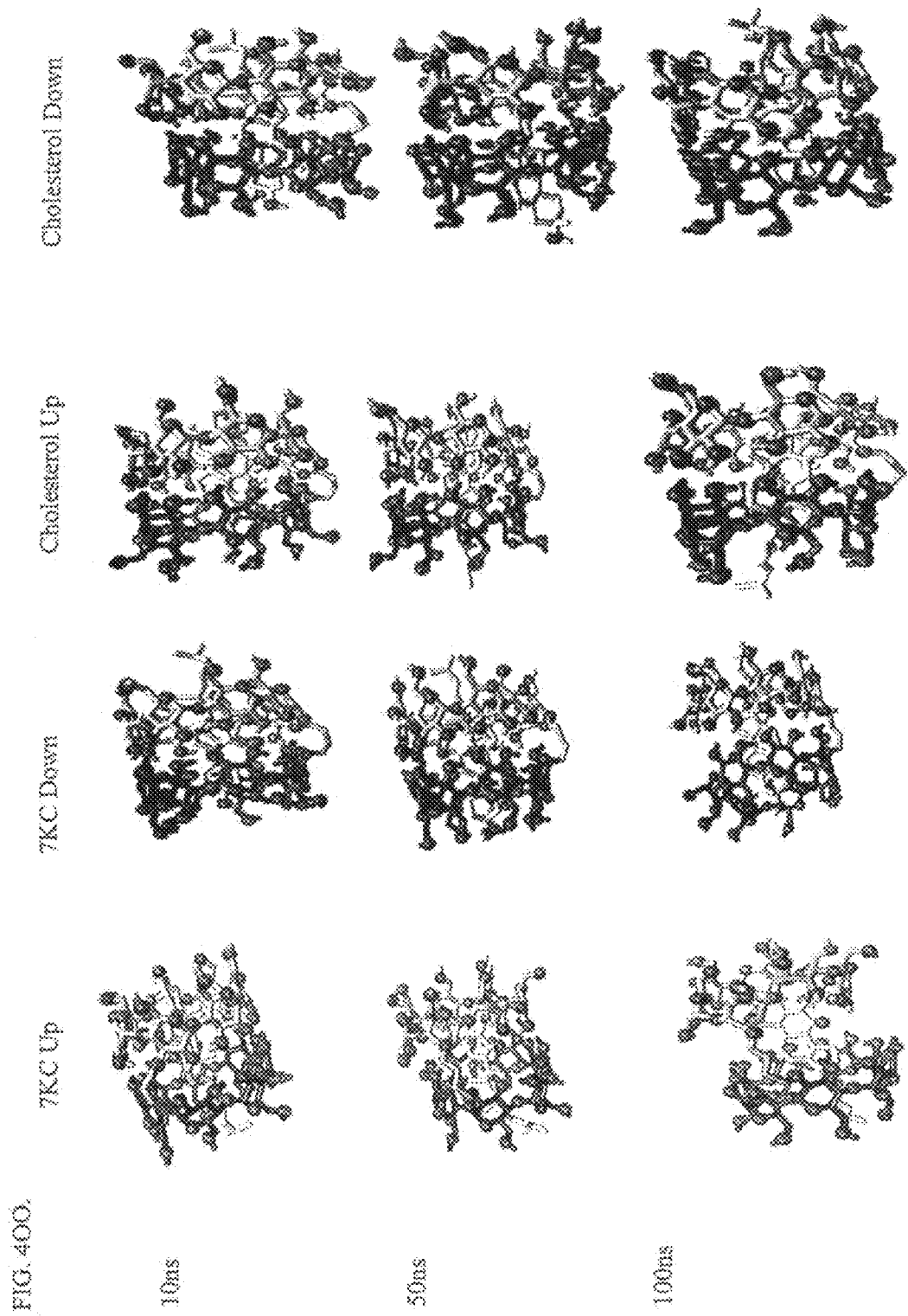
Figure 4P:
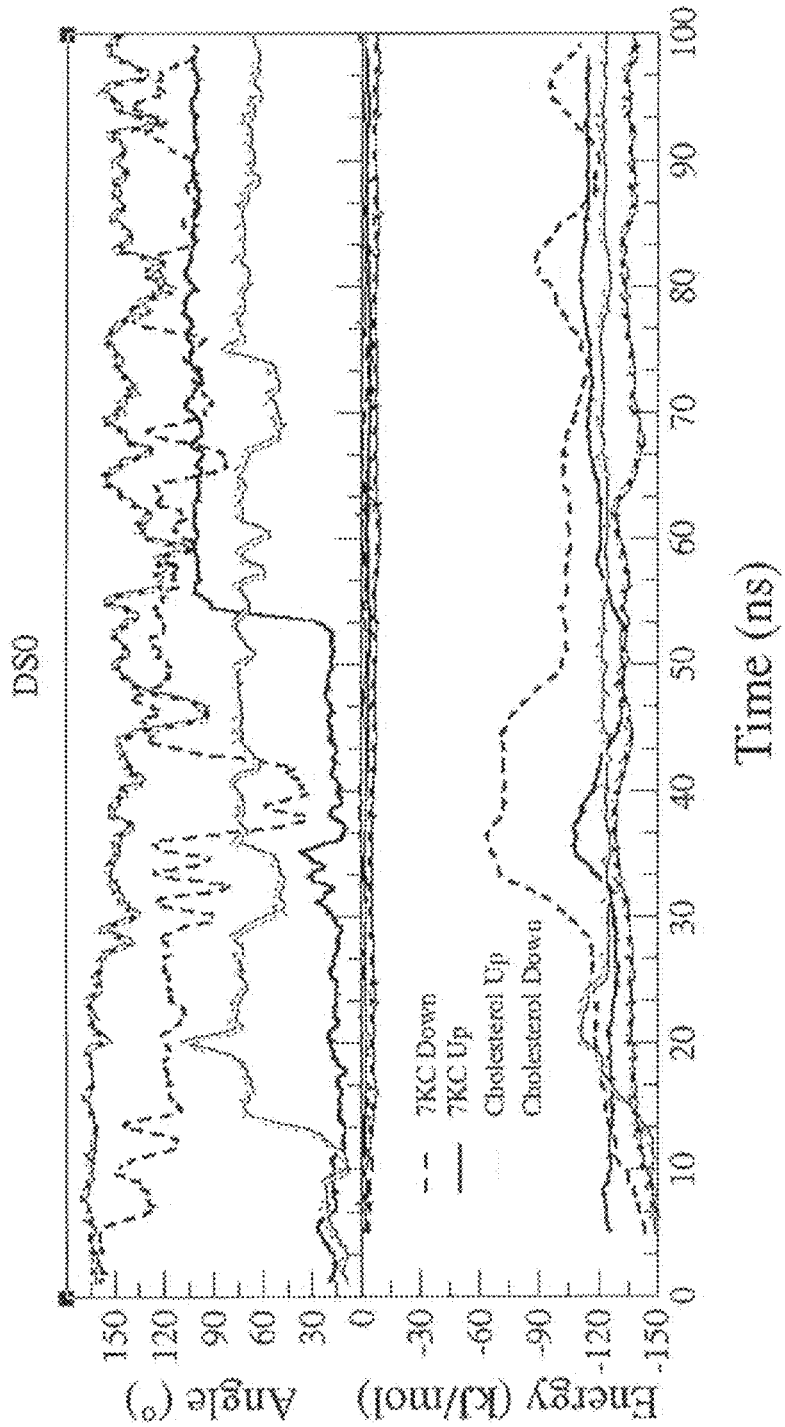
Figure 4Q:
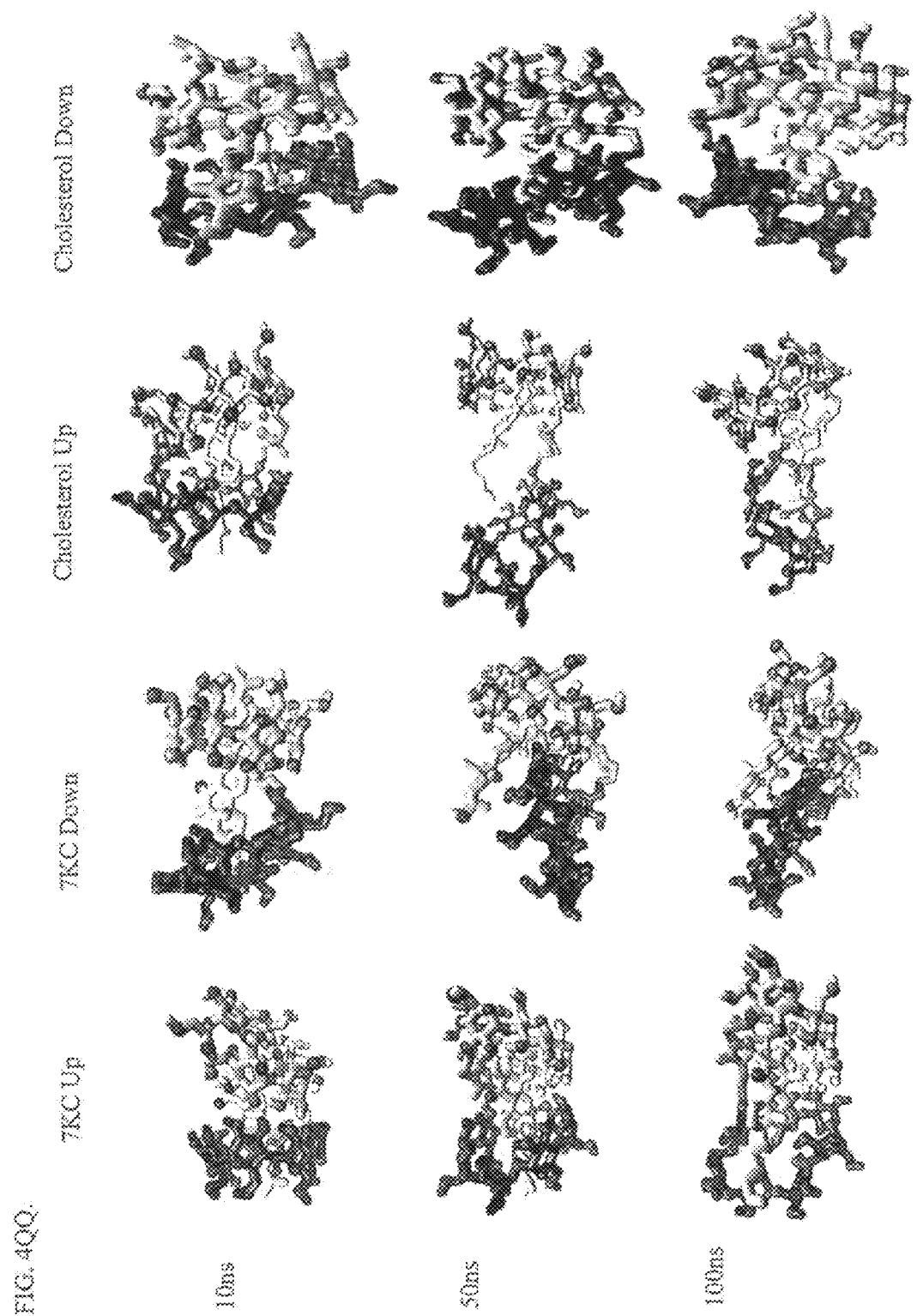
FIG. 4Q. Solubilization of ligand by native monomeric βCD in the GROMOS forcefield.
Figure 4R:
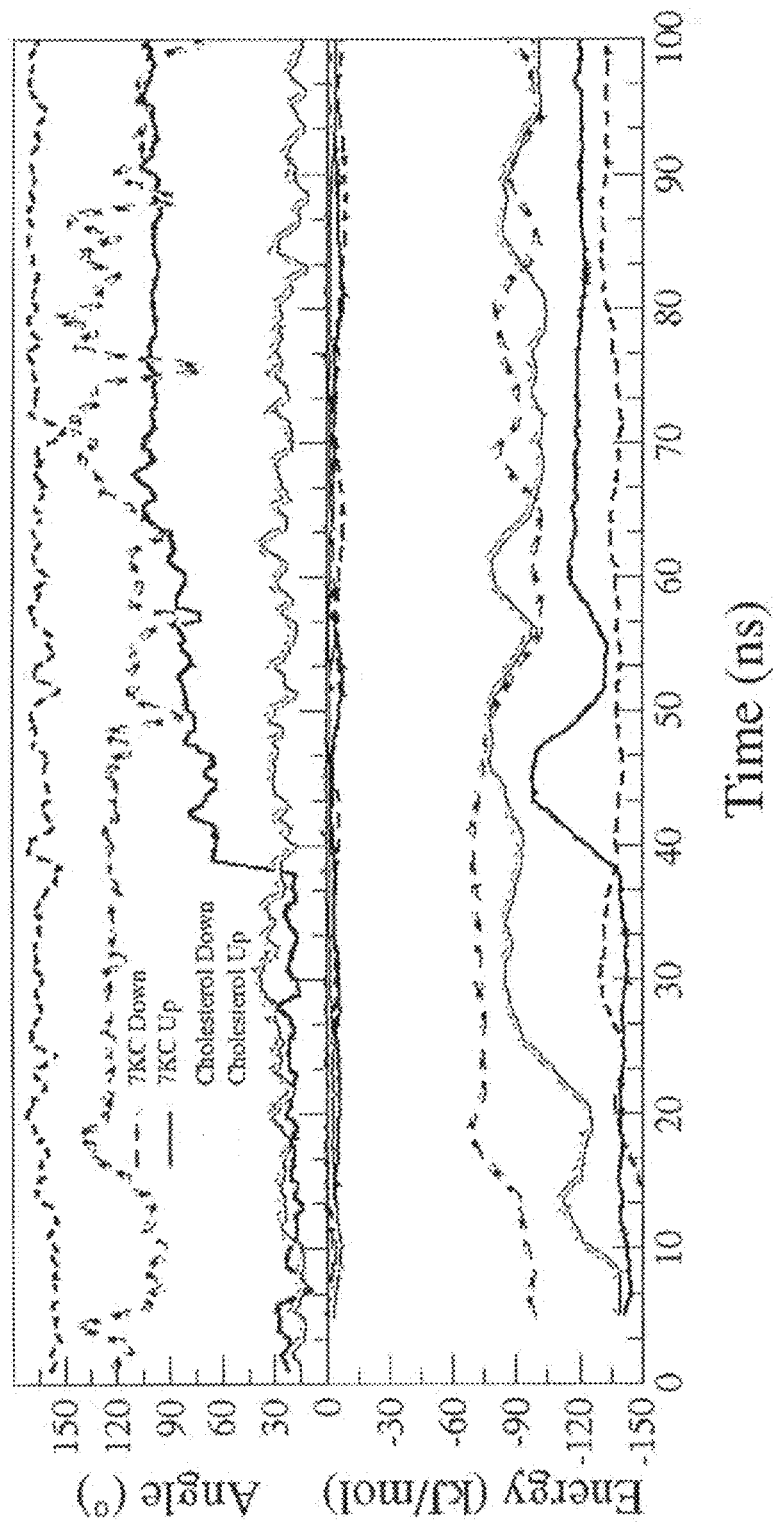
Figure 4S:
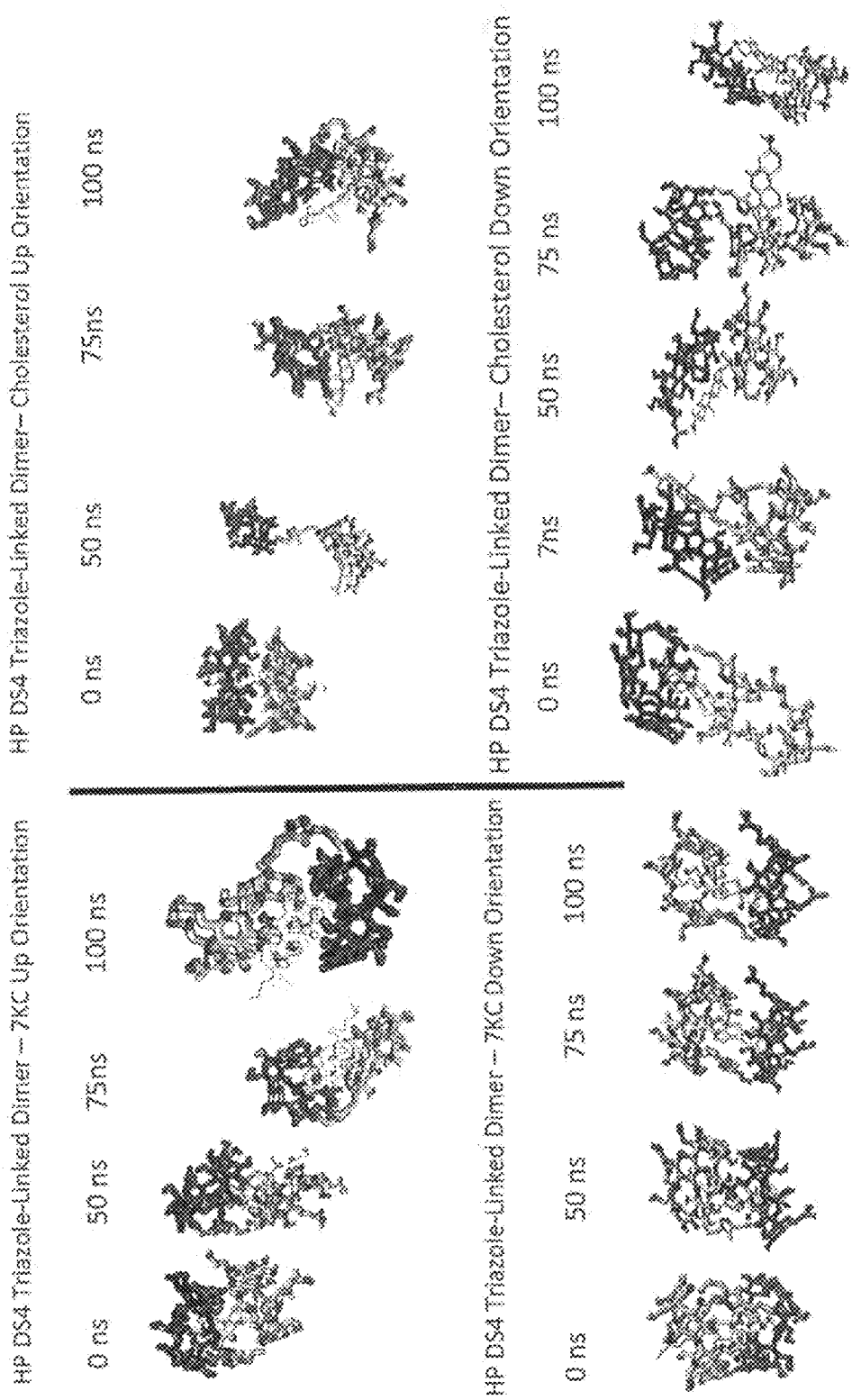

Translated Dimerized Hydroxypropyl βCD and 7KC, Up Orientation, GROMOS Forcefield:

FIG. 4JJ shows that the dimerized complex begins with translated 7KC in the up orientation snugly nestled in the cavity of both CD monomers. The complex stretches at about 140 ns, causing the first variations at this time in FIG. 4GG, but quickly reforms. The complex continues to stretch and distort periodically, as seen by variations in FIG. 4GG, but 7KC remains inside both cavities until the tail releases its monomer at about 700 ns. 7KC does not re-enter both cavities simultaneously for the rest of the trajectory.

Translated Dimerized Hydroxypropyl βCD and Cholesterol, Up Orientation, GROMOS Forcefield:

FIG. 4JJ shows that translated cholesterol in the up orientation starts complexed with the dimer, which begins to distort at about 100 ns (considerably more than the 7KC complex). The large angle change in FIG. 4GG for cholesterol at about 180 ns is caused when one monomer, associated through the secondary face to the head cholesterol, entirely flips around to the other side of the second monomer, associating a somewhat distorted secondary face (associated with cholesterol) to the somewhat distorted primary face of the second monomer, creating a somewhat distorted head-to-tail dimer. This head-to-tail dimer never fully forms a complex with cholesterol, however, and the headgroup of cholesterol remains associated with the monomer it was originally associated with. This is the only trajectory that creates a head-to-tail dimer and this configuration does not appear to effectively complex with cholesterol.

Translated Dimerized Hydroxypropyl βCD and 7KC, Down Orientation, GROMOS Forcefield:

Translated 7KC in the down position begins associated to both monomers in the center of the CD dimer. FIG. 4JJ shows that one monomer stretches far away from the tail of 7KC at 230 ns, then 7KC totally leaves the dimer at 355 ns (note that this is also where the consistency in FIG. 4GG breaks). At 400 ns, 7KC reassociates the headgroup with one monomer. The head of 7KC remains associated with this monomer for the remainder of the trajectory, but the tail never reinserts into the second monomer.

Translated Dimerized Hydroxypropyl βCD and Cholesterol, Down Orientation, GROMOS Forcefield:

Cholesterol, translated in the down orientation, forms a complex with the CD dimer for about 162 ns. At this point, the dimerized complex begins to stretch and deform, then the headgroup of cholesterol releases its monomer at 190 ns. By 210 ns cholesterol is not associated with either monomer's cavity but remains between the two, separated monomers. Cholesterol stays closely associated with the dimer until 320 ns when it fully disassociates. As seen in FIG. 4JJ, cholesterol does not re-enter both cavities, nor does the dimerized complex completely reform for the rest of the trajectory, but cholesterol does occasionally associate the headgroup with the secondary face of one monomer as in the configuration at 640 ns.

Translated Dimerized Hydroxypropyl βCD and 7KC, Up Orientation, AMBER Forcefield:

FIG. 4MM details how 7KC remains nestled inside the cavity formed by the two monomers for the whole trajectory. The complex flexes somewhat around 7KC, but 7KC stays in almost exactly the same place for the whole trajectory.

Translated Dimerized Hydroxypropyl βCD and Cholesterol, Up Orientation, AMBER Forcefield:

FIG. 4MM details how cholesterol remains nestled inside the cavity formed by the two monomers for the whole trajectory. The complex and cholesterol move somewhat during the trajectory, particularly the monomer associated with the head of cholesterol, but cholesterol never fully disassociates from either monomer. Cholesterol is complexed with the CD dimer for the whole trajectory.

Translated Dimerized Hydroxypropyl βCD and 7KC, Down Orientation, AMBER Forcefield:

FIG. 4MM details how 7KC remains nestled inside the cavity formed by the two monomers for the whole trajectory. The complex flexes somewhat around 7KC, but 7KC stays in almost exactly the same place for the whole trajectory. 7KC is complexed with the CD dimer for the whole trajectory.

Translated Dimerized Hydroxypropyl βCD and Cholesterol, Down Orientation, AMBER Forcefield:

FIG. 4MM details how cholesterol remains nestled inside the cavity formed by the two monomers for the whole trajectory. The complex flexes somewhat around cholesterol, but cholesterol stays in almost exactly the same place for the whole trajectory. Cholesterol is complexed with the CD dimer for the whole trajectory.

Additionally, a short analysis was done for a DS0 βCD dimer with both butyl and triazole linkers (FIG. 4NN-QQ) and a hydroxypropyl dimer with a triazole linker (FIG. 4RR-SS). The DS0 simulations show that the triazole linker somewhat destabilizes the complex, however this allows some additional specificity for 7KC to be conveyed. The slightly different, but still strong and favorable, interactions bode well for both linker types.

The triazole-linked HPβCD dimer (FIG. 4RR) showed slightly weaker interactions than the butyl-linked hydroxypropylated dimer and a strong preference for 7KC in the down orientation. Cholesterol interactions were weaker than those with 7KC, showing some specificity for 7KC, and 7KC in the down orientation is by far the most stable complex formed. Addition of a triazole group made the 7KC stable in the down orientation while all other complexes broke at some point.

Additional MD Analysis

Additional, abbreviated MD analyses were also conducted for triazole and butyl-linked methyl βCD, sulfobutyl βCD, and quaternary ammonium βCD, all at DS4 (FIGS. 5B-C, 6B-C, 7A-B). The methyl dimers showed the most stable complexes with the butyl linker and appeared to favor the up orientation in both linker cases, however the interactions are quite similar for the two methyl dimers tested. It is difficult to distinguish which is more practically effective, but both types of linker easily form complexes with both ligands for methyl substitutions. The trajectory revealed that the headgroup of 7KC was not entirely within the cavity of the dimer but remained stably between the two sister monomers. The complex with 7KC in the down orientation stayed associated for about 50 ns before 7KC moved out of the cavity and only the headgroup remained associated with one monomer for the rest of the trajectory.

The negatively-charged sulfobutyl dimers show a similar pattern to the methyl and hydroxypropyl dimers, where the triazole linker creates a slightly less stable complex which then allows for 7KC specificity. The charged, bulky sulfobutyl groups appear to interact quite favorably with both 7KC and cholesterol, but in both linker cases the only complex which breaks is that of cholesterol. This indicates that sulfobutyl dimers likely have very good specificity for 7KC as compared to methyl and hydroxypropyl.

To further evaluate the use of charged substitution groups, an MD analysis of DS4 positively-charged quaternary ammonium βCD was conducted. These trajectories elucidated strong binding between QA βCD and sterols, as no sterol was released at any point for either linker. Strong energies of interaction and association with at least one sister monomer for the entire trajectory for both ligands and linkers implies that DS4 QA βCD is well suited, much like other types of substitutions, to bind sterols and solubilize them.

In the final MD analysis, HPβCD with a single O-linker (FIG. 8H) was tested. The O-linked dimer (FIG. 8H) showed good 7KC specificity as only 7KC in the up orientation remained complexed for the full 100 ns. The energy of interaction is slightly lower in magnitude for the O-linked compared to butyl-linked, but overall specificity appears to be better for linker O because both cholesterol complexes break by 100 ns. The interactions are similar to the butyl-linked dimer, but they appear to give slightly better 7KC specificity, apparently due to the nitrogen in the linker interacting with the carbonyl of 7KC.

Additional Docking Screen

Docking simulations allow us to quickly model many different possible molecules without requiring their synthesis. For this reason, a "screen" of many different substitution types, linker types, substitution number, and substitution position was conducted using these docking techniques (FIGS. 8-9). This screen allows us to determine if certain modifications yield better or worse specificity for 7KC.

Figure 8A:
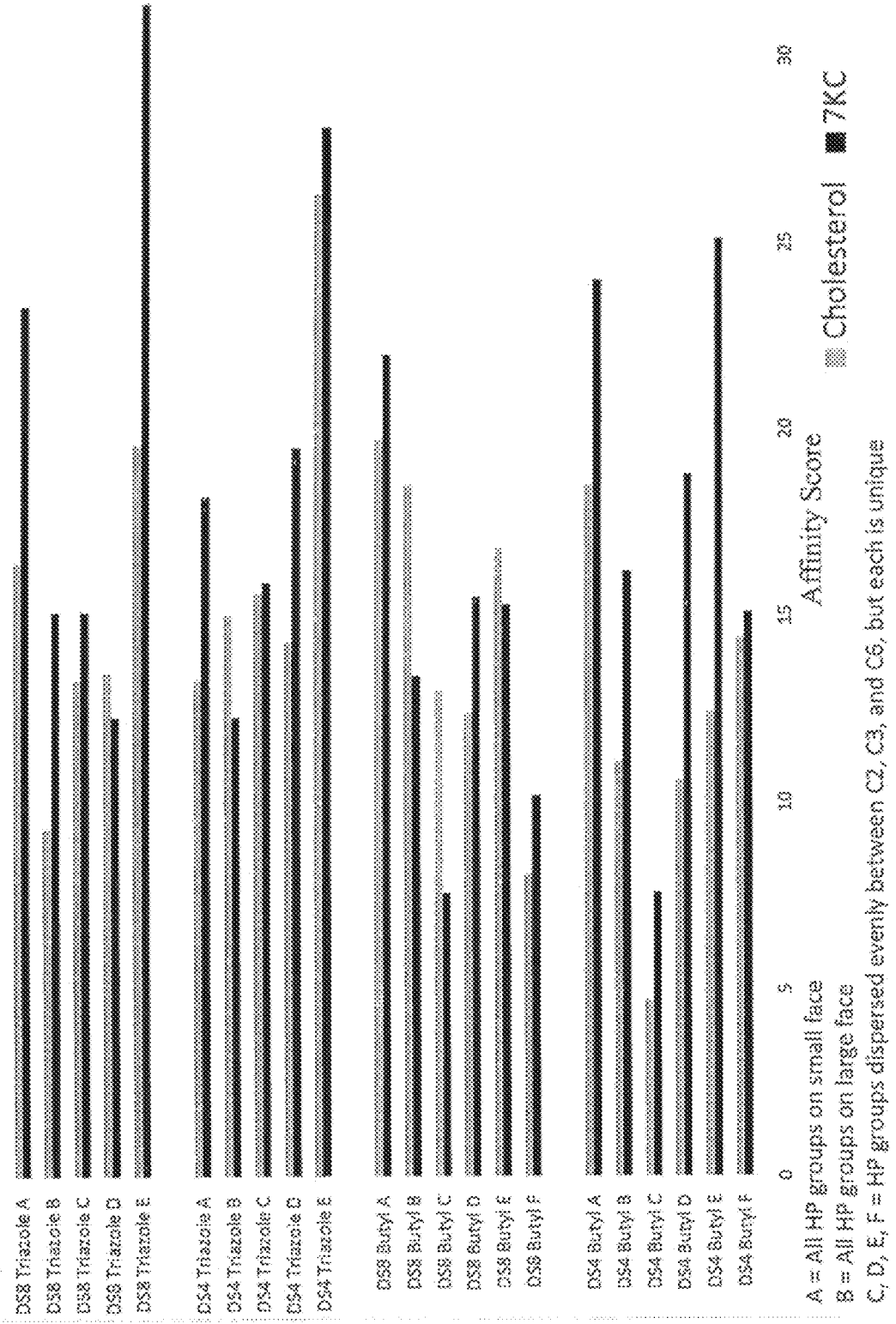
FIG. 8A. Varied hydroxypropylation sites for DS8 and DS4 triazole and butyl linked dimers, including hydroxypropylation of only the small or large face. Docking calculations were carried out for various hydroxypropylation sites in HPβCD dimers to determine the effects of changing the location of hydroxypropyl groups on sterol binding. The sites of hydroxypropylation are variable in practice, due to the stochastic nature of substitutions onto a mostly symmetrical molecule. Labels "C", "D", and "E" refer to different (distinct from one another) variant structures having an equal distribution of HP groups between the small and large faces of the CD monomers. Legend: upper (light grey) bars represent values for cholesterol and lower (dark) bars represent values for 7KC.
Figure 8B:
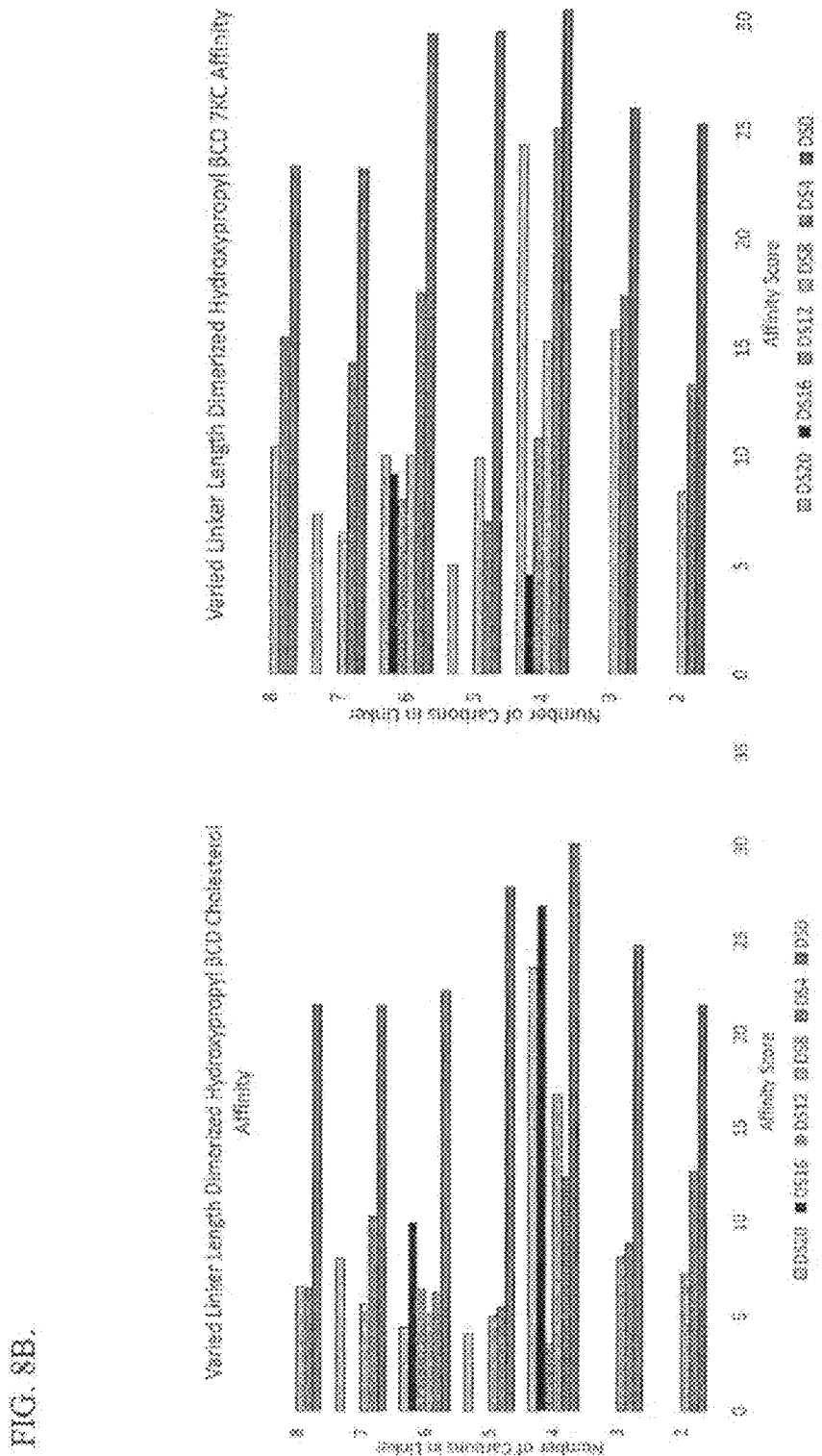
FIG. 8B. Varied length of alkyl-linked HPβCD DS5 dimers. Docking calculations were carried out for various degrees of hydroxypropylation and various lengths of a carbon-only linker. Bars within each group, ordered from top to bottom, are DS20, DS16, DS12, DS8, DS4, and DS0.
Figure 8C:
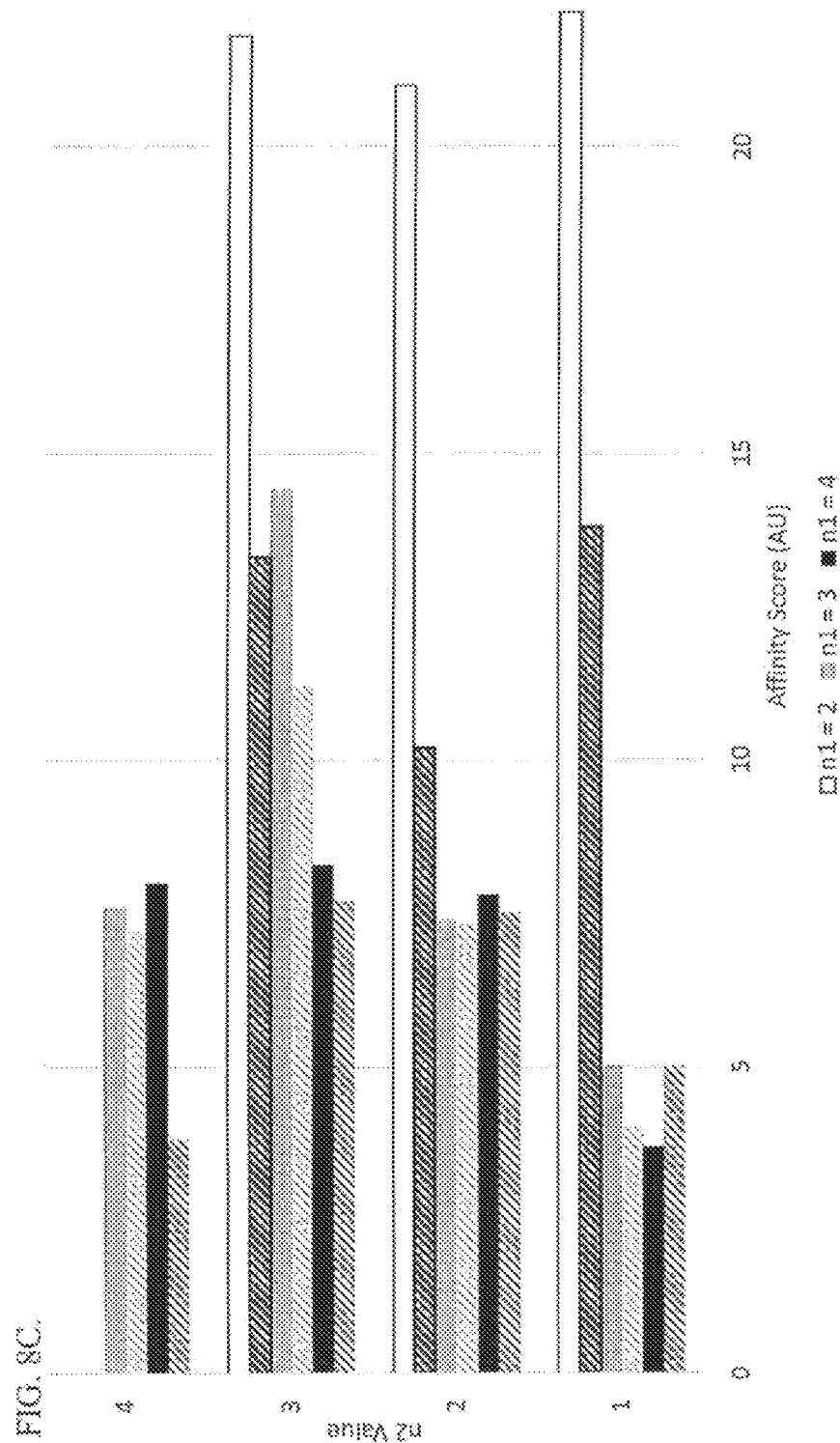
FIG. 8C. Varied length of triazole linked HPβCD DS5 dimers. Docking calculations were carried out for various lengths of the triazole linker by changing the number of carbons on either side of the triazole ring. The length of each side of the linker is distinguished by n1 or n2, and cholesterol is represented as striped bars while 7KC is solid bars. Bars within each group, ordered from top to bottom, are N1=2 and 7KC; N1=2 and cholesterol; N1=3 and 7KC; N1=3 and cholesterol; N1=4 and 7KC; and N1=4 and cholesterol.
Figure 8D:
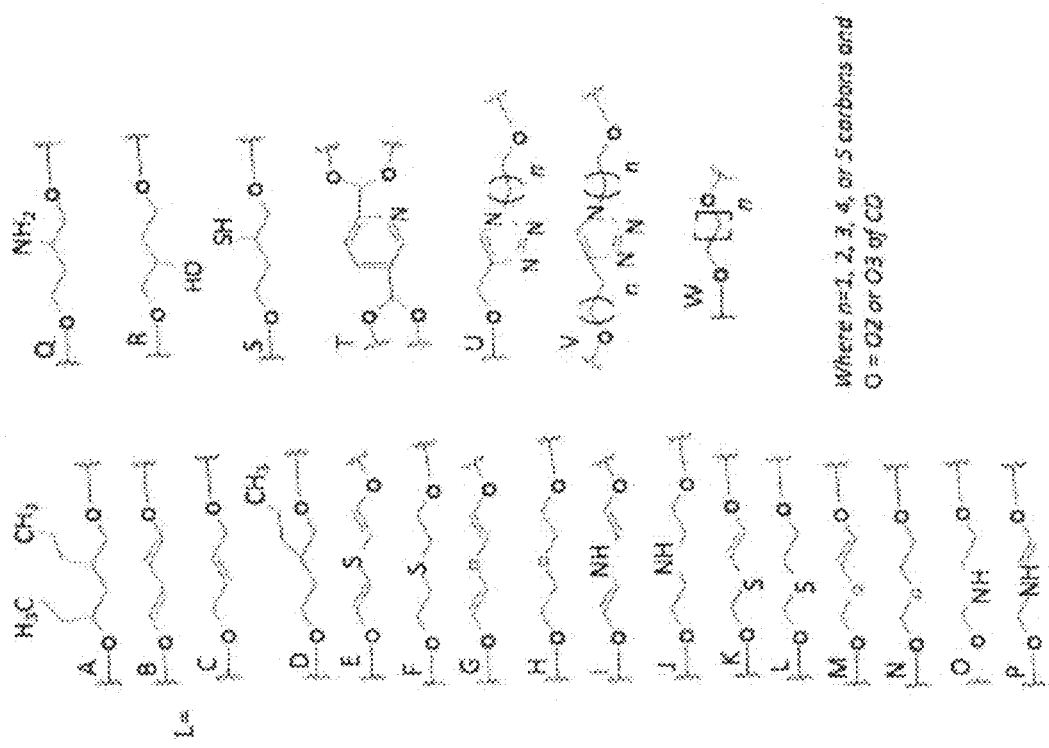
FIG. 8D. Linkers tested by docking calculations (FIG. 8E) to determine linker-dependent variation in sterol binding. Linked HPβCD dimer composition for hydroxypropyl DS4 and DS8 dimers, based on the addition of various side chains, rings, double bonds, and/or substituting in sulfur, nitrogen, and/or oxygen atoms for the linker composition compared to the four-carbon linker (linker W where n=3 carbons) and triazole-linked dimers (linker U where n=1 carbon and linker V where n=1 carbon).
Figure 8E:
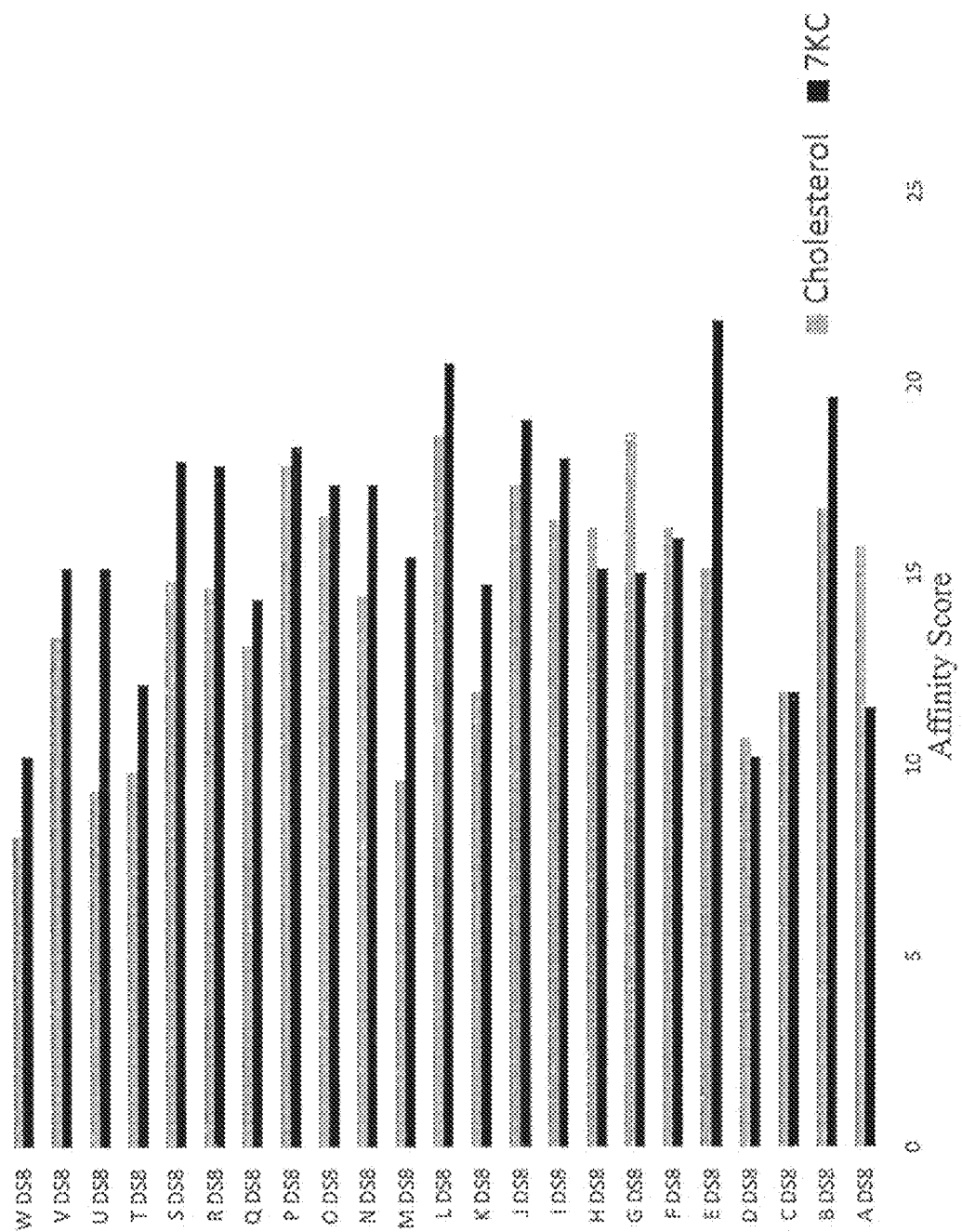
FIG. 8E. Docking results for various HPβCD dimers with different linkers. Linked HPβCD dimer 7KC preference for hydroxypropyl DS4 and DS8 dimers, based on linkers A-W (FIG. 8D) compared to the four-carbon linker (linker W where n=3 carbons) and the triazole-linked dimers (linker U where n=1 carbon and linker V where n=1 carbon). Legend: upper (light grey) bars represent values for cholesterol and lower (dark) bars represent values for 7KC.
Figure 8F:
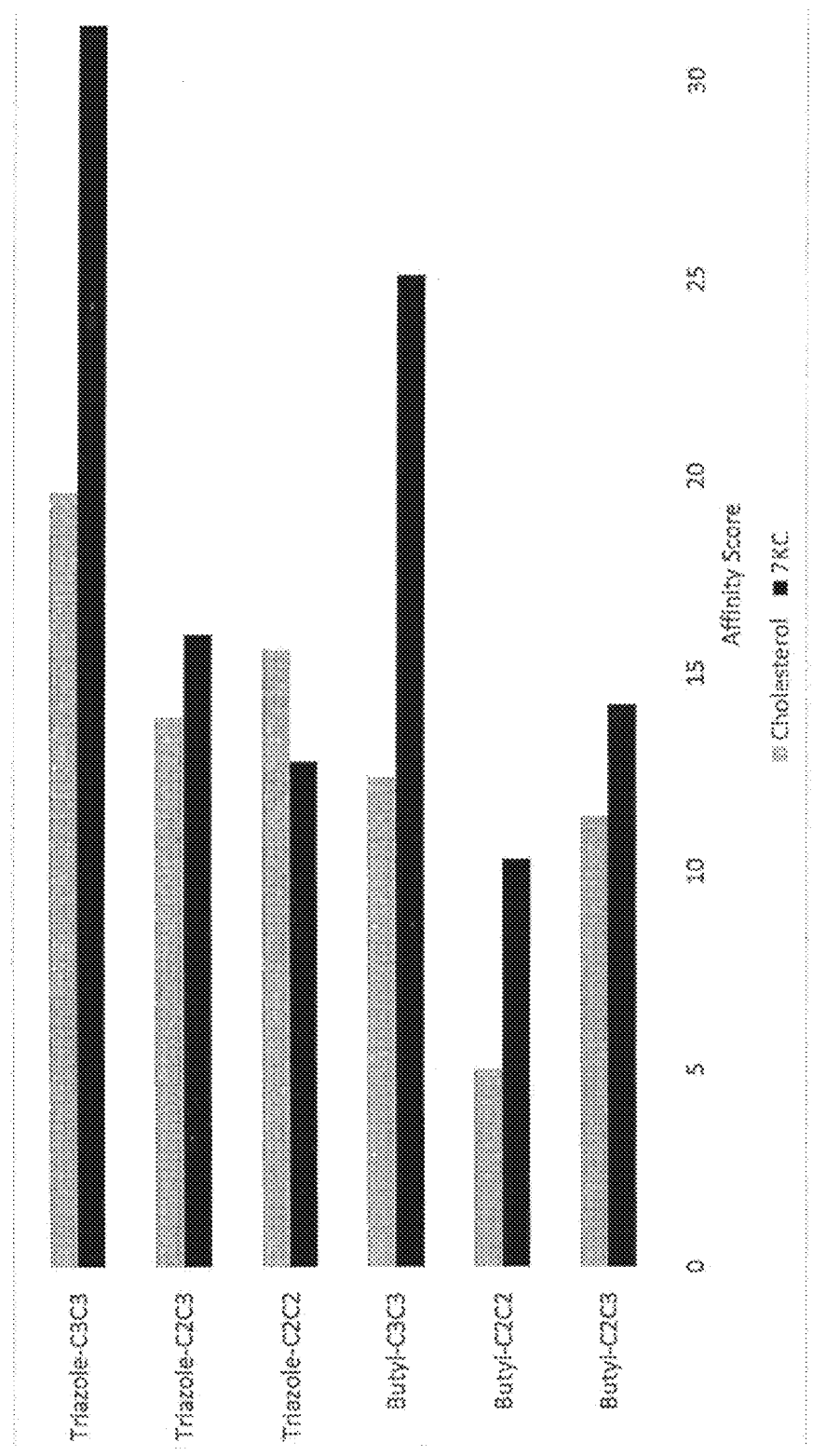
FIG. 8F. Effect of CD attachment site on molecular docking projections of triazole-linked and butyl-linked dimers on cholesterol and 7KC projected affinities. Docking calculations were performed on dimers linked by the symmetric butyl and triazole linkers, thus three possible linkages are possible. C2-C2, C3-C3, and C2-C3 which is the same as a C3-C2 linked dimer because of the symmetry in the linker. Legend: upper (light grey) bars represent values for cholesterol and lower (dark) bars represent values for 7KC.
Figure 8G:
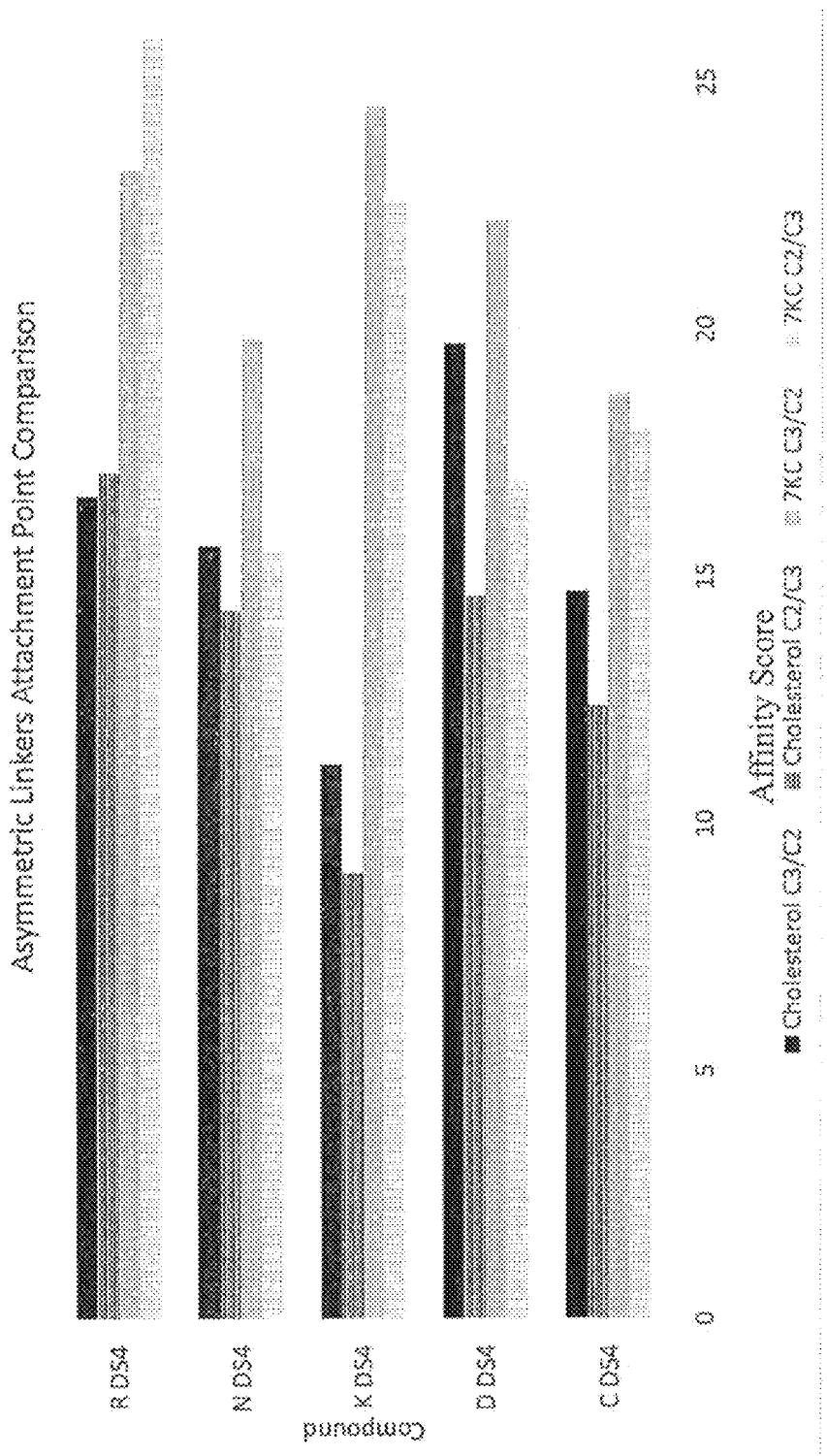
FIG. 8G. Asymmetric linkers variation in attachment point. Docking calculations were performed on dimers linked by the asymmetric four-atoms linkers C, D, K, N, and R (see FIG. 8D). For these asymmetric linkers, four possible linkages are possible: C2-C2, C3-C3, C2-C3, and C3-C2. C3-C2 is not the same as C2-C3 in these cases due to asymmetry in the linker. Legend: each group of bars, from top to bottom, represents cholesterol with C3/C2 linkage; cholesterol with C2/C3 linkage; 7KC with C3/C2 linkage, and 7KC with C2/C3 linkage.
Figure 8H:
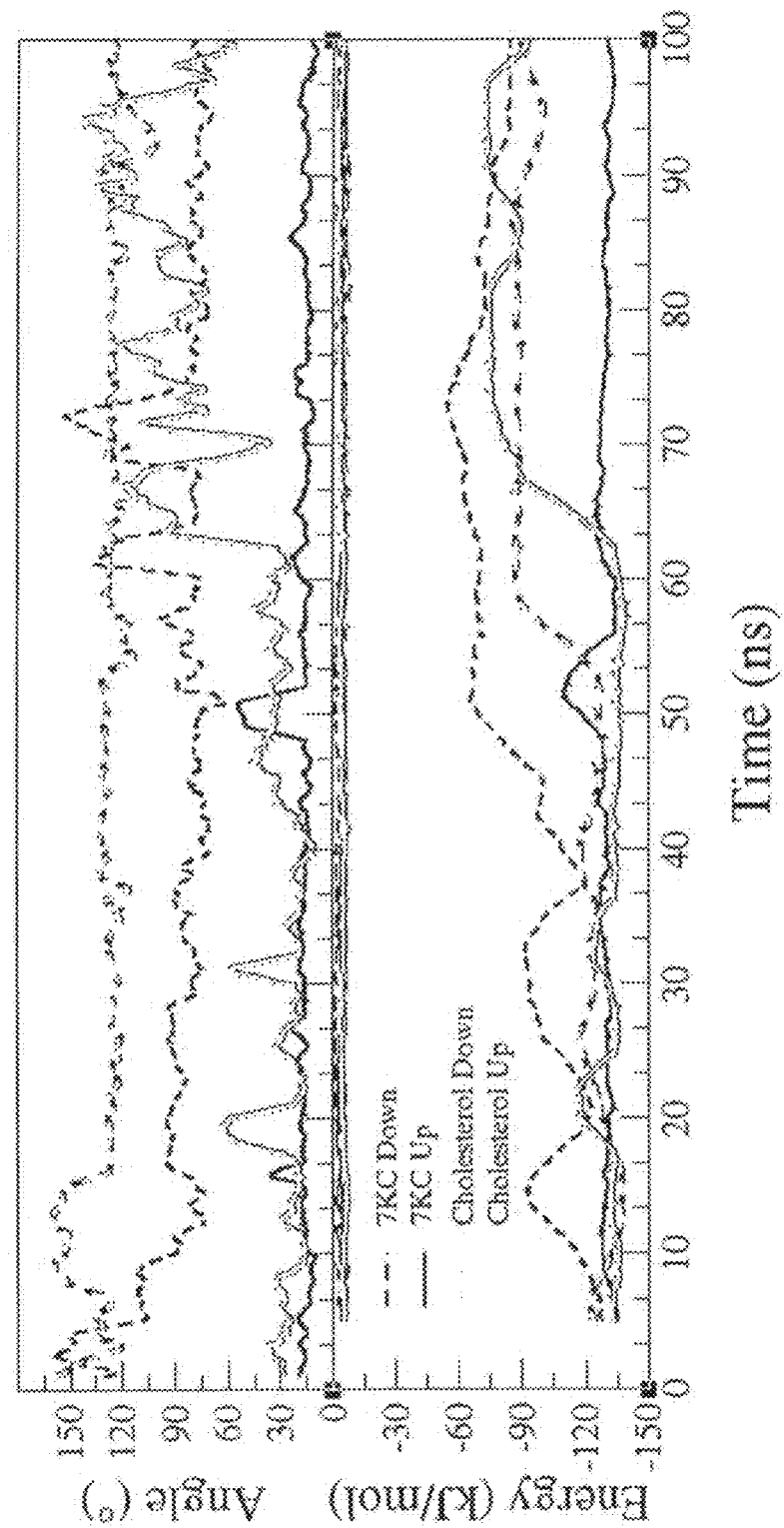
FIG. 8H. MD simulation describing 100 ns of interaction between a nitrogen-linked DS4 hydroxypropyl βCD dimer and 7KC/cholesterol in both orientations (Linker O). Legend is as in FIG. 5B.
Figure 9A:
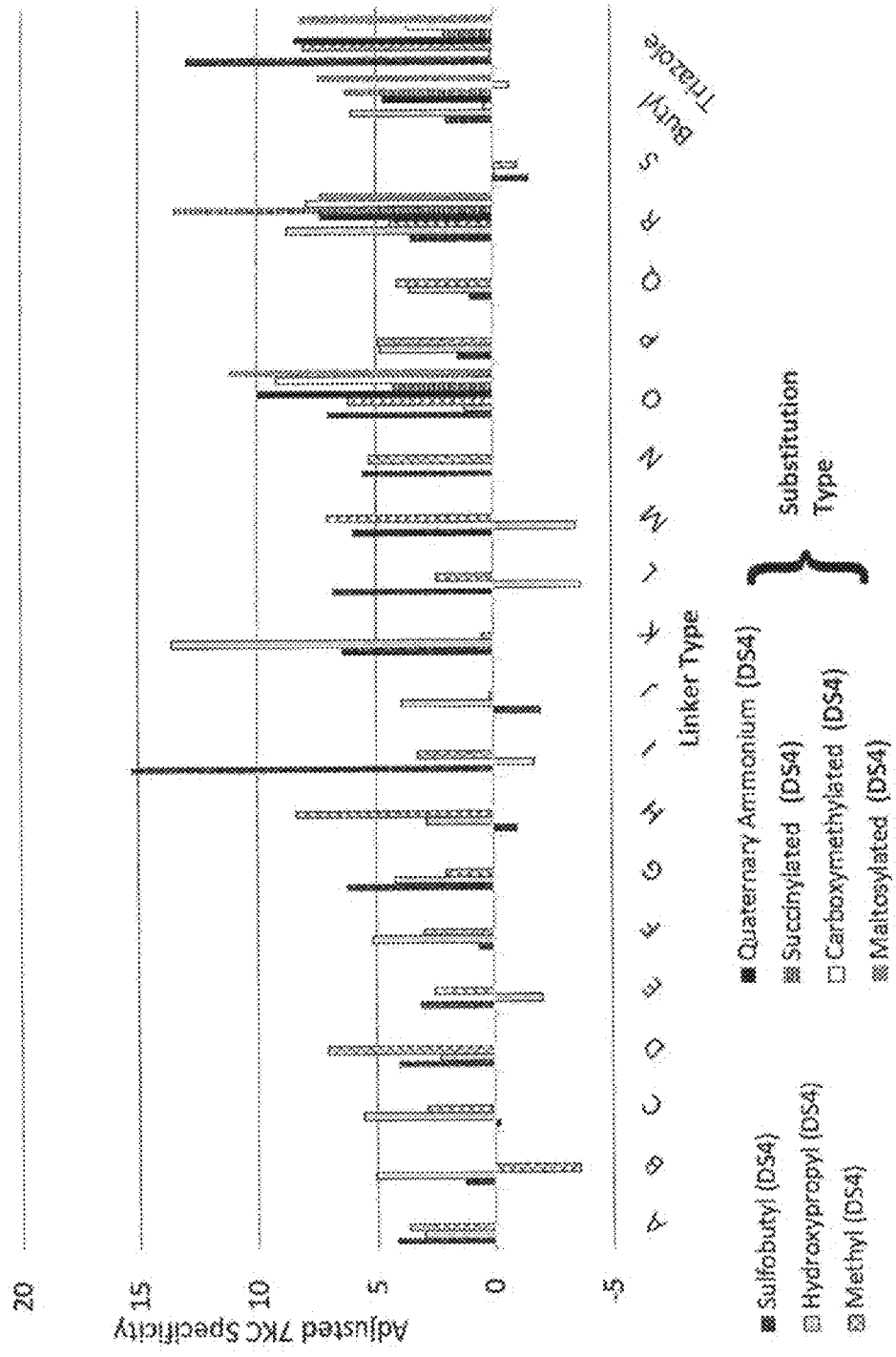
FIG. 9A. Predicted 7KC specificity for a wide range of linked dimers by molecular docking. 7KC specificity is maintained over a wide variety of linkers and substitution types for βCD dimers. Order of bars within each group, from left to right, is: sulfobutyl (DS4); hydroxypropyl (DS4); methyl (DS4); quaternary ammonium (DS4); succinyl (DS4); carboxymethyl (DS4); maltosyl (DS4).

FIG. 8E describes an assessment of the dependence of our HPβCD dimer on the composition and attachment points of the linker, variation in hydroxypropylation site, variation in linker length, as well as varying the chemical composition of the linker. Linker attachment sites were tested in silico as they are not easily controllable during the chemical synthesis of cyclodextrins. Docking calculations were carried out for various hydroxypropylation sites (FIG. 8A), various lengths of carbon-only linkers (chain length of two to eight carbons, FIG. 8B) and triazole linkers (varying n1 and n2 values surrounding triazole ring, FIG. 8C), and different attachment points to the O2 and/or O3 oxygen(s) of dimerized HPβCD (FIG. 8F-G), as well as different linker types altogether (FIG. 9A). The results show that there is little effect on 7KC preference and minimal effect on overall sterol binding when the location of the hydroxypropyl groups is varied. The linker length between 3 and 5 carbons showed the greatest affinity and specificity for 7KC (FIG. 8B).

Various triazole linkers modeled in AutoDock are shown in FIG. 8C. For these linked dimers, n1 refers to the number of carbons on the right of the ring while n2 refers to the number of carbons to the left of the azide ring. Based on these results, variations on the length of the triazole linker less than 4 on each side of the ring are predicted to have the greatest affinity for 7KC.

In FIG. 8E we performed docking calculations for HPβCD dimers with 7KC for 23 different possible alternative linkers (depicted in FIG. 8D). Based on these results, most linked dimers tested are predicted to maintain good affinity for 7KC.

We also considered the fact that the linkers can attach to the secondary face of the cyclodextrin at either the C2 or C3 carbons. We tested by molecular docking whether this would impact predicted affinities (FIG. 8F). We also investigated whether there might be more pronounced differences in affinity for sterols linked by asymmetrical linkers with variable attachment sites. These calculations show the propensity to bind 7KC and cholesterol for all three possible linkage sites, which are all present in roughly equal quantities in a typical synthesis. These calculations show the propensity to bind 7KC and cholesterol for all four possible linkages present in the synthesis of dimers linked by five different asymmetric linkers. By and large we observed no major differences between C2 and C3 attachment sites.

Our molecular modeling revealed differences in levels of specificity for 7KC for different numbers of substitutions. Of particular interest were linked HPβCDs containing 3, 4, or 5 hydroxypropyl groups, which showed the greatest specificity for 7KC of any butyl dimer that we modeled (FIG. 4B). We synthesized a variety of butyl and triazole linked HPβCD dimers, including DS-3. Consistent with our predictions, HPβCD-butyl-DS3 and HPβCD-triazole-DS3 had the greater specificity for 7KC over cholesterol (FIGS. 16A-C).

Upon completion of the hydroxypropyl CD dimer docking analysis, docking was done for a variety of different CD dimers with various degrees of substitution with various linkers against 7KC and cholesterol to see how these factors affect 7KC and cholesterol binding (FIGS. 5A, 6A, and 9). Methyl and sulfobutyl substitutions were tested from DS1 to DS20 with butyl and triazole linkers (FIG. 5A, 6A) and the results were promising enough to spur additional molecular dynamics analysis, and eventually synthesis.

We observe in FIGS. 5A and 6A that 7KC specificity is best at low DS (2-6) for both sulfobutyl and methyl substitutions. DS4 MeβCD and SBβCD behave most similarly to HPβCD DS5, where 7KC is well solubilized but cholesterol is not. It seems that 7KC specificity becomes less and less pronounced as DS increases for both linkers and all substitutions. When it appeared that ~DS4 obtained maximum 7KC specificity for all of the tested substitution types, only DS4 was tested with other linker types.

Substitutions other than hydroxypropyl, methyl, or sulfobutyl were tested only at low DS with only the butyl linker, triazole linker, linker O, and linker R (FIG. 9A). While some linkers or substitution types do show more or less specificity than others, the vast majority still show at least some specificity for 7KC. This suggests that among the tested compounds, 7KC specificity does not depend on the type of linker or substitution, but rather the number of substitutions on the βCD rings. Although a few substitution types did show negative specificity with a few linker types, the average 7KC specificity was still well above 0 for these 23 linkers and seven substitution types at low DS (4).

Figure 9B:
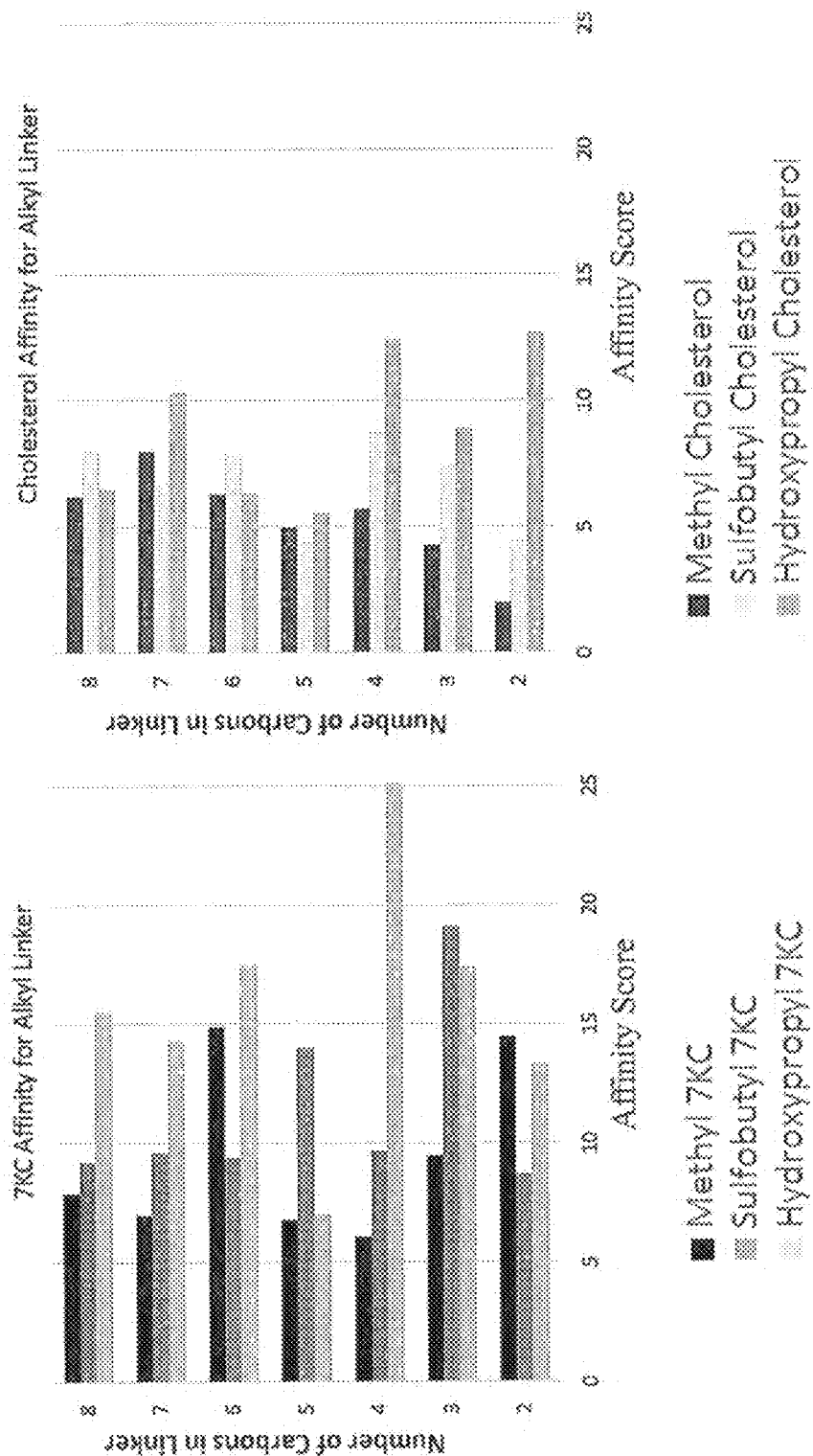
FIG. 9B. Sterol affinity for various lengths of alkyl linkers with hydroxypropyl, methyl, and sulfobutyl substitutions (DS4); as modeled by molecular docking. Order of bars within each group, from top to bottom, is methyl, sulfobutyl, and hydroxypropyl.

Using molecular docking, we were able to test how the length of the triazole or alkyl linker affects 7KC specificity of cyclodextrin dimers containing hydroxypropyl, methyl, and sulfobutyl substitutions (FIG. 9B-C). We showed that as the length of the linker increases, the specificity decreased. Without intent to be limited by theory, it is believed that for linkers of greater length, the CD subunits are allowed to separate to a greater distance, and thus spend less time in a conformation that is able to effectively encapsulate a molecule the size of 7KC or cholesterol. Based on these results, we conclude that dimers having a linker length that allows the guest (7KC or cholesterol) to fit into the two CD subunits will show more solubilization of such molecules, e.g., linker lengths of 7 atoms or fewer.

Figure 5B:
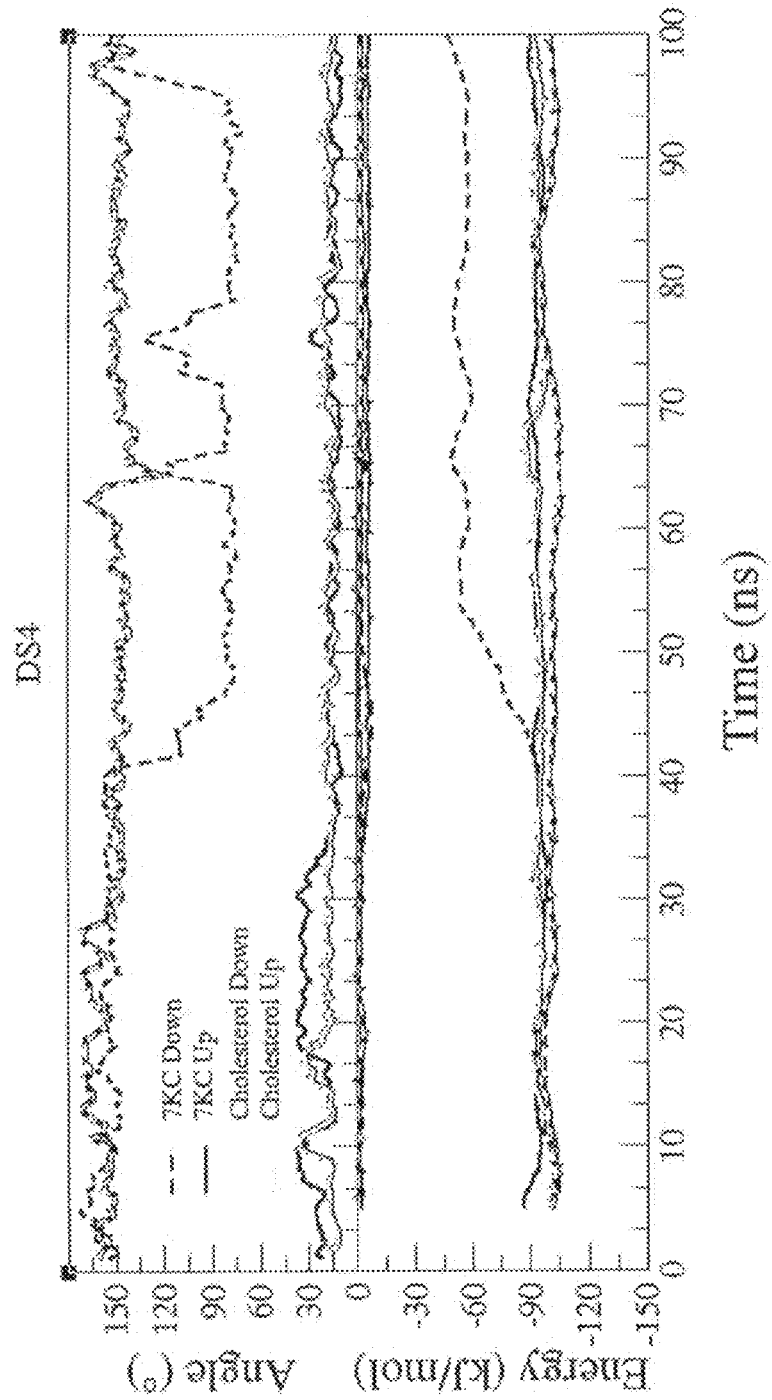
FIG. 5B. MD simulation describing 100 ns of interaction between a butyl-linked DS4 methyl βCD dimer and 7KC/cholesterol in both up and down orientations. Legend: 7KC (dark lines) and cholesterol (light grey lines), with dashed lines for down orientation and solid lines for up orientation.
Figure 5C:
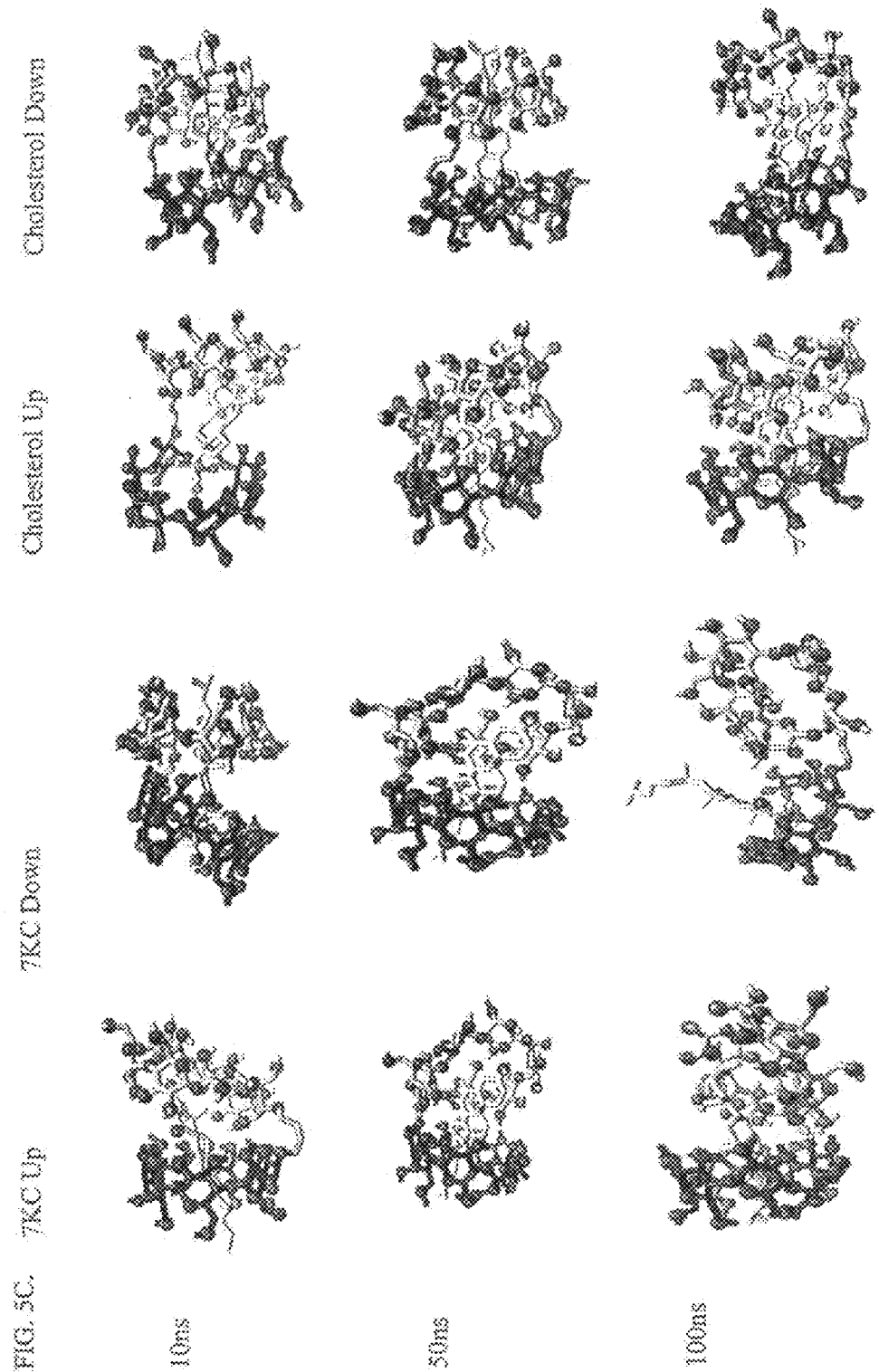
FIG. 5C. Visual trajectories of butyl-linked DS4 methyl βCD dimer and 7KC/cholesterol in both up and down orientations.
Figure 5D:
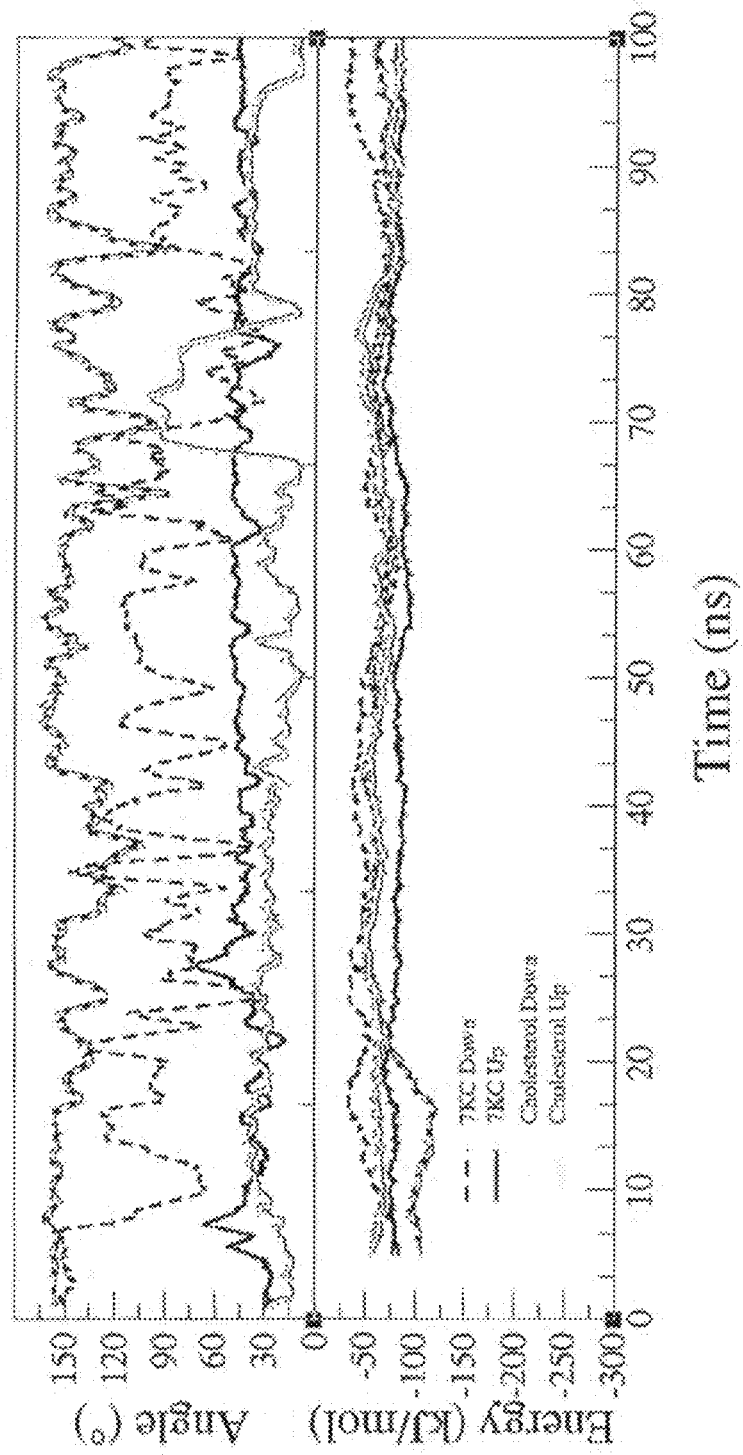
FIG. 5D. MD simulation describing 100 ns of interaction between a triazole-linked DS4 methyl βCD dimer and 7KC/cholesterol in both up and down orientations. Legend as in FIG. 5B.
Figure 5E:
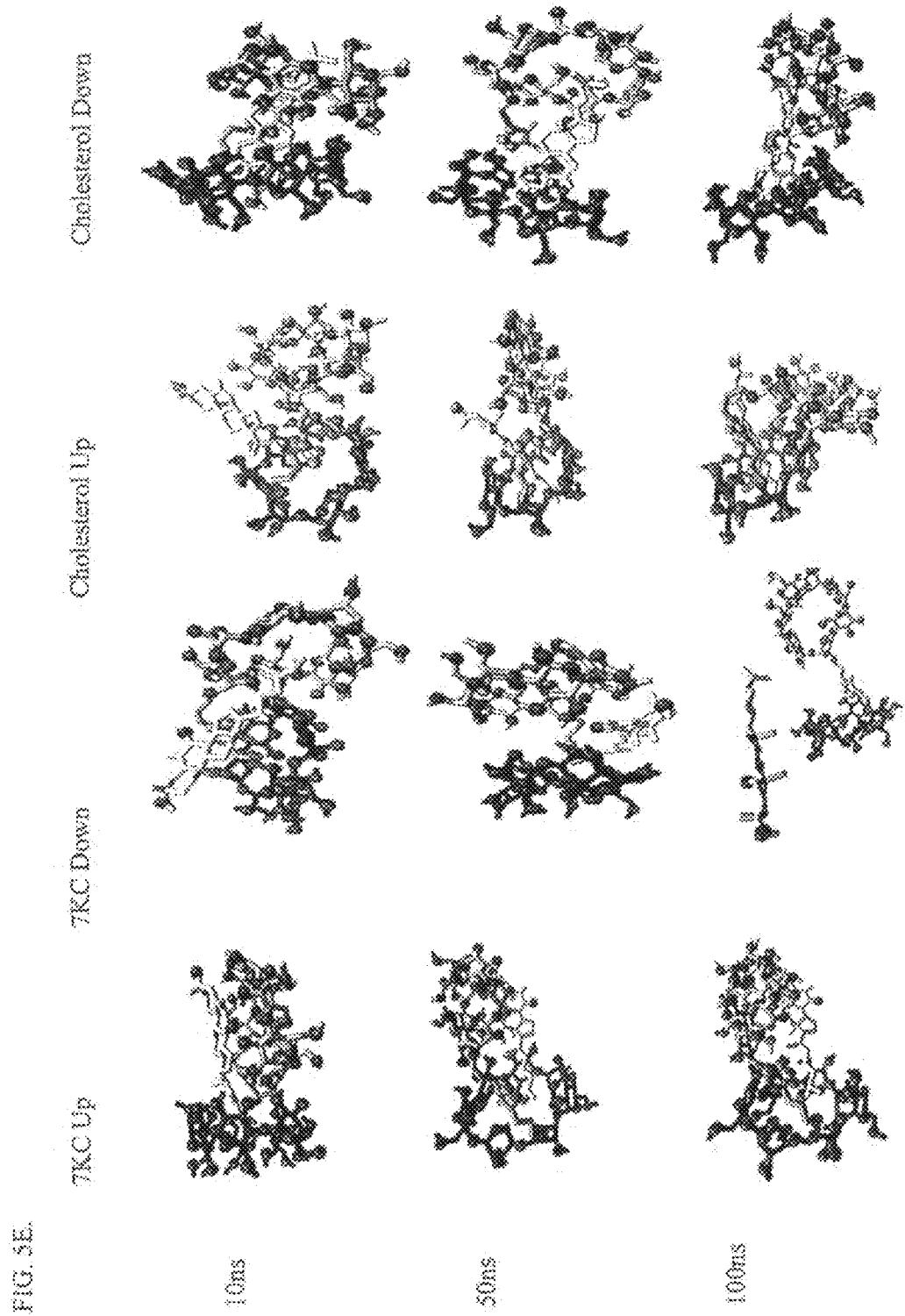
FIG. 5E. Visual trajectories of triazole-linked DS4 methyl βCD dimer and 7KC/cholesterol in both up and down orientations.
Figure 9D:
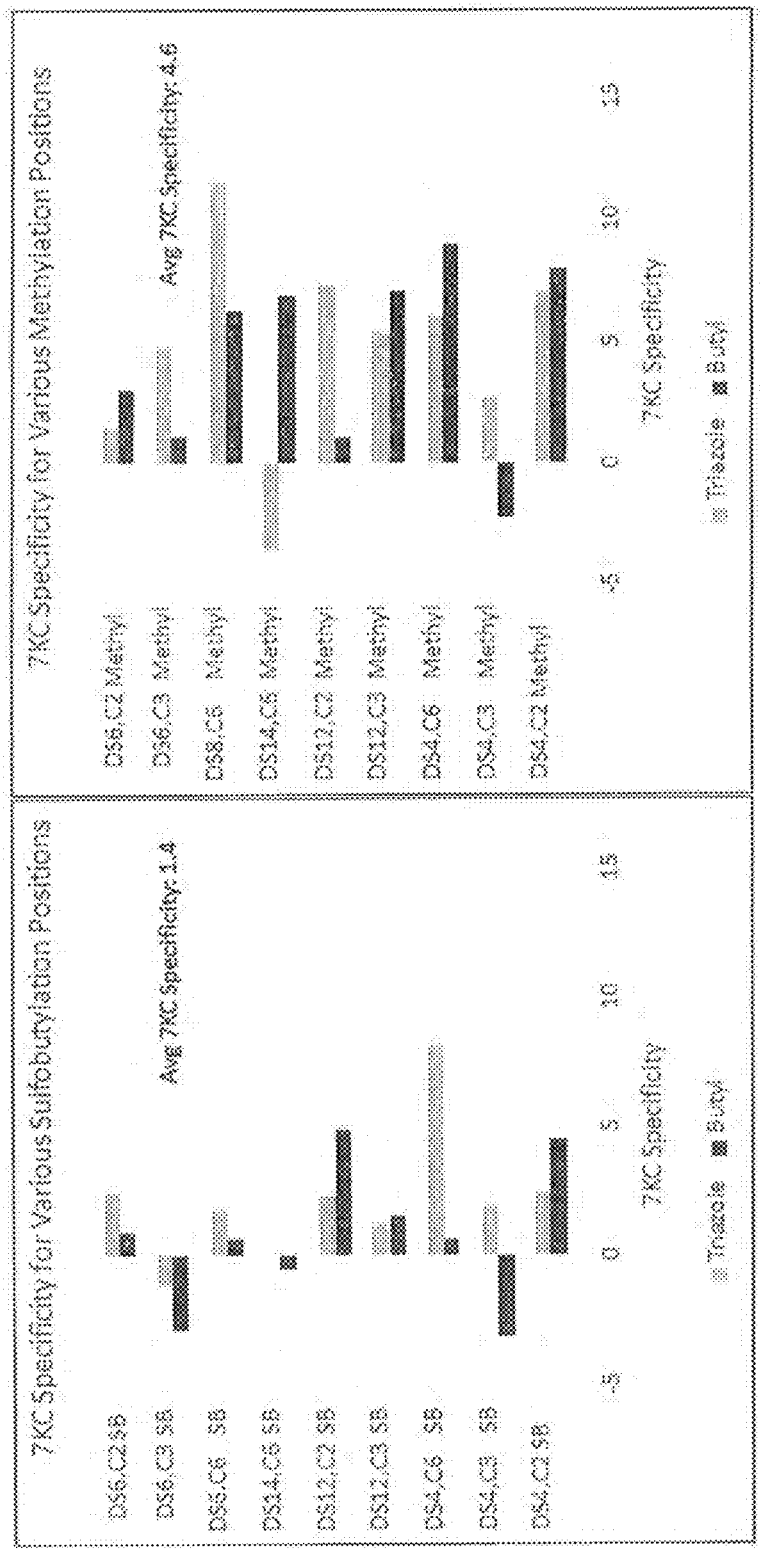
FIG. 9D. Predicted 7KC specificity of butyl and triazole linked βCD dimers for multiple positions of substitutions; as modeled by molecular docking. X-axis is fold affinity for 7KC over cholesterol. In each group the upper bars represent triazole and the lower bars represent butyl.
Figure 9E:
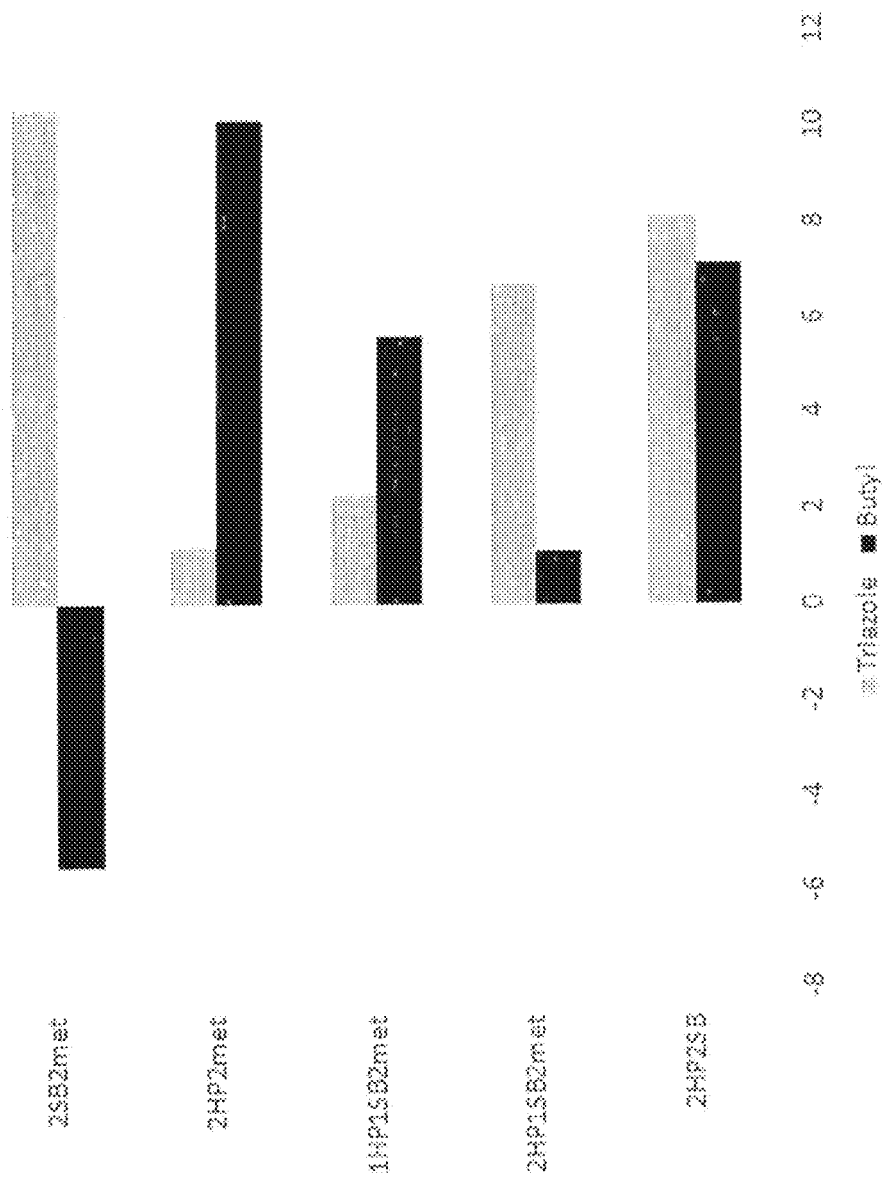
FIG. 9E. Docking screen of other βCD variants. 7KC specificity is seen for butyl and triazole-linked βCD dimers even for combinations of substitutions; as modeled by molecular docking. X-axis is fold affinity for 7KC over cholesterol. Order of bars as in FIG. 9D.

We have also tested whether the specificity of CD dimers for 7KC have dependence on substitution positions by creating many different substitution patterns with sulfobutyl, hydroxypropyl, and methyl substitutions as well as a combination of the three (FIG. 9D-E). We have found that when a single substitution type or even multiple types of substitutions are present on one CD dimer, 7KC specificity is largely maintained when DS is ~4. The type and position of these substitutions did not greatly affect 7KC specificity. Results of the docking simulations suggest that while the composition of both the linker and the substitutions affect how well a given CD can solubilize guests, the degree of specificity for 7KC depends most on the number of substitutions on the CD rings. As can be seen in FIGS. 4B and 5A-B, butyl linked dimers showed the highest specificity for 7KC at approximately DS 2-5 for methyl, sulfobutyl, and hydroxypropyl substitutions. This held true for the triazole linker as well, bolstering the idea that multiple linker and substitution types can show similar specificity for 7KC for degrees of substitution between 2 and 5. Additionally, a wide range of 23 different linkers and 14 different substitution patterns/combinations were docked to determine if linker or substitution pattern had an effect on 7KC specificity (FIG. 9A). Both of these analyses showed variation in the degree of 7KC specificity but the average specificity was still well above zero.

The conducted docking and molecular dynamics screen served to identify whether certain linker types or substitution number, type, and position affected 7KC specificity. The only modification with a large effect on binding (affinity) was the actual dimerization of the cyclodextrin (compared with docked monomers, FIG. 2E, dimers showed much better binding of sterols). By contrast, the number of substitutions present on the dimer had the greatest effect on 7KC binding specificity. Docking simulations indicate that once βCD is dimerized and substituted with approximately 4 compatible functional groups, the specificity for 7KC is mostly maintained for a vast number of different substitution types, patterns, and linkers.

Because methyl, sulfobutyl, and hydroxypropyl groups are all quite different from each other, and the range of linkers tested contained significant variability, we believe it is not unreasonable that other substitution types with a linker of length similar to the sterol guest would behave similarly to a butyl-linked CD dimer with hydroxypropyl groups. Although the substitution and linker type may have some effects on other properties such as solubility and toxicity, the specificity for 7KC is predicted to be present for other molecules of this class as well.

Example 3. Synthesis of HPβCD Substituted Cyclodextrin Dimers

FIGS. 3A-D illustrate the molecules to be synthesized in FIG. 10 below.

This example describes the synthesis of substituted cyclodextrin dimers, first linked by a butyl linker and then a triazole-containing linker.

For DS measurement, 1H and 2D NMR spectra are recorded on Varian VXR-600 at 600 MHz, using residual solvent signal as an internal reference. The sample is dissolved in DMSO-$d_6$/$D_2O$ for the structure elucidation. The FID signals are recorded with at least 16 scans so as to obtain a spectral window comprised, at least, between 0 ppm and +10 ppm. The calculation of the average degree of substitution (DS) can be accomplished by setting to fourteen the integral of the anomeric region (fourteen being the number of the anomeric protons for a beta-cyclodextrin dimer) and by dividing by three the integral of the alkyl region (see FIG. 10J).

General Description of Synthesis and Characterization HP(βCD-BUT-βCD)

The preparation of hydroxypropylated 3-cyclodextrin dimers was accomplished through a three-step synthesis (see FIG. 10A). The starting material is monomeric β-cyclodextrin protected on the primary side with tert-butyldimethylsilyl groups (TBDMS-βCD, CycloLab, Budapest, Hungary).

The secondary face dimerization was achieved by using TBDMS-βCD, anhydrous conditions, and sodium hydride as base. The dialkylating agent was added dropwise to the heterogeneous reaction mixture and exhaustively reacted at room temperature.

The primary side protected βCD dimer (TBDMS-βCD-BUT-βCD-TBDMS) was purified by chromatography with isocratic elution (chloroform:methanol:water=50:8:0.8 (v/v/v) as eluent). The MALDI analysis of the compound confirmed the identity of the product (FIG. 10D).

The desilylation was performed in THF with tetrabutylammonium fluoride at room temperature. The βCD dimer (βCD-BUT-βCD) was purified by chromatography with isocratic elution (1,4-dioxane:$NH_3$=10:7 (v/v) as eluent). The MALDI and TLC analysis of the compound confirmed the identity of the product (FIGS. 10E-10F).

The hydroxypropylation of the βCD dimer was achieved in aqueous conditions by using sodium hydroxide as base at room temperature. The purification of the hydroxypropylated βCD dimer (HP(βCD-BUT-βCD)) was based on ion exchange resins treatment, charcoal clarification and extensive dialysis. The MALDI and NMR analyses of the compound confirmed the identity and the structure of the product (FIGS. 10G-10N).

HP(βCD-Triazole-βCD)

The preparation of hydroxypropylated β-cyclodextrin dimers connected through secondary face with one triazole moiety may be performed in a four part procedure (FIG. 10B). The first part is the preparation of the azido-linker (3-azido-1-bromo-propane) as this reagent is not commercially available. The second part is the preparation of the two βCD monomers, 2-O-propargyl-β-CD and 2-O-(3-azidopropyl)-βCD, respectively. The third synthetic part is the build-up of the dimer-core by copper-assisted azide-alkyne cycloaddition, and the final part was is preparation of a series of 2-hydroxypropylated triazole-linked dimer according to the classical alkylation approach.

In particular, the preparation of the azido-linker can be achieved by strictly limiting the amount of sodium azide and by elongating the addition time of the limiting reagent. The azido-linker is then characterized by NMR spectroscopy and TLC (FIG. 10R).

The syntheses of the two monomers is accomplished by using lithium hydride as selective base for deprotonation of the secondary side. In particular, according to this approach only the hydroxyl groups located on C2 are activated. As a consequence, monomers prepared by this method are exclusively substituted on the O2 (they are single isomers). The two monomers are characterized by NMR spectroscopy, MALDI and TLC (FIGS. 10S-U).

The preparation of the dimer-core is then achieved by reacting the two monomers. The resulting compound, a single isomer, (BCD-(TRIAZOLE)$_1$-BCD DS=0) is characterized by NMR spectroscopy (FIG. 10V) and MALDI (FIG. 10O).

Hydroxypropylation of BCD-triazole-BCD was accomplished using propylene oxide and alkaline aqueous conditions. The series of hydroxypropylated compounds was characterized by MALDI (FIG. 10P-Q).

Detailed Description of Synthesis (HP(βCD-BUT-βCD))

Step 1: Secondary Face Dimerization of TBDMS-βCD

Dried TBDMS-βCD (10 g, 5.17 mmol) was solubilized in THF (400 mL) under inert atmosphere and sodium hydride (2.5 g, 50 mmol) was carefully added portion wise (in 30 min). The addition of sodium hydride caused hydrogen formation and intense bubbling of the suspension. After 15 min stirring, the reaction mixture gelified, and stirring became difficult. In order to destroy the gel, the reaction mixture was heated until a gentle reflux occurred, and kept at reflux for 30 min. The yellowish, heterogeneous suspension became more stirrable, and the gel-like architecture disappeared. The reaction mixture was cooled down to room temperature with a water bath. The alkylating agent, 1,4-dibromobutane (1.25 mL, 2.25 g, 10.5 mmol), was added dropwise (15 min) and the color of the reaction mixture turned to dark orange.

The brownish suspension was stirred overnight under inert atmosphere. The conversion rate was estimated by TLC between 10-15% (eluent: chloroform:methanol:water=50:10:1, v/v/v, see FIG. 10C) and considered acceptable for work-up.

The reaction mixture was quenched with methanol (30 mL), concentrated under reduced pressure (~20 mL) and precipitated with water (200 mL). The reaction crude was filtered on a sintered glass filter and extensively washed with water (3×300 mL). The crude material was dried until constant weight in a drying box in the presence of KOH and $P_2O_5$ (12.1 g).

The reaction crude was purified by chromatography, fractions containing the products were collected and evaporated until dryness under reduced pressure based on TLC analysis (FIG. 10C), yielding a white material that was dried until constant weight in a drying box in the presence of KOH and $P_2O_5$ (TBDMS-βCD-BUT-βCD-TBDMS, 3.5 g).

Step 2: Deprotection of TBDMS-βCD Butyl Linked Dimer

Dried TBDMS-βCD-BUT-βCD-TBDMS (3.5 g, 0.89 mmol) was solubilized in THF (250 mL) under inert atmosphere and tetrabutylammonium fluoride (8.75 g, 33.47 mmol) was added in one portion to the yellowish solution. After 30 min stirring at room temperature, the color of the reaction mixture turned to dark green. The reaction mixture was stirred at room temperature overnight. TLC analysis (1,4-dioxane:$NH_3$=10:7 (v/v)) revealed that the reaction was not completed and a second portion of tetrabutylammonium fluoride (4 g, 13.3 mmol) was added to the vessel. The reaction mixture was warmed to a gentle reflux and refluxed for two hours. The reaction conversion at this stage was exhaustive as no starting material could be detected by TLC. The reaction mixture was cooled-down to room temperature, concentrated under reduced pressure (to ~10 mL) and addition of methanol (200 mL) yielded a white precipitate. The solid was filtered-out, analyzed by TLC and dried until constant weight in a drying box in the presence of KOH and $P_2O_5$ (1.2 g). According to TLC analysis the material contained a negligible (<3%) amount of tetrabutylammonium fluoride. The mother liquor was concentrated under reduced pressure (to ~10 mL) and purified by chromatography (eluent: 1,4-dioxane:$NH_3$=10:7 v/v), fractions containing the products were collected and evaporated until dryness under reduced pressure, yielding a white material that was dried until constant weight in a drying box in the presence of KOH and $P_2O_5$ (βCD-BUT-βCD, 0.55 g).

Step 3: Hydroxypropylation of βCD-BUT-βCD

βCD-BUT-βCD (0.5 g, 0.21 mmol) was suspended in water (10 mL), sodium hydroxide (0.1 g, 2.5 mmol) was added to the reaction vessel and the color of the mixture turned to slight yellow solution. The reaction mixture was cooled with water bath (10° C.) and propylene oxide (0.5 mL, 0.415 g, 7.14 mmol) was added in one portion. The reaction vessel was flushed with argon, sealed and stirred for two days at room temperature. The reaction mixture was concentrated under reduced pressure until obtaining a viscous syrup that was precipitated with acetone (50 mL). The white solid was filtered on a sintered glass filter and extensively washed with acetone (3×15 mL). The material was solubilized with water (50 mL), treated with ion exchange resins (in order to remove the salts), clarified with charcoal, membrane filtered and dialyzed for one day against purified water. The retentate was evaporate under reduced pressure until dryness yielding a white solid (0.8 g).

Detailed Description of Synthesis (HP(βCD-Triazole-βCD))

Step 1: Preparation of the Azido-Linker 1,3-Dibromopropane (10 mL, 20.18 g, 0.1 mol) is solubilized in 40 mL DMSO under vigorous stirring. A solution of sodium azide (6.7 g, 0.1 mol) in DMSO (240 mL) is prepared and added dropwise (2 hours addition) to the solution of dihalopropane. The solution is stirred at room temperature overnight. The reaction crude is then extracted with n-hexane (3×100 mL), the collected n-hexane phases are retro-extracted with water (3×50 mL), and the organic phases are carefully evaporated under reduced pressure (at 40° C., 400 mbar strictly, otherwise the target compound may distillate out). The residue, an oil, is purified by chromatography (n-hexane-EtAc=98:2 as eluent, isocratic elution). The appropriate fractions are collected, concentrated under reduced pressure and the target compound is obtained as a viscous oil (which may be stored under inert atmosphere in a dark, refrigerated container). The compound is visualized by dipping the TLC plate in a triphenylphosphine solution in dichloromethane (10%) for ~15 s, drying the TLC plate below 60° C., dipping the TLC in a ninhydrin ethanol solution (2%) for ~15 s and final drying of the TLC plate below 60° C. The target compound appears as a violet spot on the TLC plate.

Step 2.1: Preparation of 2-O-Propargyl-βCD

Lithium hydride (212 mg, 26.432 mmol) is added to a solution of β-cyclodextrin (20 g, 17.62 mmol) in dry DMSO (300 mL). The resulting suspension is stirred under Na at room temperature until it becomes clear (12-24 h). Propargyl bromide (1.964 mL, 17.62 mmol) and a catalytic amount of lithium iodide (~20 mg) are then added and the mixture is stirred at 55° C. in the absence of light for 5 h. TLC (10:5:2 $CH_3CN$—$H_2O$-25% v/v aqueous $NH_3$) is used to characterize the products and is shows spots corresponding to monopropargylated and nonpropargylated β-cyclodextrin, respectively. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica (25×6 cm), and chromatography (10:5:2 $CH_3CN$—$H_2O$-25% v/v aqueous $NH_3$) to yield, after freeze-drying, 2-O-propargyl-β-CD as a solid. The 2-O-propargyl-β-CD was analyzed by MALDI and NMR (FIG. 10T and FIG. 10U).

Step 2.2: Synthesis of 2-O-(3-azidopropyl)-βCD

Lithium hydride (212 mg, 26.432 mmol) is added to a solution of β-cyclodextrin (20 g, 17.62 mmol) in dry DMSO (300 mL). The resulting suspension is stirred under Na at room temperature until it becomes clear (12-24 h). 3-Azido-1-bromo-propane (3 mL) and a catalytic amount of lithium iodide (~20 mg) are then added and the mixture is stirred at 55° C. in the absence of light for 5 h. TLC (10:5:2 $CH_3CN$—$H_2O$-25% v/v aqueous $NH_3$) is used to characterize the products and is shows spots corresponding to 2-O-(3-azidopropyl)-βCD and βCD. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue was obtained. This crude mixture is applied on top of a column of silica and chromatography (10:5:2 $CH_3CN$—$H_2O$-25% v/v aqueous $NH_3$) to yield, after drying, 2-O-(3-azidopropyl)-O-CD as a solid.

Step 3: Synthesis of βCD-triazole-βCD Dimer

2-O-Propargyl-β-CD and 2-O-(3-azidopropyl)-β-CD are suspended in water (300 mL) under vigorous stirring (each at a concentration of between about 8-12 mM). Dimethylformamide (DMF) (approx. 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be after about 1 hour (eluent: $CH_3CN$:$H_2O$:$NH_3$=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% v/v aqueous $NH_3$) to yield, after drying, BCD-(TRIAZOLE)$_1$-BCD DIMER. A preparation of BCD-(TRIAZOLE)$_1$-BCD DIMER was characterized by NMR (FIG. 10V).

Step 4: HP(βCD-triazole-βCD)

βCD-(TRIAZOLE)$_1$-βCD DIMER, which may be obtained according to steps 1-3 above or by other methods, (1 g, 0.418 mmol) was suspended in water (50 mL), sodium hydroxide (DS3=0.32 g, 8 mmol; DS6=0.74 g, 18.5 mmol; DS7=0.87 g, 21.75 mmol) was added to the reaction vessel and the mixture turned to a slight yellow solution. The reaction mixture was cooled by water bath (10° C.) and propylene oxide (DS3=0.49 mL, 0.42 g, 7.25 mmol; DS6=1.21 mL, 1.04 g, 17.9 mmol; DS7=1.46 mL, 1.7 g, 29.3 mmol) was added in one portion. The reaction vessel was flushed with argon, sealed and stirred for two days at room temperature. The solution was concentrated under reduced pressure until obtaining a viscous syrup that was precipitated with acetone (50 mL). The white solid was filtered on a sintered glass filter and extensively washed with acetone (3×15 mL). The material was solubilized with water (50 mL), treated with ion exchange resins (in order to remove the salts), clarified with charcoal, membrane filtered and dialyzed for one day against purified water. The retentate was evaporated under reduced pressure until dryness yielded a white solid (0.8 g). HP(βCD-triazole-βCD) products were analyzed by NMR (FIG. 10W, FIG. 10X, and FIG. 10Y) and the degree of substitution thereof was calculated for each as shown in the figures.

Example 4. Synthesis of Methyl Substituted Cyclodextrin Dimers

FIG. 3E illustrates the molecule to be synthesized.

This example describes the synthesis of methyl substituted cyclodextrin dimers with a triazole-containing linker.

Methyl(βCD-(TRIAZOLE)$_1$-βCD) Dimer
(Exemplary Synthesis)

The preparation of the methylated β-cyclodextrin dimer was accomplished in a one-step reaction (see FIG. 11A). The βCD-(TRIAZOLE)$_1$-βCD DIMER core is prepared according the synthetic strategy described in Example 3 above.

Synthesis

βCD-(TRIAZOLE)$_1$-βCD DIMER core (1.1 g, 0.46 mmol) was suspended in deionized H$_2$O (100 mL) under vigorous stirring and sodium hydroxide (0.35 g, 8.8 mmol) was added. The resulting slightly yellow suspension was stirred for 30 min until complete solubilization. When the temperature of the yellowish, transparent solution was stabilized at ~20° C., methyl iodide (0.5 mL, 1.14 g, 8.03 mmol) was added in one portion under vigorous stirring (NOTE: methyl iodide is not miscible with the reaction mixture and, as a consequence, a vigorous stirring was used to achieve more efficient). The reaction mixture was stirred for 24 h at room temperature, then it was treated with ion exchange resins: H+ resin (6 g) and OH– (6 g) resin were added to the solution, stirred for 15 min and filtered-off (the resins were washed with deionized water 3×15 mL). The resulting filtrate (final pH=7) was clarified with activated charcoal: under vigorous stirring, activated charcoal (0.2 g) was added to the solution, stirred for 30 min and filtered-off (the charcoal pad was washed with deionized water 3×15 mL). Evaporation of the colorless solution under reduced pressure (40° C.) yielded the title compound as white powder (~1 g).

Characterization

The reaction process was monitored by TLC (FIG. 11B) and the resulting material was characterized by MALDI-TOF and NMR analysis as in FIGS. 11C-N.

Example 5. Synthesis of Sulfobutyl Substituted Cyclodextrin Dimers

FIG. 12F illustrates the molecule to be synthesized.

This example describes the synthesis of sulfobutyl substituted cyclodextrin dimers with a triazole-containing linker.

The preparation of the SB-DIMERS was achieved in one-step reaction (FIG. 12A).
Synthesis (SB LOW DS)

βCD-(TRIAZOLE)1-βCD DIMER core (1.2 g, 0.5 mmol) was suspended in deionized H$_2$O (60 mL) under vigorous stirring. Sodium hydroxide (0.39 g, 9.75 mmol) was added to the mixture and the obtained solution was heated at 60° C. Butane sultone (0.88 mL, 1.17 g, 8.6 mmol) was added dropwise at 60° C. and the solution was heated at the same temperature for 3 h. The reaction was then heated to 90° C. for 1 additional hour in order to destroy the residual butane sultone. The reaction mixture was cooled down and treated with ion exchange resins. Cationic exchange resin (H+ resin, 2 g) and anionic exchange resin (OH– resin, 2 g) were added to the solution, stirred for 15 min and filtered-off (the resins were washed with deionized water 3×15 mL). The resulting filtrate (final pH=7) was clarified with activated charcoal: under vigorous stirring, activated charcoal (0.3 g) was added to the solution, stirred for 30 min and filtered-off (the charcoal pad was washed with deionized water 3×15 mL). Evaporation of the colorless solution under reduced pressure (40° C.) yielded a white powder (1.47 g).

Characterization

The reactions were monitored by TLC analysis (FIG. 12B) and the resulting material was characterized by MALDI-TOF and NMR analysis as in FIGS. 12C-K.
Synthesis (HIGH DS)

(βCD-(TRIAZOLE)1-βCD) DIMER core (1.2 g, 0.5 mmol) was suspended in deionized H$_2$O (60 mL) under vigorous stirring. Sodium hydroxide (1.22 g, 30.5 mmol) was added to the mixture and the obtained solution was heated at 60° C. Butane sultone (2.8 mL, 3.72 g, 27.35 mmol) was added dropwise at 60° C. and the solution was heated at the same temperature for 3 h. The reaction was then heated at 90° C. for 1 additional hour in order to destroy the residual butane sultone. The reaction mixture was cooled and treated with ion exchange resins. Cationic exchange resin (H+ resin, 4 g) and anionic exchange resin (OH-resin, 4 g) were added to the solution, stirred for 15 min and filtered-off (the resins were washed with deionized water 3×15 mL). The resulting filtrate (final pH=7) was clarified with activated charcoal: under vigorous stirring, activated charcoal (0.5 g) was added to the solution, stirred for 30 min and filtered (the charcoal pad was washed with deionized water 3×15 mL). Evaporation of the colorless solution under reduced pressure (40° C.) yielded a white powder (1.51 g).

Characterization

The resulting material was characterized by MALDI-TOF and NMR analysis as in FIGS. 12M-P.

Example 6. Synthesis of Quaternary Ammonium Substituted Cyclodextrin Dimers

FIGS. 3I and 13G illustrates the molecule to be synthesized.

This example describes the synthesis of quaternary ammonium substituted cyclodextrin dimers with a triazole-containing linker.

Quaternary Ammonium (βCD-(TRIAZOLE)$_1$-βCD) Dimer (Exemplary Synthesis)

The preparation of the QA-DIMER was accomplished in one-step reaction (see FIG. 13A). The βCD-(TRIAZOLE)$_1$-βCD DIMER core is prepared according the synthetic strategy described in Example 2 above.

Synthesis (BCD-(TRIAZOLE)1-BCD) DIMER core (1.2 g, 0.5 mmol) was suspended in deionized H2O (100 mL) under vigorous stirring and sodium hydroxide (0.39 g, 9.8 mmol) was added. The resulting slightly yellow suspension was stirred for 30 min until complete solubilization. The temperature of the yellowish, transparent solution got stabilized at 5-10° C. and glycidyltrimethylammonium chloride (1.17 mL, 1.32 g, 8.7 mmol) was added in one portion under vigorous stirring. The reaction mixture was stirred for 24 h at room temperature, then the temperature of solution was stabilized at 5-10° C. and a second portion of glycidyltrimethylammonium chloride was added (0.4 mL, 0.45 g, 3 mmol). The reaction mixture was heated at 50° C. for 3 hours, then cooled-down and treated with ion exchange resins: H+ resin (6 g) and OH− (6 g) resin were added to the solution, stirred for 15 min and filtered (the resins were washed with deionized water 3×15 mL). The resulting filtrate (final pH=7) was clarified with activated charcoal: under vigorous stirring, activated charcoal (0.2 g) was added to the solution, stirred for 30 min and filtered-off (the charcoal pad was washed with deionized water 3×15 mL). Evaporation of the colorless solution under reduced pressure (40° C.) yielded the title compound as white powder (~800 mg).

Characterization

The resulting material was characterized by MALDI-TOF and NMR analysis as in FIGS. 13B-K.

In the case of QA-BCD derivatives the typical Gaussian distribution with regular patterns observed for random substituted derivatives is missing, while irregular patterns of fragmentation are detectable. The identification/assignment of these irregular peaks is complicated as no simple pattern of fragmentation can be predicted. The irregular pattern observed in the MALDI spectrum is most probably due to the instability of the trimethylammonium moieties under the experimental conditions. In particular, the elimination products (see FIG. 2) are the results of trimethylammonium moieties cleavage, while the desmethylation products (see FIG. 2) are the results of the progressive cleavage of the methyl groups from the cationic side-chains. It is reasonable to conclude that the MALDI conditions are not suitable for the determination of the DS of QA-BCD derivatives as uninformative peaks generate during the laser desorption. However, the DS of QA-BCD derivatives can be determined by NMR (FIG. 13I) and was estimated to be about 2.1.

Example 7. Synthesis of Succinyl Substituted Cyclodextrin Dimers

FIGS. 3G and 14G illustrates the molecule to be synthesized. The preparation of the Succinyl substituted Dimer (Succ-DIMER) was achieved in one-step reaction (FIG. 14A).

Synthesis (βCD-(TRIAZOLE)1-βCD) DIMER core (1.2 g, 0.5 mmol) was suspended in pyridine (23 mL) under vigorous stirring and inert atmosphere. The suspension was heated at 40° C. for 1 h in order to increase the solubility of the (βCD-(TRIAZOLE)1-βCD) DIMER, however, a complete solubilization was not achieved. A second portion of pyridine (23 mL) was added to suspension, but dilution did not improve the solubility of the (βCD-(TRIAZOLE)1-βCD) DIMER further. Succinic anhydride (0.1 g, 1 mmol) was added at r.t. and the reaction mixture was stirred for 24 h. The reaction crude was concentrated under reduced pressure, solubilized in water (a clear solution was not achieved) (50 mL) and treated with ion exchange resins: H+ resin (2 g) and OH− (2 g) resin were added to the solution, stirred for 15 min and filtered (the resins were washed with deionized water 3×15 mL). The resulting filtrate (final pH=7) was clarified with activated charcoal: under vigorous stirring, activated charcoal (0.5 g) was added to the solution, stirred for 30 min and filtered (the charcoal pad was washed with deionized water 3×15 mL). Evaporation of the colorless solution under reduced pressure (40° C.) yielded the title compound as white powder (~900 mg).

Characterization

The resulting material was characterized by MALDI-TOF and NMR analysis as in FIGS. 14B-K.

As in the case of the QA-DIMER, MALDI analysis proved unfavorable for the DS determination and the DS was determined by NMR (FIG. 14I) and was estimated to be about 2.1.

Example 8. Extraction of 7KC and Cholesterol from Blood Cells with βCD Dimers and Monomers

Methods

Blood was collected from healthy volunteers by licensed phlebotomists. The test substances or PBS alone (negative control) were added to whole blood at various concentrations and incubated for 3 hours at 37 C. Blood was then spun down and serum collected. Serum was frozen and then processed for mass spec.

Plasma free 7-ketocholesterol was determined by LC-MS/MS following protein precipitation and extraction with acetonitrile and derivatization with the novel quaternary aminooxy (QAO) mass tag reagent, Amplifex Keto Reagent (AB Sciex, Framingham, MA, USA), which has been used in the analysis of testosterone (Star-Weinstock [et al.], *Analytical Chemistry*, 84(21):9310-9317. (2012)).

A 50 µL sample of plasma was spiked with 0.5 ng of the internal standard, $d_7$-7-ketocholesterol (Toronto Research Chemicals, North York, Ontario, CA) prepared at 0.1 ng/in ethanol. The sample was treated with 250 µL of acetonitrile, vortex mixed, centrifuged to remove protein at 12,000×g for 10 min. The supernatant was dried under vacuum and then treated with 75 µL of QAO reagent. The working reagent was prepared by mixing 0.7 mL of Amplifex keto reagent with 0.7 mL of Amplifex keto diluent to prepare a 10 mg/mL stock. This stock was then diluted 1:4 with 5% acetic acid in methanol to a final working concentration of 2.5 mg/mL. The mixture was allowed to react at room temperature for two days before LC-MS/MS analysis.

Standards of 7-ketocholesterol (Toronto Research Chemicals, North York, Ontario, CA) were prepared from 1 to 100 ng/ml in charcoal stripped plasma, SP1070, (Golden West Biological, Temecula, CA, USA) and in phosphate buffered saline. There was residual 7-ketocholesterol detected in the stripped plasma, so the standards from PBS were used.

QAO-7-ketocholesterol derivatives were analyzed using a 4000 Q-TRAP hybrid/triple quadrupole linear ion trap mass spectrometer (SCIEX, Framingham, MA, USA) with electrospray ionization (ESI) in positive mode. The mass spectrometer was interfaced to a Shimadzu (Columbia, MD) SIL-20AC XR auto-sampler followed by 2 LC-20AD XR LC pumps.

The instrument was operated with the following settings: source voltage 4500 kV, GS1 50, GS2 50, CUR 20, TEM 550 and CAD gas medium. Compounds were quantified with multiple reaction monitoring (MRM) and transitions optimized by infusion of pure derivatized compounds as presented in Table 1 below. The bold transitions were used for quantification.

| Q1 mass (Da) | Q3 mass (Da) | Dwell Time (msec) | Compound | Declustering Potential | Entrance Potential | Collision Energy | Collision Cell Exit Potential |
|---|---|---|---|---|---|---|---|
| 515.5 | 58.8 | 150 | QAO-7-ketocholesterol | 106 V | 10 V | 99 V | 8 V |
| 515.5 | 456.3 | 150 | QAO-7-ketocholesterol | 106 V | 10 V | 43 V | 12 V |
| 522.5 | 463.4 | 150 | QAO-d7-ketocholesterol | 61 V | 10 V | 45 V | 14 V |
| 522.5 | 432.8 | 150 | QAO-d7-ketocholesterol | 61 V | 10 V | 31 V | 14 V |

Separation was achieved using a Gemini 3μ C6-phenyl 110 Å, 100×2 mm column (Phenomenex, Torrance, CA, USA) kept at 35° C. using a Shimadzu (Columbia, MD) CTO-20AC column oven. The gradient mobile phase was delivered at a flow rate of 0.5 ml/min, and consisted of two solvents, A: 0.1% formic acid in water, B: 0.1% formic acid in acetonitrile. The initial concentration of solvent B was 20% followed by a linear increase to 60% B in 10 min, then to 95% B in 0.1 min, held for 3 minutes, decreased back to starting 20% B over 0.1 min, and then held for 4 min. The retention time for 7-ketocholesterol was 8.46 min.

Data were acquired using Analyst 1.6.2 (SCIEX, Framingham, MA, USA) and analyzed with Multiquant 3.0.1 (SCIEX, Framingham, MA, USA) software. Sample values were calculated from standard curves generated from the peak area ratio of the analyte to internal standard versus the analyte concentration that was fit to a linear equation with 1/x weighting. The lower limit of quantification was 1 ng/mL with an accuracy of 102% and precision (relative standard deviation) of 8.5%. Signal to noise (S/N) was 19:1. At a concentration of 100 ng/mL accuracy was 98% and precision was 0.5% with a S/N of 24:1.

Results

FIGS. 15A and 15B demonstrate that HPβCD dimers (DS-8 as determined by both MALDI and NMR, see FIGS. 10I and 10J) can remove 7KC from blood cells (whole blood) much more efficiently than HPβCD monomers. This is an ex vivo assay on human subjects which allows us to achieve results that could predict the effects on human patients with even more accuracy than experiments on non-human animals. FIG. 15C demonstrates that this does not appreciably impact plasma cholesterol levels. This implies that the HPβCD dimers are not removing large quantities of cholesterol from blood cells. Removal of too much cholesterol from cells could potentially lead to rupturing of cell and organelle membranes and cause cell death. We wished to investigate this directly and therefore performed hemolysis assays.

Example 9. Hemolysis Induced Only by High Concentrations of Cyclodextrin Dimers

Methods

For the test solutions, the amount of PBS varied depending on the concentration of cyclodextrin being tested. Samples were tested in triplicate. 50 μL of blood was added to each sample with PBS and cyclodextrin solution (stocks also made in PBS) to achieve the appropriate concentration in a final volume of 200 ul. 5% Triton X-100 was used as the positive control and PBS was the negative control. Once all the samples were mixed the samples were placed into a 37 C incubator for three hours with agitation. The positive control was 100% hemolyzed by Triton X-100 detergent. Once the samples were out of incubation, they were diluted by the same factor in a 96 hydrograde plate and normalized to the positive control absorbance, which is around 1.1. The absorbance is read at 540 nm. The average of the samples was then corrected by subtracting the negative control. The experiment was run three times, and the error bars are the standard error of the mean (Melanga [et al.], *Journal of Pharmaceutical Sciences*, 105(9):2921-31. (2016)), (Kiss [et al.], *European Journal of Pharmaceutical Sciences*, 40(4):376-80. (2010)).

FIGS. 15D-15E demonstrate that butyl and triazole-linked dimer toxicity to blood cells remains quite low and have no appreciable toxicity in the pharmacological range of less than 1 mM. FIG. 15D shows hemolysis by butyl-linked HP-dimers of three different DS (DS determined by MALDI in FIGS. 10G-10I and DS confirmed by NMR in FIG. 10J), a DS-3 triazole-linked HP dimer (characterized in FIGS. 10P and 10W; label based on MALDI), and a DS-3 triazole-linked Me dimer (characterized in FIGS. 11I and 11L). At higher concentrations only the three butyl-linked dimers demonstrated measurable hemolysis. In FIG. 15E we tested for hemolysis in various other substitutions of triazole-linked βCD dimers. We tested unsubstituted, quaternary ammonium (DS-2, characterized in FIG. 13I), succinyl (DS-2, characterized in FIG. 14I), and sulfobutyl (DSes characterized by both NMR and MALDI in FIGS. 12E, 12H, 12K and 12N; MALDI DSes used in labels). Only unsubstituted dimers were tested up to 7.5 mM, at which concentration we can detect ~5% hemolysis. The other dimers were only tested up to 5 mM and no significant hemolysis was detected at any of the concentrations tested.

It would appear that the triazole dimerized forms of βCD are less hemolytic at high concentrations than the HPβCD butyl dimers tested, but both linkers and all substitution types show very low lysis, suggesting low toxicity.

Example 10. Solubilization of Sterols and Sterol-Like Compounds by Cyclodextrin Dimers Lipophilic compounds were tested for solubilization by the dimers described in Examples 2-6. Test compounds included cholesterol precursor (desmosterol), other oxysterols, steroid hormones, and sterol vitamins.

Methods for In Vitro Solubility Assay (Turbidity Assay)

Sterol stock solutions (including oxysterols, hormones, and vitamins) were suspended in 100% ethanol. Final concentration of suspensions: 3% ethanol, 300 uM sterol, in PBS with various concentrations of cyclodextrins. Samples were incubated for 30 mins at 37 C, and then absorbance was measured in a spectrophotometer plate reader at 350 nm. Samples were prepared in quadruplicate using a Beckman Biomek 2000 liquid handler, and plates with a hydrophilic coating were used to minimize sterol binding to the surfaces of the well. All experiments were run 3 or more times, and error bars are the standard error of the mean.

Turbidity values were normalized to the percentage of the turbidity measured in the absence of cyclodextrins.

Results

We tested our new dimers against 7-ketocholesterol in an in vitro spectrometry assay. In FIG. 16A DS3 is the butyl-linked dimer with an average of ~3 hydroxypropyl groups (quantified by MALDI in FIG. 10G), DS6 is the butyl-linked dimer with an average of ~6 substitutions (MALDI FIG. 10H), and DS8 is the butyl-linked dimer with an average of ~8 hydroxypropyl substitutions (MALDI FIG. 10I). The sterol concentration was always held constant at 300 tested against various concentrations of HPβCD dimers. HP(CD-triazole-CD) are the triazole-linked cyclodextrin dimers of the noted average number of substitutions as determined by MALDI (FIG. 10P) while HP(CD-but-CD) denotes the butyl-linked dimers of noted DS.

FIGS. 16A-B show that all HPβCD dimers that we synthesized solubilize both 7KC and cholesterol much more efficiently than HPβCD monomers. This is consistent with our computational models and predictions illustrating how two linked monomers can completely surround the sterol, protect it from water, maintain binding for long periods of time, and recover it if it is lost. At some low concentrations of dimer it is possible to compare the solubilization achieved to that achieved by high concentrations of monomers and approximate that the same solubilization is achieved with approximately $\frac{1}{10}^{th}$ of the molar concentration. This implies that the affinity for cholesterol/7KC might be in the approximately 10 times higher than that of the monomers, though we must await the results of other experiments to rigorously determine the affinity constants. We then further sought to determine whether these dimerized HPβCDs could bind 7KC with favorable affinity.

We found that several different HPβCD dimers could indeed bind 7KC favorably (FIGS. 16A-B). FIG. 16B shows that triazole dimers labeled DS 3 bind 7KC with greater specificity than DS 6 or DS 7 dimers. These DS values were determined by MALDI. We further discovered that these HPβCDs could bind 7KC more favorably than cholesterol. We noted that some dimers seemed to solubilize 7KC more favorably than others and investigated this in FIGS. 16E-H.

As described above in FIG. 15C we found that, in human blood, DS8 HPβCD dimers removed substantial quantities of 7KC from the cells of donors while serum cholesterol levels seem to be unperturbed. This implies that, while the affinity for cholesterol may result in the removal of cholesterol from cells at the concentrations tested, it was not sufficient to perturb plasma cholesterol levels from the normal range.

FIGS. 16C-D show how dimers interact with various other sterols and steroid hormones with varying affinity as defined by relative turbidity.

FIG. 16C shows that the HP(βCD-(BUTYL)$_1$-βCD) dimer can efficiently encapsulate vitamin D3 (cholecalciferol), but not vitamin D2. It has been previously observed that βCD monomers can encapsulate vitamin D3 (Szejtli [et al.], Drugs of the Future, 9:675-676. (1984)) but our dimers seem to solubilize vitamin D3 many times more efficiently than HPβCD monomers (FIG. 2A vs. FIG. 16C. Note the concentration range is 10 times smaller in the dimer experiments).

We also wished to test the ability of our dimers to solubilize oxysterols other than 7KC.

FIG. 16C shows that HPβCD-butyl linked dimer (DS8) solubilizes various oxysterols to various extents. It seems to solubilize cholesterol epoxide particularly well.

FIG. 16D demonstrates the ability of the butyl dimers to bind various hormones. As with monomeric HPβCD, our dimers bind the 3 estrogens variously well. It should be noted that while the progesterone solubilization appears to be dramatic here, progesterone solubility is naturally much higher than the other hormones tested and therefore this method of normalizing the data is somewhat deceptive in this one case.

We observed that the dimers with the lowest DS had the highest specificity for 7KC over cholesterol, so we performed a more detailed analysis of the least substituted molecules of each linked dimer. FIGS. 16E and 16F go into more detail for the two HP dimers that showed the best specificity for 7KC. We confirmed, in greater detail, that both head-to-head linked cyclodextrin dimers with ~3 HP substitutions preferentially solubilized 7KC over cholesterol. These dimers show substantial affinity and specificity for 7KC at concentrations below 0.5 mM.

We further noted that CD dimers substituted with another groups that confers solubility and low toxicity vastly increases the affinity of CD for 7KC (FIGS. 16G-H). The methylated triazole-linked dimer contained a similar number of substitutions (~3) as the HPβCD dimer from FIG. 16F. We re-tested the HPβCD DS3 dimer along-side the methyl DS3 dimer and found that they had remarkably similar abilities to solubilize both 7KC and cholesterol, maintaining a similar specificity for 7KC.

Based on the prediction that dimerized βCDs with other substitution groups with similar degrees of substitution would also bind 7KC and cholesterol with similar affinity and specificity, new substituted triazole-linked dimers were synthesized (Examples 5-7 above). We utilized a set of charged functional groups (quaternary ammonium (QA), sulfobutyl (SB), and succinyl (SUCC)) typically used as substitutions on cyclodextrins. These low-substitution compounds resulted in comparable or improved affinity and specificity for 7KC (FIG. 16H) as compared to unsubstituted, hydroxypropyl, or methyl substituted triazole-linked dimers (FIG. 16B, FIGS. 16E-G). Conversely, highly substituted SB dimers did not bind either cholesterol or 7KC well. This is likely caused by the many bulky SB groups limiting access to the binding cavity of the CD dimer.

Taking the monomer and dimer turbidity data together with the computational data we can make two generalized conclusions: that low substitutions (likely most important on the secondary face) promote specificity for certain interactions, particularly with 7KC. The modeling data show that hydrogen bonding between secondary face hydroxyl groups and the 7-keto group may promote this specificity. Further, in general, the modeling data show that bulky substitutions can block access to the cavity of any potential guest molecules indiscriminately if present in sufficiently high DS levels. Thus non-bulky groups such as methyl groups added to a CD dimer at high substitution levels are predicted to bind sterol molecules such as cholesterol and 7KC with high affinity, but not particularly high selectivity for 7KC as compared to cholesterol, while a low substitution methyl beta cyclodextrin dimer is predicted to bind 7KC with high specificity as compared to cholesterol. Conversely, cyclodextrin dimers containing bulky substitutions such as SB are predicted to bind 7KC with specificity over cholesterol at low substitution levels, but at high substitution levels not to bind either cholesterol or 7KC, and likely no other sterols either, due to blocking access to the binding cavity. A somewhat less bulky group such as HP is predicted to behave similarly to SB, but in general a higher number of HP groups than SB groups would be required to block access to the cavity.

Based on the foregoing results, we predict that randomly methyl-substituted bCD dimers preferentially bind 7KC over cholesterol up to a substitution level of at least DS 10. Beyond this DS level, the specificity for 7KC over cholesterol may gradually decrease owing to the decreasing number of hydroxyl groups on the secondary face that are available for hydrogen bonding to 7KC as the degree of methyl substitution increases; however, binding to both 7KC and cholesterol are still expected to occur.

By contrast, randomly SB-substituted βCD dimers are predicted to preferentially bind 7KC over cholesterol up to a substitution level of at least DS 4 to DS 5, with the hydroxyl groups in the secondary face again contributing hydrogen bonds to 7KC and promoting stronger binding relative to cholesterol. However, beyond this DS level, specificity for 7KC may gradually decrease and additionally binding to both 7KC and cholesterol as well as other similar guest molecules is expected to decrease due to steric interference with guest access to the βCD cavity. In our data DS over 14 seems to nearly abolish binding to either cholesterol or 7KC.

For similar reasons, HP-substituted dimers are predicted to preferentially bind 7KC over cholesterol up to a substitution level of at least DS 4 or DS 5, while from above this level up to about DS 20 binding specificity for 7KC over cholesterol is expected to gradually decrease with both being bound, and above DS 20 binding to both 7KC and cholesterol is expected to decrease due to steric interference with guest access to the βCD cavity.

SUCC-substituted and QA-substituted βCD dimers are also predicted to preferentially bind 7KC over cholesterol up to a substitution level of at least DS 4 or DS 5, with the hydroxyl groups in the secondary face again contributing hydrogen bonds to 7KC and promoting stronger binding relative to cholesterol. However, beyond this DS level, specificity for 7KC may decrease and additionally binding to both 7KC and cholesterol is expected to gradually decrease due to steric interference with guest access to the βCD cavity over a certain DS level, perhaps over DS 15.

Our wet lab data validate these models as follows: all commonly used substitutions that we placed on our variously synthetic βCD dimers in low quantities (~DS 3-4) demonstrated specificity for 7KC over cholesterol. Increasing the DS of HP groups over 4 and up to 8 reduced affinity for 7KC, but not for cholesterol. Increasing the DS of SB dimers to ~15 severely reduced binding to both cholesterol and 7KC.

What is claimed is:
1. A cyclodextrin dimer having the structure:

CD-L-CD wherein L is a linker that is linked to the large (secondary) face of each CD molecule through a C2 carbon (in place of an $R^1$) and/or C3 carbon (in place of an $R^2$) of each CD subunit;

wherein each CD has the structure of Formula X:

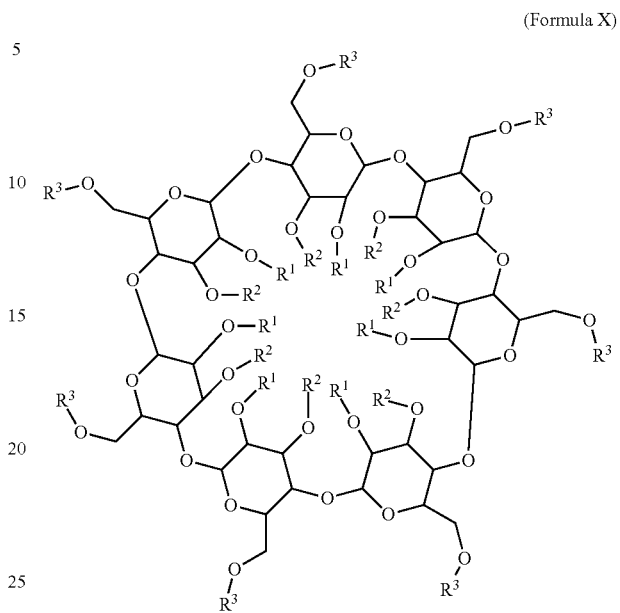

(Formula X)

wherein L has a length of no more than 22 atoms, wherein said no more than 22 atoms are each C, N, O, or S;

wherein $R^1$, $R^2$, and $R^3$ are each independently selected from H, methyl, hydroxypropyl, sulfobutyl, succinyl, quaternary ammonium, —$CH_2CH(OH)CH_2N(CH_3)_3^+$, alkyl, lower alkyl, alkenyl, alkoxy, alkoxyalkyl, alkoxyalkoxyalkyl, alkylcarbonyloxyalkyl, alkylcarbonyl, alkylsulfonyl, alkylsulfonylalkyl, alkylamino, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, aralkyloxy, cyanoalkyl, cycloalkyl, cycloalkenyl, cycloalkylalkyl, cycloalkylene, cycloalkylalkylene, glucosyl, heteroalkyl, heteroaryl, heteroarylalkyl, heteroaryloxy, heteroaralkyloxy, heterocyclylalkoxy, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carboxy, sulfite, sulfuryl, phosphoryl, phenoxy, acetyl group, fatty acid, palmitoyl group, monosaccharide, or disaccharide, wherein between 1 and 40 of said R1, R2, and R3 groups are not H, optionally between 1 and 28 of said R1, R2, and R3 groups are not H, optionally between 2 and 15, or between 4 and 20 of said R1, R2, and R3 groups are not H; and optionally said CD monomers have one or more additional substitutions, wherein no more than 20 of said R1, R2, and/or R3 groups are methyl groups, and further wherein, when L comprises a substituted or unsubstituted alkylene linker having 2-5 atoms, between 1 and 8 of said R1, R2, and R3 groups are not H, optionally between 2 and 5 of said R1, R2, and R3 groups are not H.

2. The cyclodextrin dimer of claim 1, wherein:
(a) R1, R2, and R3 are each independently selected from H, methyl, hydroxypropyl, sulfobutyl, succinyl, maltosyl, carboxymethyl, quaternary ammonium, —CH$_2$CH(OH)CH$_2$N(CH$_3$)$_3$$^+$, glucosyl, palmitoyl, phosphoryl, sulfite, sulfuryl, alkyl, ethyl, propyl, isopropyl, butyl, isobutyl;
(b) wherein R1, R2, and R3 are each independently selected from H, methyl, hydroxypropyl, sulfobutyl, succinyl, maltosyl, carboxymethyl, quaternary ammonium, —CH$_2$CH(OH)CH$_2$N(CH$_3$)$_3$;
(c) the CD monomers are hydroxypropyl (HP) substituted with between 1 and 28 HP groups, optionally between 2 and 15 HP groups or between 4 and 20 HP groups, between 2 and 5 HP groups, and optionally said CD monomers have one or more additional substitutions;
(d) the CD monomers are methyl (Me) substituted with between 1 and 20 Me groups, optionally between 2 and 15 Me groups or between 4 and 20 Me groups, or between 2 and 10 Me groups, and optionally said CD monomers have one or more additional substitutions;
(e) the CD monomers are sulfobutyl substituted with between 1 and 28 sulfobutyl groups, between 1 and 14 sulfobutyl groups, optionally between 2 and 10 sulfobutyl groups, or between 2 and 5 sulfobutyl groups, and optionally said CD monomers have one or more additional substitutions;
(f) the CD monomers are succinyl substituted with between 1 and 28 succinyl groups, optionally between 2 and 15 succinyl groups or between 4 and 20 succinyl groups, or between 2 and 5 succinyl groups, and optionally said CD monomers have one or more additional substitutions; or
(g) the CD monomers are quaternary ammonium substituted with between 1 and 28 quaternary ammonium groups, optionally between 2 and 15 quaternary ammonium groups, or between 4 and 20 quaternary ammonium groups, or between 2 and 5 quaternary ammonium groups, wherein said quaternary ammonium groups comprises —CH$_2$CH(OH)CH$_2$N(CH$_3$)$_3$$^+$, and optionally said CD monomers have one or more additional substitutions.

3. The cyclodextrin dimer of claim 1, wherein:
L has the structure:

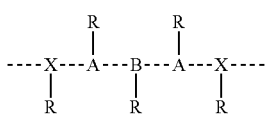

each R is independently selected from H, X, SH, NH$_2$, or OH, or is absent;
the linkage of each CD to the linker is through an O linked to a C2 or a C3 carbon thereof, or through an acetal attachment through two adjacent oxygens of the CD;
each X is a substituted or unsubstituted alkane, alkene, or alkyne;
each A is independently selected from a single, double, or triple covalent bond, S, N, NH, O, or a substituted or unsubstituted alkane, alkene, or alkyne; and
B is a substituted or unsubstituted 5 or 6 membered ring, S, N, NH, NR, O, or absent.

4. The cyclodextrin dimer of any one of claim 1, wherein said linker is an unsubstituted alkyl, a substituted or unsubstituted butyl linker, said linker comprises a triazole, said linker comprises the structure:

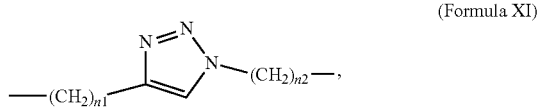

(Formula XI)

wherein n1 and n2 are each between 1 and 8, or each between 1 and 4, or wherein n1 is 1 and n2 is 3, or said linker comprises any one of the following linkers U, V, or W:

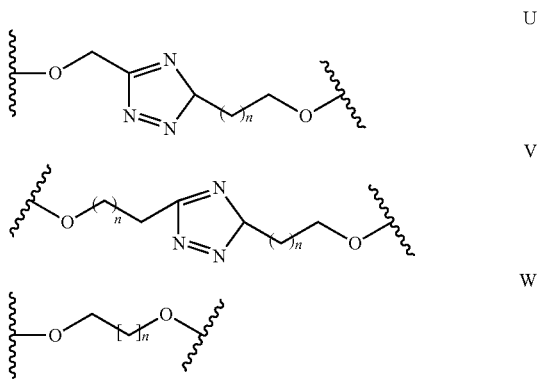

wherein the depicted oxygen atoms at each end of each linker form part of the cyclodextrin monomers to which the linker is linked, and wherein n is between 1 and 7.

5. A cyclodextrin dimer having the structure:
CD-L-CD
wherein L is a linker that is linked to the large (secondary) face of each CD molecule through a C2 carbon (in place of an R$^1$) and/or C3 carbon (in place of an R$^2$) of each CD subunit;
wherein each CD has the structure of Formula X:

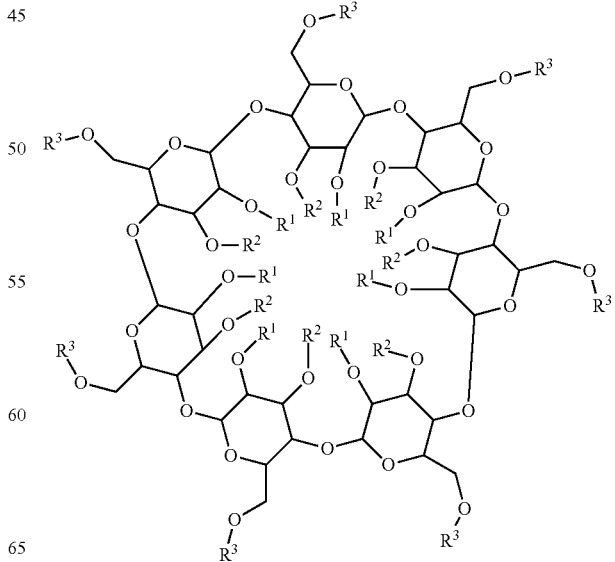

(Formula X)

wherein L comprises a triazole and has a length of no more than 12 atoms;

wherein R¹, R², and R³ are each independently selected from H, methyl, hydroxypropyl, sulfobutyl, succinyl, quaternary ammonium, —CH$_2$CH(OH)CH$_2$N(CH$_3$)$_3^+$, alkyl, lower alkyl, alkenyl, alkoxy, alkoxyalkyl, alkoxyalkoxyalkyl, alkylcarbonyloxyalkyl, alkylcarbonyl, alkylsulfonyl, alkylsulfonylalkyl, alkylamino, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, aralkyloxy, cyanoalkyl, cycloalkyl, cycloalkenyl, cycloalkylalkyl, cycloalkylene, cycloalkylalkylene, glucosyl, heteroalkyl, heteroaryl, heteroarylalkyl, heteroaryloxy, heteroaralkyloxy, heterocyclylalkoxy, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carboxy, sulfite, sulfuryl, phosphoryl, phenoxy, acetyl group, fatty acid, palmitoyl group, monosaccharide, or disaccharide; and wherein the CD monomers are each independently unsubstituted or optionally substituted.

6. The cyclodextrin dimer of claim 5, wherein said linker comprises the structure:

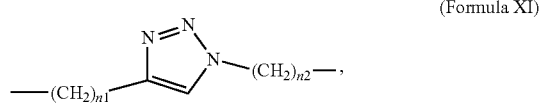

(Formula XI)

wherein n1 and n2 are each between 1 and 8, such as between 1 and 4, or wherein n1 is 1 and n2 is 3.

7. The cyclodextrin dimer of claim 1, which is further substituted with
   (a) at least one methyl, hydroxypropyl, sulfobutyl, succinyl, or quaternary ammonium group, —CH$_2$CH(OH)CH$_2$N(CH$_3$)$_3^+$, and/or
   (b) at least one alkyl, lower alkyl, alkenyl, alkoxy, alkoxyalkyl, alkoxyalkoxyalkyl, alkylcarbonyloxyalkyl, alkylcarbonyl, alkylsulfonyl, alkylsulfonylalkyl, alkylamino, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, aralkyloxy, cyanoalkyl, cycloalkyl, cycloalkenyl, cycloalkylalkyl, cycloalkylene, cycloalkylalkylene, heteroalkyl, heteroaryl, heteroarylalkyl, heteroaryloxy, heteroaralkyloxy, heterocyclylalkoxy, haloalkyl, haloalkoxy, heterocycloamino, heterocyclyl, heterocyclylalkyl, heterocyclyloxy, heterocyclylalkoxy, hydroxyalkoxy, hydroxyalkylamino, hydroxyalkylaminoalkyl, hydroxyalkyl, hydroxycarbonylalkyl, hydroxyalkyloxycarbonylalkyl, hydroxyalkyl, hydroxycycloalkyl, ureido, carboxy, phenoxy, acetyl group, glucosyl, sulfite, sulfuryl, phosphoryl, fatty acid, palmitoyl group, monosaccharide, or disaccharide and/or
   (c) at least one methyl, hydroxypropyl, sulfobutyl, succinyl, maltosyl, carboxymethyl, quaternary ammonium, —CH$_2$CH(OH)CH$_2$N(CH$_3$)$_3^+$, glucosyl, palmitoyl, phosphoryl, sulfite sulfuryl, alkyl, ethyl, propyl, isopropyl, butyl, or isobutyl group.

8. The cyclodextrin dimer of claim 1, wherein L is a linker that is linked to a C2 carbon of each CD monomer, wherein L is linked to a C3 carbon of each CD monomer, or wherein L is linked to a C2 carbon of one CD monomer and a C3 of the other CD monomer.

9. The cyclodextrin dimer of claim 1, wherein said cyclodextrin dimer exhibits greater affinity for 7KC than cholesterol, wherein optionally said greater affinity is determined by a turbidity test, optionally wherein said cyclodextrin dimer exhibits at least 1.1-fold, 1.5-fold, 2-fold, 3-fold, 4-fold, 5-fold, or 10-fold greater affinity for 7KC than cholesterol.

10. A composition comprising a mixture of cyclodextrin dimers according to claim 1 and having an average degree of substitution of between 2 and 10, between 4 and 8, or between 2 and 5; or having a degree of substitution with hydroxypropyl, sulfobutyl, succinyl, or quaternary ammonium groups of between 2 and 5, about 2, about 3, about 4, or about 5; or having a degree of substitution with methyl groups of between 2 and 10, wherein said degree of substitution is measured by NMR or by mass spectrometry, or by MALDI.

11. A pharmaceutical composition comprising a cyclodextrin dimer according to claim 1 and a pharmaceutically acceptable carrier, wherein optionally said cyclodextrin dimer is the only active ingredient for the treatment of atherosclerosis in said composition.

12. The pharmaceutical composition of claim 11, wherein said cyclodextrin dimer is the only active ingredient for the treatment of atherosclerosis in said composition.

13. A therapeutic method comprising administration of an effective amount of a cyclodextrin dimer according to claim 1 to a subject in need thereof, wherein optionally the subject in need thereof is suffering from harmful or toxic effects of 7KC.

14. A method for reducing the amount of 7KC in a subject in need thereof comprising administration of an effective amount of a cyclodextrin dimer according to claim 1 to a subject in need thereof.

15. The method of claim 13, which prevents, treats, ameliorates the symptoms of one or more of atherosclerosis/coronary artery disease, arteriosclerosis, coronary atherosclerosis due to calcified coronary lesion, heart failure (all stages), Alzheimer's disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosi, X-linked adrenoleukodystrophy, sickle cell disease, Niemann-Pick Type A disease, Niemann-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy.

16. A method of purification of oxysterols, comprising: contacting a composition comprising oxysterols with a cyclodextrin dimer according to claim 1, thereby solubilizing said oxysterols in said cyclodextrin dimer; and recovering said cyclodextrin dimer and solubilized oxysterols.

17. An in vitro method of removing oxysterols from a sample, comprising: contacting a sample comprising oxysterols with a cyclodextrin dimer according to claim 1, thereby solubilizing said oxysterols in said cyclodextrin dimer; and separating said sample from said cyclodextrin dimer and solubilized sterols, and optionally reintroducing said sample into a subject from which said sample is obtained.

18. A method of producing a reduced cholesterol product, comprising: contacting a product comprising cholesterol with a cyclodextrin dimer according to claim 1, thereby solubilizing said cholesterols in said cyclodextrin dimer; and removing said cyclodextrin dimer and solubilized cholesterol from said product.

19. A method of making a cyclodextrin dimer according to claim 1, comprising:
   (a) reacting β-cyclodextrin that is protected on the primary side with a dialkylating agent, thereby producing a primary-protected βCD dimer linked through the secondary face, and optionally purifying said primary protected βCD dimer;
   (b) deprotecting said primary protected βCD dimer, thereby producing a deprotected βCD dimer, and optionally purifying said deprotected βCD dimer; and
   (c) linking said deprotected βCD to one or more hydroxypropyl, methyl, succinyl, sulfobutyl, and/or quaternary ammonium, —$CH_2CH(OH)CH_2N(CH_3)_3^+$ groups, thereby producing said cyclodextrin dimer, and optionally purifying said cyclodextrin dimer.

20. A method of making a cyclodextrin dimer according to claim 5, comprising (a) reacting a 2-O-(n-azidoalkyl)-βCD and a 2-O-(n-alkyne)-βCD, thereby forming a βCD-triazole-βCD dimer having the structure βCD-alk1-triazole-alk2-βCD, and optionally (b) purifying said βCD-triazole-βCD dimer.

* * * * *